US011078228B2

(12) United States Patent
Chen et al.

(10) Patent No.: US 11,078,228 B2
(45) Date of Patent: Aug. 3, 2021

(54) ECTONUCLEOTIDASE INHIBITORS AND METHODS OF USE THEREOF

(71) Applicant: Calithera Biosciences, Inc., South San Francisco, CA (US)

(72) Inventors: Lijing Chen, Cupertino, CA (US); Roland Joseph Billedeau, Santa Clara, CA (US); Jim Li, San Francisco, CA (US)

(73) Assignee: Calithera Biosciences, Inc., South San Francisco, CA (US)

( * ) Notice: Subject to any disclaimer, the term of this patent is extended or adjusted under 35 U.S.C. 154(b) by 0 days.

(21) Appl. No.: 16/447,159

(22) Filed: Jun. 20, 2019

(65) Prior Publication Data

US 2019/0389899 A1    Dec. 26, 2019

Related U.S. Application Data

(60) Provisional application No. 62/827,505, filed on Apr. 1, 2019, provisional application No. 62/688,225, filed on Jun. 21, 2018.

(51) Int. Cl.
*C07H 19/167* (2006.01)
*C07H 19/23* (2006.01)
*C07H 19/067* (2006.01)

(52) U.S. Cl.
CPC ......... *C07H 19/167* (2013.01); *C07H 19/067* (2013.01); *C07H 19/23* (2013.01)

(58) Field of Classification Search
CPC ..... C07H 19/23; C07H 19/067; C07H 19/167
USPC ......................................................... 514/46
See application file for complete search history.

(56) References Cited

U.S. PATENT DOCUMENTS

| | | | |
|---|---|---|---|
| 5,635,608 A | 6/1997 | Haugland et al. | |
| 6,426,337 B1 | 7/2002 | Cox et al. | |
| 8,962,636 B2 * | 2/2015 | Pfrengle | A61K 31/522 514/263.21 |
| 10,472,364 B2 * | 11/2019 | Chen | A61P 25/16 |
| 10,570,167 B2 * | 2/2020 | Billedeau | C07H 19/06 |
| 2010/0249055 A1 * | 9/2010 | Mueller | A61P 35/00 514/47 |
| 2013/0323836 A1 | 12/2013 | Manoharan et al. | |
| 2017/0044203 A1 | 2/2017 | Cacatian et al. | |
| 2018/0186827 A1 | 7/2018 | Billedeau et al. | |
| 2019/0389899 A1 | 12/2019 | Chen et al. | |
| 2020/0087310 A1 | 3/2020 | Chen et al. | |
| 2020/0223882 A1 | 7/2020 | Billedeau et al. | |

FOREIGN PATENT DOCUMENTS

| | | |
|---|---|---|
| EP | 0572669 A1 | 12/1993 |
| EP | 1860113 A1 | 11/2007 |
| WO | WO-1994/10128 A1 | 5/1994 |
| WO | WO-1998/34943 A1 | 8/1998 |
| WO | WO-2004/096233 A2 | 11/2004 |
| WO | WO-2008/011406 A2 | 1/2008 |
| WO | WO-2009/061781 A1 | 5/2009 |
| WO | WO-2012/006351 A1 | 1/2012 |
| WO | WO-2012/151142 A2 | 11/2012 |
| WO | WO-2014/079903 A1 | 5/2014 |
| WO | WO 2015/164572 A1 * | 10/2015 | ........... C07D 473/40 |
| WO | WO-2015/164573 A1 | 10/2015 |
| WO | WO-2017/066781 A1 | 4/2017 |
| WO | WO-2017/066782 A1 | 4/2017 |
| WO | WO-2017/066791 A1 | 4/2017 |
| WO | WO-2017/079195 A1 | 5/2017 |
| WO | WO-2018/049145 A1 | 3/2018 |
| WO | WO-2018/119284 A1 | 6/2018 |
| WO | WO-2019/246403 A1 | 12/2019 |
| WO | WO-2020/257429 A1 | 12/2020 |

OTHER PUBLICATIONS

Debarge, et. al., Journal of Organic Chemistry, 2011,76(1), 105-126.*
Bonaate et al., "Discovery and development of clofarabine: a nucleoside analogue for treating cancer," Nat Rev Drug Discov, 5(10): 855-863 (2006).
CAS Registry No. 1259875-56-3; STN Entry Date: Jan. 19, 2011.
CAS Registry No. 1260067-78-4; STN Entry Date: Jan. 20, 2011.
CAS Registry No. 1260067-82-0; STN Entry Date: Jan. 20, 2011.
Debarge et al., "Design and Synthesis of α-Carboxy Phosphononucleosides," J Org Chem, 76(1): 105-126 (2011).
Hladezuk et al., "Development of O-H Insertion for the Attachment of Phosphonates to Nucleosides; Synthesis of α-carboxy phosphononucleosides," Tetrahedron, 68(7):1894-1909 (2012).
International Search Report and Written Opinion for International Application No. PCT/US2017/050659 dated Jan. 10, 2018.
International Search Report and Written Opinion for International Application No. PCT/US2017/067980 dated Mar. 28, 2018.
Jordheim et al., "Determination of the enzymatic activity of cytosolic 5'-nucleotidase cN-II in cancer cells: development of a simple analytical method and related cell line models," Anal Bioanal Chem, 407(19):5747-5758 (2015).
Périgaud et al., "Nucleoside analogues as chemotherapeutic agents: a review," Nucleos Nucleot, 11(2-4):903-945 (1992).
Allard et al., "Targeting CD73 Enhances the Antitumor Activity of Anti-PD-1 and Anti-CTLA-4 mAbs," Clinical Cancer Research, 19(20): 5626-5635 (2013).
Berkow et al., "The Merck Manual," 16th Edition: 1403-04, 1488-1489, 1493-1494 (1992).
Bhattarai et al., "α, β-Methylene-ADP (AOPCP) Derivatives and Analogs: Development of Potent and Selective ecto-5'-Nucleotidase (CD73) Inhibitors," J Med Chem, 58(15):6248-6263 (2015).

(Continued)

*Primary Examiner* — Ganapathy Krishnan
(74) *Attorney, Agent, or Firm* — David P. Halstead; Foley Hoag LLP

(57) ABSTRACT

The invention relates to novel heterocyclic compounds and pharmaceutical preparations thereof. The invention further relates to methods of treating or preventing cancer using the novel heterocyclic compounds of the invention.

35 Claims, 36 Drawing Sheets

(56) References Cited

OTHER PUBLICATIONS

Extended European Search Report for EP Application No. 17849598.2 dated May 4, 2020.
Extended European Search Report for EP Application No. 17883974.2 dated May 12, 2020.
Gura., "Systems for Identifiying New Drugs Are Often Faulty," Science, 278(5340): 1041-1042 (1997).
International Search Report and Written Opinion for International Application No. PCT/US2019/038245 dated Sep. 22, 2019.
Mawe., "Colitis-induced neuroplasticity disrupts motility in the inflamed and post-inflamed colon," The Journal of Clinical Investigation, 125(3): 949-955 (2015).
International Search Report and Written Opinion for International Application No. PCT/US2020/038395 dated Nov. 12, 2020.

* cited by examiner

| Assay | IC$_{50}$ (nM) |
|---|---|
| Human Recombinant CD73 | 0.17 |
| Human Plasma CD73 | 0.38 |
| Human Cell Surface CD73 | 0.21 |
| Mouse Recombinant CD73 | 1.3 |
| Mouse Plasma CD73 | 1.0 |

CT26 anti-PD-L1 Combo

Cmpd. 9

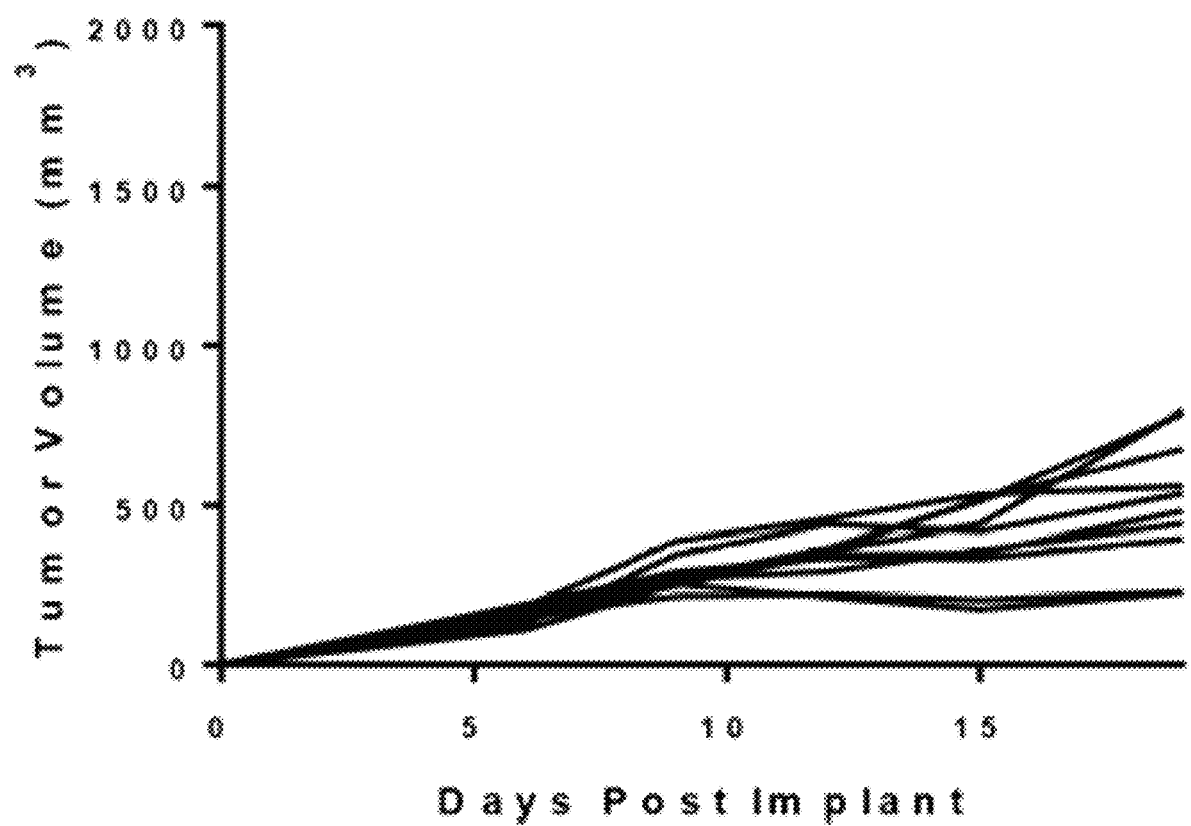

ECTONUCLEOTIDASE INHIBITORS AND METHODS OF USE THEREOF

RELATED APPLICATIONS

This application claims the benefit of U.S. Provisional Application No. 62/688,225, filed Jun. 21, 2018, and U.S. Provisional Application No. 62/827,505, filed Apr. 1, 2019, each of which is hereby incorporated by reference in its entirety.

BACKGROUND

CD73, also referred to as 5'-nucleotidase (5'-NT) or ecto-5'-nucleotidase (Ecto 5'NTase), is a membrane-bound cell surface enzyme whose primary role is to catalyze the conversion of extracellular nucleotides (e.g., AMP) to their corresponding nucleosides (e.g., adenosine). CD73 is found in most tissues and expressed on lymphocytes, endothelial cells, and epithelial cells. It is also widely expressed in many tumor cell lines and, notably, is upregulated in cancerous tissues (Antonioli et al., *Nat. Rev. Cancer,* 13: 842-857, 2013).

In tandem with CD39 (ecto-ATPase), CD73 generates adenosine from ATP/AMP, which is often released from damaged or inflamed cells into the extracellular environment. Extracellular adenosine produced by CD73 interacts with G-protein coupled receptors on target cells. An important downstream effect of this signaling is increased immunosuppression via a number of pathways. For example, CD73 is a co-signaling molecule on T lymphocytes. Under normal circumstances, extracellular adenosine levels promote a self-limiting immune response that prevents excessive inflammation and tissue damage. For tumors, an advantage of abnormally increased CD73 is that the resulting increased CD73-catalyzed adenosine levels yield inhibition of anti-tumor immune system responses.

Even though CD73 plays a role in cancer immunosuppression, higher expression of CD73 is associated with a variety of stages of tumor progression, including tumor vascularization, invasiveness, and metastasis, and with shorter breast cancer patient survival time. Some of these observations result from CD73's enzyme-independent function as an adhesion molecule required for lymphocyte binding to the endothelium.

Overall, CD73 has become an important target for developing new cancer therapies, either as single agents or in combination with other cancer therapies. Indeed, combining CD73 monoclonal antibodies with antibodies for other chemotherapy targets enhances response and survival in animal cancer models (Allard et al., *Clin. Cancer Res.,* 19:5626-35, 2013).

Many of the current cancer treatments and chemotherapeutic agents fail to successfully treat all patients or all symptoms in treated patients, and many of these therapies are associated with undesirable side effects. As certain cancers develop resistance to various chemotherapeutic agents, alternate cancer therapies are needed. Thus, there is a need for additional compounds and methods for treating cancer and other diseases.

SUMMARY

Disclosed herein are compounds of Formula (I):

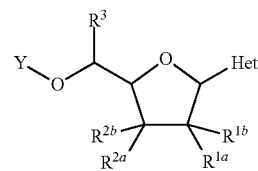

(I)

or a pharmaceutically acceptable salt and/or prodrug thereof, wherein

Y is

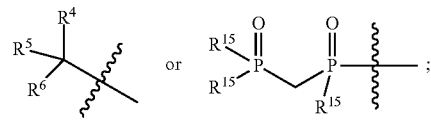

Het is heterocyclyl or heteroaryl;

$R^{1a}$ is selected from H, halo, hydroxy, cyano, azido, amino, $C_{1-6}$alkyl, hydroxy$C_{1-6}$alkyl, amino-$C_{1-6}$alkyl, —O—C(O)—O—$C_{1-6}$alkyl, $C_{1-6}$acyloxy, $C_{1-6}$alkoxy, $C_{2-6}$alkenyl, and $C_{2-6}$alkynyl;

$R^{1b}$ is selected from H, halo, $C_{1-6}$alkyl, hydroxy-$C_{1-6}$alkyl, amino-$C_{1-6}$alkyl, $C_{2-6}$alkenyl, and $C_{2-6}$alkynyl;

$R^{2a}$ is selected from halo, hydroxy, cyano, azido, amino, $C_{1-6}$alkyl, hydroxy-$C_{1-6}$alkyl, amino-$C_{1-6}$alkyl, $C_{1-6}$acyloxy, —O—C(O)—O—$C_{1-6}$alkyl, $C_{1-6}$alkoxy, $C_{2-6}$alkenyl, and $C_{2-6}$alkynyl;

$R^{2b}$ is selected from halo, $C_{1-6}$alkyl, $C_{2-6}$alkenyl, and $C_{2-6}$alkynyl, preferably substituted or unsubstituted $C_2$alkynyl, most preferably unsubstituted $C_2$alkynyl;

$R^3$ is selected from H and alkyl;

$R^4$ is selected from H, alkyl, CN, aryl, heteroaryl, —C(O)OR$^9$, —C(O)NR$^{11}$R$^{12}$, —S(O)$_2$R$^{10}$, —P(O)(OR$^{11}$)(OR$^{12}$), and —P(O)(OR$^{11}$)(NR$^{13}$R$^{14}$);

$R^5$ is selected from H, cyano, alkyl, cycloalkylalkyl, heterocyclylalkyl, aralkyl, heteroaralkyl, and —C(O)OR$^9$;

$R^6$ is selected from —C(O)OR$^9$, —C(O)NR$^{16}$R$^{17}$, and —P(O)(OR$^{11}$)(OR$^{12}$);

$R^9$ is independently selected from H, alkyl, cycloalkyl, cycloalkylalkyl, heterocyclyl, heterocyclylalkyl, aryl, aralkyl, heteroaryl, and heteroaralkyl;

$R^{10}$ is independently selected from alkyl, alkenyl, alkynyl, amino, cycloalkyl, cycloalkylalkyl, heterocyclyl, heterocyclylalkyl, aryl, aralkyl, heteroaryl, and heteroaralkyl; and each $R^{11}$ and $R^{12}$ is independently selected from H, alkyl, cycloalkyl, cycloalkylalkyl, heterocyclyl, heterocyclylalkyl, aryl, aralkyl, heteroaryl, heteroaralkyl; or $R^{11}$ and $R^{12}$, together with the nitrogen atom to which they are attached, form a 5- to 7-membered heterocyclyl;

$R^{13}$ is H or alkyl;

$R^{14}$ is alkyl or aralkyl;

each $R^{15}$ is independently selected from hydroxy, alkoxy acyloxy and NR$^{13}$R$^{14}$;

each $R^{16}$ and $R^{17}$ is independently selected from H, hydroxy, alkyl, cycloalkyl, cycloalkylalkyl, heterocyclyl, heterocyclylalkyl, aryl, aralkyl, heteroaryl, heteroaralkyl; or $R^{16}$ and $R^{17}$, together with the nitrogen atom to which they are attached, form a 5- to 7-membered heterocyclyl.

In certain preferred embodiments of Formula I, the included compounds meet the terms of a) and b); or a) and c);
wherein:
a) the compound is not
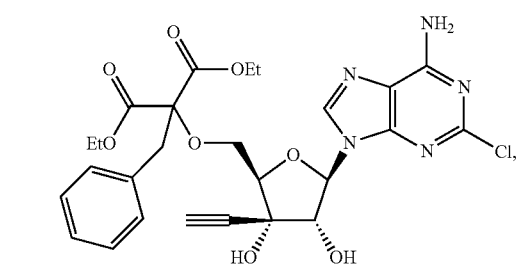
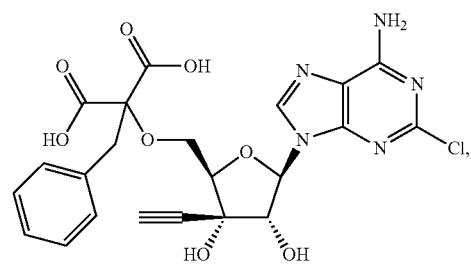
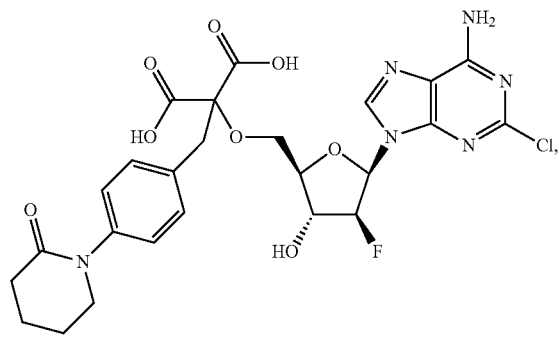
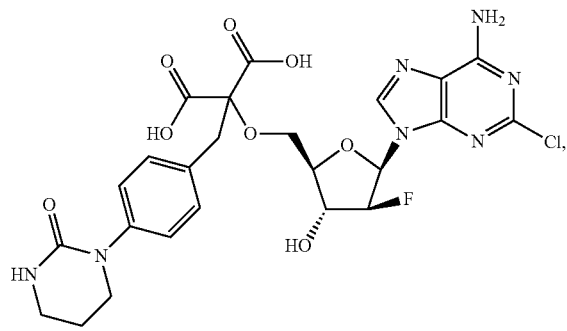
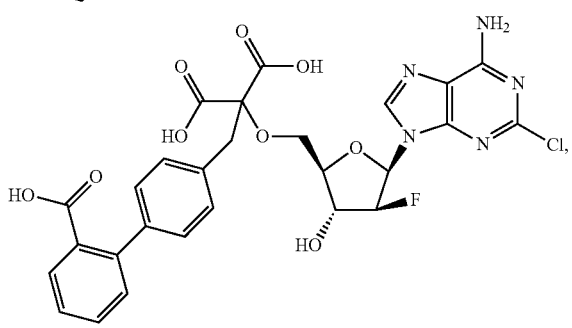
-continued
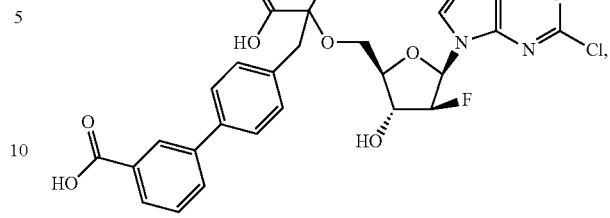
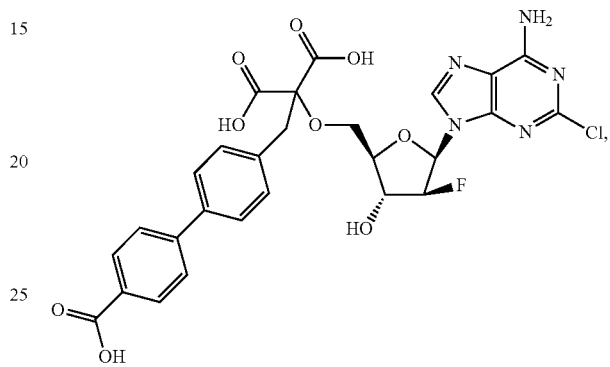
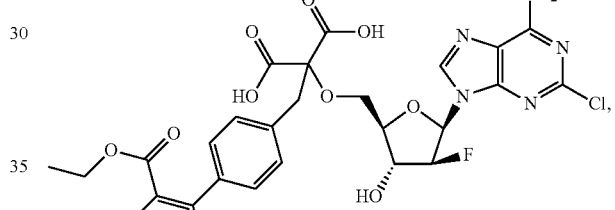
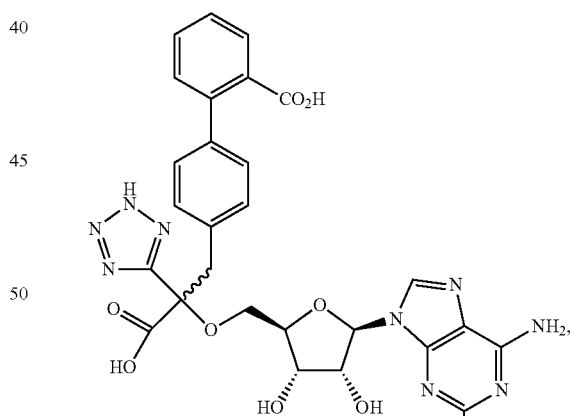
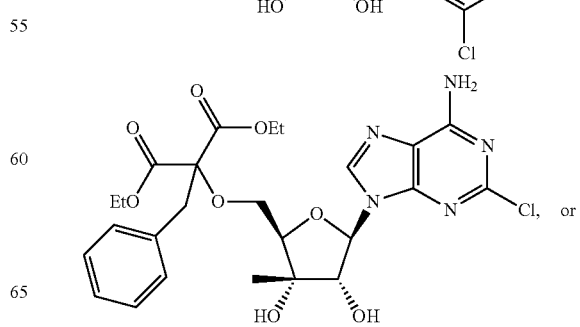
or

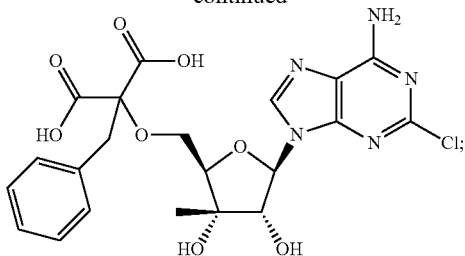

b) if R[4] and R[6] are each —C(O)OH and R[5] is benzyl substituted on the phenyl ring with a heterocyclyl or heteroaryl substituent, then the phenyl ring substituent is selected from unsubstituted or substituted pyrrolidinyl, piperazinonyl, piperidonyl, tetrahydropyrimidonyl, pyridonyl, and pyridyl; and c) if R[4] is —C(O)OH or tetrazolyl, R[6] is —C(O)OH, and R[5] is benzyl substituted on the phenyl ring with a second phenyl ring, then either the benzyl phenyl ring or the second phenyl ring is substituted with —C(O)OR[9] where R[9] is H or alkyl.

In some embodiments, Y is

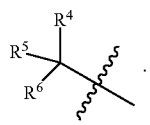

In other embodiments, Y is

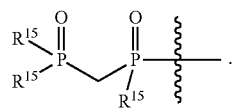

In certain preferred embodiments:
a) the compound is not

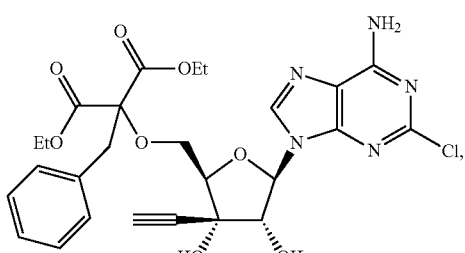

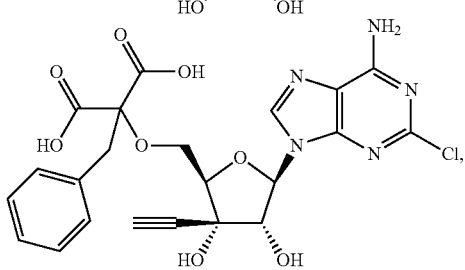

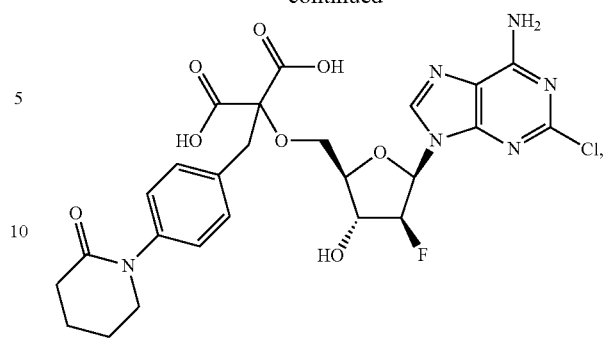

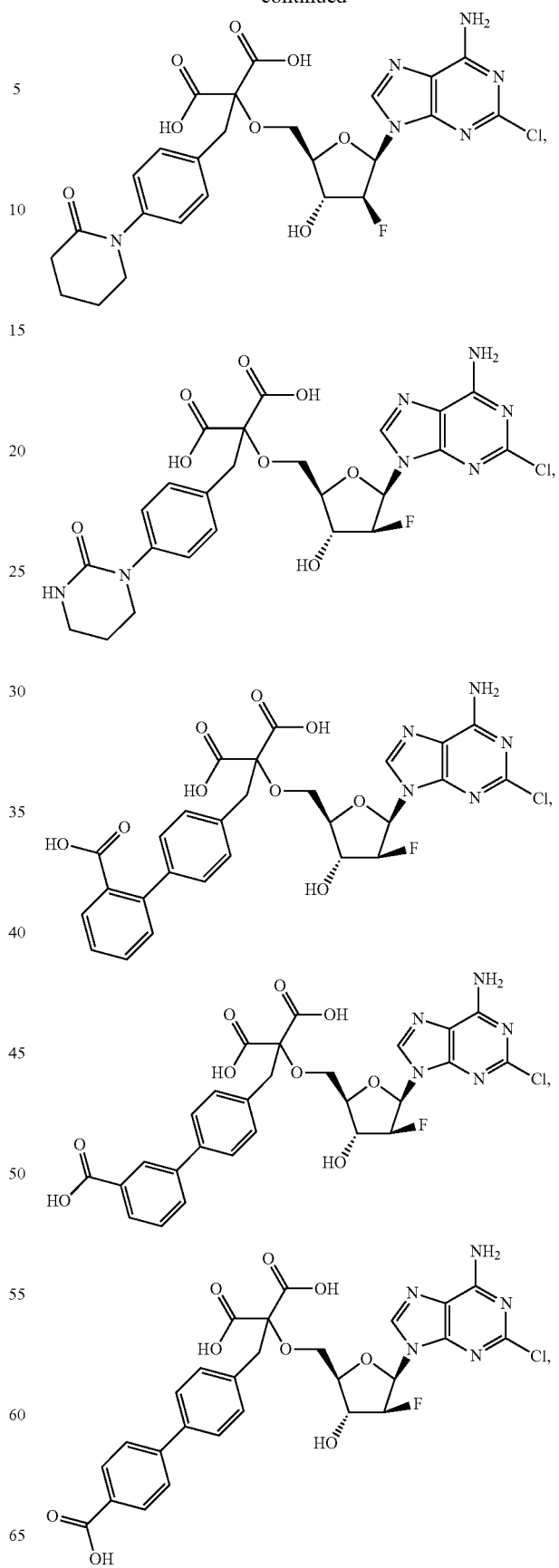

-continued

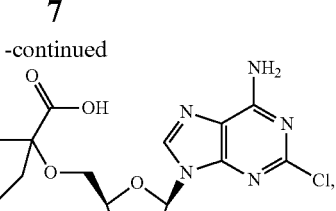

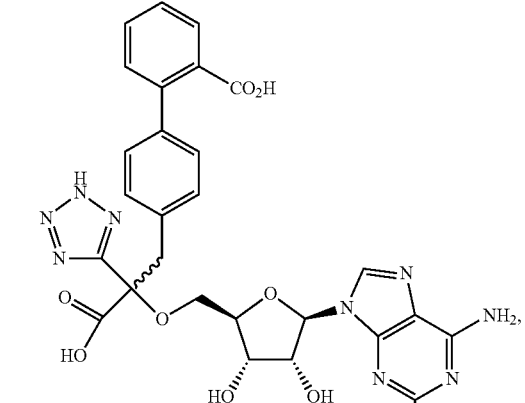

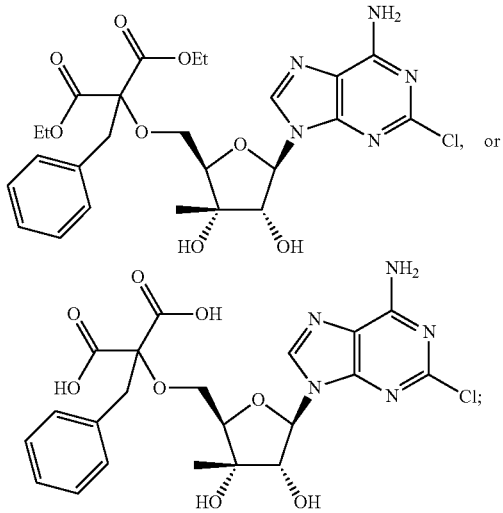

and b) $R^{2b}$ is selected from halo, $C_{2-6}$alkyl, $C_{2-6}$alkenyl, and $C_{2-6}$alkynyl, preferably substituted or unsubstituted $C_2$alkynyl, most preferably unsubstituted $C_2$alkynyl; and either c) $R^5$ is benzyl substituted on the phenyl ring with a substituent selected from unsubstituted or substituted piperidonyl, tetrahydropyrimidonyl, pyridonyl, and pyridyl, or d) $R^5$ is benzyl substituted on the phenyl ring with a second phenyl ring substituted with —C(O)OR$^9$ where $R^9$ is H or alkyl.

In certain embodiments, the present invention provides a pharmaceutical composition suitable for use in a subject in the treatment or prevention of cancer comprising an effective amount of any of the compounds described herein (e.g., a compound of the invention, such as a compound of Formula (I), or a pharmaceutically acceptable salt thereof, and one or more pharmaceutically acceptable excipients. In certain embodiments, the pharmaceutical preparations may be for use in treating or preventing a condition or disease as described herein.

Disclosed herein are methods of treating diseases and conditions that benefit from the inhibition of CD73, comprising administering to a subject in need thereof an effective amount of a compound as disclosed herein (e.g., a compound of Formula (I) or any of the embodiments thereof disclosed herein). In certain embodiments, the human subject is in need of such treatment. These diseases include, but are not limited to, cancers, such as lung cancer, kidney cancer, skin cancer, breast cancer, and ovarian cancer. Other diseases and conditions that can be treated using the methods described herein include, but are not limited to, neurological, neurodegenerative and CNS disorders and diseases such as depression and Parkinson's disease, cerebral and cardiac ischemic diseases, sleep disorders, fibrosis, immune and inflammatory disorders.

Provided herein are combination therapies of compounds of formula (I) with monoclonal antibodies and other chemotherapeutic agents that can enhance the therapeutic benefit beyond the ability of the adjuvant therapy alone.

BRIEF DESCRIPTION OF THE FIGURES

FIG. 7B is vehicle. FIG. 7C is anti-PD-L1 antibody. FIG. 7D is Compound 9. FIG. 7E is Compound 9+ Anti-PD-L1.

FIG. 8B is vehicle. FIG. 8C is oxaliplatin. FIG. 8D is Compound 9. FIG. 8E is Compound 9+oxaliplatin.

FIGS. 9B-9E show individual replications of this measurement for each dosing. FIG. 9B is vehicle. FIG. 9C is doxorubicin. FIG. 9D is Compound 9. FIG. 9E is Compound 9+doxorubicin.

FIG. 12B shows vehicle. FIG. 12C is Compound 9. FIG. 12D is docetaxel. FIG. 12E is Compound 9+docetaxel.

FIG. 13B is vehicle. FIG. 13C is dosing of Compound 9 started on day 1. FIG. 13D is Compound 9 started on day 6.

DETAILED DESCRIPTION

Definitions

Figure 1A:
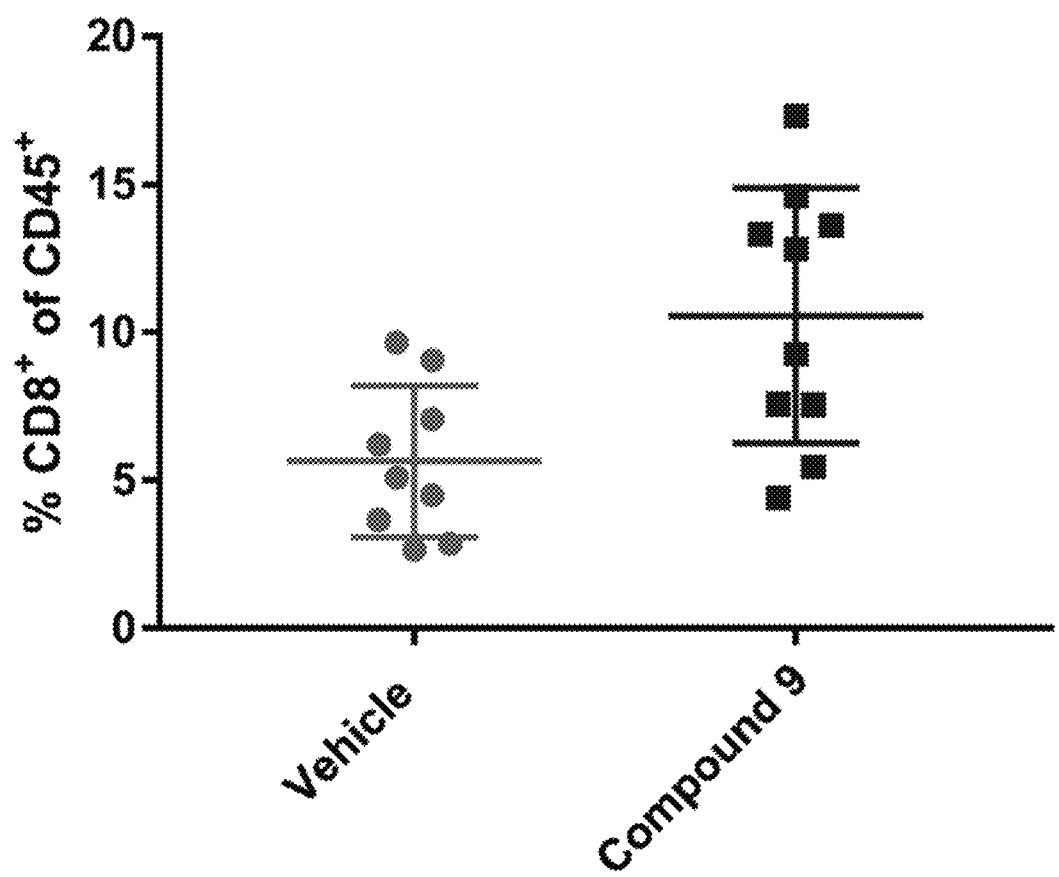
FIG. 1A depicts the increase in % CD8+ cells of CD45+ cells in EG7 tumors from mice treated with Compound 9.

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In some embodiments, chemical structures are disclosed with a corresponding chemical name. In case of conflict, the chemical structure controls the meaning, rather than the name.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited are not substantially changed by the presence of more than that which is recited, but excludes prior art embodiments.

Unless specifically stated or obvious from context, as used herein, the term "or" is understood to be inclusive. Unless specifically stated or obvious from context otherwise, as used herein, the terms "a", "an", and "the" are understood to be singular or plural.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

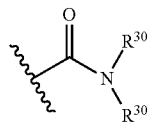

wherein each $R^{30}$ independently represents a hydrogen or hydrocarbyl group, or two $R^{30}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

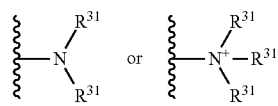

wherein each $R^{31}$ independently represents a hydrogen or a hydrocarbyl group, or two $R^{31}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

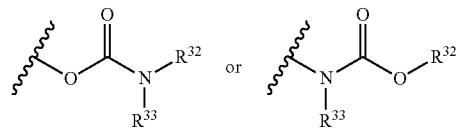

wherein $R^{32}$ and $R^{33}$ independently represent hydrogen or a hydrocarbyl group, such as an alkyl group, or $R^{32}$ and $R^{33}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^{34}$, wherein $R^{34}$ represents a hydrocarbyl group.

The term "carboxy", as used herein, refers to a group represented by the formula —$CO_2H$.

The term "ester", as used herein, refers to a group —$C(O)OR^{35}$ wherein $R^{35}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical.

Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms.

Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

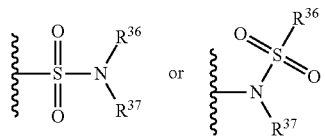

wherein $R^{36}$ and $R^{37}$ independently represent hydrogen or hydrocarbyl, such as alkyl, or $R^{36}$ and $R^{37}$ taken together with the intervening atom(s) complete a heterocycle having from 4 to 8 atoms in the ring structure.

The term "sulfoxide" is art-recognized and refers to the group —S(O)—$R^{38}$, wherein $R^{38}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^{39}$, wherein $R^{39}$ represents a hydrocarbyl.

The term "thioalkyl", as used herein, refers to an alkyl group substituted with a thiol group.

The term "thioester", as used herein, refers to a group —C(O)SR$^{40}$ or —SC(O)R$^{40}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

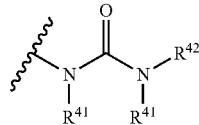

wherein $R^{41}$ and $R^{42}$ independently represent hydrogen or a hydrocarbyl, such as alkyl, or either occurrence of $R^{41}$ taken together with $R^{42}$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

In certain embodiments, compounds of the invention may be racemic. In certain embodiments, compounds of the invention may be enriched in one enantiomer. For example, a compound of the invention may have greater than about 30% ee, about 40% ee, about 50% ee, about 60% ee, about 70% ee, about 80% ee, about 90% ee, or even about 95% or greater ee. In certain embodiments, compounds of the invention may have more than one stereocenter. In certain such embodiments, compounds of the invention may be enriched in one or more diastereomer. For example, a compound of the invention may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (I)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I)). A diastereomerically enriched mixture may comprise, for example, at least about 60 mol percent of one diastereomer, or more preferably at least about 75, about 90, about 95, or even about 99 mol percent.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the subject of one or more of the disclosed compositions. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of Formula (I)). A common method for making a prodrug is to include one or more selected moieties which are hydrolyzed under physiologic conditions to reveal the desired molecule. In other embodiments, the prodrug is converted by an enzymatic activity of the subject. For example, esters or carbonates (e.g., esters or carbonates of alcohols or carboxylic acids) are preferred prodrugs of the present invention. In certain embodiments, some or all of the compounds of Formula (I) in a formulation represented above can be replaced with the corresponding suitable prodrug, e.g., wherein a hydroxyl in the parent compound is presented as an ester or a carbonate or carboxylic acid.

An "effective amount", as used herein, refers to an amount that is sufficient to achieve a desired biological effect. A "therapeutically effective amount", as used herein, refers to an amount that is sufficient to achieve a desired therapeutic effect. For example, a therapeutically effective amount can refer to an amount that is sufficient to improve at least one sign or symptom of cancer.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others.

In some embodiments, the invention provides a compound of formula (I):

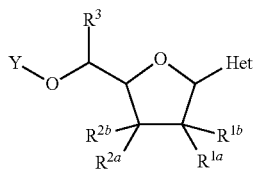
(I)

or a pharmaceutically acceptable salt and/or prodrug thereof, wherein

Y is

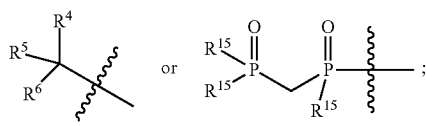

Het is heterocyclyl or heteroaryl;

$R^{1a}$ is selected from H, halo, hydroxy, cyano, azido, amino, $C_{1-6}$alkyl, hydroxyC$_{1-6}$alkyl, amino-C$_{1-6}$alkyl, —O—C(O)—O—C$_{1-6}$alkyl, C$_{1-6}$acyloxy, C$_{1-6}$alkoxy, C$_{2-6}$alkenyl, and C$_{2-6}$alkynyl;

$R^{1b}$ is selected from H, halo, C$_{1-6}$alkyl, hydroxy-C$_{1-6}$alkyl, amino-C$_{1-6}$alkyl, C$_{2-6}$alkenyl, and C$_{2-6}$alkynyl;

$R^{2a}$ is selected from halo, hydroxy, cyano, azido, amino, C$_{1-6}$alkyl, hydroxy-C$_{1-6}$alkyl, amino-C$_{1-6}$alkyl, C$_{1-6}$acyloxy, —O—C(O)—O—C$_{1-6}$alkyl, C$_{1-6}$alkoxy, C$_{2-6}$alkenyl, and C$_{2-6}$alkynyl;

$R^{2b}$ is selected from halo, C$_{1-6}$alkyl, C$_{2-6}$alkenyl, and C$_{2-6}$alkynyl, preferably substituted or unsubstituted C$_2$alkynyl, most preferably unsubstituted C$_2$alkynyl;

$R^3$ is selected from H and alkyl;

$R^4$ is selected from H, alkyl, CN, aryl, heteroaryl, —C(O)OR$^9$, —C(O)NR$^{11}$R$^{12}$, —S(O)$_2$R$^{10}$, —P(O)(OR$^{11}$)(OR$^{12}$), and —P(O)(OR$^{11}$)(NR$^{13}$R$^{14}$);

$R^5$ is selected from H, cyano, alkyl, cycloalkylalkyl, heterocyclylalkyl, aralkyl, heteroaralkyl, and —C(O)OR$^9$;

$R^6$ is selected from —C(O)OR$^9$, —C(O)NR$^{16}$R$^{17}$, and —P(O)(OR$^{11}$)(OR$^{12}$);

$R^9$ is independently selected from H, alkyl, cycloalkyl, cycloalkylalkyl, heterocyclyl, heterocyclylalkyl, aryl, aralkyl, heteroaryl, and heteroaralkyl;

$R^{10}$ is independently selected from alkyl, alkenyl, alkynyl, amino, cycloalkyl, cycloalkylalkyl, heterocyclyl, heterocyclylalkyl, aryl, aralkyl, heteroaryl, and heteroaralkyl; and each $R^{11}$ and $R^{12}$ is independently selected from H, alkyl, cycloalkyl, cycloalkylalkyl, heterocyclyl, heterocyclylalkyl, aryl, aralkyl, heteroaryl, heteroaralkyl; or $R^{11}$ and $R^{12}$, together with the nitrogen atom to which they are attached, form a 5- to 7-membered heterocyclyl;

$R^{13}$ is H or alkyl;

$R^{14}$ is alkyl or aralkyl;

each $R^{15}$ is independently selected from hydroxy, alkoxy acyloxy and NR$^{13}$R$^{14}$;

each $R^{16}$ and $R^{17}$ is independently selected from H, hydroxy, alkyl, cycloalkyl, cycloalkylalkyl, heterocyclyl, heterocyclylalkyl, aryl, aralkyl, heteroaryl, heteroaralkyl; or $R^{16}$ and $R^{17}$, together with the nitrogen atom to which they are attached, form a 5- to 7-membered heterocyclyl.

In certain preferred embodiments of Formula I, the included compounds meet the terms of a) and b); or a) and c);

wherein:

a) the compound is not

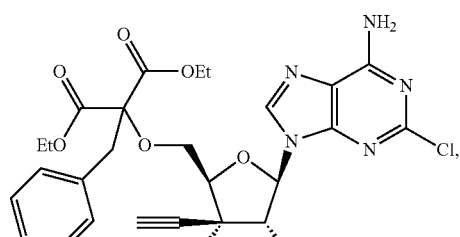

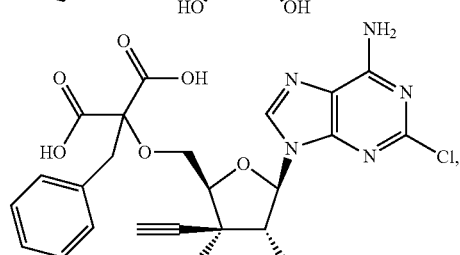

-continued

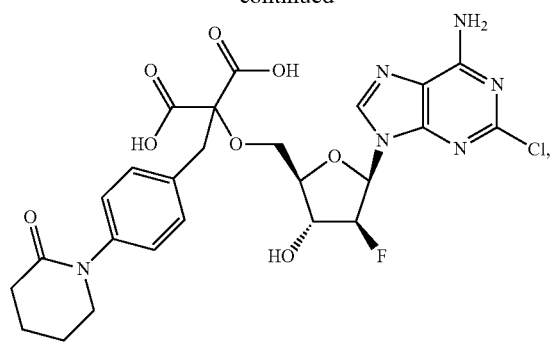

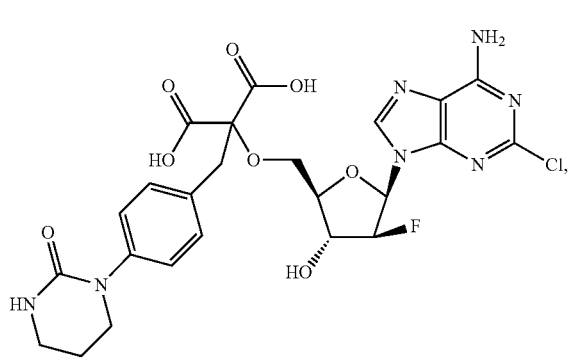

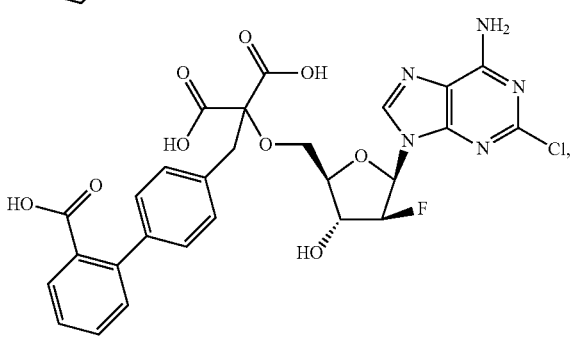

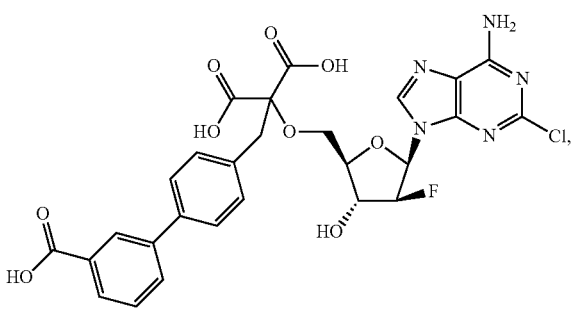

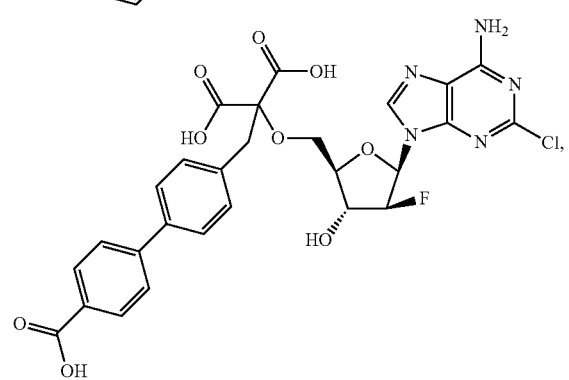

-continued

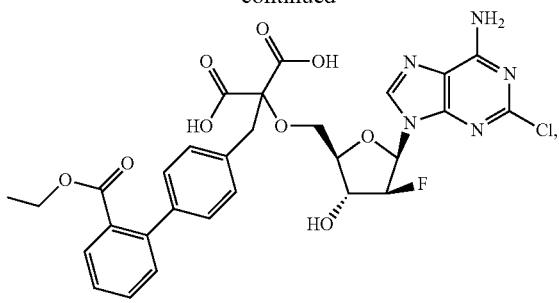

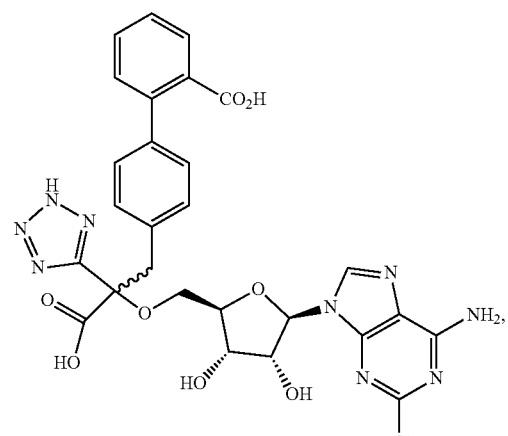

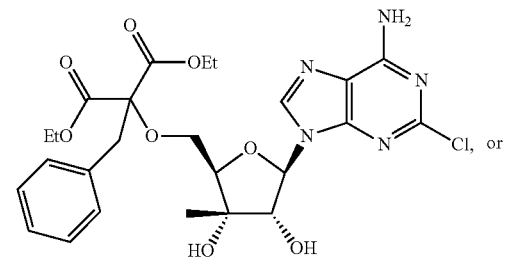

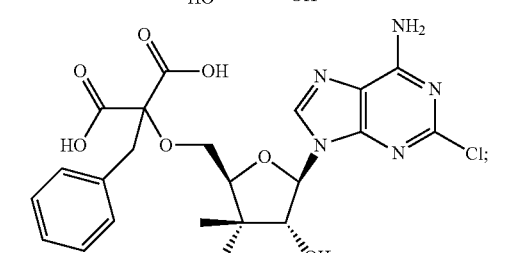

b) if $R^4$ and $R^6$ are each —C(O)OH and $R^5$ is benzyl substituted on the phenyl ring with a heterocyclyl or heteroaryl substituent, then the phenyl ring substituent is selected from unsubstituted or substituted pyrrolidinyl, piperazinonyl, piperidonyl, tetrahydropyrimidonyl, pyridonyl, and pyridyl; and c) if $R^4$ is —C(O)OH or tetrazolyl, $R^6$ is —C(O)OH, and $R^5$ is benzyl substituted on the phenyl ring with a second phenyl ring, then either the benzyl phenyl ring or the second phenyl ring is substituted with —C(O)$OR^9$ where $R^9$ is H or alkyl.

In some embodiments, the invention provides a compound of formula (II):

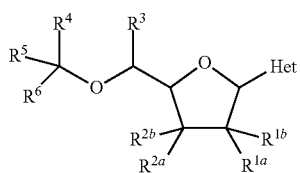

(II)

or a pharmaceutically acceptable salt and/or prodrug thereof, wherein

Het is heterocyclyl or heteroaryl;

$R^{1a}$ is selected from H, halo, hydroxy, cyano, azido, amino, $C_{1-6}$alkyl, hydroxyC$_{1-6}$alkyl, amino-C$_{1-6}$alkyl, —O—C(O)—O—C$_{1-6}$alkyl, C$_{1-6}$acyloxy, C$_{1-6}$alkoxy, C$_{2-6}$alkenyl, and C$_{2-6}$alkynyl;

$R^{1b}$ is selected from H, halo, C$_{1-6}$alkyl, hydroxy-C$_{1-6}$alkyl, amino-C$_{1-6}$alkyl, C$_{2-6}$alkenyl, and C$_{2-6}$alkynyl;

$R^{2a}$ is selected from halo, hydroxy, cyano, azido, amino, C$_{1-6}$alkyl, hydroxy-C$_{1-6}$alkyl, amino-C$_{1-6}$alkyl, C$_{1-6}$acyloxy, —O—C(O)—O—C$_{1-6}$alkyl, C$_{1-6}$alkoxy, C$_{2-6}$alkenyl, and C$_{2-6}$alkynyl;

$R^{2b}$ is selected from H, halo, C$_{1-6}$alkyl, C$_{2-6}$alkenyl, and C$_{2-6}$alkynyl;

$R^3$ is selected from H and alkyl;

$R^4$ is selected from alkyl, aryl, heteroaryl, —C(O)OR$^9$, —C(O)NR$^{11}$R$^{12}$, —S(O)$_2$R$^{10}$, —P(O)(OR$^{11}$)(OR$^{12}$), and —P(O)(OR$^{11}$)(NR$^{13}$R$^{14}$);

$R^5$ is selected from H, cyano, alkyl, cycloalkylalkyl, heterocyclylalkyl, aralkyl, heteroaralkyl, and —C(O)OR$^9$;

$R^6$ is selected from —C(O)OR$^9$, —C(O)NR$^{11}$R$^{12}$ and —P(O)(OR$^{11}$)(OR$^{12}$);

$R^9$ is independently selected from H, alkyl, alkenyl, alkynyl, cycloalkyl, cycloalkylalkyl, heterocyclyl, heterocyclylalkyl, aryl, aralkyl, heteroaryl, and heteroaralkyl;

$R^{11}$ is independently selected from alkyl, alkenyl, alkynyl, amino, cycloalkyl, cycloalkylalkyl, heterocyclyl, heterocyclylalkyl, aryl, aralkyl, heteroaryl, and heteroaralkyl; and each $R^{11}$ and $R^{12}$ is independently selected from H, alkyl, cycloalkyl, cycloalkylalkyl, heterocyclyl, heterocyclylalkyl, aryl, aralkyl, heteroaryl, heteroaralkyl; or $R^{11}$ and $R^{12}$, together with the nitrogen atom to which they are attached, form a 5- to 7-membered heterocyclyl;

$R^{13}$ is H or alkyl; and $R^{14}$ is alkyl or aralkyl;

provided that a), b) and c); or a), b) and d);

a) the compound is not

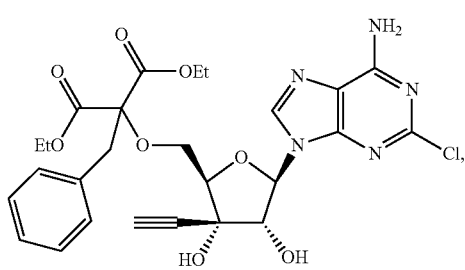 [SMILES: C[C@@]1(O)[C@@H](COC(Cc2ccccc2)(C(=O)O)C(=O)O)O[C@@H](n2cnc3c(N)nc(Cl)nc32)[C@@H]1O]

-continued

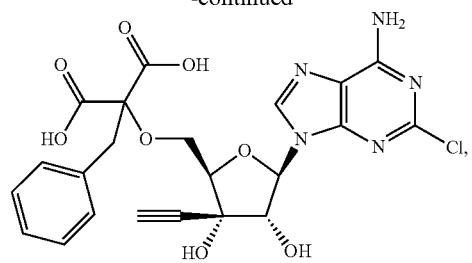

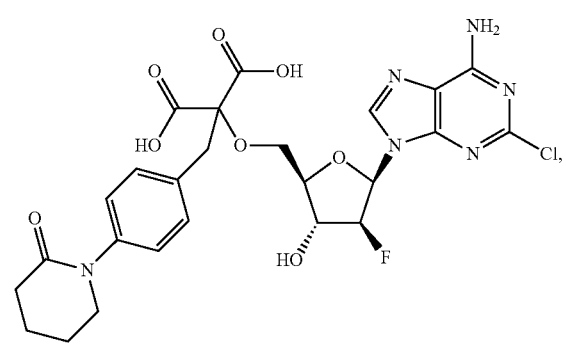

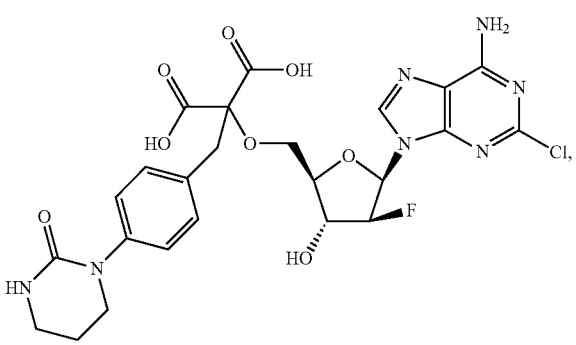

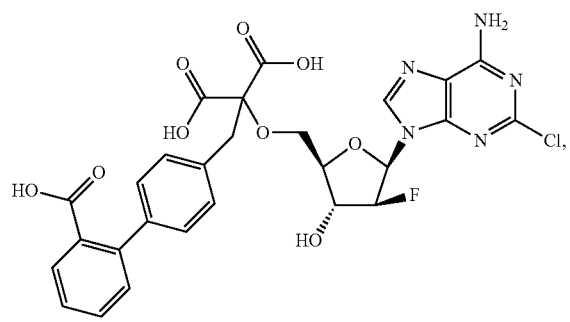

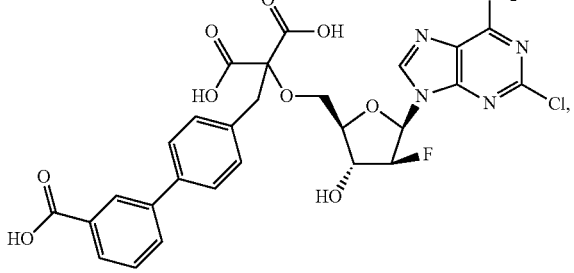

-continued

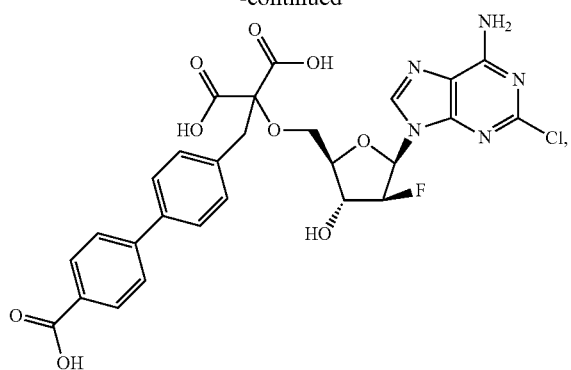

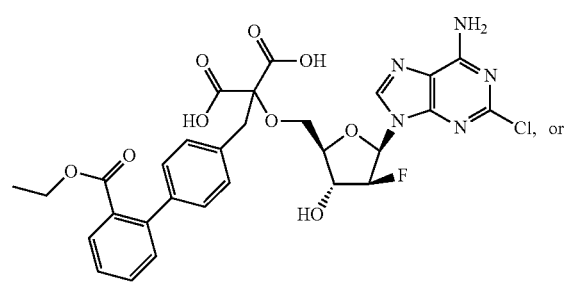

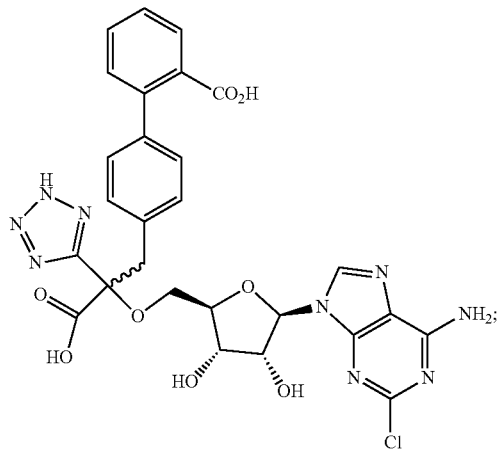

and b) $R^{2b}$ is selected from halo, $C_{2-6}$alkyl, $C_{2-6}$alkenyl, and $C_{2-6}$alkynyl, preferably substituted or unsubstituted $C_2$alkynyl, most preferably unsubstituted $C_2$alkynyl, c) if $R^4$ and $R^6$ are each —C(O)OH and $R^5$ is benzyl substituted on the phenyl ring with a heterocyclyl or heteroaryl substituent, then the phenyl ring substituent is selected from unsubstituted or substituted piperidonyl, tetrahydropyrimidonyl, pyridonyl, and pyridyl; and d) if $R^4$ is —C(O)OH or tetrazolyl, $R^6$ is —C(O)OH, and $R^5$ is benzyl substituted on the phenyl ring with a second phenyl ring, then either the benzyl phenyl ring or the second phenyl ring is substituted with —C(O)OR$^9$ where $R^9$ is H or alkyl.

In certain preferred embodiments:

a) the compound is not

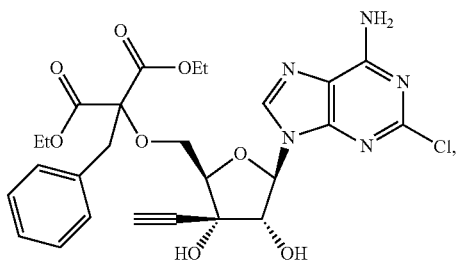

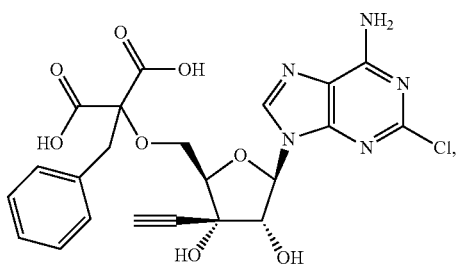

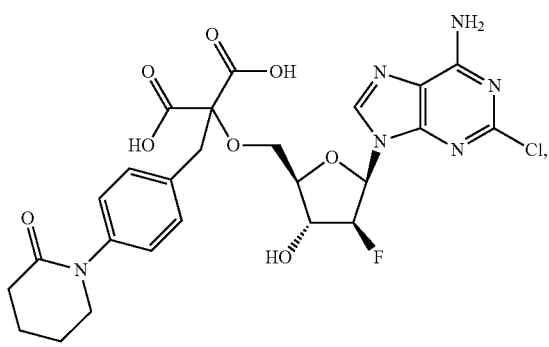

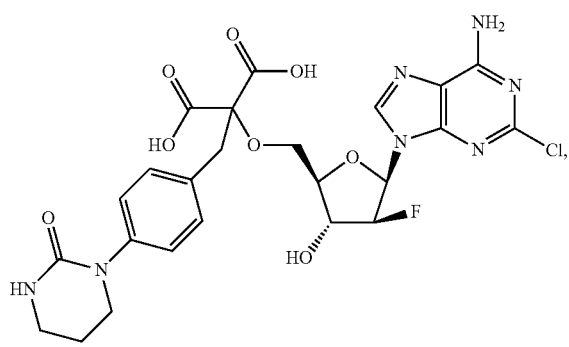

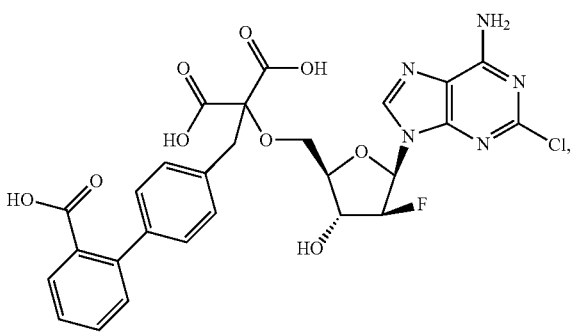

25
-continued

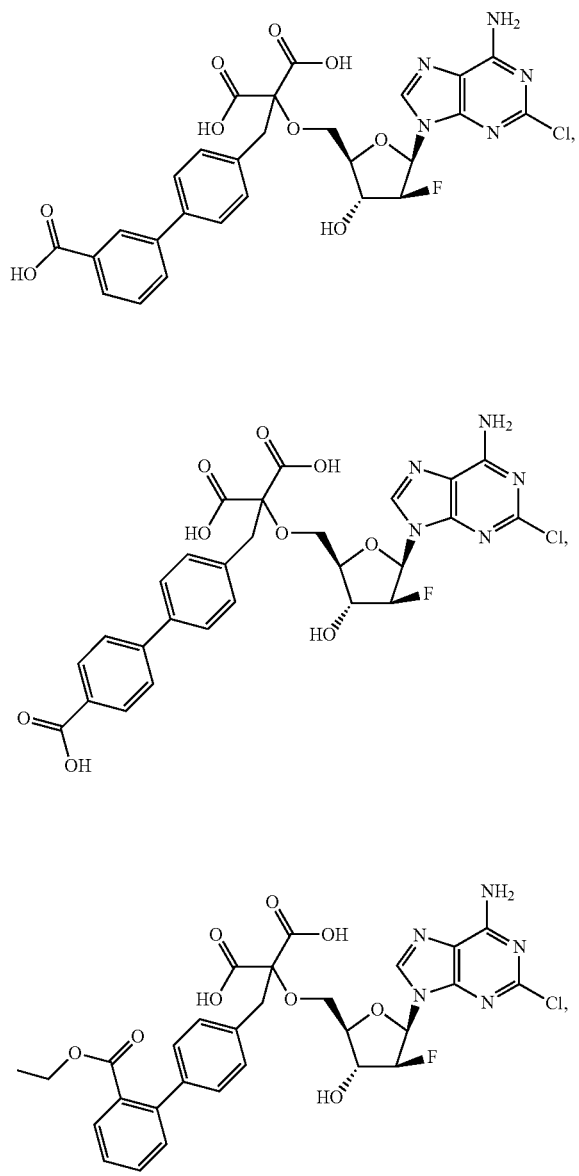

26
-continued

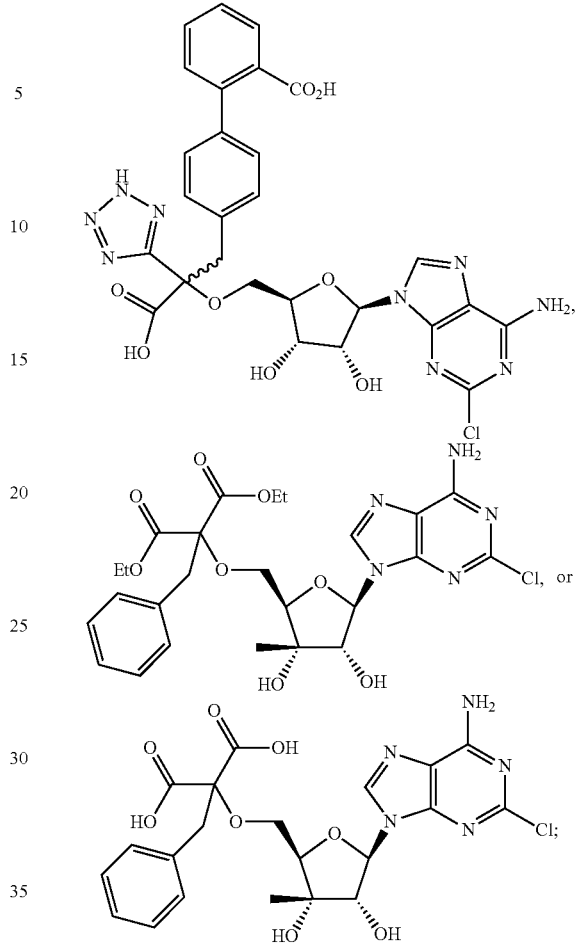

and b) $R^{2b}$ is selected from halo, $C_{2-6}$alkyl, $C_{2-6}$alkenyl, and $C_{2-6}$alkynyl, preferably substituted or unsubstituted $C_2$alkynyl, most preferably unsubstituted $C_2$alkynyl; and either c) $R^5$ is benzyl substituted on the phenyl ring with a substituent selected from unsubstituted or substituted piperidonyl, tetrahydropyrimidonyl, pyridonyl, and pyridyl, or d) $R^5$ is benzyl substituted on the phenyl ring with a second phenyl ring substituted with —C(O)OR$^9$ where $R^9$ is H or alkyl.

The following paragraphs describe various embodiments of compounds of Formula I or II, which may be combined in any combination as consistent with the formulas as defined above.

In certain embodiments, $R^{1a}$ is H or hydroxy. In certain embodiments, $R^{1b}$ is H or hydroxyl. In other embodiments, $R^{1a}$ is hydroxy and $R^{1b}$ is H.

In some embodiments, $R^{2a}$ is hydroxy or $C_{1-6}$alkyl. In certain embodiments, $R^{2b}$ is $C_{2-6}$alkyl, $C_{2-6}$alkenyl or $C_{2-6}$alkynyl, preferably substituted or unsubstituted $C_2$alkynyl, such as ethynyl. In certain preferred embodiments, $R^{2a}$ is Me and $R^{2b}$ is ethynyl. In some embodiments, $R^{2a}$ is hydroxy and $R^{2b}$ is ethyl or vinyl. In other preferred embodiments, $R^{2a}$ is hydroxy and $R^{2b}$ is ethynyl. In some embodiments, $R^{2b}$ is propynyl, butynyl,

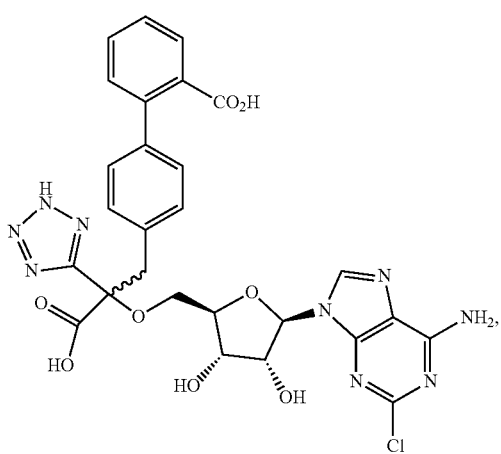

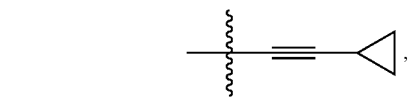 [SMILES: *C#CC1CC1]

or unsubstituted or substituted

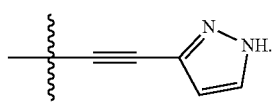 [SMILES: *C#Cc1cc[nH]n1]

In certain preferred embodiments, $R^3$ is H.

In certain embodiments, the compound of Formula (I) has the following structure:

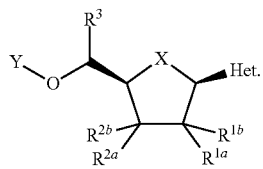

In certain embodiments, the compound of Formula (II) has the following structure:

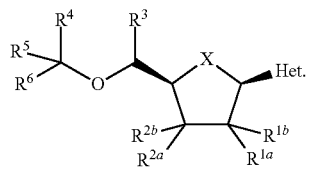

In certain such embodiments, $R^{1a}$ is in the α-configuration. For example, the compound of Formula (I) may have the structure (IA):

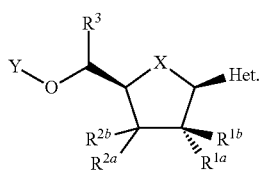

(IA)

Further, the compound of Formula (II) may have the structure (IIAa):

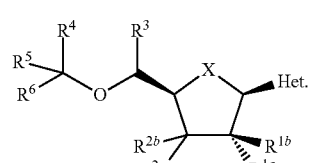

(IIAa)

In alternative embodiments, $R^{1a}$ is in the β-configuration. In some such embodiments, the compound of Formula (I) has the structure (IB):

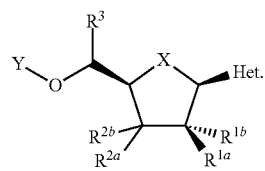

(IB)

In some such embodiments, the compound of Formula (II) has the structure (IIBa):

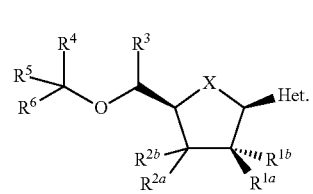

(IIBa)

In further embodiments of compounds of Formula (I), e.g., as described above, $R^{2a}$ is in the α-configuration. For example, the compound of Formula (I) may have the structure (IC):

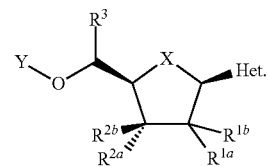

(IC)

In further preferred embodiments, the compound of Formula (II) has the structure (IICa):

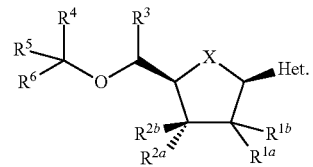

(IICa)

In alternative embodiments, $R^{2a}$ is in the β-configuration. In some such embodiments, the compound of Formula (I) has the structure (ID):

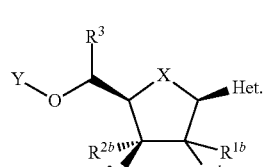

(ID)

In further preferred embodiments, the compound of Formula (II) has the structure (IIDa):

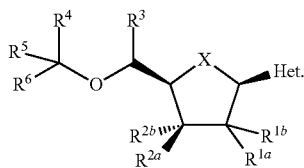

(IIDa)

In certain preferred embodiments, the compound of Formula (I) has the structure (IE):

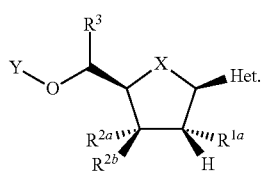

(IE)

In further preferred embodiments, the compound of Formula (II) has the structure (IIEa):

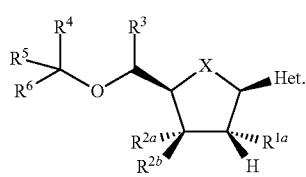

(IIEa)

In particularly preferred such embodiments, $R^{1a}$ is hydroxy and $R^{2a}$ is hydroxy and $R^{2b}$ is selected from methyl, ethyl, vinyl, and ethynyl, most preferably ethynyl. In most preferred embodiments of the compound of Formula (IE), $R^{1a}$ is hydroxy, $R^{2a}$ is hydroxy, and $R^{2b}$ is ethynyl. In some preferred embodiments of the compound of Formula (IIEa), $R^{1a}$ is hydroxy, $R^{2a}$ is hydroxy, and $R^{2b}$ is ethynyl.

In certain embodiments, Y is

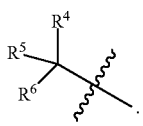

In certain embodiments, $R^4$ is selected from —C(O)OR$^9$, —C(O)NR$^{11}$R$^{12}$, —S(O)$_2$R$^{10}$, and —P(O)(OR$^{11}$)(OR$^{12}$). In some embodiments, $R^4$ is —C(O)OR$^9$ and R$^9$ is H or alkyl. In other embodiments, $R^4$ is —C(O)NR$^{11}$R$^{12}$. In certain embodiments, each $R^{11}$ and $R^{12}$ is independently selected from H and alkyl; or $R^{11}$ and $R^{12}$, together with the nitrogen atom to which they are attached, form a 5- to 7-membered heterocyclyl. In other embodiments, $R^4$ is —S(O)$_2$R$^{10}$ and $R^{10}$ is alkyl or aryl.

In some embodiments, $R^6$ is —C(O)OR$^9$ and R$^9$ is H or alkyl, e.g., H or C$_{1-6}$alkyl. In other embodiments, $R^6$ is —C(O)NR$^{11}$R$^{12}$. In certain such embodiments, each $R^{11}$ and $R^{12}$ is independently selected from H and alkyl; or $R^{11}$ and $R^{12}$, together with the nitrogen atom to which they are attached, form a 5- to 7-membered heterocyclyl.

In preferred embodiments, $R^4$ and $R^6$ are each —C(O)OH, most preferably wherein $R^5$ is benzyl, e.g., as discussed in greater detail below.

In certain embodiments, $R^5$ is selected from H, alkyl, aralkyl and heteroaralkyl. In certain such embodiments, each alkyl, aralkyl and heteroaralkyl at $R^5$ is unsubstituted or substituted with one or more substituents selected from halo, alkyl, alkoxy, carbonyl, amino, amido, cycloalkyl, heterocyclyl, and heteroaryl. In other embodiments, the substituents on the alkyl, aralkyl and heteroaralkyl at $R^5$ are selected from halo, haloalkyl, alkoxy, carbonyl, aryl, heterocyclyl, and heteroaryl. In certain embodiments, $R^5$ is aralkyl, e.g., substituted on the aryl ring with a 5- to 7-membered heterocyclyl or a 5- to 7-membered heteroaryl. In certain particular embodiments, $R^5$ is selected from H, methyl, ethyl, —CH$_2$-ethynyl, and —CH$_2$-vinyl. In other embodiments, $R^5$ is selected from benzyl, —CH$_2$-pyridyl, —CH$_2$-pyridazinyl, —CH$_2$-oxazolyl, —CH$_2$-thiophenyl, —CH$_2$-furanyl, —CH$_2$-thiazolyl, and —CH$_2$-benzothiazolyl, preferably benzyl and —CH$_2$-thiophenyl.

In certain preferred embodiments, $R^5$ is benzyl substituted on the phenyl ring (e.g., at a para position) with a heterocyclyl or heteroaryl substituent, preferably wherein the phenyl ring substituent is selected from substituted piperidonyl, tetrahydropyrimidonyl, pyridonyl, and pyridyl. In some embodiments, the phenyl ring substituent is piperazinonyl. In certain such embodiments, the piperidonyl, tetrahydropyrimidonyl, pyridonyl, or pyridyl is substituted with one or more of alkyl, hydroxyalkyl or alkoxyalkyl.

In certain embodiments, $R^5$ is aralkyl or heteroaralkyl with a para substituent on the aryl or heteroaryl ring selected from heterocyclyl, heteroaryl, and aryl; and $R^{2b}$ is methyl, ethyl, or C$_{2-6}$alkynyl.

In certain preferred embodiments, $R^5$ is benzyl substituted on the phenyl ring (e.g., at the 4-position) with

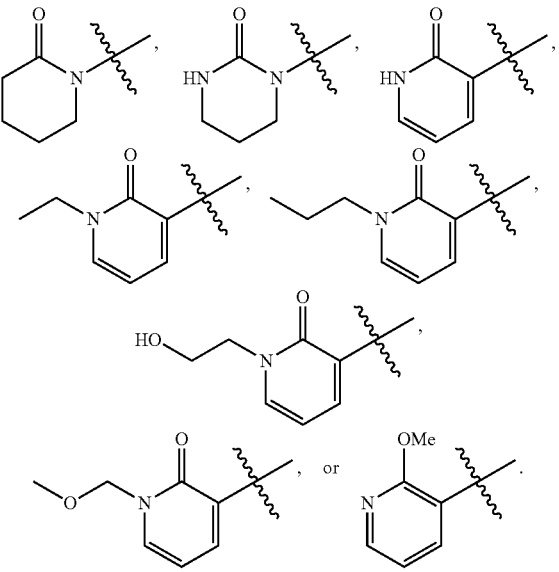

In certain embodiments, certain preferred embodiments, $R^5$ is benzyl substituted on the phenyl ring (e.g., at the 4-position) with

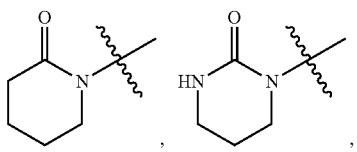

-continued
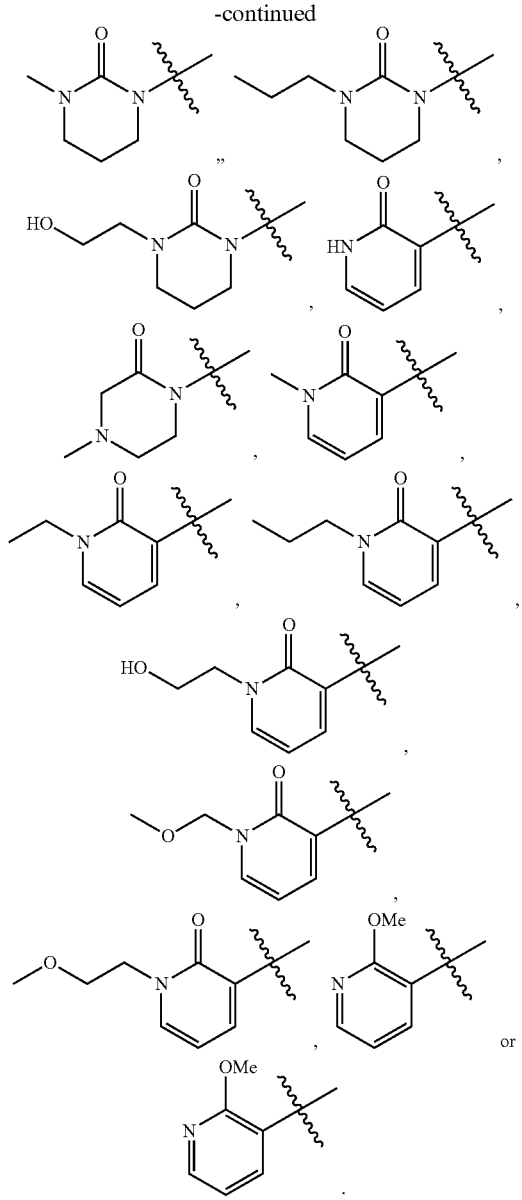
In some embodiments,
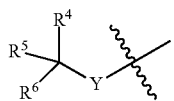
represents
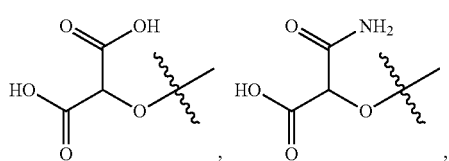
-continued
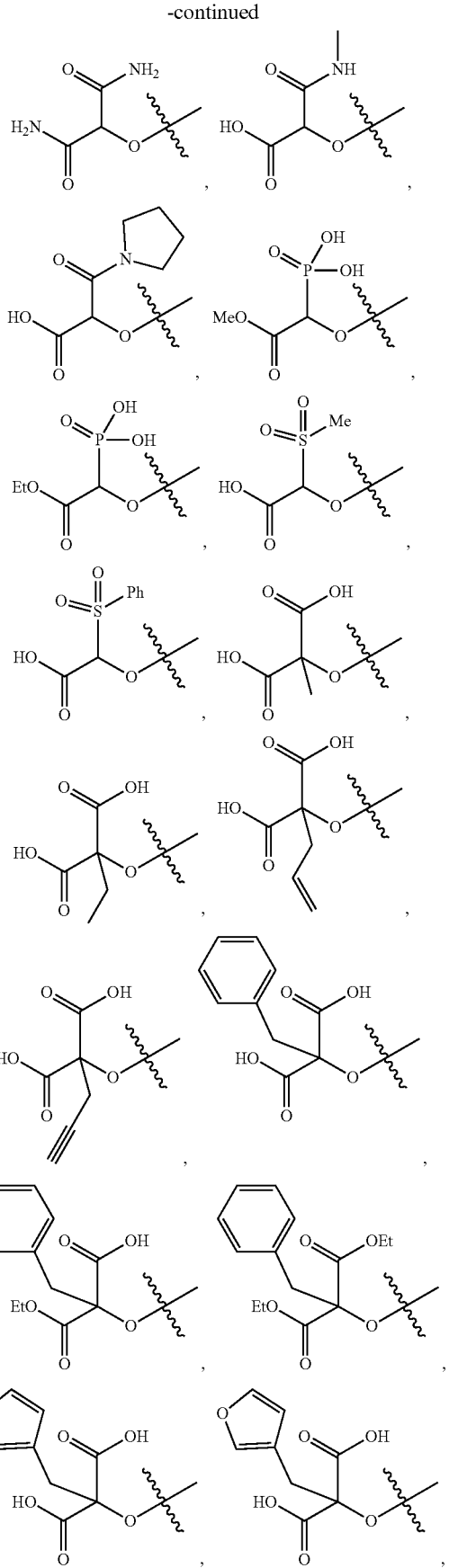

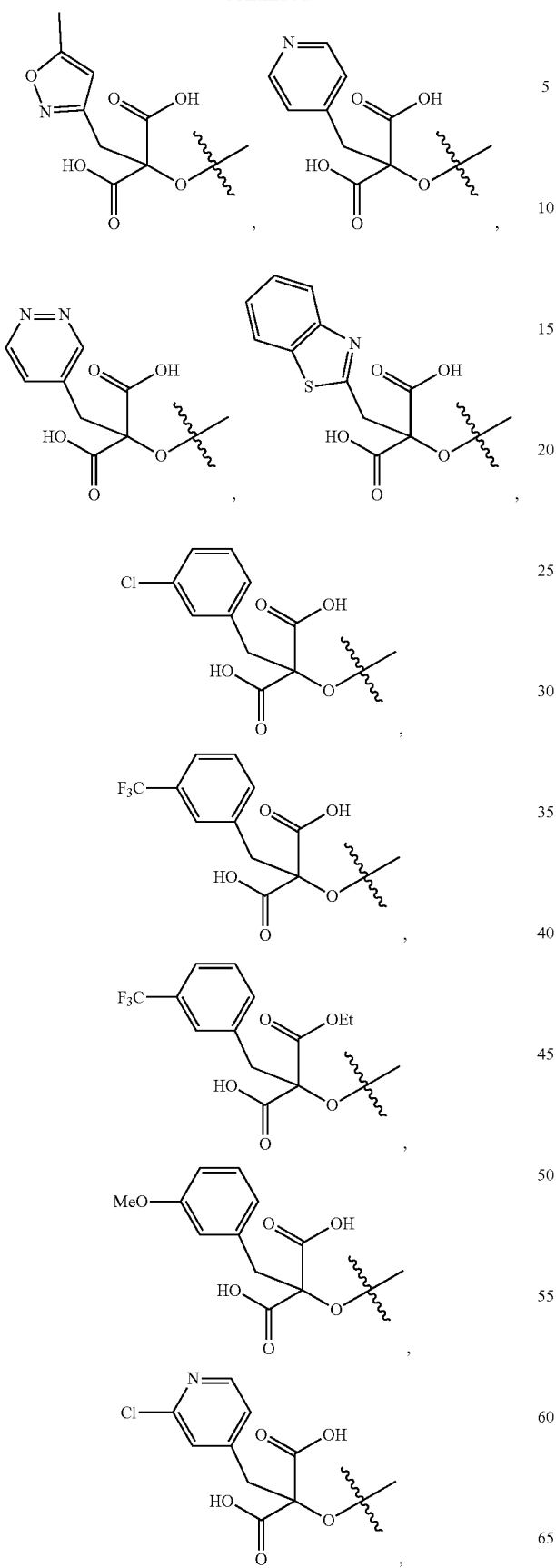

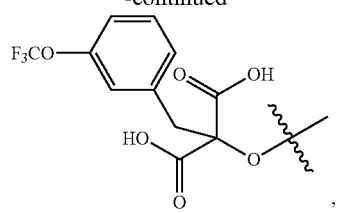
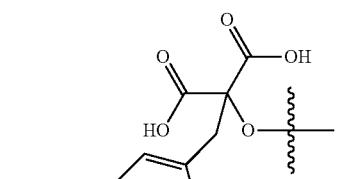
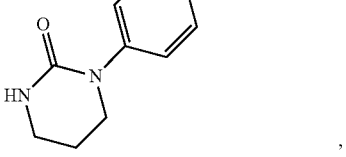
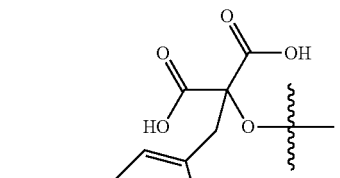
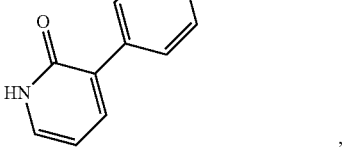
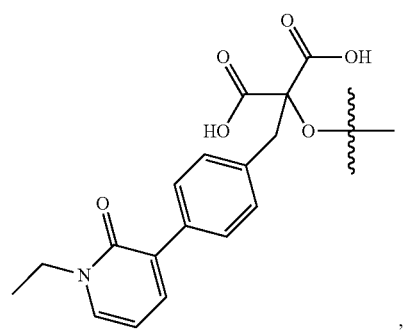
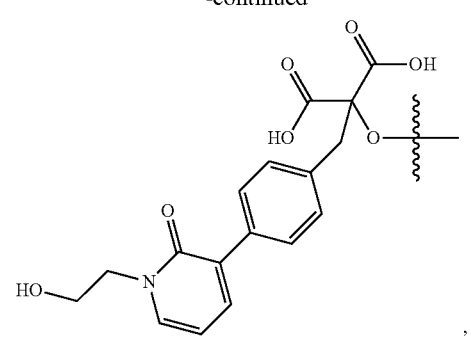
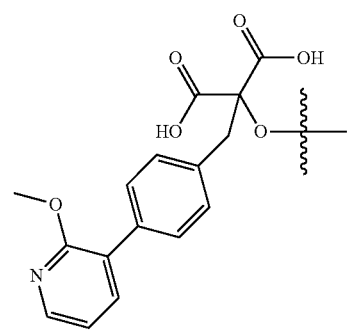
In some embodiments,
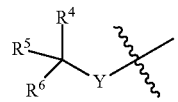
represents
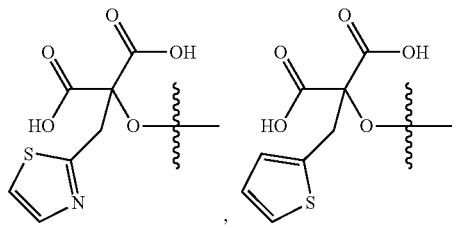
, or
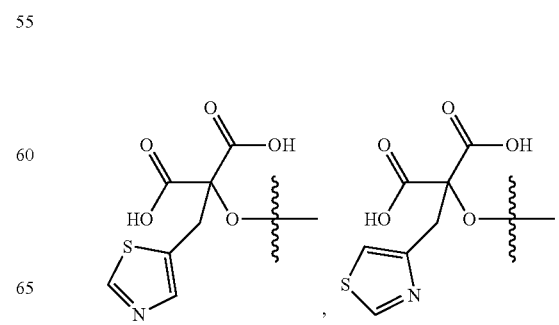
, 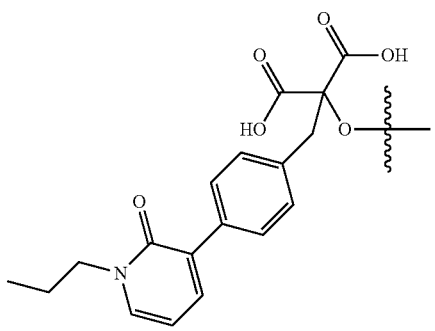

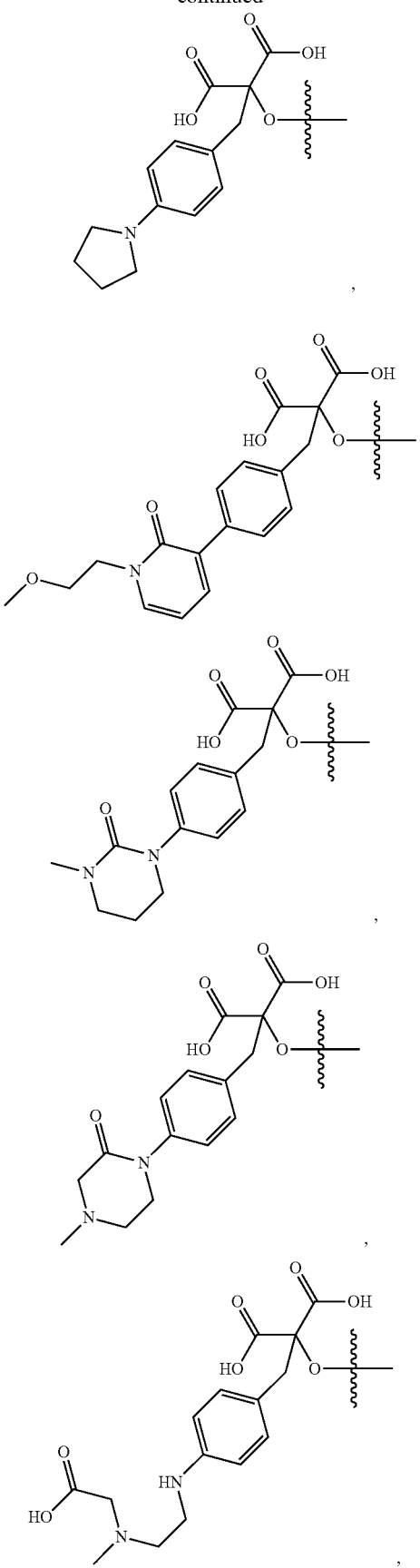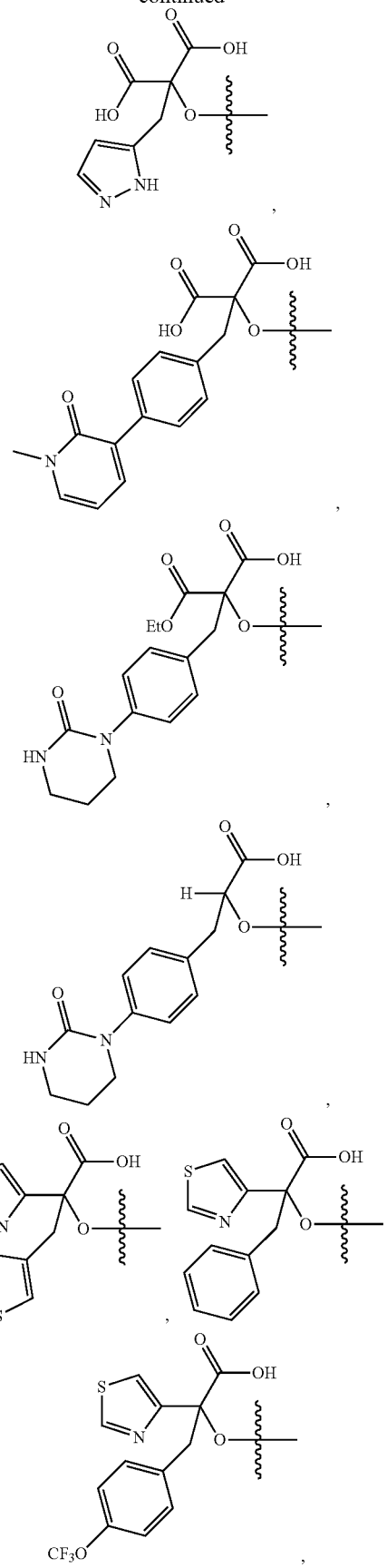

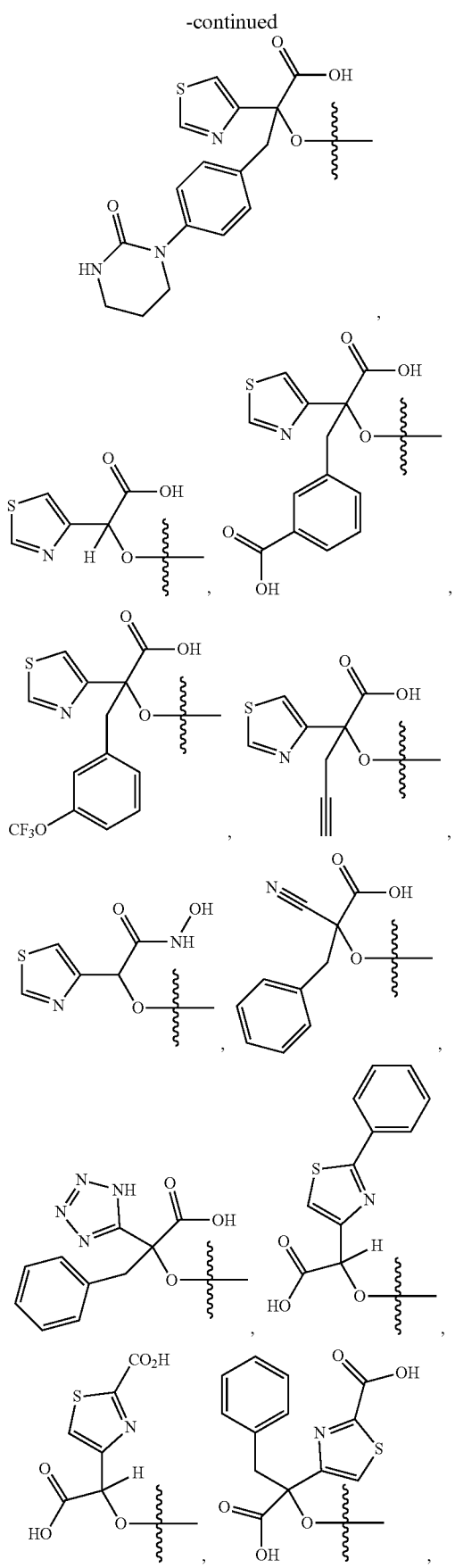

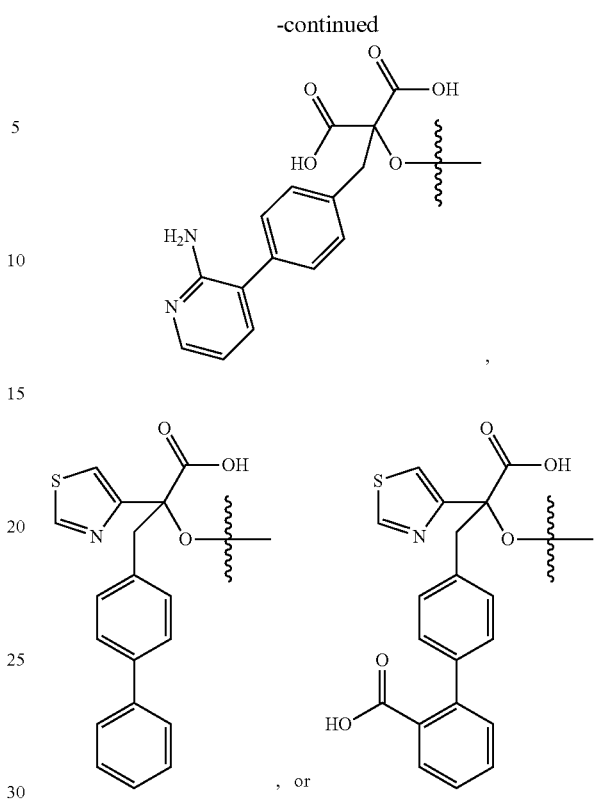

or

In some embodiments, Y is

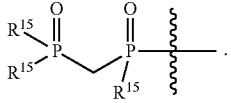

In certain embodiments, each $R^{15}$ is hydroxy.

In certain embodiments, Het is selected from a 6- to 10-membered aryl, a 5- to 8-membered heterocyclyl, a 5- to 8-membered monocyclic or 5- to 10-membered bicyclic heteroaryl, and may be unsubstituted or substituted with one or more substituents selected from halo, alkyl, haloalkyl, alkoxy, carbonyl, amino, amido, alkylthio, alkoxycarbonyl, cycloalkyl, aryl, heterocyclyl and heteroaryl. In some embodiments, the Het substituents are selected from halo, haloalkyl, amino, and heterocyclyl. In certain embodiments, Het is a nitrogen-containing heterocyclyl or heteroaryl, preferably attached to the core ring via a nitrogen atom of the heterocyclyl or heteroaryl ring. In some embodiments, Het is

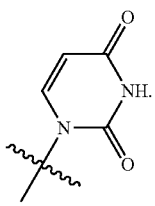 [SMILES: *n1ccc(=O)[nH]c1=O]

In other embodiments, Het is

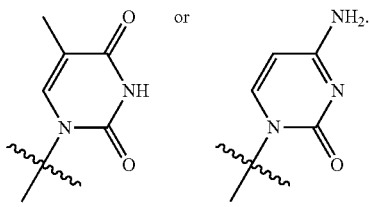

In other embodiments, Het is

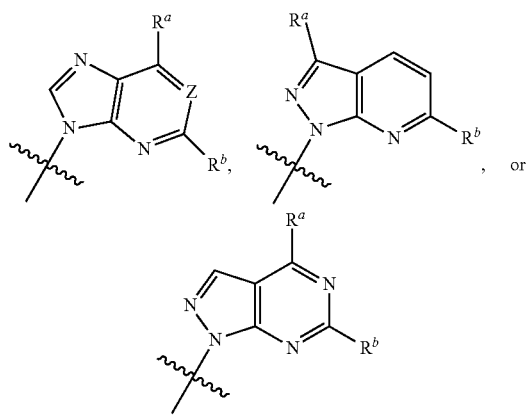

wherein

Z is CH or N;

$R^a$ is selected from H, halo, hydroxy, alkyl, thiophenyl, —$NR^7R^8$, aralkyl, aryl, and heteroaryl, preferably from H, Cl, —$NR^7R^8$, and phenyl;

$R^b$ is selected from halo, alkyl, haloalkyl, hydroxyalkyl, alkylthio, amido, carbonyl, amido, and heteroaryl;

$R^7$ is selected from H, hydroxy, alkyl, aralkyl, heteroaralkyl, cycloalkyl, and heterocyclyl; and $R^8$ is H or alkyl; or $R^7$ and $R^8$, together with the nitrogen atom to which they are attached, form a 4- to 7-membered heterocyclyl ring.

In some embodiments, Het if

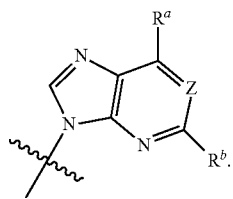

In certain embodiments, Z is CH. In other embodiments, Z is N.

In certain embodiments, $R^a$ is selected from H, halo, alkyl, thienyl, —$NR^7R^8$, aryl, and heteroaryl, preferably from H, Cl, —$NR^7R^8$, and phenyl. In some embodiments, $R^a$ is —$NR^7R^8$.

In certain embodiments, $R^b$ is selected from halo, alkyl, hydroxyalkyl, haloalkyl, amido, carbonyl, amido, and heteroaryl. In some embodiments, $R^b$ is selected from Cl, —$CF_3$, carbonyl and —$CONH_2$.

In some embodiments, Het is

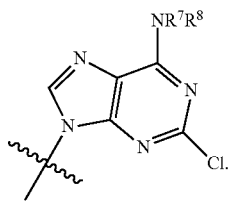

In some embodiments, $R^7$ is selected from H, alkyl, aralkyl, heteroaralkyl, cycloalkyl, and heterocyclyl. In certain embodiments, $R^7$ is alkyl or cycloalkyl, e.g., where the alkyl or cycloalkyl is unsubstituted or substituted with one or more substituents selected from hydroxy, alkoxy, aryl, amino, and cycloalkyl. In other embodiments, $R^7$ is aralkyl or heteroaralkyl, e.g., where the aralkyl or heteroaralkyl is unsubstituted or substituted with halo or alkyl.

In some embodiments, $R^8$ is selected from H, methyl, and ethyl.

In other embodiments, $R^7$ and $R^8$, together with the nitrogen atom to which they are attached, form a heterocyclyl ring, e.g., selected from azetidinyl, morpholino, pyrrolidinyl, and azepanyl.

Methods of Use

Provided herein are methods of inhibiting CD73 in a cell, comprising contacting the cell with a compound of the invention, such as a compound of formula (I), or a pharmaceutically acceptable salt thereof. In certain embodiments, contacting the cell occurs in a subject in need thereof, thereby treating a disease or disorder mediated by adenosine.

Also, disclosed herein are methods of treating a disease or a disorder mediated by adenosine comprising administering a compound the invention, such as a compound of Formula (I), or a pharmaceutically acceptable salt thereof. In some embodiments, disclosed herein are methods of treating cancer comprising administering a compound the invention, such as a compound of Formula (I), or a pharmaceutically acceptable salt thereof.

Adenosine acts on a variety of immune cells to induce immunosuppression, and the immunosuppressive effects of ectonucleotidases that enhance adenosine levels are also associated with enhanced infections of mammalian cells by parasites, fungi, bacteria, and viruses. Apart from immunosuppressive effects, adenosine also has a role in modulating the cardiovascular system (as a vasodilator and cardiac depressor), the central nervous system (CNS) (inducing sedative, anxiolytic and antiepileptic effects), the respiratory system (inducing bronchoconstriction), the kidney (having biphasic action; inducing vasoconstriction at low concentrations and vasodilation at high doses), fat cells (inhibiting lipolysis), and platelets (as an anti-aggregant). Furthermore, adenosine also promotes fibrosis (excess matrix production) in a variety of tissues. Therefore, improved treatments targeting CD73 would provide therapies for treating a wide range of conditions in addition to cancer, including cerebral and cardiac ischemic disease, fibrosis, immune and inflammatory disorders (e.g., inflammatory gut motility disorder), neurological, neurodegenerative and CNS disorders and diseases (e.g., depression, Parkinson's disease), and sleep disorders.

In some embodiments, the disease or the disorder mediated by adenosine is selected from cerebral ischemic disease, cancer, cardiac ischemic disease, depression, fibrosis, an immune disorder, an inflammatory disorder (e.g., inflammatory gut motility disorder), neurological disorder or disease, neurodegenerative disorder or disease (e.g., Parkinson's disease), CNS disorders and diseases, and sleep disorders.

The methods described herein are useful for the treatment of a wide variety of cancers, including bladder cancer, bone cancer, brain cancer (including glioblastoma), breast cancer, cardiac cancer, cervical cancer, colon cancer, colorectal cancer, esophageal cancer, fibrosarcoma, gastric cancer, gastrointestinal cancer, head & neck cancer, Kaposi's sarcoma, kidney cancer (including renal cell adenocarcinoma), leukemia, liver cancer, lung cancer (including non-small cell lung cancer, small cell lung cancer, and mucoepidermoid pulmonary carcinoma), lymphoma, melanoma, myeloma, ovarian cancer (including ovarian adenocarcinoma), pancreatic cancer, penile cancer, prostate cancer, testicular germ-cell cancer, thymoma and thymic carcinoma.

In some embodiments, the subject has a cancer selected from breast cancer, brain cancer, colon cancer, fibrosarcoma, kidney cancer, lung cancer, melanoma, ovarian cancer, and prostate cancer. In certain embodiments, the subject has a cancer selected from breast cancer, colon cancer, fibrosarcoma, melanoma, ovarian cancer, and prostate cancer. In other embodiments, the subject has a cancer selected from brain cancer, breast cancer, kidney cancer, lung cancer, melanoma, and ovarian cancer. In some embodiments, the subject has head and neck squamous cell carcinoma, ovarian cancer, breast cancer or esophageal cancer. In other embodiments, the subject has pancreatic cancer, esophageal cancer, stomach cancer, head and neck cancer, colon cancer, lung cancer or kidney cancer. In yet other embodiments, the subject has breast cancer. In some embodiments, the breast cancer is breast adenocarcinoma. In certain embodiments, the breast cancer is triple-negative breast cancer.

In certain embodiments, the methods for treating or preventing cancer can be demonstrated by one or more responses such as increased apoptosis, inhibition of tumor growth, reduction of tumor metastasis, inhibition of tumor metastasis, reduction of microvessel density, decreased neovascularization, inhibition of tumor migration, tumor regression, and increased survival of the subject.

In certain embodiments, the disease or the disorder mediated by adenosine is a disease or disorder mediated by CD73 activity. In some embodiments, the compounds of the invention, such as compounds of Formula (I), are useful as inhibitors of CD73.

In some embodiments, the methods described herein treat or prevent cardiovascular disease using inhibitors of CD73. Mutant genes encoding CD73 lead to extensive calcification of lower-extremity arteries and small joint capsules, which is associated with increased risk of cardiovascular disease (Hilaire et al., *N. Engl. J. Med.*, 364(5): 432-442, 2011).

In some embodiments, the methods disclosed herein treat or prevent cancer using inhibitors of CD73. A CD73 small interfering RNA and anti-CD73 monoclonal antibodies showed a significant effect in treating or preventing cancer (Antonioli et al., *Nat. Rev. Cancer*, 13: 842-857, 2013). A tight correlation exists between CD73 expression and the ability of cancer cells to migrate, invade, and adhere to the extracellular matrix (ECM) (Antonioli 2013; Antonioli et al., *Trends Cancer*, 2(2): 95-109, 2016).

In some embodiments, the treatment or prevention of cancer by inhibitors of CD73 can be demonstrated by one or more responses selected from activation, clonal expansion, and homing of tumor-specific T cells (Antonioli 2016). In other embodiments, the methods disclosed herein increase the number of effector T lymphocytes (e.g., cytolytic effector T lymphocytes).

Combination Treatments

In some embodiments, the method of treating or preventing cancer may comprise administering a CD39 inhibitor conjointly with one or more other chemotherapeutic agent(s). In one embodiment, the CD73 inhibitor is a compound of the invention, such as a compound of Formula (I). Other chemotherapeutic agents can include CD73-specific monoclonal antibodies which enhance the effects of other antibodies and therapies because of increased overall immune system activity (lower T-regulatory function and higher T-effector function, etc.) (Antonioli 2016).

In certain embodiments, the method of treating or preventing cancer may comprise administering a compound of the invention conjointly with one or more other chemotherapeutic agent(s).

Chemotherapeutic agents that may be conjointly administered with compounds of the invention include: 1-amino-4-phenylamino-9,10-dioxo-9,10-dihydroanthracene-2-sulfonate (acid blue 25), 1-amino-4-[4-hydroxyphenylamino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, ABT-263, afatinib dimaleate, axitinib, aminoglutethimide, amsacrine, anastrozole, APCP, asparaginase, AZD5363, *Bacillus* Calmette-Gudrin vaccine (bcg), bicalutamide, bleomycin, bortezomib, β-methylene-ADP (AOPCP), buserelin, busulfan, cabazitaxel, cabozantinib, campothecin, capecitabine, carboplatin, carfilzomib, carmustine, ceritinib, chlorambucil, chloroquine, cisplatin, cladribine, clodronate, cobimetinib, colchicine, crizotinib, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, eribulin, erlotinib, estradiol, estramustine, etoposide, everolimus, exemestane, filgrastim, fludarabine, fludrocortisone, fluorouracil, fluoxymesterone, flutamide, gefitinib, gemcitabine, genistein, goserelin, GSK1120212, hydroxyurea, idarubicin, ifosfamide, imatinib, interferon, irinotecan, ixabepilone, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, mutamycin, N-(4-sulfamoylphenylcarbamothioyl) pivalamide, NF279, NF449, nilutamide, nocodazole, octreotide, olaparib, oxaliplatin, paclitaxel, pamidronate, pazopanib, pemexetred, pentostatin, perifosine, PF-04691502, plicamycin, pomalidomide, porfimer, PPADS, procarbazine, quercetin, raltitrexed, ramucirumab, reactive blue 2, rituximab, rolofylline, romidepsin, rucaparib, selumetinib, sirolimus, sodium 2,4-dinitrobenzenesulfonate, sorafenib, streptozocin, sunitinib, suramin, talazoparib, tamoxifen, temozolomide, temsirolimus, teniposide, testosterone, thalidomide, thioguanine, thiotepa, titanocene dichloride, tonapofylline, topotecan, trametinib, trastuzumab, tretinoin, veliparib, vinblastine, vincristine, vindesine, vinorelbine, and vorinostat (SAHA). In other embodiments, chemotherapeutic agents that may be conjointly administered with compounds of the invention include: ABT-263, dexamethasone, 5-fluorouracil, PF-04691502, romidepsin, and vorinostat (SAHA). In other embodiments, chemotherapeutic agents that may be conjointly administered with compounds of the invention include: 1-amino-4-phenylamino-9,10-dioxo-9,10-dihydroanthracene-2-sulfonate (acid blue 25), 1-amino-4-[4-hydroxyphenyl-amino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, APCP, β-methylene-ADP (AOPCP), capecitabine, cladribine, cytarabine, fludarabine, doxorubicin, gemcitabine, N-(4-sulfamoylphenylcarbamothioyl) pivalamide, NF279, NF449, PPADS, quercetin, reactive blue 2, rolofylline sodium 2,4-dinitrobenzenesulfonate, sumarin, and tonapofylline.

Many combination therapies have been developed for the treatment of cancer. In certain embodiments, compounds of the invention (e.g., compounds of Formula (I)) may be conjointly administered with a combination therapy. Examples of combination therapies with which compounds of the invention may be conjointly administered are included in Table 1.

TABLE 1

Exemplary combinatorial therapies for the treatment of cancer

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocyte leukemia) | Chlorambucil, Prednisone |

TABLE 1-continued

Exemplary combinatorial therapies for the treatment of cancer

| Name | Therapeutic agents |
|---|---|
| CP (Ovarian Cancer) | Cyclophosphamide, Cisplatin |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |

TABLE 1-continued

Exemplary combinatorial therapies for the treatment of cancer

| Name | Therapeutic agents |
|---|---|
| PA-CI | Cisplatin, Doxorubicin |
| PCV | Lomustine, Procarbazine, Vincristine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In some embodiments, the chemotherapeutic agents that may be conjointly administered with compounds of the invention, such as a compound of Formula (I), include a CD39 inhibitor. CD39 or ecto-nucleoside triphosphate diphosphohydrolase 1 (E-NTPDase1 or ENTPD 1) is a membrane-bound enzyme that catalyzes the conversion of extracellular adenosine triphosphate (ATP) and/or ADP (adenosine diphosphate) to adenosine monophosphate (AMP). In one embodiment, the CD39 inhibitor is polyoxometalate-1 (POM-1).

In other embodiments, the chemotherapeutic agents that may be conjointly administered with compounds of the invention, such as a compound of Formula (I), include known CD73 inhibitors. In some embodiments, the CD73 inhibitor is an anthraquinone derivative (Baqi et al., J. Med. Chem., 53(5): 2076-2086, 2010, herein incorporated by reference). In other embodiments, the CD73 inhibitor is an sulfonic acid derivative (Raza et al., Med. Chem., 8: 1133-1139, 2012, herein incorporated by reference). In yet other embodiments, the CD73 inhibitor is selected from 1-amino-4-phenylamino-9,10-dioxo-9,10-dihydroanthracene-2-sulfonate (acid blue 25), 1-amino-4-[4-hydroxyphenylamino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, sodium 2,4-dinitrobenzenesulfonate, N-(4-sulfamoylphenylcarbamothioyl) pivalamide, APCP, β-methylene-ADP (AOPCP), PPADS, NF279, NF449, quercetin, reactive blue 2, and sumarin (Baqi 2010; Raza 2012).

In certain embodiments, the combination of a compound of the invention, such as a compound of Formula (I), with a second CD73 inhibitor or a CD39 inhibitor may have a synergistic effect in the treatment of cancer and other diseases or disorders mediated by adenosine. Without wishing to be bound by any theory, this synergy may be observed because CD39 and CD73 are often on different cell types. The hypoxic tumor microenvironment also induces greater levels of CD39 and CD73.

In some embodiments, the chemotherapeutic agents that may be conjointly administered with compounds of the invention, such as a compound of Formula (I), include an adenosine receptor inhibitor. In other embodiments, the adenosine receptor inhibitor is selected from rolofylline, tonapofylline, ATL-444, istradefylline, MSX-3, preladenant, SCH-58,261, SCH-412,348, SCH-442,416, ST-1535, VER-6623, VER-6947, VER-7835, vipadenant, and ZM-241,385. In some embodiments, the adenosine receptor inhibitor targets the $A_{2A}$ receptor as this subtype is predominantly expressed in most immune cells.

In other embodiments, the chemotherapeutic agents that may be conjointly administered with compounds of the invention, such as a compound of Formula (I), include a nucleoside-based drug. In certain embodiments, the nucleoside-based drug is selected from gemcitabine, capecitabine, cytarabine, fludarabine and cladribine.

In further embodiments, the combination therapy comprises a compound of the invention, such as a compound of Formula (I), conjointly administered with an anthracycline. In other embodiments, the combination therapy comprises a compound of the invention, such as a compound of Formula (I), conjointly administered with doxorubicin. Combination treatment with an anti-CD73 antibody and doxorubicin has demonstrated a significant chemotherapeutic effect (Young et al., Cancer Discov., 4(8): 1-10, 2014, herein incorporated by reference).

In certain embodiments, the combination therapy comprises a compound of the invention, such as a compound of Formula (I), conjointly administered with an $A_{2A}$ receptor inhibitor and an anthracycline. In some embodiments, the anthracycline is doxorubicin. Combination treatment with an anti-CD73 antibody, an $A_{2A}$ receptor inhibitor, and doxorubicin has demonstrated an increased chemotherapeutic effect (Antonioli 2013).

In certain embodiments, the conjoint therapies of the invention comprise conjoint administration with other types of chemotherapeutic agents, such as immuno-oncology agents. Cancer cells often have specific cell surface antigens that can be recognized by the immune system. Thus, immuno-oncology agents, such as monoclonal antibodies, can selectively bind to cancer cell antigens and effect cell death. Other immuno-oncology agents can suppress tumor-mediated inhibition of the native immune response or otherwise activate the immune response and thus facilitate recognition of the tumor by the immune system. Exemplary antibody immuno-oncology agents, include, but are not limited to, abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, and tremelimumab. In some embodiments, the antibody immune-oncology agents are selected from anti-CD73 monoclonal antibody (mAb), anti-CD39 mAb, anti-PD-1 mAb, and anti-CTLA4 mAb. Thus, in some embodiments, the methods of the invention comprise conjoint administration of one or more immuno-oncology agents, such as the agents mentioned above.

In some embodiments, the combination therapy comprises a compound of the invention, such as a compound of Formula (I), conjointly administered with anti-PD-1 therapy and anti-CTLA4 therapy. Combination treatment with an anti-CD73 monoclonal antibody (mAb), anti-PD-1 mAb, and anti-CTLA4 mAb showed a significant chemotherapeutic effect (Young 2014; Antonioli 2013).

In some embodiments, the combination therapy comprises conjoint administration of a compound of the invention, such as a compound of Formula (I), with anti-PD-1 therapy. In certain embodiments, the combination therapy comprises conjoint administration of a compound of the invention, such as a compound of Formula (I), with oxaliplatin. In other embodiments, the combination therapy comprises conjoint administration of a compound of the invention, such as a compound of Formula (I), with doxorubicin.

In certain embodiments, a compound of the invention may be conjointly administered with non-chemical methods of cancer treatment. In certain embodiments, a compound of the invention may be conjointly administered with radiation therapy. In certain embodiments, a compound of the invention may be conjointly administered with surgery, with thermoablation, with focused ultrasound therapy, with cryotherapy, or with any combination of these.

In certain embodiments, compounds of the invention may be conjointly administered with one or more other compounds of the invention. Moreover, such combinations may be conjointly administered with other therapeutic agents, such as other agents suitable for the treatment of cancer, immunological or neurological diseases, such as the agents identified above. In certain embodiments, conjointly administering one or more additional chemotherapeutic agents with a compound of the invention provides a synergistic effect. In certain embodiments, conjointly administering one or more additional chemotherapeutic agents provides an additive effect.

Pharmaceutical Compositions

In certain embodiments, the present invention provides a pharmaceutical preparation suitable for use in a human patient, comprising any of the compounds shown above (e.g., a compound of the invention, such as a compound of formula (I), and one or more pharmaceutically acceptable excipients. In certain embodiments, the pharmaceutical preparations may be for use in treating or preventing a condition or disease as described herein. Any of the disclosed compounds may be used in the manufacture of medicaments for the treatment of any diseases or conditions disclosed herein.

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, the dosing follows a 3+3 design. The traditional 3+3 design requires no modeling of the dose-toxicity curve beyond the classical assumption for cytotoxic drugs that toxicity increases with dose. This rule-based design proceeds with cohorts of three patients; the first cohort is treated at a starting dose that is considered to be safe based on extrapolation from animal toxicological data, and the subsequent cohorts are treated at increasing dose levels that have been fixed in advance. In some embodiments, the three doses of a compound of formula (I) range from about 100 mg to about 1000 mg orally, such as about 200 mg to about 800 mg, such as about 400 mg to about 700 mg, such as about 100 mg to about 400 mg, such as about 500 mg to about 1000 mg, and further such as about 500 mg to about 600 mg. Dosing can be three times a day when taken with without food, or twice a day when taken with food. In certain embodiments, the three doses of a compound of formula (I) range from about 400 mg to about 800 mg, such as about 400 mg to about 700 mg, such as about 500 mg to about 800 mg, and further such as about 500 mg to about 600 mg twice a day. In certain preferred embodiments, a dose of greater than about 600 mg is dosed twice a day.

If none of the three patients in a cohort experiences a dose-limiting toxicity, another three patients will be treated at the next higher dose level. However, if one of the first three patients experiences a dose-limiting toxicity, three more patients will be treated at the same dose level. The dose escalation continues until at least two patients among a cohort of three to six patients experience dose-limiting toxicities (i.e., ≥about 33% of patients with a dose-limiting toxicity at that dose level). The recommended dose for phase II trials is conventionally defined as the dose level just below this toxic dose level.

In certain embodiments, the dosing schedule can be about 40 mg/m$^2$ to about 100 mg/m$^2$, such as about 50 mg/m$^2$ to about 80 mg/m$^2$, and further such as about 70 mg/m$^2$ to about 90 mg/m$^2$ by IV for 3 weeks of a 4 week cycle.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., compound of formula I or Ia) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

General Synthetic Procedures

Compound numbers 1-129 as used in the general synthesis section below refer only to genus structures in this section and do not apply to compounds disclosed elsewhere in this application. Compounds disclosed herein can be made by methods depicted in the reaction schemes below.

The starting materials and reagents used in preparing these compounds are either available from commercial supplier such as Aldrich Chemical Co., Bachem, etc., or can be made by methods well known in the art. The schemes are merely illustrative of some methods by which the compounds disclosed herein can be synthesized and various modifications to these schemes can be made and will be suggested to POSITA having referred to this disclosure. The starting materials and the intermediates and the final products of the reacton may be isolated and purified if desired using conventional techniques, including but not limited to filtration, distillation, crystallization, chromatography, and the like and may be characterized using conventional means, including physical constants and spectral data.

Unless specified otherwise, the reactions described herein take place at atmospheric pressure over a temperature range from about −78° C. to about 150° C.

General Schemes

Compounds of Formula (I) having the structure:

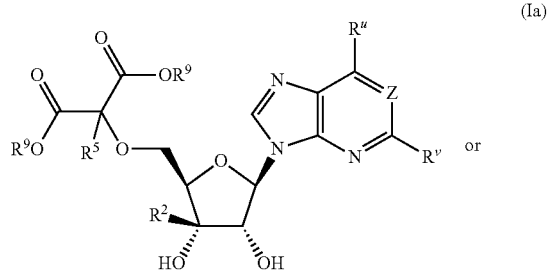

or

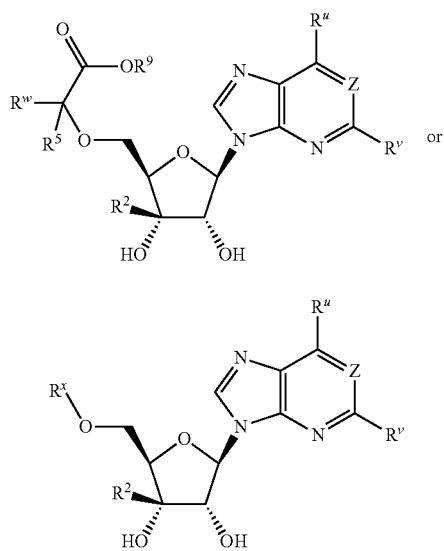
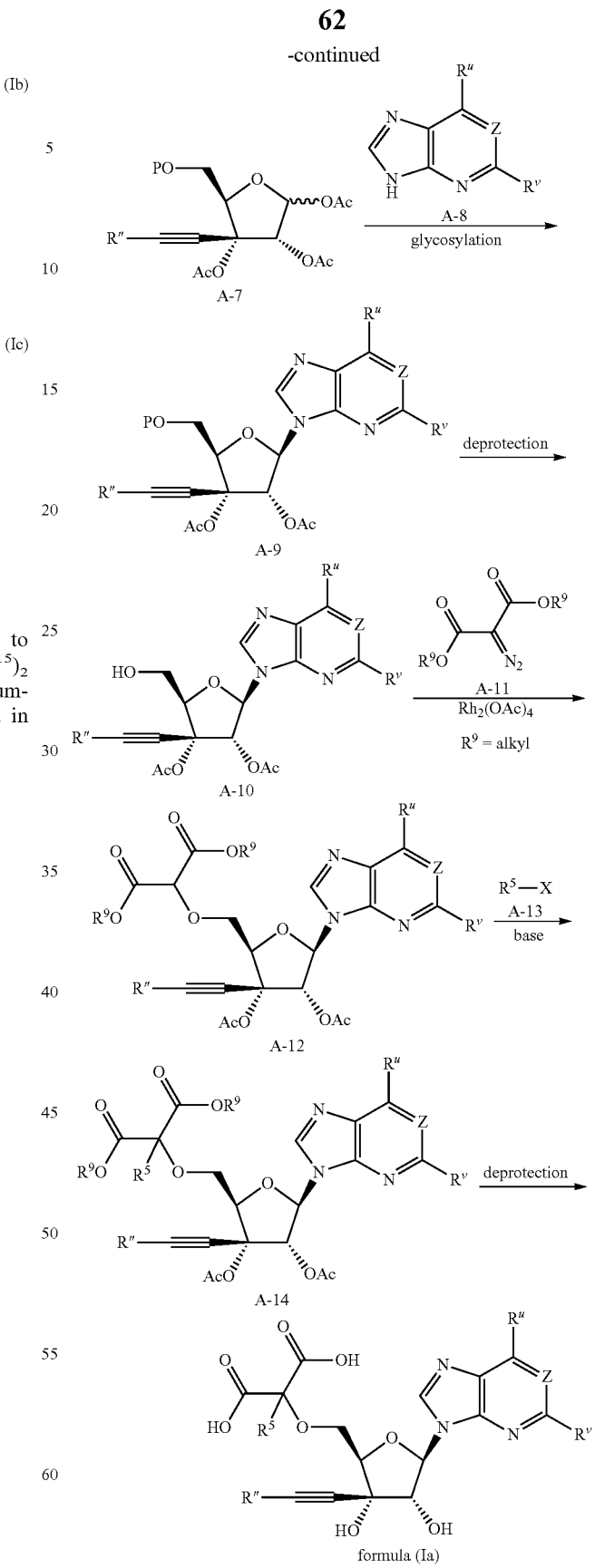
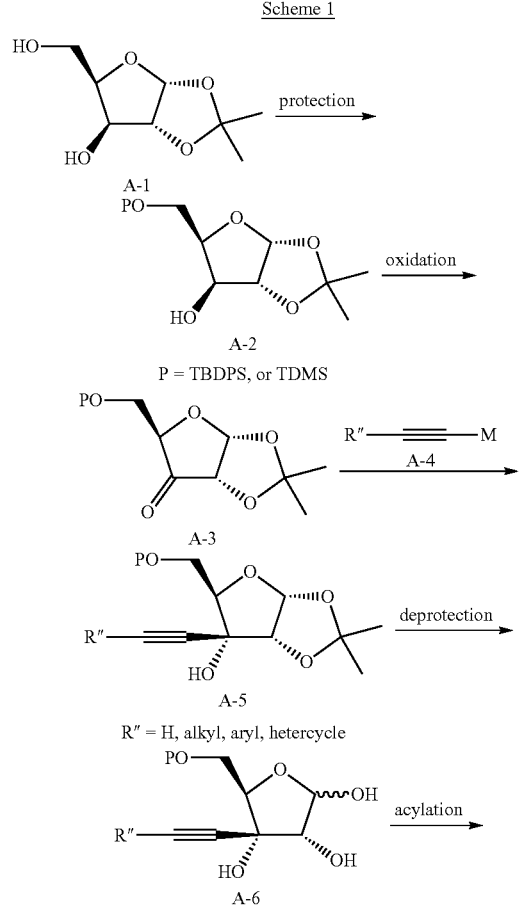
where Z, $R^u$, $R^v$, $R^w$, $R^x$, $R^5$, and $R^9$ are analogous to variables Z, $R^a$, $R^b$, $R^w$, $R^5$, $R^9$ and $R^x$ is —$CH_2P(O)(OR^{15})_2$ or —$OP(O)(OH)CH_2P(O)(OR^{15})_2$ as defined in the Summary, can be synthesized as illustrated and described in Scheme 1:
Ketone A-3 is prepared from commercially available diol A-1 via selective protecting the primary alcohol with a suitable group such as TBDPS, TBDMS, Ac and Bz, and followed by oxidizing the secondary alcohol in A-2 where R″ is H, alkyl, TMS, or heterocycles. Stereoselective addition of the corresponding ethynyl nucleophile A-4, such as Grignard reagents or Li reagents, to ketone A-3 to provide propargylic alcohol A-5. Removal of the acetonide protecting group is accomplished with diluted aq. acid, such as TFA, HCl, $H_2SO_4$, $HClO_4$, PPTS, CSA or other Lewis acids. Acylation of triol A-6 with reagents, such as $Ac_2O$, acetyl chloride, and BzCl, in the presence of a base, such as pyridine, and catalytic 4-DMAP to provide tri-ester such as tri-acetate A-7. Glycosylation under conditions (N,O-bis (trimethylsilyl)-acetamide and TMSOTf) or (TfOH and DBU) in solvent (MeCN, dichloroethane or toluene), between donor A-7 and acceptor A-8, such as 2-chloroadenine, 6-amino-2-chloroadenine, 2,6-dichloroadenine, 5,7-dichloro-1H-imidazo[4,5-b]pyridine, 5-chloro-3H-imidazo [4,5-b]pyridine, uracil, thymine, cytosine or guanine, to provide the nucleoside product A-9. In the case when $R^u$ is $NH_2$, it is protected as $N(Boc)_2$ with $Boc_2O$ in the presence of TEA and catalytic 4-DMAP. Removal of the protecting group in A-9, in the case of P is TBDMS or TBDPS group, treatment with TBAF to give the primary alcohol A-10 which then is undergone an insertion reaction with diazo reagent A-11 in the presence of catalyst such as $Rh_2(OAc)_4$ or $Cu(OAc)_2$ to provide A-12. Alkylation with an electrophile A-13 such as alkyl halide, triflate, tosylate or mesylate in the presence of base such as $Cs_2CO_3$, $K_2CO_3$, LiHMDS, DBU or NaH, to provide A-14. The ester groups in A-14 is finally removed by base such as LiOH, NaOH, and KOH in water to provide A-15 in formula (Ia).

Alternatively, the alkynyl group at the 3'-position in intermediate A-5 can be substituted with either alkyl or vinyl groups by using the corresponding alkyl or vinyl lithium and Grignard reagents at Step 3 in Scheme 1.

Scheme 2

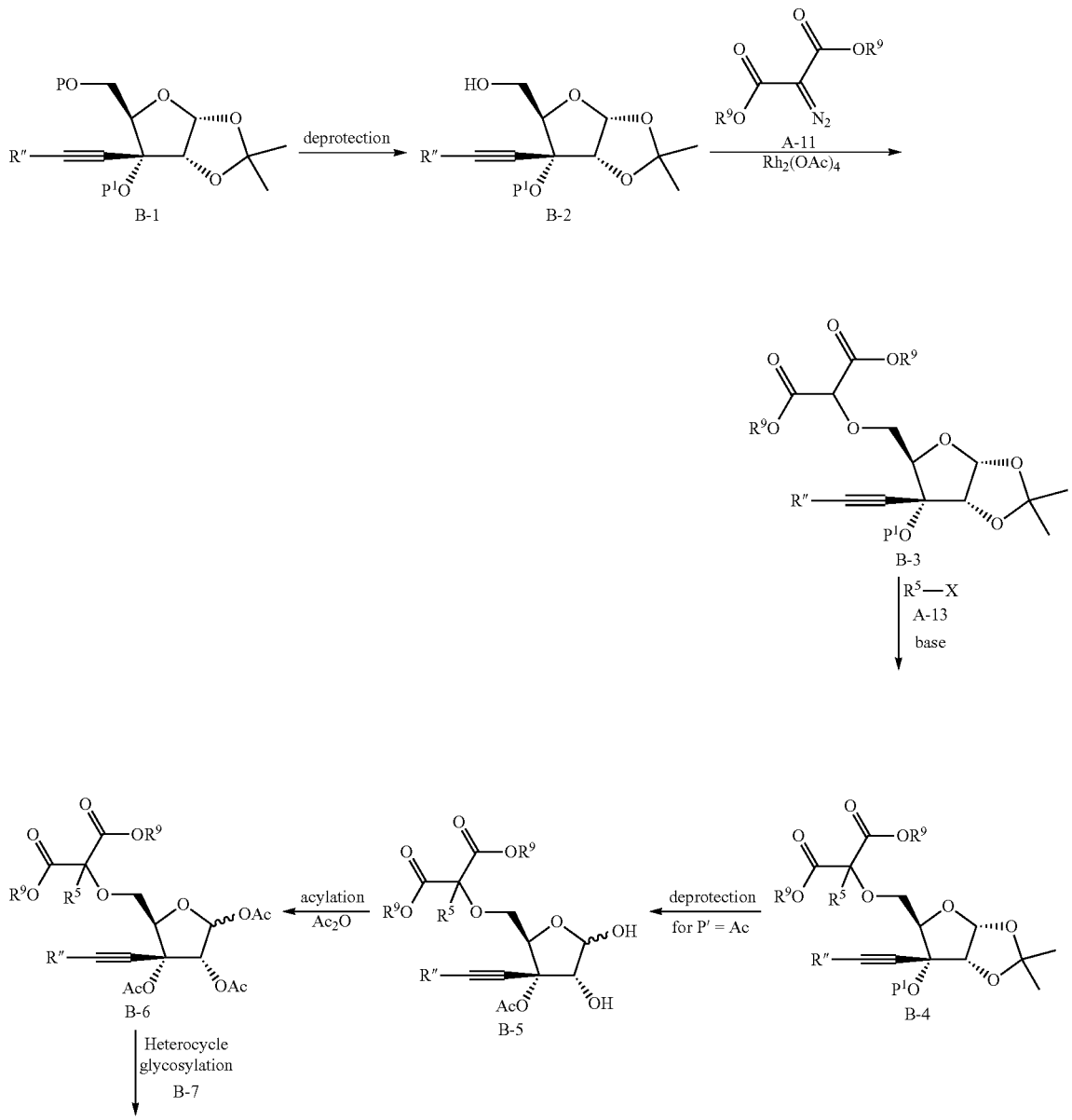

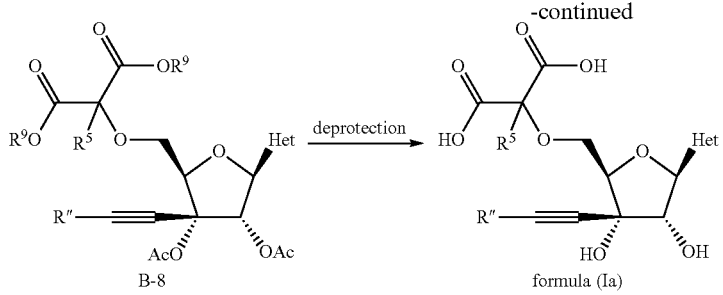

Compounds in formula (Ia) can also be prepared according to Scheme 2. The suitable protecting group such as P is a silyl group (TBDPS or TBDMS) in precursor B-1 can be selectively removed by reagent such as TBAF or HF in THF while the $P^1$ protecting group such as Ac, Bz and MOM group remains. The resulting primary alcohol B-2 can react with diazo reagent A-11 in solvent such as benzene, toluene, DCM and dichloroethane in the presence of metal catalyst such as $Rh_2(OAc)_4$ to give intermediate B-3. Alkylation of B-3 with electrophile A-13 such as halide, triflate, mesylate or sulfonate is accomplished in the presence of a base such as $K_2CO_3$, $Cs_2CO_3$, LiHMDS, NaH and DBU to give intermediate B-4. Removing the acetonide protecting group in B-4 is done by an acid treatment such as aq. TFA, HCl, $H_2SO_4$ or $HClO_4$ in solvent such as DCM, acetone, THF or dioxane to provide diol B-5. Acylation of B-5 with reagent such as $Ac_2O$ or acetyl chloride in the presence of pyridine, TEA or DIPEA and catalytic 4-DMAP to give tri-acetate B-6 (for $P^1$=OAc) as a glycosylation donor. This intermediate B-6 is reacted with a glycosylation acceptor heterocycle B-7 such as 2-chloroadenine, 6-amino-2-chloroadenine, 2,6-dichloroadenine, 5,7-dichloro-1H-imidazo[4,5-b]pyridine, 5-chloro-3H-imidazo[4,5-b]pyridine, uracil, thymine, cytosine and guanine under the influence of conditions such as [N, O-bis(trimethylsilyl)-acetamide and TMSOTf] or (TfOH and DBU) in solvent (MeCN, dichloroethane or DME) to provide nucleoside intermediate B-8. Finally removal of the ester protecting groups in B-8 with the treatment of aq. LiOH, NaOH, and KOH in solvent such as THF, dioxane, MeOH or EtOH to provide the desired final product in the formula (Ia).

Scheme 3

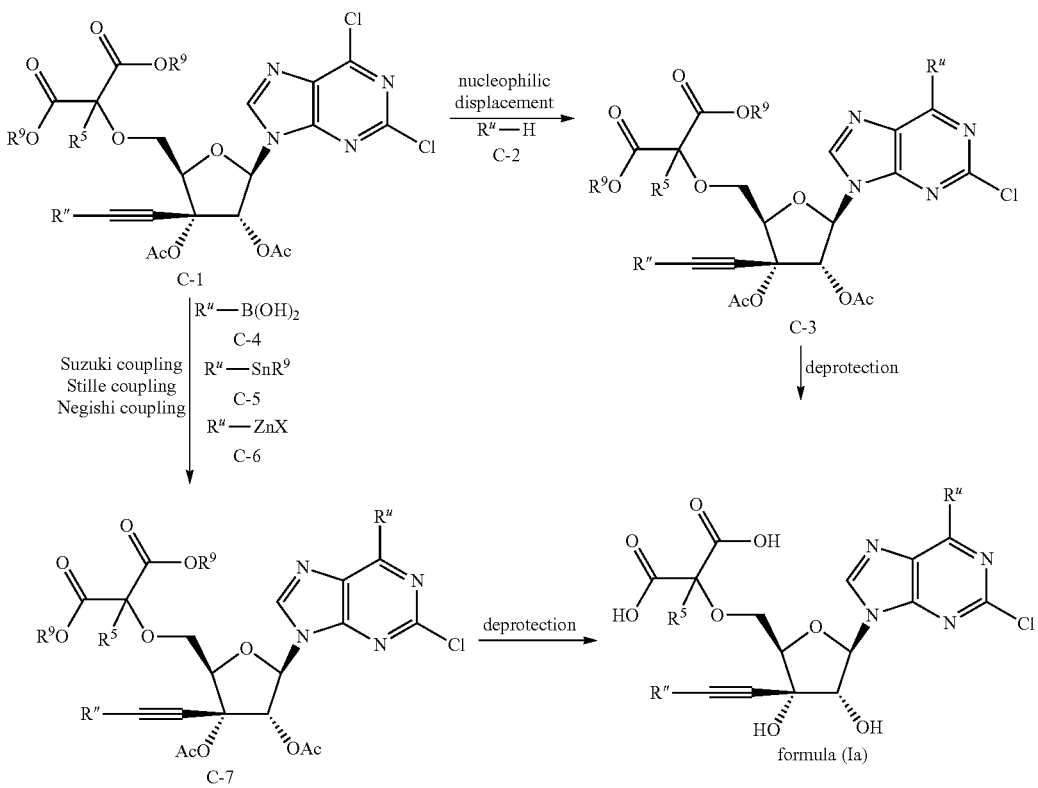

Compounds in formula (Ia) can also be prepared according to Scheme 3. 2,6-Dichloroadenine C-1 prepared according to Scheme 1 can proceed into several synthetic transformations. Selective nucleophilic displacement of the 6-chloro group in precursor 1 with nucleophile $R^u$—H (C-2)

such as amines, alkoxides or thiolates in solvent such as DMF, THF, dioxane, alcohols or NMP to provide intermediate C-3. Precursor C-1 also can undergo a coupling reaction such as Suzuki, Stille or Negishi reaction with the corresponding reagent such as boronic acids (C-4), boronic esters, Tin reagents (C-5) or Zinc reagents (C-6) to provide intermediate C-7, respectively. Treatment of both intermediates C-3 and C-7 with aq. LiOH, NaOH, KOH, NaOMe, NaOEt or KOEt in solvent such as THF, dioxane, MeOH or EtOH to provide the desired final products in the formula (Ia).

Compounds in formula (Ia) can also be prepared via C-1 according to Scheme 4. In this method, treatment of A-7 with 2,6-dichloropurine, TMSOTf and N, O-bis(trimethylsilyl)acetamide via the Vorbrüggen reaction gives protected nucleoside D-2. Selective removal of the tert-butyldiphenylsilyl moiety from the 5'-hydoxyl group gives alcohol D-3. Coupling with a desired substituted acyldiazo-reagent D-4 gives substituted nucleoside D-5. A wide variety of diazo reagents can be used in this reaction. Some examples include those where $R^w$ is $CO_2R^9$, $SOR^9$, $SO_2R^9$, $P(O)(OR^9)_2$, and CN and $R^9$ is defined as in the Summary. If an alkyl

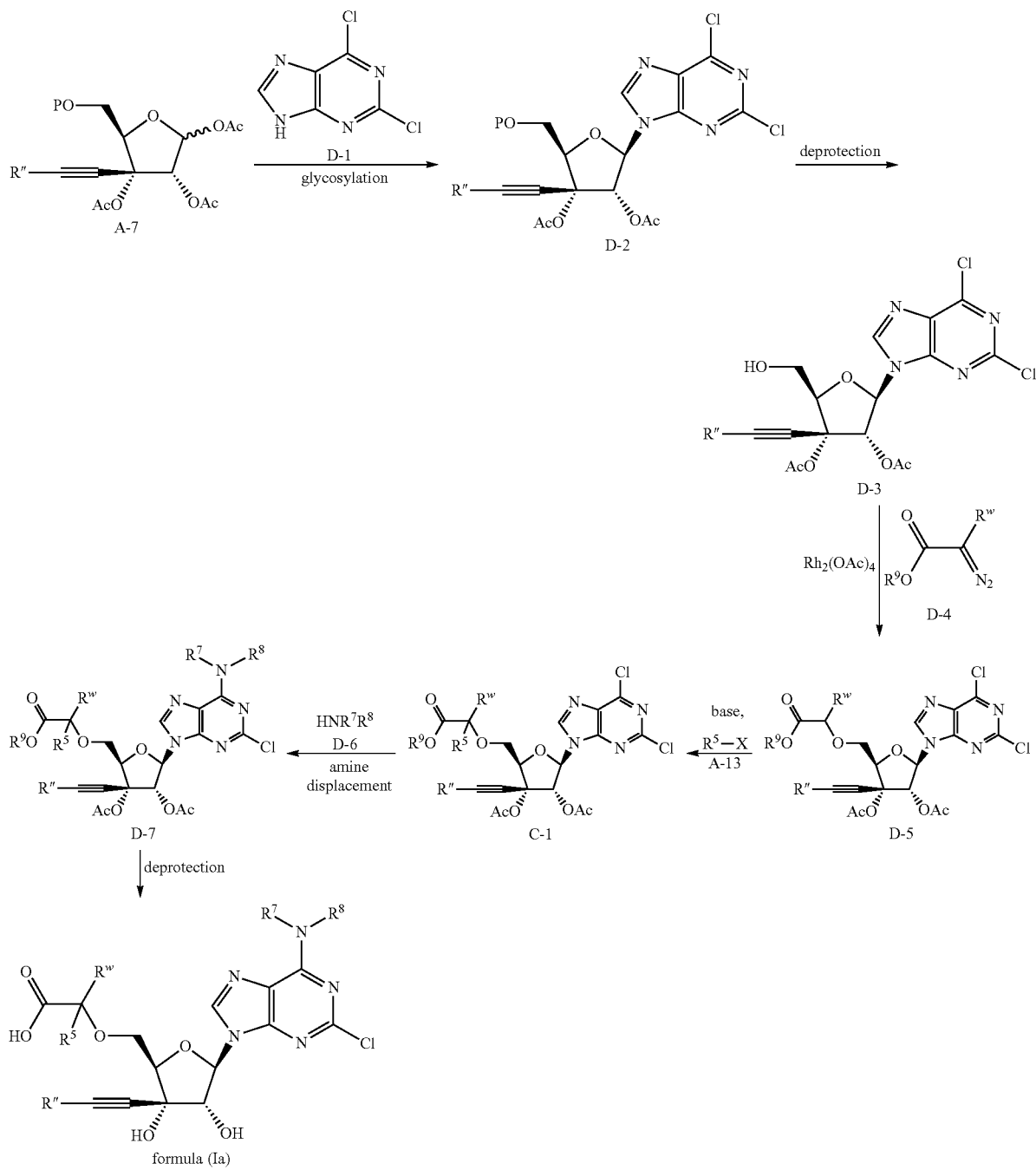

substituent R⁵ is desired, it can be conveniently introduced using an alkylation reaction where a nucleophile such as R⁵—X (X=halide, OTf, OMs or OTs) is used with a base like cesium carbonate in a polar aprotic solvent like THF or DMF to give key intermediate C-1. A substituent such as an amine can be added to the purine base by displacing the chlorine at the 6-position to give intermediate D-7 with variety of amines D-6 in a solvent such as EtOH, THF or dioxane. Final deprotection of D-7 by using an aqueous hydrolysis with a base such as lithium hydroxide gives target compound in the structure of formula (1).

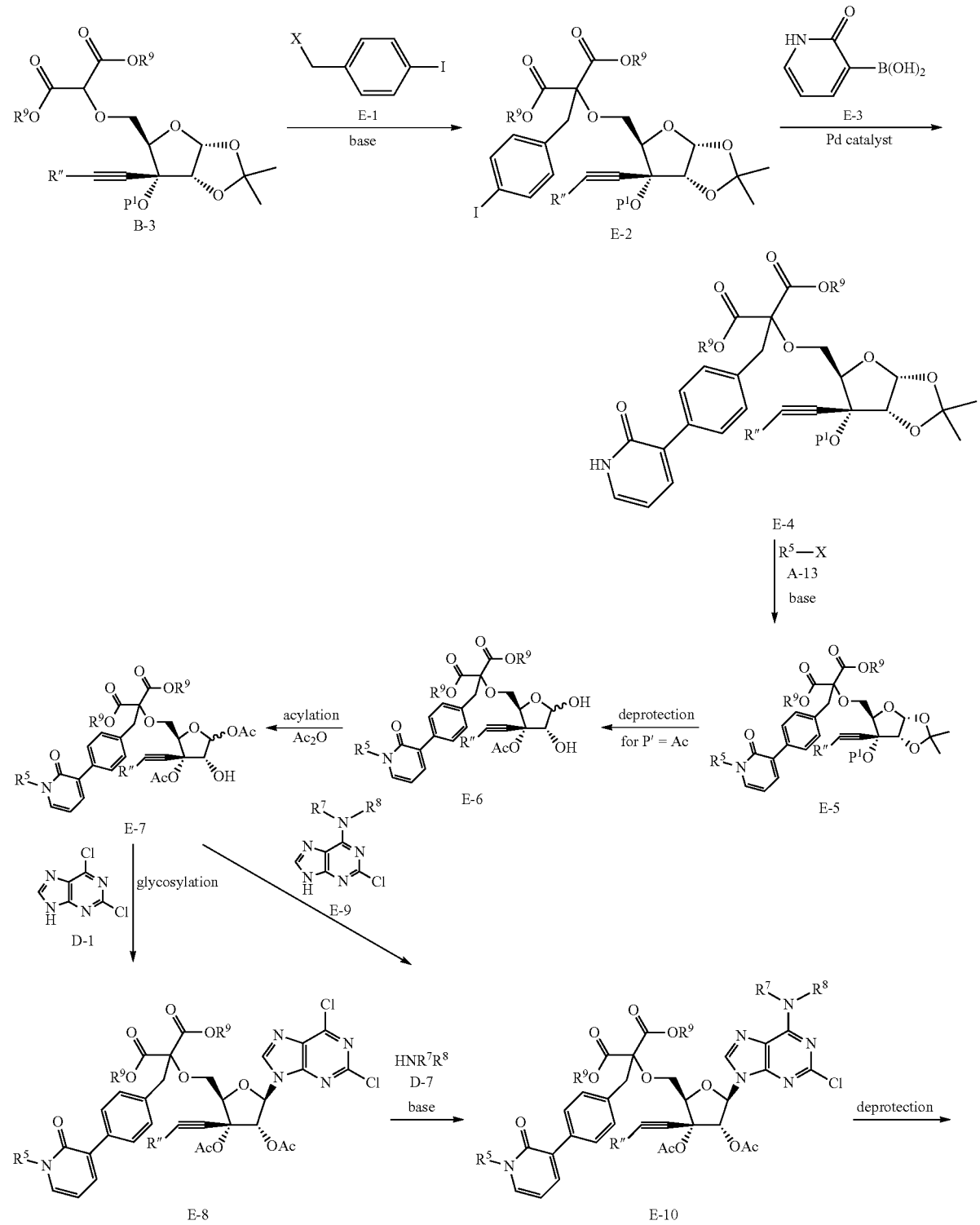

Scheme 5

-continued

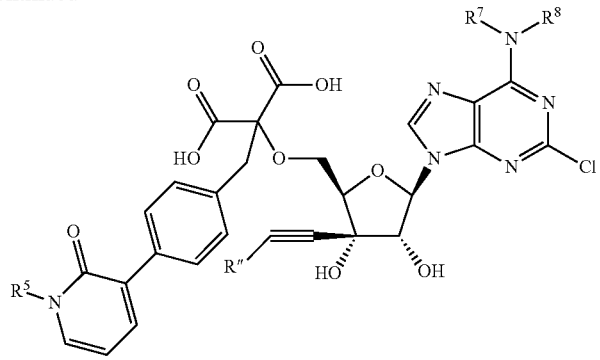

formula (Ia)

Compounds in formula (Ia) can also be prepared according to Scheme 5. Alkylation of precursor B-3 from Scheme 2 above with an electrophile E-1 such as 4-iodobenzyl halide (Br, Cl, or I) or the corresponding OTf, OMs or OTs with base such as $K_2CO_3$, $Cs_2CO_3$, NaH or LiHMDS in solvent like DMF or THF leads to intermediate E-2 which can couple with various boronic acids such as (2-oxo-1,2-dihydropyridin-3-yl)boronic acid (E-3) illustrated here. The resulting pyridone product E-4 is alkylated with various alkyl halides (A-13) in the presence of base such as $K_2CO_3$, $Cs_2CO_3$, NaH or LiHMDS in solvent like DMF and THF to give E-5. The acetonide protecting group in E-5 is removed with the treatment of aq. TFA, HCl, $H_2SO_4$ or AcOH in a solvent such as DCM, acetone, dioxane or THF to give diol E-6 which is acetylated with $Ac_2O$ or acetyl chloride with a catalytic amount of 4-DMAP and a base such as pyridine, TEA or DIPEA in solvent like DCM to provide an anomeric mixture E-7 as a glycosylation donor. Intermediate E-7 can either react with heterocyclic acceptor 2,6-dichloroadenine (D-1) or N-substituted 6-amino-2-chloroadenine (E-9) which is formed from displacing the 6-chloro group in D-1 with the suitable amines (D-7). Both glycosylation can be done under the activation conditions such as [(N, O-bis(trimethylsilyl)-acetamide and TMSOTf] or (TfOH and DBU) in solvent (MeCN, dichloroethane or toluene), between donor E-7 and acceptors D-1 or E-9 to provide the corresponding nucleoside products, E-8 or E-10 respectively. Nucleoside E-8 is converted into E-10 via a nucleophilic displacement with various amines (D-7). Finally, desired compounds in formula (Ia) is produced from E-10 via the deprotection of all its ester groups with treatment of aq. LiOH, NaOH, and KOH in a solvent such as THF, dioxane, MeOH or EtOH.

Scheme 6

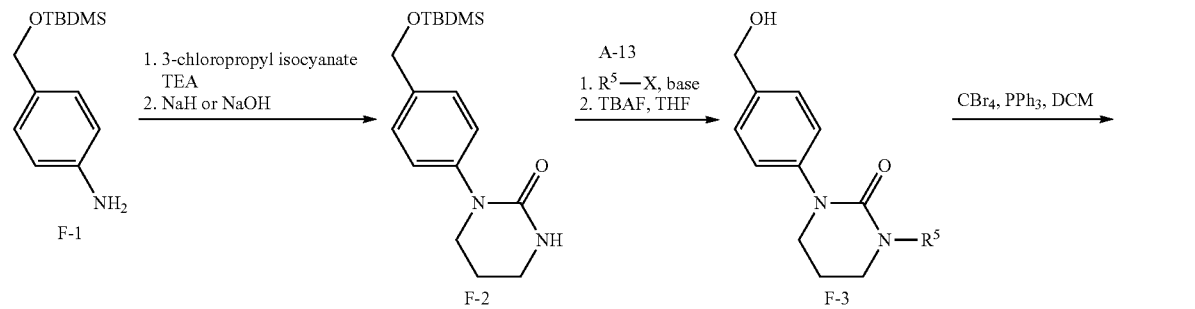

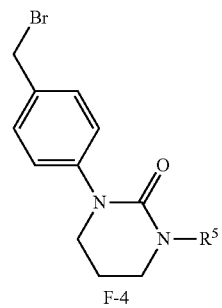

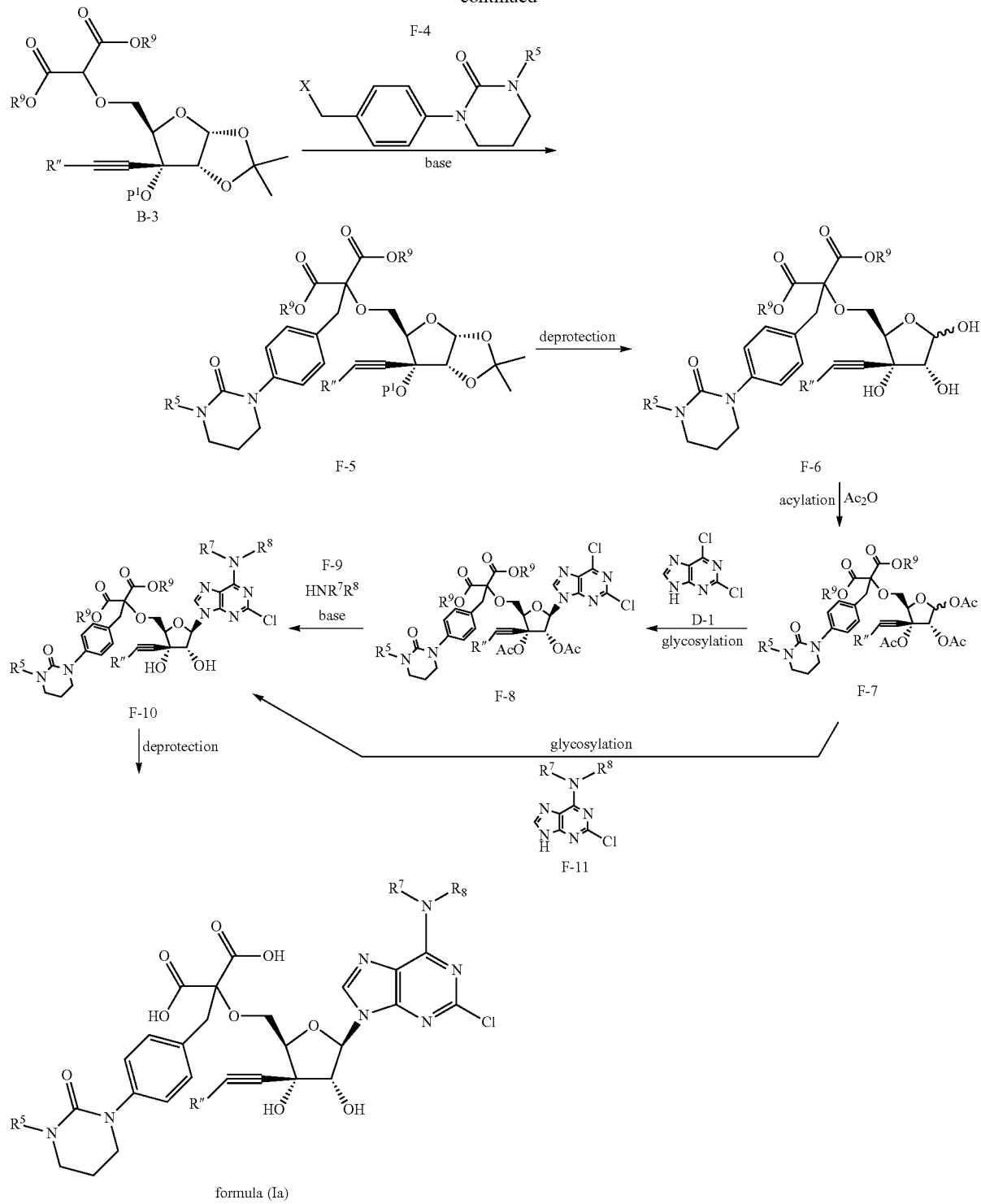

Compounds in formula (Ia) can also be prepared according to Scheme 6. Alkylation with benzyl halide F-4 with various alkyl side chains ($R^5$) and precursor B-3 in the presence of base such as $K_2CO_3$, $Cs_2CO_3$, LiHMDS or NaH in suitable solvent like DMF or THF leads to intermediate F-5. Triacetate F-7 is formed via a two-step transformation from F-5 via a deprotection (aq. TFA in DCM) and acylation ($Ac_2O$ or acetyl chloride in pyridine) as described aforementioned schemes. Glycosylation between F-7 and various acceptors such as 2,6-dichloroadenine (D-1) under an activation conditions [(N, O-bis(trimethylsilyl)-acetamide and TMSOTf] or (TfOH and DBU) in solvent (MeCN, dichloroethane or toluene) to provide nucleoside F-8 which is converted to amino analogs F-10 with various amines (F-9) in the presence of base such as pyridine, TEA or DIPEA in appropriate solvent like dioxane, DMF, or THF. Finally, desired molecules in formula (1) is obtained from F-10 with the treatment of aq. LiOH, NaOH, and KOH in a solvent such as THF, dioxane, MeOH or EtOH. Alternatively, intermediate F-10 can also directly produced from glycosylation between donor F-7 and other acceptors such as N-substituted 6-amino-2-chloroadenines (F-11).

The required benzyl halides F-4 is prepared from 4-(((tert-butyldimethylsilyl)oxy)-methyl)aniline (F-1) via a five-step transformation. The cyclic urea ring is initially formed from aniline F-1 reacting with 3-chloropropyl isocyanate and followed by cyclization under the influence of a base such as NaH, NaOH or LiHMDS in solvent like DMF or THF to generate F-2. Intermediate F-2 is then led to F-3 by removal of the TBDMS group with TBAF and proceeds to the final product by converting the primary alcohol to the bromide with $CBr_4$ and $PPh_3$ in solvent such as DCM or THF.

Alternatively, key intermediate F-5 is also prepared from precursor B-3 according to Scheme 7. Alkylation of precursor B-3 with halides such as 4-nitrobenzyl bromide in the presence of base such $K_2CO_3$ or $Cs_2CO_3$ in DMF to provide the nitro intermediate which is then reduced to the aniline with Fe in aq. $NH_4Cl$. Cyclic urea formation is carried out from aniline with 3-chloropropyl isocyanate in the presence of base such as TEA in THF and followed by intramolecular ring closure with the treatment of base such as NaH or LiHMDS. Introduction of the N-alkyl side chains is accomplished with electrophile such as A-13 to provide key intermediate F-5.

Formula (Ib) can be prepared according to Scheme 8. The required diazo reagent G-2 which $R^w$ is an aryl or heteroaryl group, can be prepared from ester G-1 with the suitable sulfonyl azide reagent, such as 4-acetmidobenzenesulfonyl azide in the presence of a base, such as $Et_3N$ and DBU, in MeCN or dioxane. Coupling of diazo reagent G-2 and alcohol A-9 from Scheme 1 via the insertion reaction catalyzed by Rh or Cu catalyst such as $Rh_2(OAc)_4$, in a solvent such as toluene, DCM or dichloroethane to give product G-3. Alkylation of G-3 with an electrophile A-13 such as alkyl halide, triflate, tosylate or mesylate in the presence of base such as $Cs_2CO_3$, $K_2CO_3$, LiHMDS, DBU or NaH, to provide G-4. The ester groups in G-4 is finally removed by an aq. base such as LiOH, NaOH, and KOH to provide the desired product in formula (Ib).

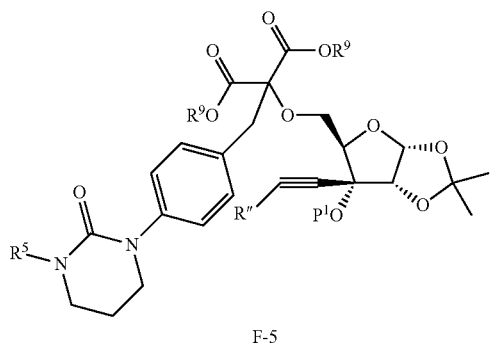

F-5

Scheme 7

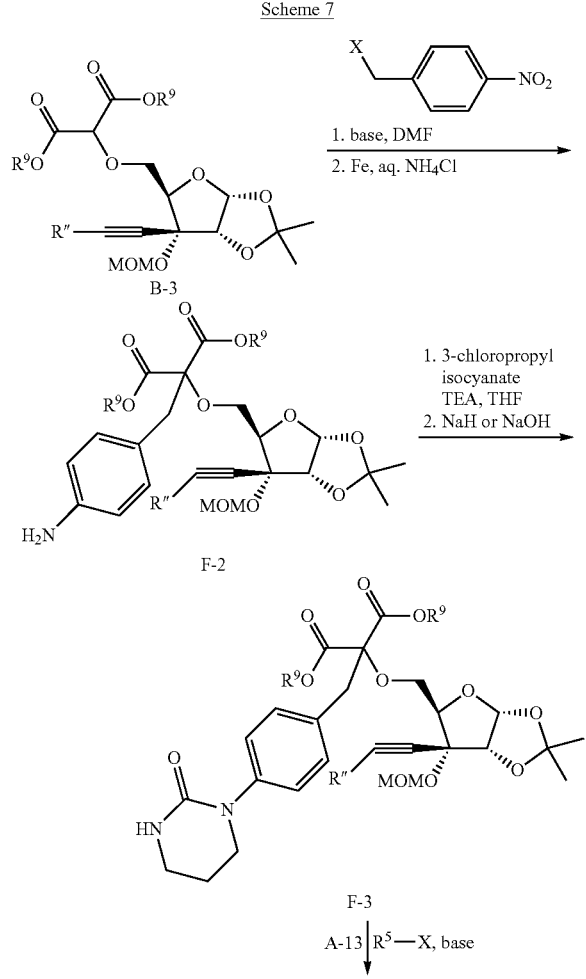

Scheme 8

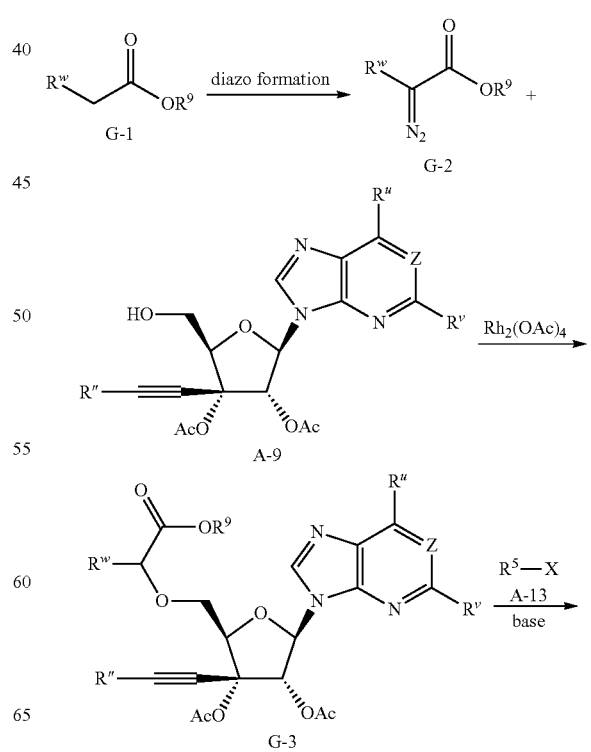

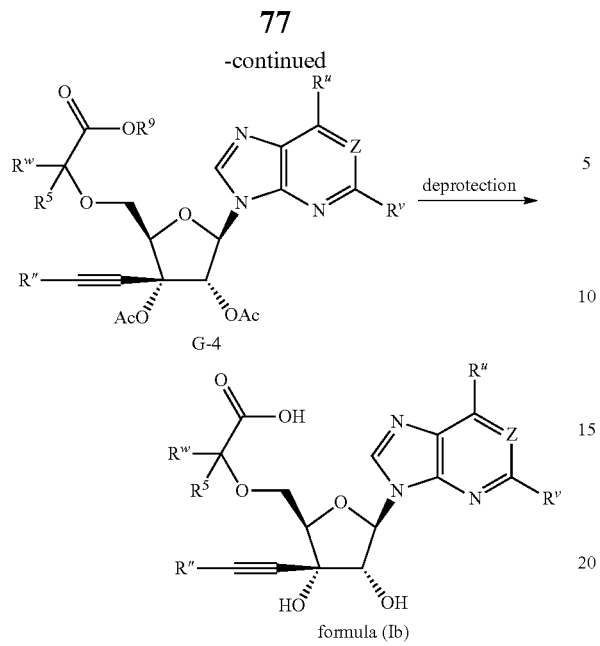

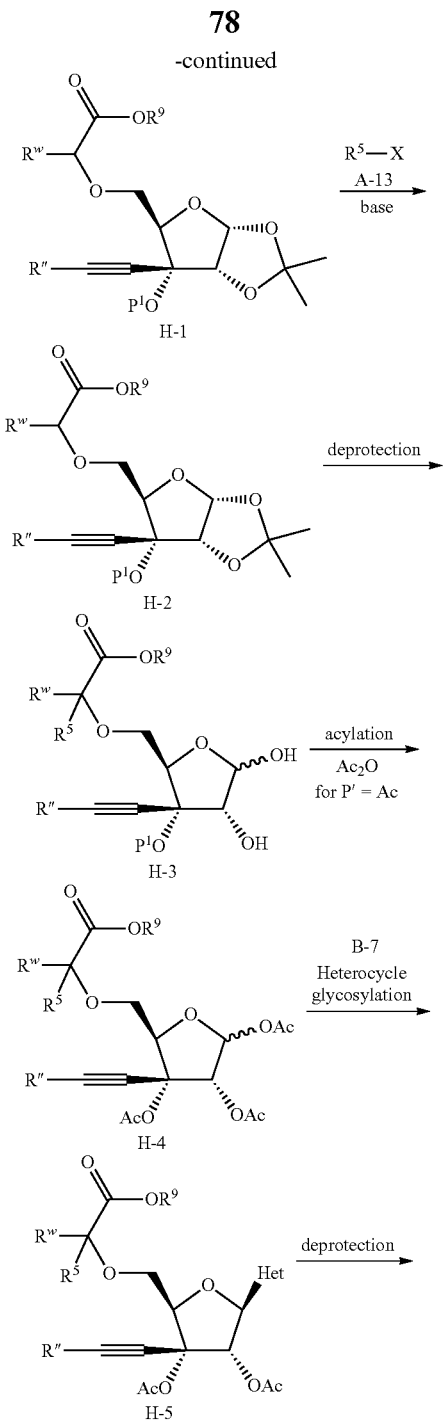

Compounds in formula (Ib) can also be prepared according to Scheme 9. The primary alcohol B-2 can react with diazo reagent G-2 from Scheme 8 in the presence of a metal catalyst such as Rh$_2$(OAc)$_4$ in a solvent such as benzene, toluene, DCM or dichloroethane to give intermediate H-1. Alkylation of H-1 with an electrophile A-13 such as halide, triflate, mesylate or sulfonate is accomplished in the presence of base such as K$_2$CO$_3$, Cs$_2$CO$_3$, LiHMDS, NaH and DBU to give intermediate H-2. Removing the acetonide protecting group in H-2 is done by acid treatment such as aq. TFA, HCl, H$_2$SO$_4$, HClO$_4$ or CSA in solvent such as DCM, acetone, THF or dioxane to provide diol H-3. Acylation of H-3 with a reagent such as Ac$_2$O or acetyl chloride in the presence of pyridine, TEA or DIPEA and catalytic 4-DMAP to give tri-acetate H-4 as a glycosylation donor. This intermediate H-4 is reacted with a glycosylation acceptor heterocycle B-7 such as 2-chloroadenine, 6-amino-2-chloroadenine, 2,6-dichloroadenine, 5,7-dichloro-1H-imidazo[4,5-b]pyridine, 5-chloro-3H-imidazo[4,5-b]pyridine, uracil, thymine, cytosine and guanine under the conditions such as [N, O-bis(trimethylsilyl)-acetamide and TMSOTf] or (TfOH and DBU) in a solvent (MeCN, dichloroethane or DME) to provide nucleoside intermediate H-5. Finally removal of the ester protecting groups in H-5 with the treatment of aq. LiOH, NaOH, and KOH in a solvent such as THF, dioxane, MeOH or EtOH to provide the desired final product in the formula (Ib).

Scheme 9

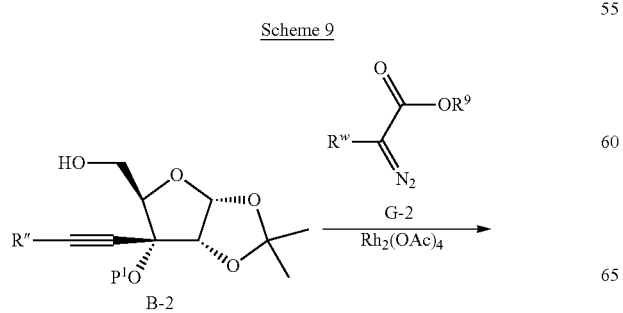

Compounds in formula (Ic) can also be prepared according to Scheme 10. Tertiary alcohol I-2 where R$^1$ is methyl (prepared according to the procedure reported by Franchetti, P. et al. *J. Med. Chem.* 2005, 48, 4983-4989) or other alkyl groups; ethynyl (prepared according to the procedure by Hulpia, F. et al. *Bioorg. Med. Chem. Lett.* 2016, 26, 1970-1972) or other alkynyl groups; and vinyl groups, was converted into I-4 either directly by treatment of acetylation reagent such as $Ac_2O$ and catalytic amount of $H_2SO_4$ in AcOH or vai a 2-step process involving deprotetion of the acetonide group with treatment of aq. TFA or other acid in DCM first and followed by acetylation of the resulting diol I-3 with a reagent such as $Ac_2O$ or acetyl chloride. Glycosylation of I-4 with a heteroaromatic glycosyl acceptor such as heterocycle B-7 described in Scheme 2 where $R^u$ is H, Cl, $NH_2$, N-alkyl group such as 2-chloroadenine, 6-amino-2-chloroadenine, 2,6-dichloroadenine, 5,7-dichloro-1H-imidazo[4,5-b]pyridine, 5-chloro-3H-imidazo[4,5-b]pyridine, uracil, thymine, cytosine and guanine under the conditions such as [N, O-bis(trimethylsilyl)-acetamide and TMSOTf] or (TfOH and DBU) in a solvent (MeCN, dichloroethane or DME) to provide nucleoside intermediate I-5. Removal of the silyl protecting group in I-5 with a source of fluoride such as TBAF in THF to give primary alcohol I-6 which was further converted into triol I-7 with aq. LiOH or NaOH in solvent such as THF, MeOH or EtOH. Finally, treatment of I-7 with methylenebis(phosphonic dichloride) and trimethylphosphate before it is followed by triethylammonium carbonate to provide the desired final product in the formula (Ic).

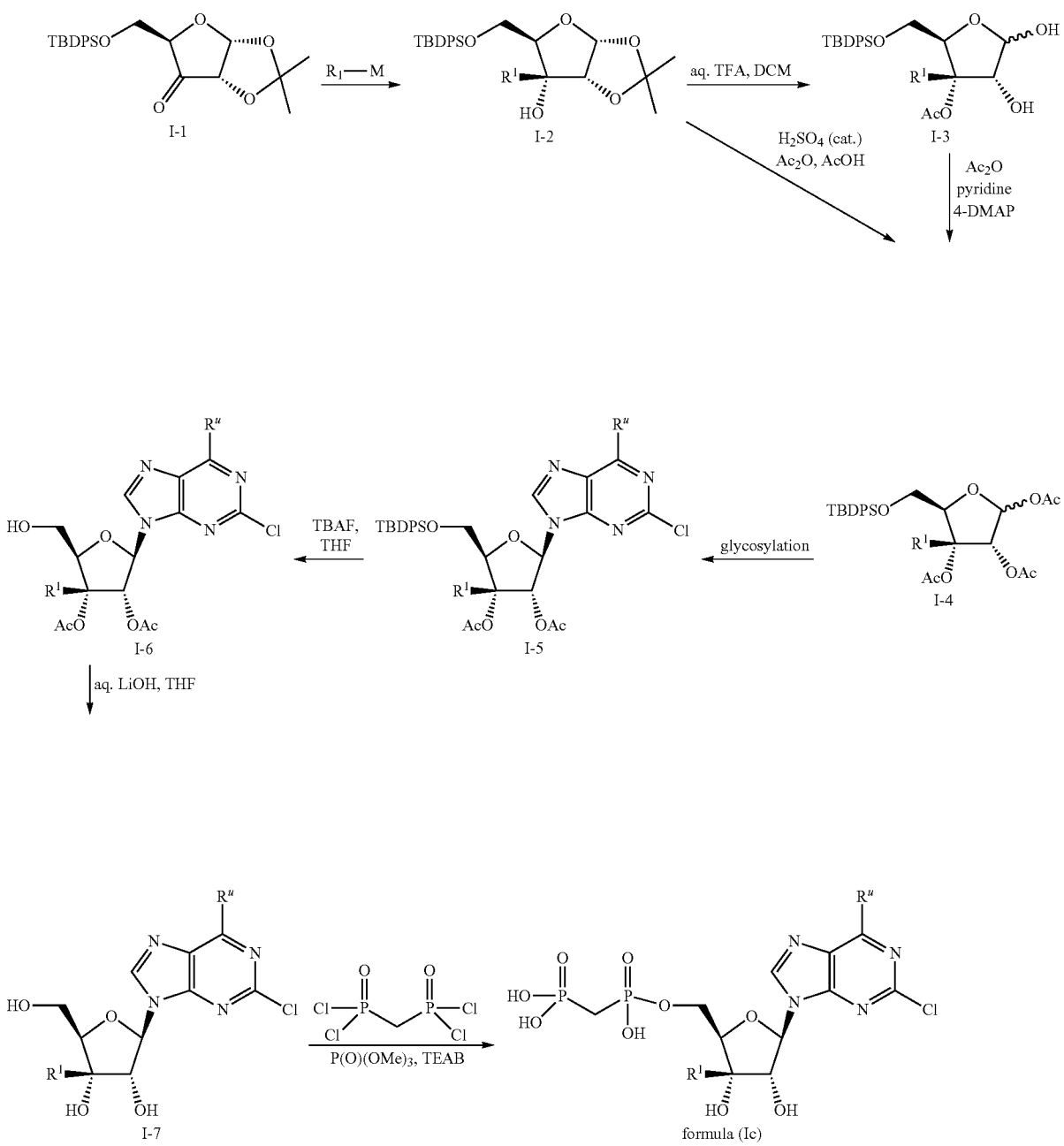

Scheme 10

Compounds in formula (Ic) can be prepared according to Scheme 11. Primary alcohol I-6 (where R"=Cl) is alkylated with electrophile J-1 such as (diethoxyphosphoryl)methyl trifluoromethanesulfonate or diethyl (iodomethyl)phosphonate in the presence of a base, such as TEA, DIPEA, NaH and Cs₂CO₃ in a solvent such as THF, DMF, dioxane or NMP to give intermediate J-2. Installation of the amino group in J-4 via nucleophilic displacement of the chloro group in J-2 with R⁷R⁸NH (J-3) where R⁷ and R⁸ are H or alkyl groups, in the presence of a base such as TEA or DIPEA in solvent such as dioxane, THF, or DMF. A two-step deprotection sequence (TMSBr and aq. LiOH or NaOH) is required to convert J-4 to the desired product in formula (Ic).

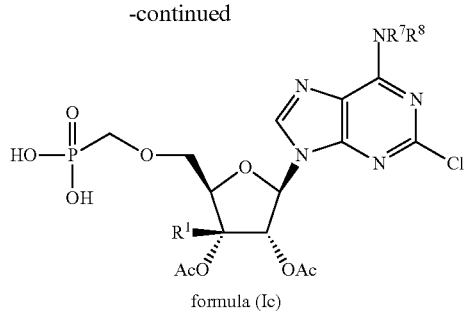

formula (Ic)

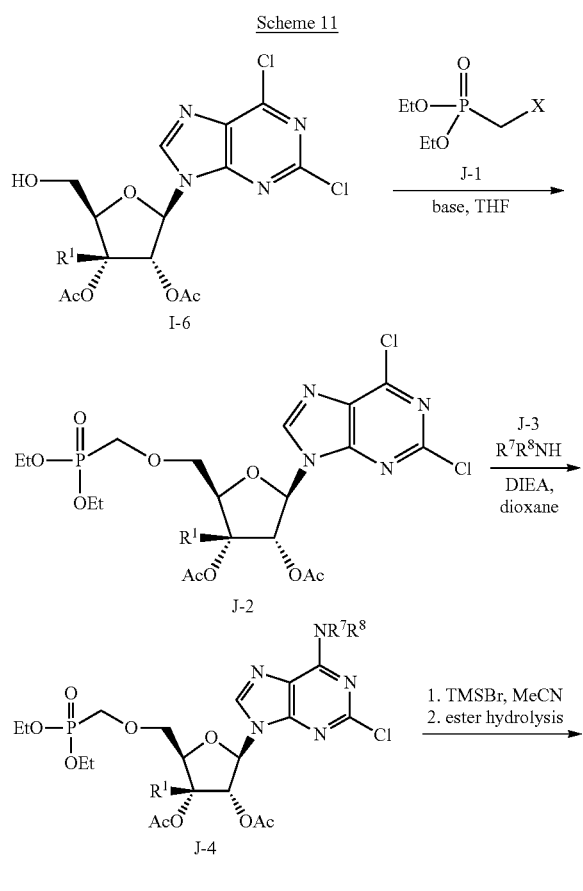

Those having skill in the art will recognize that the starting materials and reaction conditions may be varied, the sequence of the reactions altered, and additional steps employed to produce compounds encompassed by the present invention, as demonstrated by the following examples. In some cases, protection of certain reactive functionalities may be necessary to achieve some of the above transformations. In general, the need for such protecting groups as well as the conditions necessary to attach and remove such groups will be apparent to experienced organic chemists. The disclosures of all articles and references mentioned in this application, including patents, are incorporated herein by reference.

The preparation of the compounds of the present invention is illustrated further by the following examples, which are not to be construed as limiting the invention in scope or spirit to the specific procedures and compounds described in them.

SYNTHETIC EXAMPLES

Example 1

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-benzylmalonic acid

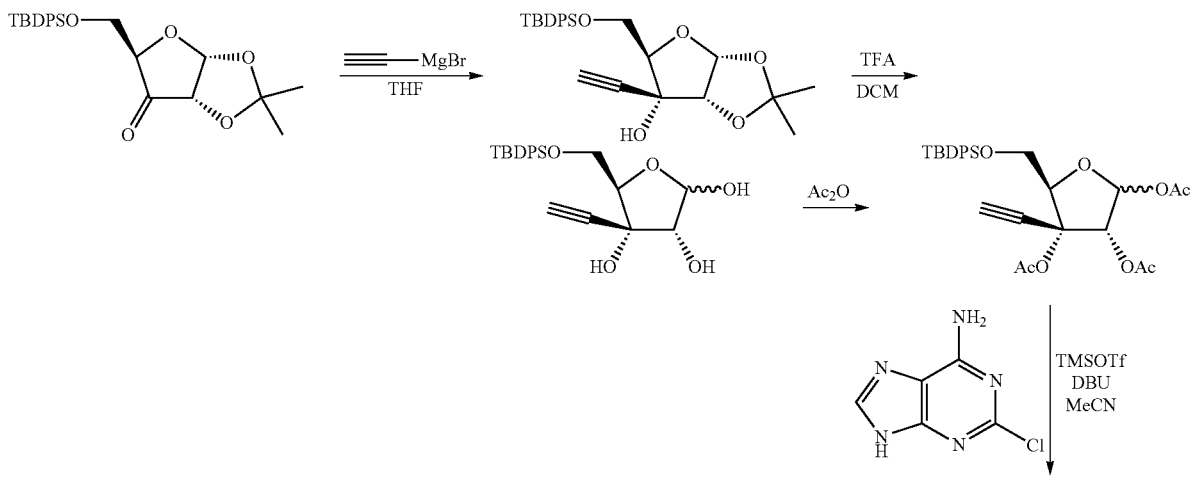

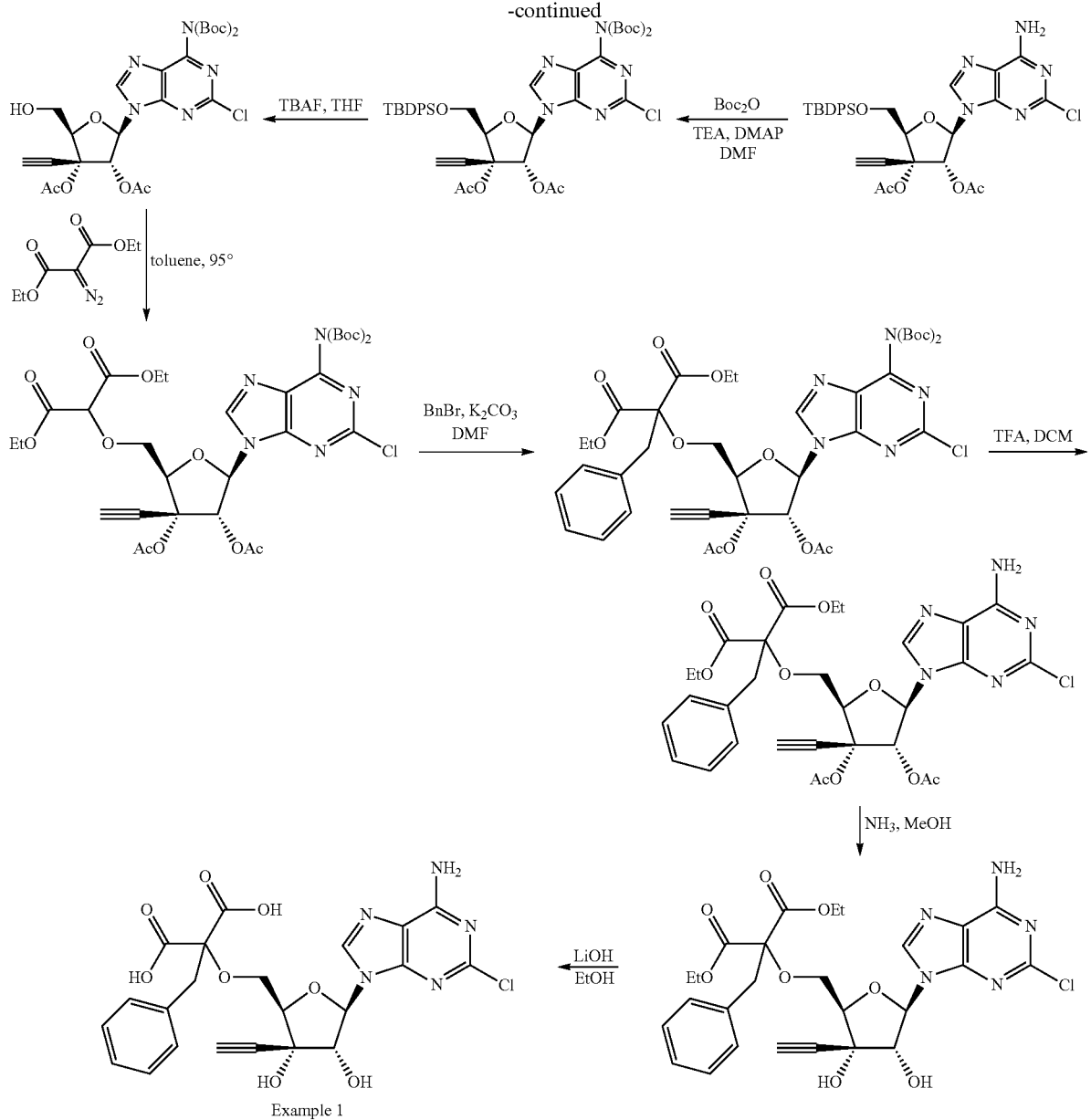

Example 1

Step 1:

To a mixture of (3aR,5R,6aS)-5-(((tert-butyldiphenylsilyl)oxy)methyl)-2,2-dimethyldihydrofuro[2,3-d][1,3]dioxol-6(3aH)-one (10 g, 23.44 mmol, 1 eq) in THF (100 mL) was added ethynylmagnesium bromide (0.5 M, 328.19 mL, 7 eq) at 15° C. under N₂ atmosphere. The mixture was stirred for 16 h before additional ethynylmagnesium bromide (0.5 M, 125 mL, 3 eq) was added. The mixture was stirred further for 3 h before it was diluted with saturated aq. NH₄Cl (250 mL) and extracted with EtOAc (3×250 mL). The combined organic layer was washed with brine (250 mL), dried over Na₂SO₄, filtered and concentrated to dryness. The crude product was purified by flash silica gel column chromatography (petroleum ether:EtOAc=1:0-4:1) to provide (3aR,5R, 6R,6aR)-5-(((tert-butyldiphenylsilyl)oxy)methyl)-6-ethynyl-2,2-dimethyl-tetrahydrofuro[2,3-d][1,3]dioxol-6-ol (19.47 g, 92% yield) as a yellow solid.

Step 2:

To a solution of (3aR,5R,6R,6aR)-5-(((tert-butyldiphenylsilyl)oxy)methyl)-6-ethynyl-2,2-dimethyltetrahydrofuro[2,3-d][1,3]dioxol-6-ol (9.47 g, 20.92 mmol, 1 eq) in DCM (100 mL) was added H₂O (10 mL) and TFA (100 mL) at 0° C. The mixture was stirred at 25° C. for 1 h before it was quenched with saturated aq. NaHCO₃ to pH 7 and then extracted with DCM (2×300 mL). The combined organic layer was washed with brine (200 mL), dried over Na₂SO₄, filtered and concentrated to dryness. The crude product was purified by flash silica gel column chromatography (petroleum ether:EtOAc=1:0-0:1) to provide (3R,4S,5R)-5-(((tert-butyldiphenylsilyl)oxy)methyl)-4-ethynyltetrahydro-furan-2,3,4-triol (5.17 g, 60% yield) as a yellow gum.

Step 3:

To a solution of (3R,4S,5R)-5-(((tert-butyldiphenylsilyl)oxy)methyl)-4-ethynyltetra-hydrofuran-2,3,4-triol (5.17 g, 12.53 mmol, 1 eq) in pyridine (50 mL) at 15° C. was added 4-DMAP (4.59 g, 37.60 mmol, 3 eq) and Ac₂O (11.74 mL, 125.32 mmol, 10 eq). The mixture was stirred at 15° C. for 16 h before H₂O (500 mL) was added to the mixture. The reaction mixture was extracted with EtOAc (3×200 mL). The combined organic layer was washed with brine (200 mL), dried over Na₂SO₄, filtered and concentrated to dryness. The crude product was purified by flash silica gel column chromatography (petroleum ether:EtOAc=1:0-1:1) to provide (3R,4R,5R)-5-(((tert-butyldiphenylsilyl)oxy)methyl)-4-ethynyltetra-hydrofuran-2,3,4-triyl triacetate (7.19 g, 79% yield) as a yellow gum.

Step 4:

To a solution of (3R,4R,5R)-5-(((tert-butyldiphenylsilyl)oxy)methyl)-4-ethynyltetra-hydrofuran-2,3,4-triyl triacetate (6.89 g, 12.79 mmol, 1 eq) in MeCN (5 mL) at 0° C. was added 2-chloroadenine (2.39 g, 14.07 mmol, 1.1 eq), DBU (5.78 mL, 38.37 mmol, 3 eq) and TMSOTf (11.56 mL, 63.96 mmol, 5 eq). The mixture was stirred at 0° C. for 0.5 h and then stirred at 65° C. for 1 h before it was diluted with saturated aq. NaHCO₃ solution (500 mL). The aqueous phase was extracted with EtOAc (2×350 mL). The combined organic layer was washed with brine (350 mL), dried over Na₂SO₄, filtered and concentrated to dryness. The crude product was purified by flash silica gel column chromatography (petroleum ether:EtOAc=1:0-0:1) to provide (2R,3R,4R,5R)-5-(6-amino-2-chloro-9H-purin-9-yl)-2-(((tert-butyldiphenylsilyl)oxy)methyl)-3-ethynyltetrahydrofuran-3,4-diyl diacetate (4.52 g, 44% yield) as a yellow solid.

Step 5:

To a solution of (2R,3R,4R,5R)-5-(6-amino-2-chloro-9H-purin-9-yl)-2-(((tert-butyldiphenylsilyl)oxy)methyl)-3-ethynyltetrahydrofuran-3,4-diyl diacetate (4.5 g, 6.94 mmol, 1 eq) in DMF (50 mL) at 20° C. was added TEA (4.83 mL, 34.71 mmol, 5 eq), 4-DMAP (254 mg, 2.08 mmol, 0.3 eq) and Boc₂O (7.58 g, 34.71 mmol, 5 eq). The mixture was stirred at 20° C. for 1 h before H₂O (250 mL) was added to the mixture. The reaction mixture was extracted with EtOAc (3×230 mL). The combined organic layer was washed with brine (250 mL), dried over Na₂SO₄, filtered and concentrated. The crude product was purified by flash silica gel column chromatography (petroleum ether:EtOAc=1:0-1:1) to provide (2R,3R,4R,5R)-5-(6-(bis-(tert-butoxycarbonyl)amino)-2-chloro-9H-purin-9-yl)-2-(((tert-butyldiphenylsilyl)oxy)methyl)-3-ethynyltetrahydrofuran-3,4-diyl diacetate (3.26 g, 46% yield) as a yellow foam.

Step 6:

To a solution of (2R,3R,4R,5R)-5-(6-(bis-(tert-butoxycarbonyl)amino)-2-chloro-9H-purin-9-yl)-2-(((tert-butyldiphenylsilyl)oxy)methyl)-3-ethynyltetrahydrofuran-3,4-diyl diacetate (3.24 g, 3.82 mmol, 1 eq) in THF (35 mL) at 0° C. was added TBAF (1 M, 5.73 mL, 1.5 eq). The reaction mixture was stirred at 0° C. for 1 h before it was diluted with H₂O (150 mL). The reaction mixture was extracted with EtOAc (3×130 mL). The combined organic layer was washed with brine (150 mL), dried over Na₂SO₄, filtered and concentrated. The crude product was purified by flash silica gel column chromatography (petroleum ether:EtOAc=1:0-1:2) to provide (2R,3R,4R,5R)-5-(6-N,N'-(bis-(tert-butoxycarbonyl)amino)-2-chloro-9H-purin-9-yl)-3-ethynyl-2-(hydroxymethyl)tetrahydrofuran-3,4-diyl diacetate (1.51 g, 54% yield) as a yellow foam.

Step 7:

To a solution of (2R,3R,4R,5R)-5-(6-N,N'-(bis-(tert-butoxycarbonyl)amino)-2-chloro-9H-purin-9-yl)-3-ethynyl-2-(hydroxymethyl)tetrahydrofuran-3,4-diyl diacetate (1.48 g, 2.43 mmol, 1 eq) in toluene (10 mL) at 20° C. under N₂ atmosphere was added Rh₂(OAc)₄ (214 mg, 485.24 umol, 0.2 eq) and diethyl diazomalonate (903 mg, 4.85 mmol, 2 eq) in toluene (3 mL). The mixture was stirred at 95° C. for 2 h to give a green suspension before it was cooled to room temperature and concentrated to dryness. The crude product was purified by flash silica gel column chromatography (petroleum ether:EtOAc=1:0-3:1) to provide diethyl 2-(((2R,3R,4R,5R)-3,4-diacetoxy-5-(6-N,N'-(bis-(tert-butoxycarbonyl)amino)-2-chloro-9H-purin-9-yl)-3-ethynyltetrahydrofuran-2-yl)methoxy)malonate (517 mg, 20% yield) as a yellow foam.

Step 8:

To a solution of diethyl 2-(((2R,3R,4R,5R)-3,4-diacetoxy-5-(6-N,N'-(bis-(tert-butoxy-carbonyl)amino)-2-chloro-9H-purin-9-yl)-3-ethynyltetrahydrofuran-2-yl)methoxy)malonate (497.00 mg, 647.00 umol, 1 eq) in DMF (5 mL) at 25° C. was added K₂CO₃ (178.84 mg, 1.29 mmol, 2 eq). The reaction mixture was stirred for 30 min and followed by addition of benzyl bromide (221.32 mg, 1.29 mmol, 153.69 uL, 2 eq). The mixture was stirred at 25° C. for 15.5 h before additional K₂CO₃ (100 mg) and BnBr (100 uL) were added to the mixture. The resulting mixture was stirred at 25° C. for 24 h before H₂O (50 mL) was added to the reaction. The reaction mixture was extracted with EtOAc (2×50 mL). The combined organic layer was washed with brine (50 mL), dried over Na₂SO₄, filtered and concentrated. The crude product was purified by flash silica gel column chromatography (petroleum ether:EtOAc=1:0-3:1) to provide diethyl 2-benzyl-2-(((2R,3R,4R, 5R)-3,4-diacetoxy-5-(6-(bis-(tert-butoxycarbonyl)amino)-2-chloro-9H-purin-9-yl)-3-ethynyltetrahydrofuran-2-yl)methoxy)-malonate (266 mg, 37% yield) as a yellow foam.

Step 9:

To a solution of diethyl 2-benzyl-2-(((2R,3R,4R,5R)-3,4-diacetoxy-5-(6-(bis-(tert-butoxycarbonyl)amino)-2-chloro-9H-purin-9-yl)-3-ethynyltetrahydrofuran-2-yl)methoxy)-malonate (266 mg, 309.92 umol, 1 eq) in DCM (3 mL) was added TFA (0.45 mL) at 0° C. The mixture was stirred at 25° C. for 16 h before it was treated with saturated aq. NaHCO₃ solution to pH 7. The reaction mixture was extracted with DCM (2×50 mL). The combined organic layer was washed with brine (50 mL), dried over Na₂SO₄, filtered and concentrated to provide crude diethyl 2-benzyl-2-(((2R,3R,4R,5R)-3,4-diacetoxy-5-(6-amino-2-chloro-9H-purin-9-yl)-3-ethynyltetrahydrofuran-2-yl)methoxy)malonate (195 mg) as a yellow foam.

Step 10:

The mixture of crude diethyl 2-benzyl-2-(((2R,3R,4R, 5R)-3,4-diacetoxy-5-(6-amino-2-chloro-9H-purin-9-yl)-3-ethynyltetrahydrofuran-2-yl)methoxy)malonate (195 mg, 296.33 umol, 1 eq) in saturated NH₃ in MeOH (3 mL) was stirred at 10° C. for 16 h before it was concentrated to dryness directly. The crude product was purified by preparative TLC (EtOAc) to provide diethyl 2-(((2R,3S,4R,5R)-5-(6-amino-2-chloro-9H-purin-9-yl)-3-ethynyl-3,4-dihydroxytetrahydrofuran-2-yl)methoxy)-2-benzylmalonate (91.7 mg, 49% yield) as a yellow foam.

Step 11:

To a solution of diethyl 2-(((2R,3S,4R,5R)-5-(6-amino-2-chloro-9H-purin-9-yl)-3-ethynyl-3,4-dihydroxytetrahydrofuran-2-yl)methoxy)-2-benzylmalonate (81 mg, 141.12 umol, 1 eq) in EtOH (2 mL) was added LiOH.H₂O (30 mg, 705.60 umol, 5 eq) in H₂O (0.2 mL) at 10° C. The mixture was stirred at 50° C. for 4 h before it was concentrated to dryness. The residue was dissolved in H₂O (50 ml) and extracted with EtOAc (2×50 mL). The organic layers were discarded and the aqueous phase was acidified to pH ~2.5 with 1N aq. HCl solution. The aqueous phase was extracted with EtOAc (3×50 mL). The combined organic layer was washed with brine (50 mL), dried over $Na_2SO_4$, filtered and concentrated to provide the title compound (55.4 mg, 74% yield) as a white solid.
$^1$H NMR (400 MHz, DMSO-$d_6$) δ ppm 8.39 (s, 1H), 7.79 (br s, 2H), 7.20 (br d, J=7.03 Hz, 2H), 7.01-7.12 (m, 3H), 5.82 (d, J=7.53 Hz, 1H), 4.87 (d, J=7.78 Hz, 1H), 4.16 (dd, J=5.27, 2.51 Hz, 1H), 3.99-4.07 (m, 2H), 3.83 (br d, J=8.03 Hz, 1H), 3.56 (s, 1H), 3.25 (dd, J=6.78 Hz, 2H); LC/MS [M+H]=518.0.
Example 2
Synthesis of 2-(((2S,3R,4R,5R)-5-(6-amino-2-chloro-9H-purin-9-yl)-3-ethynyl-4-hydroxytetrahydrofuran-2-yl)methoxy)-2-benzylmalonic acid
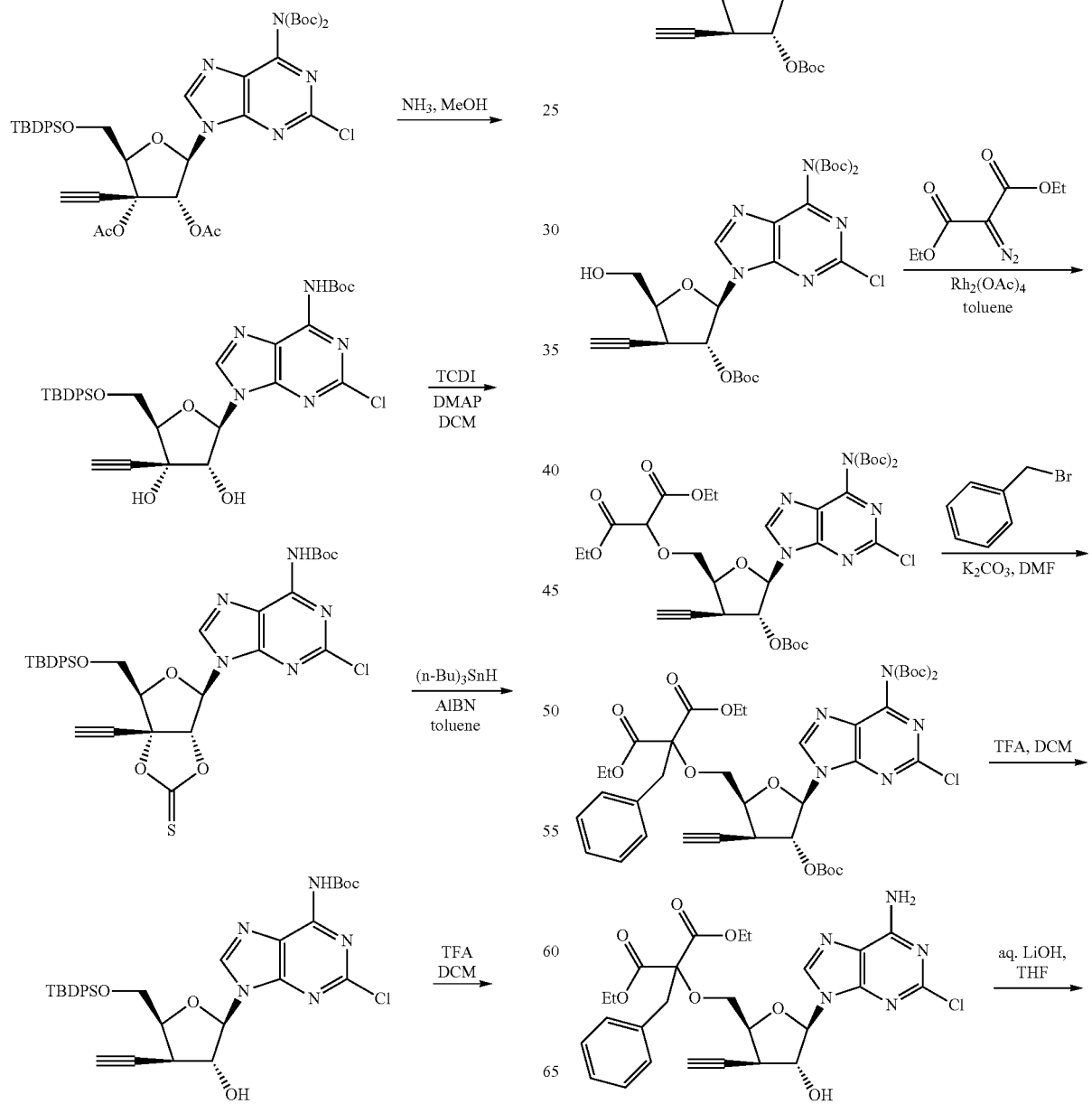

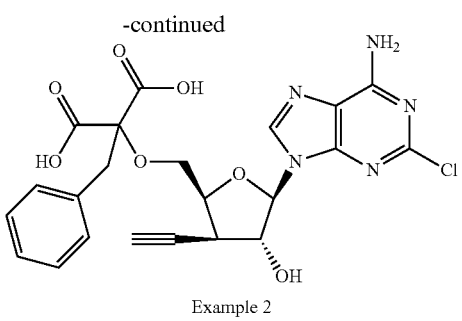

Example 2

Step 1:

To a solution of (2R,3R,4R,5R)-5-(6-(bis-(tert-butoxycarbonyl)amino)-2-chloro-9H-purin-9-yl)-2-(((tert-butyldiphenylsilyl)oxy)methyl)-3-ethynyltetrahydrofuran-3,4-diyl diacetate (5 g, 5.89 mmol, 1 eq) was added 2M NH$_3$ in MeOH (50 mL) at 0° C. The reaction mixture was stirred at 25° C. for 16 h before it was concentrated. The crude was purified by flash silica gel column chromatography (0-50% EtOAc in petroleum ether) to provide tert-butyl (9-((2R,3R,4S,5R)-5-(((tert-butyldiphenylsilyl)oxy)methyl)-4-ethynyl-3,4-dihydroxy-tetrahydrofuran-2-yl)-2-chloro-9H-purin-6-yl)carbamate (3.78 g, 90% yield) as a yellow foam.

Step 2:

To a solution of tert-butyl (9-((2R,3R,4S,5R)-5-(((tert-butyldiphenylsilyl)oxy)-methyl)-4-ethynyl-3,4-dihydroxytetrahydrofuran-2-yl)-2-chloro-9H-purin-6-yl)carbamate (3.78 g, 5.29 mmol, 1 eq) in DCM (40 mL) at 0° C. under N$_2$ atmosphere was added 4-DMAP (258.63 mg, 2.12 mmol, 0.4 eq) and TCDI (4.72 g, 26.46 mmol, 5 eq). The reaction mixture was stirred at 25° C. for 16 h before it was concentrated. The crude was purified by flash silica gel column chromatography (0-33% EtOAc in petroleum ether) to provide tert-butyl (9-((3aR,4R,6R,6aR)-6-(((tert-butyldiphenylsilyl)oxy)methyl)-6a-ethynyl-2-thioxotetrahydrofuro[3,4-d][1,3]dioxol-4-yl)-2-chloro-9H-purin-6-yl)carbamate (1.4 g, 37% yield) as a yellow foam.

Step 3:

To a solution of tert-butyl (9-((3aR,4R,6R,6aR)-6-(((tert-butyldiphenylsilyl)oxy)-methyl)-6a-ethynyl-2-thioxotetrahydrofuro[3,4-d][1,3]dioxol-4-yl)-2-chloro-9H-purin-6-yl)carbamate (500 mg, 707.93 umol, 1 eq) in toluene (5 mL) was added AIBN (11.62 mg, 70.79 umol, 0.1 eq) at 20-25° C. The reaction mixture was then heated to 60° C. and followed by addition of (n-Bu)$_3$SnH (561.96 uL, 2.12 mmol, 3 eq). The reaction mixture was stirred at 60° C. for 1.5 h before it was concentrated. The crude was purified by flash silica gel column chromatography (0-33% EtOAc in petroleum ether) to provide tert-butyl (9-((2R,3R,4R,5S)-5-(((tert-butyldiphenylsilyl)oxy)methyl)-4-ethynyl-3-hydroxytetrahydro-furan-2-yl)-2-chloro-9H-purin-6-yl)carbamate (220 mg, 47% yield) as a white foam.

Step 4:

To a solution of tert-butyl (9-((2R,3R,4R,5S)-5-(((tert-butyldiphenylsilyl)oxy)-methyl)-4-ethynyl-3-hydroxytetrahydrofuran-2-yl)-2-chloro-9H-purin-6-yl)carbamate (220 mg, 339.39 umol, 1 eq) in DCM (1.4 mL) at 0° C. was added TFA (0.7 mL, 9.45 mmol, 28 eq). The reaction mixture was stirred at 25° C. for 1 h before it was diluted with DCM (3×5 mL) and extracted with saturated aq. NaHCO$_3$ solution (15 mL) and extracted with DCM (3×5 mL). The combined organic layer was washed with brine (10 mL), dried over Na$_2$SO$_4$, filtered and concentrated to provide crude (2R,3R,4R,5S)-2-(6-amino-2-chloro-9H-purin-9-yl)-5-(((tert-butyldiphenyl-silyl)oxy)methyl)-4-ethynyltetrahydrofuran-3-ol (260 mg) as a yellow foam.

Step 5:

To a solution of (2R,3R,4R,5S)-2-(6-amino-2-chloro-9H-purin-9-yl)-5-(((tert-butyldiphenylsilyl)oxy)methyl)-4-ethynyltetrahydrofuran-3-ol (260 mg, 474.36 umol, 1 eq, crude) in DMF (2.5 mL) was added Boc$_2$O (931.75 mg, 4.27 mmol, 9 eq), TEA (660.25 uL, 4.74 mmol, 10 eq) and 4-DMAP (5.80 mg, 47.44 umol, 0.1 eq) at 0° C. The reaction mixture was stirred at 25° C. for 1.5 h before it was diluted with H$_2$O (20 mL) and extracted with EtOAc (3×5 mL). The combined organic layer was washed with brine (10 mL), dried over Na$_2$SO$_4$, filtered and concentrated to provide crude (2R,3R,4S,5S)-2-(6-(N,N'-bis-((tert-butoxycarbonyl)amino)-2-chloro-9H-purin-9-yl)-5-(((tert-butyldiphenylsilyl)oxy)methyl)-4-ethynyltetrahydrofuran-3-yl tert-butyl carbonate (560 mg) as an orange gum.

Step 6:

To a solution of crude (2R,3R,4S,5S)-2-(6-(N,N'-bis-((tert-butoxycarbonyl)amino)-2-chloro-9H-purin-9-yl)-5-(((tert-butyldiphenylsilyl)oxy)methyl)-4-ethynyltetrahydrofuran-3-yl tert-butyl carbonate (560 mg, 660.02 umol, 1 eq, crude) in THF (6 mL) at 0° C. was added TBAF in THF (1 M, 1 mL, 1.52 eq). The reaction mixture was stirred at 0° C. for 1 h. The reaction mixture was diluted with H$_2$O (10 mL) and extracted with EtOAc (3×5 mL). The combined organic layer was washed with brine (10 mL), dried over Na$_2$SO$_4$, filtered and concentrated. The crude was purified by preparative TLC (petroleum ether:EtOAc=2:1) to provide (2R,3R,4S,5S)-2-(6-(N,N'-bis-((tert-butoxycarbonyl)amino)-2-chloro-9H-purin-9-yl)-4-ethynyl-5-(hydroxymethyl)tetrahydrofuran-3-yl tert-butyl carbonate (93 mg, 45% yield over 3 steps) as a yellow foam.

Step 7:

To a solution of (2R,3R,4S,5S)-2-(6-(N,N'-bis-((tert-butoxycarbonyl)amino)-2-chloro-9H-purin-9-yl)-4-ethynyl-5-(hydroxymethyl)tetrahydrofuran-3-yl tert-butyl carbonate (93 mg, 152.45 umol, 1 eq) in toluene (1 mL) at 25° C. under N$_2$ atmosphere was added Rh$_2$(OAc)$_4$ (6.74 mg, 15.24 umol, 0.1 eq). The reaction mixture was heated to 90° C. and followed by addition of diethyl 2-diazomalonate (85.14 mg, 457.34 umol, 3 eq) in toluene (1 mL). The reaction mixture was stirred at 90° C. for 3 h before it was concentrated. The crude residue was purified by flash column chromatography on silica gel to provide diethyl 2-(((2S,3S,4R,5R)-5-(6-(N,N'-bis-((tert-butoxy-carbonyl)amino)-2-chloro-9H-purin-9-yl)-4-((tert-butoxycarbonyl)oxy)-3-ethynyltetrahydrofuran-2-yl)methoxy)malonate (180 mg) as a gum.

Step 8:

To a solution of crude diethyl 2-(((2S,3S,4R,5R)-5-(6-(N,N'-bis-((tert-butoxy-carbonyl)amino)-2-chloro-9H-purin-9-yl)-4-((tert-butoxycarbonyl)oxy)-3-ethynyltetrahydrofuran-2-yl)methoxy)malonate (117.11 mg, 152.45 umol, 1 eq) in DMF (3 mL) was added K$_2$CO$_3$ (421.39 mg, 3.05 mmol, 20 eq) at 20-25° C. The reaction mixture was stirred for 0.5 h and followed by addition of benzyl bromide (271.61 uL, 2.29 mmol, 15 eq). The reaction was then stirred further for 16 h before it was diluted with H$_2$O (20 mL) and extracted with EtOAc (3×10 mL). The combined organic layer was washed with brine (15 mL), dried over Na$_2$SO$_4$, filtered and concentrated. The crude was purified by flash silica gel column chromatography (petroleum ether:EtOAc=1:0-2:1 gradient) to provide diethyl 2-(((2S,3S,4R,5R)-5-(6-(N,N'-bis-((tert-butoxycarbonyl)amino)-2-chloro-9H-purin-9-yl)-4-((tert-butoxycarbonyl)oxy)-3-ethynyltetrahydrofuran-2-yl)methoxy)-2-benzylmalonate (90 mg) as an off-white gum.

Step 9:

To a solution of diethyl 2-(((2S,3S,4R,5R)-5-(6-(N,N'-bis-((tert-butoxycarbonyl)-amino)-2-chloro-9H-purin-9-yl)-4-((tert-butoxycarbonyl)oxy)-3-ethynyltetrahydrofuran-2-yl)methoxy)-2-benzylmalonate (90 mg, 104.86 umol, 1 eq) in DCM (0.6 mL) at 0° C. was added TFA (0.3 mL, 4.05 mmol, 39 eq). The reaction mixture was stirred at 25° C. for 1 h before it was diluted with saturated aq. NaHCO$_3$ solution (5 mL) and extracted with DCM (3×3 mL). The combined organic layer was washed with brine (5 mL), dried over Na$_2$SO$_4$, filtered and concentrated. The crude residue was purified by preparative TLC (petroleum ether:EtOAc=1:1) to provide diethyl 2-(((2S,3R,4R,5R)-5-(6-amino-2-chloro-9H-purin-9-yl)-3-ethynyl-4-hydroxytetrahydrofuran-2-yl)methoxy)-2-benzylmalonate (19 mg, 13% yield for 3 steps) as a yellow gum.

Step 10:

To a solution of diethyl 2-(((2S,3R,4R,5R)-5-(6-amino-2-chloro-9H-purin-9-yl)-3-ethynyl-4-hydroxytetrahydrofuran-2-yl)methoxy)-2-benzylmalonate (19 mg, 34.05 umol, 1 eq) in THF (0.2 mL) was added LiOH.H$_2$O (7.14 mg, 170.26 umol, 5 eq) in H$_2$O (70 uL) at 25° C. The reaction mixture was stirred for 5.5 h before it was diluted with H$_2$O (5 mL) and then acidified to pH 2-3 with 1N aq. HCl. The mixture was extracted with EtOAc (3×5 mL). The combined organic layer was washed with brine (15 mL), dried over anhydrous Na$_2$SO$_4$, filtered, and concentrated. The crude residue was dissolved in a mixture of H$_2$O (3 mL) and MeCN (2 mL) and then lyophilized to provide the title compound as a white solid.

$^1$H NMR (400 MHz, CD3OD) δ ppm 8.30 (s, 1H) 7.27 (br d, J=5.27 Hz, 2H) 7.17-7.24 (m, 1H) 7.15 (br d, J=6.78 Hz, 2H) 5.87-5.96 (m, 1H) 4.94 (br s, 1H) 4.68 (br s, 1H) 3.96-4.11 (m, 2H) 3.34-3.40 (m, 2H) 2.57 (d, J=2.51 Hz, 1H) 2.32 (s, 1H); LC/MS [M+H]=502.0.

Example 3

Synthesis of 2-(((2R,3S,4R,5R)-5-(6-amino-2-chloro-9H-purin-9-yl)-3,4-dihydroxy-3-(prop-1-yn-1-yl)tetrahydrofuran-2-yl)methoxy)-2-benzylmalonic acid

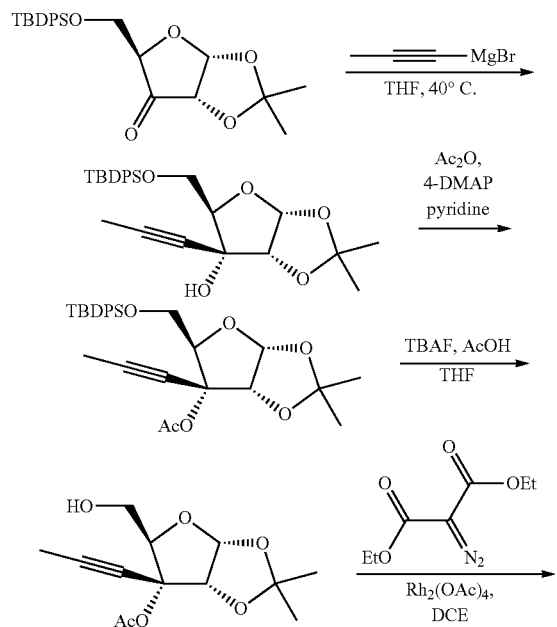

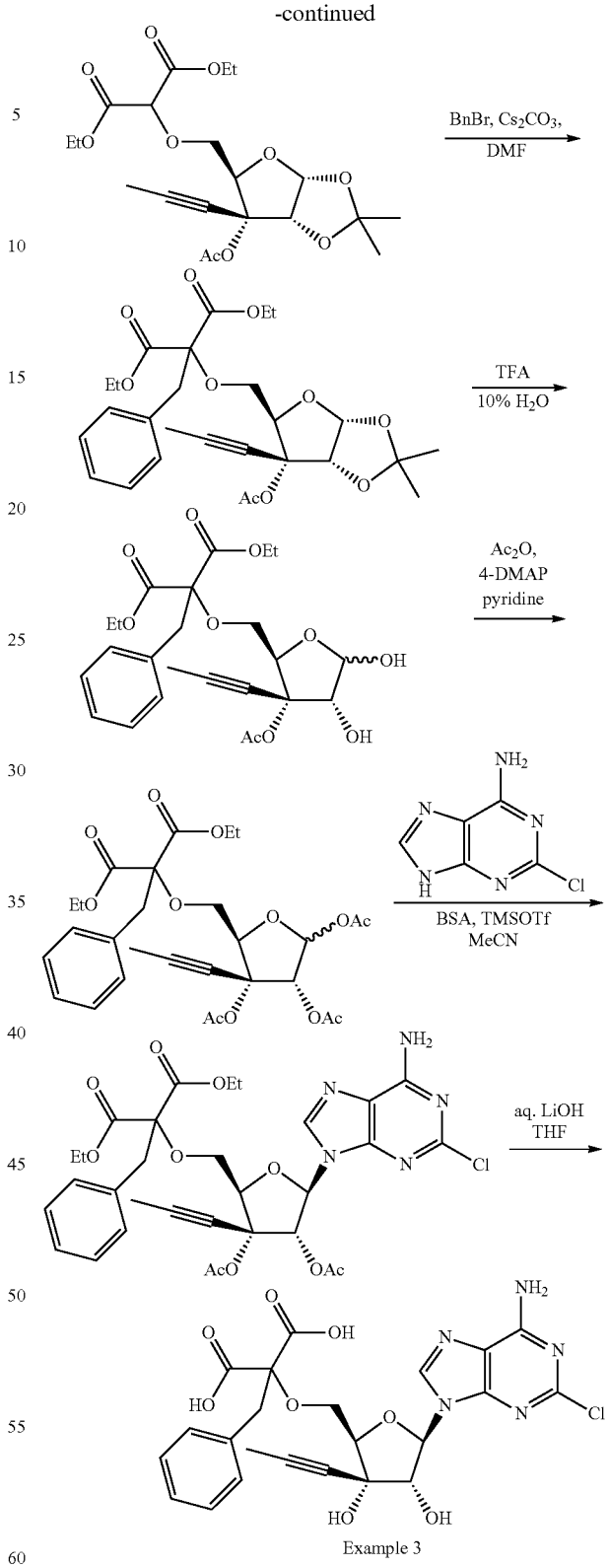

Example 3

Step 1:

To a solution of (3aR,5R,6aS)-5-(((tert-butyldiphenylsilyl)oxy)methyl)-2,2-dimethyldihydrofuro[2,3-d][1,3]dioxol-6(3aH)-one (10 g, 23.44 mmol, 1 eq) in THF (100 mL) at 20° C. under N$_2$ atmosphere was added (prop-1-ynyl) magnesium bromide (0.5 M, 93.77 mL, 2 eq). The mixture was stirred at 40° C. for 2 h before it was diluted with saturated aq. NH₄Cl solution (250 mL). The aqueous phase was extracted with EtOAc (3×200 mL). The combined organic layer was washed with brine (200 mL), dried over Na₂SO₄, filtered and concentrated to give crude (3aR,5R, 6R,6aR)-5-(((tert-butyldiphenylsilyl)oxy)methyl)-2,2-dimethyl-6-(prop-1-yn-1-yl)tetrahydrofuro[2,3-d][1,3]dioxol-6-ol (11.81 g) as a yellow gum.

Step 2:

To a solution of crude (3aR,5R,6R,6aR)-5-(((tert-butyldiphenylsilyl)oxy)-methyl)-2,2-dimethyl-6-(prop-1-yn-1-yl)tetrahydrofuro[2,3-d][1,3]dioxol-6-ol (12.2 g, 26.14 mmol, 1 eq) in pyridine (120 mL) at 20° C. was added 4-DMAP (3.51 g, 28.76 mmol, 1.1 eq) and Ac₂O (4.90 mL, 52.29 mmol, 2 eq). The mixture was stirred at 20° C. for 16 h before it was diluted with H₂O (200 mL) and extracted with EtOAc (3×100 mL). The combined organic layer was washed with brine (250 mL), dried over Na₂SO₄ and filtered. The filtrate was concentrated to give crude (3aR,5R,6R, 6aR)-5-(((tert-butyldiphenylsilyl)oxy)methyl)-2,2-dimethyl-6-(prop-1-yn-1-yl)tetrahydrofuro[2,3-d][1,3]dioxol-6-yl acetate (15 g) as a yellow gum.

Step 3:

To a solution of crude (3aR,5R,6R,6aR)-5-(((tert-butyldiphenylsilyl)oxy)-methyl)-2,2-dimethyl-6-(prop-1-yn-1-yl)tetrahydrofuro[2,3-d][1,3]dioxol-6-yl acetate (15 g, 29.49 mmol, 1 eq) in THF (300 mL) at 0° C. under N₂ atmosphere was added a mixture of TBAF (1 M, 44.23 mL, 1.5 eq) and AcOH (1.26 mL, 22.12 mmol, 0.75 eq). The mixture was stirred at 20° C. for 7 h before it was diluted with saturated aq. NH₄Cl solution (300 mL) and extracted with EtOAc (3×200 mL). The combined organic layer was washed with brine (300 mL), dried over Na₂SO₄, filtered and concentrated. The crude product was purified by flash silica gel column chromatography (petroleum ether:EtOAc=1:0-1:1) to provide (3aR,5R,6R,6aR)-5-(hydroxymethyl)-2,2-dimethyl-6-(prop-1-yn-1-yl)tetrahydrofuro[2,3-d][1,3]dioxol-6-yl acetate (5.78 g, 72.5% yield) as a white solid.

Step 4:

To a solution of (3aR,5R,6R,6aR)-5-(hydroxymethyl)-2, 2-dimethyl-6-(prop-1-yn-1-yl)tetrahydrofuro[2,3-d][1,3]dioxol-6-yl acetate (5.78 g, 21.39 mmol, 1 eq) in dichloroethane (60 mL) at 15° C. under N₂ atmosphere was added Rh₂(OAc)₄ (945.21 mg, 2.14 mmol, 0.1 eq) and diethyl diazomalonate (7.96 g, 42.77 mmol, 2 eq). The mixture was stirred at 40° C. for 7 h before it was concentrated to dryness. The crude product was purified by flash silica gel column chromatography (0-25% EtOAc in petroleum ether) to provide diethyl 2-(((3aR,5R,6R,6aR)-6-acetoxy-2,2-dimethyl-6-(prop-1-yn-1-yl)tetrahydrofuro[2,3-d][1,3]-dioxol-5-yl)methoxy)malonate as a yellow gum.

Step 5:

To a solution of diethyl 2-(((3aR,5R,6R,6aR)-6-acetoxy-2,2-dimethyl-6-(prop-1-yn-1-yl)tetrahydrofuro[2,3-d][1,3]dioxol-5-yl)methoxy)malonate (7.28 g, 16.99 mmol, 1 eq) in DMF (70 mL) at 20° C. was added Cs₂CO₃ (11.07 g, 33.98 mmol, 2 eq) and BnBr (3.03 mL, 25.49 mmol, 1.5 eq). The mixture was stirred at 20° C. for 2 h before it was diluted with H₂O (300 mL) and extracted with EtOAc (3×100 mL). The combined organic layer was washed with brine (200 mL), dried over Na₂SO₄, filtered and concentrated. The crude product was purified by flash silica gel gel column chromatography (petroleum ether:EtOAc=1:0-3:1) to provide diethyl 2-(((3aR,5R,6R,6aR)-6-acetoxy-2,2-dimethyl-6-(prop-1-yn-1-yl)tetrahydrofuro[2,3-d][1,3]dioxol-5-yl)methoxy)-2-benzylmalonate (7.67 g, 87% yield) as a yellow gum.

Step 6:

To a solution of diethyl 2-(((3aR,5R,6R,6aR)-6-acetoxy-2,2-dimethyl-6-(prop-1-yn-1-yl)tetrahydrofuro[2,3-d][1,3]dioxol-5-yl)methoxy)-2-benzylmalonate (7.67 g, 14.79 mmol, 1 eq) in TFA (80 mL) at 20° C. was added H₂O (6.97 mL, 387.05 mmol, 26 eq). The mixture was stirred at 20° C. for 8 h before it was quenched with saturated aq. NaHCO₃ solution to pH 7 and partitioned with EtOAc (3×100 mL). The combined organic layer was washed with brine (200 mL), dried over Na₂SO₄ and filtered. The filtrate was concentrated to dryness to provide crude diethyl 2-benzyl-2-(((2R,3S,4R)-3,4,5-trihydroxy-3-(prop-1-yn-1-yl)tetra-hydrofuran-2-yl)methoxy)malonate (5.95 g) as a yellow gum.

Step 7:

To a solution of crude diethyl 2-benzyl-2-(((2R,3S,4R)-3,4,5-trihydroxy-3-(prop-1-yn-1-yl)tetrahydrofuran-2-yl) methoxy)malonate (5.95 g, 13.63 mmol, 1 eq) in pyridine (60 mL) at 20° C. was added 4-DMAP (5.00 g, 40.90 mmol, 3 eq) and Ac₂O (6.38 mL, 68.16 mmol, 5 eq). The mixture was stirred at 20° C. for 16 h before it was diluted with H₂O (300 mL) and extracted with EtOAc (3×150 mL). The combined organic layer was washed with brine (300 mL), dried over Na₂SO₄, filtered and concentrated. The crude product was purified by flash silica gel column chromatography (petroleum ether:EtOAc=1:0-3:1) to provide diethyl 2-benzyl-2-(((2R,3R,4R)-3,4,5-triacetoxy-3-(prop-1-yn-1-yl)tetrahydrofuran-2-yl)methoxy)malonate (5.76 g, 66% yield) as a yellow gum.

Step 8:

To a solution of diethyl 2-benzyl-2-(((2R,3R,4R)-3,4,5-triacetoxy-3-(prop-1-yn-1-yl)tetrahydrofuran-2-yl) methoxy)malonate (1 g, 1.78 mmol, 1 eq) in MeCN (10 mL) at 20° C. was added N,O-bis(trimethylsilyl)acetamide (BSA) (1.32 mL, 5.33 mmol, 3 eq) and 2-chloroadenine (301.43 mg, 1.78 mmol, 1 eq). The mixture was stirred at 65° C. for 30 min before it was cooled to 0° C. and followed by addition of TMSOTf (642 uL, 3.56 mmol, 2 eq) dropwise. The mixture was stirred at 0° C. for 10 min and then at 65° C. for 2 h before it was quenched with saturated aq. NaHCO₃(100 mL) and extracted with EtOAc (2×60 mL). The combined organic layer was washed with brine (100 mL) and dried over Na₂SO₄, filtered and concentrated. The crude product was purified by flash silica gel column chromatography (0-33% EtOAc in petroleum ether) to provide diethyl 2-benzyl-2-(((2R,3R,4R,5R)-3,4-diacetoxy-5-(6-amino-2-chloro-9H-purin-9-yl)-3-(prop-1-yn-1-yl)tetrahydrofuran-2-yl)methoxy)malonate (218 mg, 18% yield) as a yellow foam.

Step 9:

To a solution of diethyl 2-benzyl-2-(((2R,3R,4R,5R)-3,4-diacetoxy-5-(6-amino-2-chloro-9H-purin-9-yl)-3-(prop-1-yn-1-yl)tetrahydrofuran-2-yl)methoxy)malonate (218 mg, 324.37 umol, 1 eq) in THF (2 mL) was added LiOH.H₂O (136.12 mg, 3.24 mmol, 10 eq) in H₂O (2 mL) at 20° C. The mixture was heated at 45° C. for 2 h before it was diluted with H₂O (10 mL) and extracted with EtOAc (10 mL). The organic layer was discarded and the aqueous phase was acidified with 2 N aq. HCl to pH 2-3. Then the aqueous phase was extracted with EtOAc (3×20 mL). The combined organic layer was washed with brine (30 mL), dried over Na₂SO₄, filtered and concentrated. The crude product was purified by preparative HPLC to provide the title compound (39.8 mg, 23% yield) as a white solid.

¹H NMR (DMSO-d₆, 400 MHz) δ ppm 12.70-14.12 (m, 2H), 8.37 (s, 1H), 7.80 (br s, 2H), 7.19 (br d, J=7.03 Hz, 2H), 7.00-7.11 (m, 3H), 5.88-6.03 (m, 2H), 5.81 (d, J=7.53 Hz, 1H), 4.78 (br s, 1H), 4.12 (dd, J=4.52, 3.01 Hz, 1H), 3.95 (br dd, J=9.91, 4.89 Hz, 1H), 3.82 (br d, J=8.53 Hz, 1H), 3.25 (s, 2H), 1.81 (s, 3H); LC/MS [M+H]=532.0.

Example 4

Synthesis of 2-(((2R,3S,4R,5R)-5-(6-amino-2-chloro-9H-purin-9-yl)-3-(cyclopropylethynyl)-3,4-dihydroxytetrahydrofuran-2-yl)methoxy)-2-benzyl-malonic acid

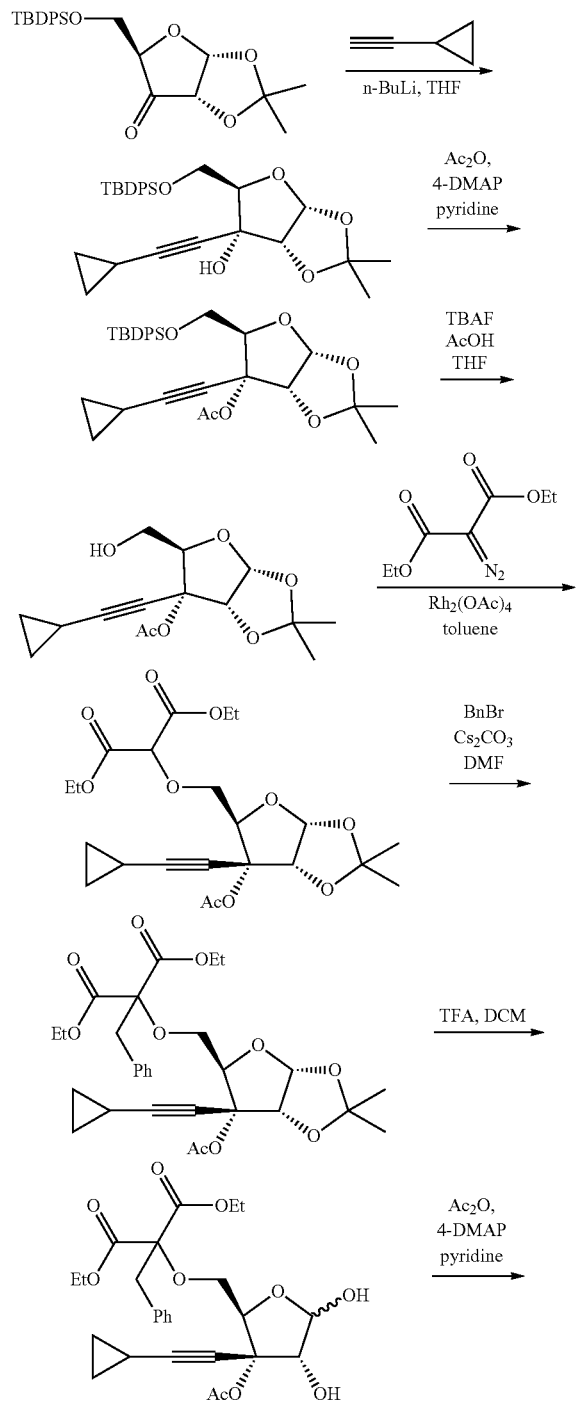

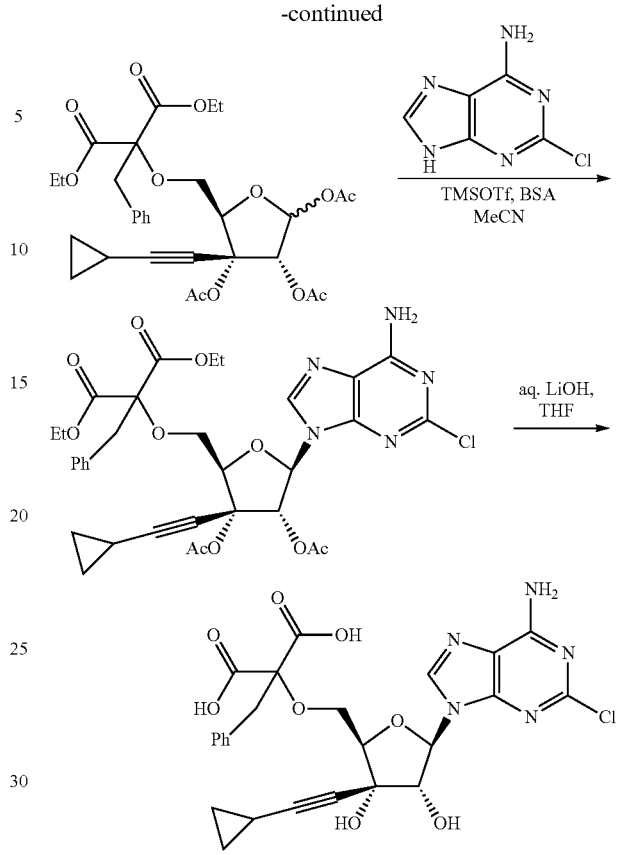

Example 4

Step 1:

To a solution of ethynylcyclopropane (4.96 g, 75.02 mmol, 6.22 mL, 2 eq) in THF (80 mL) at −78° C. under N₂ atmosphere was added n-BuLi (2.5 M, 30.01 mL, 2 eq) dropwise. The solution was stirred at −78° C. for 0.5 h and followed by addition of a solution of (3aR,5R,6aS)-5-(((tert-butyldiphenylsilyl)oxy)methyl)-2,2-dimethyldihydrofuro[2,3-d][1,3]-dioxol-6(3aH)-one (16.0 g, 37.51 mmol, 1 eq) in THF (60 mL) dropwise. Then the solution was allowed to warm to 20° C. and stirred for 1 h before it was then cooled to 0° C. and quenched with water (120 mL). The mixture was extracted with EtOAc (2×120 mL). The combined organic layer was washed with brine (200 mL), and dried by Na₂SO₄, filtered and concentrated. The crude was purified by Combi-flash on silica gel (0-15% ethyl acetate in petroleum ether) to give (3aR,5R,6R,6aR)-5-(((tert-butyldiphenylsilyl)oxy)-methyl)-6-(cyclopropylethynyl)-2,2-dimethyltetrahydrofuro[2,3-d][1,3]dioxol-6-ol (15.8 g, 86% yield) as a syrup.

Step 2:

To a solution of (3aR,5R,6R,6aR)-5-(((tert-butyldiphenylsilyl)oxy)methyl)-6-(cyclo-propylethynyl)-2,2-dimethyltetrahydrofuro[2,3-d][1,3]dioxol-6-ol (15.8 g, 32.07 mmol, 1 eq) in pyridine (160 mL) at 20° C. was added 4-DMAP (4.70 g, 38.48 mmol, 1.2 eq) and Ac₂O (9.01 mL, 96.21 mmol, 3 eq). The solution was stirred for 3 h before it was diluted with water (200 mL) and extracted with ethyl acetate (2×200 mL). The combined organic layer was washed with brine (400 mL), dried by Na₂SO₄, filtered and concentrated. The crude residue was purified by Combi-flash on silica gel (0-15% ethyl acetate in petroleum ether)

to give (3aR,5R,6R,6aR)-5-(((tert-butyldiphenylsilyl)oxy)methyl)-6-(cyclopropylethynyl)-2,2-dimethyltetrahydrofuro[2,3-d][1,3]dioxol-6-yl acetate (14.7 g, 86% yield) as a clear syrup.

Step 3:

To a solution of (3aR,5R,6R,6aR)-5-(((tert-butyldiphenylsilyl)oxy)methyl)-6-(cyclopropylethynyl)-2,2-dimethyltetrahydrofuro[2,3-d][1,3]dioxol-6-yl acetate (14.7 g, 27.49 mmol, 1 eq) in THF (150 mL) at 0° C. was added a solution of TBAF (1 M, 41.24 mL, 1.5 eq) and AcOH (1.18 mL, 20.62 mmol, 0.75 eq). The solution was stirred at 20° C. for 16 h before it was diluted with water (300 mL) and extracted with ethyl acetate (2×200 mL). The combined organic layer was washed with water (400 mL), brine (400 mL), dried by $Na_2SO_4$, filtered and concentrated. The crude was purified by Combi-flash on silica gel (20-60% ethyl acetate in petroleum ether) to give (3aR,5R,6R,6aR)-6-(cyclopropylethynyl)-5-(hydroxymethyl)-2,2-dimethyltetrahydrofuro[2,3-d][1,3]dioxol-6-yl acetate (8.15 g, 100% yield) as a white solid.

Step 4:

To a solution of (3aR,5R,6R,6aR)-6-(cyclopropylethynyl)-5-(hydroxymethyl)-2,2-dimethyltetrahydrofuro[2,3-d][1,3]dioxol-6-yl acetate (8.15 g, 27.50 mmol, 1 eq) in dichloroethane (80 mL) at 20° C. under $N_2$ atmosphere was added $Rh_2(OAc)_4$ (1.00 g, 2.26 mmol, 0.08 eq) and a solution of diethyl diazomalonate (10.24 g, 55.01 mmol, 2 eq) in dichloroethane (20 mL). The green solution was stirred for 16 h before it was concentrated. The crude was purified by Combi-flash on silica gel (15-50% ethyl acetate in petroleum ether) to give diethyl 2-(((3aR,5R,6R,6aR)-6-acetoxy-6-(cyclopropylethynyl)-2,2-dimethyl-tetrahydrofuro[2,3-d][1,3]dioxol-5-yl)methoxy)malonate (9.52 g, 76% yield) as a yellow oil.

Step 5:

To a solution of diethyl 2-(((3aR,5R,6R,6aR)-6-acetoxy-6-(cyclopropylethynyl)-2,2-dimethyltetrahydrofuro[2,3-d][1,3]dioxol-5-yl)methoxy)malonate (4.50 g, 9.90 mmol, 1 eq) in DMF (50 mL) at 20° C. was added $Cs_2CO_3$ (9.68 g, 29.71 mmol, 3 eq) and benzyl bromide (1.76 mL, 14.85 mmol, 1.5 eq). The suspension was stirred for 16 h before it was diluted with water (80 mL) and extracted with ethyl acetate (3×80 mL). The combined organic layer was washed with water (200 mL), brine (200 mL), dried by $Na_2SO_4$, filtered and concentrated. The crude was purified by Combi-flash on silica gel (15-50% ethyl acetate in petroleum ether) to give diethyl 2-(((3aR,5R,6R,6aR)-6-acetoxy-6-(cyclopropylethynyl)-2,2-dimethyltetrahydrofuro[2,3-d][1,3]dioxol-5-yl)methoxy)-2-benzyl-malonate (4.10 g, 76% yield) as a colorless syrup.

Step 6:

To a solution of diethyl 2-(((3aR,5R,6R,6aR)-6-acetoxy-6-(cyclopropylethynyl)-2,2-dimethyltetrahydrofuro[2,3-d][1,3]dioxol-5-yl)methoxy)-2-benzylmalonate (4.10 g, 7.53 mmol, 1 eq) in DCM (50 mL) at 0° C. was added $H_2O$ (10 mL) and TFA (50 mL). The solution was stirred at 20° C. for 2 h before it was quenched with saturated aq. $NaHCO_3$ (80 mL) to pH ~7. The reaction mixture was exacted with DCM (100 mL). The organic layer was washed with brine (10 mL), dried by $Na_2SO_4$, filtered and concentrated to give crude diethyl 2-(((2R,3S,4R)-3-acetoxy-3-(cyclopropyl-ethynyl)-4,5-dihydroxytetrahydrofuran-2-yl)methoxy)-2-benzylmalonate (3.80 g) as a yellow gum.

Step 7:

To a solution of crude diethyl diethyl 2-(((2R,3S,4R)-3-acetoxy-3-(cyclopropyl-ethynyl)-4,5-dihydroxytetrahydrofuran-2-yl)methoxy)-2-benzylmalonate (3.80 g, 7.53 mmol, 1 eq) in pyridine (40 mL) at 20° C. was added 4-DMAP (2.76 g, 22.60 mmol, 3 eq) and $Ac_2O$ (5.64 mL, 60.25 mmol, 8 eq). The solution was stirred for 16 h before it was diluted with water (80 mL) and extracted with ethyl acetate (2×80 mL). The combined organic layer was washed with water (150 mL), brine (150 mL), dried by $Na_2SO_4$, filtered and concentrated. The crude was purified by Combi-flash on silica gel (10-50% ethyl acetate in petroleum ether) to give diethyl 2-benzyl-2-(((2R,3R,4R)-3,4,5-triacetoxy-3-(cyclopropylethynyl)-tetrahydro-furan-2-yl)methoxy)malonate (2.91 g, 66% yield) as a yellow gum.

Step 8:

To a solution of diethyl 2-benzyl-2-(((2R,3R,4R)-3,4,5-triacetoxy-3-(cyclopropylethynyl)tetrahydrofuran-2-yl)methoxy)malonate (980 mg, 1.66 mmol, 1 eq) in MeCN (24 mL) at 25° C. was added 2-chloroadenine (338.80 mg, 2.00 mmol, 1.2 eq) and BSA (987.71 uL, 4.00 mmol, 2.4 eq). The suspension was stirred at 65° C. for 0.5 h as it turned clear. The resulting solution was cooled down to 0° C. and followed by addition of TMSOTf (444.06 mg, 2.00 mmol, 361.03 uL, 1.2 eq) dropwise. The reaction mixture was stirred at 40° C. for 4 h before it was allowed to cool to room temperature. The reaction mixture was diluted with water (20 mL) and extracted with ethyl acetate (3×20 mL). The combined organic layer was washed with brine (50 mL), dried by $Na_2SO_4$, filtered and concentrated. The crude was purified by Combi-flash on silica gel (30-80% ethyl acetate in petroleum ether) to give diethyl 2-benzyl-2-(((2R,3R,4R,5R)-3,4-diacetoxy-5-(6-amino-2-chloro-9H-purin-9-yl)-3-(cyclopropylethynyl)tetrahydrofuran-2-yl)methoxy)malonate (270 mg, 23% yield) as a yellow gum.

Step 9:

To a solution of diethyl 2-benzyl-2-(((2R,3R,4R,5R)-3,4-diacetoxy-5-(6-amino-2-chloro-9H-purin-9-yl)-3-(cyclopropylethynyl)tetrahydrofuran-2-yl)-methoxy)malonate (270 mg, 386.75 umol, 1 eq) in THF (8 mL) was added aq. LiOH solution (1 M, 5.80 mL, 15 eq). The mixture was stirred at 20° C. for 16 h before it was treated with 1N HCl to adjust the pH to 5. The mixture was concentrated. The crude residue was purified by preparative HPLC to give the title compound (23 mg, 11% yield) as a white solid.

$^1$H NMR (400 MHz, CD3OD) δ ppm 8.04 (s, 1H) 7.14-7.27 (m, 2H) 7.01-7.08 (m, 3H) 5.92 (d, J=6.63 Hz, 1H) 4.70-4.83 (m, 1H) 4.24 (t, J=3.50 Hz, 1H) 4.02 (t, J=3.31 Hz, 2H) 3.31-3.45 (m, 2H) 1.25-1.33 (m, 1H) 0.72-0.79 (m, 2H) 0.63-0.71 (m, 2H); LC/MS [M+H]=559.0.

Example 5

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-((2-chloropyridin-4-yl)methyl)malonic acid

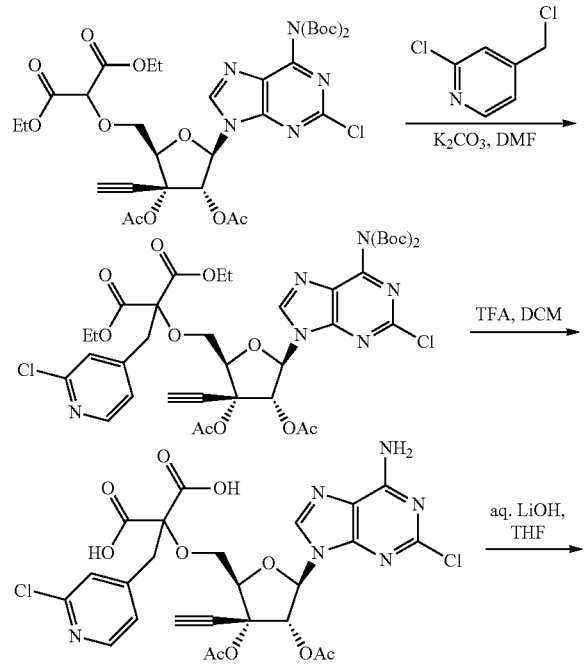

Proceeding as described in Example 1 above by substituting BnBr with 2-chloro-4-(chloromethyl)pyridine provided the title compound as a white solid.

$^1$H NMR (CD3OD, 400 MHz) δ ppm 8.40 (s, 1H), 8.00 (d, J=5.13 Hz, 1H), 7.36 (s, 1H), 7.23 (d, J=5.13 Hz, 1H), 6.01 (d, J=7.63 Hz, 1H), 5.08 (d, J=7.63 Hz, 1H), 4.39 (dd, J=4.88, 2.75 Hz, 1H), 4.16 (dd, J=10.07, 5.19 Hz, 1H), 4.05 (dd, J=10.01, 2.63 Hz, 1H), 3.47 (s, 2H), 3.05 (s, 1H); LC/MS [M+H]=553.1.

Example 6

Synthesis of 2-benzyl-2-(((2R,3S,4R,5R)-5-(2,4-dioxo-3,4-dihydropyrimidin-(2H)-yl)-3-ethynyl-3,4-dihydroxytetrahydrofuran-2-yl)methoxy)malonic acid

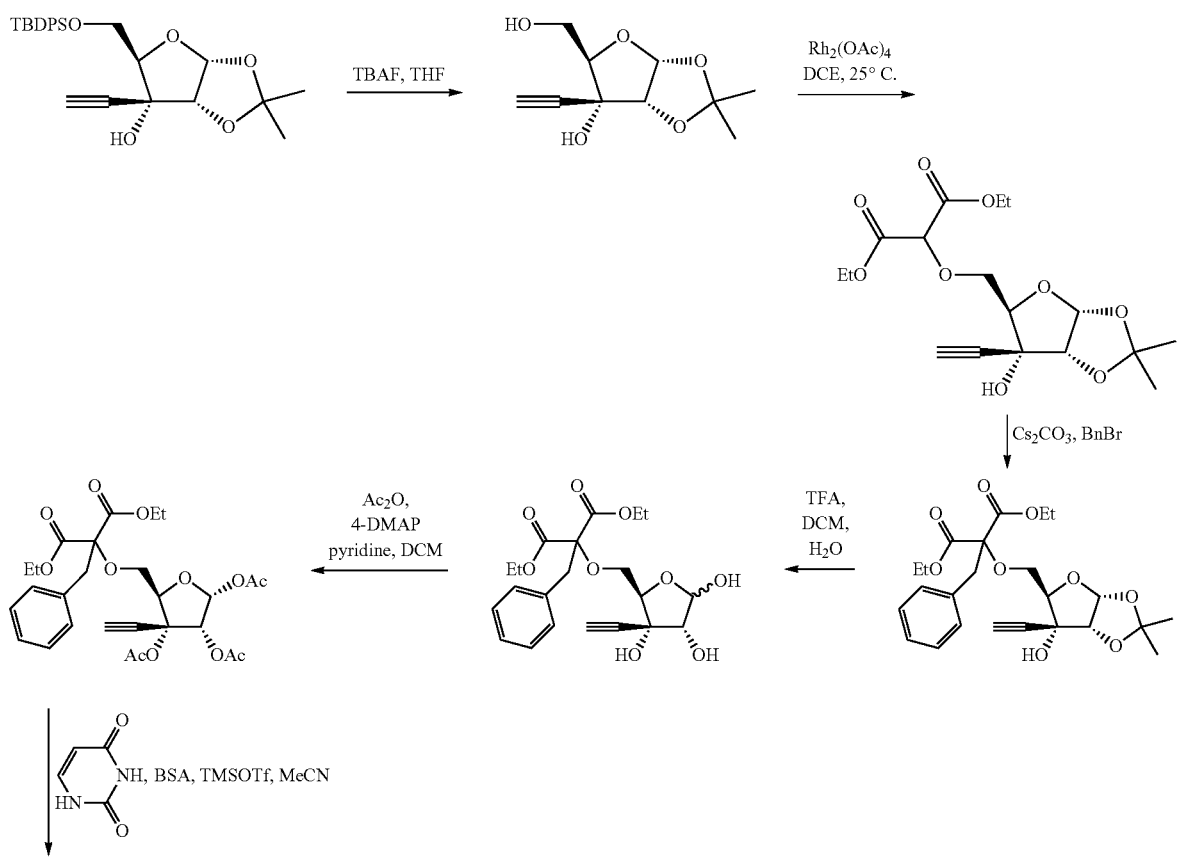

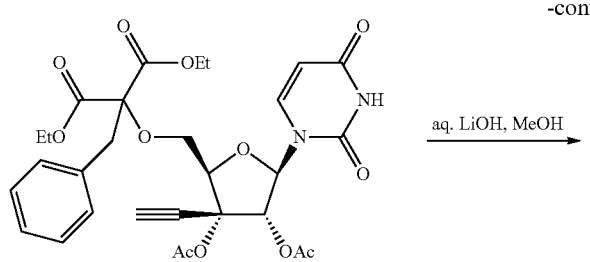
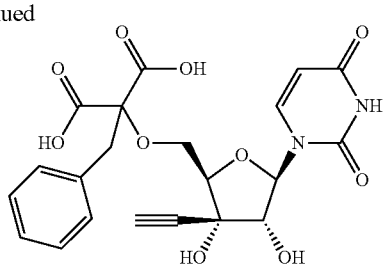

Example 6

Step 1:
To a mixture of (3aR,5R,6R,6aR)-5-(((tert-butyldiphenylsilyl)oxy)methyl)-6-ethynyl-2,2-dimethyltetrahydrofuro[2,3-d][1,3]dioxol-6-yl acetate (27.4 g, 55.39 mmol, 1 eq) in THF (250 mL) at 0° C. was added AcOH (2.38 mL, 41.54 mmol, 0.75 eq) in TBAF (1 M, 83.09 mL, 1.5 eq). The mixture was stirred at 15° C. for 15 h before it was partitioned between water (800 mL) and EtOAc (300 mL). The aqueous phase was further extracted with EtOAc (3×200 mL). The combined organic layer was washed with brine (300 mL), dried over anhydrous $Na_2SO_4$, filtered and concentrated under reduced pressure to give a residue. The residue was purified by column chromatography on $SiO_2$ (11-33% EtOAc in petroleum ether) to give (3aR,5R,6R,6aR)-6-ethynyl-5-(hydroxymethyl)-2,2-dimethyl-tetrahydrofuro-[2,3-d][1,3]dioxol-6-yl acetate (15.2 g, 91% yield) as a light yellow solid.

Step 2:
To a mixture of (3aR,5R,6R,6aR)-6-ethynyl-5-(hydroxymethyl)-2,2-dimethyltetrahydrofuro[2,3-d][1,3]dioxol-6-yl acetate (15.2 g, 59.32 mmol, 1 eq) in dichloroethane (150 mL) at 0° C. was added $Rh_2(OAc)_4$ (1.31 g, 2.97 mmol, 0.05 eq) and diethyl diazomalonate (13.25 g, 71.18 mmol, 1.2 eq) in dichloroethane (30 mL). The mixture was stirred at 15° C. under $N_2$ atmosphere for 15 h before additional amount of diethyl diazomalonate (6 g) in dichloroethane (15 mL) was added. The mixture was stirred further at 15° C. for 2 h before it was concentrated under reduced pressure. The residue was purified by column chromatography on silica gel (11-33% EtOAc in petroleum ether) to give diethyl 2-(((3aR,5R,6R,6aR)-6-acetoxy-6-ethynyl-2,2-dimethyltetra-hydrofuro-[2,3-d][1,3]dioxol-5-yl)methoxy)malonate (15 g, 61% yield) as a white solid.

Step 3:
To a mixture of diethyl 2-(((3aR,5R,6R,6aR)-6-acetoxy-6-ethynyl-2,2-dimethyltetra-hydrofuro[2,3-d][1,3]dioxol-5-yl)methoxy)malonate (14 g, 33.78 mmol, 1 eq) in DMF (140 mL) at 25° C. was added $Cs_2CO_3$ (22.01 g, 67.57 mmol, 2 eq) and BnBr (6.02 mL, 50.68 mmol, 1.5 eq). The mixture was stirred at 25° C. for 3 h before it was filtered and the filter cake was washed with EtOAc (50 mL). The filtrate was diluted with water (400 mL) and extracted with EtOAc (3×150 mL). The combined organic layer was washed with brine (200 mL), dried over anhydrous $Na_2SO_4$, filtered and concentrated under reduced pressure. The residue was purified by flash silica gel column chromatography (0-33% EtOAc in petroleum ether) to give diethyl 2-(((3aR,5R,6R,6aR)-6-acetoxy-6-ethynyl-2,2-dimethyltetra-hydrofuro[2,3-d][1,3]dioxol-5-yl)methoxy)-2-benzylmalonate (13.3 g, 78% yield) as a colorless oil.

Step 4:
To a mixture of diethyl 2-(((3aR,5R,6R,6aR)-6-acetoxy-6-ethynyl-2,2-dimethyltetra-hydrofuro[2,3-d][1,3]dioxol-5-yl)methoxy)-2-benzylmalonate (13.20 g, 26.16 mmol, 1 eq) in DCM (100 mL) and $H_2O$ (20 mL, 1.11 mol, 42 eq) was added TFA (100 mL, 1.35 mol, 52 eq). The mixture was stirred at 15° C. for 12 h before water (200 mL) was added. The aqueous phase was extracted with DCM (2×100 mL). The combined organic extract was washed with saturated aq. $NaHCO_3$ (2×100 mL), brine (100 mL), dried over anhydrous $Na_2SO_4$, filtered and concentrated under reduced pressure. The residue was purified by flash column chromatography ($SiO_2$, petroleum ether:Ethyl acetate=10:1 to 1:3) to give diethyl 2-benzyl-2-(((2R,3S,4R)-3-ethynyl-3,4,5-trihydroxytetrahydrofuran-2-yl)methoxy)malonate (7.8 g, 71% yield) as a colorless oil.

Step 5:
To a mixture of diethyl 2-benzyl-2-(((2R,3S,4R)-3-ethynyl-3,4,5-trihydroxytetrahydrofuran-2-yl)methoxy)malonate (7.8 g, 18.46 mmol, 1 eq) in pyridine (70 mL) at 15° C. was added 4-DMAP (6.77 g, 55.39 mmol, 3 eq) and $Ac_2O$ (17.29 mL, 184.65 mmol, 10 eq). The mixture was stirred for 15 h before water (400 mL) was added. The mixture was extracted with EtOAc (3×200 mL). The combined organic layer was washed with 1N aq. HCl (2×200 mL), saturated aq. $NaHCO_3$ (300 mL), brine (300 mL), dried over anhydrous $Na_2SO_4$, filtered and concentrated under reduced pressure. The residue was purified by flash silica gel column chromatography (petroleum ether:Ethyl acetate=1:0 to 2:1) to give the desired product (7 g). This product was triturated with EtOH (10 mL) and filtered to give diethyl 2-benzyl-2-(((2R,3R,4R)-3,4,5-triacetoxy-3-ethynyltetrahydrofuran-2-yl)methoxy)-malonate (3.79 g, 37% yield) as a white solid. The filtrate was concentrated under reduced pressure to give slightly impure additional product (3 g).

Step 6:
To a solution of diethyl 2-benzyl-2-(((2R,3R,4R)-3,4,5-triacetoxy-3-ethynyltetra-hydrofuran-2-yl)methoxy)malonate (116 mg, 0.21 mmol, 1.0 eq) in MeCN (3 mL) at 25° C. was added uracil (28 mg, 0.25 mmol, 1.2 eq) and followed by N,O-bis(trimethylsilyl)-acetamide (BSA) (124 uL, 0.51 mmol, 2.4 eq). The resulting suspension was heated at 65° C. for 30 min as it became clear. The reaction mixture was cooled to 0° C. and followed by dropwise addition of TMSOTf (46 uL, 0.25 mmol, 1.2 eq). The reaction mixture was allowed to warm up and heated at 65° C. for 3 h as all of the starting material was consumed. The reaction was quenched with cold saturated aq. $NaHCO_3$ solution (3 mL) and diluted with EtOAc (15 mL). The organic layer was separated, washed with $H_2O$ (2×10 mL), brine, dried ($MgSO_4$), filtered and concentrated. The crude residue was purified by flash silica gel column chromatography (0-75% EtOAc in hexanes) to provide the product diethyl 2-benzyl-2-(((2R,3R,4R,5R)-3,4-diacetoxy-5-(2,4-dioxo-3,4-dihydro-pyrimidin-1 (2H)-yl)-3-ethynyl-tetrahydrofuran-2-yl)methoxy)malonate (104 mg, 82% yield).

Step 7:

To a solution of diethyl 2-benzyl-2-(((2R,3R,4R,5R)-3,4-diacetoxy-5-(2,4-dioxo-3,4-dihydropyrimidin-1(2H)-yl)-3-ethynyltetrahydrofuran-2-yl)methoxy)-malonate (100 mg, 0.166 umol, 1 eq) in a mixture of THF (1 mL) and MeOH (2 mL) was added aq. LiOH solution (1 M, 3 mL). The mixture was stirred at 40° C. for 24 h before the organic volatile was removed under reduced pressure. The residue was diluted with water (2 mL) and treated with 1N HCl to adjust the pH to 4. The mixture was extracted with EtOAc (3×10 mL). The combined organic layer was washed with brine, dried (MgSO₄), filtered and concentrated to provide the title compound (67 mg) as a white solid.

¹H NMR (CD₃OD, 300 MHz) δ 8.09 (bs, 1H), 7.86 (d, J=8 Hz, 1H), 7.33-7.16 (m, 5H), 6.01 (d, J=7 Hz, 1H), 5.07 (d, J=8 Hz, 1H), 4.45 (d, J=7 Hz, 1H), 4.22 (bs, 1H), 4.11-3.94 (m, 2H), 3.55-3.31 (m, 2H), 2.95 (s, 1H); LC/MS [M+H]=461.0.

Example 7

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(pyridin-4-ylmethyl) malonic acid

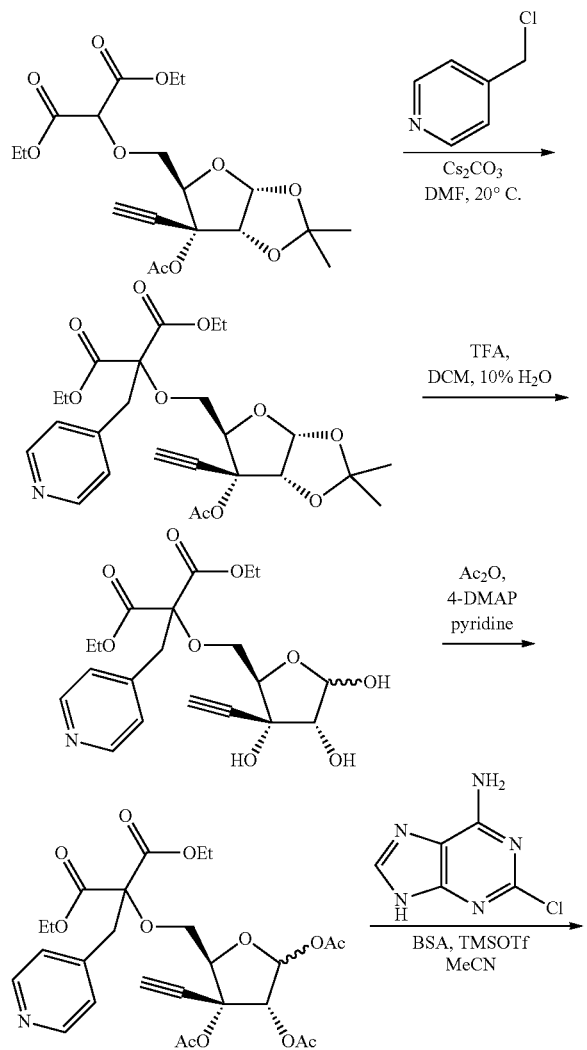

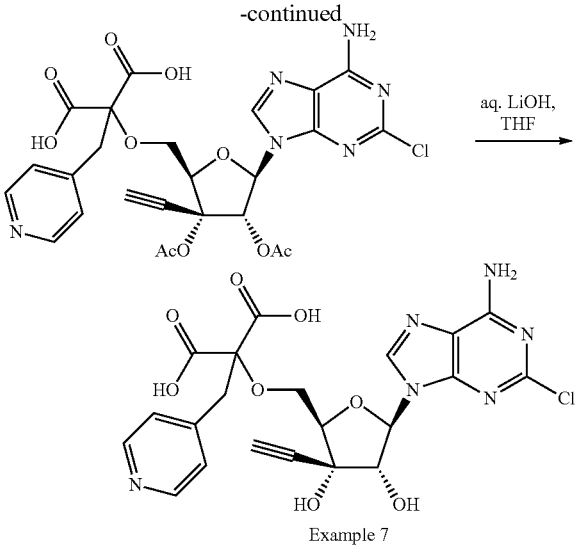

Example 7

Step 1:

To a mixture of diethyl 2-(((3aR,5R,6R,6aR)-6-acetoxy-6-ethynyl-2,2-dimethyltetra-hydrofuro[2,3-d][1,3]dioxol-5-yl)methoxy)malonate (1.2 g, 2.90 mmol, 1 eq) in DMF (20 mL) at 20° C. was added Cs₂CO₃ (6.60 g, 20.27 mmol, 7 eq) and 4-(chloromethyl) pyridine hydrochloride (1.90 g, 11.58 mmol, 4 eq). The mixture was stirred for 2 h before it was filtered and the filter cake was washed with EtOAc (20 mL). The filtrate was diluted with water (60 mL) and extracted with EtOAc (3×50 mL). The combined extract was washed with water (2×50 mL), saturated aq. NH₄Cl (50 mL), brine (50 mL), dried over anhydrous Na₂SO₄, filtered and concentrated under reduced pressure. The residue was purified by column chromatography on SiO₂ (14-33% EtOAc in petroleum ether) to give diethyl 2-(((3aR,5R,6R,6aR)-6-acetoxy-6-ethynyl-2,2-dimethyltetrahydrofuro[2,3-d][1,3]-dioxol-5-yl)methoxy)-2-(pyridin-4-ylmethyl)malonate (900 mg, 61% yield) as a yellow oil.

Step 2:

To a mixture of diethyl 2-(((3aR,5R,6R,6aR)-6-acetoxy-6-ethynyl-2,2-dimethyltetra-hydrofuro[2,3-d][1,3]dioxol-5-yl)methoxy)-2-(pyridin-4-ylmethyl)-malonate (900 mg, 1.78 mmol, 1 eq) in DCM (5 mL) and H₂O (1 mL, 55.51 mmol, 31.18 eq) was added TFA (5 mL, 67.53 mmol, 37.93 eq). The mixture was stirred at 20° C. for 12 h before it was concentrated under reduced pressure. The crude residue was azeotroped with DCM (3×10 mL) under reduced pressure to provide crude diethyl 2-(((2R,3S,4R)-3-ethynyl-3,4,5-trihydroxytetrahydrofuran-2-yl)methoxy)-2-(pyridin-4-ylmethyl)malonate (1.1 g) as a brown oil.

Step 3:

To a mixture of crude diethyl 2-(((2R,3S,4R)-3-ethynyl-3,4,5-trihydroxy-tetrahydro-furan-2-yl)methoxy)-2-(pyridin-4-ylmethyl)malonate (1.1 g, 2.60 mmol, 1 eq) in pyridinie (8 mL) at 20° C. was added 4-DMAP (952.17 mg, 7.79 mmol, 3 eq) and Ac₂O (2.43 mL, 25.98 mmol, 10 eq). The mixture was stirred for 12 h before it was partitioned between water (30 mL) and EtOAc (20 mL). The aqueous phase was further extracted with EtOAc (2×20 mL). The combined extract was washed with water (20 mL), 0.5 N aq. HCl (2×10 mL), and brine (20 mL), dried over anhydrous Na₂SO₄, filtered and concentrated under reduced pressure. The residue was purified by flash column chromatography on SiO₂ (25-50% EtOAc in petroleum ether) to give diethyl 2-(pyridin-4-ylmethyl)-2-(((2R,3R,4R)-3,4,5-triacetoxy-3-ethynyl-tetrahydrofuran-2-yl)methoxy)malonate (640 mg, 45% yield) as a brown syrup.

Step 4:

To a mixture of diethyl 2-(pyridin-4-ylmethyl)-2-(((2R,3R,4R)-3,4,5-triacetoxy-3-ethynyltetrahydrofuran-2-yl)methoxy)malonate (40 mg, 72.79 umol, 1 eq) and 2-chloroadenine (13.58 mg, 80.07 umol, 1.1 eq) in MeCN (1.5 mL) was added BSA (44.98 uL, 181.98 umol, 2.5 eq) at 25° C. under $N_2$ atmosphere. The mixture was stirred at 65° C. for 0.5 h before it was cooled to 0° C. and followed by dropwise addition of TMSOTf (26.31 uL, 145.58 umol, 2 eq). The mixture was stirred at 0° C. for 0.5 h and then at 65° C. for 2 h. The reaction mixture was cooled to room temperature and quenched with saturated aq. $NaHCO_3$ (6 mL). The mixture was extracted with EtOAc (3×8 mL). The combined organic layer was washed with brine (5 mL), dried over anhydrous $Na_2SO_4$, filtered and concentrated under reduced pressure. The residue was purified by preparative TLC (EtOAc) to provide diethyl 2-(((2R,3R,4R,5R)-3,4-diacetoxy-5-(6-amino-2-chloro-9H-purin-9-yl)-3-ethynyltetrahydrofuran-2-yl)methoxy)-2-(pyridin-4-ylmethyl)-malonate (13 mg, 26% yield) was obtained as a yellow gum.

Step 5:

To a mixture of diethyl 2-(((2R,3R,4R,5R)-3,4-diacetoxy-5-(6-amino-2-chloro-9H-purin-9-yl)-3-ethynyltetrahydrofuran-2-yl)methoxy)-2-(pyridin-4-ylmethyl)-malonate (50 mg, 75.87 umol, 1 eq) in THF (1 mL) was added 1N aq. LiOH (1 mL). The mixture was stirred at 50° C. for 1 h before it was cooled to room temperature and adjusted the pH 6-7 with 2N aq. HCl solution. The mixture was concentrated under reduced pressure and the residue was purified by preparative reverse-phase HPLC to provide the title compound (34 mg) as a white solid.

$^1$H NMR (CD$_3$OD, 300 MHz) δ 8.50 (bs, 1H), 8.32 (d, J=4 Hz, 2H), 7.50 (d, J=5 Hz, 2H), 6.01 (d, J=7 Hz, 1H), 4.80 (d, J=6 Hz, 1H), 4.38 (q, J=3 Hz, 1H), 4.10-3.95 (m, 2H), 3.45 (bs, 2H), 3.06 (s, 1H); LC/MS [M+H]=519.0.

Example 8

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(furan-3-ylmethyl)malonic acid

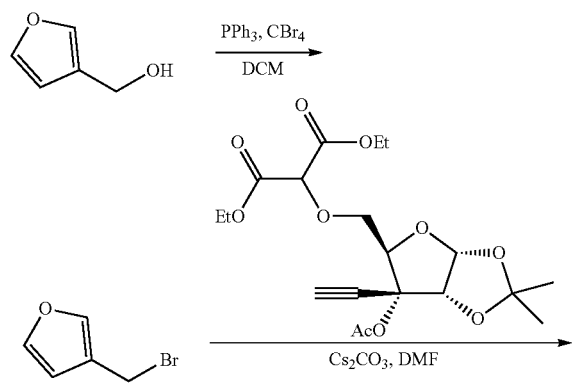

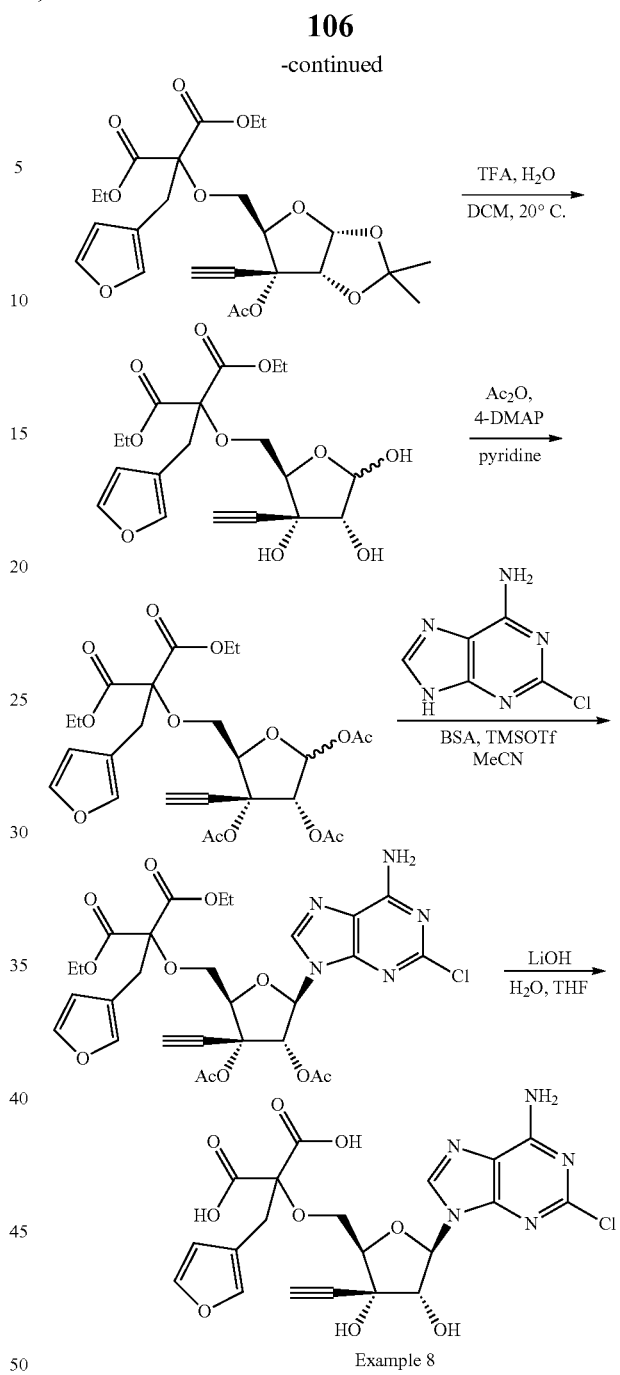

Example 8

Step 1:

To a mixture of PPh$_3$ (4.28 g, 16.31 mmol, 1.6 eq) and CBr$_4$ (4.06 g, 12.23 mmol, 1.2 eq) in DCM (20 mL) at 0° C. under N$_2$ atmosphere was added furan-3-ylmethanol (1 g, 10.19 mmol, 1 eq) in DCM (5 mL) dropwise. The mixture was stirred at 20° C. for 2 h before it was quenched with saturated aq. NaHCO$_3$ (30 mL) and then extracted with EtOAc (2×15 mL). The combined organic layer was washed with brine (30 mL), dried over anhydrous Na$_2$SO$_4$, filtered and concentrated under reduced pressure to provide crude 3-(bromomethyl)furan (2.9 g) as yellow gum which was used in the next step directly without further purification.

Step 2:

To a solution of diethyl 2-(((3aR,5R,6R,6aR)-6-acetoxy-6-ethynyl-2,2-dimethyltetra-hydrofuro[2,3-d][1,3]dioxol-5- yl)methoxy)malonate (1 g, 2.41 mmol, 1 eq) in DMF (5 mL) at 20° C. was added $Cs_2CO_3$ (2.36 g, 7.24 mmol, 3 eq) and crude 3-(bromomethyl)furan (2.9 g) in DMF (6 mL). The mixture was stirred for 2 h before it was partitioned between water (30 mL) and EtOAc (30 mL). The aqueous phase was extracted with EtOAc (3×15 mL). The combined organic extract was washed with water (20 mL), saturated aq. $NH_4Cl$ (2×20 mL), brine (20 mL), dried over anhydrous $Na_2SO_4$, filtered and concentrated under reduced pressure. The residue was purified by column chromatography on $SiO_2$ (10-25% EtOAc in petroleum ether) to give diethyl 2-(((3aR, 5R,6R,6aR)-6-acetoxy-6-ethynyl-2,2-dimethyltetra-hydrofuro[2,3-d][1,3]dioxol-5-yl)methoxy)-2-(furan-3-ylmethyl)malonate (375 mg, 31% yield) as a light yellow oil.

Step 3:

To a mixture of diethyl 2-(((3aR,5R,6R,6aR)-6-acetoxy-6-ethynyl-2,2-dimethyltetra-hydrofuro[2,3-d][1,3]dioxol-5-yl)methoxy)-2-(furan-3-ylmethyl)-malonate (375 mg, 758.36 umol, 1 eq) in DCM (2 mL) and $H_2O$ (0.4 mL, 22.20 mmol, 29 eq) was added TFA (2 mL, 27.01 mmol, 36 eq). The mixture was stirred at 20° C. for 12 h before it was concentrated under reduced pressure to provide crude diethyl 2-(((2R,3S,4R)-3-ethynyl-3,4,5-trihydroxy-tetrahydrofuran-2-yl)methoxy)-2-(furan-3-ylmethyl)malonate (420 mg) as an oil which was used in next step without further purification.

Step 4:

To a mixture of crude diethyl 2-(((2R,3S,4R)-3-ethynyl-3,4,5-trihydroxytetrahydro-furan-2-yl)methoxy)-2-(furan-3-ylmethyl)malonate (420 mg, 1.02 mmol, 1 eq) in pyridine (4 mL) at 20° C. was added $Ac_2O$ (954 uL, 10.18 mmol, 10 eq) and 4-DMAP (373 mg, 3.06 mmol, 3 eq). The mixture was stirred for 12 h before it was partitioned between water (15 mL) and EtOAc (10 mL). The aqueous phase was extracted with EtOAc (2×20 mL). The combined organic extract was washed with water (10 mL), 0.5N aq. HCl (2×5 mL), brine (10 mL), dried over anhydrous $Na_2SO_4$, filtered and concentrated. The residue was purified by preparative TLC (petroleum ether:EtOAc=3:1) to give diethyl 2-(furan-3-ylmethyl)-2-(((2R,3R,4R)-3,4,5-triacetoxy-3-ethynyltetrahydrofuran-2-yl)methoxy)malonate (95 mg, 17% yield) as a yellow oil.

Step 5:

To a mixture of diethyl 2-(furan-3-ylmethyl)-2-(((2R,3R, 4R)-3,4,5-triacetoxy-3-ethynyltetrahydrofuran-2-yl) methoxy)malonate (50 mg, 92.85 umol, 1 eq) and 2-chloroaddenine (17.32 mg, 102.14 umol, 1.1 eq) in MeCN (1.2 mL) was added BSA (57.38 uL, 232.13 umol, 2.5 eq) at 25° C. under $N_2$ atmosphere. The mixture was stirred at 65° C. for 0.5 h before it was cooled to 0° C. and followed by dropwise addition of TMSOTf (33.56 uL, 185.70 umol, 2 eq). The mixture was stirred at 0° C. for 0.5 h and then at 65° C. for 2 h before it was cooled to room temperature and quenched with saturated aq. $NaHCO_3$ solution (2 mL). The mixture was extracted with EtOAc (3×2 mL). The combined organic layer was washed with brine (2 mL), dried over anhydrous $Na_2SO_4$, filtered and concentrated under reduced pressure. The residue was purified by preparative TLC (petroleum ether:EtOAc=1:1) to provide diethyl 2-(((2R,3R, 4R,5R)-3,4-diacetoxy-5-(6-amino-2-chloro-9H-purin-9-yl)-3-ethynyltetrahydrofuran-2-yl)methoxy)-2-(furan-3-ylmethyl)malonate (17 mg, 29% yield) as a yellow gum.

Step 6:

To a mixture of diethyl 2-(((2R,3R,4R,5R)-3,4-diacetoxy-5-(6-amino-2-chloro-9H-purin-9-yl)-3-ethynyltetrahydrofuran-2-yl)methoxy)-2-(furan-3-ylmethyl)-malonate (33 mg, 50.92 umol, 1 eq) in THF (1 mL) was added 1N aq. LiOH (1 mL). The mixture was stirred at 20° C. for 3 h before it was extracted with EtOAc (2 mL). The organic layer was discarded. The aqueous phase was adjusted the pH 2-3 with 2N aq. HCl before it was extracted with EtOAc (4×5 mL). The combined organic extract was washed with brine (3 mL), dried over anhydrous $Na_2SO_4$, filtered and concentrated under reduced pressure. The residue was dissolved in a mixture of MeCN (1 mL) and $H_2O$ (1 mL) and then dried by lyophilization to provide the title compound (10.0 mg, 37% yield) as a white solid.

$^1$H NMR (400 MHz, DMSO-$d_6$) δ ppm 8.48 (s, 1H) 7.81 (br s, 2H) 7.35 (s, 2H) 6.29 (s, 1H) 6.22 (br s, 1H) 6.02 (br d, J=6.50 Hz, 1H) 5.83 (d, J=7.50 Hz, 1H) 4.75-4.90 (m, 1H) 4.16 (dd, J=4.75, 2.75 Hz, 1H) 3.92 (br dd, J=10.07, 5.07 Hz, 1H) 3.77 (br d, J=8.00 Hz, 1H) 3.48 (s, 1H) 3.08 (s, 2H); LC/MS [M+H]=507.9.

Example 9

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(2-oxotetrahydropyrimidin-1 (2H)-yl)benzyl)malonic acid

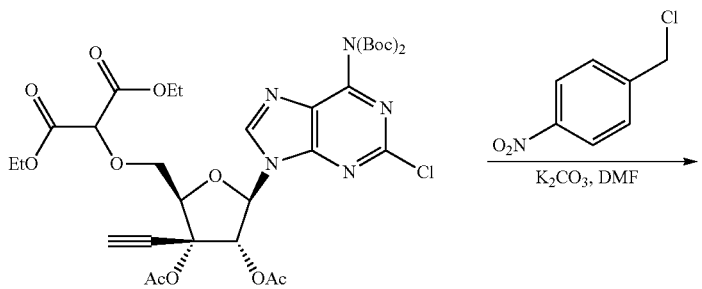

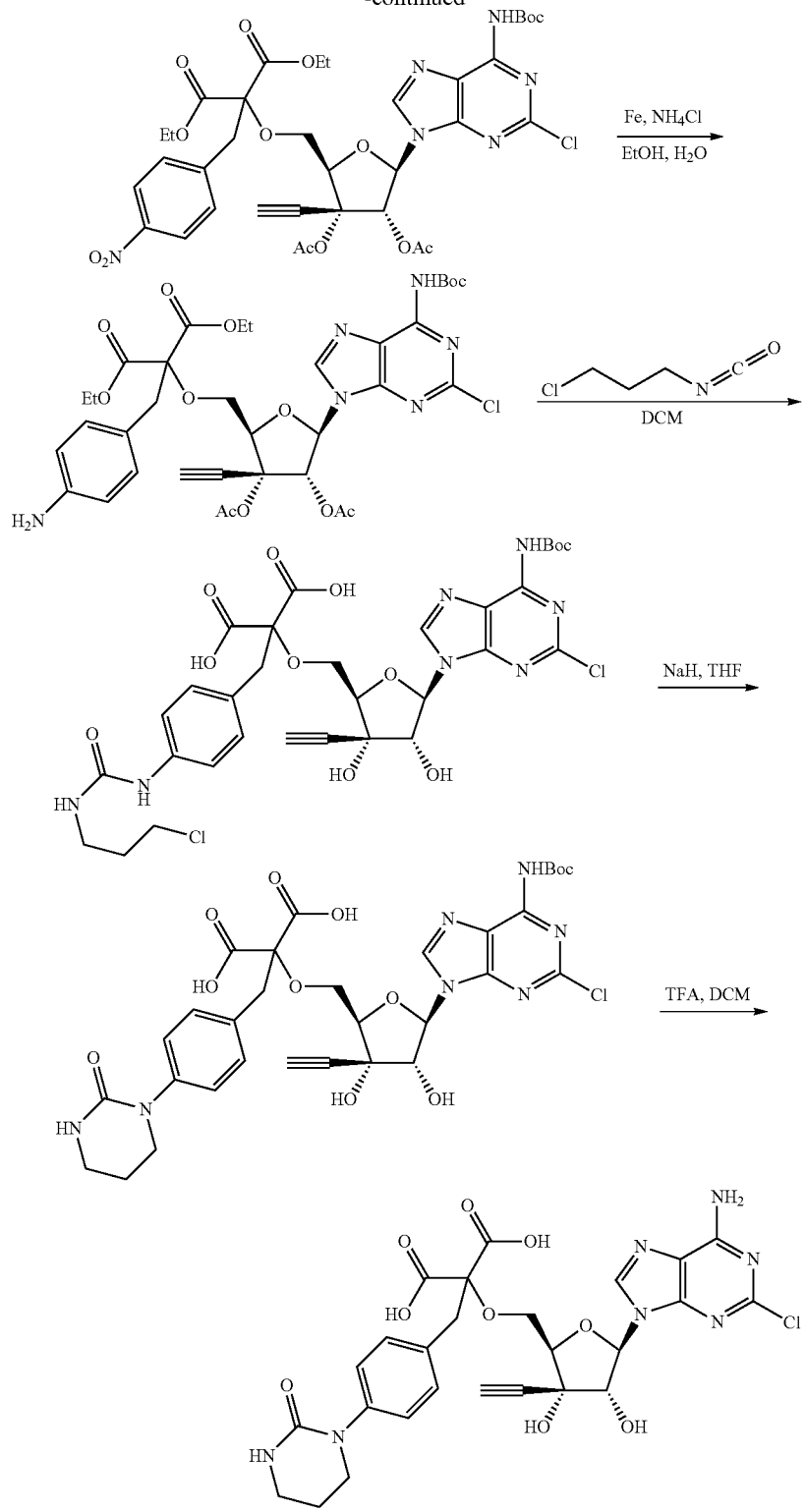
Example 9
Step 1:
To a solution of diethyl 2-(((2R,3R,4R,5R)-3,4-diacetoxy-5-(6-N,N'-(bis-(tert-butoxycarbonyl)amino)-2-chloro-9H-purin-9-yl)-3-ethynyltetrahydrofuran-2-yl)methoxy-)malonate (7.26 g, 4.92 mmol, 1 eq) in DMF (80 mL) at 25° C. was added $K_2CO_3$ (13.60 g, 98.40 mmol, 20 eq). The reaction mixture was stirred for 0.5 h and followed by addition of 1-(bromomethyl)-4-nitro-benzene (15.94 g, 73.80 mmol, 15 eq). The reaction mixture was stirred for 24 h before it was diluted with H₂O (300 mL) and extracted with EtOAc (3×60 mL). The combined organic layer was washed with brine (100 mL), dried over Na₂SO₄, filtered and concentrated. The crude residue was purified by flash silica gel column chromatography (petroleum ether:EtOAc=10:1-2:1) to provide diethyl 2-(((2R,3R,4R,5R)-3,4-diacetoxy-5-(6-((tert-butoxycarbonyl)amino)-2-chloro-9H-purin-9-yl)-3-ethynyltetra-hydrofuran-2-yl)methoxy)-2-(4-nitrobenzyl)malonate (2.36 g) was obtained as a brown gum.

Step 2:

To a solution of diethyl 2-(((2R,3R,4R,5R)-3,4-diacetoxy-5-(6-((tert-butoxycarbonyl)-amino)-2-chloro-9H-purin-9-yl)-3-ethynyltetra-hydrofuran-2-yl)methoxy)-2-(4-nitrobenzyl)-malonate (2.26 g, 2.81 mmol, 1 eq) in EtOH (23 mL) at 0° C. was added Fe (786 mg, 14.07 mmol, 5 eq) and NH₄Cl (151 mg, 2.81 mmol, 1 eq) in H₂O (8.5 mL). The reaction mixture was stirred at 50° C. for 4 h before it was filtered and the filtrate was concentrated. The crude residue was purified by flash silica gel column chromatography (petroleum ether:EtOAc=1:0-1:1) to provide diethyl 2-(4-aminobenzyl)-2-(((2R,3R,4R,5R)-3,4-diacetoxy-5-(6-((tert-butoxycarbonyl)-amino)-2-chloro-9H-purin-9-yl)-3-ethynyltetra-hydrofuran-2-yl)methoxy)-malonate (280 mg) as a yellow foam.

Step 3:

To a solution of diethyl 2-(4-aminobenzyl)-2-(((2R,3R,4R,5R)-3,4-diacetoxy-5-(6-((tert-butoxycarbonyl)amino)-2-chloro-9H-purin-9-yl)-3-ethynyltetrahydrofuran-2-yl)methoxy)malonate (280 mg, 362.14 umol, 1 eq) in DCM (3 mL) at 0° C. was added 1-chloro-3-isocyanatopropane (86.59 mg, 724.28 umol, 2 eq). The reaction mixture was stirred at 25° C. for 16 h before it was concentrated. The crude residue was purified by preparative TLC (petroleum ether:EtOAc=1:0-1:1) to provide diethyl 2-(4-(3-(3-chloropropyl)ureido)-benzyl)-2-(((2R,3R,4R,5R)-3,4-diacetoxy-5-(6-((tert-butoxycarbonyl)amino)-2-chloro-9H-purin-9-yl)-3-ethynyltetrahydrofuran-2-yl)methoxy)malonate (120 mg, 33% yield) as a foam.

Step 4:

To a solution of diethyl 2-(4-(3-(3-chloropropyl)ureido) benzyl)-2-(((2R,3R,4R,5R)-3,4-diacetoxy-5-(6-((tert-butoxycarbonyl)amino)-2-chloro-9H-purin-9-yl)-3-ethynyltetra-hydrofuran-2-yl)methoxy)malonate (120 mg, 134.42 umol, 1 eq) in THF (1.2 mL) at 0° C. was added NaH (11 mg, 268.84 umol, 60% in mineral oil, 2 eq). The reaction mixture was stirred at 25° C. for 2 h before it was quenched with H₂O (0.2 mL) at 0° C. The reaction mixture was then stirred at 25° C. for 16 h. The reaction mixture was acidified to pH 3-4 with 1N aq. HCl solution and then extracted with EtOAc (3×5 mL). The combined organic layer was washed with brine (15 mL), dried over anhydrous Na₂SO₄, filtered and concentrated to provide crude 2-(((2R,3S,4R,5R)-5-(6-((tert-butoxycarbonyl)amino)-2-chloro-9H-purin-9-yl)-3-ethynyl-3,4-dihydroxytetrahydrofuran-2-yl)methoxy)-2-(4-(2-oxo-tetrahydropyrimidin-1(2H)-yl)benzyl)malonic acid (77 mg, 73% yield) as a white solid.

Step 5:

To a solution of crude 2-(((2R,3S,4R,5R)-5-(6-((tert-butoxycarbonyl)amino)-2-chloro-9H-purin-9-yl)-3-ethynyl-3,4-dihydroxytetrahydrofuran-2-yl)methoxy)-2-(4-(2-oxotetrahydropyrimidin-1(2H)-yl)benzyl)malonic acid (76 mg, 106.13 umol, 1 eq) in DCM (0.5 mL) at 0° C. was added TFA (0.25 mL, 3.38 mmol, 32 eq). The reaction mixture was stirred at 25° C. for 2 h before it was concentrated. The residue was re-dissolved with saturated aq. NaHCO₃ solution (5 mL) and extracted EtOAc (3×5 mL). The combined organic layer was washed with brine (15 mL), dried over anhydrous Na₂SO₄, filtered and concentrated. The crude residue was purified by preparative reversed-phase HPLC to provide the title compound (8.6 mg, 12% yield) as a white solid.

¹H NMR (CD₃OD, 300 MHz) δ 8.28 (s, 1H), 7.11 (d, J=8.52 Hz, 2H), 7.02 (d, J=8.52 Hz, 2H), 5.99 (d, J=7.44 Hz, 1H), 4.79 (d, J=7.41 Hz, 1H), 4.29 (t, J=2.76 Hz, 1H), 4.01-3.91 (m, 2H), 3.54-3.41 (m, 4H), 3.36-3.32 (m, 2H), 3.05 (s, 1H), 2.03-1.94 (m, 2H); LC/MS [M+H]=616.2.

Example 10

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(2-oxopiperidin-1-yl)benzyl)malonic acid

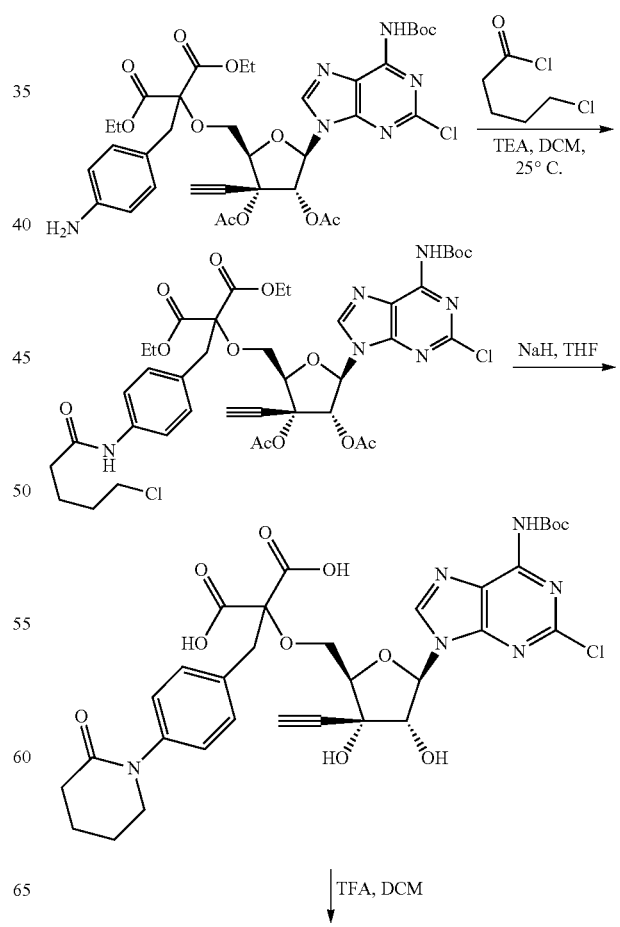

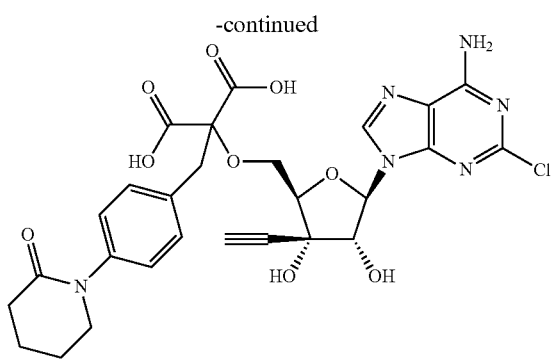

Example 10

Step 1:

To a solution of crude diethyl 2-(4-aminobenzyl)-2-(((2R,3R,4R,5R)-3,4-diacetoxy-5-(6-((tert-butoxycarbonyl)amino)-2-chloro-9H-purin-9-yl)-3-ethynyltetrahydrofuran-2-yl)-methoxy)malonate (140 mg, 160 umol, 1 eq) in DCM (2 mL) at 25° C. was added TEA (107 mg, 1.06 mmol, 147 uL, 6.59 eq) and followed by 5-chloropentanoyl chloride (24.9 uL, 192 umol, 1.2 eq). The mixture was stirred for 1 h before it was partitioned between DCM (20 mL) and H$_2$O (20 mL). The organic phase was washed with H$_2$O (10 mL), dried over Na$_2$SO$_4$, filtered and concentrated under reduced pressure. The residue was purified by preparative TLC (petroleum ether:EtOAc=1:1) to give diethyl 2-(4-(5-chloropentanamido)-benzyl)-2-(((2R,3R,4R,5R)-3,4-diacetoxy-5-(6-((tert-butoxycarbonyl)amino)-2-chloro-9H-purin-9-yl)-3-ethynyltetrahydrofuran-2-yl)methoxy)malonate (130 mg, 69% yield) as a yellow gum.

Step 2:

To a solution of diethyl 2-(4-(5-chloropentanamido)-benzyl)-2-(((2R,3R,4R,5R)-3,4-diacetoxy-5-(6-((tert-butoxycarbonyl)amino)-2-chloro-9H-purin-9-yl)-3-ethynyltetrahydro-furan-2-yl)methoxy)malonate (104 mg, 105 umol, 1 eq) in THF (2 mL) at 25° C. was added NaH (25.2 mg, 630 umol, 60% in mineral oil, 6 eq). The mixture was stirred for 4 h before it was quenched with H$_2$O (1 mL). The reaction mixture was stirred at 20° C. for 14 before it was partitioned between EtOAc (10 mL) and water (20 mL). The aqueous phase was acidified to pH 5-6 with 2N aq. HCl solution before it was partitioned between EtOAc (20 mL) and brine (10 mL), dried over anhydrous Na$_2$SO$_4$, filtered and concentrated under reduced pressure to give crude 2-(((2R,3S,4R,5R)-5-(6-((tert-butoxycarbonyl)amino)-2-chloro-9H-purin-9-yl)-3-ethynyl-3,4-dihydroxytetrahydrofuran-2-yl)methoxy)-2-(4-(2-oxopiperidin-1-yl)benzyl)malonic acid (58 mg) as a colorless gum.

Step 3:

To a mixture of crude 2-(((2R,3S,4R,5R)-5-(6-((tert-butoxycarbonyl)amino)-2-chloro-9H-purin-9-yl)-3-ethynyl-3,4-dihydroxytetrahydrofuran-2-yl)methoxy)-2-(4-(2-oxopiperidin-1-yl)benzyl)malonic acid (58 mg, 81 umol, 1 eq) in DCM (500 uL) was added TFA (400 uL, 5.40 mmol, 67 eq). The mixture was stirred at 20° C. for 2 h before it was quenched with 2N aq. LiOH (500 uL). The mixture was partitioned between EtOAc (10 mL) and water (10 mL). The aqueous phase was adjusted to pH 5-6 with 2M aq. HCl solution. The aqueous phase was partitioned between EtOAc (2×20 mL) and brine (5 mL), dried over anhydrous Na$_2$SO$_4$, filtered and concentrated under reduced pressure. The crude product was purified by preparative HPLC and lyophilized to give the title compound (6.9 mg, 14% yield) as a white solid.

$^1$H NMR (400 MHz, DMSO-d$_6$) δ ppm 8.32 (s, 1H) 7.33 (d, J=8.53 Hz, 2H) 6.98 (d, J=8.28 Hz, 2H) 5.98 (d, J=7.53 Hz, 1H) 4.79 (m, 1H) 4.28 (t, J=2.76 Hz, 1H) 4.04 (br s, 2H) 3.39-3.54 (m, 4H) 3.05 (s, 1H) 2.43 (m, 2H) 1.88 (br t, J=2.89 Hz, 4H); LC/MS [M+H]=615.3.

Example 11

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(1-(methoxymethyl)-2-oxo-1,2-dihydropyridin-3-yl)benzyl)malonic acid

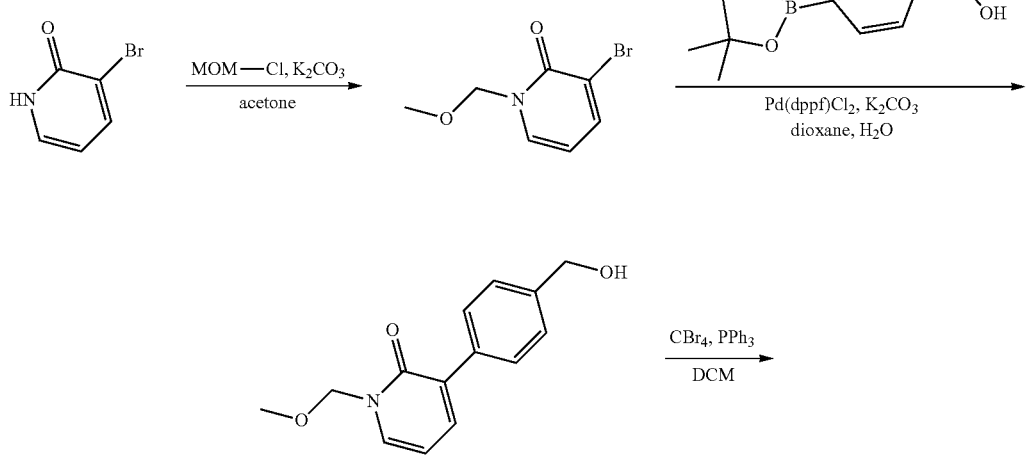

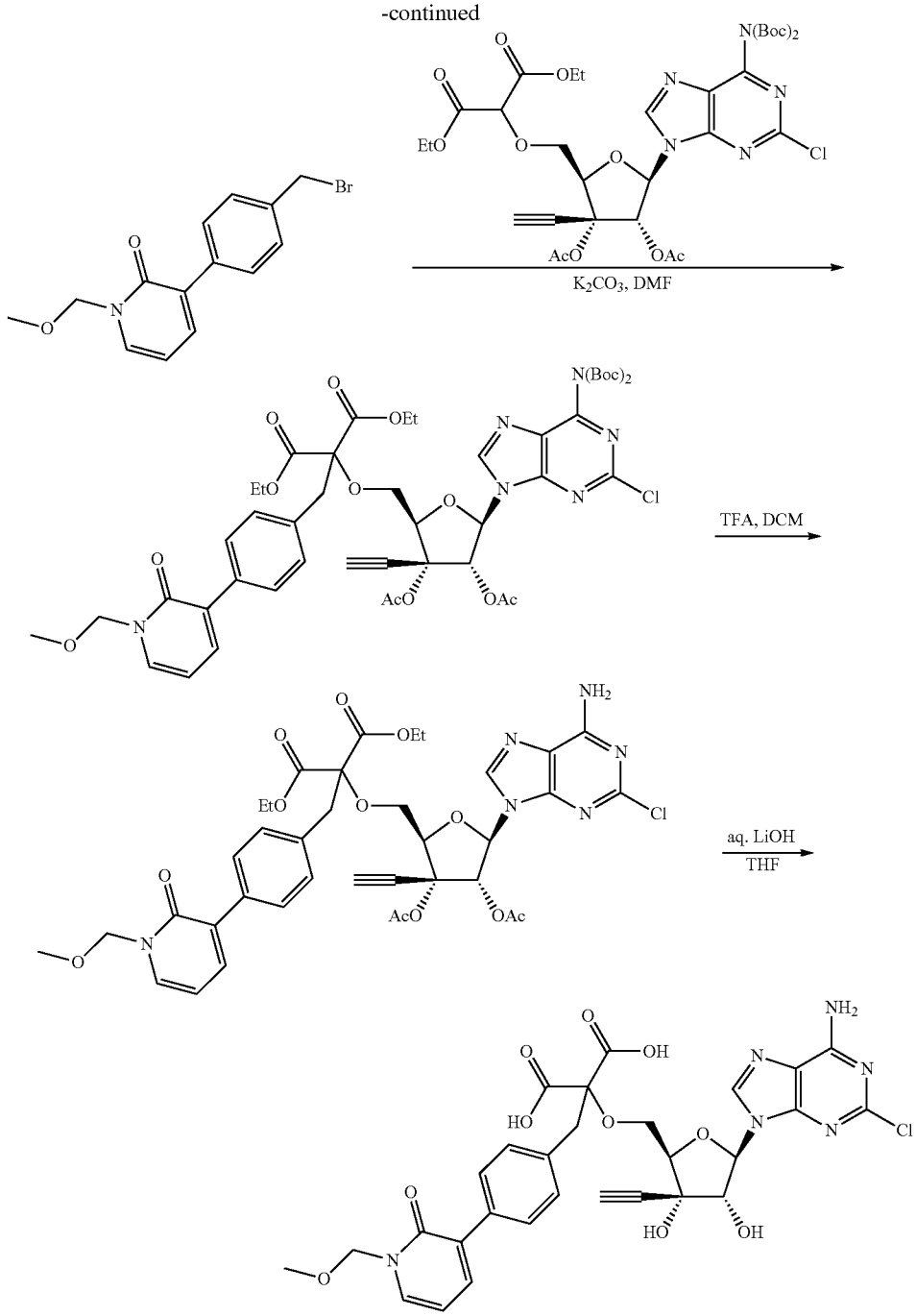

Example 11

Step 1:

To a solution of 3-bromopyridin-2(1H)-one (2.25 g, 12.93 mmol, 1 eq) in acetone (40 mL) at 25° C. was added $K_2CO_3$ (4.47 g, 32.33 mmol, 2.5 eq). The suspension was stirred for 0.5 h and followed by addition of MOM-$C_1$ (2.79 mL, 36.76 mmol, 2.84 eq) dropwise. The mixture was stirred at 25° C. for 15 h before it was diluted with water (40 mL) and extracted with ethyl acetate (2×30 mL). The combined organic layer was washed with brine (50 mL), dried by $Na_2SO_4$, filtered and concentrated. The crude residue was purified by Combi-flash on silica gel (20-60% ethyl acetate in petroleum ether) to provide 3-bromo-1-(methoxymethyl)-pyridin-2(1H)-one (1.22 g, 43% yield) as a clear oil.

Step 2:

To a solution of 3-bromo-1-(methoxymethyl)pyridin-2 (1H)-one (1.38 g, 6.33 mmol, 1 eq) and (4-(4,4,5,5-tetramethyl-1,3,2-dioxaborolan-2-yl)phenyl)methanol (1.06 g, 6.96 mmol, 1.1 eq) in dioxane (12 mL) was added $K_2CO_3$ (2.62 g, 18.99 mmol, 3 eq), Pd(dppf)$Cl_2$ (463 mg, 632.89 umol, 0.1 eq) and $H_2O$ (4 mL). The mixture was de-gassed with $N_2$ for 10 min before it was then heated at 80° C. for 16 h under $N_2$ atmosphere. The reaction was diluted with water (10 mL) and extracted with ethyl acetate (3×10 mL).

The combined organic layer was washed with brine (25 mL), dried by $Na_2SO_4$, filtered and concentrated. The crude residue was purified by Combi-flash on silica gel (50-100% ethyl acetate in petroleum ether) to provide 3-(4-(hydroxymethyl)phenyl)-1-(methoxymethyl)pyridin-2(1H)-one (1.30 g, 84% yield) as a yellow gum.

Step 3:

To a solution of $PPh_3$ (8.34 g, 31.80 mmol, 6 eq) in DCM (50 mL) at −25° C. was added $CBr_4$ (10.55 g, 31.80 mmol, 6 eq). The yellow suspension was stirred at −25° C. for 1 h and followed by addition of a solution of 3-(4-(hydroxymethyl)phenyl)-1-(methoxymethyl)-pyridin-2(1H)-one (1.30 g, 5.30 mmol, 1 eq) in DCM (10 mL) dropwise. The yellow suspension was stirred at −25° C. for 0.5 h before it was diluted with MTBE (180 mL). The precipitate was filtered off and the filtrate was concentrated to give crude (2.8 g) as a yellow gum. The crude residue was purified by Combi-flash on silica gel (30-100% ethyl acetate in petroleum ether) to provide 3-(4-(bromomethyl)phenyl)-1-(methoxymethyl)-pyridin-2(1H)-one (760 mg, 46% yield) as a white solid.

Step 4:

To a solution of diethyl 2-(((2R,3R,4R,5R)-3,4-diacetoxy-5-(6-N,N'-(bis-(tert-butoxycarbonyl)amino)-2-chloro-9H-purin-9-yl)-3-ethynyltetrahydrofuran-2-yl)-methoxy)-malonate (100 mg, 130.18 umol, 1 eq) in DMF (1.5 mL) at 20° C. was added $K_2CO_3$ (53.97 mg, 390.54 umol, 3 eq). The suspension was stirred for 0.5 h and followed by addition of 3-(4-(bromomethyl)phenyl)-1-(methoxymethyl)pyridin-2(1H)-one (44.13 mg, 143.20 umol, 1.1 eq). The suspension was stirred at 20° C. for 16 h before it was diluted with water (2 mL) and extracted with ethyl acetate (3×2 mL). The combined organic layer was dried by $Na_2SO_4$, filtered and concentrated. The crude residue was purified by preparative TLC (petroleum ether: ethyl acetate=1:1) to provide diethyl 2-(((2R,3R,4R,5R)-3,4-diacetoxy-5-(6-(N,N'-bis-(tert-butoxy-carbonyl)amino)-2-chloro-9H-purin-9-yl)-3-ethynyltetrahydro-furan-2-yl)methoxy)-2-(4-(1-(methoxymethyl)-2-oxo-1,2-dihydropyridin-3-yl)benzyl)-malonate (71 mg, 55% yield) as a clear syrup.

Step 5:

To a solution of diethyl 2-(((2R,3R,4R,5R)-3,4-diacetoxy-5-(6-(N,N'-bis-(tert-butoxy-carbonyl)amino)-2-chloro-9H-purin-9-yl)-3-ethynyltetrahydrofuran-2-yl)-methoxy)-2-(4-(1-(methoxymethyl)-2-oxo-1,2-dihydropyridin-3-yl)benzyl)-malonate (68 mg, 68.31 umol, 1 eq) in DCM (1.7 mL) at 0° C. was added TFA (0.3 mL, 4.05 mmol, 59 eq). The mixture was stirred at 20° C. for 2 h before it was quenched with saturated aq. $NaHCO_3$ solution to adjust the pH to 9. The mixture was extracted with ethyl acetate (3×8 mL). The combined organic layer was concentrated to give crude (98 mg) as a yellow gum. The crude residue was purified by preparative TLC (ethyl acetate) to provide diethyl 2-(((2R,3R,4R,5R)-3,4-diacetoxy-5-(6-amino-2-chloro-9H-purin-9-yl)-3-ethynyltetrahydro-furan-2-yl)-methoxy)-2-(4-(1-(methoxymethyl)-2-oxo-1,2-dihydropyridin-3-yl)-benzyl)-malonate (21 mg, 38% yield) as a colorless syrup.

Step 6:

To a solution of diethyl 2-(((2R,3R,4R,5R)-3,4-diacetoxy-5-(6-amino-2-chloro-9H-purin-9-yl)-3-ethynyltetrahydrofuran-2-yl)methoxy)-2-(4-(1-(methoxy-methyl)-2-oxo-1,2-dihydropyridin-3-yl)benzyl)malonate (20 mg, 25.15 umol, 1 eq) in THF (1 mL) was added 1M aq. LiOH (503 uL, 20 eq). The mixture was stirred at 18° C. for 22 h before it was acidified to pH 2 with 1N aq. HCl and concentrated. The crude residue was purified by preparative HPLC and the fraction was dried by lyophilization to provide the title compound (2.1 mg, 13% yield) as a white solid.

$^1$H NMR (400 MHz, DMSO-$d_6$) δ ppm 8.45 (br s, 1H), 7.81 (br s, 2H), 7.67 (dd, J=6.75, 1.75 Hz, 1H), 7.51 (br d, J=6.75 Hz, 1H), 7.36 (br d, J=6.88 Hz, 2H), 7.20 (br d, J=7.50 Hz, 2H), 6.33 (t, J=6.75 Hz, 1H), 6.20 (br s, 1H), 6.01 (br d, J=6.88 Hz, 1H), 5.82 (d, J=7.50 Hz, 1H), 5.28 (s, 2H), 4.65-4.89 (m, 1H), 4.06-4.23 (m, 1H) 3.88-4.06 (m, 1H), 3.67-3.86 (m, 1H), 3.40-3.52 (m, 3H), 3.18-3.30 (m, 2H); LC/MS [M+H]=655.1.

Example 12

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(2-oxo-1,2-dihydropyridin-3-yl)benzyl)malonic acid

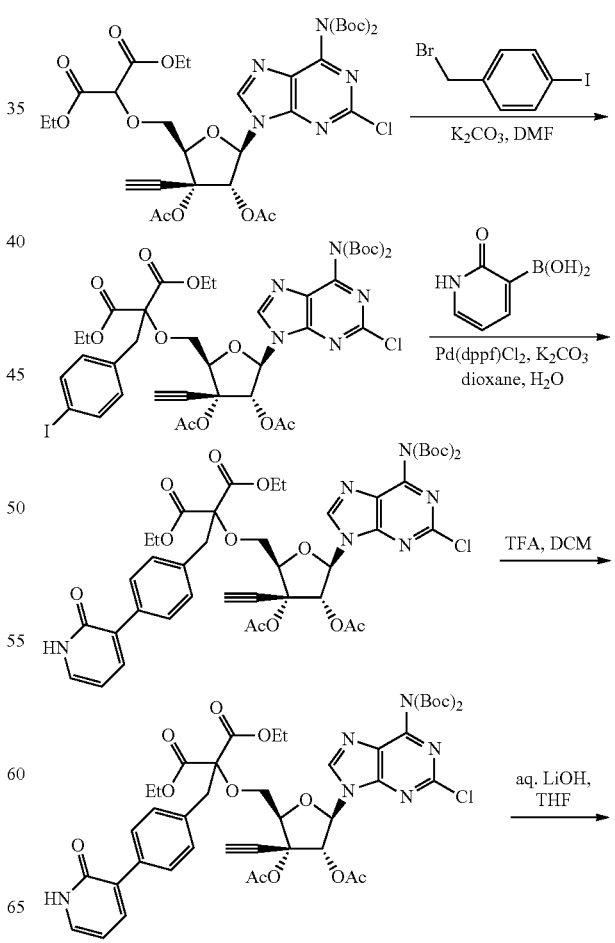

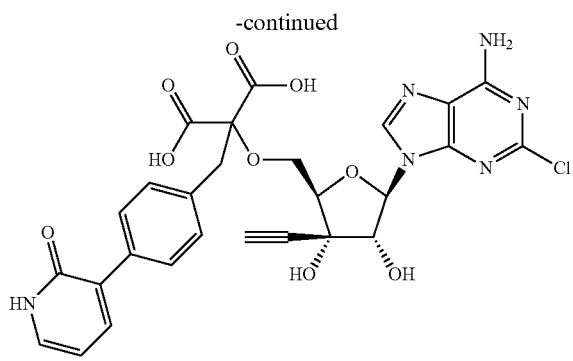

Example 12

Step 1:

To a solution of diethyl 2-(((2R,3R,4R,5R)-3,4-diacetoxy-5-(6-N,N'-bis-(tert-butoxy-carbonyl)amino)-2-chloro-9H-purin-9-yl)-3-ethynyltetrahydrofuran-2-yl)-methoxy)-malonate (12.59 g, 16.39 mmol, 1 eq) and 1-(bromomethyl)-4-iodo-benzene (48.67 g, 163.90 mmol, 10 eq) in DMF (120 mL) at 20° C. was added K₂CO₃ (33.98 g, 245.85 mmol, 15 eq). The solution was stirred for 16 h before it was diluted with water (200 mL) and extracted with ethyl acetate (3×200 mL). The combined organic layer was washed with water (400 mL), brine (400 mL), dried by Na₂SO₄, filtered and concentrated. The crude residue was purified by Combi-flash on silica gel (15-40% ethyl acetate in petroleum ether) to give diethyl 2-(((2R,3R,4R,5R)-3,4-diacetoxy-5-(6-N,N'-(bis-(tert-butoxycarbonyl)-amino)-2-chloro-9H-purin-9-yl)-3-ethynyltetra-hydrofuran-2-yl)methoxy)-2-(4-iodobenzyl)-malonate (2.94 g, 18% yield) as a yellow solid.

Step 2:

To a solution of diethyl 2-(((2R,3R,4R,5R)-3,4-diacetoxy-5-(6-N,N'-(bis-(tert-butoxy-carbonyl)amino)-2-chloro-9H-purin-9-yl)-3-ethynyltetrahydrofuran-2-yl)-methoxy)-2-(4-iodobenzyl)malonate (1.10 g, 1.12 mmol, 1 eq) and (2-oxo-1,2-dihydropyridin-3-yl)boronic acid (310.53 mg, 2.24 mmol, 2 eq) in dioxane (12 mL) was added K₂CO₃ (463.41 mg, 3.35 mmol, 3 eq), Pd(dppf)Cl₂ (81.78 mg, 111.77 umol, 0.1 eq) and H₂O (4 mL). The mixture was degassed with N₂ for 10 min and then stirred at 80° C. for 1 h under N₂ atmosphere. The dark mixture was diluted with water (10 mL) and extracted with ethyl acetate (3×10 mL). The combined organic layer was washed with brine (30 mL), dried by Na₂SO₄, filtered and concentrated. The crude residue was purified by Combi-flash on silica gel (40-100% ethyl acetate in petroleum ether) to give diethyl 2-(((2R,3R,4R,5R)-3,4-diacetoxy-5-(6-N,N'-(bis-(tert-butoxy-carbo-nyl)amino)-2-chloro-9H-purin-9-yl)-3-ethynyltetrahydro-furan-2-yl)-methoxy)-2-(4-(2-oxo-1,2-dihydropyridin-3-yl)benzyl)malonate (220 mg, 21% yield) as a yellow gum.

Step 3:

To a solution of diethyl 2-(((2R,3R,4R,5R)-3,4-diacetoxy-5-(6-N,N'-bis-(tert-butoxy-carbonyl)amino)-2-chloro-9H-purin-9-yl)-3-ethynyltetrahydrofuran-2-yl)-methoxy)-2-(4-(2-oxo-1,2-dihydropyridin-3-yl)benzyl)malonate (180 mg, 189.20 umol, 1 eq) in DCM (2.4 mL) was added TFA (0.6 mL, 8.10 mmol, 43 eq). The yellow solution was stirred at 20° C. for 2.5 h before it was quenched with saturated aq. NaHCO₃ (5 mL) and extracted with ethyl acetate (3×4 mL). The combined organic layer was concentrated to give crude (108 mg) as a yellow gum. The crude residue was purified by preparative TLC (ethyl acetate) to give diethyl 2-(((2R,3R,4R,5R)-3,4-diacetoxy-5-(6-amino-2-chloro-9H-purin-9-yl)-3-ethynyltetra-hydrofuran-2-yl) methoxy)-2-(4-(2-oxo-1,2-dihydropyridin-3-yl)benzyl)-malonate (23 mg, 16% yield) as a yellow solid.

Step 4:

To a solution of diethyl 2-(((2R,3R,4R,5R)-3,4-diacetoxy-5-(6-amino-2-chloro-9H-purin-9-yl)-3-ethynyltetra-hydrofuran-2-yl)methoxy)-2-(4-(2-oxo-1,2-dihydropyridin-3-yl)benzyl)malonate (23 mg, 30.62 umol, 1 eq) in THF (2.5 mL) was added 1M aq. LiOH (0.6 mL, 20 eq). The reaction mixture was stirred at 20° C. for 4 h before it was acidified to pH 6 with 1N aq. HCl and concentrated to give crude (32 mg) as a yellow gum. The crude residue was purified by preparative HPLC (column: YMC-Triart Prep C18 150*40 mm*7 um; Mobile phase: [water (0.225% FA)-CAN]; B %: 15%-35%, 10 min). The product was dried by lyophilization to give the title compound (2.1 mg, 11% yield) as a white solid.

¹H NMR (400 MHz, CD3OD) δ ppm 8.24 (s, 1H), 7.46 (dd, J=6.88, 1.63 Hz, 1H), 7.28-7.34 (m, 5H), 6.39 (t, J=6.75 Hz, 1H), 5.96 (d, J=7.38 Hz, 1H), 4.77-4.84 (m, 1H), 4.29 (t, J=2.88 Hz, 1H), 4.03 (d, J=2.75 Hz, 2H), 3.38-3.51 (m, 2H), 3.04 (s, 1H); LC/MS [M+H]=611.0.

Example 13

Synthesis of 2-(((2R,3S,4R,5R)-5-(6-amino-2-chloro-9H-purin-9-yl)-3-ethynyl-3,4-dihydroxytetra-hydrofuran-2-yl)methoxy)-2-((2-carboxy-[1,1'-bi-phenyl]-4-yl)methyl)malonic acid

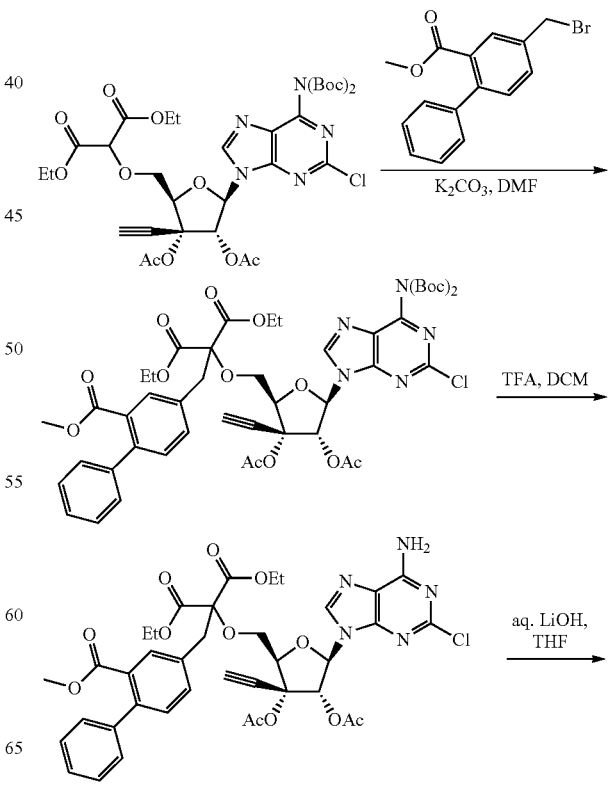

-continued

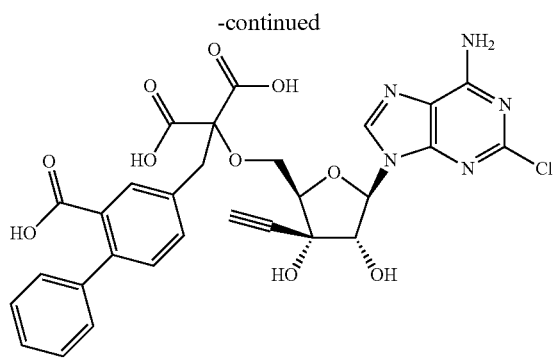

Example 13

Step 1:

To a mixture of diethyl 2-(((2R,3R,4R,5R)-3,4-diacetoxy-5-(6-N,N'-(bis-(tert-butoxycarbonyl)amino)-2-chloro-9H-purin-9-yl)-3-ethynyltetrahydrofuran-2-yl)methoxy)-malonate (99.87 mg, 130.01 umol, 1 eq) in DMF (0.5 mL) was added $K_2CO_3$ (53.90 mg, 390.03 umol, 3 eq). The mixture was stirred at 40° C. for 0.5 h and followed by addition of methyl 4-(bromomethyl)-[1,1'-biphenyl]-2-carboxylate (79.35 mg, 260.02 umol, 2 eq) which was prepared according to the reported procedure by D. Stoermer et al (*J. of Med. Chem.* 2012, 55, 5922-5932). The mixture was stirred at 40° C. for 15.5 h before it was diluted with water (4 mL) and extracted with EtOAc (3×5 mL). The combined organic layer was washed with water (2×5 mL) and brine (5 mL), dried over anhydrous $Na_2SO_4$, filtered and concentrated. The crude residue was purified by preparative TLC (petroleum ether:EtOAc=1:1) to give diethyl 2-(((2R,3R,4R,5R)-3,4-diacetoxy-5-(6-N,N'-(bis-(tert-butoxycarbonyl)-amino)-2-chloro-9H-purin-9-yl)-3-ethynyltetrahydrofuran-2-yl)methoxy)-2-((2-(methoxy-carbonyl)-[1,1'-biphenyl]-4-yl)methyl)malonate (70 mg, 53% yield) as a colorless syrup.

Step 2:

To a solution of diethyl 2-(((2R,3R,4R,5R)-3,4-diacetoxy-5-(6-N,N'-(bis-(tert-butoxycarbonyl)amino)-2-chloro-9H-purin-9-yl)-3-ethynyltetrahydrofuran-2-yl)methoxy)-2-((2-(methoxycarbonyl)-[1,1'-biphenyl]-4-yl)methyl)malonate (70 mg, 70.53 umol, 1 eq) in DCM (2 mL) was added TFA (0.5 mL, 6.75 mmol, 96 eq). The mixture was stirred at 20° C. for 2 h before it was quenched with saturated aq. $NaHCO_3$ to pH 7-8 and extracted with EtOAc (3×10 mL). The combined organic layer was washed with water (2×8 mL) and brine (8 mL), dried over anhydrous $Na_2SO_4$, filtered and concentrated. The crude residue was purified by preparative TLC (petroleum ether:EtOAc=1:1) to give diethyl 2-(((2R,3R,4R,5R)-3,4-diacetoxy-5-(6-amino-2-chloro-9H-purin-9-yl)-3-ethynyltetrahydro-furan-2-yl)-methoxy)-2-((2-(methoxycarbonyl)-[1,1'-biphenyl]-4-yl)methyl)malonate (40 mg, 71% yield) as a colorless syrup.

Step 3:

To a solution of diethyl 2-(((2R,3R,4R,5R)-3,4-diacetoxy-5-(6-amino-2-chloro-9H-purin-9-yl)-3-ethynyltetrahydrofuran-2-yl)methoxy)-2-((2-(methoxy-carbonyl)-[1,1'-biphenyl]-4-yl)methyl)malonate (30 mg, 37.87 umol, 1 eq) in THF (1 mL) was added 1M aq. LiOH (568 uL, 15 eq). The mixture was stirred at 25° C. for 20 h before it was diluted with water (1 mL) and extracted with EtOAc (3×2 mL). The organic layer was discarded. The pH of the water phase was adjusted to 2 with 2N aq. HCl to produce a precipitate. The precipitate was collected by filtration to give desired product (28 mg) as the first crop. The aq. phase was further extracted with EtOAc (4×2 mL). The combined organic layer was dried over anhydrous $Na_2SO_4$, filtered and concentrated to provide the second crop (10 mg) as a white solid. These two crops were combined and purified by preparative HPLC and the fraction was lyophilized to give the title compound (8.0 mg, 33% yield) as a white solid.

$^1$H NMR (400 MHz, CD3OD) δ ppm 8.21 (s, 1H), 7.66 (s, 1H), 7.46 (br d, J=7.6 Hz, 1H), 7.24-7.32 (m, 3H), 7.12 (dd, J=7.1, 2.3 Hz, 2H), 7.07 (d, J=7.9 Hz, 1H), 5.99 (d, J=7.4 Hz, 1H), 4.84 (br s, 1H), 4.33 (br s, 1H), 4.02-4.16 (m, 2H), 3.43-3.60 (m, 2H), 3.03 (s, 1H); LC/MS [M+H]=638.2.

Example 14

Synthesis of 2-benzyl-2-(((2R,3S,4R,5R)-5-(2-chloro-6-phenyl-9H-purin-9-yl)-3-ethynyl-3,4-dihydroxytetrahydrofuran-2-yl)methoxy)malonic acid

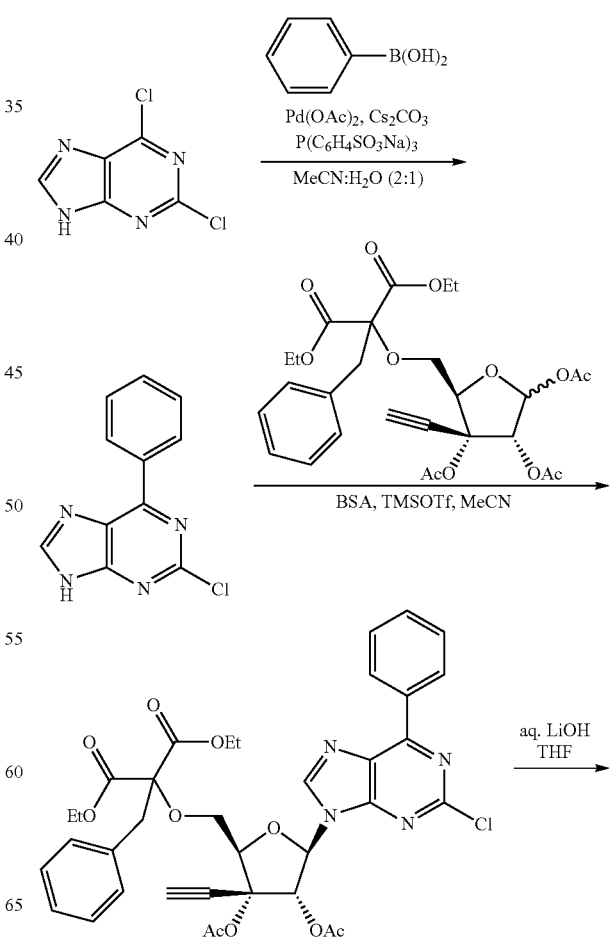

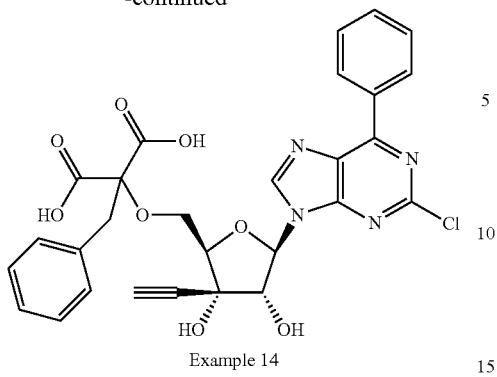

Example 14

Step 1:
To a solution of 2,6-dichloroadenine (0.8 g, 4.23 mmol, 1 eq) in H$_2$O (10 mL) and MeCN (5 mL) was added phenylboronic acid (464.49 mg, 3.81 mmol, 0.9 eq), Cs$_2$CO$_3$ (3.45 g, 10.58 mmol, 2.5 eq), Pd(OAc)$_2$ (47.51 mg, 211.64 umol, 0.05 eq) and trisodium; 3-bis(3-sulfonatophenyl)phosphanylbenzenesulfonate (601.50 mg, 1.06 mmol, 0.25 eq) at 20° C. under N$_2$ atmosphere. The mixture was stirred at 110° C. for 2 h before it was allowed to cool and diluted with H$_2$O (50 mL). The reaction mixture was extracted with EtOAc (5×50 mL). The combined organic layer was washed with brine (50 mL), dried over Na$_2$SO$_4$, filtered and concentrated. The crude product was triturated with a mixture of petroleum ether (9 mL) and EtOAc (3 mL) to provide 2-chloro-6-phenyl-9H-purine (140 mg, 14% yield) as a yellow solid.

Step 2:
To a solution of 2-chloro-6-phenyl-9H-purine (321.05 mg, 585.30 umol, 1 eq) in MeCN (0.5 mL) was added diethyl 2-benzyl-2-(((2R,3R,4R)-3,4,5-triacetoxy-3-ethynyltetra-hydrofuran-2-yl)methoxy)malonate (135 mg, 585.30 umol, 1 eq) and BSA (347 uL, 1.40 mmol, 2.4 eq) at 15° C. The mixture was stirred at 65° C. for 30 min as it became clear. The mixture was cooled to 0° C. and followed by dropwise addition of TMSOTf (126.91 uL, 702.35 umol, 1.2 eq). The mixture was stirred for 0° C. 10 min and then at 65° C. for 3 h before it was cooled and quenched with saturated aq. NaHCO$_3$ (40 mL). The reaction mixture was extracted with EtOAc (2×30 mL). The combined organic layer was washed with brine (40 mL) and dried over Na$_2$SO$_4$, filtered and concentrated. The crude product was purified by flash silica gel column chromatography (petroleum:EtOAc=1:0-1:1) first and then by preparative TLC (petroleum:EtOAc=1:1) to provide diethyl 2-benzyl-2-(((2R,3R,4R,5R)-3,4-diacetoxy-5-(2-chloro-6-phenyl-9H-purin-9-yl)-3-ethynyltetrahydrofuran-2-yl)methoxy)malonate (135 mg) as a yellow gum.

Step 3:
To a solution of diethyl 2-benzyl-2-(((2R,3R,4R,5R)-3,4-diacetoxy-5-(2-chloro-6-phenyl-9H-purin-9-yl)-3-ethynyltetrahydrofuran-2-yl)methoxy)malonate (135 mg, 187.73 umol, 1 eq) in THF (2 mL) was added LiOH.H$_2$O (78.77 mg, 1.88 mmol, 10 eq) in H$_2$O (0.2 mL) at 20° C. The mixture was stirred at 45° C. for 2 h before it was diluted with H$_2$O (10 mL) and with EtOAc (2 mL). The organic layer was discarded and the aqueous phase was acidified with 2N aq. HCl to pH 2-3. Then the aqueous phase was extracted with EtOAc (3×20 mL). The combined organic layer was washed with brine (30 mL), dried over Na$_2$SO$_4$, filtered and concentrated. The crude product was purified by preparative HPLC to provide the title compound (27.6 mg, 24% yield) as a white solid.

$^1$H NMR (400 MHz, DMSO-d$_6$) δ ppm 9.23 (s, 1H), 8.75-8.81 (m, 2H), 7.61-7.68 (m, 3H), 7.07-7.22 (m, 5H), 6.03 (d, J=6.53 Hz, 1H), 4.62 (d, J=6.53 Hz, 1H), 4.20 (dd, J=6.90, 2.64 Hz, 1H), 3.72 (br dd, J=9.91, 7.15 Hz, 2H), 3.55 (s, 1H), 3.03 (br d, J=1.51 Hz, 2H); LC/MS [M+H]=579.1.

Example 15

Synthesis of 2-allyl-2-(((2R,3S,4R,5R)-5-(6-amino-2-chloro-9H-purin-9-yl)-3-ethynyl-3,4-dihydroxytetrahydrofuran-2-yl)methoxy)malonic acid

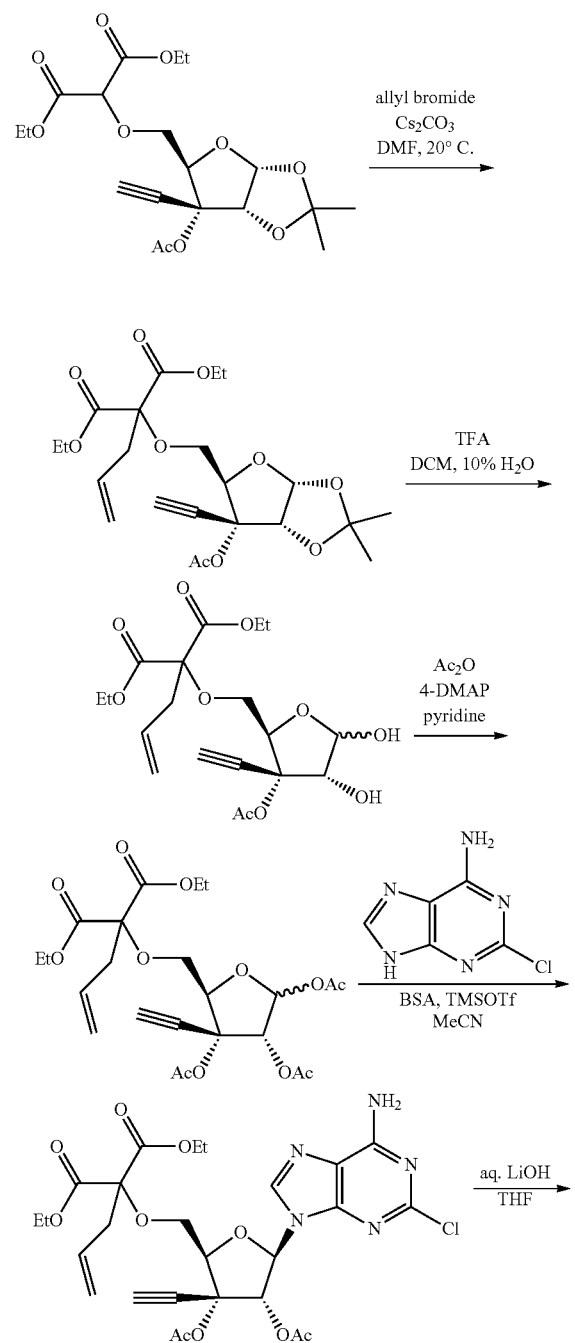

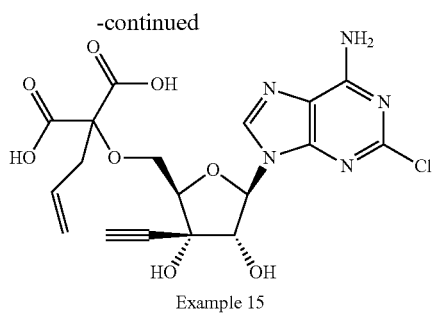

Example 15

Step 1:

To a solution of diethyl 2-(((3aR,5R,6R,6aR)-6-acetoxy-6-ethynyl-2,2-dimethyltetra-hydrofuro[2,3-d][1,3]dioxol-5-yl)methoxy)malonate (600 mg, 1.45 mmol, 1 eq) in DMF (1 mL) was added allyl bromide (263 mg, 2.17 mmol, 1.5 eq) and $Cs_2CO_3$ (943 mg, 2.90 mmol, 2 eq). The mixture was stirred at 20° C. for 2 h before it was diluted with water (15 mL) and extracted with EtOAc (4×10 mL). The combined organic phase was washed with water (10 mL), brine (10 mL), dried over anhydrous $Na_2SO_4$, filtered and concentrated to provide crude diethyl 2-(((3aR,5R,6R,6aR)-6-acetoxy-6-ethynyl-2,2-dimethyltetrahydro-furo[2,3-d][1,3]-dioxol-5-yl)methoxy)-2-allylmalonate (685 mg) as a colorless gum.

Step 2:

To a solution of crude diethyl 2-(((3aR,5R,6R,6aR)-6-acetoxy-6-ethynyl-2,2-dimethyltetrahydrofuro[2,3-d][1,3]dioxol-5-yl)methoxy)-2-allylmalonate (685 mg, 1.51 mmol, 1 eq) in DCM (5 mL) was added TFA (5 mL, 67.53 mmol, 45 eq) and $H_2O$ (1 mL, 55.51 mmol, 37 eq). The mixture was stirred at 20° C. for 16 h before it was diluted with water (15 mL) and adjusted the pH to 7-8 with solid $NaHCO_3$. The reaction mixture was extracted with a mixture of DCM and MeOH (4×12 mL; 10:1/v:v). The combined extract was washed with saturated aq. $NaHCO_3$ (8 mL), brine (8 mL), dried over anhydrous $Na_2SO_4$, filtered and concentrated under reduced pressure to give crude diethyl 2-(((2R,3S,4R)-3-acetoxy-3-ethynyl-4,5-dihydroxytetrahydrofuran-2-yl)methoxy)-2-allylmalonate (580 mg) as a yellow gum.

Step 3:

To a solution of crude diethyl 2-(((2R,3S,4R)-3-acetoxy-3-ethynyl-4,5-dihydroxytetra-hydrofuran-2-yl)methoxy)-2-allylmalonate (580 mg, 1.40 mmol, 1 eq) in pyridine (5 mL) was added $Ac_2O$ (1.31 mL, 14.00 mmol, 10 eq) and 4-DMAP (513 mg, 4.20 mmol, 3 eq). The mixture was stirred at 20° C. for 15 before it was diluted with water (15 mL) and extracted with EtOAc (3×10 mL). The combined extract was washed with 0.5 N aq. HCl (2×8 mL), $NaHCO_3$ (2×8 mL), brine (8 mL), dried over anhydrous $Na_2SO_4$, filtered and concentrated under reduced pressure. The crude product was purified by silica gel column chromatography (petroleum ether:EtOAc=5:1-2:1) to give (420 mg, 60% yield) as a colorless gum.

Step 4:

To a mixture of diethyl 2-allyl-2-(((2R,3R,4R)-3,4,5-triacetoxy-3-ethynyltetra-hydrofuran-2-yl)methoxy)malonate (360 mg, 722.20 umol, 1 eq) and 2-chloro-9H-purin-6-amine (135 mg, 794.42 umol, 1.1 eq) in MeCN (5 mL) was added BSA (446.28 uL, 1.81 mmol, 2.5 eq) at 25° C. under $N_2$ atmosphere. The mixture was stirred at 65° C. for 0.5 h. The reaction mixture was cooled to 0° C. and followed by dropwise addition of TMSOTf (261.00 uL, 1.44 mmol, 2 eq) in MeCN (1 mL). The mixture was stirred at 65° C. for 3 h before it was allowed to cooled and quenched with saturated aq. $NaHCO_3$ solution (15 mL). Then the mixture was extracted with EtOAc (4×10 mL), washed with saturated brine (8 mL), dried over anhydrous $Na_2SO_4$, filtrated and concentrated. The crude product was purified by Combi-flash on silica gel (20-40% EtOAc in petroleum ether) to give diethyl 2-allyl-2-(((2R,3R,4R,5R)-3,4-diacetoxy-5-(6-amino-2-chloro-9H-purin-9-yl)-3-ethynyltetra-hydrofuran-2-yl)methoxy)malonate (190 mg) as a colorless gum.

Step 5:

To a solution of diethyl 2-allyl-2-(((2R,3R,4R,5R)-3,4-diacetoxy-5-(6-amino-2-chloro-9H-purin-9-yl)-3-ethynyltetrahydrofuran-2-yl)methoxy)malonate (100 mg, 164.47 umol, 1 eq) in THF (0.5 mL) was added $LiOH \cdot H_2O$ (6.90 mg, 164.47 umol, 1 eq). The mixture was stirred at 50° C. for 1 h before it was diluted with water (6 mL) and extracted with EtOAc (3×4 mL). The organic layer was discarded. The pH of the aq. phase was adjusted to 2 with 2N aq. HCl solution. The aq. phase was then extracted with EtOAc (4×6 mL). The combined organic phases was washed with brine (6 mL), dried over anhydrous $Na_2SO_4$, filtered and concentrated to provide a solid. The solid was dissolved in a mixture of MeCN (1 mL) and water (1 mL) and then lyophilizied directly to give the title compound (65.2 mg, 83% yield) as a white solid.

$^1$H NMR (400 MHz, CD3OD) δ ppm 8.83 (s, 1H) 6.05 (d, J=7.5 Hz, 1H) 5.84 (br dd, J=17.2, 10.2 Hz, 1H) 5.15 (dd, J=17.2, 1.6 Hz, 1H) 4.99-5.05 (m, 2H) 4.27 (t, J=2.5 Hz, 1H) 4.00 (dd, J=10.2, 2.6 Hz, 1H) 3.79 (dd, J=10.3, 2.8 Hz, 1H) 3.06 (s, 1H) 2.88 (d, J=7.3 Hz, 2H); LC/MS [M+H]=467.9.

Example 16

Synthesis of 2-(((2R,3S,4R,5R)-5-(6-amino-2-chloro-9H-purin-9-yl)-3-ethynyl-3,4-dihydroxytetra-hydrofuran-2-yl)methoxy)-2-ethylmalonic acid

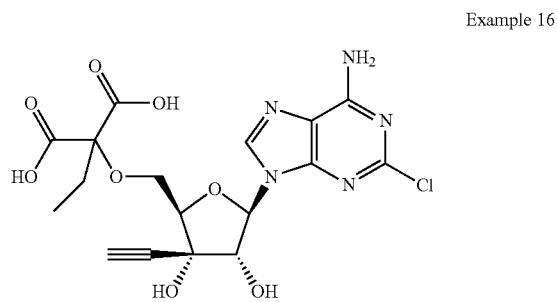 [SMILES: C#C[C@@]1(O)[C@@H](COC(CC)(C(=O)O)C(=O)O)O[C@@H](n2cnc3c(N)nc(Cl)nc32)[C@@H]1O]

Example 16

Proceeding as described in Example 15 above but substituting allyl bromide with EtBr provided the title compound as a white solid.

$^1$H NMR (400 MHz, DMSO-$d_6$) δ ppm 8.53-8.83 (m, 1H) 7.81 (br s, 2H) 5.91-6.40 (m, 2H) 5.83 (d, J=7.88 Hz, 1H) 4.91 (d, J=7.75 Hz, 1H) 4.14 (t, J=2.88 Hz, 1H) 3.75 (dd, J=10.26, 3.25 Hz, 1H) 3.56 (s, 1H) 3.47-3.51 (m, 1H) 1.93-2.04 (m, 2H) 0.76 (t, J=7.38 Hz, 3H); LC/MS [M+H]= 455.9.

Example 17

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-methylmalonic acid

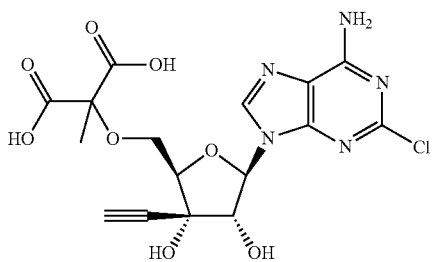

Example 17

Proceeding as described in Example 15 above but substituting allyl bromide with methyl bromide provided the title compound as a white solid.

$^1$H NMR (400 MHz, DMSO-d$_6$) δ ppm 13.38 (br s, 2H) 8.69 (s, 1H) 7.82 (br s, 2H) 6.17 (br s, 1H) 5.98 (br d, J=7.25 Hz, 1H) 5.82 (d, J=7.63 Hz, 1H) 4.85 (brt, J=6.94 Hz, 1H) 4.15 (t, J=2.75 Hz, 1H) 3.83 (dd, J=10.13, 3.25 Hz, 1H) 3.53-3.65 (m, 2H) 1.52 (s, 3H); LC/MS [M+H]=441.8.

Example 18

Synthesis of 2-benzyl-2-(((2R,3S,4R,5R)-5-(2-chloro-6-(thiophen-2-yl)-9H-purin-9-yl)-3-ethynyl-3,4-dihydroxytetrahydrofuran-2-yl)methoxy)malonic acid

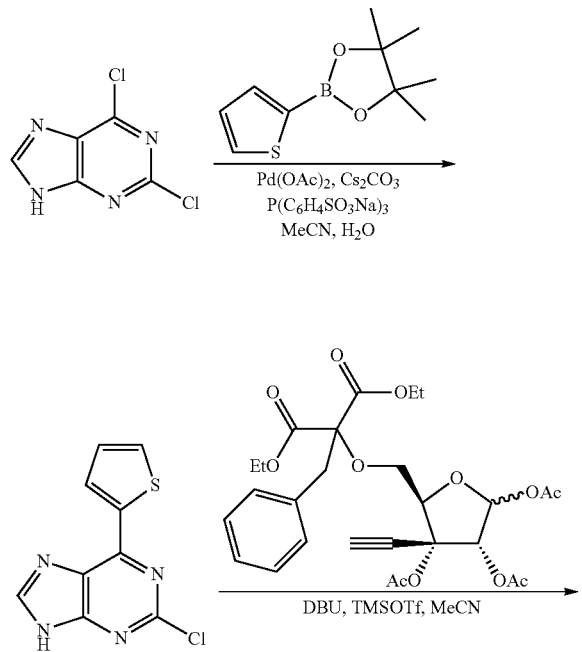

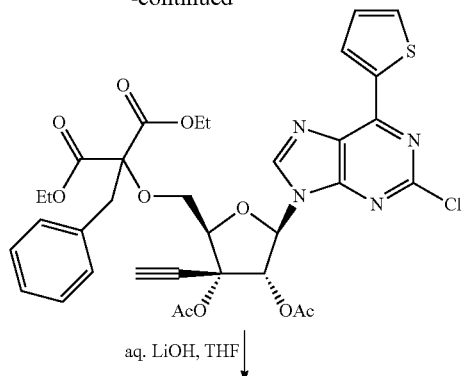

aq. LiOH, THF

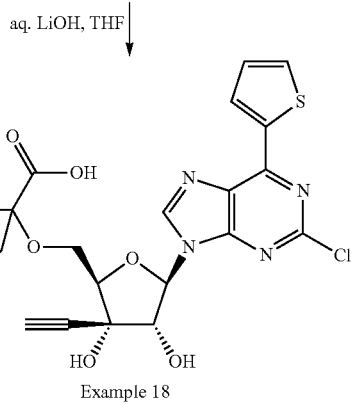

Example 18

Step 1:

To a mixture of 2-chloroadenine (800 mg, 4.23 mmol, 1 eq) in MeCN (5 mL) and H$_2$O (10 mL) at 20° C. under N$_2$ atmosphere was added 4,4,5,5-tetramethyl-2-(thiophen-2-yl)-1,3,2-dioxaborolane (800.37 mg, 3.81 mmol, 0.9 eq), Pd(OAc)$_2$ (47.51 mg, 211.64 umol, 0.05 eq), Cs$_2$CO$_3$ (3.45 g, 10.58 mmol, 2.5 eq) and triphenylphosphine-3,3'-3''-trisulfonic acid trisodium salt (601.50 mg, 1.06 mmol, 0.25 eq). The mixture was stirred at 110° C. for 3 h before it was allowed to cool and partitioned between EtOAc (3×20 mL) and H$_2$O (10 mL). The combined organic phase was washed with H$_2$O (2×10 mL), dried over Na$_2$SO$_4$, filtered and concentrated under reduced pressure. The crude product was triturated with (petroleum ether:EtOAc=3:1) and left standing for for 14 h. The precipitate was collected by suction filtration and dried to provide 2-chloro-6-(thiophen-2-yl)-9H-purine (190 mg, 19% yield) as a yellow solid.

Step 2:

To a mixture of 2-chloro-6-(thiophen-2-yl)-9H-purine (140 mg, 591.51 umol, 1 eq) and diethyl 2-benzyl-2-(((2R,3R,4R)-3,4,5-triacetoxy-3-ethynyltetrahydrofuran-2-yl)methoxy)malonate (324.47 mg, 591.51 umol, 1 eq) in MeCN (3 mL) at 0° C. was added DBU (267 uL, 1.77 mmol, 3 eq). The mixture was stirred at 0° C. for 10 min and followed by dropwise addition of TMSOTf (481 uL, 2.66 mmol, 4.5 eq). The mixture was stirred at 0° C. for 30 min and then at 65° C. under N$_2$ atmosphere for 14 h. The reaction mixture was allowed to cool and partitioned between EtOAc (3×20 mL) and saturated aq. NaHCO$_3$ (2×10 mL). The combined organic phase was washed with brine (2×20 mL), dried over Na$_2$SO$_4$, filtered and concentrated. The crude product was purified by preparative TLC (petroleum ether:EtOAc=2:1) to provide diethyl 2-benzyl-2-(((2R,3R,4R,5R)-3,4-diacetoxy-5-(2-chloro-6-(thiophen-2-yl)-9H-purin-9-yl)-3-ethynyltetrahydrofuran-2-yl)methoxy)-malonate (150 mg, 31% yield) as a white solid.

Step 3:

To a mixture of diethyl 2-benzyl-2-(((2R,3R,4R,5R)-3,4-diacetoxy-5-(2-chloro-6-(thiophen-2-yl)-9H-purin-9-yl)-3-ethynyltetrahydrofuran-2-yl)methoxy)malonate (150 mg, 206.85 umol, 1 eq) in THF (2 mL) was added LiOH.H$_2$O (2 M, 2 mL, 19.34 eq). The mixture was stirred at 25° C. for 2 h before it was partitioned between EtOAc (10 mL) and water (10 mL). The aqueous phase was adjusted to pH ~2 with 2M aq. HCl solution. The aqueous phase was partitioned between EtOAc (40 mL) and brine (20 mL), dried over anhydrous Na$_2$SO$_4$, filtered and concentrated under reduced pressure. The crude product was purified by preparative HPLC (column: YMC-Triart Prep C18 150*40 mm*7 um; mobile phase: [water (0.225% FA)-ACN]; B %: 43%-63%, 10 min) and lyophilized to provide the title compound (31.6 mg, 26% yield) as a white solid.

$^1$H NMR (400 MHz, DMSO-d$_6$) δ ppm 8.87 (s, 1H) 8.60 (dd, J=3.76, 1.25 Hz, 1H) 8.02 (dd, J=5.02, 1.00 Hz, 1H) 7.36 (dd, J=4.89, 3.89 Hz, 1H) 7.16-7.28 (m, 2H) 6.93-7.10 (m, 3H) 6.31 (br s, 1H) 6.11 (br d, J=6.02 Hz, 1H) 5.99 (d, J=7.53 Hz, 1H) 4.88-4.97 (m, 1H) 4.23 (dd, J=4.27, 2.76 Hz, 1H) 3.99 (br dd, J=10.42, 4.39 Hz, 1H) 3.84 (br d, J=8.53 Hz, 1H) 3.56 (s, 1H) 3.26 (s, 2H); LC/MS [M+H]=585.0.

Example 19

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(2-oxo-1-propy-1,2-dihydropyridin-3-yl)benzyl)malonic acid

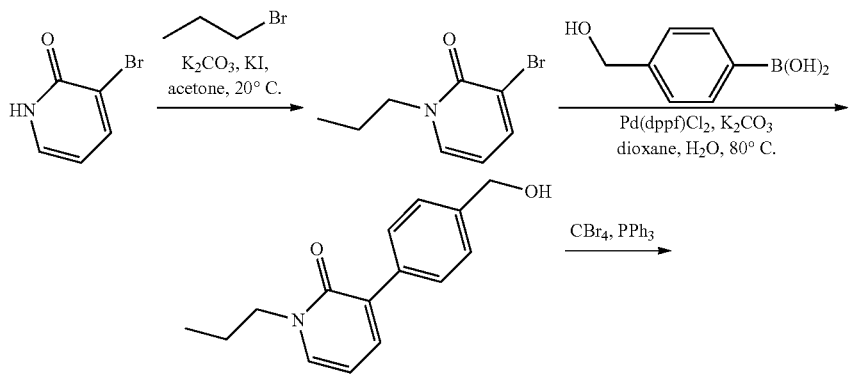

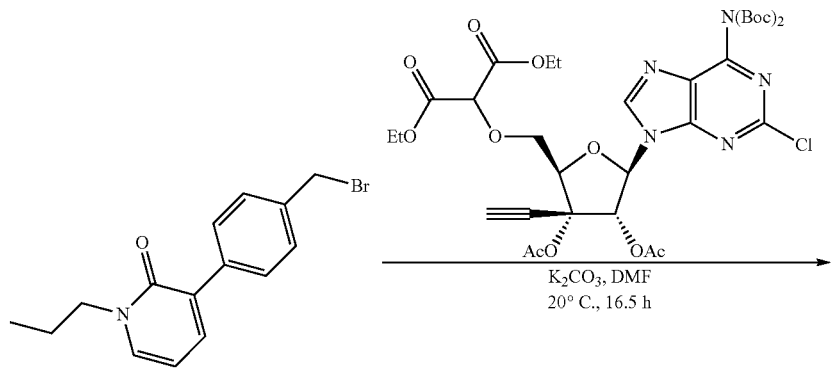

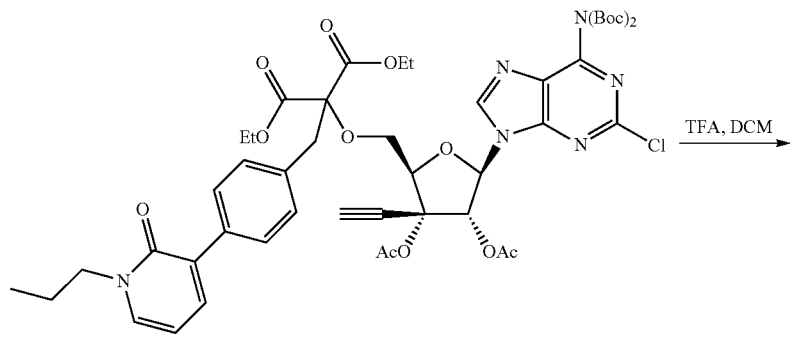

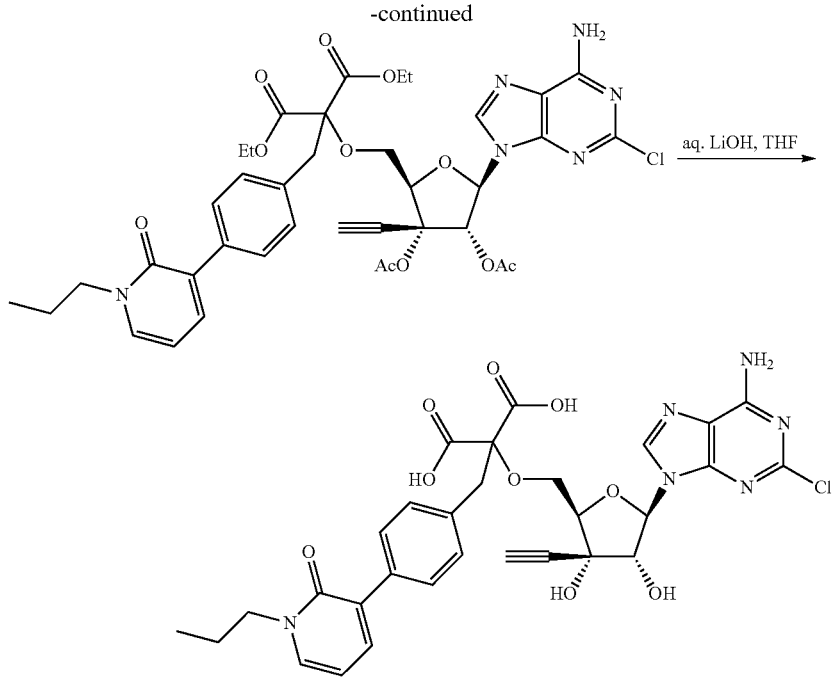

Example 19

Step 1:

To a solution of 3-bromopyridin-2(1H)-one (3 g, 17.24 mmol, 1 eq) in acetone (100 mL) was added $K_2CO_3$ (11.91 g, 86.21 mmol, 5 eq). The suspension was stirred at 20° C. for 0.5 h and followed by addition of 1-bromopropane (4.71 mL, 51.73 mmol, 3 eq) and KI (859 mg, 5.17 mmol, 0.3 eq). The mixture was stirred at 20° C. for 16 h. Additional amount of 1-bromopropane (1.0 g) was added to the reaction mixture and the mixture was stirred further at 20° C. for 3 h. The reaction was diluted with water (50 mL) and extracted with EtOAc (3×40 mL). The combined organic layer was washed with brine (100 mL), and dried over anhydrous $Na_2SO_4$, filtered and concentrated. The residue was purified by Combi-Flash (silica gel, 20-60% EtOAc in petroleum ether) to provide 3-bromo-1-propylpyridin-2(1H)-one (1.23 g, 33% yield) as a clear oil.

Step 2:

To a solution of 3-bromo-1-propylpyridin-2(1H)-one (1.79 g, 8.28 mmol, 1 eq) and (4-(hydroxymethyl)phenyl) boronic acid (1.38 g, 9.11 mmol, 1.1 eq) in dioxane (18 mL) was added $K_2CO_3$ (3.43 g, 24.84 mmol, 3 eq), Pd(dppf)$Cl_2$ (606 mg, 828.00 umol, 0.1 eq) and $H_2O$ (6 mL). The mixture was degassed with $N_2$ for 10 min and then stirred at 80° C. for 16 h under $N_2$ atmosphere. The reaction mixture was cooled and filtered. The filtrate was concentrated. The residue was purified by Combi Flash (silica gel, 30-50% of EtOAc in petroleum ether) to provide 3-(4-(hydroxymethyl) phenyl)-1-propylpyridin-2(1H)-one (1.84 g, 91% yield) as a brown solid.

Step 3:

To a solution of $PPh_3$ (1.94 g, 7.40 mmol, 6 eq) in DCM (15 mL) was added $CBr_4$ (2.45 g, 7.40 mmol, 6 eq) at −25° C. The yellow solution was stirred at −25° C. for 1 h and followed by addition of 3-(4-(hydroxymethyl)phenyl)-1-propylpyridin-2(1H)-one (300 mg, 1.23 mmol, 1 eq) in DCM (3 mL) dropwise. The yellow suspension was stirred at −25° C. for 0.5 h to produce a yellow suspension. The reaction mixture was diluted with MTBE (50 mL) to produce more precipitate. The precipitate was filtered off and the filtrate was concentrated. The residue was purified by CombiFlash (silica gel column, 10-100% of EtOAc in petroleum ether) to provide 3-(4-(bromomethyl)phenyl)-1-propylpyridin-2(1H)-one (243 mg, 64% yield) as a clear oil.

Step 4:

To a solution of diethyl 2-(((2R,3R,4R,5R)-3,4-diacetoxy-5-(6-N,N'-(bis-(tert-butoxycarbonyl)amino)-2-chloro-9H-purin-9-yl)-3-ethynyltetrahydrofuran-2-yl) methoxy)-malonate (554 mg, 721.20 umol, 1 eq) in DMF (5 mL) was added $K_2CO_3$ (299.03 mg, 2.16 mmol, 3 eq). The mixture was stirred at 20° C. for 0.5 h and followed by addition of 3-(4-(bromomethyl)phenyl)-1-propylpyridin-2 (1H)-one (242.91 mg, 793.32 umol, 1.1 eq). The mixture was stirred at 20° C. for 16 h before it was diluted with water (30 mL) and extracted by EtOAc (4×20 mL). The combined organic layer was washed with water (100 mL), dried over anhydrous $Na_2SO_4$, filtered and concentrated. The residue was purified by Combi Flash (silica gel, 20-30% of EtOAc in petroleum ether to provide diethyl 2-(((2R,3R,4R,5R)-3, 4-diacetoxy-5-(6-N,N'-(bis-(tert-butoxycarbonyl)amino)-2-chloro-9H-purin-9-yl)-3-ethynyl-tetrahydrofuran-2-yl) methoxy)-2-(4-(2-oxo-1-propyl-1,2-dihydropyridin-3-yl) benzyl)-malonate (209 mg) as a colorless gum.

Step 5:

To a solution of diethyl 2-(((2R,3R,4R,5R)-3,4-diacetoxy-5-(6-N,N'-(bis-(tert-butoxy-carbonyl)amino)-2-chloro-9H-purin-9-yl)-3-ethynyltetrahydrofuran-2-yl) methoxy)-2-(4-(2-oxo-1-propyl-1,2-dihydropyridin-3-yl) benzyl)malonate (209 mg, 210.38 umol, 1 eq) in DCM (2 mL) at 0° C. was added TFA (0.7 mL, 9.45 mmol, 44.94 eq). The solution was stirred at 20° C. for 2 h before it was quenched by saturated aq. $NaHCO_3$(5 mL) and extracted with EtOAc (4×10 mL). The combined organic layer was dried over anhydrous $Na_2SO_4$, filtered and concentrated. The residue was purified by Combi Flash (silica gel, 30-70% of EtOAc in petroleum ether) to provide diethyl 2-(((2R, 3R,4R, S5R)-3,4-diacetoxy-5-(6-amino-2-chloro-9H-purin-9-yl)-3-ethynyltetrahydrofuran-2-yl)methoxy)-2-(4-(2-oxo-1-propyl-1,2-dihydro-pyridin-3-yl)benzyl)malonate (91 mg, 55% yield) as a white solid.

Step 6:

To a solution of diethyl 2-(((2R,3R,4R,5R)-3,4-diacetoxy-5-(6-amino-2-chloro-9H-purin-9-yl)-3-ethynyltetrahydrofuran-2-yl)methoxy)-2-(4-(2-oxo-1-propyl-1,2-dihydro-pyridin-3-yl)benzyl)malonate (91 mg, 114.72 umol, 1 eq) in THF (1 mL) was added 1N aq.

LiOH (1 mL). The mixture was stirred at 20° C. for 2.5 h before it was diluted with water (5 mL) and the resulting solution was washed with EtOAc (2×10 mL). The organic extract was discarded. The aqueous layer acidified to pH 2 with 2N aq. HCl and then extracted with EtOAc (4×8 mL). The combined organic layer was dried over anhydrous Na₂SO₄, filtered and concentrated. The residue was dissolved in a mixture of MeOH (5 mL) and water (20 mL) and was dried by lyophilization to provide thet title compound (51 mg, 67% yield) as a white solid.

¹H NMR (400 MHz, CD₃OD) δ ppm 8.08 (s, 1H), 7.53 (dd, J=6.80, 2.0 Hz, 1H), 7.28-7.39 (m, 5H), 6.34 (t, J=6.9 Hz, 1H), 5.96 (d, J=7.6 Hz, 1H), 4.77 (d, J=7.6 Hz, 1H), 4.28 (s, 1H), 4.07-4.15 (m, 1H), 4.01 (dd, J=10.3, 2.8 Hz, 1H), 3.92 (t, J=7.4 Hz, 2H), 3.39-3.58 (m, 2H), 3.06 (s, 1H), 1.65-1.80 (m, 2H), 0.94 (t, J=7.4 Hz, 3H); LC/MS [M+H]= 653.1.

Example 20

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(1-ethyl-2-oxo-1,2-dihydropyridin-3-yl)benzyl)malonic acid

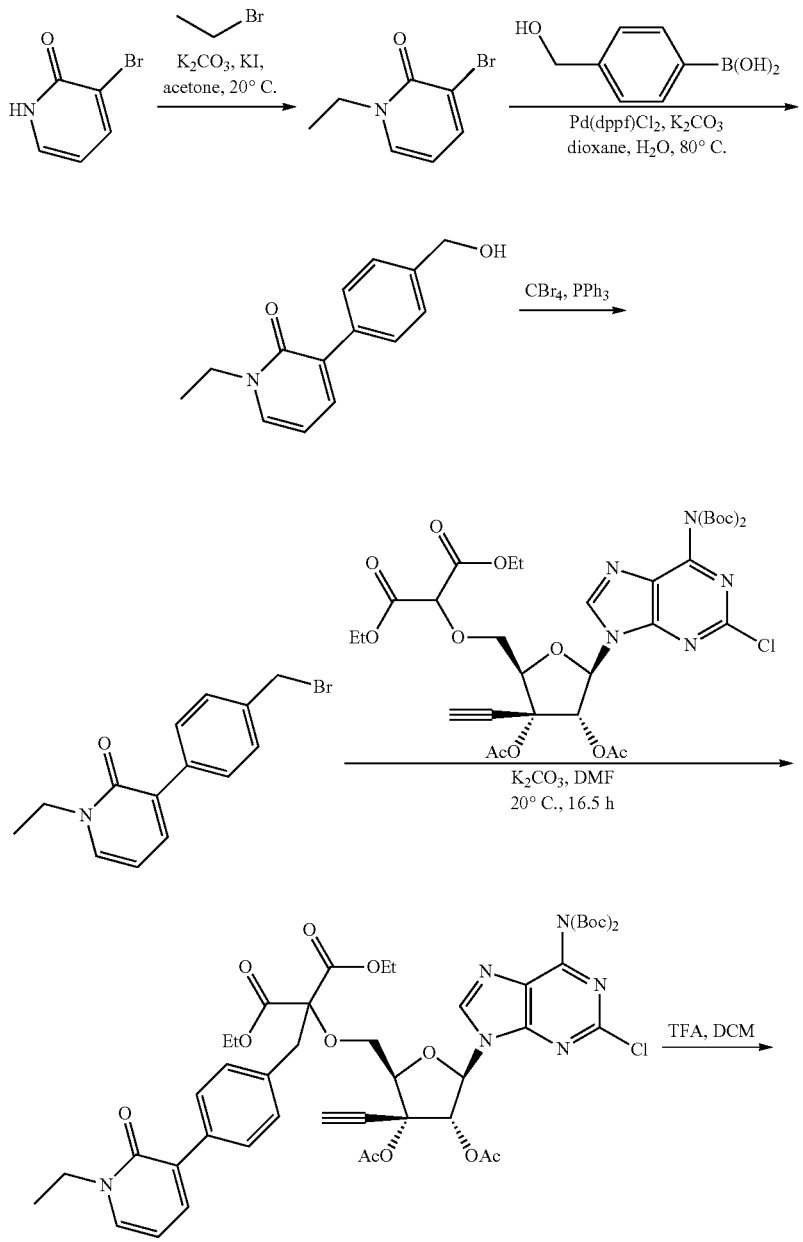

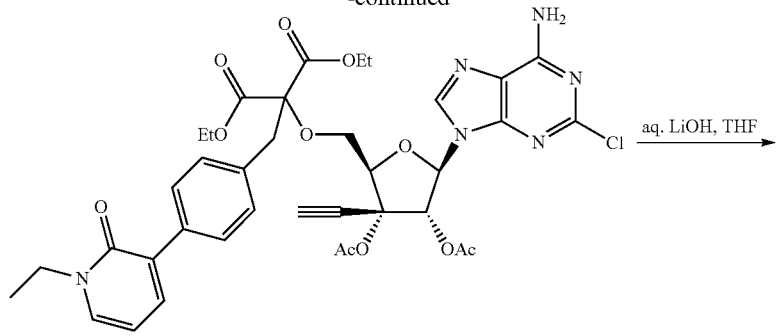

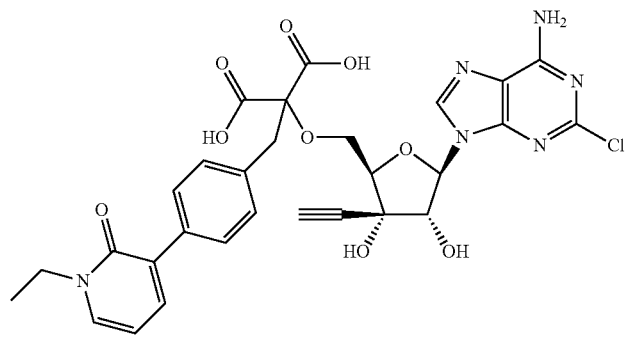

Example 20

Proceeding as described in Example 19 above but substituting propyl bromide with ethyl bromide provided the title compound as a white solid.

$^1$H NMR (400 MHz, CD3OD) δ ppm 8.15 (s, 1H), 7.53 (dd, J=6.6, 1.3 Hz, 1H), 7.25-7.38 (m, 5H), 6.32 (t, J=6.9 Hz, 1H), 5.96 (d, J=7.6 Hz, 1H), 4.78 (d, J=7.5 Hz, 1H), 4.30 (s, 1H), 4.09-4.15 (m, 1H), 3.95-4.04 (m, 3H), 3.39-3.58 (m, 2H), 3.06 (s, 1H), 1.28-1.32 (m, 3H); LC/MS [M+H]=639.1.

Example 21

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(1-(2-hydroxyethyl)-2-oxo-1,2-dihydropyridin-3-yl)benzyl)malonic acid

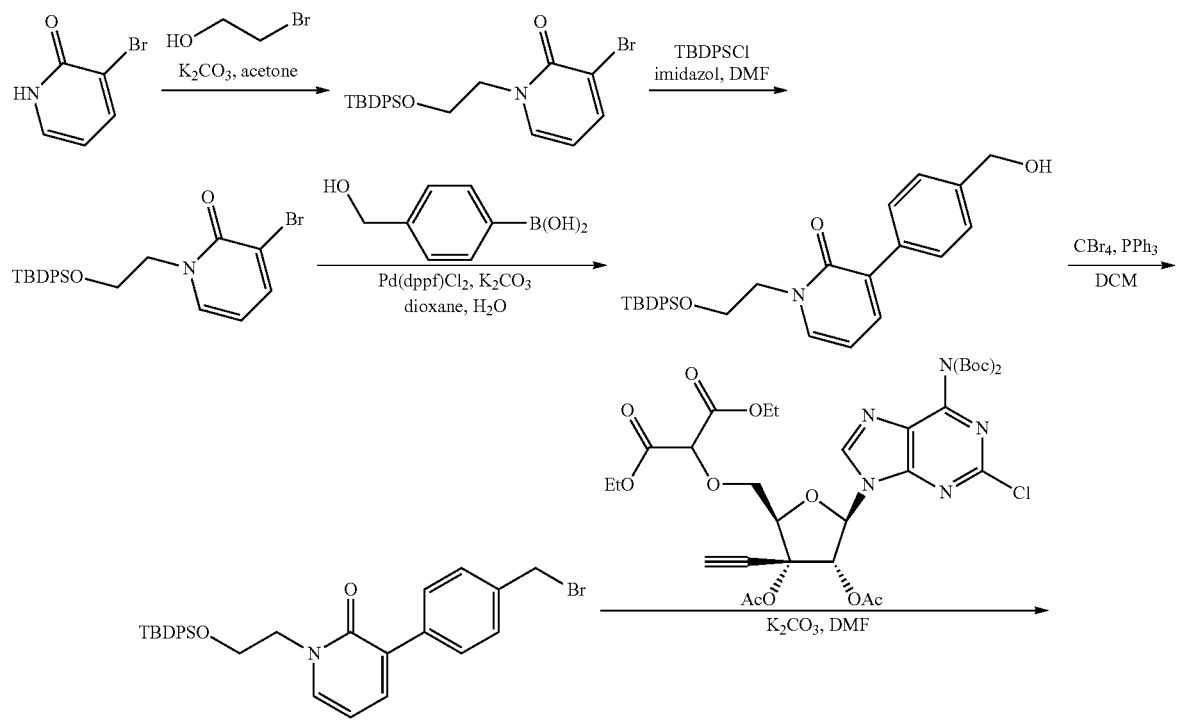

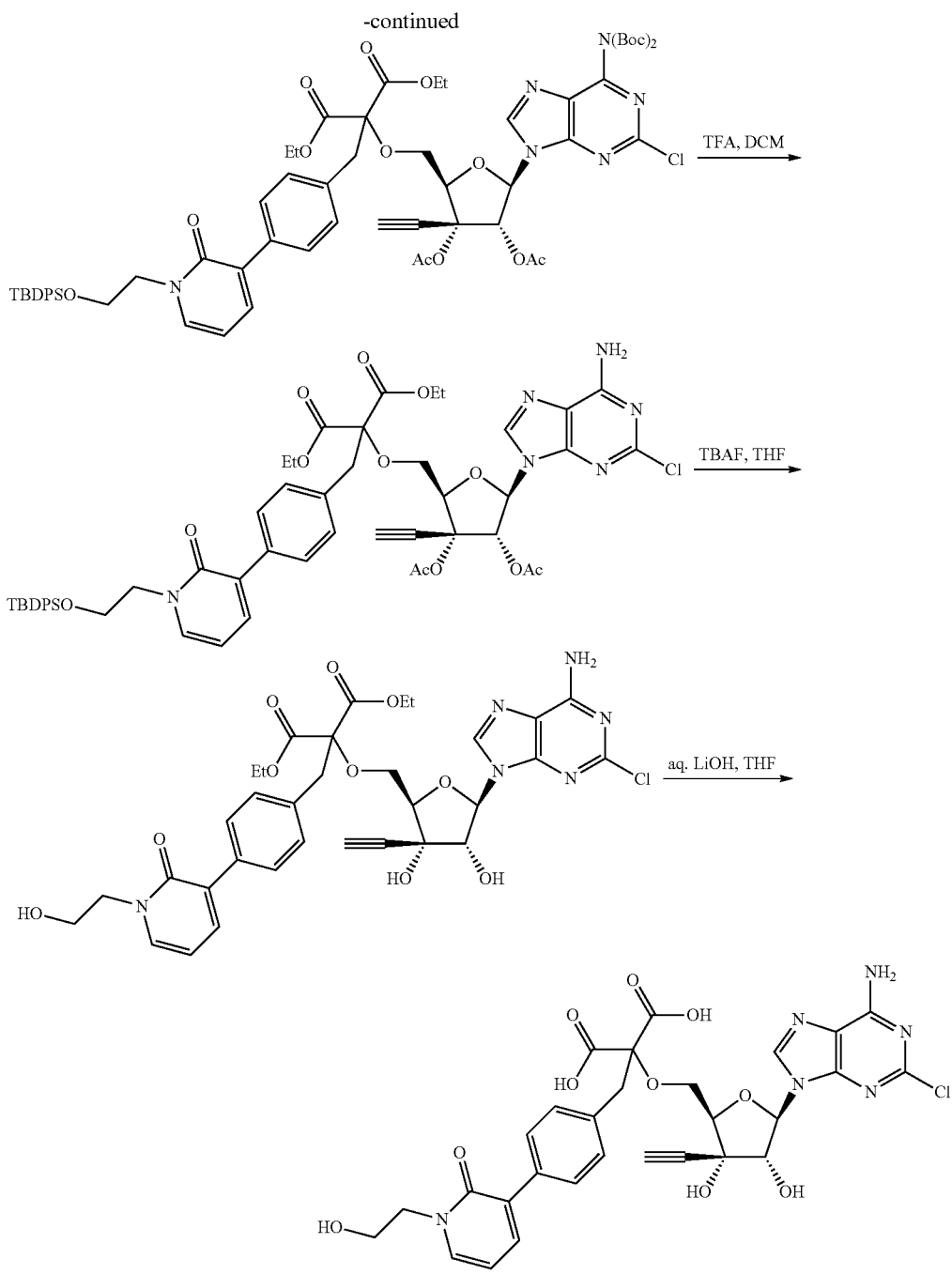

Example 21

Step 1:

To a mixture of 3-bromopyridin-2(1H)-one (3 g, 17.24 mmol, 1 eq) in acetone (100 mL) at 20° C. was added KI (859 mg, 5.17 mmol, 0.3 eq), $K_2CO_3$ (5.96 g, 43.10 mmol, 2.5 eq) and 2-bromoethanol (4.90 mL, 68.97 mmol, 4 eq). The mixture was stirred for 4 before it was filtered and the filter cake was washed with EtOAc (100 mL). The filtrate was concentrated under reduced pressure to give a residue. The residue was purified by flash silica gel column chromatography (petroleum ether:EtOAc=5:1 to 0:1) to provide 3-bromo-1-(2-hydroxyethyl)pyridin-2(1H)-one (2.2 g, 59% yield) as a yellow gum.

Step 2:

To a mixture of 3-bromo-1-(2-hydroxyethyl)pyridin-2 (1H)-one (2.2 g, 10.09 mmol, 1 eq) in DMF (15 mL) at 20° C. was added imidazole (1.72 g, 25.22 mmol, 2.5 eq) and TBDPSCl (5.18 mL, 20.18 mmol, 2 eq). The mixture was stirred for 2 h before it was diluted with $H_2O$ (60 mL) and extracted with EtOAc (3×30 mL). The combined extract was washed with saturated aq. $NH_4Cl$ (2×30 mL), brine (30 mL), dried over anhydrous $Na_2SO_4$, filtered and concentrated under reduced pressure. The residue was purified by flash silica gel column chromatography (petroleum ether:

EtOAc=1:0 to 6:1) to provide 3-bromo-1-(2-((tert-butyldiphenylsilyl)oxy)ethyl)-pyridin-2(1H)-one (3.75 g, 79% yield) as a light yellow oil.

Steps 3-8:

Proceeding as described in Example 19 above but substituting 3-(4-(bromomethyl)-phenyl)-1-propylpyridin-2(1H)-one with 3-bromo-1-(2-((tert-butyldiphenylsilyl)oxy)ethyl)-pyridin-2(1H)-one provided the title compound as a white solid.

¹H NMR (400 MHz, CD3OD) δ ppm 8.33 (s, 1H), 7.50-7.57 (m, 1H), 7.41-7.47 (m, 1H), 7.39 (d, J=8.13 Hz, 2H), 7.29 (br d, J=8.13 Hz, 2H), 6.35 (t, J=6.88 Hz, 1H), 5.98 (d, J=7.13 Hz, 1H), 4.71 (d, J=7.00 Hz, 1H), 4.30 (br s, 1H), 3.93-4.16 (m, 4H), 3.83 (m, 2H), 3.36-3.50 (m, 2H), 3.05 (s, 1H); LC/MS [M+H]=655.1.

Example 22

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(2-methoxypyridin-3-yl)benzyl)malonic acid

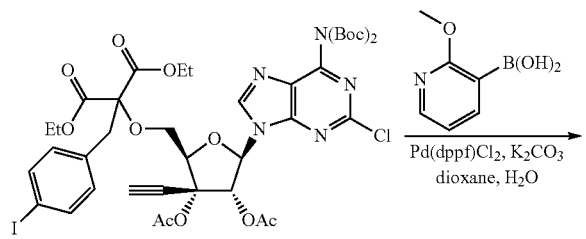

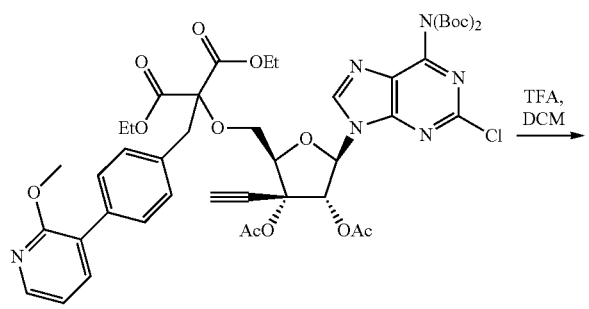

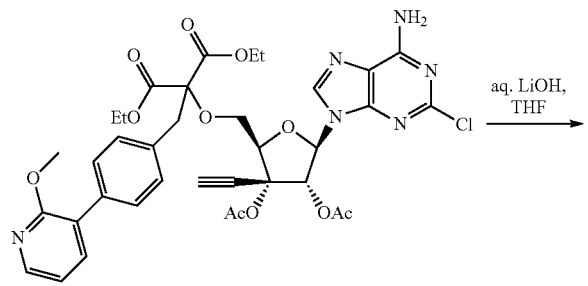

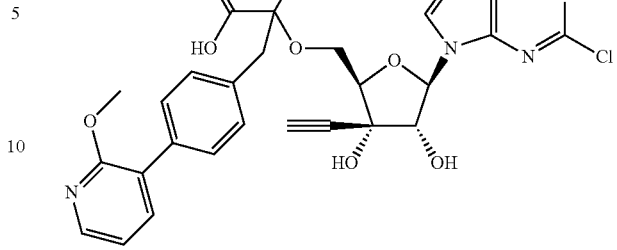

Example 22

Step 1:

To a solution of diethyl 2-(((2R,3R,4R,5R)-3,4-diacetoxy-5-(6-N,N'-(bis-(tert-butoxy-carbonyl)amino)-2-chloro-9H-purin-9-yl)-3-ethynyltetrahydrofuran-2-yl)methoxy)-2-(4-iodobenzyl)malonate (900 mg, 914.47 umol, 1 eq) and (2-methoxy-3-pyridyl)boronic acid (168 mg, 1.10 mmol, 1.2 eq) in dioxane (9 mL) 25° C. was added K₂CO₃ (379 mg, 2.74 mmol, 3 eq), Pd(dppf)Cl₂ (67 mg, 91.45 umol, 0.1 eq) and H₂O (3 mL). The mixture was degassed with N₂ for a while and then heated to 80° C. for 16 h before it was diluted with water (10 mL), and extracted with ethyl acetate (2×10 mL). The combined organic layer was dried by Na₂SO₄, filtered and concentrated. The crude product was purified by Combi-flash (silica gel, 10-50% of EtOAc in petroleum ether) to give diethyl 2-(((2R,3R,4R,5R)-3,4-diacetoxy-5-(6-N,N'-(bis-(tert-butoxycarbonyl)amino)-2-chloro-9H-purin-9-yl)-3-ethynyltetrahydro-furan-2-yl)methoxy)-2-(4-(2-methoxypyridin-3-yl)benzyl)malonate (117 mg, 13% yield) as a yellow gum.

Step 2:

To a solution of diethyl 2-(((2R,3R,4R,5R)-3,4-diacetoxy-5-(6-N,N'-(bis-(tert-butoxycarbonyl)amino)-2-chloro-9H-purin-9-yl)-3-ethynyltetrahydrofuran-2-yl)methoxy)-2-(4-(2-methoxypyridin-3-yl)benzyl)malonate (90 mg, 93.23 umol, 1 eq) in DCM (3 mL) was added TFA (0.4 mL, 5.40 mmol, 58 eq). The solution was stirred at 20° C. for 2 h before it was quenched with saturated aq. NaHCO₃ (4 mL) and extracted with EtOAc (3×4 mL). The combined organic layer was concentrated to give crude diethyl 2-(((2R,3R,4R,5R)-3,4-diacetoxy-5-(6-amino-2-chloro-9H-purin-9-yl)-3-ethynyltetrahydrofuran-2-yl)methoxy)-2-(4-(2-methoxypyridin-3-yl)benzyl)-malonate (42 mg) as a yellow gum.

Step 3:

To a solution of crude diethyl 2-(((2R,3R,4R,5R)-3,4-diacetoxy-5-(6-amino-2-chloro-9H-purin-9-yl)-3-ethynyltetrahydrofuran-2-yl)methoxy)-2-(4-(2-methoxy-pyridin-3-yl)benzyl)malonate (42 mg, 54.89 umol, 1 eq) in THF (2.5 mL) was added 1M aq. LiOH (0.8 mL, 15 eq). The reaction mixture was stirred at 20° C. for 4 h before it was acidified to pH 6 with 1N aq. HCl and concentrated. The crude product was purified by preparative HPLC and the fraction was dried by lyophilization to give the title compound (6 mg, 17% yield) as a white solid.

¹H NMR (400 MHz, CD3OD) δ ppm 8.10 (s, 1H), 8.01 (dd, J=4.94, 1.69 Hz, 1H), 7.48 (dd, J=7.25, 1.63 Hz, 1H), 7.24-7.35 (m, 4H), 6.93 (dd, J=7.32, 5.07 Hz, 1H), 5.97 (d, J=7.50 Hz, 1H), 4.89-4.96 (m, 1H), 4.29 (br s, 1H), 4.05 (br d, J=5.00 Hz, 2H), 3.76 (s, 3H), 3.51 (br d, J=14.76 Hz, 1H), 3.42 (br d, J=14.51 Hz, 1H), 3.01 (s, 1H); LC/MS [M+H]= 625.1.

Example 23

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(3-(trifluoromethoxy)benzyl)malonic acid

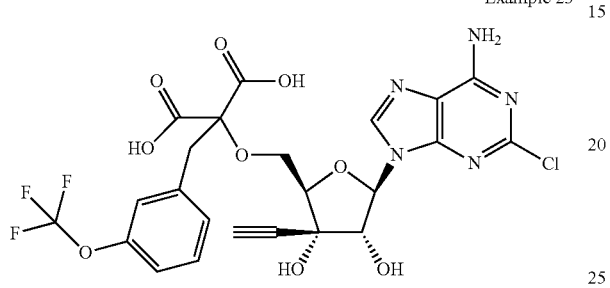

Example 23

Proceeding as described in Example 1 above but substituting benzyl bromide with 1-(bromomethyl)-4-(trifluoromethoxy)benzene provided the title compound as a white solid.

$^1$H NMR (CD$_3$OD, 300 MHz) δ 8.43 (s, 1H), 7.09-7.25 (m, 3H), 6.95-6.98 (d, J=8.1 Hz, 1H), 6.01-6.04 (d, J=7.32 Hz, 1H), 5.00-5.03 (d, J=7.41 Hz, 1H), 4.35-4.37 (t, J=3.33 Hz, 1H), 4.05-4.15 (m, 2H), 3.38-3.53 (q, J=15 Hz, 2H), 2.99 (s, 1H); LC/MS [M+H]=602.0.

Example 24

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(thiophen-3-ylmethyl)malonic acid

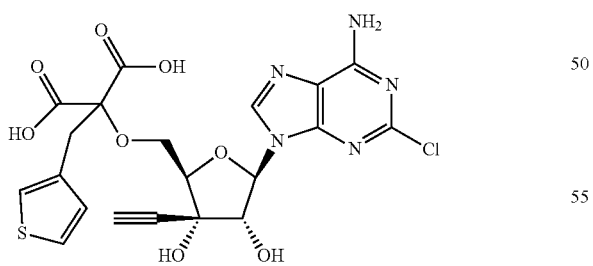

Example 24

Proceeding as described in Example 1 above but substituting benzyl bromide with 3-(bromomethyl)thiophene provided the title compound as a white solid.

$^1$H NMR (CD$_3$OD, 300 MHz) δ 8.39 (s, 1H), 7.09-7.17 (m, 2H), 6.98-7.00 (d, J=5.04.0 Hz, 1H), 6.01-6.04 (d, J=7.47 Hz, 1H), 5.00-5.02 (d, J=7.29 Hz, 1H), 4.32-4.34 (t, J=2.76 Hz, 1H), 4.01-4.11 (m, 2H), 3.41-3.54 (q, J=15 Hz, J=9.03 Hz, 2H), 2.98 (s, 1H); LC/MS [M+H]=524.0.

Example 25

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(prop-2-yn-1-yl)malonic acid

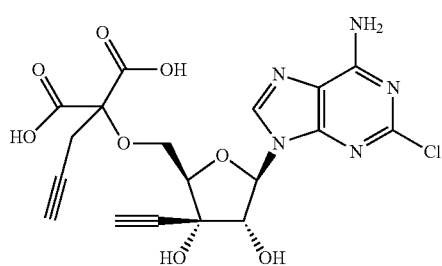

Example 25

Proceeding as described in Example 1 above but substituting benzyl bromide with propargyl bromide provided the title compound as a white solid.

$^1$H NMR (CD$_3$OD, 300 MHz) δ 8.96 (s, 1H), 6.07-6.09 (d, J=7.53 Hz, 1H), 5.01-5.04 (d, J=7.53 Hz, 1H), 4.29-4.30 (m, 1H), 3.92-4.05 (m, 2H), 3.01-3.15 (m, 2H), 2.99 (s, 1H), 2.28-2.30 (t, J=2.58 Hz, 1H); LC/MS [M+H]=467.

Example 26

Synthesis of 2-(((2R,3S,4R,5R)-5-(6-amino-2-chloro-9H-purin-9-yl)-3-ethynyl-3,4-dihydroxytetrahydrofuran-2-yl)methoxy)malonic acid

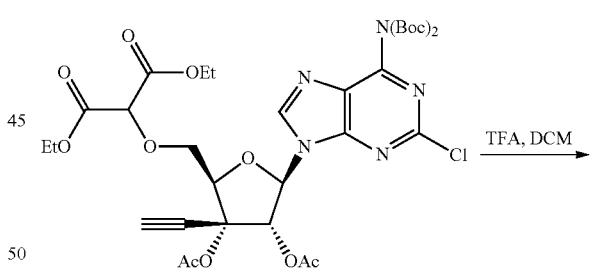

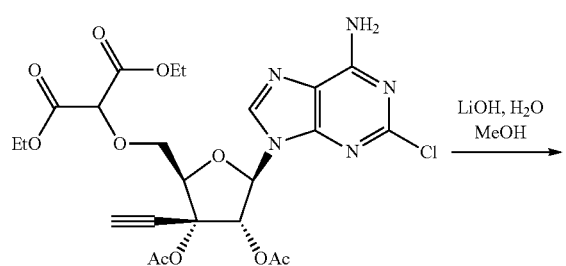

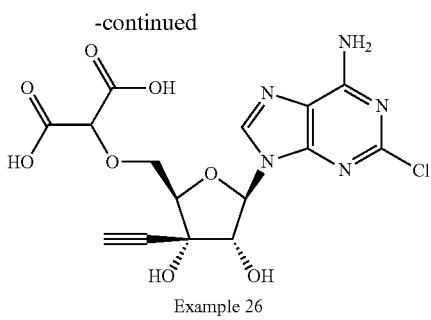

Example 26

Step 1:
A solution of diethyl 2-(((2R,3R,4R,5R)-3,4-diacetoxy-5-(6-N,N'-(bis-(tert-butoxy-carbonyl)amino)-2-chloro-9H-purin-9-yl)-3-ethynyltetrahydrofuran-2-yl)methoxy)malonate (200 mg, 0.26 mmol) in $CH_2Cl_2$ (1 mL) under argon atmosphere at 0° C. was added TFA (0.5 mL). The mixture was stirred for 5 minutes and allowed to warm up and stirred for 1 h. Additional amount of TFA (0.4 mL) was added to the reaction mixture and it was stirred further 1.5 h before it was concentrated. The residue was azeotroped with DCM (5×5 mL) under reduced pressure to provide crude diethyl 2-(((2R,3R,4R,5R)-3,4-diacetoxy-5-(6-amino-2-chloro-9H-purin-9-yl)-3-ethynyltetrahydro-furan-2-yl)methoxy)malonate which was used in the next step without further purification.

Step 2:
To a solution of crude diethyl 2-(((2R,3R,4R,5R)-3,4-diacetoxy-5-(6-amino-2-chloro-9H-purin-9-yl)-3-ethynyltetrahydrofuran-2-yl)methoxy)malonate (0.26 mmol) from the previous step in a mixture of MeOH (8.5 mL) and water (1.5 mL) was added powdered lithium hydroxide monohydrate (86 mg, 2.08 mmol). The resulting mixture was stirred for 16 h before the organic volatile was removed under reduced pressure. The residue was diluted with additional water (11 mL) and extracted with EtOAc (12 mL). The organic layer was discarded. The aqueous phase was acidified to pH ~2.5 with 1N aq. HCl solution and extracted with EtOAc (3×12 mL). The combined organic layer was dried ($Na_2SO_4$), filtered and concentrated to provide the title compound (45.5 mg) as a light brown solid.
$^1$H NMR ($CD_3OD$, 300 MHz): δ 8.94 (s, 1H), 6.08 (d, J=7.52 Hz, 1H), 5.05 (d, J=7.52 Hz, 1H), 4.65 (s, 1H), 4.29 (t, J=2.40 Hz, 1H), 4.06 (dd, J=10.7, 2.5 Hz, 1H), 3.93 (dd, J=10.64, 2.50 Hz, 1H), 3.12 (s, 1H); LC/MS [M+H]=428.

Example 27

Synthesis of 2-(((2R,3S,4R,5R)-3-((1H-pyrazol-3-yl)ethynyl)-5-(6-amino-2-chloro-9H-purin-9-yl)-3,4-dihydroxytetrahydrofuran-2-yl)methoxy)malonic acid

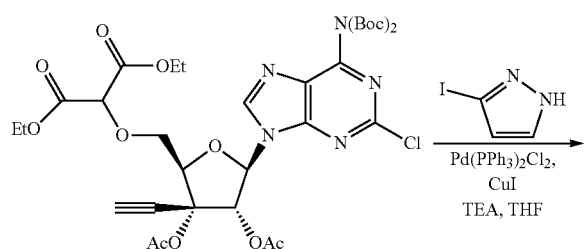

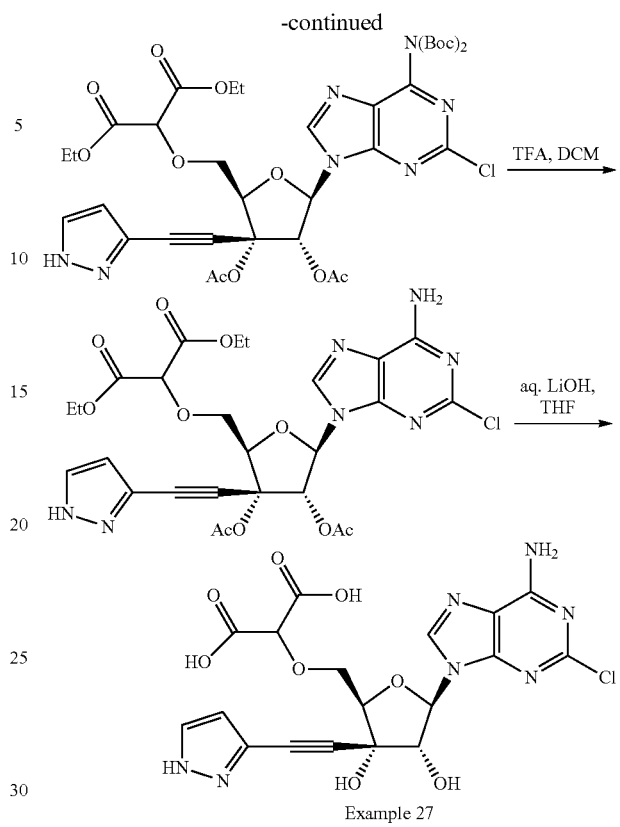

Example 27

Step 1:
To a mixture of 3-iodo-1H-pyrazole (407 mg, 2.1 mmol), $PdCl_2(PPh_3)_2$ (82 mg, 0.12 mmol), CuI (22 mg, 0.12 mmol), and $Et_3N$ (10 mL) in THF (10 mL) under argon atmosphere was added diethyl 2-(((2R,3R,4R,5R)-3,4-diacetoxy-5-(6-N,N'-(bis-(tert-butoxycarbonyl)-amino)-2-chloro-9H-purin-9-yl)-3-ethynyltetrahydrofuran-2-yl)methoxy)malonate (1 g, 1.2 mmol). The resulting mixture was stirred at 60° C. overnight before it was allowed to cool to room temperature and the organic volatile was removed under reduced pressure. The resulting crude residue was purified by flash silica gel column chromatography (60-100% EtOAc in hexanes) to provide diethyl 2-(((2R,3R,4R,5R)-3-((1H-pyrazol-3-yl)ethynyl)-3,4-diacetoxy-5-(6-N,N'-(bis-(tert-butoxycarbonyl)amino)-2-chloro-9H-purin-9-yl)tetrahydro-furan-2-yl)methoxy)malonate as a solid.

Step 2:
To a solution of diethyl 2-(((2R,3R,4R,5R)-3-((1H-pyrazol-3-yl)ethynyl)-3,4-diacetoxy-5-(6-N,N'-(bis-(tert-butoxycarbonyl)amino)-2-chloro-9H-purin-9-yl)tetrahydrofuran-2-yl)methoxy)malonate (100 mg, 0.12 mmol) in a DCM (3 mL) was added TFA (1 mL). The resulting mixture was stirred at 25° C. for 4 h before it was concentrated to provide crude diethyl 2-(((2R,3R,4R,5R)-3-((1H-pyrazol-3-yl)ethynyl)-3,4-diacetoxy-5-(6-amino-2-chloro-9H-purin-9-yl)tetrahydrofuran-2-yl)methoxy)malonate which was used in the next step without further purification.

Step 3:
To a solution of crude diethyl 2-(((2R,3R,4R,5R)-3-((1H-pyrazol-3-yl)ethynyl)-3,4-diacetoxy-5-(6-amino-2-chloro-9H-purin-9-yl)tetrahydrofuran-2-yl)methoxy)malonate in a mixture of THF (5 mL) and $H_2O$ (2 mL) was added $LiOH·H_2O$ (50 mg, 1.2 mmol). The resulting mixture was stirred at 25° C. for 24 h before it was cooled to 0° C. and acidified to pH 6.5 with 1N aq. HCl. The reaction mixture was concentrated. The crude residue was purified by preparative reversed-phase HPLC and dried by lyophilization to provide the title compound as a white solid.

¹H NMR (CD₃OD, 300 MHz) δ 8.96 (s, 1H), 7.56-7.76 (m, 1H), 6.50-6.57 (m, 1H), 6.12-6.14 (d, J=7.14 Hz, 1H), 5.13-5.15 (d, J=6.78 Hz, 1H), 4.63-4.70 (m, 1H), 4.38 (s, 1H), 3.99-4.13 (m, 2H); LC/MS [M+H]=495.

Examples 28 & 29

Synthesis of 2-(((2R,3S,4R,5R)-5-(6-amino-2-chloro-9H-purin-9-yl)-3-((1-benzyl-1H-pyrazol-3-yl)ethynyl)-3,4-dihydroxytetrahydrofuran-2-yl)methoxy)malonic acid & 2-(((2R,3S,4R,5R)-5-(6-amino-2-chloro-9H-purin-9-yl)-3-((1-benzyl-1H-pyrazol-5-yl)ethynyl)-3,4-dihydroxytetrahydrofuran-2-yl)methoxy)malonic acid

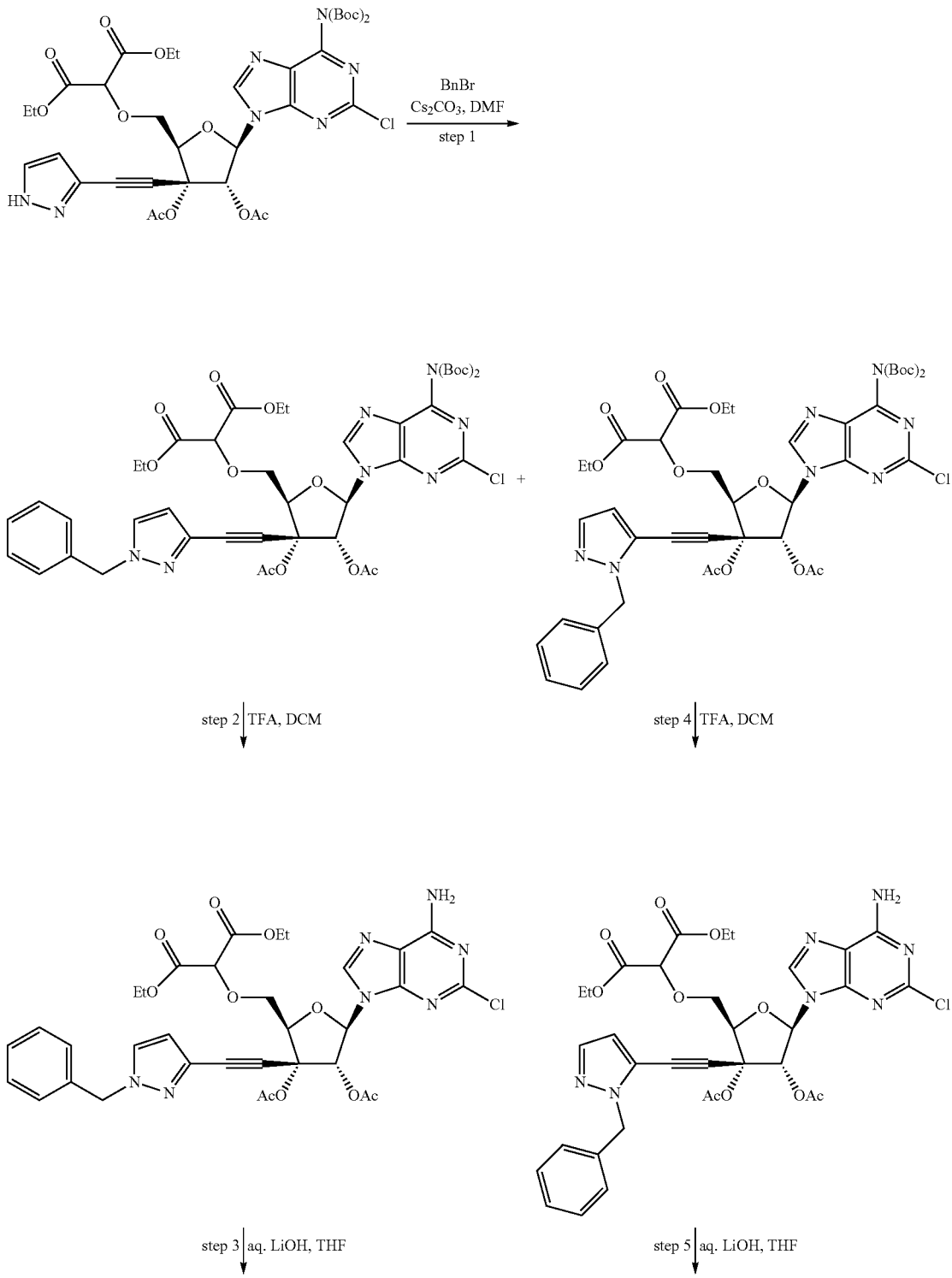

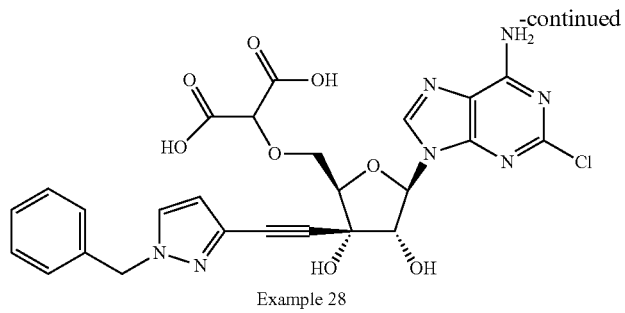

Example 28

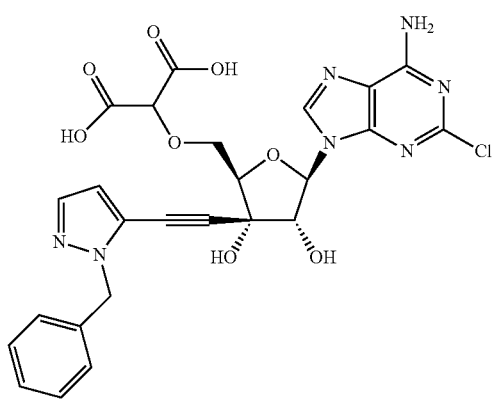

Example 29

Step 1:

To a solution of diethyl 2-(((2R,3R,4R,5R)-3-((1H-pyrazol-3-yl)ethynyl)-3,4-diacetoxy-5-(6-N,N'-(bis-(tert-butoxycarbonyl)amino)-2-chloro-9H-purin-9-yl)tetrahydrofuran-2-yl)methoxy)malonate (100 mg, 0.12 mmol), in anhydrous DMF (2 mL) under argon atmosphere at 0° C. was added oven dried Cs₂CO₃ (78 mg, 0.24 mmole). The mixture was stirred at room temperature for 20 minutes followed by addition of benzyl bromide (29 ul, 0.24 mmole). The resulting mixture was stirred at room temperature for 2 h before it was diluted with EtOAc (15 mL) and H₂O (5 mL). The organic layer was separated, washed with H₂O (20 mL), brine, dried over Na₂SO₄ and concentrated. The crude residue was purified by flash silica gel column chromatography (0-50% EtOAc in hexanes) to provide diethyl 2-(((2R, 3R,4R,5R)-3,4-diacetoxy-3-((1-benzyl-1H-pyrazol-3-yl)ethynyl)-5-(6-N,N'-(bis-(tert-butoxycarbonyl)amino)-2-chloro-9H-purin-9-yl)tetrahydrofuran-2-yl)methoxy)-malonate and diethyl 2-(((2R,3R,4R,5R)-3,4-diacetoxy-3-((1-benzyl-1H-pyrazol-5-yl)ethynyl)-5-(6-N,N'-(bis-(tert-butoxycarbonyl)amino)-2-chloro-9H-purin-9-yl)tetrahydrofuran-2-yl)methoxy)malonate.

Steps 2-3:

Proceeding as described in Example 27 above but substituting diethyl 2-(((2R,3R,4R,5R)-3-((1H-pyrazol-3-yl)ethynyl)-3,4-diacetoxy-5-(6-N,N'-(bis-(tert-butoxycarbonyl)amino)-2-chloro-9H-purin-9-yl)tetrahydrofuran-2-yl)methoxy)malonate with diethyl 2-(((2R,3R,4R,5R)-3,4-diacetoxy-3-((1-benzyl-1H-pyrazol-3-yl)ethynyl)-5-(6-N, N'-(bis-(tert-butoxycarbonyl)amino)-2-chloro-9H-purin-9-yl)tetrahydrofuran-2-yl)methoxy)-malonate provided the title compound (Example 28) acid as a white solid.

¹H NMR (CD₃OD, 300 MHz) δ 8.95 (s, 1H), 7.685 (s, 1H), 7.22-7.38 (m, 5H), 6.50 (s, 1H), 6.10-6.13 (d, J=7.05 Hz, 1H), 5.35 (s, 2H), 5.16-5.18 (d, J=7.35 Hz, 1H), 4.68-4.76 (m, 1H), 4.38 (s, 1H), 3.96-4.16 (dd, J=9.84 Hz, J=17 Hz, 2H); LC/MS [M+H]=585.

Steps 4-5:

Proceeding as described in Example 27 above but substituting diethyl 2-(((2R,3R,4R,5R)-3-((1H-pyrazol-3-yl) ethynyl)-3,4-diacetoxy-5-(6-N,N'-(bis-(tert-butoxy-carbonyl)amino)-2-chloro-9H-purin-9-yl)tetrahydrofuran-2-yl) methoxy)malonate with diethyl 2-(((2R,3R,4R,5R)-3,4-diacetoxy-3-((1-benzyl-1H-pyrazol-5-yl)ethynyl)-5-(6-N, N'-(bis-(tert-butoxycarbonyl)amino)-2-chloro-9H-purin-9-yl)tetrahydrofuran-2-yl)methoxy)-malonate provided the title compound (Example 29) as a white solid.

¹H NMR (CD₃OD, 300 MHz) δ 8.88 (s, 1H), 7.53 (s, 1H), 7.23-7.35 (m, 5H), 6.59 (s, 1H), 6.10-6.13 (d, J=6.09 Hz, 1H), 5.46 (s, 2H), 5.15-5.17 (d, J=6.9 Hz, 1H), 4.35-4.41 (m, 2H), 3.71-4.01 (dd, J=10.71, J=33, 2H); LC/MS [M+H]= 585.

Examples 30 & 31

Synthesis of 2-benzyl-2-(((2R,3S,4R,5R)-5-(5-chloro-7-(isopropylamino)-3H-imidazo[4,5-b]pyridin-3-yl)-3-ethynyl-3,4-dihydroxytetrahydrofuran-2-yl)methoxy)malonic acid & 2-benzyl-2-(((2R,3S, 4R,5R)-5-(2-chloro-6-(dimethylamino)-9H-purin-9-yl)-3-ethynyl-3,4-dihydroxytetrahydrofuran-2-yl) methoxy)malonic acid

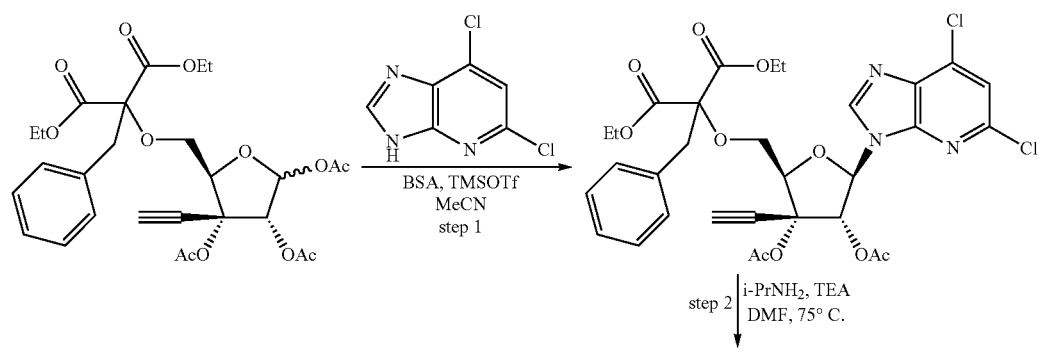

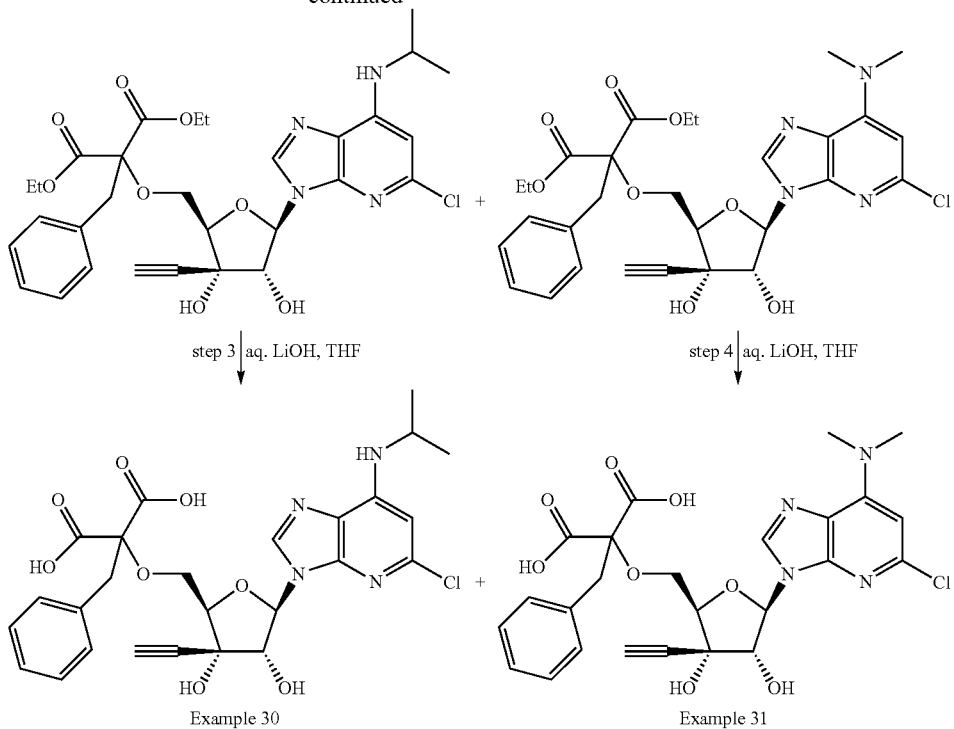

Example 30

Example 31

Step 1:

To a solution of diethyl 2-benzyl-2-(((2R,3R,4R)-3,4,5-triacetoxy-3-ethynyltetra-hydrofuran-2-yl)methoxy)malonate (500 mg, 0.91 mmol) in MeCN (6 mL) at 25° C. was added 5,7-dichloro-1H-imidazo[4,5-b]pyridine (223 mg, 1.18 mmol) and followed by N,O-bis(trimethylsilyl)acetamide (BSA) (535 uL, 2.19 mmol). The resulting suspension was heated at 85° C. for 15 min as it became clear. The reaction mixture was allowed to cool to room temperature followed by addition of TMSOTf (262 mg, 1.18 mmol) dropwise. The reaction mixture was then refluxed at 85° C. for 3 h as all of the starting material was consumed. The reaction was quenched with cold saturated aq. NaHCO$_3$ solution and diluted with EtOAc (15 mL). The organic layer was separated, washed with H$_2$O (20 mL), brine, dried over Na$_2$SO$_4$ and concentrated. The crude residue was purified by flash silica gel column chromatography (0-50% EtOAc in hexanes) to provide diethyl 2-benzyl-2-(((2R,3R,4R,5R)-3,4-diacetoxy-5-(5,7-dichloro-3H-imidazo[4,5-b]pyridin-3-yl)-3-ethynyl-tetrahydrofuran-2-yl)methoxy)malonate as a foam.

Step 2:

To a sealed tube containing diethyl 2-benzyl-2-(((2R,3R,4R,5R)-3,4-diacetoxy-5-(5,7-dichloro-3H-imidazo[4,5-b]pyridin-3-yl)-3-ethynyltetrahydrofuran-2-yl)methoxy)malonate (80 mg, 0.12 mmol) in anhydrous DMF (1 mL) was added isopropyl amine (0.5 mL, 5.9 mmol) and Et$_3$N (1 mL, 7.1 mmol). The reaction mixture was heated at 75° C. for 72 h before it was allowed to cool and diluted with EtOAc (15 mL) and H$_2$O (5 mL). The organic layer was separated, washed with H$_2$O (20 mL), brine, dried over Na$_2$SO$_4$ and concentrated. The residue was purified by flash silica gel column chromatography (0-50% EtOAc in hexanes) to provide diethyl 2-benzyl-2-(((2R,3S,4R,5R)-5-(5-chloro-7-(isopropylamino)-3H-imidazo-[4,5-b]pyridin-3-yl)-3-ethynyl-3,4-dihydroxytetrahydrofuran-2-yl)methoxy)malonate and diethyl 2-benzyl-2-(((2R,3S,4R,5R)-5-(5-chloro-7-(dimethylamino)-3H-imidazo[4,5-b]-pyridin-3-yl)-3-ethynyl-3,4-dihydroxytetrahydrofuran-2-yl)methoxy)malonate as foam.

Step 3:

To a solution of diethyl 2-benzyl-2-(((2R,3S,4R,5R)-5-(5-chloro-7-(isopropylamino)-3H-imidazo[4,5-b]pyridin-3-yl)-3-ethynyl-3,4-dihydroxytetra-hydrofuran-2-yl)methoxy)-malonate (10 mg, 0.016 mmol) in a mixture of THF (3 mL) and H$_2$O (1 mL) was added LiOH.H$_2$O (10 mg, 0.24 mmol). The resulting mixture was stirred at 25° C. for 24 h before it was cooled to 0° C. and acidified to pH 6.5 with 1N aq. HCl. The crude residue was purified by preparative reversed-phase HPLC and dried by lyophilization to provide 2-benzyl-2-(((2R,3S,4R,5R)-5-(5-chloro-7-(isopropylamino)-3H-imidazo[4,5-b]pyridin-3-yl)-3-ethynyl-3,4-dihydroxytetrahydrofuran-2-yl)methoxy)malonic acid as a white solid.

$^1$H NMR (CD$_3$OD, 300 MHz) δ 8.25 (s, 1H), 7.25-7.28 (m, 2H), 7.05 (m, 3H), 6.43 (s, 1H), 6.06-6.08 (d, J=7.17 Hz, 1H), 4.95-4.98 (d, J=7.05 Hz, 1H), 4.32 (s, 1H), 4.05-4.11 (m, 2H), 3.89-3.93 (m, 1H), 3.31-3.39 (m, 2H), 2.99 (s, 1H), 1.30-1.33 (m, 6H); LC/MS [M+H]=560.

Step 4:

To a solution of diethyl 2-benzyl-2-(((2R,3S,4R,5R)-5-(5-chloro-7-(dimethyl-amino)-3H-imidazo[4,5-b]pyridin-3-yl)-3-ethynyl-3,4-dihydroxytetrahydrofuran-2-yl)methoxy)-malonate (21 mg, 0.035 mmol) in a mixture of THF (3 mL) and H$_2$O (1 mL) was added LiOH.H$_2$O (30 mg, 0.71 mmol). The resulting mixture was stirred at 25° C. for 24 h before it was cooled to 0° C. and acidified to pH 6.5 with 1N aq. HCl. The reaction mixture was concentrated. The crude residue was purified by preparative reversed-phase HPLC and dried by lyophilization to provide the title compound as a white solid.

$^1$H NMR (CD$_3$OD, 300 MHz) δ 8.68 (s, 1H), 7.21-7.24 (m, 2H), 6.99-7.03 (m, 3H), 6.49 (s, 1H), 6.15-6.17 (d, J=7.08 Hz, 1H), 4.99-5.02 (d, J=7.17 Hz, 1H), 4.35-4.37 (t, J=3.12 Hz, 1H), 4.07-4.08 (m, 2H), 3.36-3.50 (m, 8H), 2.99 (s, 1H); LC/MS [M+H]=546.

Example 32

Synthesis of 2-(((2R,3S,4R,5R)-5-(2-chloro-6-((2-hydroxyethyl)amino)-9H-purin-9-yl)-3-ethynyl-3,4-dihydroxytetrahydrofuran-2-yl)methoxy)-2-(thiophen-3-ylmethyl)malonic acid

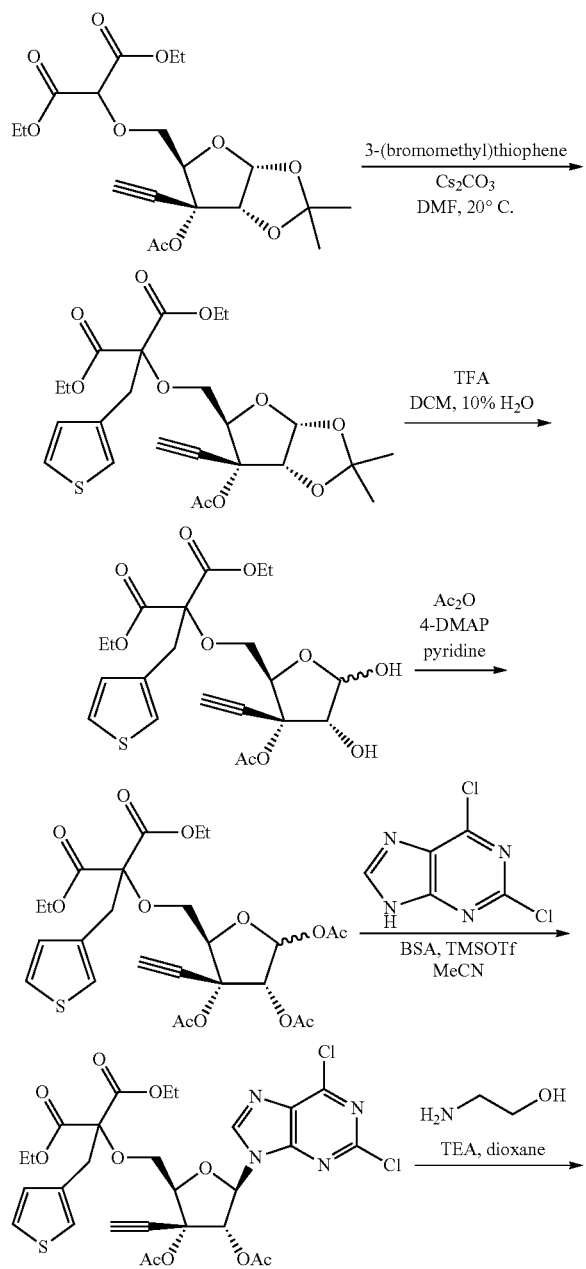

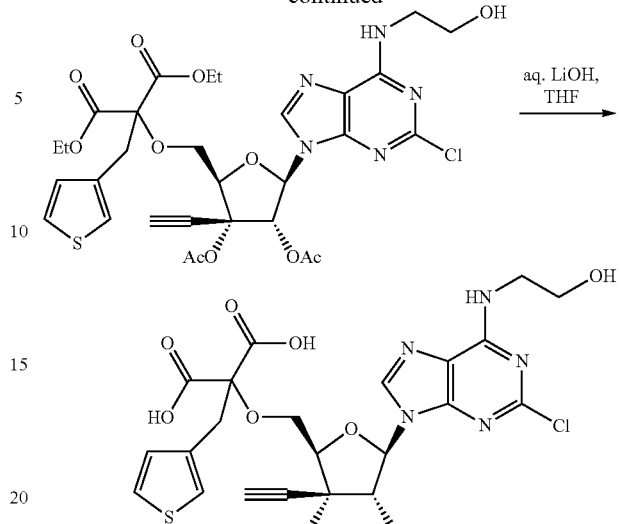

Example 32

Steps 1-3:

Proceeding as described in Example 15 above but substituting allyl bromide with 3-(bromomethyl)thiophene provided diethyl 2-(thiophen-3-ylmethyl)-2-(((2R,3R,4R)-3,4,5-triacetoxy-3-ethynyltetrahydrofuran-2-yl)methoxy) malonate as a solid.

Step 4:

To a solution of 5,7-dichloro-1H-imidazo[4,5-b]pyridine (238 mg, 1.26 mmol) in MeCN (6 mL) at 25° C. was added N,O-bis(trimethylsilyl)acetamide (BSA) (571 uL, 2.34 mmol). The resulting suspension was heated at 85° C. for 15 min as it became clear. The reaction mixture was allowed to cool to room temperature followed by addition of diethyl 2-(thiophen-3-ylmethyl)-2-(((2R,3R,4R)-3,4,5-triacetoxy-3-ethynyltetrahydrofuran-2-yl)-methoxy)malonate (540 mg, 0.97 mmol) and TMSOTf (228 ul, 1.26 mmol) dropwise. The reaction mixture was then refluxed at 85° C. for 2.5 h as all of the starting material was consumed. The reaction was quenched with cold saturated aq. NaHCO$_3$ solution and diluted with EtOAc (15 mL). The organic layer was separated, washed with H$_2$O (20 mL), brine, dried over Na$_2$SO$_4$ and concentrated. The crude residue was purified by flash silica gel column chromatography (0-50% EtOAc in hexanes) to provide diethyl 2-(((2R,3R,4R,5R)-3,4-diacetoxy-5-(2,6-dichloro-9H-purin-9-yl)-3-ethynyltetrahydrofuran-2-yl)methoxy)-2-(thiophen-3-ylmethyl)malonate as a foam.

Step 5:

To a solution of diethyl 2-(((2R,3R,4R,5R)-3,4-diacetoxy-5-(2,6-dichloro-9H-purin-9-yl)-3-ethynyltetrahydrofuran-2-yl)methoxy)-2-(thiophen-3-ylmethyl)malonate (100 mg, 0.146 mmol) in 1,4-dioxane (2 mL) was added TEA (20 uL, 0.146 mmol) followed by ethanolamine (13 ul, 0.219 mmole). The resulting mixture was stirred at 25° C. for 2 h before it was diluted with EtOAc (15 mL) and H$_2$O (5 mL). The organic layer was separated, washed with H$_2$O (20 mL), brine, dried over Na$_2$SO$_4$ and concentrated to provide crude diethyl 2-(((2R,3R,4R,5R)-3,4-diacetoxy-5-(2-chloro-6-((2-hydroxyethyl)amino)-9H-purin-9-yl)-3-ethynyltetrahydrofuran-2-yl)methoxy)-2-(thiophen-3-ylmethyl)malonate which was used in the next step without further purification.

Step 6:

To a solution of crude diethyl 2-(((2R,3R,4R,5R)-3,4-diacetoxy-5-(2-chloro-6-((2-hydroxyethyl)amino)-9H-purin-9-yl)-3-ethynyltetrahydrofuran-2-yl)methoxy)-2-(thiophen-3-ylmethyl)malonate in a mixture of THF (4 mL) and H₂O (1 mL) was added LiOH.H₂O (80 mg, 1.91 mmol). The resulting mixture was stirred at 25° C. for 24 h before it was cooled to 0° C. and acidified to pH 6.5 with 1N aq. HCl. The reaction mixture was concentrated. The crude residue was purified by preparative reversed-phase HPLC and dried by lyophilization to provide the title compound as a white solid.

¹H NMR (CD₃OD, 300 MHz) δ 8.32 (s, 1H), 7.09-7.16 (m, 2H), 6.97-6.99 (m, 1H), 6.00-6.03 (d, J=7.41 Hz, 1H), 4.99-5.02 (d, J=7.38 Hz, 1H), 4.32-4.34 (t, J=3.03 Hz, 1H), 4.00-4.11 (m, 2H), 3.65-3.79 (m, 4H), 3.40-3.53 (q, J=15.42 Hz, J=5.79 Hz, 2H), 2.98 (s, 1H); LC/MS [M+H]=568.0.

Example 33

Synthesis of 2-(((2R,3S,4R,5R)-5-(2-chloro-6-(isopropylamino)-9H-purin-9-yl)-3-ethynyl-3,4-dihydroxytetrahydrofuran-2-yl)methoxy)-2-(thiophen-3-ylmethyl)malonic acid

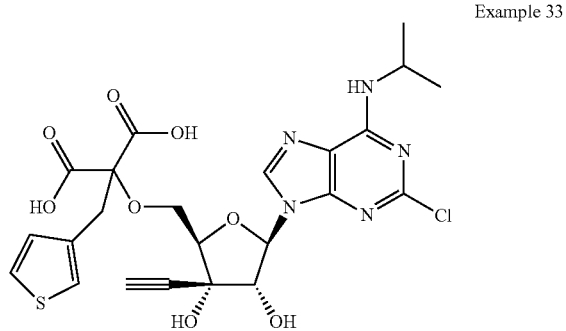 [SMILES: C#C[C@@]1(O)[C@@H](COC(Cc2ccsc2)(C(=O)O)C(=O)O)O[C@@H](n2cnc3c(NC(C)C)nc(Cl)nc32)[C@@H]1O]

Example 33

Proceeding as described in Example 32 above but substituting ethanolamine with i-PrNH₂ provided the title compound as a white solid.

¹H NMR (CD₃OD, 300 MHz) δ 8.28 (s, 1H), 7.08-7.16 (m, 2H), 6.97-6.99 (m, 1H), 5.99-6.02 (d, J=7.38 Hz, 1H), 5.00-5.02 (d, J=7.35 Hz, 1H), 4.31-4.43 (m, 2H), 4.00-4.12 (m, 2H), 3.40-3.53 (q, J=15.63 Hz, J=5.4 Hz, 2H), 2.98 (s, 1H), 1.27-1.32 (m, 6H); LC/MS [M+H]=566.0.

Example 34

Synthesis of 2-benzyl-2-(((2R,3S,4R,5R)-5-(2-chloro-6-((3-hydroxypropyl)amino)-9H-purin-9-yl)-3-ethynyl-3,4-dihydroxytetrahydrofuran-2-yl)methoxy)malonic acid

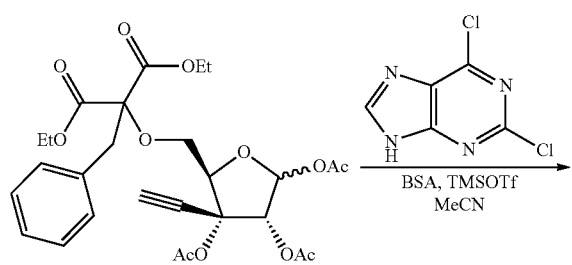

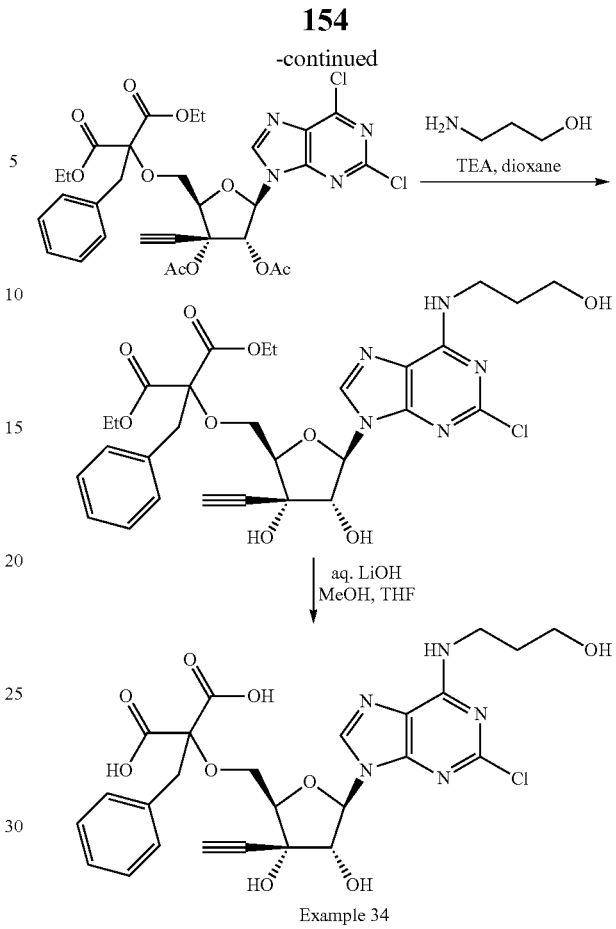

Example 34

Step 1:

To a solution of 2,6-dichloro-9H-purine (690 mg, 3.65 mmol) in dry CH₃CN (15 mL) was added N, O-bis(trimethylsilyl)acetamide (0.28 mL, 1.12 mmol) via syringe. The mixture was heated to 95° C. under argon atmosphere for 5 minutes and then cooled to ambient. To this mixture was added diethyl 2-benzyl-2-(((2R,3R,4R)-3,4,5-triacetoxy-3-ethynyltetra-hydrofuran-2-yl)methoxy)malonate (2 g, 3.65 mmol) and followed by TMSOTf (0.09 mL, 0.494 mmol). The resulting mixture was heated at 95° C. for 2.5 h before it was cooled to ambient temperature and diluted with water (60 mL) and EtOAc (60 mL). The organic phase was washed successively with equal volumes of saturated NaHCO₃ solution and brine. The aqueous phase was further extracted with EtOAc (2×30 mL). The combined organic phase was dried (MgSO₄), filtered and concentrated. The crude residue was purified by flash silica gel column chromatography (5-60% EtOAc in hexane) to provide diethyl 2-benzyl-2-(((2R,3R,4R,5R)-3,4-diacetoxy-5-(2,6-dichloro-9H-purin-9-yl)tetrahydrofuran-2-yl)-methoxy)malonate (1.61 g) as an off-white solid.

Step 2:

To a solution of diethyl 2-benzyl-2-(((2R,3R,4R,5R)-3,4-diacetoxy-5-(2,6-dichloro-9H-purin-9-yl)tetrahydrofuran-2-yl)methoxy)malonate (102 mg, 0.15 mmol) in dry dioxane (1 mL) was added triethylamine (0.02 mL, 0.15 mmol) and 3-aminopropanol (16 mg, 0.212 mmol). The resulting mixture was stirred for 1.5 h before it was diluted with water (15 mL) and DCM (15 mL). and the organic phase was collected. The organic layer was washed with brine (15 mL). The aqueous phase were further extracted with EtOAc (2×10 mL). The combined organic layer was dried over MgSO₄, filtered and concentrated to provide crude diethyl 2-benzyl-2-(((2R,3R,4R,5R)-3,4-diacetoxy-5-(2-chloro-6-((3-hydroxypropyl)amino)-9H-purin-9-yl)tetrahydrofuran-2-yl)methoxy)malonate as a clear viscous oil.

Step 3:

To a solution of crude diethyl 2-benzyl-2-(((2R,3R,4R,5R)-3,4-diacetoxy-5-(2-chloro-6-((3-hydroxypropyl)amino)-9H-purin-9-yl)tetrahydrofuran-2-yl)methoxy)malonate (0.15 mmol) in H$_2$O (0.2 mL), MeOH (1 mL) and THF (0.28 mL) was added powdered LiOH mono-hydrate (43 mg, 1.05 mmol)). The mixture was stirred for 4 h and then sonicated for 30 minutes. Additional LiOH monohydrate (7 mg) was added and sonication continued for 1 h before the organic volatile was removed under reduced pressure and the residue was diluted with water (10 mL) and EtOAc (10 mL). The mixture was cooled at 0° C. and acidified to pH ~3 with 1N aq. HCl. The organic phase was collected and the aqueous phase was further extracted with EtOAc (2×10 mL). The combined EtOAc phases were dried over MgSO$_4$, filtered and concentrated. The crude residue was purified by preparative reversed-phase HPLC to provide the title compound as a off-white solid.

$^1$H NMR (CD$_3$OD, 300 MHz) δ 8.19 (bs, 1H), 7.21-7.3 (m, 2H), 7.00-7.10 (m, 3H), 6.00 (d, J=7.36 Hz, 1H), 4.98 (d, J=7.36 Hz, 1H), 4.33 (t, J=3.18 Hz, 1H), 4.02-4.15 (m, 2H), 3.68 (t, J=6.18 Hz, 2H), 3.59-3.72 (m, 2H), 3.47 (d, J=14.95 Hz, 1H), 3.38 (d, J=14.95 Hz, 1H), 2.99 (s, 1H), 1.84-1.95 (m, 2H); LC/MS [M+H]=576.0.

Example 35

Synthesis of 2-benzyl-2-(((2R,3S,4R,5R)-5-(2-chloro-6-(((R)-2-hydroxypropyl)amino)-9H-purin-9-yl)-3-ethynyl-3,4-dihydroxytetrahydrofuran-2-yl)methoxy)malonic acid

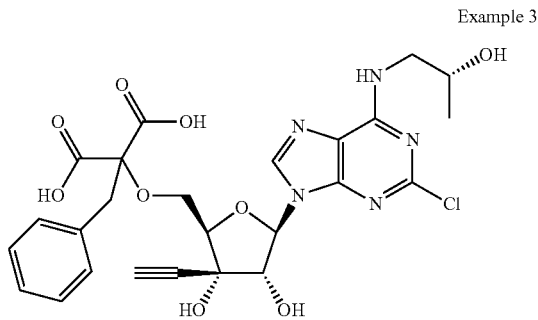

Example 35

Proceeding as described in Example 34 above but substituting propanolamine with (R)-1-aminopropan-2-ol and followed by ester hydrolysis with LiOH provided the title compound as a white solid.

$^1$H NMR (CD$_3$OD, 300 MHz) δ 8.19 (bs, 1H), 7.22-7.30 (m, 2H), 7.02-7.10 (m, 3H), 6.01 (d, J=7.38 Hz, 1H), 4.98 (d, J=7.38 Hz, 1H), 4.33 (t, J=3.17 Hz, 1H), 3.99-4.13 (m, 3H), 3.58-3.69 (m, 1H), 3.43 (qt, J=14.64 Hz, 2H), 3.41-3.55 (m, 1H), 2.99 (s, 1H), 1.24 (d, J=6.30 Hz, 3H); LC/MS [M+H]=576.0.

Example 36

Synthesis of 2-benzyl-2-(((2R,3S,4R,5R)-5-(2-chloro-6-(((S)-2-hydroxypropyl)amino)-9H-purin-9-yl)-3-ethynyl-3,4-dihydroxytetrahydrofuran-2-yl)methoxy)malonic acid

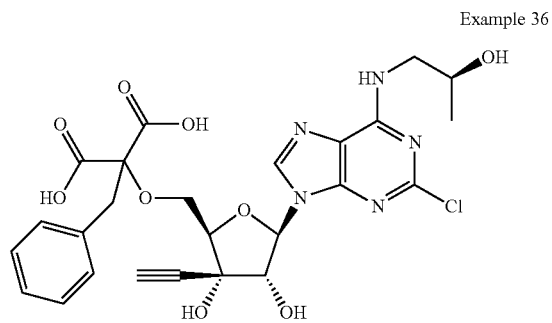 [SMILES: C#C[C@@]1(O)[C@@H](COC(Cc2ccccc2)(C(=O)O)C(=O)O)O[C@@H](n2cnc3c(NC[C@H](C)O)nc(Cl)nc32)[C@@H]1O]

Example 36

Proceeding as described in Example 34 above but substituting propanolamine with (S)-1-aminopropan-2-ol and followed by ester hydrolysis with LiOH provided the title compound as a white solid.

$^1$H NMR (CD$_3$OD, 300 MHz) δ 8.19 (bs, 1H), 7.23-7.29 (m, 2H), 7.03-7.10 (m, 3H), 6.00 (d, J=7.35 Hz, 1H), 4.96 (d, J=7.35 Hz, 1H), 4.32 (t, J=3.30 Hz, 1H), 3.98-4.13 (m, 3H), 3.59-3.68 (m, 1H), 3.35-3.55 (m, 3H), 2.99 (s, 1H), 1.25 (d, J=6.30 Hz, 3H); LC/MS [M+H]=576.0.

Example 37

Synthesis of 2-benzyl-2-(((2R,3S,4R,5R)-5-(6-(bis(2-hydroxyethyl)amino)-2-chloro-9H-purin-9-yl)-3-ethynyl-3,4-dihydroxytetrahydrofuran-2-yl)methoxy)malonic acid

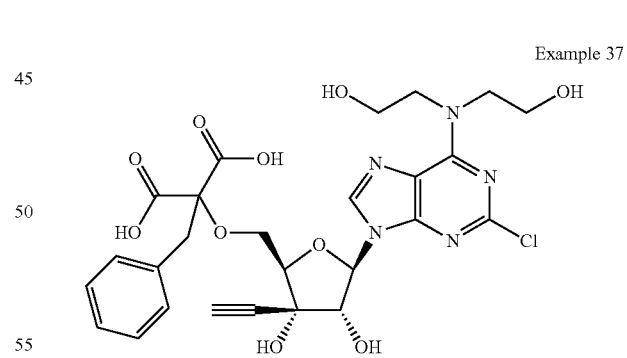

Example 37

Proceeding as described in Example 34 above but substituting propanolamine with diethanolamine and followed by ester hydrolysis with LiOH provided the title compound as a white solid.

$^1$H NMR (CD$_3$OD, 300 MHz) δ 8.16 (s, 1H), 7.22-7.29 (m, 2H), 6.99-7.09 (m, 3H), 6.02 (d, J=7.33 Hz, 1H), 4.97 (d, J=7.33 Hz, 1H), 4.00-4.37 (m, 2H), 4.29-4.34 (m, 2H), 4.03-4.13 (m, 3H), 3.84-3.91 (m, 4H), 3.46 (d, J=14.92 Hz, 1H), 3.37 (d, J=14.92 Hz, 1H), 2.98 (s, 1H); LC/MS [M+H]=606.0.

Example 38

Synthesis of 2-benzyl-2-(((2R,3S,4R,5R)-5-(2-chloro-6-((2-methoxyethyl)amino)-9H-purin-9-yl)-3-ethynyl-3,4-dihydroxytetrahydrofuran-2-yl)methoxy)malonic acid

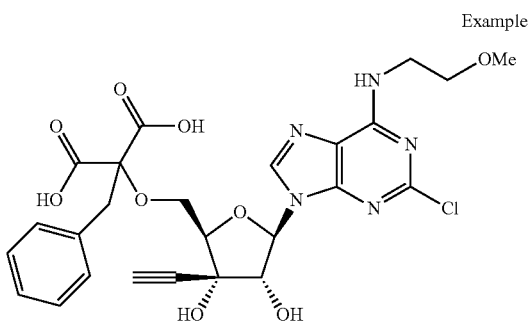

Example 38

Proceeding as described in Example 34 above but substituting propanolamine with 2-methoxyethylamine and followed by ester hydrolysis with LiOH provided the title compound as a white solid.

$^1$H NMR (CD$_3$OD, 300 MHz) δ 8.17 (bs, 1H), 7.22-7.30 (m, 2H), 7.01-7.09 (m, 3H), 6.01 (d, J=7.33 Hz, 1H), 4.98 (d, J=7.33 Hz, 1H), 4.33 (t, J=3.20 Hz, 1H), 4.03-4.13 (m, 2H), 3.69-3.79 (m, 2H), 3.62 (t, J=5.13 Hz, 2H), 3.47 (d, J=14.89 Hz, 1H), 3.40 (s, 3H), 3.38 (d, J=14.89 Hz, 1H), 2.99 (s, 1H); LC/MS [M+H]=576.0.

Example 39

Synthesis of 2-benzyl-2-(((2R,3S,4R,5R)-5-(2-chloro-6-((2-methoxyethyl)-(methyl)amino)-9H-purin-9-yl)-3-ethynyl-3,4-dihydroxytetrahydrofuran-2-yl)methoxy)malonic acid

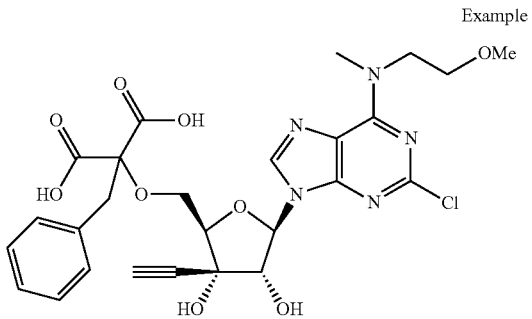

Example 39

Proceeding as described in Example 34 above but substituting propanolamine with (2-methoxyethyl)methylamine and followed by ester hydrolysis with LiOH provided the title compound as a white solid.

$^1$H NMR (CD$_3$OD, 300 MHz) δ 8.18 (bs, 1H), 7.22-7.29 (m, 2H), 6.99-7.09 (m, 3H), 6.02 (d, J=7.21 Hz, 1H), 4.98 (d, J=7.21 Hz, 1H), 4.32 (t, J=3.41 Hz, 1H), 4.03-4.14 (m, 2H), 3.68 (t, J=5.42 Hz, 2H), 3.34-3.49 (m, 7H), 3.36 (s, 3H), 2.99 (s, 1H); LC/MS [M+H]=590.0.

Example 40

Synthesis of 2-benzyl-2-(((2R,3S,4R,5R)-5-(2-chloro-6-(((1-hydroxycyclobutyl)-methyl)amino)-9H-purin-9-yl)-3-ethynyl-3,4-dihydroxytetrahydrofuran-2-yl)methoxy)malonic acid

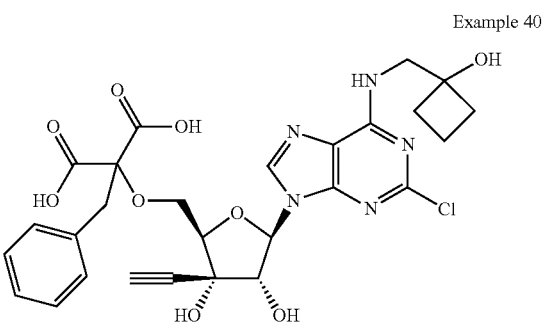 [SMILES: C#C[C@@]1(O)[C@@H](COC(Cc2ccccc2)(C(=O)O)C(=O)O)O[C@@H](n2cnc3c(NCC4(O)CCC4)nc(Cl)nc32)[C@@H]1O]

Example 40

Proceeding as described in Example 34 above but substituting propanolamine with 1-(aminomethyl)cyclobutanol and followed by ester hydrolysis with LiOH provided the title compound as a white solid.

$^1$H NMR (CD$_3$OD, 300 MHz) δ 8.18 (bs, 1H), 7.23-7.29 (m, 2H), 7.01-7.09 (m, 3H), 6.01 (d, J=7.36 Hz, 1H), 4.98 (d, J=7.36 Hz, 1H), 4.32 (t, J=3.21 Hz, 1H), 4.03-4.11 (m, 2H), 3.73-3.79 (m, 2H), 3.36-3.50 (m, 2H), 2.99 (s, 1H), 2.03-2.21 (m, 4H), 1.59-1.85 (m, 2H); LC/MS [M+H]=602.0.

Example 41

Synthesis of 2-benzyl-2-(((2R,3S,4R,5R)-5-(2-chloro-6-(3-hydroxyazetidin-1-yl)-9H-purin-9-yl)-3-ethynyl-3,4-dihydroxytetrahydrofuran-2-yl)methoxy)malonic acid

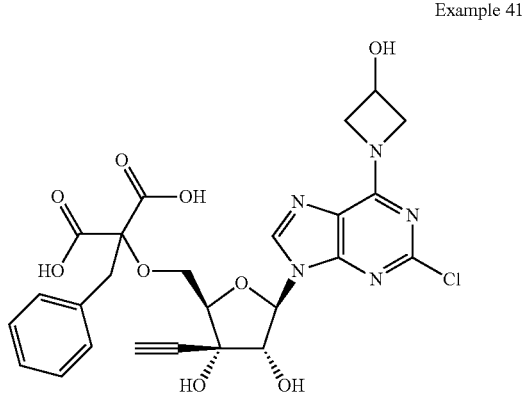 [SMILES: C#C[C@@]1(O)[C@@H](COC(Cc2ccccc2)(C(=O)O)C(=O)O)O[C@@H](n2cnc3c(N4CC(O)C4)nc(Cl)nc32)[C@@H]1O]

Example 41

Proceeding as described in Example 34 above but substituting propanolamine with azetidin-3-ol and followed by ester hydrolysis with LiOH provided the title compound as a white solid.

$^1$H NMR (CD$_3$OD, 300 MHz) δ 8.29 (bs, 1H), 7.21-7.29 (m, 2H), 6.99-7.11 (m, 3H), 6.01 (d, J=7.33 Hz, 1H), 5.01 (d, J=7.33 Hz, 1H), 4.57-4.82 (m, 3H), 4.33 (t, J=3.39 Hz, 1H), 4.14-4.27 (m, 2H), 4.07 (qd, J=4.04, 2.92 Hz, 2H), 3.30-3.50 (m, 2H), 2.98 (s, 1H); LC/MS [M+H]=574.0.

Example 42

Synthesis of 2-benzyl-2-(((2R,3S,4R,5R)-5-(2-chloro-6-(2-(hydroxymethyl)azetidin-1-yl)-9H-purin-9-yl)-3-ethynyl-3,4-dihydroxytetrahydrofuran-2-yl)methoxy)malonic acid

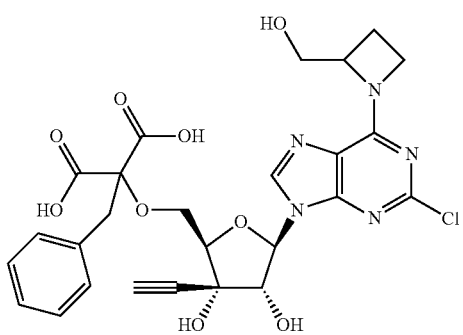

Example 42

Proceeding as described in Example 34 above but substituting propanolamine with azetidin-2-ylmethanol and followed by ester hydrolysis with LiOH provided the title compound as a white solid.

$^1$H NMR (CD$_3$OD, 300 MHz) δ 8.17-8.29 (m, 1H), 7.22-7.28 (m, 2H), 7.01-7.12 (m, 3H), 5.98-6.03 (m, 1H), 4.98 (d, J=7.30 Hz, 1H), 4.27-4.45 (m, 3H), 4.00-4.13 (m, 3H), 3.83-3.92 (m, 1H), 3.33-3.50 (m, 3H), 2.99 (s, 0.5H), 2.97 (s, 0.5H), 2.49-2.63 (m, 1H), 2.31-2.64 (m, 1H); LC/MS [M+H]=588.0.

Example 43

Synthesis of 2-benzyl-2-(((2R,3S,4R,5R)-5-(2-chloro-6-((1-(hydroxymethyl)-cyclopropyl)amino)-9H-purin-9-yl)-3-ethynyl-3,4-dihydroxytetrahydrofuran-2-yl)methoxy)malonic acid

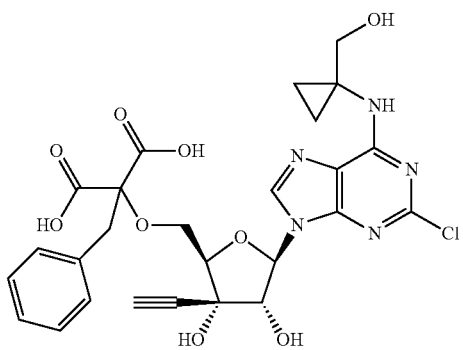

Example 43

Proceeding as described in Example 34 above but substituting propanolamine with (1-aminocyclopropyl)methanol and followed by ester hydrolysis with LiOH provided the title compound as a white solid.

$^1$H NMR (CD$_3$OD, 300 MHz) δ 8.18 (s, 1H), 7.22-7.32 (m, 2H), 7.02-7.11 (m, 3H), 6.01 (d, J=7.36 Hz, 1H), 4.96 (d, J=7.36 Hz, 1H), 4.32 (t, J=3.24 Hz, 1H), 4.02-4.14 (m, 2H), 3.76 (bs, 2H), 3.46 (d, J=15.04 Hz, 1H), 3.38 (d, J=15.04 Hz, 1H), 2.99 (s, 1H), 0.88-1.03 (m, 4H); LC/MS [M+H]=588.0.

Example 44

Synthesis of 2-benzyl-2-(((2R,3S,4R,5R)-5-(2-chloro-6-(((1-hydroxycyclopropyl)-methyl)amino)-9H-purin-9-yl)-3-ethynyl-3,4-dihydroxytetrahydrofuran-2-yl)methoxy)malonic acid

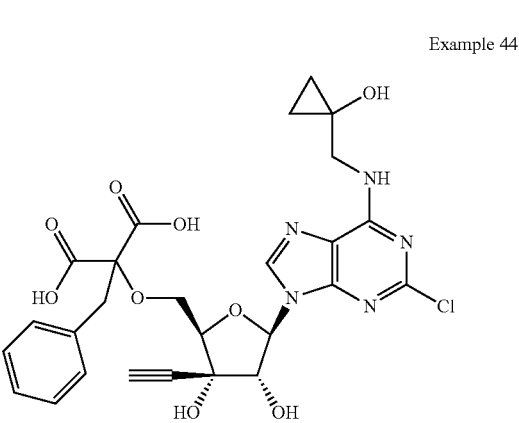 [SMILES: C#C[C@@]1(O)[C@@H](COC(Cc2ccccc2)(C(=O)O)C(=O)O)O[C@@H](n2cnc3c(NCC4(O)CC4)nc(Cl)nc32)[C@@H]1O]

Example 44

Proceeding as described in Example 34 above but substituting propanolamine with 1-(aminomethyl)cyclopropanol and followed by ester hydrolysis with LiOH provided the title compound as a white solid.

$^1$H NMR (CD$_3$OD, 300 MHz) δ 8.18 (s, 1H), 7.08-7.25 (m, 5H), 5.98-6.02 (d, J=7 Hz, 1H), 4.93-4.97 (m, 2H), 4.30 (bs, 1H), 3.98-4.10 (m, 2H), 3.71 (bs, 2H), 3.39-3.51 (m, 2H), 3.00-3.13 (s 1H), 0.71-0.80 (m, 4H); LC/MS [M+H]=588.2.

Example 45

Synthesis of 2-benzyl-2-(((2R,3S,4R,5R)-5-(2-chloro-6-((cyclobutylmethyl)amino)-9H-purin-9-yl)-3-ethynyl-3,4-dihydroxytetrahydrofuran-2-yl)methoxy)malonic acid

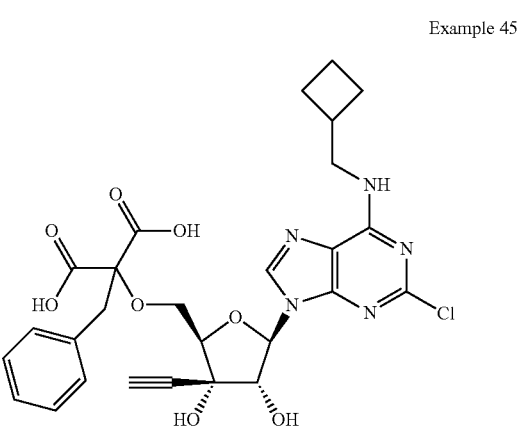 [SMILES: C#C[C@@]1(O)[C@@H](COC(Cc2ccccc2)(C(=O)O)C(=O)O)O[C@@H](n2cnc3c(NCC4CCC4)nc(Cl)nc32)[C@@H]1O]

Example 45

Proceeding as described in Example 34 above but substituting propanolamine with cyclobutylmethanamine and followed by ester hydrolysis with LiOH provided the title compound as a white solid.

¹H NMR (CD₃OD, 300 MHz) δ 8.19 (s, 1H), 7.24-7.27 (m, 2H), 7.05-7.07 (m, 3H), 5.98-6.01 (d, J=8 Hz, 1H), 4.93-4.95 (d, J=7 Hz, 1 Hz), 4.31-4.33 (bs, 1H), 4.01-4.10 (m, 2H), 3.58 (s, 2H), 3.39-3.48 (m, 2H), 3.00 (s, 1H), 2.66-2.71 (m, 1H), 2.12-2.15 (m, 2H) 1.84-1.97 (m, 4H); LC/MS [M+H]=586.2.

Example 46

Synthesis of 2-benzyl-2-(((2R,3S,4R,5R)-5-(2-chloro-6-(3-(hydroxymethyl)azetidin-1-yl)-9H-purin-9-yl)-3-ethynyl-3,4-dihydroxytetrahydrofuran-2-yl)methoxy)malonic acid

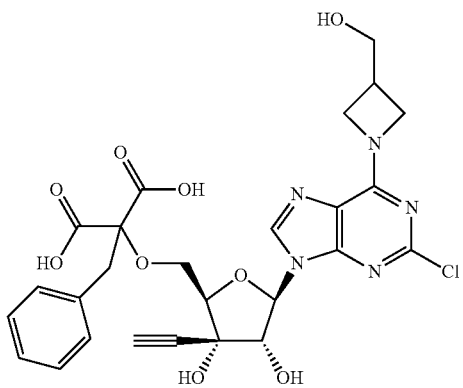

Example 46

Proceeding as described in Example 34 above but substituting propanolamine with azetidin-3-ylmethanol and followed by ester hydrolysis with LiOH provided the title compound as a white solid.

¹H NMR (CD₃OD, 300 MHz) δ 8.09 (s, 1H), 7.05-7.25 (m, 5H), 6.00-6.02 (d, J=7 Hz, 1H), 4.93-4.97 (m, 1H), 4.33 (bs, 1H), 3.96-4.11 (m, 2H), 3.78 (bs, 2H), 3.36-3.40 (m, 6H), 2.99 (bs, 2H); LC/MS [M+H]=588.2.

Example 47

Synthesis of 2-benzyl-2-(((2R,3S,4R,5R)-5-(2-chloro-6-(3-hydroxy-3-methylazetidin-1-yl)-9H-purin-9-yl)-3-ethynyl-3,4-dihydroxytetrahydrofuran-2-yl)methoxy)malonic acid

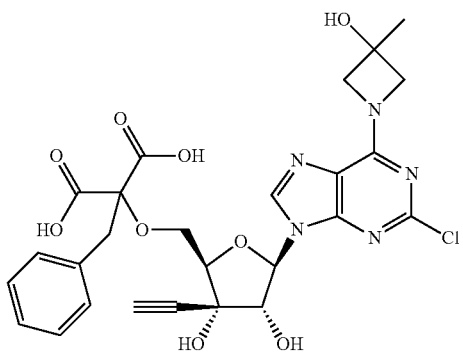

Example 47

Proceeding as described in Example 34 above but substituting propanolamine with 3-methylazetidin-3-ol and followed by ester hydrolysis with LiOH provided the title compound as a white solid.

¹H NMR (CD₃OD, 300 MHz) δ 8.30 (s, 1H), 7.08-7.25 (m, 5H), 6.00-6.03 (d, J=7 Hz, 1H), 4.98-5.01 (m, 1H), 4.33 (bs, 4H), 4.01-4.09 (m, 2H), 3.73 (bs, 1H), 3.35-3.47 (m, 2H), 2.98 (s, 1H), 1.57 (s, 3H); LC/MS [M+H]=588.2.

Example 48

Synthesis of 2-benzyl-2-(((2R,3S,4R,5R)-5-(2-chloro-6-((3-hydroxycyclobutyl)-(methyl)amino)-9H-purin-9-yl)-3-ethynyl-3,4-dihydroxytetrahydrofuran-2-yl)methoxy)malonic acid

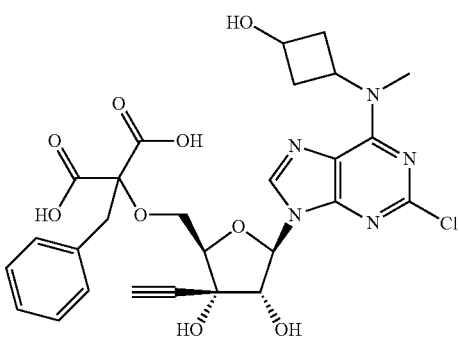

Example 48

Proceeding as described in Example 34 above but substituting propanolamine with 3-(methylamino)cyclobutanol and followed by ester hydrolysis with LiOH provided the title compound as a white solid.

¹H NMR (CD₃OD, 300 MHz) δ 8.26 (s, 1H), 6.96-7.28 (m, 5H), 6.02-6.04 (d, J=7 Hz, 1H), 5.27 (bs, 1H), 4.98-5.02 (m, 1H), 4.33 (bs, 2H), 3.95-4.15 (m, 3H), 3.36-3.51 (m, 4H), 2.99 (s, 1H), 2.67-2.69 (m, 2H), 2.22-2.25 (m, 2H); LC/MS [M+H]=602.2.

Examples 49 & 50

Synthesis of 2-(((2R,3S,4R,5R)-5-(6-amino-2-chloro-9H-purin-9-yl)-3-ethynyl-3,4-dihydroxytetrahydrofuran-2-yl)methoxy)-3-ethoxy-3-oxo-2-(3-(trifluoromethyl)-benzyl)propanoic acid & 2-(((2R,3S,4R,5R)-5-(6-amino-2-chloro-9H-purin-9-yl)-3-ethynyl-3,4-dihydroxytetrahydrofuran-2-yl)methoxy)-2-(3-(trifluoromethyl)benzyl)malonic acid

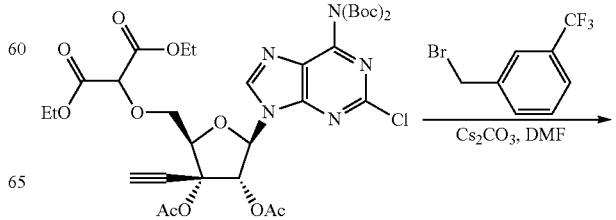

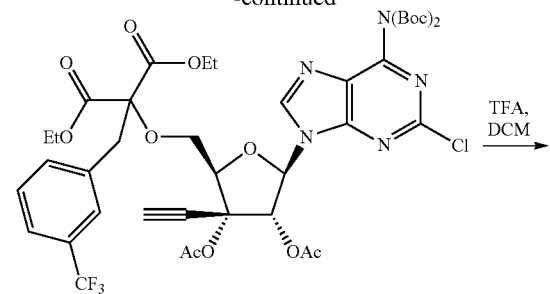

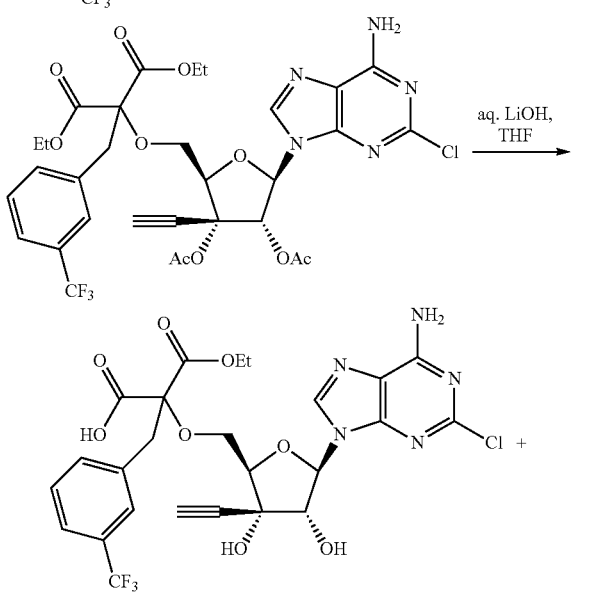

Example 49

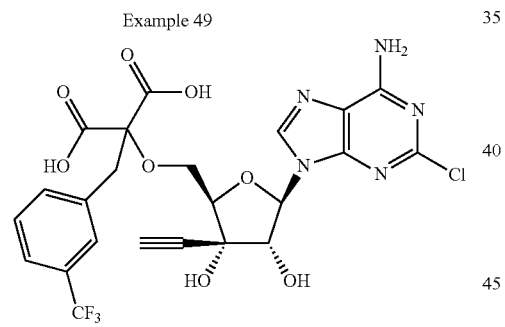

Example 50

Proceeding as described in Example 8 above but substituting furan with (3-trifluoro-methyl)benzene provided the title compounds both as white solid by preparative reversed-phase HPLC purification.

2-(((2R,3S,4R,5R)-5-(6-amino-2-chloro-9H-purin-9-yl)-3-ethynyl-3,4-dihydroxytetrahydro-furan-2-yl)methoxy)-3-ethoxy-3-oxo-2-(3-(trifluoromethyl)-benzyl)propanoic acid: $^1$H NMR (CD$_3$OD, 300 MHz) δ 8.33 (bs, 1H), 7.51-7.54 (d, J=8 Hz, 2H), 7.38-7.40 (d, J=6 Hz, 1H), 7.21-7.26 (t, J=7 Hz, 1H), 6.00-6.04 (m, 1H), 4.98-5.02 (dt, J=4.7, 52 Hz, 1H), 4.36 (bs, 1H), 4.02-4.22 (m, 4H), 3.45-3.58 (m, 2H), 3.02-3.12 (d, J=29 Hz, 1H), 1.18-1.24 (m, 3H); LC/MS [M+H]=614.2.

2-(((2R,3S,4R,5R)-5-(6-amino-2-chloro-9H-purin-9-yl)-3-ethynyl-3,4-dihydroxytetrahydro-furan-2-yl)methoxy)-2-(3-(trifluoromethyl)benzyl)malonic acid: $^1$H NMR (CD$_3$OD, 300 MHz) δ 8.30 (s, 1H), 7.52-7.54 (d, J=9 Hz, 2H), 7.37-7.39 (d, J=7 Hz, 1H), 7.23-7.25 (t, J=7 Hz, 1H), 6.01-6.03 (d, J=7 Hz, 1H), 4.97-5.00 (d, J=7 Hz, 1H), 4.37 (bs, 1H), 4.12-4.14 (m, 2H), 3.44-3.57 (m, 2H), 3.01 (s, 1H); LC/MS [M+H]=586.2.

Example 51

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(3-chlorobenzyl)malonic acid

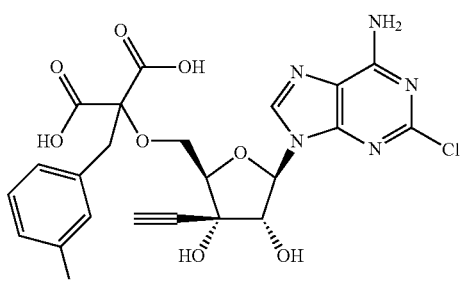

Example 51

Proceeding as described in Example 8 above but substituting furan with 3-chloro-benzene provided the title compound as a white solid by preparative reversed-phase HPLC purification.

$^1$H NMR (CD$_3$OD, 300 MHz) δ 8.42 (s, 1H), 7.27 (bs, 1H), 7.14-7.15 (d, J=6 Hz, 1H), 7.02-7.06 (m, 2H), 6.02-6.05 (d, J=8 Hz, 1H), 5.03-5.06 (d, J=7 Hz, 1H), 4.35-4.39 (m, 2H), 3.39-3.49 (m, 2H), 3.01 (s, 1H), 2.48-2.54 (t, J=8 Hz, 1H) 2.22-2.32 (m, 1H); LC/MS [M+H]=552.1.

Example 52

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(3-methoxybenzyl)malonic acid

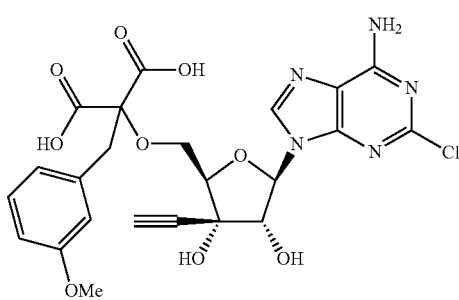

Example 52

Proceeding as described in Example 8 above but substituting furan with 3-methoxy-benzene provided the title compound as a white solid by preparative reversed-phase HPLC purification.

$^1$H NMR (CD$_3$OD, 300 MHz) δ 8.40 (s, 1H), 6.96-7.02 (t, J=8 Hz, 1H), 6.82 (bs, 2H), 6.59-6.62 (m, 1H), 6.02-6.04 (d, J=7 Hz, 1H), 5.01-5.04 (d, J=8 Hz, 1H), 4.35-4.39 (m, 2H), 3.54 (s, 3H), 3.45-3.50 (m, 1H), 2.97 (s, 1H), 2.48-2.54 (t, J=8 Hz, 1H) 2.22-2.32 (m, 1H); LC/MS [M+H]=548.1.

Example 53

Synthesis of 2-([1,1'-biphenyl]-4-ylmethyl)-2-(((2R,3S,4R,5R)-5-(6-amino-2-chloro-9H-purin-9-yl)-3-ethynyl-3,4-dihydroxytetrahydrofuran-2-yl)methoxy)malonic acid

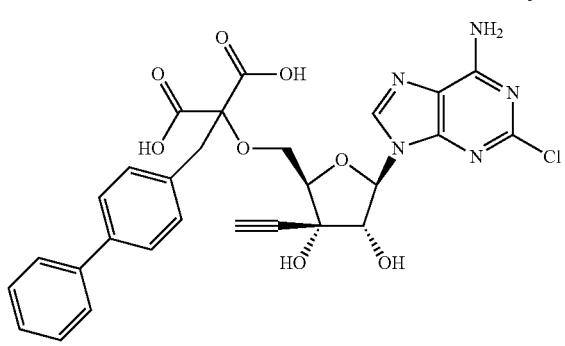

Example 53

Proceeding as described in Example 8 above but substituting furan with 3-biphenyl provided the title compound as a white solid by preparative reversed-phase HPLC purification.

$^1$H NMR (CD$_3$OD, 300 MHz) δ 8.23 (s, 1H), 7.28-7.43 (m, 9H), 5.99-6.02 (d, J=7 Hz, 1H), 4.96-4.98 (d, J=7 Hz, 1H), 4.35 (s, 1H), 4.08-4.15 (m, 2H), 3.41-3.57 (m, 2H), 3.04 (s, 1H): LC/MS [M+H]=594.2.

Example 54

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-((2'-carboxy-[1,1'-biphenyl]-4-yl)methyl)malonic acid

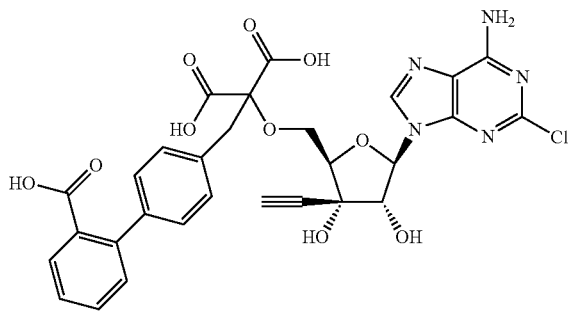

Example 54

Proceeding as described in Example 8 above but substituting furan with 3-methyl[1,1'-biphenyl]-2-carboxylate provided the title compound as a white solid by preparative reversed-phase HPLC purification.

$^1$H NMR (CD$_3$OD, 300 MHz) δ 8.27 (s, 1H), 7.71-7.73 (d, J=7 Hz, 1H), 7.29-7.48 (m, 4H), 7.14-7.16 (d, J=8 Hz, 1H), 7.08-7.10 (d, J=8 Hz, 2H), 5.99-6.01 (d, J=8 Hz, 1H), 4.88-4.91 (m, 1H), 4.30 (bs, 1H), 4.03-4.12 (m, 2H), 3.39-3.57 (m, 2H), 2.99 (s, 1H); LC/MS [M+H]=638.2.

Example 55

Synthesis of 2-(((2R,3S,4R,5R)-5-(6-amino-2-chloro-9H-purin-9-yl)-3-ethyl-3,4-dihydroxytetrahydrofuran-2-yl)methoxy)malonic acid

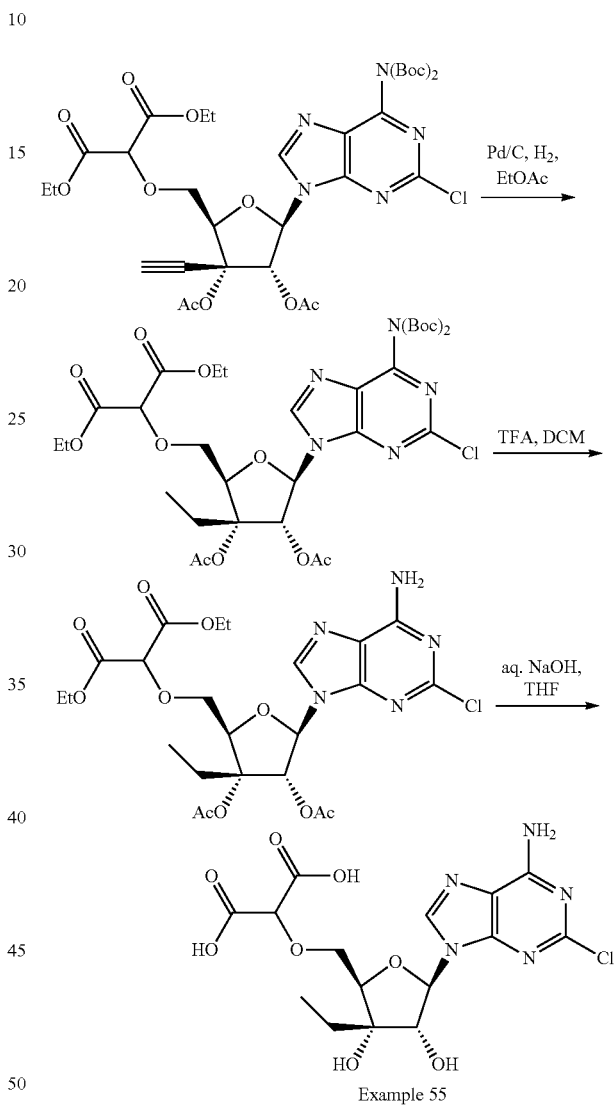

Example 55

Ddiethyl 2-(((2R,3R,4S,5R)-5-(N$_6$,N$_6$-bis-Boc-2-chloro-9H-purin-9-yl)-3-((tert-butoxycarbonyl)oxy)-4-fluorotetrahydrofuran-2-yl)methoxy)malonate (100 mg, 0.13 mmol) was dissolved in EtOAc (2 mL). The solution was purged three times with Argon gas and followed by careful addition of palladium on carbon (20 mg, 10 wt %). The resulting slurry was purged three times with Argon gas and then placed under H$_2$ (1 atm in a balloon). The reaction was held for 70 h at ambient temperature. The suspension was filtered through diatomaceous earth, washed with EtOAc (3×2 mL). The filtrate was concentrated to an oil which was then dissolved in DCM (1 mL) and followed by addition of TFA (100 μL). The resulting solution was held overnight before it was concentrated. The pale yellow oil residue was dissolved in THF (1 mL) and cooled at 0° C. To this reaction mixture was added 4M NaOH (100 μL) and the reaction was allowed to warm to ambient temperature over 14 h before it was concentrated. The crude residue was purified by preparative reversed-phase HPLC to provide the title compound as a white solid.

$^1$H NMR (CD$_3$OD, 300 MHz) δ 8.90 (s, 1H), 6.09-6.11 (d, J=7 Hz, 1H), 4.69-4.72 (d, J=8 Hz, 1H), 4.64 (bs, 1H), 4.19 (s, 1H), 3.83 (bs, 3H), 1.88-1.95 (m, 3H), 1.06-1.11 (t, J=7 Hz, 3H); LC/MS [M+H]=432.2.

Example 56

Synthesis of 2-(((2R,3S,4R,5R)-5-(6-amino-2-chloro-9H-purin-9-yl)-3-ethyl-3,4-dihydroxytetrahydrofuran-2-yl)methoxy)-2-benzylmalonic acid

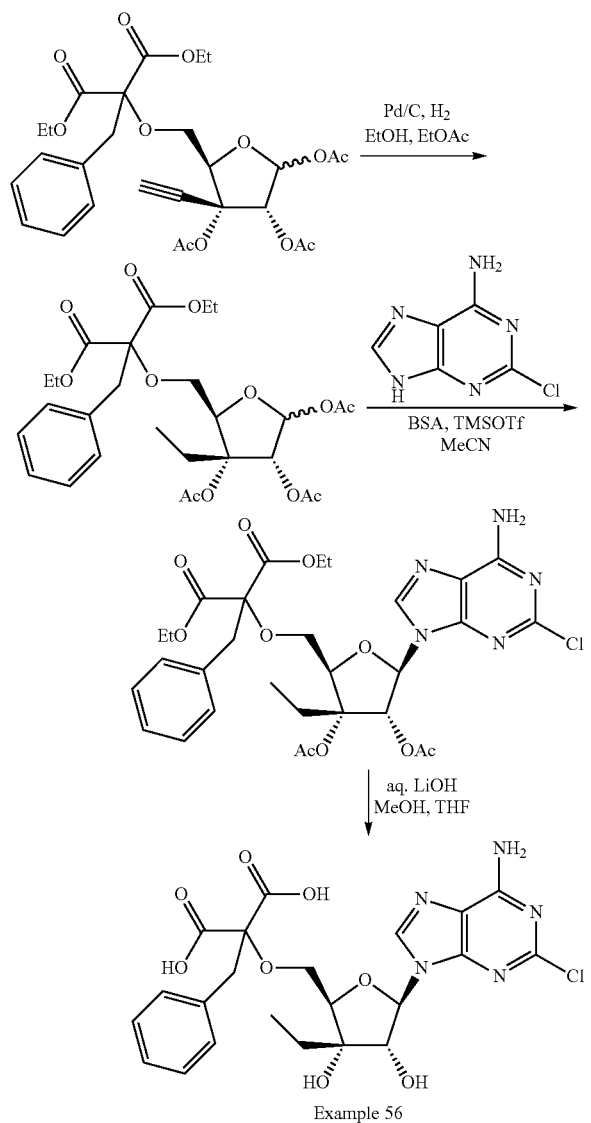

Example 56

Step 1:

A mixture of diethyl 2-benzyl-2-(((2R,3R,4R)-3,4,5-triacetoxy-3-ethynyltetrahydro-furan-2-yl)methoxy)malonate (1.0 mmol, 549 mg) and palladium on carbon (100 mg, 10 wt %) in EtOH (5 mL) and EtOAc (5 mL) under an atmosphere of H$_2$ was stirred for 24 h before it was filtered through diatomaceous earth, rinsed with EtOAc (3×5 mL). The filtrate was concentrated and purified via flash silica gel column chromatography to provide diethyl 2-benzyl-2-(((2R,3R,4R)-3,4,5-triacetoxy-3-ethyltetrahydrofuran-2-yl)methoxy)malonate.

Steps 2-3:

Proceeding as described in Example 7 above but substituting diethyl 2-(pyridin-4-ylmethyl)-2-(((2R,3R,4R)-3,4,5-triacetoxy-3-ethynyltetrahydrofuran-2-yl)methoxy)malonate with diethyl 2-benzyl-2-(((2R,3R,4R)-3,4,5-triacetoxy-3-ethyltetrahydrofuran-2-yl)methoxy)-malonate and followed by ester hydrolysis provided the title compound as a white solid via preparative reversed-phase HPLC purification.

$^1$H NMR (CD$_3$OD, 300 MHz) δ 8.46 (s, 1H), 7.18-7.20 (m, 2H), 7.04-7.09 (m, 3H), 6.01-6.04 (d, J=8 Hz, 1H), 4.63-4.66 (d, J=8 Hz, 1H), 4.21 (bs, 1H), 3.76-3.96 (m, 2H), 3.39-3.52 (m, 2H), 1.76-1.83 (m, 2H), 0.98-1.03 (t, J=7 Hz, 3H); LC/MS [M+H]=522.2.

Example 57

Synthesis of 2-(((2R,3S,4R,5R)-5-(6-amino-2-chloro-9H-purin-9-yl)-3,4-dihydroxy-3-vinyltetrahydrofuran-2-yl)methoxy)-2-benzylmalonic acid

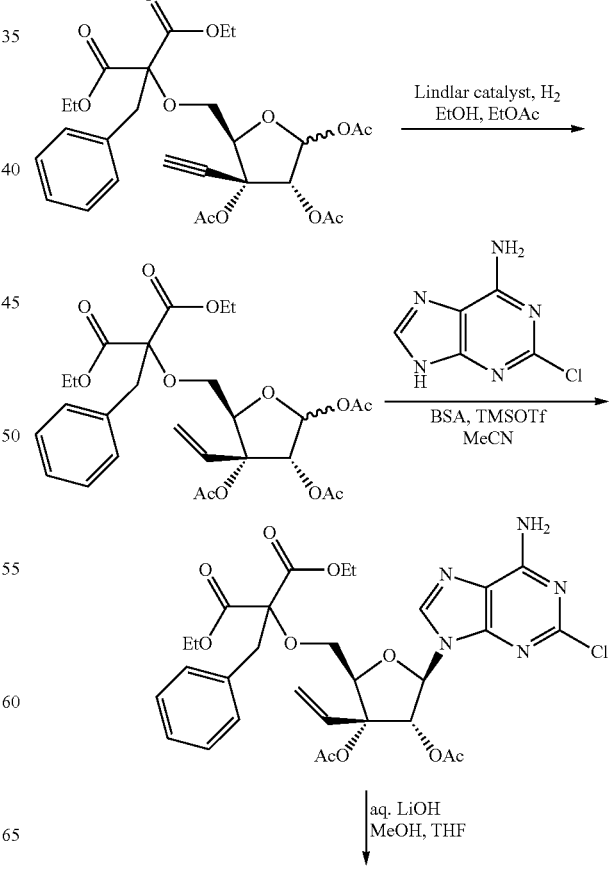

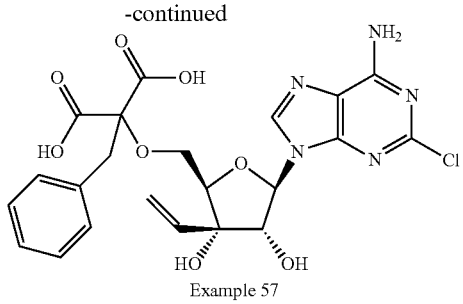

Example 57

Step 1:

A mixture of diethyl 2-benzyl-2-(((2R,3R,4R)-3,4,5-triacetoxy-3-ethynyltetra-hydrofuran-2-yl)methoxy)malonate (525 mg, 0.96 mmol) and Lindlar catalyst (105 mg, 5 wt %) in EtOH (5 mL) and EtOAc (5 mL) under an atmosphere of H₂ was stirred for 24 h before it was filtered through diatomaceous earth, rinsed with EtOAc (3×5 mL). The filtrate was concentrated and purified via flash silica gel column chromatography to provide diethyl 2-benzyl-2-(((2R,3R,4R)-3,4,5-triacetoxy-3-vinyltetrahydrofuran-2-yl)methoxy)malonate.

Steps 2-3:

Proceeding as described in Example 7 above but substituting diethyl 2-(pyridin-4-ylmethyl)-2-(((2R,3R,4R)-3,4,5-triacetoxy-3-ethynyltetrahydrofuran-2-yl)methoxy)malonate with diethyl 2-benzyl-2-(((2R,3R,4R)-3,4,5-triacetoxy-3-vinyltetrahydrofuran-2-yl)methoxy)-malonate and followed by ester hydrolysis provided the title compound as a white solid via preparative reversed-phase HPLC purification.

¹H NMR (CD₃OD, 300 MHz) δ 8.44 (s, 1H), 7.21-7.22 (m, 2H), 7.06-7.11 (m, 3H), 6.14-6.23 (m, 1H), 6.08-6.10 (d, J=8 Hz, 1H), 5.55-5.61 (m, 1H), 5.25-5.29 (m, 1H), 4.81 (s, 1H), 4.14 (bs, 1H), 3.91-3.94 (m, 1H), 3.62-3.65 (d, J=9 Hz, 1H), 3.50-3.55 (d, J=15 Hz, 1H), 3.39 (s, 1H); LC/MS [M+H]=520.1.

Example 58

Synthesis of 2-benzyl-2-(((2R,3S,4R,5R)-5-(5-chloro-3H-imidazo[4,5-b]pyridin-3-yl)-3-ethynyl-3,4-dihydroxytetrahydrofuran-2-yl)methoxy)malonic acid

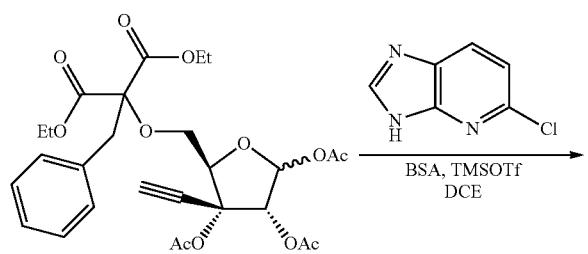

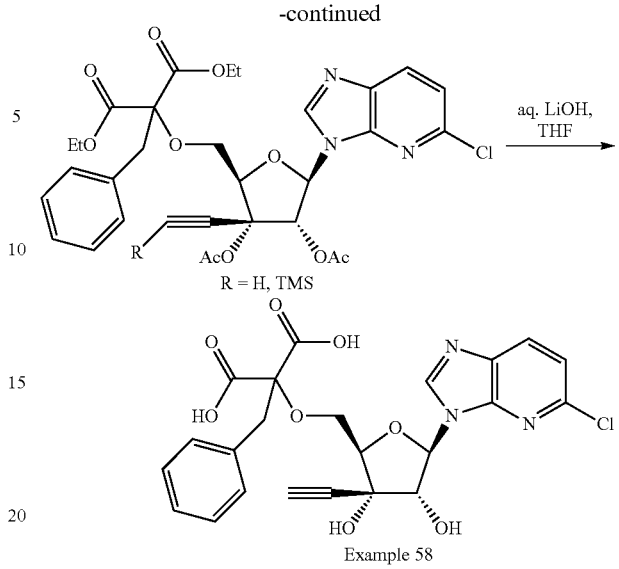

Example 58

Step 1:

To a solution of an anomeric mixture of diethyl 2-benzyl-2-(((2R,3R,4R)-3,4,5-triacetoxy-3-ethynyltetrahydrofuran-2-yl)methoxy)malonate (175 mg, 0.319 mmol) in dry dichloroethane (3.5 mL) was added 5-chloro-3H-imidazo[4,5-b]pyridine (65 mg, 0.422 mmol) and followed by addition of N,O-bis(trimethylsilyl)acetamide (BSA) (0.28 mL, 1.12 mmol) via syringe. The mixture was heated at 95° C. under argon atmosphere for 1 h before it was cooled to ambient temperature and followed by addition of TMSOTf (0.09 mL, 0.494 mmol) via syringe. The resulting mixture was heated at 95° C. for 5 h before it was allowed to cool and diluted with water (30 mL) and extracted with EtOAc (30 mL). The organic phase was washed successively with equal volumes of saturated NaHCO₃ solution and brine. The aqueous phases was further extracted with EtOAc (2×30 mL). The combined organic phase was dried (MgSO₄), filtered and concentrated. The crude residue was purification by preparative TLC (55% EtOAc in hexanes) to provide less polar diethyl 2-benzyl-2-(((2R,3R,4R,5R)-3,4-diacetoxy-5-(5-chloro-3H-imidazo[4,5-b]pyridin-3-yl)-3-((trimethyl-silyl)ethynyl)tetrahydrofuran-2-yl)methoxy)malonate (44 mg) as a viscous oil and the desired diethyl 2-benzyl-2-(((2R,3R,4R,5R)-3,4-diacetoxy-5-(5-chloro-3H-imidazo[4,5-b]pyridin-3-yl)-3-ethynyltetrahydrofuran-2-yl)methoxy)malonate (22 mg) as a viscous oil.

Step 2:

To a solution of diethyl 2-benzyl-2-(((2R,3R,4R,5R)-3,4-diacetoxy-5-(5-chloro-3H-imidazo[4,5-b]pyridin-3-yl)-3-ethynyltetrahydrofuran-2-yl)methoxy)malonate (22 mg, 0.034 mmol) in THF (0.6 mL) was added a solution of 1N aq. LiOH (0.24 mL). Additional 1N aq. LiOH (0.58 mL) was applied over a period of 2 days with a combination of periodically sonication and stirring. The reaction mixture was concentrated and diluted with water (10 mL) and EtOAc (10 mL). The reaction mixture was cooled at 0° C. and acidified to pH ~3 with 1N aq. HCl. The layers were separated and the aq. layer was further extracted with EtOAc (2×10 mL). The combined organic layer was dried over MgSO₄, filtered and concentrated. The crude residue was purified by preparative reversed-phase HPLC to provide the title compound as a off-white solid.

¹H NMR (CD₃OD, 300 MHz): δ 8.63 (bs, 1H), 8.01 (d, J=8.14 Hz, 1H), 7.34 (d, J=8.14 Hz, 1H), 7.29-7.23 (m, 2H), 7.07-6.99 (m, 3H), 6.21 (d, J=7.33 Hz, 1H), 5.04 (d, J=7.33 Hz, 1H), 4.34 (t, J=3.02 Hz, 1H), 4.14-4.03 (m, 2H), 3.48 (d, J=12.53 Hz, 1H), 3.37 (d, J=12.53 Hz, 1H), 2.99 (s, 1H); LC/MS [M+H]=502.0.

Example 59

Synthesis of 2-benzyl-2-(((2R,3S,4R,5R)-5-(6-(benzylamino)-2-chloro-9H-purin-9-yl)-3-ethynyl-3,4-dihydroxytetrahydrofuran-2-yl)methoxy)malonic acid

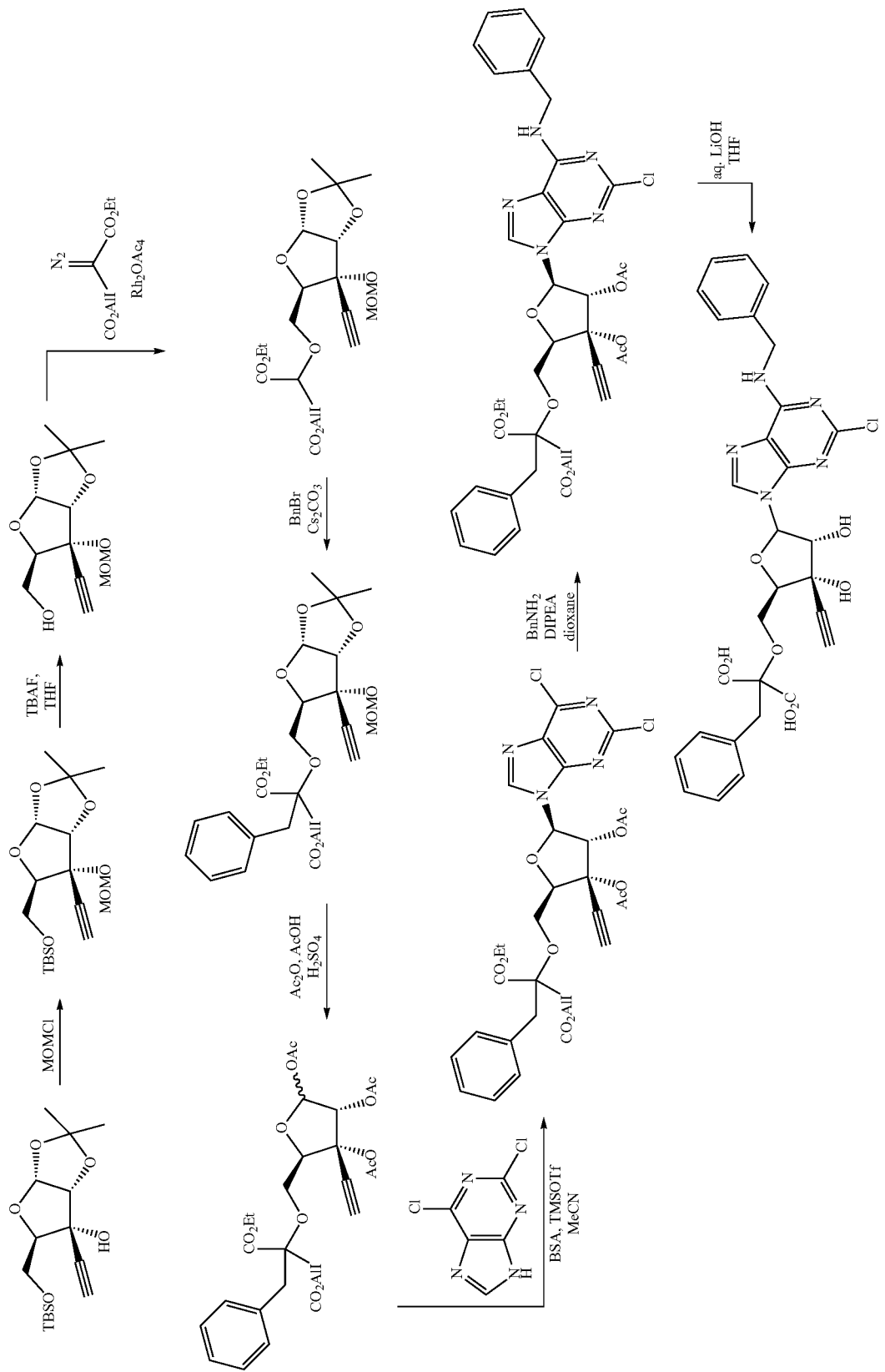

Step 1:
A suspension of sodium hydride (60%, mineral dispersion; 1.91 g, 47.7 mmoL) in anhydrous THF (150 mL) was cooled to 0° C. and treated with a second solution of (3aR,5R,6R,6aR)-5-(((tert-butyldimethylsilyl)oxy)methyl)-6-ethynyl-2,2-dimethyltetrahydro-furo[2,3-d][1,3]dioxol-6-ol (10 g, 30.4 mmoL) in THF (50 mL) over 15 minutes. After stirring 15 mins at 0° C., the mixture was warmed to room temperature and stirred for an additional 1.5 h. The mixture was then cooled back to 0° C. and treated with MOMCl (6.81 mL, 80.7 mmoL, 2.6 eq) was added dropwise. Once the addition was complete, the cooling bath was removed and stirring was continued for 2 h at room temperature. The reaction was quenched by the slow addition of saturated aqueous ammonium chloride (50 mL), washed with water and extracted with ethyl acetate (100 mL). The organic phase was dried over sodium sulfate, filtered, and concentrated. The crude product was purified via silica gel chromatography (30% ethyl acetate in hexanes) to afford tert-butyl-(((3aR,5R,6R,6aR)-6-ethynyl-6-(methoxy-methoxy)-2,2-dimethyltetrahydrofuro[2,3-d][1,3]dioxol-5-yl)methoxy)dimethylsilane (9.95 g, 88% yield) as a white solid.

Step 2:
A solution of the above alcohol (9.8 g, 26.3 mmoL) in anhydrous THF (100 mL) was cooled to 0° C. and treated with 1N solution of tetrabutylammonium fluoride in THF (37 mL, 36.8 mmoL, 1.4 eq) over 15 minutes. After the addition is complete, the reaction was warmed to room temperature and stirred for 3 h. When the reaction was complete (3 h), the volatiles were concentrated affording a viscous residual oil which was dissolved in dichloromethane (5 mL), loaded directly onto a silica gel column (~300cc) and purified via silica gel chromatography, eluting with hexanes to 50% Ethyl acetate in hexanes to afford ((3aR,5R,6R,6aR)-6-ethynyl-6-(methoxymethoxy)-2,2-dimethyltetrahydrofuro[2,3-d][1,3]-dioxol-5-yl)methanol (6.18 g, 91% yield) as a white solid.

Step 3:
A solution of the above alcohol (175 mg, 0.678 mmoL) in anhydrous benzene (8 mL) and 1-ethyl 3-(prop-1-en-1-yl) 2-diazomalonate (188 mg, 0.949 mmoL) was treated with rhodium(II) acetate (5.8 mg, 0.013 mmoL, 0.02 eq) and warmed to 60-65° C. for 2 h. Once complete, the solution is concentrated, dissolved in dichloromethane (1.5 mL) and loaded directly onto a silica gel column (~100cc) and purified via silica gel chromatography, eluting with (0-50% ethyl acetate in hexanes) to afford 1-ethyl 3-prop-1-en-1-yl 2-(((3aR,5R,6R,6aR)-6-ethynyl-6-(methoxymethoxy)-2,2-dimethyltetrahydrofuro[2,3-d][1,3]-dioxol-5-yl)methoxy)malonate (252 mg, 87%) (mixture of isomers) as a pale-yellow oil.

Step 4:
While under nitrogen, a solution of malonate from the previous step (250 mg, 0.583 mmol) and benzyl bromide (0.42 mL, 3.5 mmol, 6 eq) in anhydrous DMF (8 mL) was treated with and cesium carbonate (760 mg, 2.33 mmol) and stirred at room temperature for 4 h. Once complete, the reaction was filtered through a celite pad, washed with water and extracted with ethyl acetate. The combined organic layers were dried over sodium sulfate, filtered, and concentrated. The residual oil was dissolved in dichloromethane (2 mL), loaded onto a silica gel column (~100 cc) eluting with 30% ethyl acetate in hexanes to afford 1-ethyl 3-prop-1-en-1-yl 2-benzyl-2-(((3aR,5R,6R,6aR)-6-ethynyl-6-(methoxymethoxy)-2,2-dimethyltetrahydrofuro[2,3-d][1,3]dioxol-5-yl)methoxy)malonate (261 mg, 86%) (mixture of isomers) as a pale yellow oil.

Step 5:
While under nitrogen, a water cooled (14-17° C.) solution of the acetonide from the last step (500 mg, 0.964 mmoL) in acetic acid (3.9 mL) was treated with acetic anhydride (0.965 mL, 10.3 mmoL, 10.7 eq) and concentrated sulfuric acid (410 uL, 0.326 mmoL, 0.34 eq). The resulting solution was stirred for 4 h, diluted with water and extracted with ethyl acetate. The combined organic solution washed with sodium bicarbonate (aqueous, saturated; 100 mL), dried (Na$_2$SO$_4$), filtered, and concentrated in vacuo. The residual oil was dissolved in dichloromethane (2 mL), and purified on a Biotage flash chromatography system, eluted with hexanes to 50% ethyl acetate in hexanes. A diastereomeric mixture of 1-ethyl 3-prop-1-en-1-yl 2-benzyl-2-(((2R,3R,4R)-3,4,5-triacetoxy-3-ethynyltetrahydrofuran-2-yl)methoxy)-malonate (420 mg, 8%) (separable anomers via silica gel chromatography, 40 G silica gel column) was isolated as a clear oil.

Step 6:
A suspension of 2,6-dichloroadenine (143 mg, 0.76 mmol, 1.01 eq) and N, O-bis(trimethylsilyl)acetamide (0.24 mL, 0.97 mmol, 1.29 eq) in anhydrous acetonitrile (5 mL) was treated with a second solution of 1-ethyl 3-((E)-prop-1-en-1-yl) 2-benzyl-2-(((2R,3R,4R)-3,4,5-triacetoxy-3-ethynyltetrahydrofuran-2-yl)-methoxy)malonate (143 mg, 0.75 mmol) in anhydrous acetonitrile (15 mL), followed by dropwise addition of trimethylsilyl trifluoromethane-sulfonate (0.18 mL, 1.0 mmol, 1.33 eq). After the addition was complete, the reaction was warmed to 50° C. for 18 h, then cooled to room temperature. (Reaction begins a pale-yellow color and after 4 h turns to a transparent amber). Once complete, saturated aqueous sodium bicarbonate was added, and the mixture was stirred for 10 minutes. The crude product was then extracted with ethyl acetate (3×30 mL) and the combined organic layer is dried (Na$_2$SO$_4$), filtered, and concentrated. The residue was dissolved in dichloromethane and purified on a Biotage flash chromatography system, eluted with hexanes to 50% ethyl acetate in hexanes to give 1-ethyl 3-prop-1-en-1-yl 2-benzyl-2-(((2R,3R,4R,5R)-3,4-diacetoxy-5-(2,6-dichloro-9H-purin-9-yl)-3-ethynyltetrahydrofuran-2-yl)methoxy)malonate (as a mixture of isomers) as a white solid (400 mg, 77% yield).

Step 7:
A solution of 1-ethyl 3-prop-1-en-1-yl 2-benzyl-2-(((2R,3R,4R,5R)-3,4-diacetoxy-5-(2,6-dichloro-9H-purin-9-yl)-3-ethynyltetrahydrofuran-2-yl)methoxy)-malonate (80 mg, 0.116 mmoL) in anhydrous dioxane (2 mL) was cooled to 0° C. was treated with DIPEA (30 µL, 0.174 mmoL, 1.5 eq) and benzylamine (13 µL, 0.116 mmoL, 1 eq). Once the addition was complete, the solution was warmed to room temperature with continued stirring overnight (18H). The mixture was diluted with ethyl acetate (50 mL) and washed with water (20 mL). The organic layer was dried (Na$_2$SO$_4$), filtered, and concentrated. The crude product was purified via Biotage flash chromatography, eluting with 50% ethyl acetate in hexanes to give 1-ethyl 3-prop-1-en-1-yl 2-benzyl-2-(((2R,3R,4R,5R)-3,4-diacetoxy-5-(6-(benzylamino)-2-chloro-9H-purin-9-yl)-3-ethynyltetrahydrofuran-2-yl)methoxy)malonate (as a mixture of isomers, ~1:1) as a white solid (75 mg, 85% yield).

Step 8:
A solution of 1-ethyl 3-prop-1-en-1-yl 2-benzyl-2-(((2R,3R,4R,5R)-3,4-diacetoxy-5-(6-(benzylamino)-2-chloro-9H-purin-9-yl)-3-ethynyltetrahydrofuran-2-yl)methoxy)malonate from the last step (70 mg, 0.092 mmoL) in THF (1 mL) was treated with a LiOH solution (31 mg, 1.35 mmoL, 15 eq; in 1 mL water) and stirred overnight. The resulting solution was acidified with 2N HCl to pH 3 and the resulting suspension was stirred for 10 min., then filtered, washed with cold water and dried. The title compound was isolated as a white solid (50 mg, 89% yield).

$^1$H NMR (400 MHz, CDCl$_3$/CD$_3$OD=5:1) δ 7.98 (s. 1H), 7.25-6.84 (m, 10H), 5.85 (d, J=6.4 Hz, 1H), 4.63 (s, 2H), 4.54 (d, J=6.4 Hz, 1H), 4.17 (t, J=3.2 Hz, 1H), 3.88 (qd, J=10.3, 3.3 Hz, 2H), 3.36-3.16 (m, 2H), 2.49 (s, 1H). HPLC: 9.97 min, 97.0%. ESI-MS (m/z): [M]$^+$ calcd for C$_{29}$H$_{26}$ClN$_5$O$_8$, 608.15; found 608.1.

Example 60

Synthesis of 2-benzyl-2-(((2R,3S,4R,5R)-5-(2-chloro-6-((tetrahydro-2H-pyran-4-yl)amino)-9H-purin-9-yl)-3-ethynyl-3,4-dihydroxytetrahydrofuran-2-yl)methoxy)malonic acid

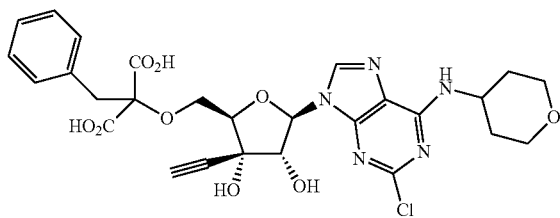

Example 60

The title compound was prepared in a manner analogous to that set forth in Example 59, except tetrahydro-2H-pyran-4-amine was used in place of benzylamine in step 7.

$^1$H NMR (400 MHz, CDCl$_3$/CD$_3$OD=5:1) δ 8.09 (s, 1H), 7.18-7.12 (m, 2H), 7.01 (dd, J=12.1, 7.2 Hz, 3H), 5.90 (d, J=6.3 Hz, 1H), 4.57 (d, J=6.3 Hz, 1H), 4.25 (t, J=3.1 Hz, 2H), 4.00-3.89 (m, 4H), 3.51 (td, J=11.6, 2.2 Hz, 2H), 3.42-3.330 (m, 2H), 2.52 (s, 1H), 1.94 (d, J=13.0 Hz, 2H), 1.57 (td, J=11.2, 3.5 Hz, 2H). ESI-MS (m/z): [M]$^+$ calcd for C$_{27}$H$_{28}$ClN$_5$O$_9$, 602.16; found 602.5.

Example 61

Synthesis of 2-benzyl-2-(((2R,3S,4R,5R)-5-(2-chloro-6-((2-(diethylamino)ethyl)-amino)-9H-purin-9-yl)-3-ethynyl-3,4-dihydroxytetrahydrofuran-2-yl)methoxy)-malonic acid

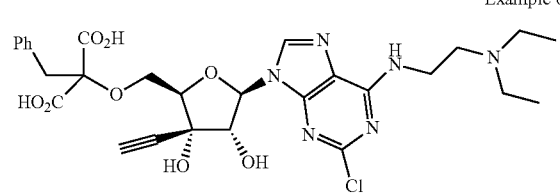

Example 61

The title compound was prepared in a manner analogous to that set forth in Example 59, except N$_1$,N$_1$-diethylethane-1,2-diamine was used in place of benzylamine in step 7.

$^1$H NMR (400 MHz, DMSO-66): 9.01 (s, 1H), 8.75 (s, 1H), 8.49 (s, 1H), 7.23-7.03 (m, 5H), 6.16 (s, 1H), 5.96 (d, J=7.0 Hz, 1H), 5.84 (d, J=6.9 Hz, 1H), 4.59 (t, J=7.1 Hz, 1H), 4.13 (dd, J=6.7, 2.7 Hz, 1H), 3.83-3.55 (m, 4H), 3.53 (s, 1H), 3.30-3.15 (m, 6H), 3.06-2.97 (m, 2H), 1.26-1.12 (m, 6H). ESI-MS (m/z): [M]$^+$ calcd for C$_{28}$H$_{33}$ClN$_6$O$_8$, 617.20; found 617.5.

Example 62

Synthesis of 2-benzyl-2-(((2R,3S,4R,5R)-5-(2-chloro-6-(((R)-1-phenylethyl)amino)-9H-purin-9-yl)-3-ethynyl-3,4-dihydroxytetrahydrofuran-2-yl)methoxy)malonic acid

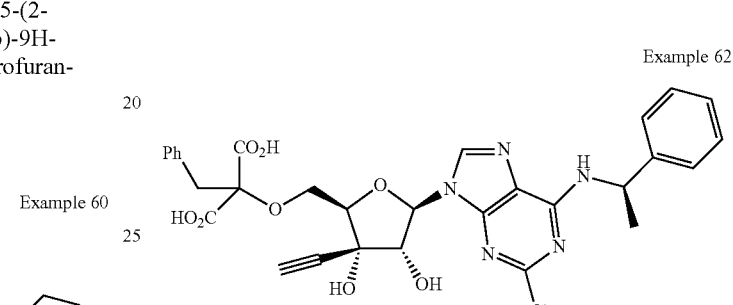

Example 62

The title compound was prepared in a manner analogous to that set forth in Example 59, except (R)-1-phenylethan-1-amine was used in place of benzylamine in step 7.

$^1$H NMR (400 MHz, CDCl$_3$/CD$_3$OD=5:1) δ 8.25 (s, 1H), 7.44-7.27 (m, 4H), 7.23-6.94 (m, 6H), 5.91 (dd, J=6.2, 1.7 Hz, 1H), 5.46 (d, J=8.0 Hz, 1H), 4.58 (d, J=6.2 Hz, 1H), 4.25 (t, J=2.4 Hz, 1H), 3.98-3.83 (m, 2H), 3.32 (dd, J=6.3, 1.7 Hz, 2H), 2.48 (d, J=1.7 Hz, 1H), 1.59 (dd, J=6.9, 1.7 Hz, 3H). ESI-MS (m/z): [M]$^+$ calcd for C$_{30}$H$_{28}$ClN$_5$O$_8$, 622.16; found 622.1.

Example 63

Synthesis of 2-benzyl-2-(((2R,3S,4R,5R)-5-(2-chloro-6-(((S)-1-phenylethyl)amino)-9H-purin-9-yl)-3-ethynyl-3,4-dihydroxytetrahydrofuran-2-yl)methoxy)malonic acid

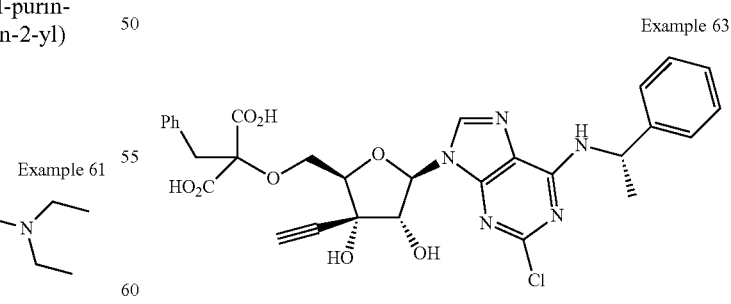

Example 63

The title compound was prepared in a manner analogous to that set forth in Example 59, except (S)-1-phenylethan-1-amine was used in place of benzylamine in step 7.

$^1$H NMR (400 MHz, CDCl$_3$/CD$_3$OD=5:1) δ 8.11 (s, 1H), 7.40-7.28 (m, 4H), 7.23-6.93 (m, 6H), 5.90 (d, J=5.8 Hz, 1H), 5.45 (s, 1H), 4.52 (d, J=5.8 Hz, 1H), 4.35-4.22 (m, 1H), 3.99 (t, J=2.4 Hz, 2H), 3.42-3.25 (m, 2H), 2.50 (s, 1H), 1.58 (d, J=6.9 Hz, 3H). ESI-MS (m/z): [M]+ calcd for $C_{30}H_{28}ClN_5O_8$, 622.16; found 622.2.

Example 64

Synthesis of 2-benzyl-2-(((2R,3S,4R,5R)-5-(2-chloro-6-((tetrahydrofuran-3-yl)-amino)-9H-purin-9-yl)-3-ethynyl-3,4-dihydroxytetrahydrofuran-2-yl)methoxy)-malonic acid

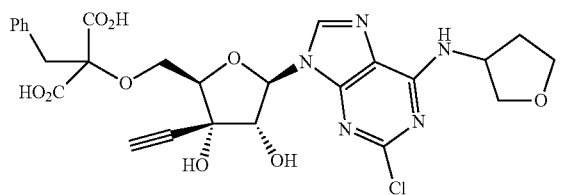

Example 64

The title compound was prepared in a manner analogous to that set forth in Example 59, except tetrahydrofuran-3-amine was used in place of benzylamine in step 7.

1H NMR (400 MHz, CDCl3/CD3OD=5:1) δ 8.10 (s, 1H), 7.19-6.92 (m, 5H), 5.90 (d, J=6.3 Hz, 1H), 4.72 (s, 1H), 4.58 (d, J=6.3 Hz, 1H) 4.25 (t, J=3.1 Hz, 1H), 3.94 (tp, J=7.0, 4.0, 3.3 Hz, 3H), 3.70 (dt, J=9.4, 3.6 Hz, 2H), 3.43-3.24 (m, 2H), 2.52 (s, 1H), 2.29 (dq, J=13.2, 7.6 Hz, 1H), 1.93 (m, 1H). ESI-MS (m/z): [M]+ calcd for $C_{26}H_{26}ClN_5O_9$, 588.14; found 588.3.

Example 65

Synthesis of 2-benzyl-2-(((2R,3S,4R,5R)-5-(2-chloro-6-((S)-3-hydroxypyrrolidin-1-yl)-9H-purin-9-yl)-3-ethynyl-3,4-dihydroxytetrahydrofuran-2-yl)methoxy)malonic acid

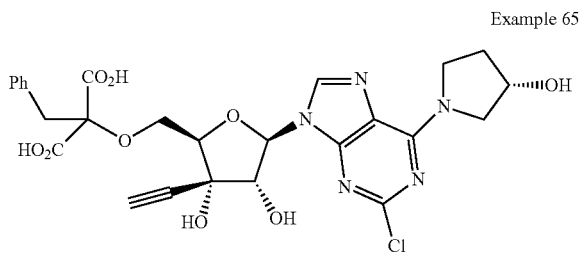 [SMILES: C#C[C@@]1(O)[C@@H](COC(Cc2ccccc2)(C(=O)O)C(=O)O)O[C@@H](n2cnc3c(N4CC[C@H](O)C4)nc(Cl)nc32)[C@@H]1O]

Example 65

The title compound was prepared in a manner analogous to that set forth in Example 59, except (S)-pyrrolidin-3-ol was used in place of benzylamine in step 7.

1H NMR (400 MHz, CDCl3/CD3OD=5:1) δ 8.10 (s, 1H), 7.22-6.92 (m, 5H), 5.92 (d, J=5.4 Hz, 1H), 4.55-4.48 (m, 2H), 4.29 (t, J=3.7 Hz, 1H), 4.25-3.85 (m, 4H), 3.80-3.65 (m, 2H), 3.35-3.24 (m, 2H), 2.51 (s, 1H), 2.08-1.98 (m, 2H). ESI-MS (m/z): [M]+ calcd for $C_{26}H_{26}ClN_5O_9$, 588.14; found 588.2.

Example 66

Synthesis of 2-benzyl-2-(((2R,3S,4R,5R)-5-(2-chloro-6-(ethyl(methyl)amino)-9H-purin-9-yl)-3-ethynyl-3,4-dihydroxytetrahydrofuran-2-yl)methoxy)malonic acid

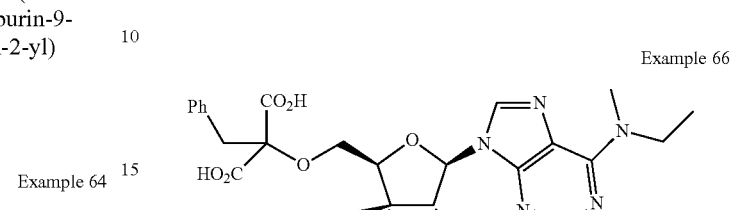

Example 66

The title compound was prepared in a manner analogous to that set forth in Example 59, except N-methylethanamine was used in place of benzylamine in step 7.

1H NMR (400 MHz, CDCl3/CD3OD=5:1) δ 8.05 (s, 1H), 7.24-7.02 (m, 5H), 5.92 (d, J=4.8 Hz, 1H), 4.46 (dd, J=4.8, 1.3 Hz, 1H), 4.32 (dd, J=4.9, 3.2 Hz, 1H), 4.05 (dd, J=8.5, 4.0 Hz, 2H), 3.44-3.30 (m, 2H), 3.10-2.85 (m, 7H), 2.53 (s, 1H), 1.22 (t, J=7.1 Hz, 3H). ESI-MS (m/z): [M]+ calcd for $C_{25}H_{26}ClN_5O_8$, 560.15; found 560.5.

Example 67

Synthesis of 2-benzyl-2-(((2R,3S,4R,5R)-5-(2-chloro-6-((2-fluorobenzyl)amino)-9H-purin-9-yl)-3-ethynyl-3,4-dihydroxytetrahydrofuran-2-yl)methoxy)malonic acid

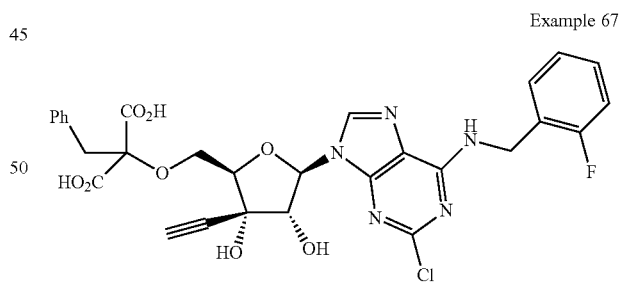

Example 67

The title compound was prepared in a manner analogous to that set forth in Example 59, except (2-fluorophenyl)methanamine was used in place of benzylamine in step 7.

1H NMR (400 MHz, CDCl3/CD3OD=5:1) δ 8.29 (s, 1H), 7.47-7.36 (m, 1H), 7.26-6.94 (m, 8H), 5.94 (d, J=6.2 Hz, 1H), 4.82-4.76 (m, 2H), 4.60 (d, J=6.2 Hz, 1H), 4.35-4.23 (m, 1H), 3.98-3.84 (m, 2H), 3.44-3.30 (m, 2H), 2.46 (s, 1H). ESI-MS (m/z): [M]+ calcd for $C_{29}H_{25}ClFN_5O_{58}$, 626.14; found 626.7.

Example 68

Synthesis of 2-benzyl-2-(((2R,3S,4R,5R)-5-(2-chloro-6-((4-fluorobenzyl)amino)-9H-purin-9-yl)-3-ethynyl-3,4-dihydroxytetrahydrofuran-2-yl)methoxy)malonic acid

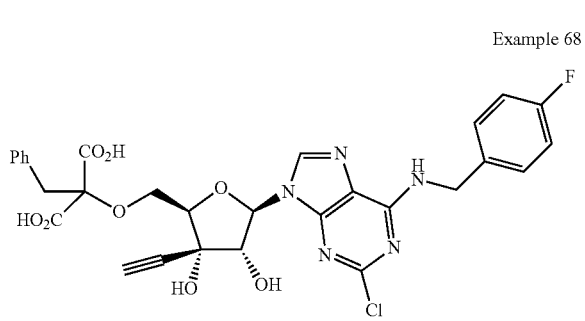 [SMILES: C#C[C@@]1(O)[C@@H](COC(Cc2ccccc2)(C(=O)O)C(=O)O)O[C@@H](n2cnc3c(NCc4ccc(F)cc4)nc(Cl)nc32)[C@@H]1O]

Example 68

The title compound was prepared in a manner analogous to that set forth in Example 59, except (4-fluorophenyl)methanamine was used in place of benzylamine in step 7.

$^1$H NMR (400 MHz, CDCl$_3$/CD$_3$OD=5:1) δ 8.49 (s, 1H), 7.37 (dd, J=8.4, 5.3 Hz, 2H), 7.24-6.89 (m, 7H), 5.97 (d, J=6.3 Hz, 1H), 4.72 (s, 2H), 4.63 (d, J=6.3 Hz, 1H), 4.7-4.28 (m, 1H), 4.06-3.87 (m, 2H), 3.46-3.26 (m, 2H), 2.54 (s, 1H). ESI-MS (m/z): [M]$^+$ calcd for C$_{29}$H$_{25}$ClFN$_5$O$_8$, 626.14; found 626.4.

Example 69

Synthesis of 2-benzyl-2-(((2R,3S,4R,5R)-5-(2-chloro-6-(((R)-2,3-dihydro-1H-inden-1-yl)amino)-9H-purin-9-yl)-3-ethynyl-3,4-dihydroxytetrahydrofuran-2-yl)methoxy)-malonic acid

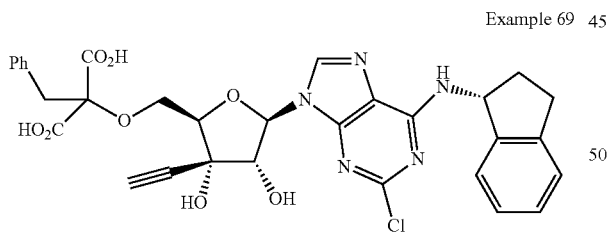

Example 69

The title compound was prepared in a manner analogous to that set forth in Example 59, except (R)-2,3-dihydro-1H-inden-1-amine was used in place of benzylamine in step 7.

$^1$H NMR (400 MHz, CDCl$_3$/CD$_3$OD=5:1) δ 8.30 (s, 1H), 7.29-6.97 (m, 9H), 5.95 (d, J=6.2 Hz, 1H), 5.81 (t, J=7.1 Hz, 1H), 4.59 (d, J=6.3 Hz, 1H), 4.25 (d, J=3.1 Hz, 1H), 3.94-3.73 (m, 2H), 3.40-3.31 (m, 2H), 3.07 (ddd, J=14.0, 8.7, 4.8 Hz, 1H), 2.89 (dt, J=15.8, 7.7 Hz, 1H), 2.69-2.58 (m, 1H), 2.45 (s, 1H), 2.00 (dd, J=13.6, 7.1 Hz, 1H). ESI-MS (m/z): [M]$^+$ calcd for C$_{31}$H$_{28}$ClN$_5$O$_8$, 634.16; found 634.8.

Example 70

Synthesis of 2-benzyl-2-(((2R,3S,4R,5R)-5-(2-chloro-6-(phenethylamino)-9H-purin-9-yl)-3-ethynyl-3,4-dihydroxytetrahydrofuran-2-yl)methoxy)malonic acid

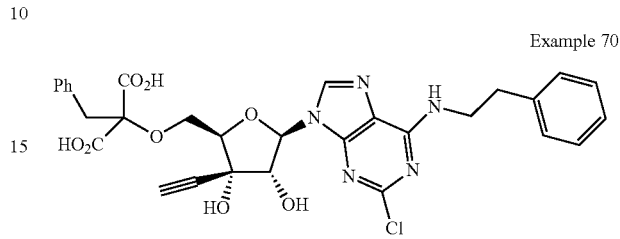

Example 70

The title compound was prepared in a manner analogous to that set forth in Example 59, except 2-phenylethan-1-amine was used in place of benzylamine in step 7.

$^1$H NMR (400 MHz, CDCl$_3$/CD$_3$OD=5:1) δ 8.14 (s, 1H), 7.26-6.91 (m, 10H), 5.91 (d, J=6.2 Hz, 1H), 4.57 (d, J=6.2 Hz, 1H), 4.27 (t, J=3.2 Hz, 1H), 3.96 (t, J=4.0 Hz, 2H), 3.78 (m, 2H), 3.45-3.29 (m, 2H), 2.93 (t, J=7.3 Hz, 2H), 2.52 (s, 1H). ESI-MS (m/z): [M]$^+$ calcd for C$_{30}$H$_{28}$ClN$_5$O$_8$, 622.16; found 622.5.

Example 71

Synthesis of 2-benzyl-2-(((2R,3S,4R,5R)-5-(2-chloro-6-(methylamino)-9H-purin-9-yl)-3-ethynyl-3,4-dihydroxytetrahydrofuran-2-yl)methoxy)malonic acid

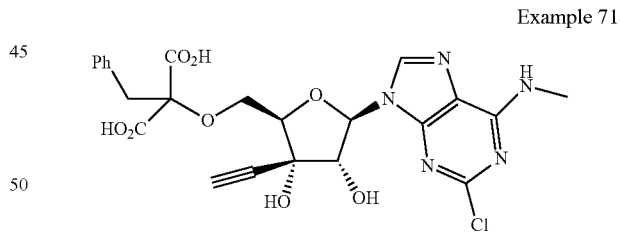

Example 71

The title compound was prepared in a manner analogous to that set forth in Example 59, except methylamine was used in place of benzylamine in step 7.

$^1$H NMR (400 MHz, CD$_3$OD) δ 8.18 (s, 1H), 7.29-7.20 (m, 2H), 7.04 (dd, J=5.1, 1.9 Hz, 3H), 5.99 (d, J=7.4 Hz, 1H), 4.99 (d, J=7 Hz, 1H), 4.30 (t, J=3.3 Hz, 1H), 4.11-4.01 (m, 2H), 3.49-3.34 (m, 2H), 3.06 (s, 3H), 2.98 (s, 1H). ESI-MS (m/z): [M]$^+$ calcd for C$_{23}$H$_{22}$ClN$_5$O$_8$, 532.12; found 532.1.

Example 72

Synthesis of 2-benzyl-2-(((2R,3S,4R,5R)-5-(2-chloro-6-(((S)-2,3-dihydro-1H-inden-1-yl)amino)-9H-purin-9-yl)-3-ethynyl-3,4-dihydroxytetrahydrofuran-2-yl)methoxy)-malonic acid

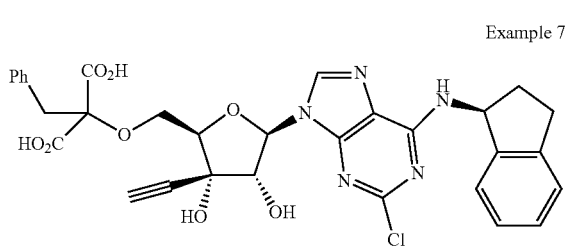

Example 72

The title compound was prepared in a manner analogous to that set forth in Example 59, except (S)-2,3-dihydro-1H-inden-1-amine was used in place of benzylamine in step 7.

$^1$H NMR (400 MHz, CD$_3$OD) δ 8.14 (s, 1H), 7.41-7.13 (m, 6H), 7.04 (t, J=3.5 Hz, 3H), 6.01 (d, J=7.4 Hz, 1H), 5.88-5.76 (m, 1H), 4.99 (d, J=7.4 Hz, 1H), 4.32 (t, J=3.3 Hz, 1H), 4.06 (dd, J=5.5, 3.3 Hz, 2H), 3.53-3.34 (m, 2H), 3.13-3.05 (m, 1H), 3.00 (s, 1H), 2.99-2.87 (m, 1H), 2.67 (dd, J=12.5, 4.2 Hz, 1H), 2.02 (dd, J=12.8, 7.7 Hz, 1H). ESI-MS (m/z): [M]$^+$ calcd for C$_{31}$H$_{28}$ClN$_5$O$_8$, 634.16; found 634.5.

Example 73

Synthesis of 2-benzyl-2-(((2R,3S,4R,5R)-5-(2-chloro-6-(ethylamino)-9H-purin-9-yl)-3-ethynyl-3,4-dihydroxytetrahydrofuran-2-yl)methoxy)malonic acid

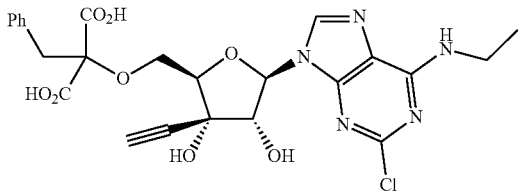

Example 73

The title compound was prepared in a manner analogous to that set forth in Example 59, except ethylamine was used in place of benzylamine in step 7.

$^1$H NMR (400 MHz, CD$_3$OD) δ 8.16 (s, 1H), 7.40-7.19 (m, 2H), 7.04 (dd, J=5.1, 1.9 Hz, 3H), 5.98 (d, J=7.4 Hz, 1H), 4.97 (d, J=7.4 Hz, 1H), 4.30 (T, J=3.3 Hz, 1H), 4.14-3.98 (m, 2H), 3.57 (d, J=7.8 Hz, 2H), 3.49-3.33 (m, 2H), 2.98 (s, 1H), 1.28 (t, J=7.2 Hz, 3H).

ESI-MS (m/z): [M]$^+$ calcd for C$_{24}$H$_{24}$ClN$_5$O$_8$, 546.13; found 546.1.

Example 74

Synthesis of 2-benzyl-2-(((2R,3S,4R,5R)-5-(6-((S)-sec-butylamino)-2-chloro-9H-purin-9-yl)-3-ethynyl-3,4-dihydroxytetrahydrofuran-2-yl)methoxy)malonic acid

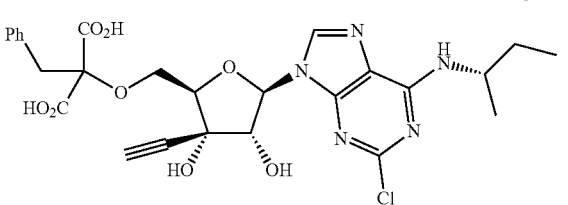

Example 74

The title compound was prepared in a manner analogous to that set forth in Example 59, except (S)-butan-2-amine was used in place of benzylamine in step 7.

$^1$H NMR (400 MHz, CD$_3$OD) δ 8.13 (s, 1H), 7.32-7.15 (m, 2H), 7.14-6.98 (m, 3H), 5.98 (d, J=7.4 Hz, 1H), 4.97 (d, J=7.4 Hz, 1H), 4.31 (t, J=3.2 Hz, 1H), 4.24 (s, 1H), 4.14-3.97 (m, 2H), 3.53-3.33 (m, 2H), 2.99 (s, 1H), 1.63 (q, J=7.2 Hz, 2H), 1.27 (d, J=6.5 Hz, 3H), 0.97 (t, J=7.4 Hz, 3H). ESI-MS (m/z): [M]$^+$ calcd for C$_{26}$H$_{28}$ClN$_5$O$_8$, 574.16; found 574.1.

Example 75

Synthesis of 2-benzyl-2-(((2R,3S,4R,5R)-5-(2-chloro-6-((cyclopropylmethyl)-(methyl)amino)-9H-purin-9-yl)-3-ethynyl-3,4-dihydroxytetrahydrofuran-2-yl)methoxy)malonic acid

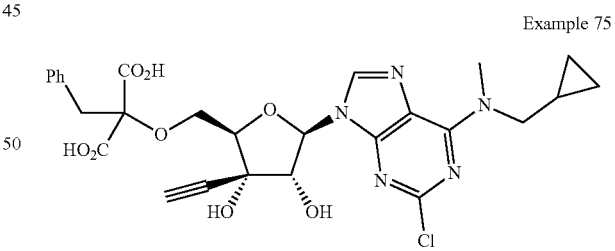

Example 75

The title compound was prepared in a manner analogous to that set forth in Example 59, except 1-cyclopropyl-N-methylmethanamine was used in place of benzylamine in step 7.

$^1$H NMR (400 MHz, CD$_3$OD) δ 8.15 (s, 1H), 7.36-7.18 (m, 2H), 7.03 (dd, J=5.2, 2.0 Hz, 3H), 6.00 (d, J=7.3 Hz, 1H), 4.97 (d, J=7.3 Hz, 1H), 4.30 (dd, J=4.1, 2.8 Hz, 1H), 4.07 (qd, J=10.2, 3.5 Hz, 2H), 3.52-3.31 (m, 7H), 2.98 (s, 1H), 1.20-1.12 (m, 1H), 0.54 (dd, J=8.2, 1.8 Hz, 2H), 0.45-0.30 (m, 2H). ESI-MS (m/z): [M]$^+$ calcd for C$_{27}$H$_{28}$ClN$_5$O$_8$, 586.16; found 586.9

Example 76

Synthesis of 2-benzyl-2-(((2R,3S,4R,5R)-5-(6-((carboxymethyl)amino)-2-chloro-9H-purin-9-yl)-3-ethynyl-3,4-dihydroxytetrahydrofuran-2-yl)methoxy)malonic acid

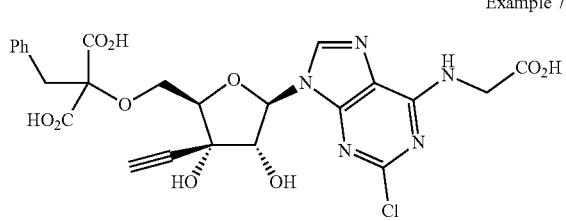

Example 76

The title compound was prepared in a manner analogous to that set forth in Example 59, except 2-amino-N,N-dimethylacetamide was used in place of benzylamine in step 7.

$^1$H NMR (400 MHz, CD$_3$OD) δ 8.21 (s, 1H), 7.38-7.14 (m, 2H), 7.12-6.98 (m, 3H), 6.11 (d, J=7.4 Hz, 1H), 4.96 (d, J=7.3 Hz, 1H), 4.30 (q, J=4.7, 4.0 Hz, 2H), 4.09-4.02 (m, 2H), 3.54-3.33 (m, 2H), 2.97 (s, 1H). ESI-MS (m/z): [M]$^-$ calcd for C$_{24}$H$_{22}$ClN$_5$O$_{10}$, 574.11; found 574.1.

Example 77

Synthesis of 2-benzyl-2-(((2R,3S,4R,5R)-5-(2-chloro-6-((2-chlorobenzyl)amino)-9H-purin-9-yl)-3-ethynyl-3,4-dihydroxytetrahydrofuran-2-yl)methoxy)malonic acid

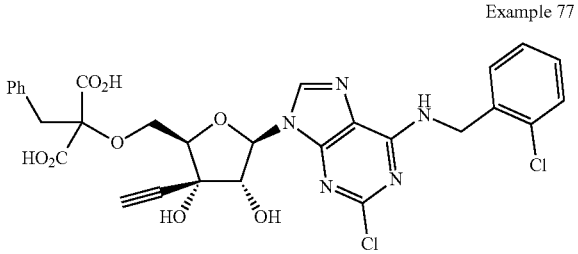 [SMILES: C#C[C@@]1(O)[C@@H](COC(Cc2ccccc2)(C(=O)O)C(=O)O)O[C@@H](n2cnc3c(NCc4ccccc4Cl)nc(Cl)nc32)[C@@H]1O]

Example 77

The title compound was prepared in a manner analogous to that set forth in Example 59, except (2-chlorophenyl)methanamine was used in place of benzylamine in step 7.

$^1$H NMR (400 MHz, CD$_3$OD) δ 8.17 (s, 1H), 7.43 (m, 2H), 7.28 (m, 3H), 7.22 (m, 1H), 7.00 (m, 3H), 5.99 (d, J=7.4 Hz, 1H), 4.98 (d, J=7.4 Hz, 1H), 4.82 (m, 2H), 4.30 (s, 1H), 4.05 (s, 2H), 3.42 (m, 2H), 2.98 (s, 1H). LC-MS: m/z=597 (M-CO$_2$H); m/z=292 (M-ribose fragment).

Example 78

Synthesis of 2-benzyl-2-(((2R,3S,4R,5R)-5-(2-chloro-6-((pyridin-4-ylmethyl)amino)-9H-purin-9-yl)-3-ethynyl-3,4-dihydroxytetrahydrofuran-2-yl)methoxy)malonic acid

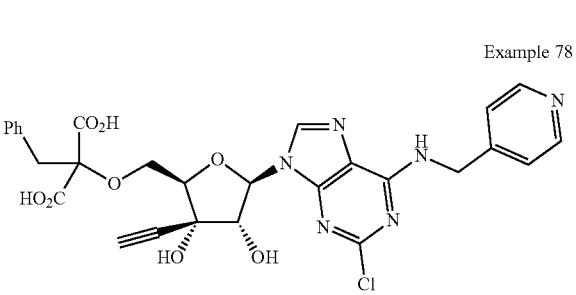 [SMILES: C#C[C@@]1(O)[C@@H](COC(Cc2ccccc2)(C(=O)O)C(=O)O)O[C@@H](n2cnc3c(NCc4ccncc4)nc(Cl)nc32)[C@@H]1O]

Example 78

The title compound was prepared in a manner analogous to that set forth in Example 59, except pyridin-4-ylmethanamine was used in place of benzylamine in step 7.

$^1$H NMR (400 MHz, CD$_3$OD) δ 9.08 (bs, 1H), 8.73 (d, J=5.7 Hz, 2H), 8.51 (s, 1H), 7.68 (d, J=5.6 Hz, 2H), 7.22 (m, 2H), 7.06 (m, 3H), 5.82 (d, J=7.7 Hz, 1H), 4.93 (d, J=6.9 Hz, 1H), 4.87 (d, J=7.6 Hz, 1H), 4.20 (m, 1H), 4.03 (m, 2H), 3.86 (m, 2H), 3.62 (s, 1H), 3.27 (m, 2H). HPLC: Room temperature=5.74 min, 97.7%. LC-MS: m/z=610 (M+); m/z=261 (M-ribose fragment).

Example 79

Synthesis of 2-benzyl-2-(((2R,3S,4R,5R)-5-(2-chloro-6-morpholino-9H-purin-9-yl)-3-ethynyl-3,4-dihydroxytetrahydrofuran-2-yl)methoxy)malonic acid

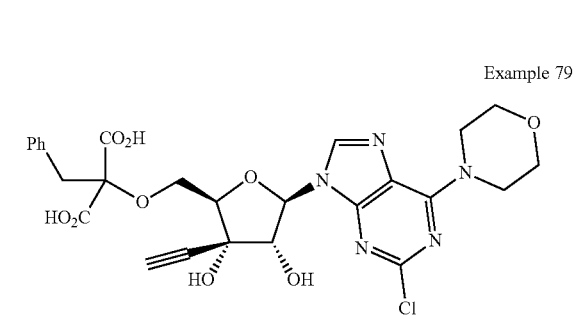 [SMILES: C#C[C@@]1(O)[C@@H](COC(Cc2ccccc2)(C(=O)O)C(=O)O)O[C@@H](n2cnc3c(N4CCOCC4)nc(Cl)nc32)[C@@H]1O]

Example 79

The title compound was prepared in a manner analogous to that set forth in Example 59, except morpholine was used in place of benzylamine in step 7.

$^1$H NMR (400 MHz, CD$_3$OD) δ 8.20 (s, 1H), 7.22 (m, 2H), 7.01 (m, 3H), 6.00 (d, J=7.6 Hz, 1H), 4.99 (d, J=7.6 Hz, 1H), 4.30 (m, 1H), 4.22 (m, 4H), 4.04 (m, 2H), 3.78 (m, 4H), 3.47 (m, 2H), 2.99 (s, 1H). HPLC: 8.16 min, 98.2%. LC-MS: m/z=588 (M+), 544 (M-CO$_2$H), m/z=240 (M-ribose fragment).

Example 80

Synthesis of 2-(((2R,3S,4R,5R)-5-(6-(azepan-1-yl)-2-chloro-9H-purin-9-yl)-3-ethynyl-3,4-dihydroxytetrahydrofuran-2-yl)methoxy)-2-benzylmalonic acid

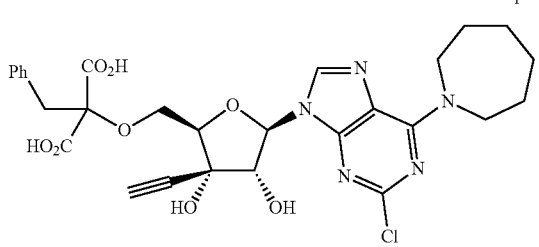

Example 80

The title compound was prepared in a manner analogous to that set forth in Example 59, except azepane was used in place of benzylamine in step 7.

$^1$H NMR (400 MHz, CD$_3$OD) δ 8.16 (s, 1H), 7.22 (m, 2H), 7.00 (m, 3H), 5.99 (d, J=7.6 Hz, 1H), 4.98 (d, J=7.6 Hz, 1H), 4.29 (m, 3H), 4.07 (m, 2H), 3.85 (m, 2H), 3.40 (m, 2H), 2.97 (s, 1H), 1.85 (m, 4H), 1.59 (m, 4H). HPLC: 9.67 min, 98.1%. LC-MS: m/z=600 (M+), m/z=556 (M-CO$_2$H), m/z=252 (M-ribose fragment).

Example 81

Synthesis of 2-benzyl-2-(((2R,3S,4R,5R)-5-(2-chloro-6-(cyclobutyl(methyl)amino)-9H-purin-9-yl)-3-ethynyl-3,4-dihydroxytetrahydrofuran-2-yl)methoxy)malonic acid

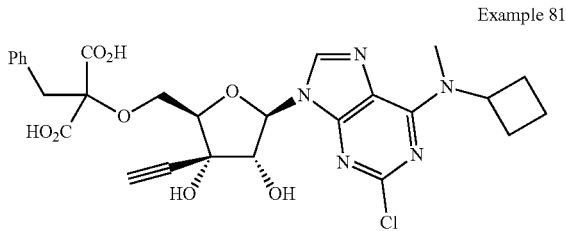 [SMILES: C#C[C@@]1(O)[C@@H](COC(Cc2ccccc2)(C(=O)O)C(=O)O)O[C@@H](n2cnc3c(N(C)C4CCC4)nc(Cl)nc32)[C@@H]1O]

Example 81

The title compound was prepared in a manner analogous to that set forth in Example 59, except N-methylcyclobutanamine was used in place of benzylamine in step 7.

$^1$H NMR (400 MHz, CD$_3$OD) δ 8.21 (s, 1H), 7.21 (dd, J=7.0, 2.6 Hz, 2H), 6.99 (m, 3H), 5.99 (d, J=7.3 Hz, 1H), 5.74 (br s, 1H), 4.96 (d, J=7.2 Hz, 1H), 4.28 (dd, J=4.1, 2.8 Hz, 1H), 4.06 (dd, J=10.2, 4.2 Hz, 1H), 4.01 (dd, J=10.2, 2.9 Hz, 1H), 3.45-3.31 (m, 5H), 2.96 (s, 1H), 2.35 (q, J=10.0 Hz, 2H), 2.23 (m, 2H), 1.87-1.63 (m, 2H); HPLC: 9.45 min, 98.9%. LC-MS: m/z=587 (M+H), 543 (M-CO$_2$H), m/z=238 (M-ribose fragment).

Example 82

Synthesis of 2-benzyl-2-(((2R,3S,4R,5R)-5-(2-chloro-6-(isopropyl(methyl)amino)-9H-purin-9-yl)-3-ethynyl-3,4-dihydroxytetrahydrofuran-2-yl)methoxy)malonic acid

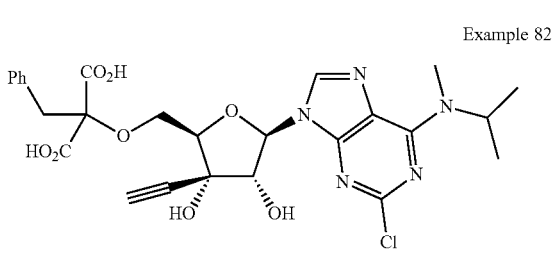 [SMILES: C#C[C@@]1(O)[C@@H](COC(Cc2ccccc2)(C(=O)O)C(=O)O)O[C@@H](n2cnc3c(N(C)C(C)C)nc(Cl)nc32)[C@@H]1O]

Example 82

The title compound was prepared in a manner analogous to that set forth in Example 59, except N-methylpropan-2-amine was used in place of benzylamine in step 7.

$^1$H NMR (400 MHz, CD$_3$OD) δ 8.17 (s, 1H), 7.21 (dd, J=7.3, 2.2 Hz, 2H), 7.03-6.94 (m, 3H), 5.98 (d, J=7.3 Hz, 1H), 4.97 (d, J=7.3 Hz, 1H), 4.28 (dd, J=4.0, 2.8 Hz, 1H), 4.04 (qd, J=10.2, 3.5 Hz, 2H), 3.45-3.31 (m, 6H), 2.96 (s, 1H), 1.25 (d, J=6.8 Hz, 6H); HPLC: 9.08 min, 99.9%. LC-MS: m/z=575 (M+H), 531 (M-CO$_2$H), m/z=226 (M-ribose fragment).

Example 83

Synthesis of 2-benzyl-2-(((2R,3S,4R,5R)-5-(2-chloro-6-(cyclopropylamino)-9H-purin-9-yl)-3-ethynyl-3,4-dihydroxytetrahydrofuran-2-yl)methoxy)malonic acid

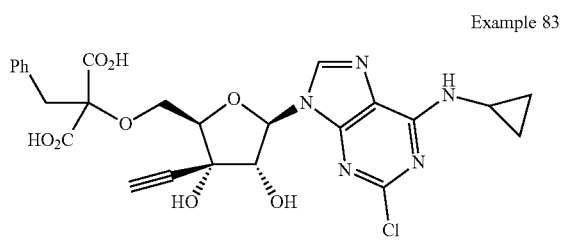 [SMILES: C#C[C@@]1(O)[C@@H](COC(Cc2ccccc2)(C(=O)O)C(=O)O)O[C@@H](n2cnc3c(NC4CC4)nc(Cl)nc32)[C@@H]1O]

Example 83

The title compound was prepared in a manner analogous to that set forth in Example 59, except cyclopropanamine was used in place of benzylamine in step 7.

$^1$H NMR (400 MHz, CD$_3$OD) δ 8.14 (s, 1H), 7.23 (dd, J=6.7, 2.8 Hz, 2H), 7.01 (m, 3H), 5.97 (d, J=7.4 Hz, 1H), 4.95 (d, J=7.4 Hz, 1H), 4.28 (t, J=3.3 Hz, 1H), 4.10-3.97 (m, 2H), 3.49-3.30 (m, 2H), 2.99 (m, 1H), 2.96 (s, 1H), 0.92-0.78 (m, 2H), 0.66-0.54 (m, 2H); HPLC: 7.83 min, 99.1%. LC-MS: m/z=559 (M+H).

Example 84

Synthesis of 2-benzyl-2-(((2R,3S,4R,5R)-5-(2-chloro-6-((pyridin-3-ylmethyl)amino)-9H-purin-9-yl)-3-ethynyl-3,4-dihydroxytetrahydrofuran-2-yl)methoxy)malonic acid

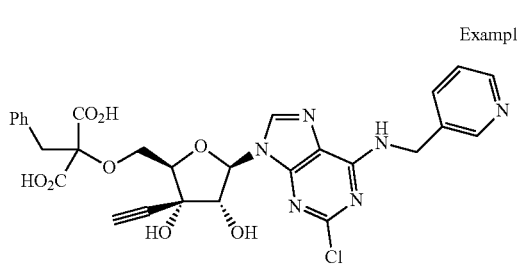

Example 84

The title compound was prepared in a manner analogous to that set forth in Example 59, except pyridin-3-ylmethanamine was used in place of benzylamine in step 7.

$^1$H NMR (400 MHz, CD$_3$OD) δ 8.87 (s, 1H), 8.70 (d, J=5.6 Hz, 1H), 8.56 (d, J=8.1 Hz, 1H), 8.22 (s, 1H), 7.97 (dd, J=8.1, 5.7 Hz, 1H), 7.21 (dd, J=6.5, 3.0 Hz, 2H), 7.07-6.90 (m, 3H), 5.97 (d, J=7.4 Hz, 1H), 4.96 (d, J=7.4 Hz, 1H), 4.92 (m, 2H), 4.29 (t, J=3.4 Hz, 1H), 4.04 (qd, J=10.2, 3.4 Hz, 2H), 3.38 (m, 2H), 2.97 (s, 1H); HPLC: 5.82 min, 99.9%. LC-MS: m/z=261 (M-ribose fragment).

Example 85

Synthesis of 2-benzyl-2-(((2R,3S,4R,5R)-5-(2-chloro-6-((3-fluorobenzyl)amino)-9H-purin-9-yl)-3-ethynyl-3,4-dihydroxytetrahydrofuran-2-yl)methoxy)malonic acid

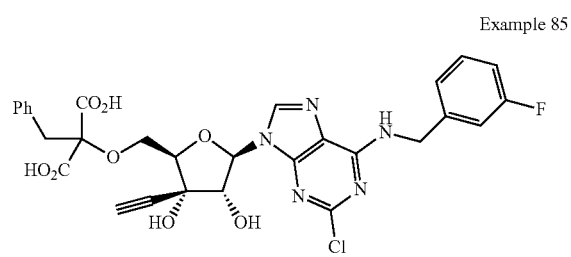 [SMILES: C#C[C@@]1(O)[C@@H](COC(Cc2ccccc2)(C(=O)O)C(=O)O)O[C@@H](n2cnc3c(NCc4cccc(F)c4)nc(Cl)nc32)[C@@H]1O]

Example 85

The title compound was prepared in a manner analogous to that set forth in Example 59, except (3-fluorophenyl)methanamine was used in place of benzylamine in step 7.

$^1$H NMR (400 MHz, CD$_3$OD) δ 8.19 (s, 1H), 7.32 (td, J=8.0, 5.9 Hz, 1H), 7.24-7.16 (m, 3H), 7.12 (dd, J=9.8, 2.3 Hz, 1H), 7.06-6.78 (m, 4H), 5.98 (d, J=7.3 Hz, 1H), 4.94 (d, J=7.3 Hz, 1H), 4.74 (m, 2H), 4.29 (t, J=3.3 Hz, 1H), 4.03 (qd, J=10.3, 3.5 Hz, 2H), 3.47-3.26 (m, 2H), 2.97 (s, 1H); HPLC: 9.04 min, 99.5%. LC-MS: m/z=627 (M+H), 583 (M-CO$_2$H), m/z=278 (M-ribose fragment).

Example 86

Synthesis of 2-benzyl-2-(((2R,3S,4R,5R)-5-(2-chloro-6-((3-chlorobenzyl)amino)-9H-purin-9-yl)-3-ethynyl-3,4-dihydroxytetrahydrofuran-2-yl)methoxy)malonic acid

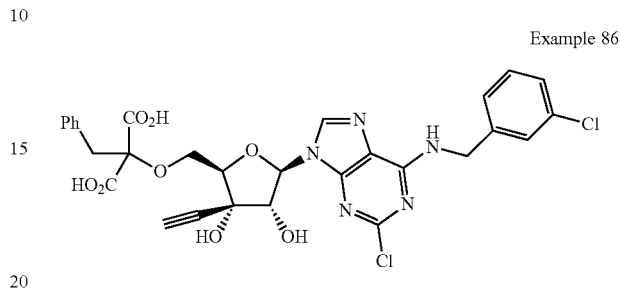

Example 86

The title compound was prepared in a manner analogous to that set forth in Example 59, except (3-chlorophenyl)methanamine was used in place of benzylamine in step 7.

$^1$H NMR (400 MHz, CD$_3$OD) δ 8.18 (s, 1H), 7.40 (s, 1H), 7.34-7.05 (m, 5H), 6.98 (m, 3H), 5.97 (d, J=7.4 Hz, 1H), 4.95 (d, J=7.4 Hz, 1H), 4.72 (m, 2H), 4.29 (t, J=3.3 Hz, 1H), 4.09-3.87 (m, 2H), 3.46-3.31 (m, 2H), 2.97 (s, 1H); HPLC: 9.45 min, 98.3%. LC-MS: m/z=643 (M+H), 598 (M-CO$_2$H), m/z=294 (M-ribose fragment).

Example 87

Synthesis of 2-benzyl-2-(((2R,3S,4R,5R)-5-(2-chloro-6-((4-chlorobenzyl)amino)-9H-purin-9-yl)-3-ethynyl-3,4-dihydroxytetrahydrofuran-2-yl)methoxy)malonic acid

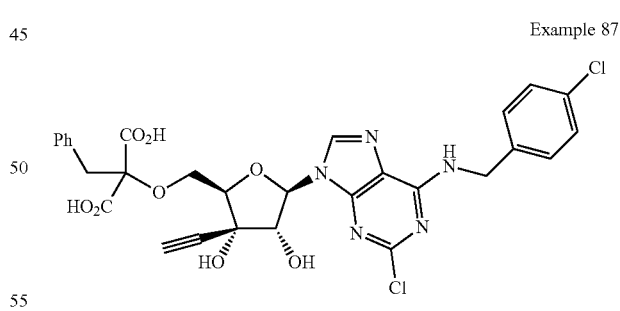

Example 87

The title compound was prepared in a manner analogous to that set forth in Example 59, except (4-chlorophenyl)methanamine was used in place of benzylamine in step 7.

$^1$H NMR (400 MHz, CD$_3$OD) δ 8.17 (s, 1H), 7.36 (d, J=8.6 Hz, 2H), 7.31 (d, J=8.5 Hz, 1H), 7.21 (dd, J=6.8, 2.8 Hz, 2H), 7.02-6.96 (m, 3H), 5.97 (d, J=7.3 Hz, 1H), 4.94 (d, J=7.3 Hz, 1H), 4.71 (m, 2H), 4.29 (t, J=3.3 Hz, 1H), 4.03 (qd, J=10.2, 3.4 Hz, 2H), 3.46-3.30 (m, 2H), 2.96 (s, 1H); HPLC: 9.50 min, 98.7%. LC-MS: m/z=643 (M+H), 598 (M-CO$_2$H), m/z=294 (M-ribose fragment).

Example 88

Synthesis of 2-(((2R,3S,4R,5R)-5-(6-(azetidin-1-yl)-2-chloro-9H-purin-9-yl)-3-ethynyl-3,4-dihydroxytetrahydrofuran-2-yl)methoxy)-2-benzylmalonic acid

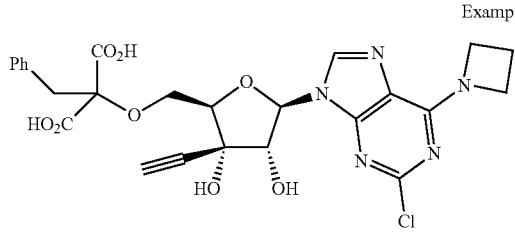

Example 88

The title compound was prepared in a manner analogous to that set forth in Example 59, except azetidine was used in place of benzylamine in step 7.

$^1$H NMR (400 MHz, CD$_3$OD) δ 8.25 (s, 1H), 7.24-7.08 (m, 2H), 7.10-6.85 (m, 3H), 5.97 (d, J=7.4 Hz, 1H), 4.98 (d, J=7.3 Hz, 1H), 4.43 (m, 4H), 4.29 (dd, J=4.1, 2.8 Hz, 1H), 4.07 (dd, J=10.2, 4.2 Hz, 1H), 4.00 (dd, J=10.2, 2.9 Hz, 1H), 3.42 (d, J=15.0 Hz, 1H), 3.34 (d, J=12.3 Hz, 2H), 2.95 (s, 1H), 2.51 (q, J=7.7 Hz, 2H); HPLC: 7.58 min, 99.5%.

LC-MS: m/z=558 (M+H), 554 (M-CO$_2$H), m/z=210 (M-ribose fragment).

Example 89

Synthesis of 2-benzyl-2-(((2R,3S,4R,5R)-5-(2-chloro-6-(dimethylamino)-9H-purin-9-yl)-3-ethynyl-3,4-dihydroxytetrahydrofuran-2-yl)methoxy)malonic acid

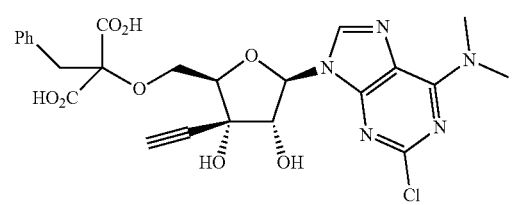

Example 89

The title compound was prepared in a manner analogous to that set forth in Example 59, except dimethylamine was used in place of benzylamine in step 7.

$^1$H NMR (400 MHz, CD$_3$OD) δ 8.17 (s, 1H), 7.22 (dd, J=7.5, 2.0 Hz, 2H), 7.05-6.89 (m, 3H), 5.98 (d, J=7.2 Hz, 1H), 4.96 (d, J=7.3 Hz, 1H), 4.28 (dd, J=4.0, 2.9 Hz, 1H), 4.04 (qd, J=10.2, 3.5 Hz, 2H), 3.55-3.31 (m, 8H), 2.95 (s, 1H); HPLC: 8.16 min, 99.9%. LC-MS: m/z=546 (M+H), 502 (M-CO$_2$H), m/z=198 (M-ribose fragment).

Example 90

Synthesis of 2-benzyl-2-(((2R,3S,4R,5R)-5-(2-chloro-6-(pyrrolidin-1-yl)-9H-purin-9-yl)-3-ethynyl-3,4-dihydroxytetrahydrofuran-2-yl)methoxy)malonic acid

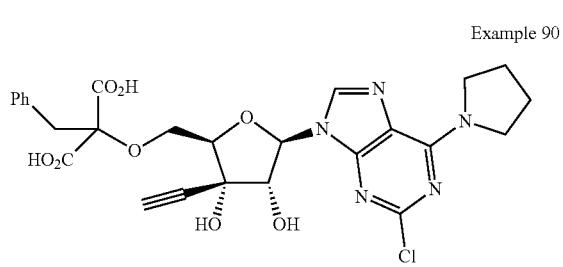 [SMILES: C#C[C@@]1(O)[C@@H](COC(Cc2ccccc2)(C(=O)O)C(=O)O)O[C@@H](n2cnc3c(N4CCCC4)nc(Cl)nc32)[C@@H]1O]

Example 90

The title compound was prepared in a manner analogous to that set forth in Example 59, except pyrrolidine was used in place of benzylamine in step 7.

$^1$H NMR (400 MHz, CD$_3$OD) δ 8.21 (s, 1H), 7.21 (dd, J=7.3, 2.3 Hz, 2H), 7.03-6.76 (m, 3H), 5.98 (d, J=7.3 Hz, 1H), 4.98 (d, J=7.3 Hz, 1H), 4.29 (dd, J=4.2, 2.8 Hz, 1H), 4.15-3.86 (m, 4H), 3.66 (m, 2H), 3.41 (d, J=15.0 Hz, 1H), 3.34 (d, J=15.0 Hz, 1H), 2.95 (s, 1H), 2.02 (m, 4H); HPLC: 8.42 min, 95.6%. LC-MS: m/z=573 (M+H), 529 (M-CO$_2$H), m/z=224 (M-ribose fragment).

Example 91

Synthesis of 2-benzyl-2-(((2R,3S,4R,5R)-5-(2-chloro-6-(cyclopentylamino)-9H-purin-9-yl)-3-ethynyl-3,4-dihydroxytetrahydrofuran-2-yl)methoxy)malonic acid

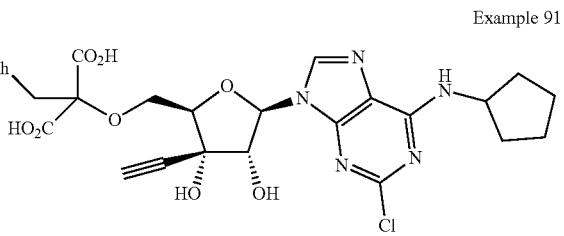

Example 91

The title compound was prepared in a manner analogous to that set forth in Example 59, except cyclopentanamine was used in place of benzylamine in step 7.

$^1$H NMR (400 MHz, CD$_3$OD) δ 8.09 (s, 1H), 7.23 (dd, J=6.7, 2.9 Hz, 2H), 7.01 (m, 3H), 5.96 (d, J=7.4 Hz, 1H), 4.94 (d, J=7.4 Hz, 1H), 4.47 (m, 1H), 4.28 (t, J=3.3 Hz, 1H), 4.04 (m, 2H), 3.43 (d, J=14.9 Hz, 1H), 3.34 (d, J=14.9 Hz, 1H), 2.96 (s, 1H), 2.19-1.98 (m, 2H), 1.78 (m, 2H), 1.72-1.64 (m, 2H), 1.62-1.52 (m, 2H); HPLC: 9.06 min, 98.9%. LC-MS: m/z=587 (M+H), 543 (M-CO$_2$H), m/z=238 (M-ribose fragment).

Example 92

Synthesis of 2-benzyl-2-(((2R,3S,4R,5R)-5-(2-chloro-6-((cyclopropylmethyl)amino)-9H-purin-9-yl)-3-ethynyl-3,4-dihydroxytetrahydrofuran-2-yl)methoxy)malonic acid

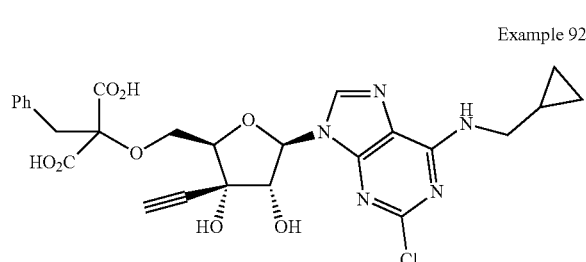

Example 92

The title compound was prepared in a manner analogous to that set forth in Example 59, except cyclopropylmethanamine was used in place of benzylamine in step 7.

$^1$H NMR (400 MHz, CD$_3$OD) δ 8.14 (s, 1H), 7.18 (d, J=6.9 Hz, 2H), 7.12-6.68 (m, 3H), 5.92 (d, J=6.1 Hz, 1H), 4.58 (d, J=6.1 Hz, 1H), 4.28 (t, J=3.2 Hz, 1H), 3.98 (qd, J=10.3, 3.2 Hz, 2H), 3.50-3.04 (m, 4H), 2.55 (s, 1H), 1.08 (m, 1H), 0.52 (m, 2H), 0.26 (m, 2H); HPLC: 8.52 min, 97.7%. LC-MS: m/z=572 (M+H), 528 (M-CO$_2$H), m/z=224 (M-ribose fragment).

Example 93

Synthesis of 2-benzyl-2-(((2R,3S,4R,5R)-5-(2-chloro-6-(isopropylamino)-9H-purin-9-yl)-3-ethynyl-3,4-dihydroxytetrahydrofuran-2-yl)methoxy)malonic acid

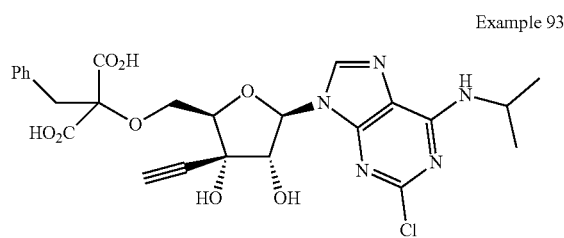 [SMILES: C#C[C@@]1(O)[C@@H](COC(Cc2ccccc2)(C(=O)O)C(=O)O)O[C@@H](n2cnc3c(NC(C)C)nc(Cl)nc32)[C@@H]1O]

Example 93

The title compound was prepared in a manner analogous to that set forth in Example 59, except propan-2-amine was used in place of benzylamine in step 7.

$^1$H NMR (400 MHz, CD$_3$OD) δ 8.05 (s, 1H), 7.23-7.12 (m, 2H), 7.09-6.78 (m, 3H), 5.91 (d, J=6.2 Hz, 1H), 4.59 (d, J=6.2 Hz, 1H), 4.37 (m, 1H), 4.28 (m, 1H), 3.42 (d, J=14.8 Hz, 1H), 3.35-3.22 (m, 3H), 2.56 (s, 1H), 1.24 (d, J=6.5 Hz, 6H); HPLC: 8.39 min, 98.9%. LC-MS: m/z=560 (M+H), 516 (M-CO$_2$H), m/z=212 (M-ribose fragment).

Example 94

Synthesis of 2-benzyl-2-(((2R,3S,4R,5R)-5-(2-chloro-6-((2-hydroxy-2-methylpropyl)amino)-9H-purin-9-yl)-3-ethynyl-3,4-dihydroxytetrahydrofuran-2-yl)methoxy)malonic acid

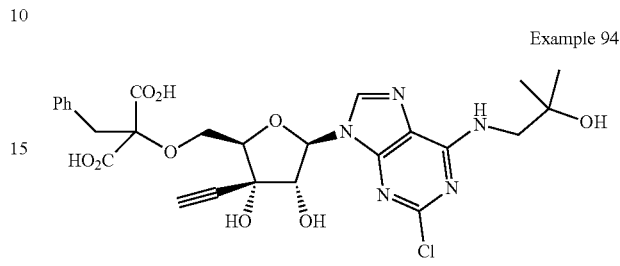

Example 94

The title compound was prepared in a manner analogous to that set forth in Example 59, except 1-amino-2-methylpropan-2-ol was used in place of benzylamine in step 7.

$^1$H-NMR (400 MHz, CD$_3$OD) δ 8.16 (s, 1H) 7.24-7.22 (m, 2H) 7.03-7.01 (m, 3H) 5.97 (d, J=7.4 Hz, 1H) 4.95 (d, J=7.4 Hz, 1H) 4.28 (t, J=3.2 Hz, 1H) 4.05-4.03 (m, 2H) 3.72-3.69 (m, 2H) 3.48-3.31 (m, 2H) 2.97 (s, 1H) 1.24 (s, 6H). ESI-MS (m/z): [M]$^-$ calcd for C$_{26}$H$_{28}$ClN$_5$O$_9$ 589.98; found 588.4.

Example 95

Synthesis of 2-benzyl-2-(((2R,3S,4R,5R)-5-(2-chloro-6-(((S)-1-hydroxypropan-2-yl)amino)-9H-purin-9-yl)-3-ethynyl-3,4-dihydroxytetrahydrofuran-2-yl)methoxy)malonic acid

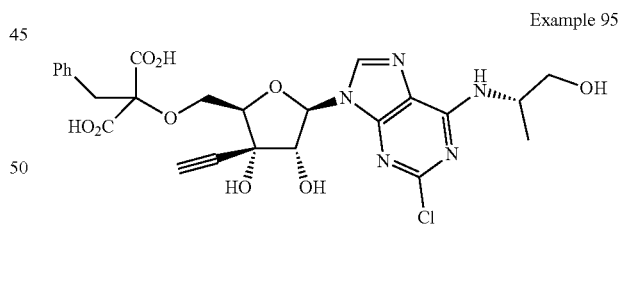

Example 95

The title compound was prepared in a manner analogous to that set forth in Example 59, except (S)-2-aminopropan-1-ol was used in place of benzylamine in step 7.

$^1$H-NMR (400 MHz, CD$_3$OD) δ 8.18 (s, 1H) 7.24-7.22 (m, 2H) 7.03-7.01 (m, 3H) 5.97 (d, J=7.4 Hz, 1H) 4.93 (d, J=7.4 Hz, 1H) 4.42-4.35 (m, 1H) 4.32-4.26 (m, 1H) 4.04 (d, J=3.2 Hz, 2H) 3.62-3.60 (m, 2H) 3.48-3.32 (m, 2H) 2.96 (s, 1H) 1.29 (d, J=6.7 Hz, 3H). ESI-MS (m/z): [M]$^-$ calcd for C$_{25}$H$_{26}$ClN$_5$O$_9$ 575.96; found 574.2.

Example 96

Synthesis of 2-benzyl-2-(((2R,3S,4R,5R)-5-(2-chloro-6-(diethylamino)-9H-purin-9-yl)-3-ethynyl-3,4-dihydroxytetrahydrofuran-2-yl)methoxy)malonic acid

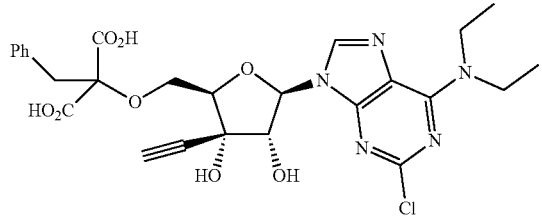

Example 96

The title compound was prepared in a manner analogous to that set forth in Example 59, except diethylamine was used in place of benzylamine in step 7.

$^1$H-NMR (400 MHz, CD$_3$OD) δ 8.15 (s, 1H) 7.23-7.20 (m, 2H) 7.00-6.98 (m, 3H) 5.98 (d, J=7.3 Hz, 1H) 4.97 (d, J=7.3 Hz, 1H) 4.29 (m, 1H) 4.15-3.83 (m, 6H) 3.43-3.33 (m, 2H) 2.96 (s, 1H) 1.24 (t, J=7.0 Hz, 6H). ESI-MS (m/z): [M]$^-$ calcd for C$_{26}$H$_{28}$ClN$_5$O$_9$ 573.98; found 572.3.

Example 97

Synthesis of 2-benzyl-2-(((2R,3S,4R,5R)-5-(2-chloro-6-((2-hydroxyethyl)amino)-9H-purin-9-yl)-3-ethynyl-3,4-dihydroxytetrahydrofuran-2-yl)methoxy)malonic acid

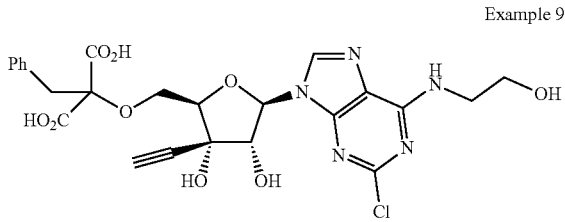

Example 97

The title compound was prepared in a manner analogous to that set forth in Example 59, except 2-aminoethan-1-ol was used in place of benzylamine in step 7.

$^1$H-NMR (400 MHz, CD$_3$OD) δ 8.20 (s, 1H) 7.24-7.22 (m, 2H) 7.04-7.02 (m, 3H) 5.97 (d, J=7.4 Hz, 1H) 4.91 (d, J=7.3 Hz, 1H) 4.29 (t, J=3.4 Hz, 1H)) 4.06-3.98 (m, 2H) 3.76-3.73 (m, 2H) 3.66-3.63 (m, 2H) 3.43-3.33 (m, 2H) 2.96 (s, 1H). ESI-MS (m/z): [M]$^-$ calcd for C$_{24}$H$_{24}$ClN$_5$O$_9$ 561.93; found 560.2.

Example 98

Synthesis of 2-benzyl-2-(((2R,3S,4R,5R)-5-(2-chloro-6-(((R)-1-hydroxypropan-2-yl)amino)-9H-purin-9-yl)-3-ethynyl-3,4-dihydroxytetrahydrofuran-2-yl)methoxy)malonic acid

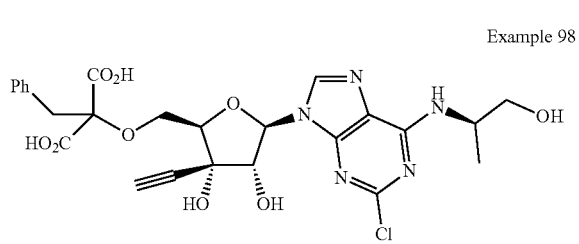 [SMILES: C#C[C@@]1(O)[C@@H](COC(Cc2ccccc2)(C(=O)O)C(=O)O)O[C@@H](n2cnc3c(N[C@H](C)CO)nc(Cl)nc32)[C@@H]1O]

Example 98

The title compound was prepared in a manner analogous to that set forth in Example 59, except (R)-2-aminopropan-1-ol was used in place of benzylamine in step 7.

$^1$H-NMR (400 MHz, CD$_3$OD) δ 8.12 (s, 1H) 7.24-7.22 (m, 2H) 7.03-7.01 (m, 3H) 5.96 (d, J=7.4 Hz, 1H) 4.95 (d, J=7.4 Hz, 1H) 4.42-4.32 (m, 1H) 4.28 (t, J=3.3 Hz, 1H) 4.08-4.00 (m, 2H) 3.66-3.58 (m, 2H) 3.45-3.33 (m, 2H) 2.97 (s, 1H) 1.27 (d, J=6.7 Hz, 3H). ESI-MS (m/z): [M]$^-$ calcd for C$_{25}$H$_{26}$ClN$_5$O$_9$ 575.96; found 574.2.

Example 99

Synthesis of 2-benzyl-2-(((2R,3S,4R,5R)-5-(2-chloro-6-(cyclopropyl(2-hydroxyethyl)amino)-9H-purin-9-yl)-3-ethynyl-3,4-dihydroxytetrahydrofuran-2-yl)methoxy)malonic acid

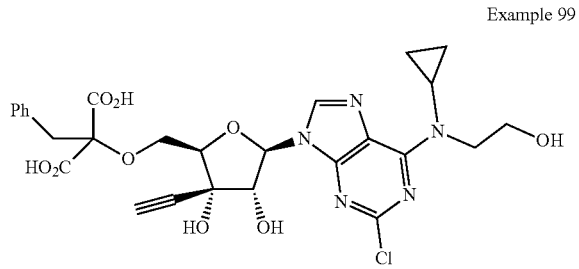 [SMILES: C#C[C@@]1(O)[C@@H](COC(Cc2ccccc2)(C(=O)O)C(=O)O)O[C@@H](n2cnc3c(N(CCO)C4CC4)nc(Cl)nc32)[C@@H]1O]

Example 99

The title compound was prepared in a manner analogous to that set forth in Example 59, except 2-(cyclopropylamino)ethan-1-ol was used in place of benzylamine in step 7.

$^1$H-NMR (400 MHz, CD$_3$OD) δ 8.23 (s, 1H) 7.24-7.22 (m, 2H) 7.04-7.01 (m, 3H) 6.02 (d, J=7.4 Hz, 1H) 4.96 (d, J=7.3 Hz, 1H) 4.30-4.28 (m, 1H) 4.10-4.04 (m, 4H) 3.78 (t, J=5.9 Hz, 2H) 3.44-3.32 (m, 2H) 3.23-3.19 (m, 1H) 2.96 (s, 1H) 1.01-0.97 (m, 2H) 0.78-0.74 (m, 2H).

Example 100

Synthesis of 2-benzyl-2-(((2R,3S,4R,5R)-5-(2-chloro-6-((R)-3-hydroxypyrrolidin-1-yl)-9H-purin-9-yl)-3-ethynyl-3,4-dihydroxytetrahydrofuran-2-yl)methoxy)malonic acid

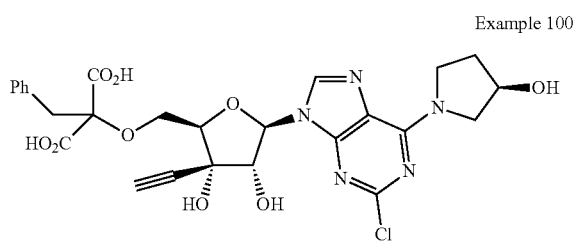 [SMILES: C#C[C@@]1(O)[C@@H](COC(Cc2ccccc2)(C(=O)O)C(=O)O)O[C@@H](n2cnc3c(N4CC[C@@H](O)C4)nc(Cl)nc32)[C@@H]1O]

Example 100

The title compound was prepared in a manner analogous to that set forth in Example 59, except (R)-pyrrolidin-3-ol was used in place of benzylamine in step 7.

$^1$H NMR (400 MHz, CD$_3$OD) δ 8.24 (s, 1H), 7.23 (d, J=7.2 Hz, 2H), 7.06-6.96 (m, 3H), 6.01 (d, J=7.3 Hz, 1H), 5.01 (s, 1H), 4.56 (d, J=26.1 Hz, 1H), 4.33-4.31 (m, 1H), 4.20 (d, J=12.5 Hz, 1H), 4.10-4.00 (m, 3H), 3.78 (m, 2H), 3.50-3.35 (m, 2H), 2.97 (s, 1H), 2.14-2.05 (m, 2H).

Example 101

Synthesis of 2-benzyl-2-(((2R,3S,4R,5R)-5-(2-chloro-6-((S)-3-(hydroxymethyl)-pyrrolidin-1-yl)-9H-purin-9-yl)-3-ethynyl-3,4-dihydroxytetrahydrofuran-2-yl)methoxy)malonic acid

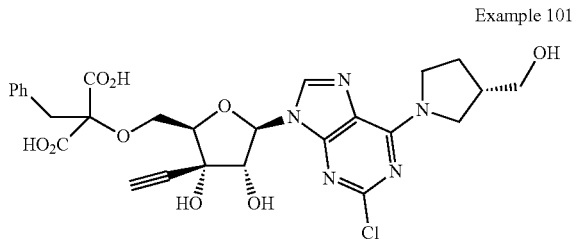 [SMILES: C#C[C@@]1(O)[C@@H](COC(Cc2ccccc2)(C(=O)O)C(=O)O)O[C@@H](n2cnc3c(N4CC[C@H](CO)C4)nc(Cl)nc32)[C@@H]1O]

Example 101

The title compound was prepared in a manner analogous to that set forth in Example 59, except (S)-pyrrolidin-3-ylmethanol was used in place of benzylamine in step 7.

$^1$H NMR (400 MHz, DMSO-d$_6$) δ 8.37 (s, 1H), 8.34 (s, 1H), 7.15 (m, 2H), 7.01 (m, 3H), 6.16 (br s, 1H), 5.96 (br s, 1H), 5.81 (d, J=7.5 Hz, 1H), 4.82 (d, J=7.4 Hz, 1H), 4.18-4.08 (m, 1H), 3.94 (m, 2H), 3.71 (m, 2H), 3.50 (m, 2H), 3.20 (s, 4H), 3.13 (s, 1H), 2.33 (m, 1H), 2.04 (m, 1H), 1.98-1.89 (m, 1H), 1.77 (m, 1H), 1.65 (m, 1H); HPLC: 7.22 min, 97.7%.

Example 102

Synthesis of 2-benzyl-2-(((2R,3S,4R,5R)-5-(2-chloro-6-((R)-3-(hydroxymethyl)-pyrrolidin-1-yl)-9H-purin-9-yl)-3-ethynyl-3,4-dihydroxytetrahydrofuran-2-yl)methoxy)malonic acid

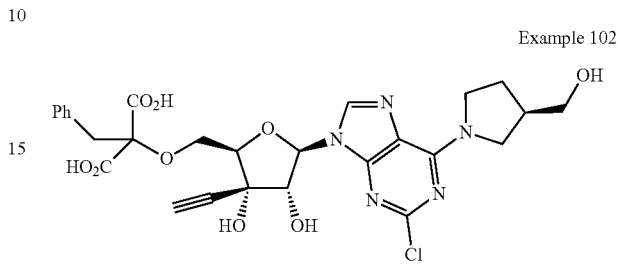

Example 102

The title compound was prepared in a manner analogous to that set forth in Example 59, except (R)-pyrrolidin-3-ylmethanol was used in place of benzylamine in step 7.

$^1$H NMR (400 MHz, DMSO-d$_6$) δ 8.37 (s, 1H), 8.34 (s, 1H), 7.21-7.11 (m, 2H), 7.01 (m, 3H), 6.16 (br s, 1H), 5.96 (br s, 1H), 5.81 (d, J=7.5 Hz, 1H), 4.82 (d, J=7.5 Hz, 1H), 4.44 (m, 1H), 4.25-4.07 (m, 3H), 3.95 (m, 2H), 3.87-3.64 (m, 3H), 3.51 (m, 2H), 3.20 (s, 1H), 2.37-2.27 (m, 1H), 2.04 (m, 1H), 1.98-1.86 (m, 1H), 1.76 (m, 1H), 1.66 (m, 1H); HPLC: Rt=7.20 min, 97.0%.

Example 103

Synthesis of 2-benzyl-2-(((2R,3S,4R,5R)-5-(2-chloro-6-((R)-2-(hydroxymethyl)-pyrrolidin-1-yl)-9H-purin-9-yl)-3-ethynyl-3,4-dihydroxytetrahydrofuran-2-yl)methoxy)malonic acid

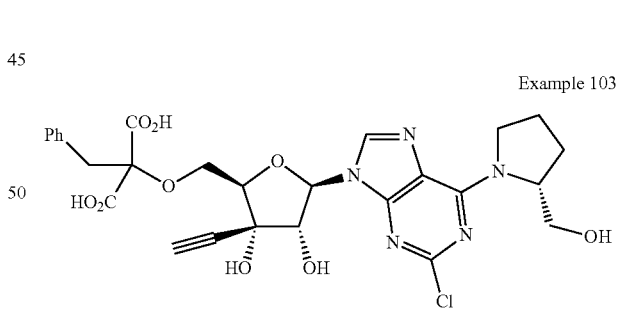

Example 103

The title compound was prepared in a manner analogous to that set forth in Example 59, except (R)-pyrrolidin-2-ylmethanol was used in place of benzylamine in step 7.

$^1$H NMR (400 MHz, CD$_3$OD) δ 8.21 (s, 1H), 7.28-7.16 (m, 2H), 7.08-6.87 (m, 3H), 5.99 (d, J=7.3 Hz, 1H), 4.97 (d, J=7.3 Hz, 1H), 4.41 (m, 1H), 4.28 (m, 1H), 4.12-3.93 (m, 4H), 3.72 (m, 2H), 3.42 (d, J=15.0 Hz, 1H), 3.33 (d, J=15.0 Hz, 2H), 2.96 (s, 1H), 2.05 (m, 4H); HPLC: 7.73 min, 98.2%; ESI-MS: m/z=254 (M-ribose fragment).

Example 104

Synthesis of 2-benzyl-2-(((2R,3S,4R,5R)-5-(2-chloro-6-((S)-2-(hydroxymethyl)-pyrrolidin-1-yl)-9H-purin-9-yl)-3-ethynyl-3,4-dihydroxytetrahydrofuran-2-yl)methoxy)malonic acid

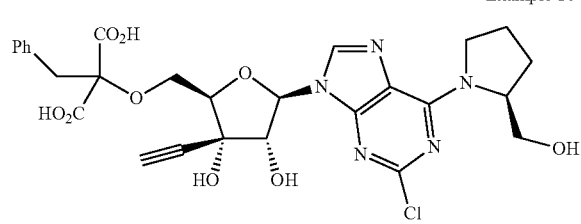

Example 104

The title compound was prepared in a manner analogous to that set forth in Example 59, except (S)-pyrrolidin-2-ylmethanol was used in place of benzylamine in step 7.

$^1$H NMR (400 MHz, CD$_3$OD) δ 8.22 (s, 1H), 7.22 (m, 2H), 7.07-6.88 (m, 3H), 5.99 (d, J=7.3 Hz, 1H), 4.98 (d, J=7.3 Hz, 1H), 4.44 (m, 1H), 4.29 (dd, J=4.0, 2.9 Hz, 1H), 4.07 (m, 2H), 4.05 (qd, J=10.2, 3.5 Hz, 2H), 3.77 (dd, J=11.0, 4.2 Hz, 1H), 3.66 (dd, J=11.1, 6.5 Hz, 1H), 3.42 (d, J=15.1 Hz, 1H), 3.33 (d, J=15.1 Hz, 1H), 2.95 (s, 1H), 2.07 (m, 4H); HPLC: 7.77 min, 99.3%; ESI-MS: m/z=642 (M+ACN).

Example 105

Synthesis of 2-benzyl-2-(((2R,3S,4R,5R)-5-(2-chloro-6-(cyclopropyl(methyl)amino)-9H-purin-9-yl)-3-ethynyl-3,4-dihydroxytetrahydrofuran-2-yl)methoxy)malonic acid

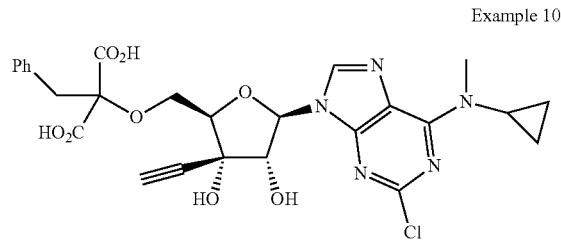

Example 105

The title compound was prepared in a manner analogous to that set forth in Example 59, except N-methylcyclopropanamine was used in place of benzylamine in step 7.

$^1$H NMR (400 MHz, CD$_3$OD) δ 8.36 (s, 1H), 7.26-7.12 (m, 2H), 7.02 (m, 3H), 6.03 (d, J=7.3 Hz, 1H), 4.97 (d, J=7.3 Hz, 1H), 4.30 (dd, J=3.9, 2.8 Hz, 1H), 4.19-3.97 (m, 2H), 3.57-3.29 (m, 5H), 3.21 (m, 1H), 2.96 (s, 1H), 1.05-0.85 (m, 2H), 0.83-0.62 (m, 2H); HPLC: Rt=8.41 min, 98.6%; ESI-MS: m/z=224 (M-ribose fragment).

Example 106

Synthesis of 2-benzyl-2-(((2R,3S,4R,5R)-5-(2-chloro-6-(((cyclopropylmethyl)amino)-9H-purin-9-yl)-3-ethynyl-3,4-dihydroxytetrahydrofuran-2-yl)methoxy)-3-(methylamino)-3-oxopropanoic acid

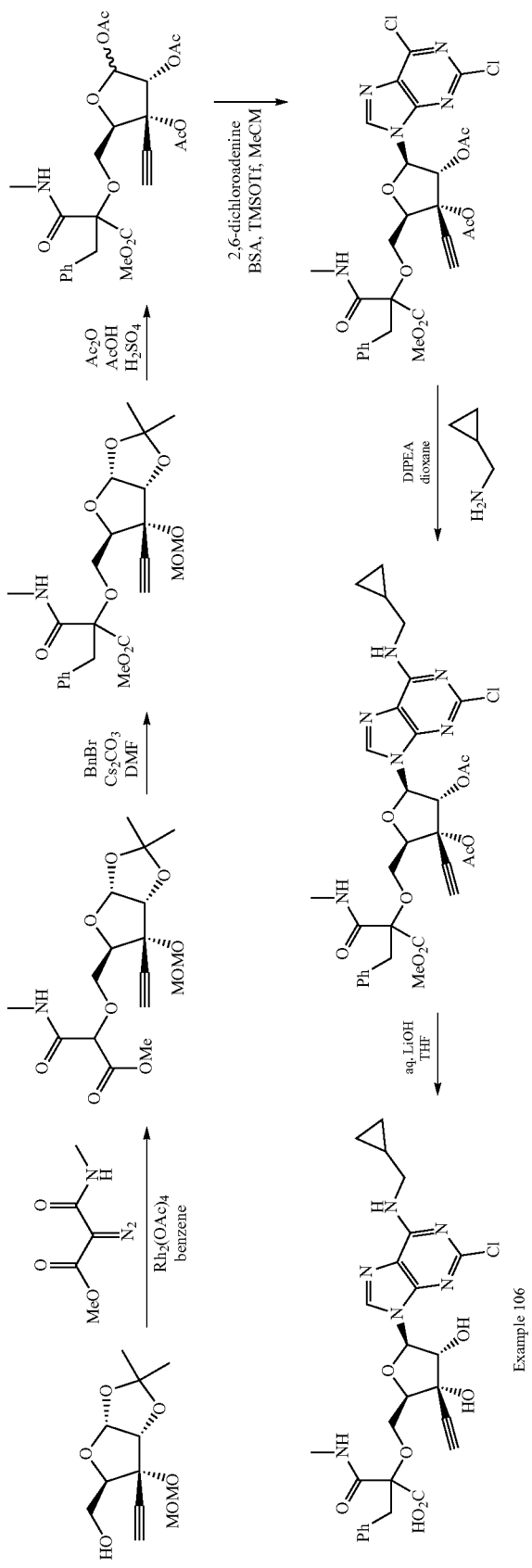

Step 1:

A stirred solution of [(3aR,5R,6R,6aR)-6-ethynyl-6-(methoxymethoxy)-2,2-dimethyl-tetrahydro-2H-furo[2,3-d][1,3]dioxol-5-yl]methanol (480 mg, 1.87 mmol) and methyl 2-diazo-2-(methylcarbamoyl)acetate (440 mg, 2.8 mmol, prepared according to literature: European Journal of Organic Chemistry, 2014 (24), 5302-5311) in anhydrous benzene (20 mL) under nitrogen was treated with rhodium tetraacetate (16 mg, 0.04 mmol) and heated to 60° C. for 4 h. The resulting mixture was cooled to room temperature and concentrated. The resulting oil was dissolved in dichloromethane, loaded onto a silica gel column eluting with 10-100% ethyl acetate in hexane to afford methyl 2-{[(3aR,5R,6R,6aR)-6-ethynyl-6-(methoxymethoxy)-2,2-dimethyl-tetrahydro-2H-furo[2,3-d][1,3]dioxol-5-yl]methoxy}-2-(methylcarbamoyl)acetate (455 mg, 63% yield) as a diastereomeric pair.

Step 2:

A solution of methyl 2-{[(3aR,5R,6R,6aR)-6-ethynyl-6-(methoxymethoxy)-2,2-dimethyl-tetrahydro-2H-furo[2,3-d][1,3]dioxol-5-yl]methoxy}-2-(methylcarbamoyl)acetate (450 mg, 116 mmol) and benzyl bromide (0.97 mL, 8.13 mmol) in anhydrous DMF (4 mL) was treated with cesium carbonate (757 mg, 2.32 mmol). The reaction mixture was stirred at room temperature overnight. The reaction was quenched with water (10 mL), diluted with diethyl ether (70 mL) and washed with saturated aqueous sodium chloride (50 mL) twice. The organic layer was dried with NaSO$_4$ and concentrated to give a yellow oil. The residue was purified by silica gel column and eluted with 10-70% ethyl acetate in hexane to afford a diastereomeric mixture methyl 2-benzyl-2-(((3aR,5R,6R,6aR)-6-ethynyl-6-(methoxy-methoxy)-2,2-dimethyltetrahydrofuro[2,3-d][1,3]dioxol-5-yl)methoxy)-3-(methylamino)-3-oxopropanoate (500 mg, 90% yield) as a clear oil as.

Step 3:

While under nitrogen, an ice cooled stirred solution of methyl 2-benzyl-2-(((3aR,5R,6R,6aR)-6-ethynyl-6-(methoxymethoxy)-2,2-dimethyltetrahydrofuro[2,3-d][1,3]-dioxol-5-yl)methoxy)-3-(methylamino)-3-oxopropanoate (500 mg, 1.05 mmol) in acetic acid (4 mL) was treated with acetic anhydride (1 mL, 11.15 mmol) and concentrated sulfuric acid (0.02, 0.35 mmol). The reaction solution was slowly warmed to room temperature. After 4 hours, reaction was diluted with water and extracted with ethyl acetate (80 mL each). The organic solution was washed with saturated sodium bicarbonate (100 mL), dried over Na$_2$SO$_4$ and concentrated. The residual oil was dissolved in dichloromethane and purified by flash chromatography to provide (3R,4R,5R)-5-(((2-benzyl-1-methoxy-3-(methylamino)-1,3-dioxo-propan-2-yl)oxy)methyl)-4-ethynyltetrahydrofuran-2,3,4-triyl triacetate as an anomer/diastereomeric mixture.

Step 4:

A suspension of 2-6-dichloroadenine (48 mg, 0.25 mmol) and N, O-bis(trimethylsilyl)-acetamide (0.08 mL, 0.32 mmol) in anhydrous acetonitrile (7 mL) was treated with a second solution of (3R,4R,5R)-5-(((2-benzyl-1-methoxy-3-(methylamino)-1,3-dioxopropan-2-yl)oxy)methyl)-4-ethynyltetrahydrofuran-2,3,4-triyl triacetate (130 mg, 0.25 mmol) in anhydrous acetonitrile (10 mL), followed by dropwise addition of trimethylsilyl trifluoromethanesulfonate (0.06 mL, 0.33 mmol). Once the addition was complete, the reaction was heated to 50° C. for 18 h, cooled to room temperature and quenched with saturated sodium bicarbonate solution (80 mL). After stirring for a 5 minutes the solution was extracted with ethyl acetate (3×80 mL), dried over Na$_2$SO$_4$ and concentrated. The residue was dissolved in dichloromethane and purified by flash chromatography to provide (2R,3R,4R,5R)-2-(((2-benzyl-1-methoxy-3-(methylamino)-1,3-dioxopropan-2-yl)oxy)methyl)-5-(2,6-dichloro-9H-purin-9-yl)-3-ethynyltetrahydrofuran-3,4-diyl diacetate (135 mg, 83% yield) as a foamy solid (diastereomer pair).

Step 5:

While under nitrogen, a solution of (2R,3R,4R,5R)-2-(((2-benzyl-1-methoxy-3-(methylamino)-1,3-dioxopropan-2-yl)oxy)methyl)-5-(2,6-dichloro-9H-purin-9-yl)-3-ethynyl-tetrahydrofuran-3,4-diyl diacetate (70 mg, 0.11 mmol) in dioxane (2 mL) was cooled to 0° C. and treated with diisopropylethylamine (0.03 mL, 0.16 mmol) and cyclopropylamine (0.01 mL, 0.13 mmol), and warmed to room temperature with stirring overnight. The reaction mixture was diluted with ethyl acetate (80 mL), washed with water (50 mL) and saturated aqueous sodium chloride (50 mL). The organic layer was dried over Na$_2$SO$_4$ then filtered and concentrated. The residue was dissolved in dichloromethane and purified by flash column chromatography to afford (2R,3R,4R,5R)-2-(((2-benzyl-1-methoxy-3-(methylamino)-1,3-dioxopropan-2-yl)oxy)methyl)-5-(2-chloro-6-((cyclopropylmethyl)amino)-9H-purin-9-yl)-3-ethynyltetrahydrofuran-3,4-diyl diacetate (70 mg, 95% yield) as an off-white solid (diastereomeric pair).

Step 6:

To solution of (2R,3R,4R,5R)-2-(((2-benzyl-1-methoxy-3-(methylamino)-1,3-dioxo-propan-2-yl)oxy)methyl)-5-(2-chloro-6-((cyclopropylmethyl)amino)-9H-purin-9-yl)-3-ethynyltetrahydrofuran-3,4-diyl diacetate (70 mg, 0.10 mmol) in THF (1 mL) was treated with LiOH (24 mg, 1.02 mmol) in water (1 mL) and stirred at room temperature overnight. Reaction pH was adjusted to 4-5 using cold 2 N HCl. Upon precipitation, the suspension was stirred for another 10 min. The solid was collected, washed with cold water and dried to provide 2-benzyl-2-(((2R,3S,4R,5R)-5-(2-chloro-6-((cyclopropylmethyl)amino)-9H-purin-9-yl)-3-ethynyl-3,4-dihydroxytetrahydro-furan-2-yl)methoxy)-3-(methylamino)-3-oxopropanoic acid (45 mg, 75% yield) as an off-white solid (diastereomeric pair).

$^1$H NMR (400 MHz, CDCl$_3$/CD$_3$OD=5:1) δ 8.01 (s, 0.45H), 7.48 (s, 0.55H), 7.22-7.03 (m, 5H), 5.86 (dd, J=4.7, 3.0 Hz, 1H), 4.43 (dd, J=8.5, 4.6 Hz, 1H), 4.31-4.06 (m, 2H), 3.84-3.72 (m, 1H), 3.45-3.21 (m, 4H), 2.62 (d, J=40.9 Hz, 1H), 2.46 (d, J=8.1 Hz, 3H), 1.05 (dq, J=8.0, 3.7 Hz, 1H), 0.51 (ddd, J=8.1, 4.0, 1.6 Hz, 2H), 0.31-0.18 (m, 2H). ESI-MS (m/z): [M]$^+$ calcd for C$_{27}$H$_{29}$ClN$_6$O$_7$, 585.18; found 585.9.

Example 107

Synthesis of 2-benzyl-2-(((2R,3S,4R,5R)-5-(6-(benzylamino)-2-chloro-9H-purin-9-yl)-3-ethynyl-3,4-dihydroxytetrahydrofuran-2-yl)methoxy)-3-(methylamino)-3-oxopropanoic acid

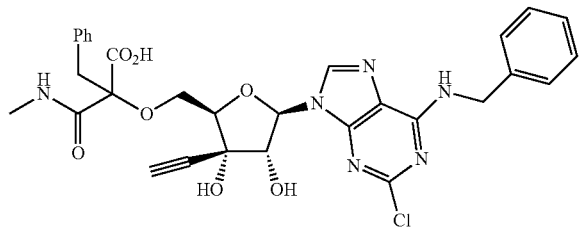

Example 107

The title compound was prepared in a manner analogous to that set forth in Example 106, except benzylamine was used in place of cyclopropylamine in step 5.

¹H NMR (400 MHz, CDCl₃/CD₃OD=5:1) δ 8.03 (s, 0.46H), 7.52 (d, J=2.7 Hz, 0.54H), 7.42-7.04 (m, 10H), 5.89 (t, J=4.3 Hz, 1H), 4.73 (m, 2H), 4.44 (dd, J=6.0, 4.5 Hz, 1H), 4.33-4.15 (m, 2H), 3.79 (dd, J=10.6, 4.5 Hz, 1H), 3.45-3.27 (m, 2H), 2.62 (d, J=36.6 Hz, 1H), 2.48 (d, J=13.2 Hz, 3H). ESI-MS (m/z): [M]⁺ calcd for $C_{30}H_{29}ClN_6O_7$, 621.18; found 621.4.

Example 108

Synthesis of 2-benzyl-2-(((2R,3S,4R,5R)-5-(2-chloro-6-((2-chlorobenzyl)amino)-9H-purin-9-yl)-3-ethynyl-3,4-dihydroxytetrahydrofuran-2-yl)methoxy)-3-ethoxy-3-oxopropanoic acid Example 108

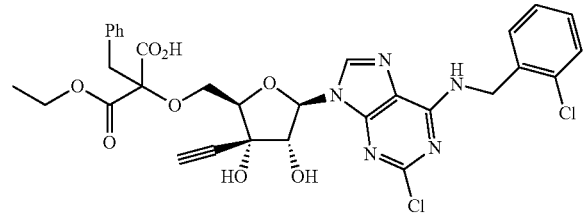

The title compounds is prepared in a manner analogous to that set forth in Example 59, except only 5 equivalents of lithium hydroxide are used in step 8.

¹H NMR (400 MHz, CD₃OD) δ 8.16 (s, 1H), 7.42 (m, 2H), 7.26 (m, 2H), 7.21 (m, 2H), 6.99 (m, 3H), 5.97 (d, J=7.6 Hz, 1H), 4.96 (d, J=7.6 Hz, 1H), 4.82 (m, 2H), 4.28 (m, 1H), 4.03 (m, 2H), 3.75 (m, 2H), 3.38 (m, 2H), 3.22 (m, 2H), 2.97 (s, 1H) 1.29 (t, J=7.6 Hz, 3H). HPLC: 9.43 min, 96.2%. LC-MS: m/z=642, 597 (M-CO₂H); m/z=292 (M-ribose fragment).

Example 109

Synthesis of 2-benzyl-2-(((2R,3S,4R,5R)-5-(2-chloro-6-((pyridin-4-ylmethyl)amino)-9H-purin-9-yl)-3-ethynyl-3,4-dihydroxytetrahydrofuran-2-yl)methoxy)-3-ethoxy-3-oxopropanoic acid Example 109

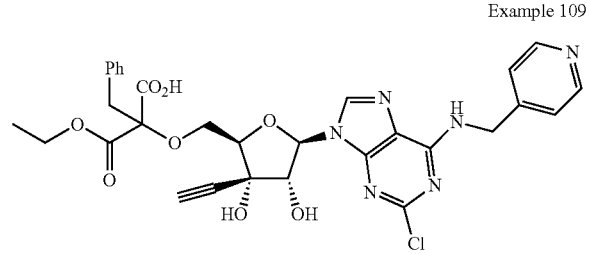 [SMILES: C#C[C@@]1(O)[C@@H](COC(Cc2ccccc2)(C(=O)O)C(=O)OCC)O[C@@H](n2cnc3c(NCc4ccncc4)nc(Cl)nc32)[C@@H]1O]

The title compounds is prepared in a manner analogous to that set forth in Example 59, except only 5 equivalents of lithium hydroxide are used in step 8. Compound was isolated as ~2:1 mixture of diastereomers.

¹H NMR (400 MHz, DMSO-d₆) of major isomer: δ 8.73 (d, J=5.9 Hz, 2H), 8.15 (s, 0.61H), 7.98 (d, J=5.9 Hz, 2H), 7.23 (m, 2H), 7.06 (m, 3H), 6.00 (m, 1H), 5.00 (m, 2H), 4.10 (m, 4H), 3.39 (m, 2H), 3.12 (s, 0.80H), 1.17 (m, 3H). 1H NMR (DMSO-d₆) of minor isomer: δ 8.73 (d, J=5.9 Hz, 2H), 8.31 (s, 0.32H), 7.98 (d, J=5.9 Hz, 2H), 7.23 (m, 2H), 7.06 (m, 3H), 6.00 (m, 1H), 5.00 (m, 2H), 4.10 (m, 4H), 3.39 (m, 2H), 3.01 (s, 0.41H), 1.17 (m, 3H). HPLC: 6.25 min, 94.8%. LC-MS: m/z=638 (M+), 594 (M-CO₂H), m/z=259 (M-ribose fragment).

Example 110

Synthesis of 2-(((2R,3S,4R,5R)-5-(2-chloro-6-(isopropylamino)-9H-purin-9-yl)-3-ethynyl-3,4-dihydroxytetrahydrofuran-2-yl)methoxy)-2-((5-methylisoxazol-3-yl)methyl)malonic acid Example 110

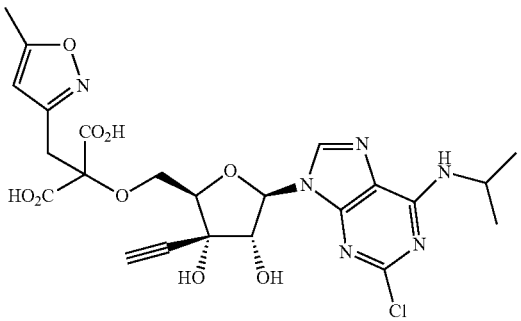

The title compound was prepared in a manner analogous to that set forth in Example 59, except 3-(bromomethyl)-5-methylisoxazole was used in place of benzyl bromide in step 4 and propan-2-amine is used in place of benzylamine in step 7.

¹H-NMR (400 MHz, CD₃OD) δ 8.46 (s, 1H) 5.99 (d, J=7.6 Hz, 1H) 5.95 (s, 1H) 5.07 (d, J=7.6 Hz, 1H) 4.41-4.38 (m, 1H) 4.31-4.29 (m, 1H) 4.07-4.05 (m, 1H) 3.99-3.88 (m, 1H) 3.50-3.38 (m, 2H) 2.95 (s, 1H) 2.05 (s, 3H) 1.27 (d, J=6.5 Hz, 6H). ESI-MS (m/z): [M]⁺ calcd for $C_{23}H_{25}ClN_6O_9$ 564.93; found 566.1.

Example 111

Synthesis of 2-(((2R,3S,4R,5R)-5-(2-chloro-6-((4-fluorobenzyl)amino)-9H-purin-9-yl)-3-ethynyl-3,4-dihydroxytetrahydrofuran-2-yl)methoxy)-2-((5-methylisoxazol-3-yl)methyl)malonic acid Example 111

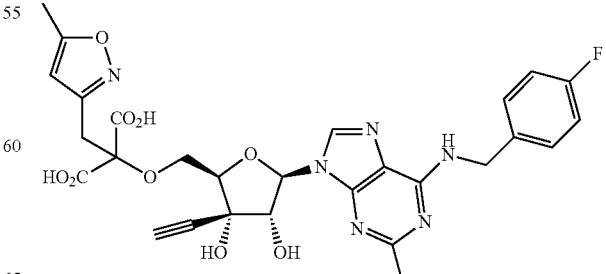

The title compound was prepared in a manner analogous to that set forth in Example 59, except 3-(bromomethyl)-5-methylisoxazole was used in place of benzyl bromide in step 4 and (4-fluorophenyl)methanamine is used in place of benzylamine in step 7.

$^1$H-NMR (400 MHz, CD$_3$OD) δ 8.62-8.58 (br s, 1H) 7.41-7.38 (m, 2H) 7.07-7.01 (m, 2H) 6.01 (d, J=7.4 Hz, 1H) 5.96 (s, 1H) 5.09 (d, J=7.3 Hz, 1H) 4.82-4.71 (m, 2H) 4.31-4.29 (m, 1H) 4.06 (dd, J=10.0, 3.8 Hz, 1H) 3.97 (dd, J=10.1, 3.1 Hz, 1H) 3.44-3.32 (m, 2H) 3.18 (s, 3H) 2.96 (s, 1H).

Example 112

Synthesis of 2-(benzo[d]thiazol-2-ylmethyl)-2-(((2R,3S,4R,5R)-5-(2-chloro-6-((4-fluorobenzyl)amino)-9H-purin-9-yl)-3-ethynyl-3,4-dihydroxytetrahydrofuran-2-yl)methoxy)malonic acid

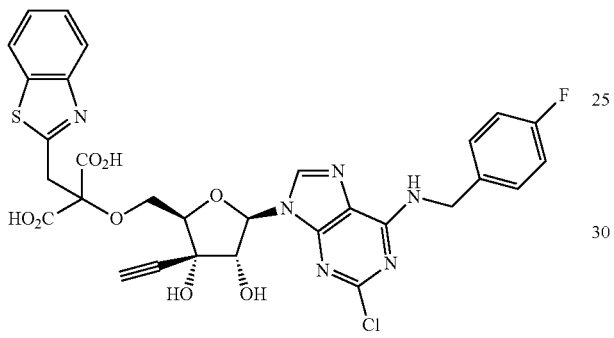

Example 112

The title compound was prepared in a manner analogous to that set forth in Example 59, except 2-(bromomethyl)benzo[d]thiazole is used in place of benzyl bromide in step 4 and (4-fluorophenyl)methanamine was used in place of benzylamine in step 7.

$^1$H-NMR (400 MHz, CD$_3$OD) δ 8.57-8.54 (br s, 1H) 7.74-7.70 (m, 2H) 7.45-7.41 (m, 2H) 7.23-7.20 (m, 1H) 7.12-7.16 (m, 1H) 7.09-7.04 (m, 2H) 5.94 (d, J=7.3 Hz, 1H) 5.15 (d, J=7.1 Hz, 1H) 4.77-4.72 (m, 2H) 4.35-4.32 (m, 1H) 4.20 (dd, J=10.1, 2.7 Hz, 1H) 4.11 (dd, J=10.1, 3.1 Hz, 1H) 3.99-3.86 (m, 2H) 2.77 (s, 1H).

Example 113

Synthesis of 2-(((2R,3S,4R,5R)-5-(6-amino-2-chloro-9H-purin-9-yl)-3-ethynyl-3,4-dihydroxytetrahydrofuran-2-yl)methoxy)-3-oxo-3-(pyrrolidin-1-yl)propanoic acid

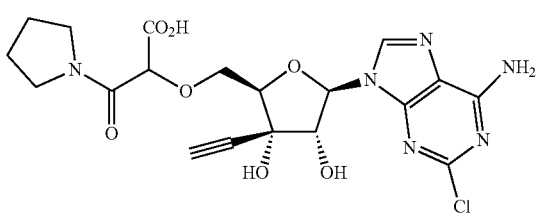

Example 113

The title compound was prepared in an analogous manner to Example 59 except ethyl 2-diazo-3-oxo-3-(pyrrolidin-1-yl)propanoate was used instead of 1-ethyl 3-(prop-1-en-1-yl) 2-diazomalonate in Step 3 and ammonia is used in place of benzylamine in Step 7. The product is isolated as a 55/45 mixture of diastereomers.

Major diastereomer $^1$H-NMR (400 MHz, CD$_3$OD) d 8.80 (s, 1H) 5.99 (d, J=7.4 Hz, 1H) 5.05 (d, J=7.4 Hz, 1H) 4.88 (s, 1H) 4.28-4.26 (m, 1H) 4.13 (dd, J=10.7, 2.5 Hz, 1H) 4.00 (dd, J=10.7, 3.9 Hz, 1H) 3.66-3.39 (m, 4H) 3.17 (s, 1H) 1.89-1.79 (m, 4H). Minor diasteomer $^1$H-NMR (400 MHz, CD$_3$OD) δ 8.89 (s, 1H) 6.03 (d, J=7.4 Hz, 1H) 5.05 (d, J=7.4 Hz, 1H) 4.86 (s, 1H) 4.28-4.26 (m, 1H) 3.90-3.86 (m, 2H) 3.66-3.39 (m, 4H) 3.16 (s, 1H) 1.89-1.79 (m, 4H). ESI-MS (m/z): [M]$^-$ calcd for C$_{19}$H$_{21}$ClN$_6$O$_7$ 480.86; found 479.1.

Example 114

Synthesis of 2-(((2R,3S,4R,5R)-5-(2-chloro-6-(cyclopentylamino)-9H-purin-9-yl)-3-ethynyl-3,4-dihydroxytetrahydrofuran-2-yl)methoxy)-3-oxo-3-(pyrrolidin-1-yl)propanoic acid

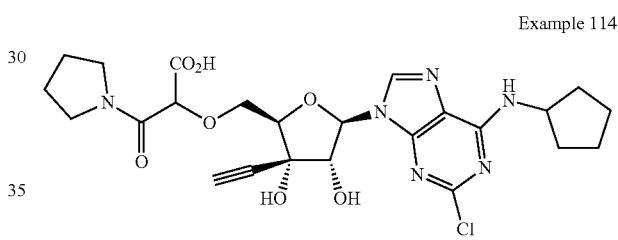

Example 114

The title compound was prepared in an analogous manner to Example 59 except ethyl 2-diazo-3-oxo-3-(pyrrolidin-1-yl)propanoate was used instead of 1-ethyl 3-(prop-1-en-1-yl) 2-diazomalonate in Step 3 and cyclopentanamine is used in place of benzylamine in Step 7. The product is isolated as a 55/45 mixture of diastereomers.

Major diastereomer. $^1$H NMR (400 MHz, CD$_3$OD) d 8.72 (s, 1H) 5.96 (d, J=7.4 Hz, 1H) 5.04 (d, J=7.4 Hz, 1H) 4.87 (s, 1H) 4.52-4.48 (m, 1H) 4.28-4.25 (m, 1H) 4.14 (d, J=10.5 Hz, 1H) 4.01 (dd, J=10.6, 5.2 Hz, 1H) 3.60-3.36 (m, 4H) 3.17 (s, 1H) 2.10-2.04 (m, 2H) 1.84-1.77 (m, 6H) 1.69-1.58 (m, 4H) Minor diastereomer $^1$H NMR (400 MHz, CD$_3$OD) δ 8.64 (s, 1H) 6.00 (d, J=7.4 Hz, 1H) 5.01 (d, J=7.4 Hz, 1H) 4.85 (s, 1H) 4.52-4.48 (m, 1H) 4.28-4.25 (m, 1H) 3.92-3.86 (m, 2H) 3.60-3.36 (m, 4H) 3.16 (s, 1H) 2.10-2.04 (m, 2H) 1.84-1.77 (m, 6H) 1.69-1.58 (m, 4H) (ESI-MS (m/z): [M]$^-$ calcd for C$_{24}$H$_{29}$ClN$_6$O$_7$ 548.98; found 547.3.

Example 115

Synthesis of 3-amino-2-(((2R,3S,4R,5R)-5-(2-chloro-6-(cyclopentylamino)-9H-purin-9-yl)-3-ethynyl-3,4-dihydroxytetrahydrofuran-2-yl)methoxy)-3-oxopropanoic acid

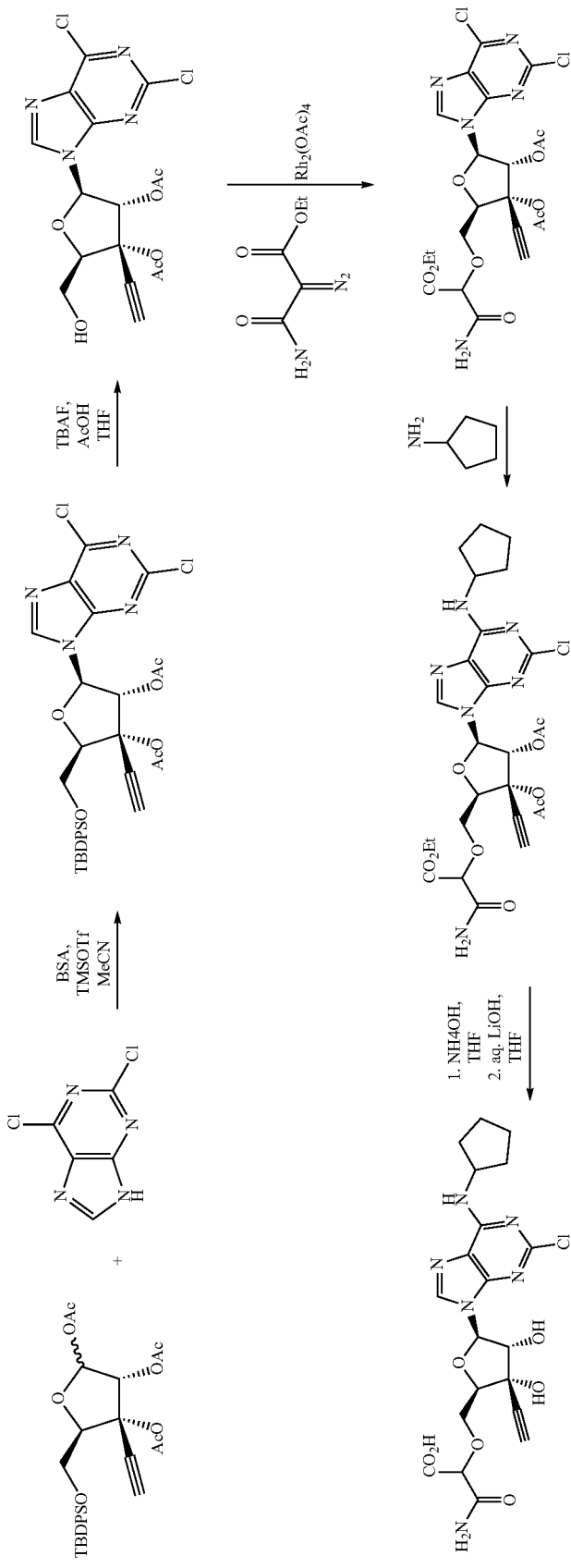

Step 1:

While under nitrogen, a suspension of 2,6-dichloroadenine (2.91 g, 15.4 mmoL, 1.01 eq) and N,O-bis(trimethylsilyl)acetamide (4.87 mL, 19.6 mmoL, 1.29 eq) in anhydrous acetonitrile (90 mL). Next, a solution of (2R,3R,4R,5R)-2,4-bis(acetyloxy)-5-{[(tert-butyldiphenylsilyl)oxy]methyl}-4-ethynyloxolan-3-yl acetate (8.2 g, 15.22 mmoL) in anhydrous acetonitrile (10 mL) was added, followed by dropwise addition of trimethylsilyl trifluoromethanesulfonate (3.67 mL, 20.3 mmoL, 1.33 eq). The reaction was warmed to 50° C. for 18 h, then cooled to room temperature. (Reaction begins a pale-yellow color and after 4 h turns to a transparent amber). Saturated aqueous sodium bicarbonate (10 mL), was added and the mixture was stirred for ten minutes. The resulting mixture was extracted with ethyl acetate (3×100 mL) and the combined organic layer was dried ($Na_2SO_4$), filtered, and concentrated. The residue was dissolved in dichloromethane/ethyl acetate (~3 mL, 1:1), loaded onto a silica gel column (~300 cc), and eluted with 0-30% ethyl acetate in hexanes to provide (2R,3R,4R,5R)-2-(((tert-butyldiphenylsilyl)oxy)methyl)-5-(2,6-dichloro-9H-purin-9-yl)-3-ethynyltetrahydrofuran-3,4-diyl diacetate (8.2 g, 81%) as a white solid.

Step 2:

A solution of (2R,3R,4R,5R)-2-(((tert-butyldiphenylsilyl)oxy)methyl)-5-(2,6-dichloro-9H-purin-9-yl)-3-ethynyltetrahydrofuran-3,4-diyl diacetate (1.6 g, 2.4 mmoL) in anhydrous THF (25 mL) was cooled to 0° C. and treated with acetic acid (0.192 mL, 3.36 mmoL, 1.4 eq) a 1 N solution of tetrabutylammonium fluoride in THF (3.36 mL, 3.36 mmoL, 1.4 eq). After the addition was complete, the reaction was warmed to room temperature with stirring for 3 h. The reaction mixture was concentrated, a purified via flash column chromatography (0 to 50% ethyl acetate in hexanes to afford (2R,3R,4R,5R)-5-(2,6-dichloro-9H-purin-9-yl)-3-ethynyl-2-(hydroxymethyl)tetrahydrofuran-3,4-diyl diacetate (0.88 g, 86%) as a white foam.

Step 3:

While under nitrogen, a solution of ((2R,3R,4R,5R)-5-(2,6-dichloro-9H-purin-9-yl)-3-ethynyl-2-(hydroxymethyl)tetrahydrofuran-3,4-diyl diacetate (172 mg, 0.40 mmol) and ethyl 3-(aminooxy)-2-diazo-3-oxopropanoate (160 mg, 1.02 mmoL, 2.5 eq) in anhydrous toluene (3 mL) was treated with rhodium (II) acetate dimer (5 mg, 0.011 mmoL, 2.8 mol %) and warmed to 80° C. for 5 h. The reaction was concentrated, and purified via flash column chromatography (25-75% ethyl acetate in dichloromethane) to afford (2R,3R,4R,5R)-2-(((1-amino-3-ethoxy-1,3-dioxopropan-2-yl)oxy)methyl)-5-(2,6-dichloro-9H-purin-9-yl)-3-ethynyltetrahydrofuran-3,4-diyl diacetate (101 mg, 45% in ~85:15 mixture of diastereomers) as a colorless glass.

Step 4:

While under nitrogen, a solution of (2R,3R,4R,5R)-2-(((1-amino-3-ethoxy-1,3-dioxo-propan-2-yl)oxy)methyl)-5-(2,6-dichloro-9H-purin-9-yl)-3-ethynyltetrahydrofuran-3,4-diyl diacetate (157 mg, 0.28 mmol) in dioxane (2.5 mL) was treated with diisopropylethylamine (0.100 mL, 0.61 mmoL, 2.2 eq) and cyclopentylamine (0.065 mL, 0.066 mmoL, 2.33 eq). After stirring at room temperature for 18 h, the mixture was diluted with ethyl acetate (20 mL), washed with water (10 mL), dried ($Na_2SO_4$), filtered, and concentrated to provide crude (2R,3R,4R,5R)-2-(((1-amino-3-ethoxy-1,3-dioxopropan-2-yl)oxy)methyl)-5-(2-chloro-6-(cyclopentylamino)-9H-purin-9-yl)-3-ethynyltetrahydrofuran-3,4-diyl diacetate.

Step 5:

The resulting residue from the previous step was stirred in ammonium hydroxide and ethanol (1:1/v:v, 10 mL) at room temperature overnight. The mixture was concentrated, dissolved in THF (2.5 mL) and treated with lithium hydroxide (23 mg, 0.96 mmoL, 3.4 eq) dissolved in water (2.5 mL). The mixture was stirred at room temperature with occasional gentle heating for ~3 h, then neutralized with 1N HCl to pH-6 and concentrated in vacuo. The crude product was dissolved in water and purified by reverse phase HPLC and dried by lyophilization to provide the title compound (52 mg, 37% for 3 steps) as a voluminous white solid.

$^1$H NMR (400 MHz, $D_2O$) of major isomer: δ 8.30 (s, 1H), 5.81 (m, 1H), 4.88 (d, J=6.6 Hz, 1H), 4.80 (d, J=6.8 Hz, 1H), 4.24 (m, 2H), 4.20 (bs, 1H), 3.83 (m, 2H), 3.01 (s, 1H), 1.85 (m, 2H), 1.49 (m, 6H). 1H NMR (400 MHz, $D_2O$) of minor isomer: δ 8.39 (s, 1H), 5.81 (m, 1H), 4.88 (d, J=6.6 Hz, 1H), 4.80 (d, J=6.8 Hz, 1H), 4.24 (m, 2H), 4.20 (bs, 1H), 3.83 (m, 2H), 2.99 (s, 1H), 1.85 (m, 2H), 1.49 (m, 6H). HPLC: Rt=7.08 min, 93.0%. ESI-MS for $C_{20}H_{23}ClN_6O_7$ calcd. 494.13, found 493.2 (M−); ESI-MS for $C_{10}H_{11}ClN_5$ calcd. 236.07, found 236.0 (M-ribose fragment).

Example 116

Synthesis of 2-(((2R,3S,4R,5R)-5-(2-chloro-6-(cyclopentylamino)-9H-purin-9-yl)-3-ethynyl-3,4-dihydroxytetrahydrofuran-2-yl)methoxy)malonamide

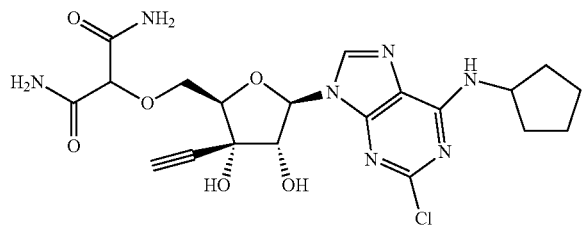

Example 116

The title compound was prepared as a second product from step 5 in the synthesis of example 115. It was isolated as a voluminous white solid (8.5 mg, 6%).

$^1$H NMR (400 MHz, DMSO-$d_6$): 8.57 (s, 0.5H), 8.31 (s, 1H), 7.73 (s, 1H), 7.38 (m, 1.5H), 7.21 (m, 1.5H), 7.05 (m, 0.5H), 6.87 (n, 0.5H), 6.20 (m, 1H), 6.02 (d, J=7.0 Hz, 1H), 5.79 (d, J=7.8 Hz, 1H), 5.02 (s, 1H), 4.73 (s, 1H), 4.39 (m, 1H), 4.18 (m, 1H), 3.79 (m, 1H), 3.68 (s, 1H), 1.85 (m, 2H), 1.49 (m, 6H). HPLC: Rt=6.64 min, 97.1%. ESI-MS for $C_{20}H_{24}ClN_7O_6$ calcd. 493.15, found 492.3 (M−); ESI-MS for $C_{10}H_{11}ClN_5$ calcd. 236.1, found 236.1 (M-ribose fragment).

Example 117

Synthesis of 2-(((2R,3S,4R,5R)-5-(2-chloro-6-(methylamino)-9H-purin-9-yl)-3-ethynyl-3,4-dihydroxytetrahydrofuran-2-yl)methoxy)malonic acid

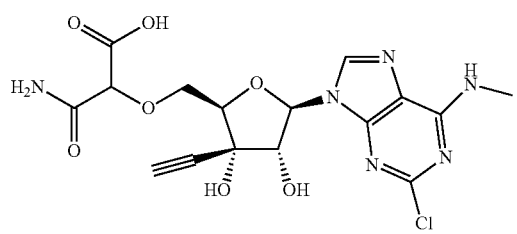

Example 117

The title compound was prepared in a manner analogous to that set forth in Example 59, except methylamine was used in place of benzylamine in step 7 and step 4 is eliminated.

$^1$H NMR (400 MHz, CD$_3$OD) δ 8.88 (s, 1H), 6.05 (d, J=7.6 Hz, 1H), 5.03 (d, J=7.6 Hz, 1H), 4.62 (s, 1H), 4.26 (m, 1H), 4.04 (m, 1H), 3.90 (m, 1H), 3.11 (s, 1H), 3.07 (s, 3H). HPLC: Rt=5.92 min, 97.9%. ESI-MS for C$_{16}$H$_{16}$ClN$_5$O$_8$ calcd. 441.07, found 442.5 (M+); ESI-MS for C$_6$H$_5$ClN$_5$ calcd. 182.02, found 184.2 (M-ribose fragment).

Example 118

Synthesis of 2-(((2R,3S,4R,5R)-5-(6-(benzylamino)-2-chloro-9H-purin-9-yl)-3-ethynyl-3,4-dihydroxytetrahydrofuran-2-yl)methoxy)malonic acid

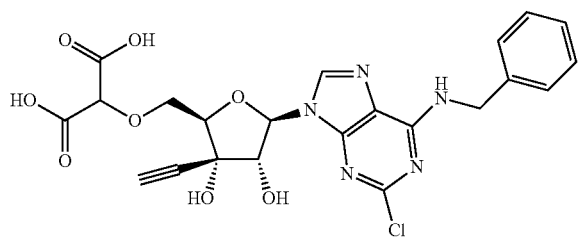

Example 18

The title compound was prepared in a manner analogous to that set forth in Example 59, except step 4 was eliminated.

$^1$H NMR (400 MHz, CD$_3$OD) δ 8.87 (s, 1H), 7.39 (m, 2H), 7.33 (m, 2H), 7.26 (m, 1H), 6.06 (d, J=7.6 Hz, 1H), 5.02 (d, J=7.6 Hz, 1H), 4.76 (m, 2H), 4.62 (s, 1H), 4.26 (s, 1H), 4.03 (m, 1H), 3.90 (m, 1H), 3.10 (s, 1H). HPLC: Rt=7.83 min, 98.2%. ESI-MS for C$_{22}$H$_{20}$ClN$_5$O$_8$ calcd. 517.10 found 516.7 (M-); ESI-MS for C$_{12}$H$_9$ClN$_5$ calcd. 258.05, found 258 (M-ribose fragment).

Example 119

Synthesis of 2-(((2R,3S,4R,5R)-5-(2-chloro-6-morpholino-9H-purin-9-yl)-3-ethynyl-3,4-dihydroxytetrahydrofuran-2-yl)methoxy)-2-(phenylsulfonyl)acetic acid

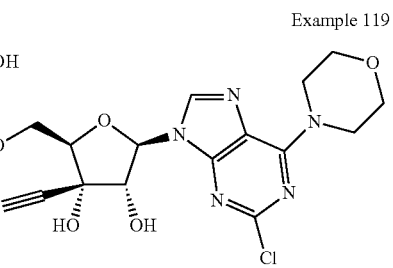

Example 119

The title compound was prepared in an analogous manner to Example 59 except ethyl 2-diazo-2-(phenylsulfonyl)acetate was used instead of 1-ethyl 3-(prop-1-en-1-yl) 2-diazomalonate in Step 3, morpholine was used in place of benzylamine in Step 7 and Step 4 is eliminated.

$^1$H NMR (400 MHz, DMSO-d$_6$) of major isomer: δ 8.40 (s, 1H), 7.83 (m, 2H), 7.66 (m, 2H), 7.53 (m, 1H), 5.83 (m, 1H), 5.50 (d, J=7.8 Hz, 1H), 4.80 (d, J=7.8 Hz, 1H), 4.16 (m, 4H), 3.98 (m, 1H), 3.76 (m, 4H), 3.63 (s, 1H). $^1$H NMR (400 MHz, DMSO-d$_6$) of minor isomer: δ 8.41 (s, 1H), 7.83 (m, 2H), 7.66 (m, 2H), 7.53 (m, 1H), 5.83 (m, 1H), 5.50 (d, J=7.8 Hz, 1H), 4.66 (d, J=7.8 Hz, 1H), 4.16 (m, 4H), 3.98 (m, 1H), 3.76 (m, 4H), 3.61 (s, 1H). HPLC: Rt=7.83 (minor), 8.18 min (major), 99.6% (40:60). ESI-MS for C$_{26}$H$_{26}$ClN$_5$O$_9$ calcd. 587.14, found 588 (M+); ESI-MS for C$_{24}$H$_{24}$ClN$_5$O$_9$S calcd. 593.10, found 592 (M-); ESI-MS for C$_{23}$H$_{23}$ClN$_5$O$_7$S calcd. 548.10, found 548 (M-CO$_2$H); ESI-MS for C$_9$H$_9$ClN$_5$O calcd. 238.05, found 240 (M-ribose fragment).

Example 120

Synthesis of 2-(((2R,3S,4R,5R)-5-(2-chloro-6-(cyclopentylamino)-9H-purin-9-yl)-3-ethynyl-3,4-dihydroxytetrahydrofuran-2-yl)methoxy)-2-(methylsulfonyl)acetic acid

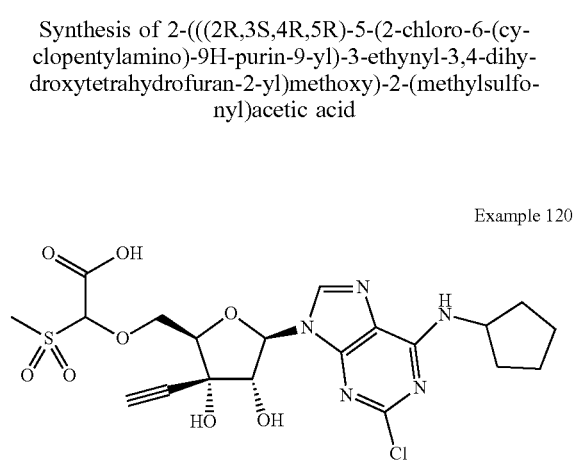

Example 120

The title compound was prepared in an analogous manner to Example 59 except ethyl 2-diazo-2-(methylsulfonyl)acetate was used instead of 1-ethyl 3-(prop-1-en-1-yl) 2- diazomalonate in Step 3, cyclopentanamine is used in place of benzylamine in Step 7 and Step 4 is eliminated.

$^1$H NMR (400 MHz, DMSO-$d_6$) of major isomer: δ 8.47 (s, 1H), 5.85 (m, 1H), 5.36 (m, 1H), 5.01 (m, 1H), 4.86 (d, J=8.0 Hz, 1H), 4.42 (m, 2H), 4.33 (m, 1H), 4.25 (m, 2H), 4.14 (m, 1H), 4.00 (m, 1H), 3.37 (s, 1H), 3.05 (s, 3H), 1.97 (m, 2H), 1.72 (m, 2H), 1.57 (m, 4H). $^1$H NMR (400 MHz, DMSO-$d_6$) of minor isomer: δ 8.39 (s, 1H), 5.83 (m, 1H), 5.36 (m, 1H), 4.68 (d, J=8.0 Hz, 1H), 4.42 (m, 2H), 4.33 (m, 1H), 4.25 (m, 2H), 4.14 (m, 1H), 4.00 (m, 1H), 3.37 (s, 1H), 3.05 (s, 3H), 1.97 (m, 2H), 1.72 (m, 2H), 1.57 (m, 4H). HPLC: Rt=8.02 min, 98.4%. ESI-MS for $C_{20}H_{24}ClN_5O_8S$ calcd. 529.10, found 530 (M+); ESI-MS for $C_{10}H_{11}ClN_5$ calcd. 236.07, found 238 (M-ribose fragment).

Examples 121 & 122

Synthesis of 2-(((2R,3S,4R,5R)-5-(6-amino-2-carbamoyl-9H-purin-9-yl)-3-ethynyl-3,4-dihydroxytetrahydrofuran-2-yl)methoxy)-2-benzyl-3-ethoxy-3-oxopropanoic acid and 2-(((2R,3S,4R,5R)-5-(6-amino-2-carbamoyl-9H-purin-9-yl)-3-ethynyl-3,4-dihydroxytetrahydrofuran-2-yl)methoxy)-2-benzylmalonic acid

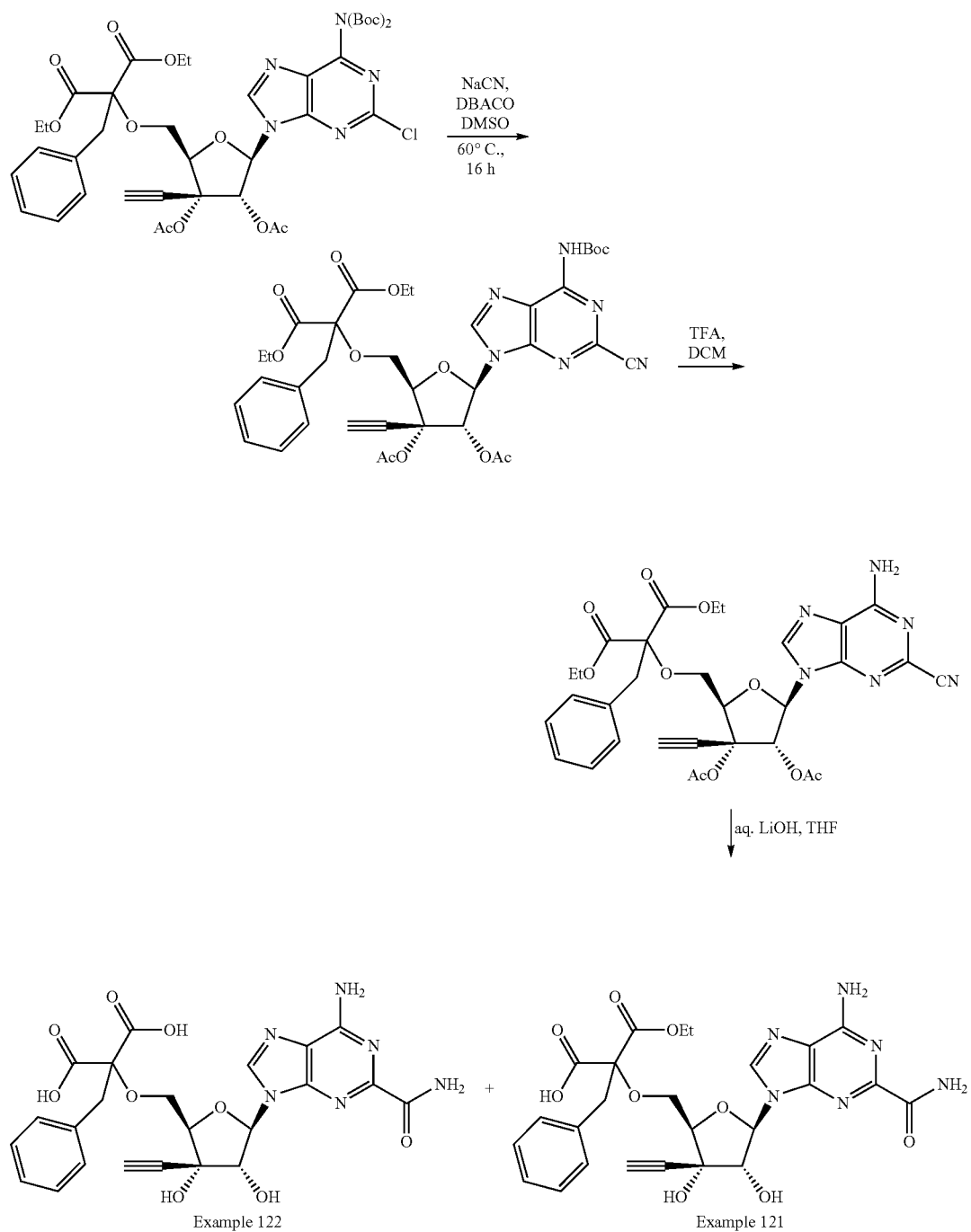

Example 122      Example 121

Step 1:
To a solution of diethyl 2-benzyl-2-(((2R,3R,4R,5R)-3,4-diacetoxy-5-(6-(N,N'-bis(tert-butoxycarbonyl)amino)-2-chloro-9H-purin-9-yl)-3-ethynyltetrahydrofuran-2-yl)methoxy)malonate (1.00 g, 1.17 mmol, 1 eq) in DMSO (10 mL) and H₂O (2 mL) was added 1,4-diazabicyclo[2.2.2]octane (128 uL, 1.17 mmol, 1 eq) and NaCN (114.20 mg, 2.33 mmol, 2 eq). The solution was stirred at 60° C. for 3 h before it was diluted with water (15 mL) and extracted with ethyl acetate (3×15 mL). The combined organic layer was washed with water (50 mL), brine (50 mL), dried by Na₂SO₄, and filtered and concentrated. The crude residue was purified by Combi-flash (silica gel, 30-70% EtOAc in petroleum ether) to give diethyl 2-benzyl-2-(((2R,3R,4R,5R)-3,4-diacetoxy-5-(6-(N,N'-bis(tert-butoxycarbonyl)-amino)-2-cyano-9H-purin-9-yl)-3-ethynyltetrahydrofuran-2-yl)methoxy)malonate (312 mg, 40% yield) as a yellow gum.

Step 2:
To a solution of diethyl 2-benzyl-2-(((2R,3R,4R,5R)-3,4-diacetoxy-5-(6-(N,N'-bis(tert-butoxycarbonyl)amino)-2-cyano-9H-purin-9-yl)-3-ethynyltetrahydrofuran-2-yl)methoxy)malonate (50 mg, 75.23 umol, 1 eq) in DCM (1.7 mL) was added TFA (0.3 mL) at 0° C. The solution was stirred at 20° C. for 1 h before it was diluted with saturated aq. NaHCO₃ to adjust the pH to 9. The mixture was extracted with ethyl acetate (3×3 mL). The organic was concentrated to give crude diethyl 2-(((2R,3S,4R,5R)-5-(6-amino-2-cyano-9H-purin-9-yl)-3-ethynyl-3,4-dihydroxytetra-hydrofuran-2-yl)methoxy)-2-benzylmalonate (45 mg) as a yellow gum.

Step 3:
To a solution of crude diethyl 2-(((2R,3S,4R,5R)-5-(6-amino-2-cyano-9H-purin-9-yl)-3-ethynyl-3,4-dihydroxytetra-hydrofuran-2-yl)methoxy)-2-benzyl-malonate (65 mg, 115.14 umol, 1 eq) in MeCN (2 mL) was added 3,4,6,7,8,9-hexahydro-2H-pyrimido[1,2-a]-pyrimidine (TBD) (1 M aq., 461 uL, 4 eq). The reaction mixture was stirred at 20° C. for 18 h before it was concentrated. The crude residue was purified by preparative HPLC and the fractions were dried by lyophilization to give 2-(((2R,3S,4R,5R)-5-(6-amino-2-carbamoyl-9H-purin-9-yl)-3-ethynyl-3,4-dihydroxytetrahydrofuran-2-yl)methoxy)-2-benzyl-3-ethoxy-3-oxopropanoic acid (Example 121) (4.1 mg, 5% yield) as a white solid and 2-(((2R,3S,4R,5R)-5-(6-amino-2-carbamoyl-9H-purin-9-yl)-3-ethynyl-3,4-dihydroxytetra-hydrofuran-2-yl)methoxy)-2-benzylmalonic acid (Example 122) (2.2 mg, 3% yield) as a white solid.

Example 121: ¹H NMR (400 MHz, CD₃OD) δ ppm 8.19-8.39 (m, 1H) 7.26 (br d, J=5.88 Hz, 2H) 7.03-7.12 (m, 3H) 6.20 (dd, J=9.69, 7.19 Hz, 1H) 4.91-4.97 (m, 1H) 4.29 (br s, 1H) 3.98-4.24 (m, 4H) 3.41-3.53 (m, 1H) 3.31-3.40 (m, 1H) 2.97-3.08 (m, 1H) 1.18 (q, J=7.25 Hz, 3H); LC/MS [M+H]=555.1.

Example 122: ¹H NMR (400 MHz, CD₃OD) δ ppm 8.504 (s, 1H) 7.16-7.28 (m, 2H) 7.07 (br s, 3H) 6.20 (d, J=5.88 Hz, 1H) 4.92-4.99 (m, 1H) 4.37 (br s, 1H) 3.97 (br d, J=3.63 Hz, 2H) 3.32-3.48 (m, 2H) 3.01 (s, 1H); LC/MS [M+H]=527.0.

Example 123

Synthesis of (1-(((2R,3S,4R,5R)-5-(6-amino-2-chloro-9H-purin-9-yl)-3-ethynyl-3,4-dihydroxytetrahydrofuran-2-yl)methoxy)-2-methoxy-2-oxoethyl) phosphonic acid

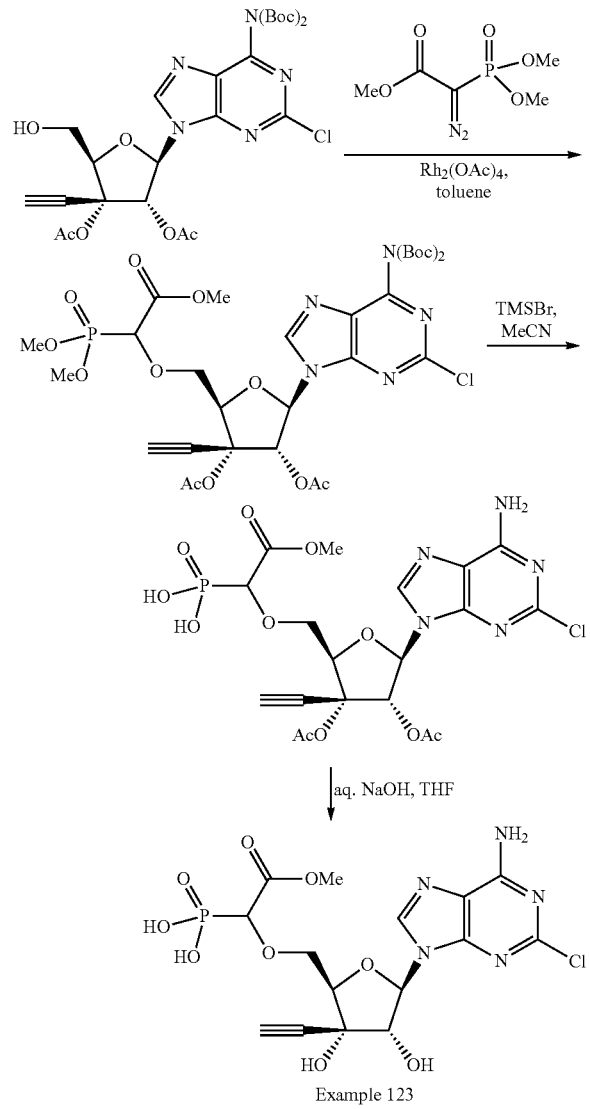

Example 123

Step 1:
A mixture of (2R,3R,4R,5R)-5-(6-(N,N'-bis(tert-butoxycarbonyl)amino)-2-chloro-9H-purin-9-yl)-3-ethynyl-2-(hydroxymethyl)tetrahydrofuran-3,4-diyl diacetate (565 mg, 0.926 mmol, 1.0 eq) and methyl 2-diazo-2-(dimethoxyphosphoryl)acetate (247 mg, 1.20 mmol, 1.3 eq) was azeotroped twice with toluene and the resulting oil was re-dissolved in toluene (5.7 mL). The reaction solution was stirred at ambient temperature under argon atmosphere and fitted with a jacketed reflux condenser. Rhodium(II) acetate (0.185 mmol, 82 mg, 0.2 eq) was added and the reaction heated at 75° C. for 9 h before it was cooled to room temperature. The reaction mixture was concentrated and the resulting oil was purified by flash silica gel column chromatography to provide (2R,3R,4R,5R)-5-(6-(N,N'-bis(tert-butoxy-carbonyl)

acetamido)-2-chloro-9H-purin-9-yl)-2-((1-(dimethoxyphosphoryl)-2-methoxy-2-oxoethoxy)methyl)-3-ethynyltetrahydrofuran-3,4-diyl diacetate.

Steps 2-3:

Deprotection of the product from the previous step was performed according to the procedure described for step 4 in Example 121. Aq. NaOH solution was used instead of KOEt that lead to the carboxylic acid. The title compound was isolated as a white solid from preparative reversed-phase HPLC.

$^1$H NMR (CD$_3$OD, 300 MHz) δ 8.08 (s, 1H), 6.06 (bs, 1H), 5.06-5.08 (d, J=5 Hz, 1H), 4.28 (s, 1H), 3.90-4.10 (m, 2H), 3.79 (s, 3H), 3.98 (bs, 2H), 3.13 (s, 1H); LC/MS [M+H]=478.2.

Example 124

Synthesis of (1-(((2R,3S,4R,5R)-5-(2-chloro-6-morpholino-9H-purin-9-yl)-3-ethynyl-3,4-dihydroxytetrahydrofuran-2-yl)methoxy)-2-ethoxy-2-oxoethyl) phosphonic acid

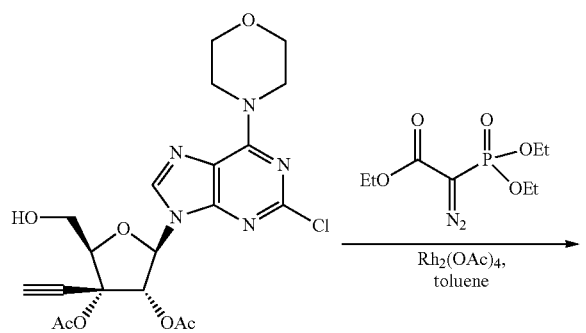

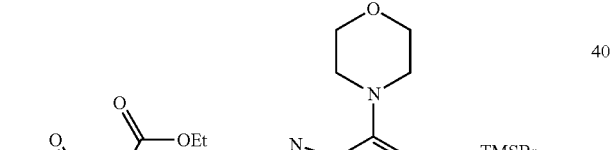

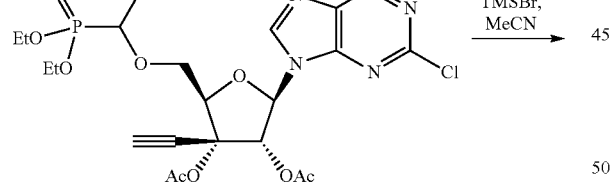

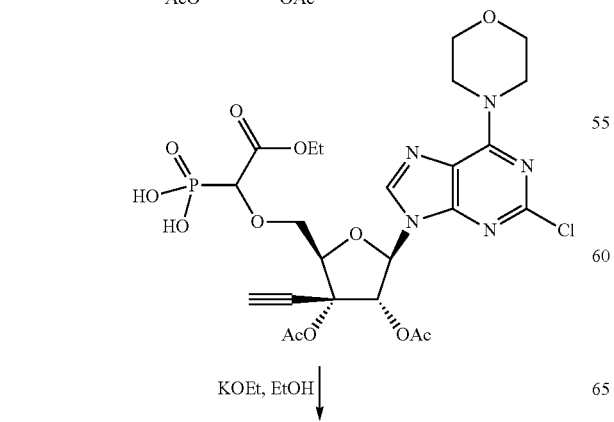

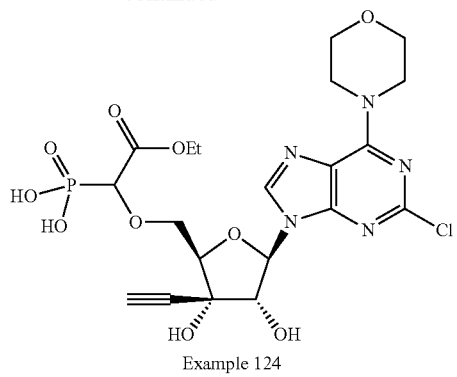

Example 124

(1-(((2R,3S,4R,5R)-5-(2-chloro-6-morpholino-9H-purin-9-yl)-3-ethynyl-3,4-dihydroxytetrahydrofuran-2-yl)methoxy)-2-ethoxy-2-oxoethyl)phosphonic acid is prepared in a manner analogous to that set forth in Example 59, except ethyl 2-diazo-2-(diethoxyphosphoryl)acetate in place of 2-diazomalonate in step 3, morpholine is used in place of benzylamine in step 7 and step 4 is eliminated. Compound was isolated as a 1:1 mixture of diastereomers.

$^1$H NMR (400 MHz, DMSO-d$_6$) of major isomer: δ 8.59 (s, 1H), 5.90 (m, 1H) 5.00 (d, J=7.0 Hz, 1H), 4.25 (m, 2H), 4.05 (m, 4H), 3.99 (m, 1H), 3.83 (m, 1H), 3.75 (m, 4H), 3.01 (s, 1H) 1.05 (t, J=7.1 Hz, 3H). 1H NMR (400 MHz, DMSO-d$_6$) of minor isomer: δ 8.48 (s, 1H), 5.88 (m, 1H), 4.94 (d, J=6.9 Hz, 1H), 4.25 (m, 2H), 4.05 (m, 4H), 3.99 (m, 1H), 3.83 (m, 1H), 3.75 (m, 4H), 3.01 (s, 1H), 0.99 (t, J=7.1 Hz, 3H). HPLC: minor isomer=6.63 min; major isomer=6.65 min, 98.6%. LC-MS: m/z=562 (M+); m/z=240 (M-ribose fragment).

Example 125

Synthesis of 2-benzyl-2-(((2R,3S,4R,5R)-3-ethynyl-3,4-dihydroxy-5-(5-(trifluoromethyl)-3H-imidazo[4,5-b]pyridin-3-yl)tetrahydrofuran-2-yl)methoxy)malonic acid

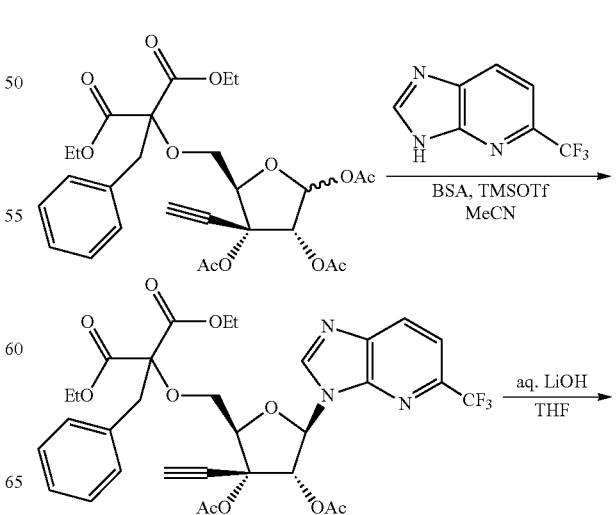

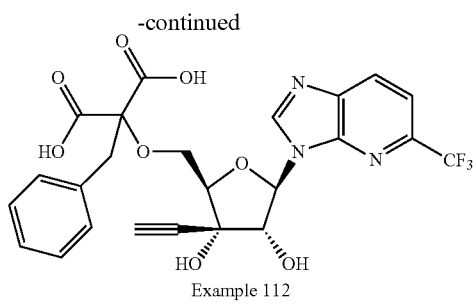

Example 112

Proceeding as described in Example 15 above but substituting 6-amino-2-chloroadenine with 5-(trifluoromethyl)-3H-imidazo[4,5-b]pyridine provided the title compound as a white solid.

$^1$H NMR (CD$_3$OD, 300 MHz) δ 8.82 (bs, 1H), 8.23 (d, J=8 Hz, 1H), 7.78 (d, J=8 Hz, 1H), 7.29-7.26 (m, 2H), 7.03-7.00 (m, 3H), 6.32 (d, J=7 Hz, 1H), 5.10 (d, J=7 Hz, 1H), 4.37-4.36 (m, 1H), 4.08 (d, J=3 Hz, 2H), 3.42 (dd, J=15, 28 Hz, 2H), 2.98 (s, 1H); LC/MS [M+H]=535.2.

Example 126

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(thiazol-4-ylmethyl) malonic acid

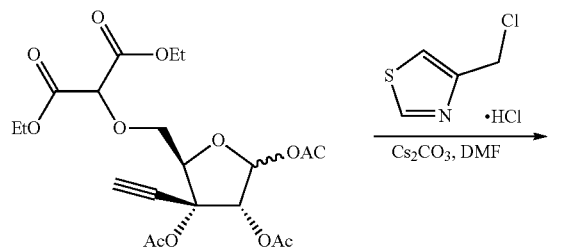

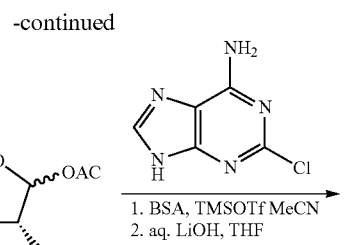

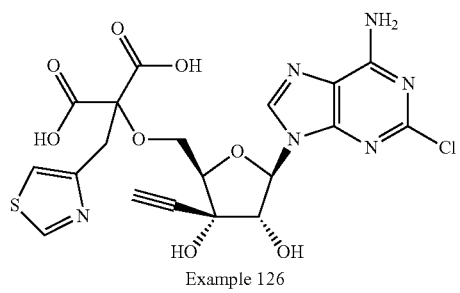

Example 126

Proceeding as described in Example 15 above but substituting allyl bromide with 4-(chloromethyl)thiazole provided the title compound as a white solid.

$^1$H NMR (CD$_3$OD, 300 MHz) δ 8.76 (bs, 1H), 8.57 (bs, 1H), 7.36 (bs, 1H), 6.00 (d, J=7 Hz, 1H), 5.00-4.95 (m, 1H), 4.35 (bs, 1H), 4.08-4.04 (m, 2H), 3.66-3.64 (m, 2H), 2.98 (s, 1H); LC/MS [M+H]=524.9.

Example 127

Synthesis of 2-(((2R,3S,4R,5R)-5-(2-acetyl-6-amino-9H-purin-9-yl)-3-ethynyl-3,4-dihydroxytetrahydrofuran-2-yl)methoxy)-2-benzylmalonic acid

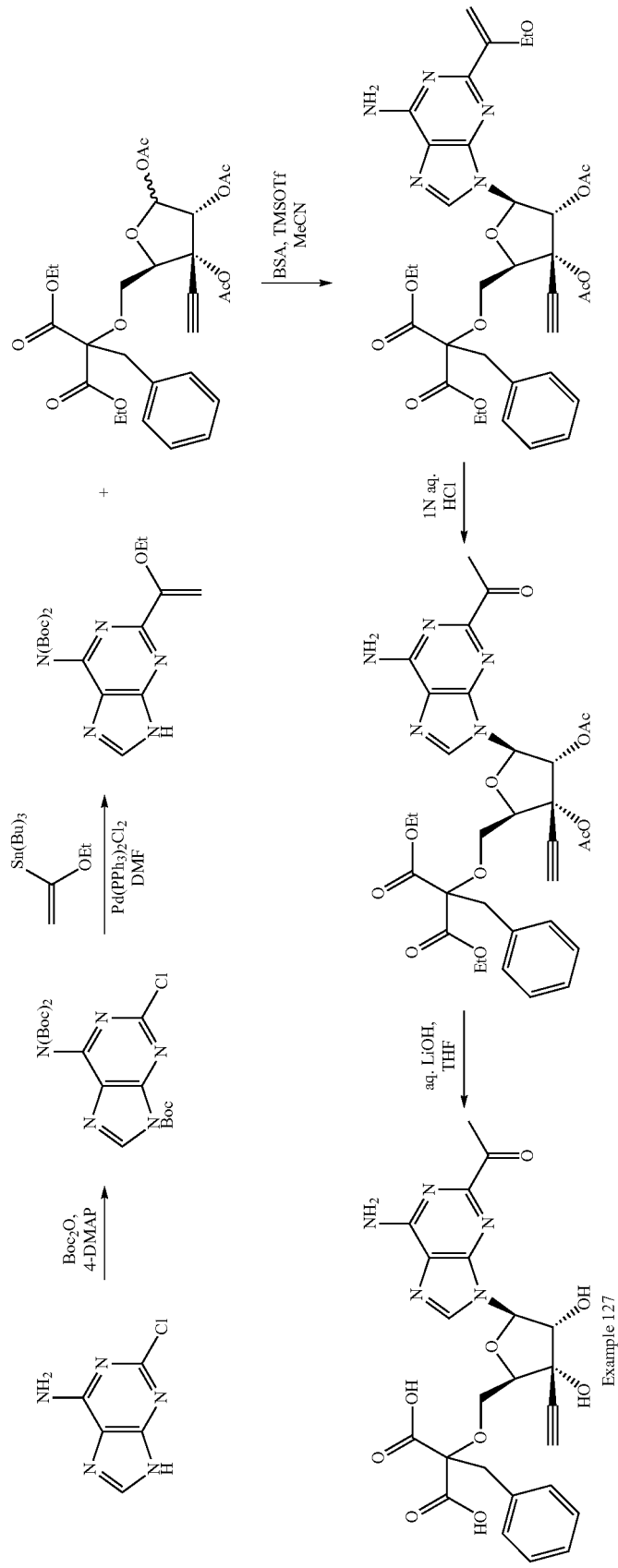

Step 1:

To a suspension of 6-amino-2-chloroadenine (3.0 g, 17.69 mmol, 1 eq) in DCM (60 mL) was added 4-DMAP (2.16 g, 17.69 mmol, 1 eq), TEA (21.48 g, 212.30 mmol, 29.55 mL, 12 eq) and (Boc)₂O (30.89 g, 141.53 mmol, 8 eq). The suspension was stirred at 20° C. for 18 h before it was diluted with saturated aq. NH₄Cl (100 mL), and extracted with ethyl acetate (2×100 mL). The combined organic layer was washed with brine (200 mL), dried by Na₂SO₄, filtered and concentrated. The crude residue was purified by Combi-flash (silica gel, 0-20% EtOAc in petroleum ether) to give tert-butyl 6-(N,N'-bis(tert-butoxycarbonyl)amino)-2-chloro-9H-purine-9-carboxylate (904 mg, 11% yield) as a yellow gum.

Step 2:

To a solution of tert-butyl 6-(N,N'-bis(tert-butoxycarbonyl)amino)-2-chloro-9H-purine-9-carboxylate (900 mg, 1.92 mmol, 1 eq) in DMF (12 mL) was added Pd(PPh₃)₂Cl₂ (134.43 mg, 191.52 umol, 0.1 eq) and tributyl(1-ethoxyvinyl)stannane (832 uL, 2.46 mmol, 1.29 eq) under N₂ atmosphere. The suspension was stirred at 95° C. for 3 h before it was diluted with saturated aq. KF solution (8 mL) and stirred at 20° C. for 1 h. The mixture was extracted with ethyl acetate (2×8 mL). The combined organic layer was washed with water (20 mL), brine (15 mL), dried by Na₂SO₄, filtered and concentrated. The crude residue was purified by Combi-flash (silica gel, 30-70% EtOAc in petroleum ether) to give tert-butyl N-(tert-butoxycarbonyl)amino-(2-(1-ethoxyvinyl)-9H-purin-6-yl)carbamate (256 mg, 33% yield) as a white solid.

Step 3:

To a solution of the product from the last step (60 mg, 109.38 umol, 1 eq) and diethyl 2-benzyl-2-(((2R,3R,4R)-3,4,5-triacetoxy-3-ethynyltetrahydrofuran-2-yl)methoxy)-malonate (53.22 mg, 131.26 umol, 1.2 eq) in MeCN (1 mL) was added BSA (65 uL, 262.52 umol, 2.4 eq). The solution was stirred at 65° C. for 0.5 h before it was cooled to 25° C. and followed by addition of TMSOTf (24 uL, 131.26 umol, 1.2 eq). The resulting solution was stirred at 65° C. for 1 h before it was diluted with saturated aq. NaHCO₃ (5 mL) and extracted with EtOAc (2×5 mL). The combined organic layer was concentrated. The crude residue was purified by preparative TLC (EtOAc) to give diethyl 2-benzyl-2-(((2R,3R,4R,5R)-3,4-diacetoxy-5-(6-amino-2-(1-ethoxyvinyl)-9H-purin-9-yl)-3-ethynyltetrahydrofuran-2-yl)-methoxy)malonate (42 mg, 55% yield) as a colorless gum.

Step 4:

To a solution of diethyl 2-benzyl-2-(((2R,3R,4R,5R)-3,4-diacetoxy-5-(6-amino-2-(1-ethoxyvinyl)-9H-purin-9-yl)-3-ethynyltetrahydrofuran-2-yl)methoxy)-malonate (40 mg, 57.66 umol, 1 eq) in THF (1.5 mL) was added 1M aq. HCl aq. (0.5 mL, 8.67 eq). The mixture was stirred at 20° C. for 21 before it was diluted with saturated aq. NaHCO₃ (5 mL) and the mixture was extracted with ethyl acetate (3×5 mL). The combined organic layer was dried by Na₂SO₄, filtered and concentrated to provide crude diethyl 2-benzyl-2-(((2R, 3R,4R,5R)-3,4-diacetoxy-5-(2-acetyl-6-amino-9H-purin-9-yl)-3-ethynyltetrahydro-furan-2-yl)methoxy)malonate (40 mg) as a light yellow gum.

Step 5:

To a solution of crude diethyl 2-benzyl-2-(((2R,3R,4R,5R)-3,4-diacetoxy-5-(2-acetyl-6-amino-9H-purin-9-yl)-3-ethynyltetrahydrofuran-2-yl)methoxy)malonate (30 mg, 45.07 umol, 1 eq) in THF (4 mL) was added 1M aq. LiOH aq. (901 uL, 20 eq). The mixture was stirred at 20° C. for 6 before it was acidified with 1N aq. HCl to pH 6 and concentrated. The crude residue was purified by preparative HPLC and the fraction was dried by lyophilization to give the title compound (1.4 mg, 6% yield) as a white solid.

¹H NMR (CD₃OD, 300 MHz) δ 8.43 (bs, 1H), 7.14-6.98 (m, 5H), 6.06 (d, J=6.4 Hz, 1H), 4.89 (d, J=6.8 Hz, 1H), 4.26 (m, 1H), 3.94-3.91 (m, 2H), 3.30-3.21 (m, 2H), 2.91 (s, 1H), 2.61 (s, 3H); LC/MS [M+H]=526.0.

Example 128

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(thiophen-2-ylmethyl) malonic acid

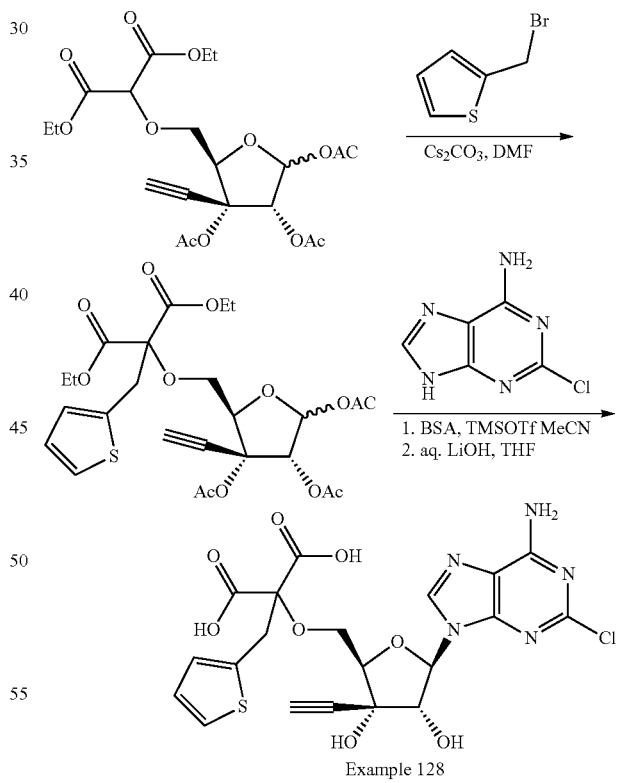

Example 128

Proceeding as described in Example 15 above but substituting allyl bromide with 2-(bromomethyl)thiophene provided the title compound as a white solid.

¹H NMR (CD₃OD, 300 MHz) δ 8.37 (bs, 1H), 7.10 (d, J=5 Hz, 1H), 6.93-6.72 (m, 2H), 6.00 (d, J=7.2 Hz, 1H), 4.98 (d, J=7.6 Hz, 1H), 4.23 (bs, 1H), 4.06 (bs, 2H), 3.62-3.58 (m, 2H), 2.94 (s, 1H); LC/MS [M+H]=523.9.

Example 129

Synthesis of 2-(((2R,3S,4R,5R)-5-(2-chloro-6-(cyclopentylamino)-9H-purin-9-yl)-3-ethynyl-3,4-dihydroxytetrahydrofuran-2-yl)methoxy)-2-(phenylsulfonyl)acetic acid Example 129

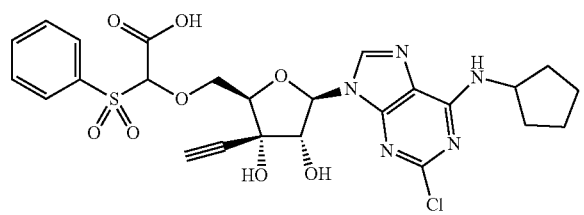

The title compound was prepared in an analogous manner to Example 59 except ethyl 2-diazo-2-(phenylsulfonyl)acetate was used instead of 1-ethyl 3-(prop-1-en-1-yl) 2-diazo malonate in Step 3, cyclopentanamine is used in place of benzylamine in Step 7 and Step 4 is eliminated.

LC/MS [M+H]=592.0.

Example 130

Synthesis of 2-(((2R,3S,4R,5R)-5-(2-chloro-6-(methylamino)-9H-purin-9-yl)-3-ethynyl-3,4-dihydroxytetrahydrofuran-2-yl)methoxy)-2-(4-(1-ethyl-2-oxo-1,2-dihydropyridin-3-yl)benzyl)malonic acid

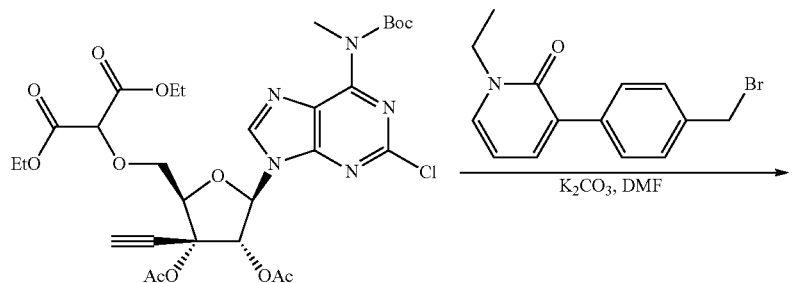

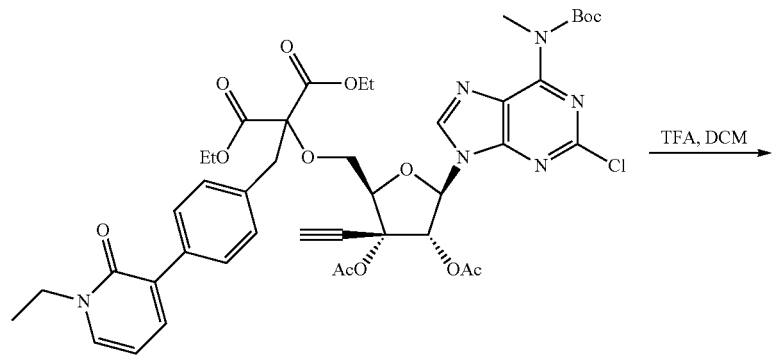

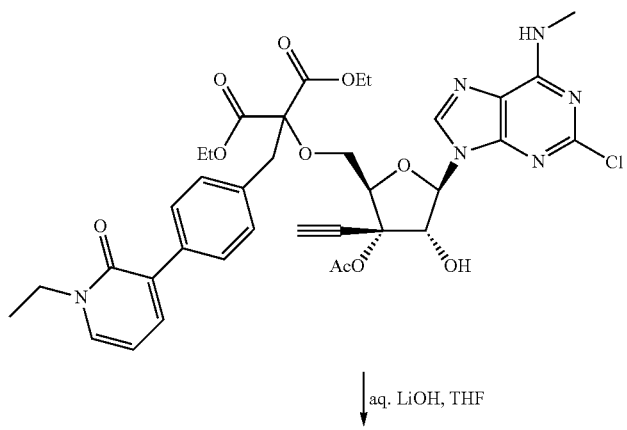

-continued

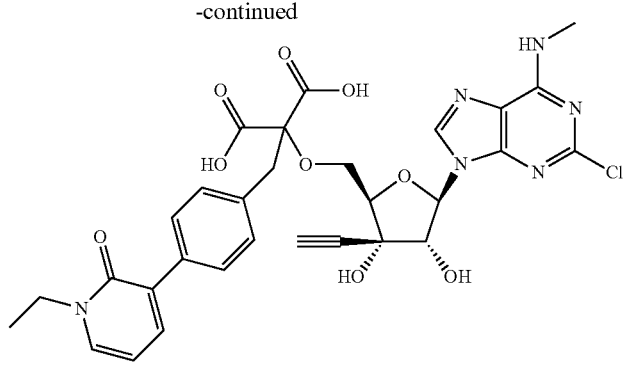

Example 130

Proceeding as described in Example 20 above but substituting diethyl 2-(((2R,3R,4R,5R)-3,4-diacetoxy-5-(6-N,N'-(bis-(tert-butoxycarbonyl)amino)-2-chloro-9H-purin-9-yl)-3-ethynyltetrahydrofuran-2-yl)methoxy)malonate with diethyl 2-(((2R,3R,4R,5R)-3,4-diacetoxy-5-(6-((tert-butoxycarbonyl)(methyl)amino)-2-chloro-9H-purin-9-yl)-3-ethynyl-tetrahydrofuran-2-yl)methoxy)malonate provided the title compound as a white solid.

$^1$H NMR (400 MHz, CD$_3$OD) δ ppm 8.04 (s, 1H), 7.58 (dd, J=6.7, 1.9 Hz, 1H), 7.27-7.38 (m, 5H), 6.35 (t, J=6.9 Hz, 1H), 5.95 (d, J=7.8 Hz, 1H), 4.77 (d, J=7.8 Hz, 1H), 4.28 (t, J=2.6 Hz, 1H), 3.96-4.13 (m, 4H), 3.38-3.57 (m, 2H), 3.05 (s, 1H) 2.99 (m, 3H), 1.32 (t, J=7.3 Hz, 3H); LC/MS [M+H]=653.1.

Example 131

Synthesis of 2-(((2R,3S,4R,5R)-5-(6-chloro-3-methyl-1H-pyrazolo[3,4-b]pyridin-1-yl)-3-ethynyl-3,4-dihydroxytetrahydrofuran-2-yl)methoxy)-2-(4-(2-oxotetrahydropyrimidin-1(2H)-yl)benzyl)malonic acid

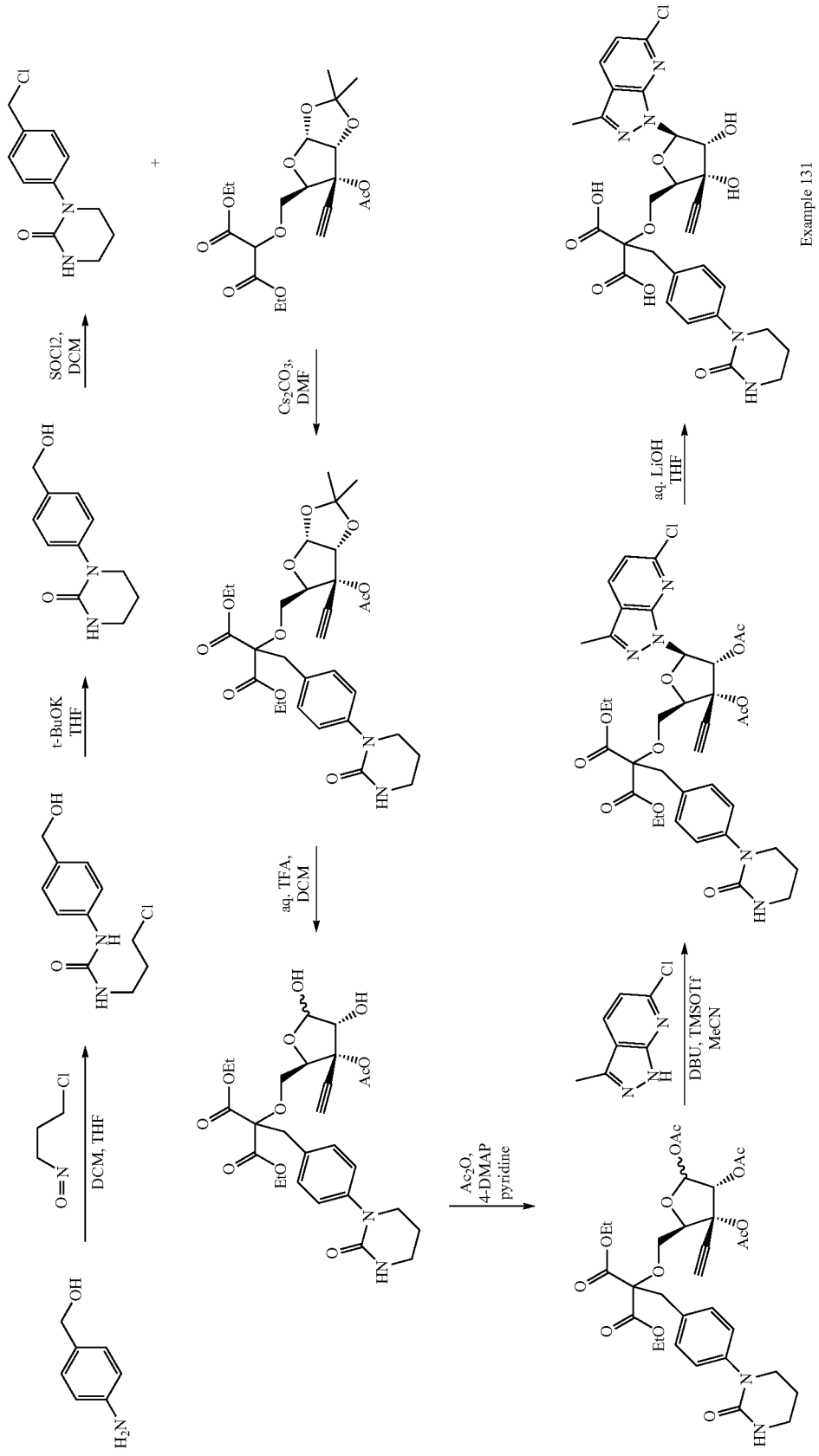

Step 1:
To a solution of (4-aminophenyl)methanol (27.65 g, 224.44 mmol, 1 eq) in a mixture of anhydrous DCM (100 mL) and anhydrous THF (50 mL) maintained at 25° C. was added 1-chloro-3-isocyanatopropane (26.83 g, 224.44 mmol, 1 eq) dropwise. The reaction mixture became slightly exothermic and turned yellow as a precipitate was formed within 15 minutes. The mixture was stirred for 1.5 h before hexanes (50 mL) was added. The mixture was stirred for additional 15 min before the solid product was collected by filtration, rinsing with a mixture of DCM and hexanes (5:1=v:v). Upon drying provided 1-(3-chloropropyl)-3-(4-(hydroxymethyl)phenyl)urea (38.45 g) as a light yellow solid.

Step 2:
To a solution of 1-(3-chloropropyl)-3-(4-(hydroxymethyl)phenyl)urea (30.00 g, 123.6 mmol, 1.0 eq) in THF (300 mL) at 25° C. was added a solution of 1M t-BuOK in THF (247.2 mL, 247.2 mmol, 2.0 eq) dropwise while stirring vigorously with a mechanical stirrer. The resulting heterogeneous mixture was stirred at 25° C. for 6 h before it was cooled to 0° C. and acidified to pH 5-6 with 2N aq. HCl. The organic volatile was then removed under reduced pressure. The crude solid was taken up in MeOH (75 mL) and concentrated. The resulting solid mixture was rinsed with a solution of 7% MeOH in DCM (220 mL) under gentle heating and the solid was filtered off. The solid was rinsed again with 7% MeOH in DCM (150 mL) and filtered. The combined rinse was concentrated to give the desired crude 1-(4-(hydroxymethyl)phenyl)tetrahydropyrimidin-2(1H)-one as a yellowish solid (27.68 g).

Step 3:
To a suspension of crude 1-(4-(hydroxymethyl)phenyl)tetrahydropyrimidin-2(1H)-one (15.00 g, 72.74 mmol, 1 eq) in DCM (250 mL) was added a solution of thionyl chloride (10.61 mL, 145.48 mmol, 2 eq) at 25° C. under a $N_2$ atmosphere. The mixture was stirred at 25° C. for 8 h before it was diluted with EtOAc (250 mL) and stirred for 30 min. The solid was collected by filtration, rinsed with EtOAc and dried to provide crude 1-(4-(chloro-methyl)phenyl)tetrahydropyrimidin-2(1H)-one (15.00 g).

Step 4:
To a solution of diethyl 2-(((3aR,5R,6R,6aR)-6-acetoxy-2,2-dimethyl-6-(prop-1-yn-1-yl)tetrahydrofuro[2,3-d][1,3]dioxol-5-yl)methoxy)malonate (7.04 g, 16.99 mmol, 1 eq) in DMF (70 mL) was added $Cs_2CO_3$ (11.07 g, 33.98 mmol, 2 eq) and crude 1-(4-(chloro-methyl)phenyl)tetrahydropyrimidin-2(1H)-one (5.09 g, 25.49 mmol, 1.5 eq) at 20° C. The mixture was stirred at 20° C. for 5 h before it was diluted with $H_2O$ (300 mL) and extracted with EtOAc (3×100 mL). The combined organic layer was washed with brine (200 mL), dried over $Na_2SO_4$, filtered and concentrated. The crude product was purified by flash silica gel column chromatography (10-40% acetone in DCM) to provide diethyl 2-(((3aR,5R,6R,6aR)-6-acetoxy-6-ethynyl-2,2-dimethyltetrahydrofuro[2,3-d][1,3]dioxol-5-yl)methoxy)-2-(4-(2-oxotetrahydropyrimidin-1 (2H)-yl)benzyl)malonate (9.62 g, 94% yield) as a solid.

Step 5:
To a solution of diethyl 2-(((3aR,5R,6R,6aR)-6-acetoxy-6-ethynyl-2,2-dimethyl-tetrahydrofuro[2,3-d][1,3]dioxol-5-yl)methoxy)-2-(4-(2-oxotetrahydropyrimidin-1(2H)-yl)benzyl)malonate (17.31 g, 28.72 mmol, 1 eq) in DCM (90 mL) was added $H_2O$ (18 mL) and TFA (90 mL, 1.22 mol, 42 eq) at 0° C. The reaction mixture was stirred at 20-25° C. for 16 h before it concentrated under reduced pressure. The residue was azeotroped with DCM (2×50 mL) under reduced pressure to provide the crude product diethyl 2-(((2R,3S,4R)-3-acetoxy-3-ethynyl-4,5-dihydroxytetrahydrofuran-2-yl)methoxy)-2-(4-(2-oxotetrahydropyrimidin-1 (2H)-yl)benzyl)malonate which was used in the next step without further purification.

Step 6:
To a solution of crude diethyl 2-(((2R,3S,4R)-3-acetoxy-3-ethynyl-4,5-dihydroxy-tetrahydrofuran-2-yl)methoxy)-2-(4-(2-oxotetrahydropyrimidin-1(2H)-yl)benzyl)malonate (17.23 g, crude) in DCM (170 mL) was added 4-DMAP (374 mg, 3.06 mmol, 0.1 eq), $Ac_2O$ (17.21 mL, 183.77 mmol, 6 eq) and pyridine (19.78 mL, 245.02 mmol, 8 eq) at 0° C. The reaction mixture was stirred at 20-25° C. for 16 h before it was concentrated under reduced pressure. The residue was re-dissolved in EtOAc (200 mL), washed with 1N aq. HCl (150 mL), 10% aq. $Cu_2SO_4$ (150 mL), saturated aq. $NaHCO_3$(150 mL) and brine (150 mL), dried over $Na_2SO_4$, filtered and concentrated to provide crude diethyl 2-(4-(2-oxotetrahydro-pyrimidin-1 (2H)-yl)benzyl)-2-(((2R,3R,4R)-3,4,5-triacetoxy-3-ethynyltetrahydrofuran-2-yl)methoxy)malonate (19.24 g) as a foam which was carried onto the next step without further purification.

Step 7:
To a suspension of crude diethyl 2-(4-(2-oxotetrahydropyrimidin-1(2H)-yl)benzyl)-2-(((2R,3R,4R)-3,4,5-triacetoxy-3-ethynyltetrahydrofuran-2-yl)methoxy)malonate (450 mg, 0.70 mmol, 1 eq) and 6-chloro-3-methyl-1H-pyrazolo[3,4-b]pyridine (128 mg, 0.77 mmol, 1.1 eq) in MeCN (4 mL) was added DBU (315 uL, 2.09 mmol, 3.0 eq) at 0° C. The solution was stirred at 0° C. for 5 min and followed by addition of a solution of TMSOTf (566 uL, 3.13 mmol, 4.5 eq) in MeCN (2 mL) dropwise. The solution was stirred at 0° C. for 0.5 h and then stirred at 70° C. for 16 h before it was allowed to cool to 25° C. and adjusted the pH to 9 with saturated aq. $NaHCO_3$. The mixture was extracted with ethyl acetate (2×40 mL). The combined organic layer was dried with $Na_2SO_4$, filtered and concentrated. The crude residue which was purified by Combi-flash on silica gel (0-10% MeOH in DCM) to give diethyl 2-(((2R,3R,4R,5R)-3,4-diacetoxy-5-(6-chloro-3-methyl-1H-pyrazolo[3,4-b]pyridin-1-yl)-3-ethynyltetrahydrofuran-2-yl)methoxy)-2-(4-(2-oxotetrahydropyrimidin-1 (2H)-yl)benzyl)-malonate (255 mg, 49% yield) as a yellow gum.

Step 8:
To a solution of diethyl 2-(((2R,3R,4R,5R)-3,4-diacetoxy-5-(6-chloro-3-methyl-1H-pyrazolo[3,4-b]pyridin-1-yl)-3-ethynyltetrahydrofuran-2-yl)methoxy)-2-(4-(2-oxotetrahydro-pyrimidin-1(2H)-yl)benzyl)malonate (296 mg, 392 umol, 1 eq) in THF (6 mL) was added aq. LiOH solution (2 M, 1.96 mL, 10 eq). The solution was stirred at 50° C. for 2 h before the organic volatile was removed under reduced pressure. To the water layer was added 1N HCl to adjust the pH to 5-6. The mixture was concentrated to give crude product which was purified by preparative HPLC (Column: YMC-Actus Triart C18 150*30 mm*5 um; mobile phase: [water (0.225% FA)-ACN]; B %: 25%-45%, 10 min). The product was isolated by lyophilization to give 2-(((2R,3S,4R,5R)-5-(6-chloro-3-methyl-1H-pyrazolo[3,4-b]pyridin-1-yl)-3-ethynyl-3,4-dihydroxytetrahydrofuran-2-yl)methoxy)-2-(4-(2-oxotetrahydropyrimidin-1(2H)-yl)benzyl)malonic acid (32 mg) as a white solid.

$^1$H NMR (400 MHz, DMSO-$d_6$) δ ppm 8.27 (d, J=8.28 Hz, 1H), 7.31 (d, J=8.28 Hz, 1H), 6.97 (d, J=8.53 Hz, 2H), 6.81 (d, J=8.53 Hz, 2H), 6.49 (s, 1H), 6.20 (s, 1H), 6.13 (d, J=7.53 Hz, 1H), 5.97 (s, 1H), 4.98 (d, J=7.53 Hz, 1H), 4.13 (dd, J=8.41, 2.64 Hz, 1H), 3.93-3.99 (m, 1H), 3.84-3.91 (m, 1H), 3.64 (s, 1H), 3.42-3.52 (t, J=5.60 Hz, 2H), 3.17-3.23 (m, 2H), 3.05-3.16 (m, 2H), 2.45 (s, 3H), 1.90 (m, 2H); LC/MS [M+H]=614.3.

Example 132

Synthesis of 2-(((2R,3S,4R,5R)-5-(2-chloro-6-oxo-1H-purin-9(6H)-yl)-3-ethynyl-3,4-dihydroxytetrahydrofuran-2-yl)methoxy)-2-(4-(2-oxotetrahydropyrimidin-1 (2H)-yl)benzyl)malonic acid

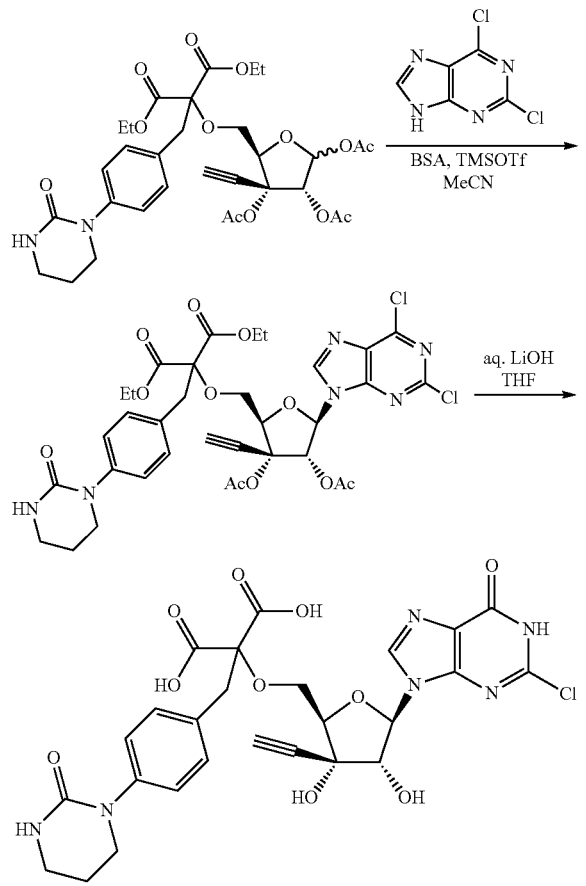

Example 132

Step 1:

To a solution of 2,6-dichloro-9H-purine (379.97 mg, 2.01 mmol) in MeCN (5 mL) was added BSA (956 uL, 3.87 mmol) at 25° C. The reaction mixture was stirred at 65° C. for 0.5 h and then cooled back to 25° C. To this mixture was added diethyl 2-(4-(2-oxotetrahydropyrimidin-1 (2H)-yl)benzyl)-2-(((2R,3R,4R)-3,4,5-triacetoxy-3-ethynyltetrahydrofuran-2-yl)methoxy)malonate (1 g) in MeCN (5 mL) and TMSOTf (419 uL, 2.32 mmol) at 25° C. and further stirred at 65° C. for 5 h. The reaction mixture was allowed to cool to 25° C. before it was quenched with saturated aq. NaHCO₃ (10 mL) and extracted with EtOAc (3×5 mL). The combined organic layer was washed brine (10 mL), dried over anhydrous Na₂SO₄, filtered and concentrated. The crude residue was purified by flash silica gel column chromatography (0-10% MeOH in DCM) to provide diethyl 2-(((2R,3R,4R,5R)-3,4-di-acetoxy-5-(2,6-dichloro-9H-purin-9-yl)-3-ethynyltetrahydrofuran-2-yl)methoxy)-2-(4-(2-oxotetrahydropyrimidin-1 (2H)-yl)benzyl)malonate (365 mg) as a foam.

Step 2:

To a solution of diethyl 2-(((2R,3R,4R,5R)-3,4-diacetoxy-5-(2,6-dichloro-9H-purin-9-yl)-3-ethynyltetrahydrofuran-2-yl)methoxy)-2-(4-(2-oxotetrahydropyrimidin-1 (2H)-yl)benzyl)malonate (180 mg) in THF (2 mL) was added LiOH.H₂O (97.39 mg, 2.32 mmol, 10 eq) in H₂O (1 mL) at 25° C. The reaction mixture was stirred at 40° C. for 2 h before the organic volatile was removed under reduced pressure. The aqueous phase was acidified to pH 5-6 with 1N aq. HCl and concentrated under reduced pressure. The crude residue was purified by preparative HPLC (column: YMC-Actus Triart C18 150*30 mm*5 um; mobile phase: [water (0.225% FA)-ACN]; B %: 13%-33%, 10 min) and dried by lyophilization to provide 2-(((2R,3S,4R,5R)-5-(2-chloro-6-oxo-1H-purin-9(6H)-yl)-3-ethynyl-3,4-dihydroxy-tetrahydrofuran-2-yl)methoxy)-2-(4-(2-oxotetrahydropyrimidin-1 (2H)-yl)benzyl)malonic acid (15 mg) as a white solid. 1H NMR (400 MHz, CD₃OD) δ ppm 8.62 (s, 1H), 7.24 (d, J=8.31 Hz, 2H), 7.03 (d, J=8.31 Hz, 2H), 6.32 (d, J=6.48 Hz, 1H), 4.61 (d, J=6.48 Hz, 1H), 4.28-4.34 (m, 1H), 3.92-4.04 (m, 2H), 3.55-3.66 (m, 2H), 3.33-3.40 (m, 4H), 3.02 (s, 1H), 1.99-2.06 (m, 2H); LC/MS [M+H]=617.2.

Example 133

Synthesis of 2-(((2R,3S,4R,5R)-3-ethynyl-3,4-dihydroxy-5-(5-methyl-2,4-dioxo-3,4-dihydropyrimidin-1 (2H)-yl)tetrahydrofuran-2-yl)methoxy)-2-(4-(2-oxotetrahydropyrimidin-1 (2H)-yl)benzyl) malonic acid

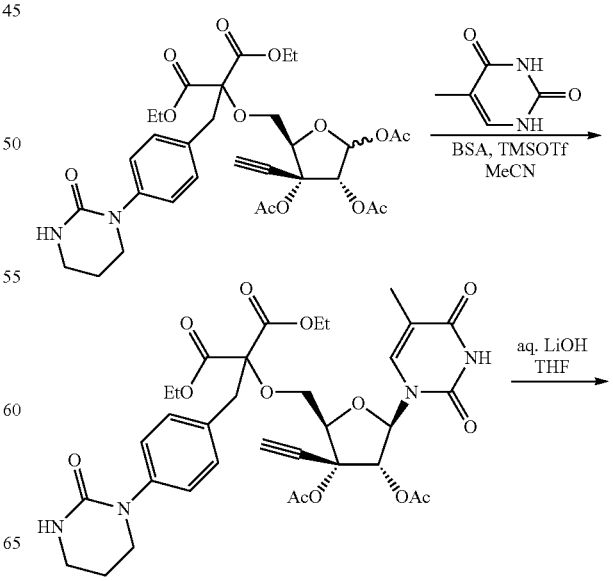

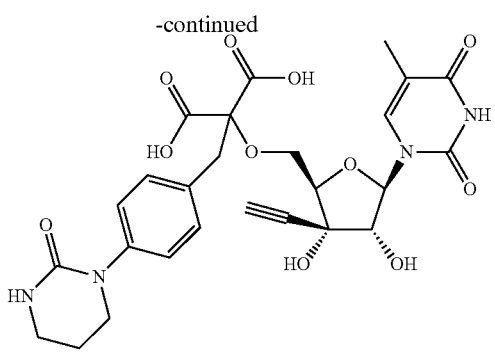

Example 133

Step 1:
To the mixture of 5-methylpyrimidine-2,4(1H,3H)-dione (100 mg, 792.94 umol, 1 eq) in MeCN (2 mL) was added BSA (490 uL, 1.98 mmol, 2.5 eq). The mixture was stirred at 85° C. for 0.5 h. The mixture was cooled to 0° C. and followed by addition of a solution of diethyl 2-(4-(2-oxo-tetra-hydropyrimidin-1(2H)-yl)benzyl)-2-(((2R,3R,4R)-3,4,5-triacetoxy-3-ethynyltetrahydrofuran-2-yl)methoxy)malonate (385 mg) in MeCN (2 mL) and TMSOTf (430 uL, 2.38 mmol, 3.0 eq) was added dropwise. The mixture was stirred at 65° C. under $N_2$ atmosphere for 5 h before it was allowed to cool to 25° C. and quenched with saturated aq. $NaHCO_3$ (10 mL). The mixture was extracted with EtOAc (3×5 mL). The organic layers were combined, dried over $Na_2SO_4$, filtered and concentrated in vacuo. The crude compound was purified by silica gel column chromatography (0-5% MeOH in DCM) to provide diethyl 2-(((2R,3R,4R,5R)-3,4-diacetoxy-3-ethynyl-5-(5-methyl-2,4-dioxo-3,4-dihydropyrimidin-1 (2H)-yl)tetrahydrofuran-2-yl)methoxy)-2-(4-(2-oxotetrahydropyrimidin-1(2H)-yl)benzyl)malonate (208 mg, 37% yield) as a solid.
Step 2:
To a solution of diethyl 2-(((2R,3R,4R,5R)-3,4-diacetoxy-3-ethynyl-5-(5-methyl-2,4-dioxo-3,4-dihydropyrimidin-1 (2H)-yl)tetrahydrofuran-2-yl)methoxy)-2-(4-(2-oxo-tetrahydro-pyrimidin-1(2H)-yl)benzyl)malonate (200 mg, 280.62 umol, 1 eq) in THF (2 mL) was added $LiOH·H_2O$ (58.88 mg, 1.40 mmol, 5 eq) in $H_2O$ (1 mL) at 20-25° C. The reaction mixture was stirred at 40° C. for 1 h before the organic volatile was removed under reduced pressure.

The aqueous phase was acidified to pH is 5-6 with 1N aq. HCl and concentrated under reduced pressure. The crude residue was purified by preparative HPLC (column: YMC-Actus Triart C18 150*30 mm*5 um; mobile phase: [water (0.225% FA)-ACN]; B %: 13%-33%, 10 min) and then followed by lyophilization to provide 2-(((2R,3S,4R,5R)-3-ethynyl-3,4-dihydroxy-5-(5-methyl-2,4-dioxo-3,4-dihydropyrimidin-1(2H)-yl)tetrahydrofuran-2-yl)methoxy)-2-(4-(2-oxotetrahydropyrimidin-1(2H)-yl)benzyl)malonic acid (49 mg) as a white solid.
$^1$H NMR (400 MHz, $CD_3OD$) δ ppm 7.83 (d, J=0.75 Hz, 1H), 7.33 (d, J=8.28 Hz, 2H), 7.11 (d, J=8.28 Hz, 2H), 6.06 (d, J=7.78 Hz, 1H), 4.44 (d, J=7.78 Hz, 1H), 4.16 (t, J=2.26 Hz, 1H), 3.92-4.05 (m, 2H), 3.47-3.65 (m, 3H), 3.33-3.41 (m, 3H), 2.98 (s, 1H), 2.04 (m, 2H), 1.62 (s, 3H); LC/MS [M+H]=573.1.

Example 134

Synthesis of 2-(((2R,3S,4R,5R)-5-(2,4-dioxo-3,4-dihydropyrimidin-1(2H)-yl)-3-ethynyl-3,4-dihydroxytetrahydrofuran-2-yl)methoxy)-2-(4-(2-oxotetrahydropyrimidin-1 (2H)-yl)benzyl)malonic acid

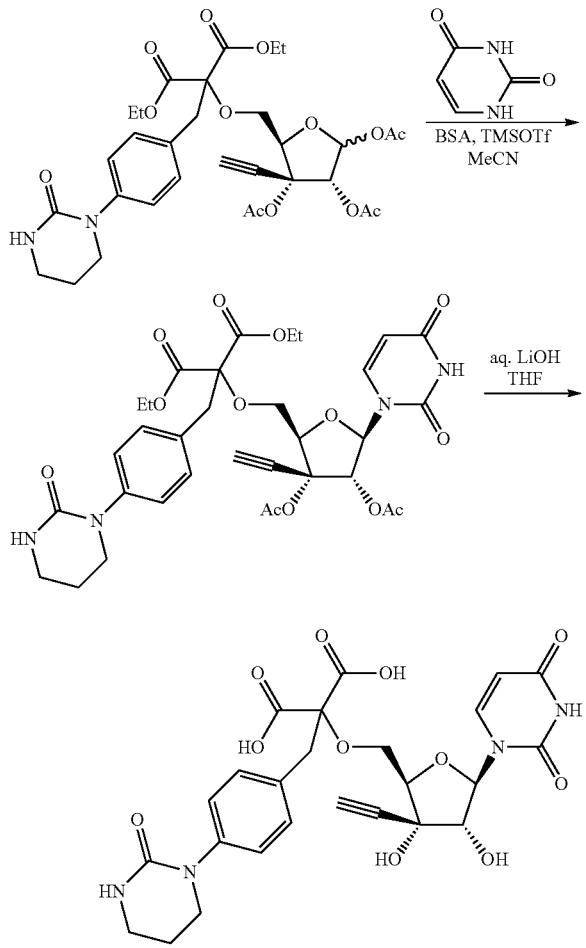

Example 134

Proceeding as described in Example 133 above but substituting thymine with uracil provided the title compound as a white solid.

$^1$H NMR (400 MHz, $CD_3OD$) δ ppm 7.91 (d, J=8.0 Hz, 1H), 7.31 (d, J=8.4 Hz, 2H), 7.15 (d, J=8.4 Hz, 2H), 6.01 (d, J=7.5 Hz, 1H), 5.20 (d, J=8.0 Hz, 1H), 4.36 (d, J=7.5 Hz, 1H), 4.17 (t, J=2.4 Hz, 1H), 3.99 (dd, J=18.8, 2.5 Hz, 2H), 3.55-3.66 (m, 2H), 3.44-3.52 (m, 1H), 3.33-3.38 (m, 3H), 3.01 (s, 1H), 1.99-2.10 (m, 2H); LC/MS [M+H]=559.1.

Example 135

Synthesis of 2-(((2R,3S,4R,5R)-5-(4-amino-2-oxopyrimidin-1(2H)-yl)-3-ethynyl-3,4-dihydroxytetrahydrofuran-2-yl)methoxy)-2-(4-(2-oxotetrahydropyrimidin-1 (2H)-yl)benzyl)malonic acid

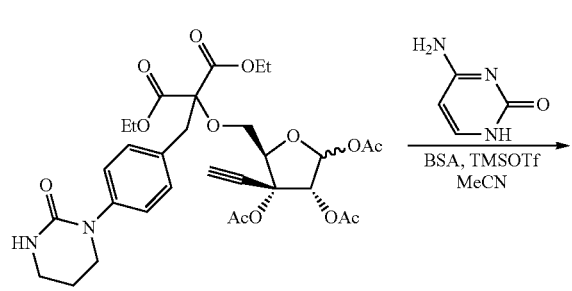

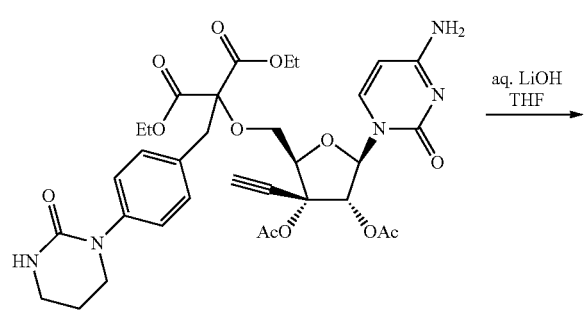

Example 135

Proceeding as described in Example 133 above but substituting thymine with cytosine provided the title compound as a white solid.

¹H NMR (400 MHz, DMSO-d₆) δ ppm 7.92-8.05 (m, 1H), 7.76-7.92 (br s, 1H), 7.45-7.62 (s, 1H), 7.03-7.19 (m, 4H), 6.55 (s, 1H), 5.91-5.99 (m, 1H), 5.87 (d, J=6.80 Hz, 1H), 5.80 (d, J=6.00 Hz, 1H), 5.57 (d, J=7.20 Hz, 1H), 4.13 (t, J=6.80 Hz, 1H), 4.02-4.08 (m, 1H), 3.68-3.82 (m, 2H), 3.50-3.57 (m, 2H), 3.22 (s, 1H), 3.19-3.22 (m, 3H), 1.82-1.99 (m, 2H); LC/MS [M+H]=558.3.

Example 136

Synthesis of 2-(((2R,3S,4R,5R)-5-(2-chloro-6-((cyclopropylmethyl)amino)-9H-purin-9-yl)-3-ethynyl-3,4-dihydroxytetrahydrofuran-2-yl)methoxy)-2-(4-(2-oxotetrahydropyrimidin-1(2H)-yl)benzyl)malonic acid

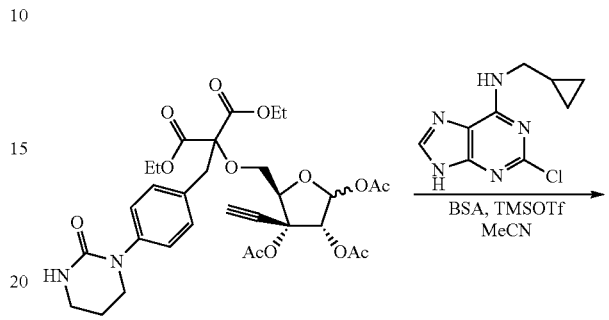

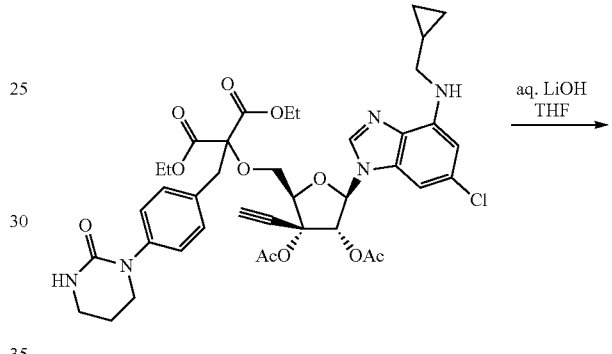

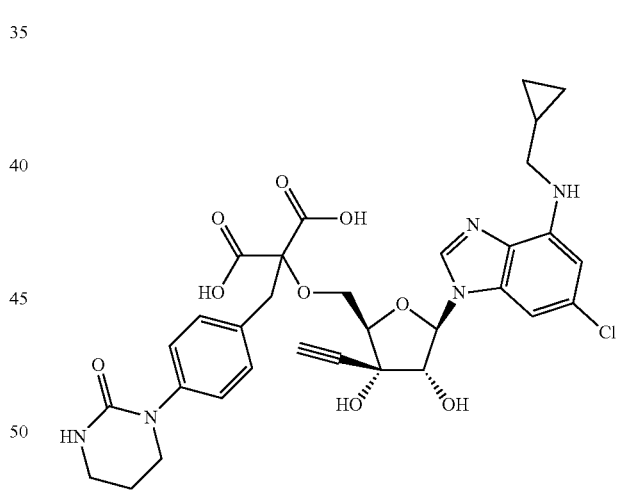

Example 136

Proceeding as described in Example 133 above but substituting thymine with 2-chloro-N-(cyclopropylmethyl)-9H-purin-6-amine provided the title compound as a white solid.

¹H NMR (400 MHz, CD₃OD) δ ppm 8.22 (s, 1H), 7.28 (br d, J=8.03 Hz, 2H), 7.03 (d, J=8.28 Hz, 2H), 5.97 (d, J=7.28 Hz, 1H), 4.72-4.77 (m, 1H), 4.28 (s, 1H), 3.95-4.05 (m, 2H), 3.34-3.52 (m, 8H), 3.05 (s, 1H), 1.92-2.02 (m, 2H), 1.11-1.20 (m, 1H), 0.51-0.59 (m, 2H), 0.34 (q, J=4.85 Hz, 2H); LC/MS [M+H]=670.1.

Example 137
Synthesis of 2-(((2R,3S,4R,5R)-5-(2-chloro-6-(methylamino)-9H-purin-9-yl)-3-ethynyl-3,4-dihydroxytetrahydrofuran-2-yl)methoxy)-2-(4-(3-(2-hydroxyethyl)-2-oxotetrahydropyrimidin-1(2H)-yl)benzyl)malonic acid
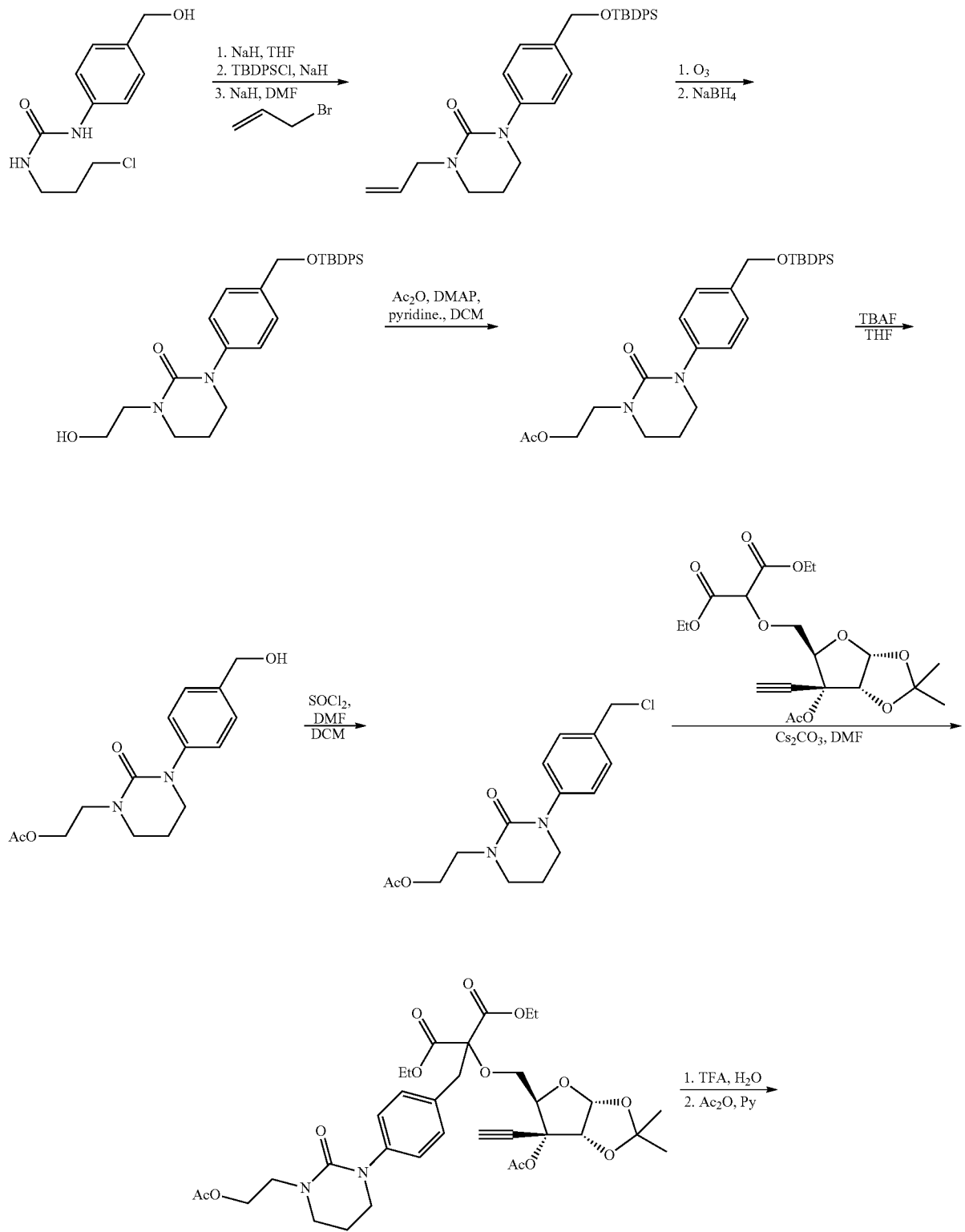

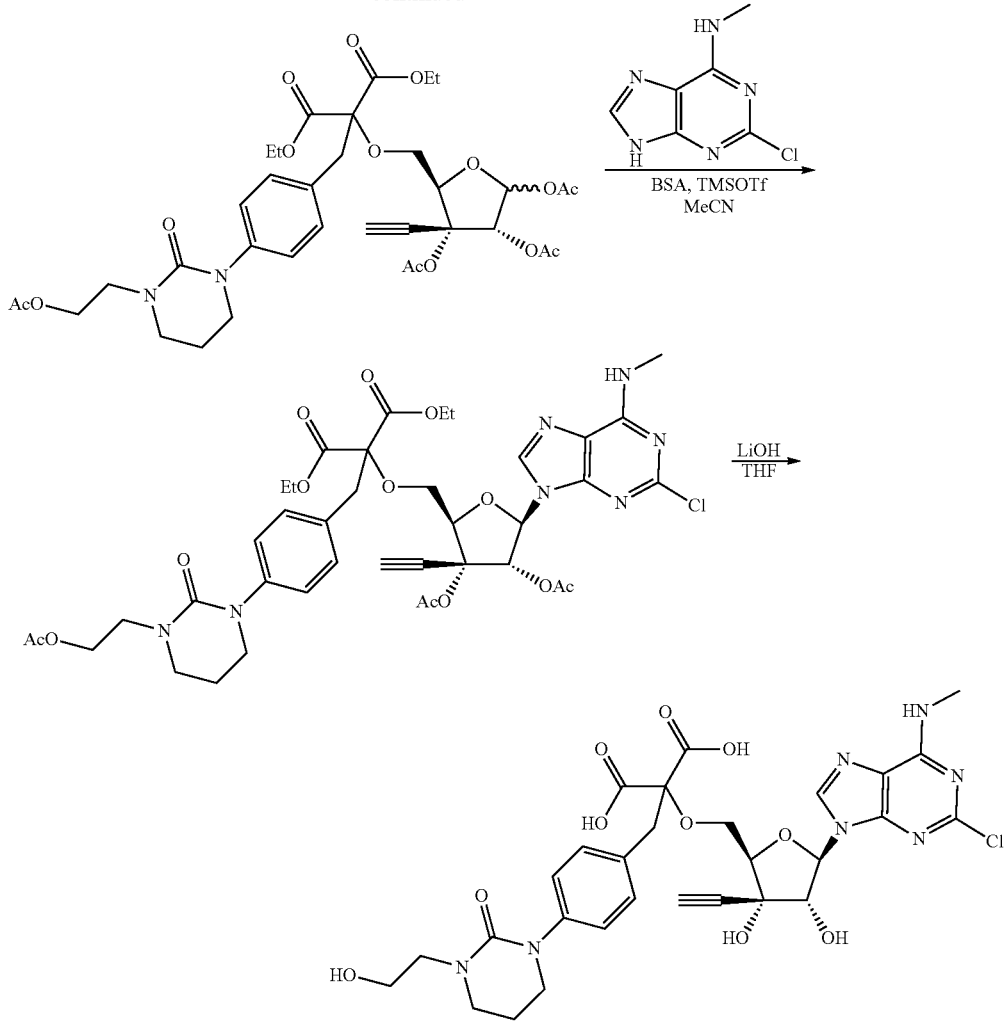

Example 137

Step 1:

To a solution of compound 1-(3-chloropropyl)-3-(4-(hydroxymethyl)phenyl)urea (5 g, 20.60 mmol, 1 eq) in THF (100 mL) at 0° C. was added NaH (9.89 g, 247.22 mmol, 60% in mineral oil, 12 eq). The reaction mixture was stirred at 25° C. for 1.5 h before it was then added TBDPSCl (6.80 g, 24.72 mmol, 1.2 eq) and stirred further for additional 1.5 h. To the reaction mixture was then added allyl bromide (9.97 g, 82.41 mmol, 4 eq) and stirred further for 16 h. To the reaction mixture was added H$_2$O (50 mL) and the resulting mixture was extracted with EtOAc (3×100 mL). The combined organic layer was washed with brine (100 mL), dried over Na$_2$SO$_4$, filtered and concentrated. The crude residue was purified by silica gel column chromatography and eluted with EtOAc in petroleum ether (0-30%) to provide 1-allyl-3-(4-(((tert-butyldiphenylsilyl)oxy)methyl)phenyl)tetrahydropyrimidin-2(1H)-one (6 g, 60% yield) as an oil.

Step 2:

To a solution of compound 1-allyl-3-(4-(((tert-butyldiphenylsilyl)oxy)methyl)-phenyl)tetrahydropyrimidin-2(1H)-one (6 g, 12.38 mmol, 1 eq) in a mixture of MeOH (60 mL) and DCM (30 mL) at −78° C., ozone (15 psi) was introduced until the blue color of the solution persisted for 20 minutes. The excess of ozone was removed by bubbling nitrogen gas for 10 minutes. To this reaction mixture was added NaBH$_4$ (937 mg, 24.76 mmol, 2 eq) and the mixture was allowed to reach 0° C. and stirred for 15 h at 25° C. The mixture was poured into 1N aq. HCl (50 mL) and extracted with EtOAc (2×100 mL). The combined organic layer was washed with water (100 mL) and brine (100 mL), dried (Na$_2$SO$_4$), filtered and concentrated to give crude 1-(4-(((tert-butyldiphenylsilyl)oxy)methyl)phenyl)-3-(2-hydroxyethyl)tetrahydropyrimidin-2(1H)-one (6.6 g) as an oil which was used directly in the next step.

Step 3:

To a solution of crude 1-(4-(((tert-butyldiphenylsilyl)oxy)methyl)phenyl)-3-(2-hydroxyethyl)tetrahydropyrimidin-2(1H)-one (12.38 mmol, 1 eq) in DCM (40 mL) and pyridine (3.00 mL, 37.14 mmol, 3 eq) at 25° C. was added Ac$_2$O (2.32 mL, 24.76 mmol, 2 eq) and 4-DMAP (151 mg, 1.24 mmol, 0.1 eq). The mixture was stirred for 2 h before it was quenched with H$_2$O (60 mL). The mixture was extracted with EtOAc (3×50 mL). The combined organic layer was washed with water (2×30 mL), brine (30 mL), dried over Na$_2$SO$_4$, filtered and concentrated to provide the crude 2-(3-(4-(((tert-butyldiphenylsilyl)-oxy)methyl)phenyl)-2-oxotetrahydropyrimidin-1 (2H)-yl)ethyl acetate which was used in the next step directly.

Step 4:

To a solution of crude 2-(3-(4-(((tert-butyldiphenylsilyl)oxy)methyl)phenyl)-2-oxotetrahydropyrimidin-1(2H)-yl)ethyl acetate (6.57 g, 12.38 mmol, 1 eq) in THF (40 mL) was added 1 M TBAF solution in THF (18.57 mL, 1.5 eq) at 0° C. The mixture was stirred at 25° C. for 1 h before $H_2O$ (100 mL) was added. The reaction mixture was extracted with EtOAc (4×100 mL). The combined organic layer was washed with brine (50 mL), dried over $Na_2SO_4$, filtered and concentrated. The water phase was further extracted with $CH_2Cl_2$ (4×100 mL). The combined organic layer was washed with brine (50 mL), dried over $Na_2SO_4$, filtered and concentrated to provide more product. Combining both batches of crude product and further purified on silica gel column chromatography (40-100% EtOAc in petroleum ether) to provide 2-(3-(4-(hydroxymethyl)phenyl)-2-oxotetrahydropyrimidin-1(2H)-yl)ethyl acetate (3.14 g) as as a white solid.

Step 5:

To a mixture of 2-(3-(4-(hydroxymethyl)phenyl)-2-oxotetrahydropyrimidin-1(2H)-yl)ethyl acetate (1.28 g, 4.38 mmol, 1 eq) and DMF (3.37 uL, 43.79 umol, 0.01 eq) in DCM (25 mL) at 0° C. was added $SOCl_2$ (5 mL, 68.92 mmol, 15.74 eq). The mixture was stirred at 50° C. for 2 h before it was concentrated to give crude 2-(3-(4-(chloromethyl)phenyl)-2-oxo-tetrahydropyrimidin-1 (2H)-yl)ethyl acetate (1.51 g) which was used in the next step without further purification.

Step 6:

To a solution of crude 2-(3-(4-(chloromethyl)phenyl)-2-oxotetrahydropyrimidin-1(2H)-yl)ethyl acetate (1.51 g, 4.38 mmol, 1 eq) and of diethyl 2-(((3aR,5R,6R,6aR)-6-acetoxy-2,2-dimethyl-6-(prop-1-yn-1-yl)tetrahydrofuro[2,3-d][1,3]dioxol-5-yl)methoxy)-malonate (1.91 g, 4.60 mmol, 1.05 eq) in DMF (8 mL) was added $Cs_2CO_3$ (4.28 g, 13.14 mmol, 3 eq). The mixture was stirred at 25° C. for 16 h before it was diluted with $H_2O$ (40 mL) and extracted with EtOAc (3×30 mL). The combined organic layer was washed with saturated aq. $NH_4Cl$ (2×15 mL), water (2×15 mL), brine (15 mL), dried over $Na_2SO_4$, filtered and concentrated. The residue was purified by column chromatography on silica gel (25-70% EtOAc in petroleum ether) to provide diethyl 2-(((3aR,5R,6R,6aR)-6-acetoxy-6-ethynyl-2,2-dimethyltetrahydrofuro[2,3-d][1,3]dioxol-5-yl)methoxy)-2-(4-(3-(2-acetoxyethyl)-2-oxotetrahydropyrimidin-1(2H)-yl)benzyl)malonate (2.20 g, 68% yield) as a yellow gum.

Step 7:

To a solution of diethyl 2-(((3aR,5R,6R,6aR)-6-acetoxy-6-ethynyl-2,2-dimethyl-tetrahydrofuro[2,3-d][1,3]dioxol-5-yl)methoxy)-2-(4-(3-(2-acetoxyethyl)-2-oxotetrahydro-pyrimidin-1(2H)-yl)benzyl)malonate (2.20 g, 3.19 mmol, 1 eq) in DCM (7.5 mL) was added TFA (7.5 mL, 101.30 mmol, 32 eq) and $H_2O$ (1.5 mL). The mixture was stirred at 25° C. for 16 h before it was diluted with water (20 mL), Then the pH of the mixture was adjusted to 7-8 with $NaHCO_3$ solid. Then the mixture was extracted with $CH_2Cl_2$ (4×20 mL). Then the organic phase was washed with brine (10 mL), dried over anhydrous $Na_2SO_4$, filtered and concentrated to provide crude diethyl 2-(((2R,3S,4R)-3-acetoxy-3-ethynyl-4,5-dihydroxy-tetrahydrofuran-2-yl)methoxy)-2-(4-(3-(2-acetoxyethyl)-2-oxotetrahydropyrimidin-1(2H)-yl)benzyl)malonate (2.1 g) as a yellow gum.

To a solution of the above crude product (2.1 g, 3.19 mmol, 1 eq) in DCM (15 mL) was added $Ac_2O$ (1.79 mL, 19.14 mmol, 6 eq), pyridine (2.06 mL, 25.52 mmol, 8 eq) and 4-DMAP (38.97 mg, 319.00 umol, 0.1 eq). The mixture was stirred at 25° C. for 2 h before it was diluted with EtOAc (100 mL), sequentially washed with 1N aq. HCl (2×30 mL). The organic layer was washed with water (20 mL), saturated aq. $NaHCO_3$ solution (2×20 mL), water (20 mL), and brine (10 mL). The organic layer was dried over $MgSO_4$ and concentrated to provide crude diethyl 2-(4-(3-(2-acetoxyethyl)-2-oxotetrahydropyrimidin-1 (2H)-yl)benzyl)-2-(((2R,3R,4R)-3,4,5-triacetoxy-3-ethynyltetrahydrofuran-2-yl)methoxy)-malonate (2.3 g) as a yellow foam.

Step 8:

To a solution of 2-chloro-N-methyl-9H-purin-6-amine (151.59 mg, 825.68 umol, 1.1 eq) in MeCN (3 mL) was added BSA (408.19 uL, 1.65 mmol, 2.2 eq). The mixture was stirred at 65° C. for 0.5 h before it was cooled to 0° C. and followed by addition of diethyl 2-(4-(3-(2-acetoxyethyl)-2-oxotetrahydropyrimidin-1 (2H)-yl)benzyl)-2-(((2R,3R,4R)-3,4,5-triacetoxy-3-ethynyltetrahydrofuran-2-yl)methoxy)malonate (550 mg, crude) in MeCN (3 mL) and TMSOTf (406.91 uL, 2.25 mmol, 3 eq). The mixture was stirred at 65° C. for 3 h before it was allowed to cool to 25° C. and quenched with saturated aq. $NaHCO_3$ (20 mL). The reaction mixture was extracted with EtOAc (4×20 mL). The combined organic layer was washed with water (10 mL), brine (10 mL), dried over $Na_2SO_4$, filtered and concentrated. The crude residue was purified by flash column chromatography on silica gel (30-70% EtOAc in petroleum ether) first and then further purified by preparative TLC (7% MeOH in DCM) to provide diethyl 2-(4-(3-(2-acetoxyethyl)-2-oxotetrahydropyrimidin-1 (2H)-yl)benzyl)-2-(((2R,3R,4R,5R)-3,4-diacetoxy-5-(2-chloro-6-(methylamino)-9H-purin-9-yl)-3-ethynyltetrahydrofuran-2-yl)methoxy)malonate (180 mg, 22% yield) as a foam.

Step 9:

To a solution of diethyl 2-(4-(3-(2-acetoxyethyl)-2-oxotetrahydropyrimidin-1(2H)-yl)benzyl)-2-(((2R,3R,4R,5R)-3,4-diacetoxy-5-(2-chloro-6-(methylamino)-9H-purin-9-yl)-3-ethynyltetrahydrofuran-2-yl)methoxy)malonate (180 mg, 210.21 umol, 1 eq) in THF (1 mL) was added saturated aq. LiOH solution (1.5 mL). The mixture was stirred at 50° C. for 2 h before the organic volatile was removed under reduced pressure. The pH of the mixture was adjusted to 2-3 with 6N aq. HCl solution and then concentrated. The crude residue was purified by preparative HPLC (column: YMC-Actus ODS-AQ 150*30 5 u; mobile phase: [water (0.225% FA)-ACN]; B %: 15%-35%,15 min) to provide 2-(((2R,3S,4R,5R)-5-(2-chloro-6-(methylamino)-9H-purin-9-yl)-3-ethynyl-3,4-dihydroxytetrahydrofuran-2-yl)methoxy)-2-(4-(3-(2-hydroxyethyl)-2-oxotetrahydropyrimidin-1 (2H)-yl)benzyl)malonic acid (71.8 mg, 50% yield) as a white solid.

$^1$H NMR (400 MHz, $CD_3OD$) δ ppm 8.14 (s, 1H), 7.27 (d, J=8.0 Hz, 2H), 6.98 (d, J=8.0 Hz, 2H), 5.96 (d, J=7.5 Hz, 1H), 4.76 (d, J=7.4 Hz, 1H), 4.26 (br s, 1H), 4.04 (s, 2H), 3.66 (t, J=5.6 Hz, 2H), 3.36-3.55 (m, 8H), 3.05 (m, 4H), 1.96-2.04 (m, 2H); LC/MS [M+H]=674.1.

Example 138

Synthesis of 2-((((2R,3S,4R,5R)-5-(2-chloro-6-((cyclopropylmethyl)amino)-9H-purin-9-yl)-3-ethynyl-3,4-dihydroxytetrahydrofuran-2-yl)methoxy)-2-(4-(3-(2-hydroxyethyl)-2-oxotetrahydropyrimidin-1(2H)-yl)benzyl)malonic acid

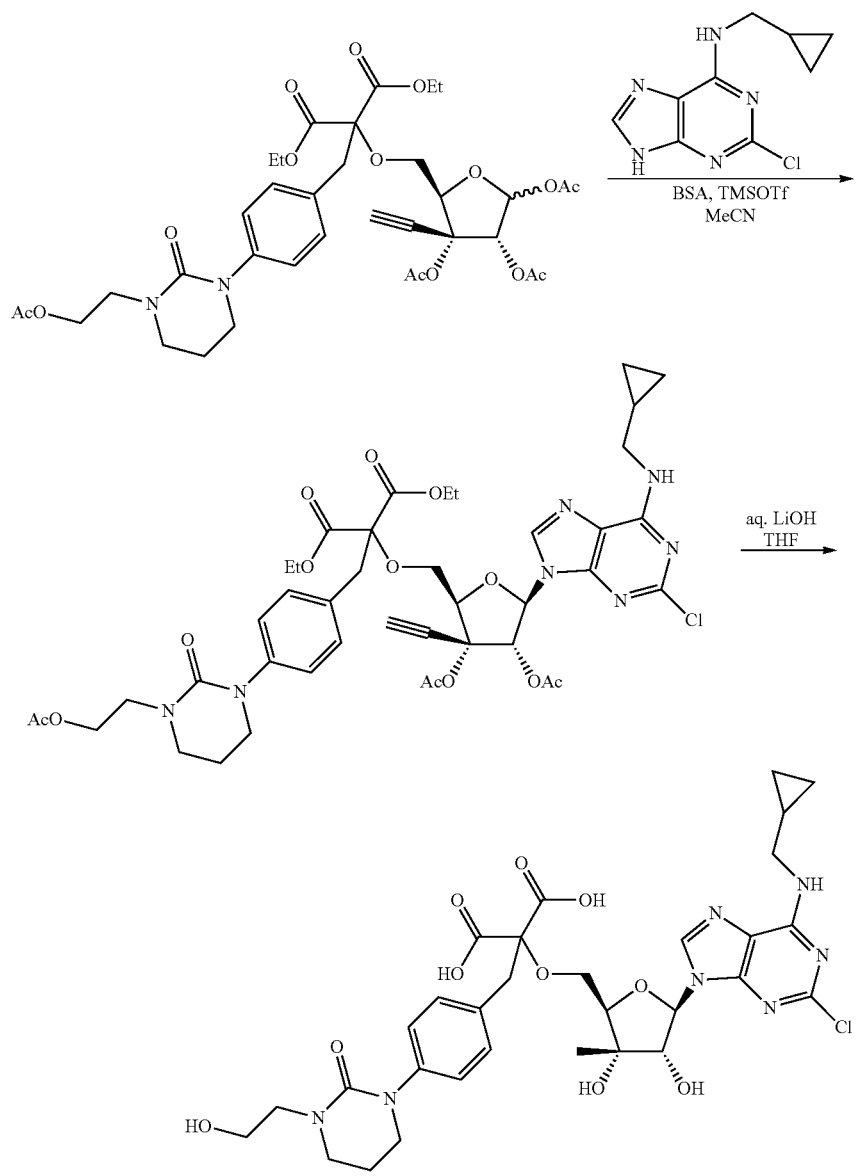

Example 138

Proceeding as described in Example 137 above but substituting 2-chloro-N-methyl-9H-purin-6-amine with 2-chloro-N-(cyclopropylmethyl)-9H-purin-6-amine provided the title compound as a white solid.

$^1$H NMR (400 MHz, CD$_3$OD) δ ppm 8.09 (s, 1H), 7.28 (d, J=8.3 Hz, 2H), 7.01 (d, J=8.3 Hz, 2H), 5.96 (d, J=7.5 Hz, 1H), 4.74 (d, J=7.3 Hz, 1H), 4.26 (t, J=2.8 Hz, 1H), 4.04 (d, J=2.3 Hz, 2H), 3.62-3.69 (m, 2H), 3.45-3.54 (m, 4H), 3.34-3.42 (m, 6H), 3.06 (s, 1H) 1.97-2.05 (m, 2H), 1.09-1.21 (m, 1H), 0.52-0.61 (m, 2H), 0.34 (q, J=4.8 Hz, 2H); LC/MS [M+H]=714.1.

Example 139

Synthesis of 2-(((2R,3S,4R,5R)-5-(2-chloro-6-(isopropylamino)-9H-purin-9-yl)-3-ethynyl-3,4-dihydroxytetrahydrofuran-2-yl)methoxy)-2-(4-(3-(2-hydroxyethyl)-2-oxotetrahydropyrimidin-1(2H)-yl)benzyl)malonic acid

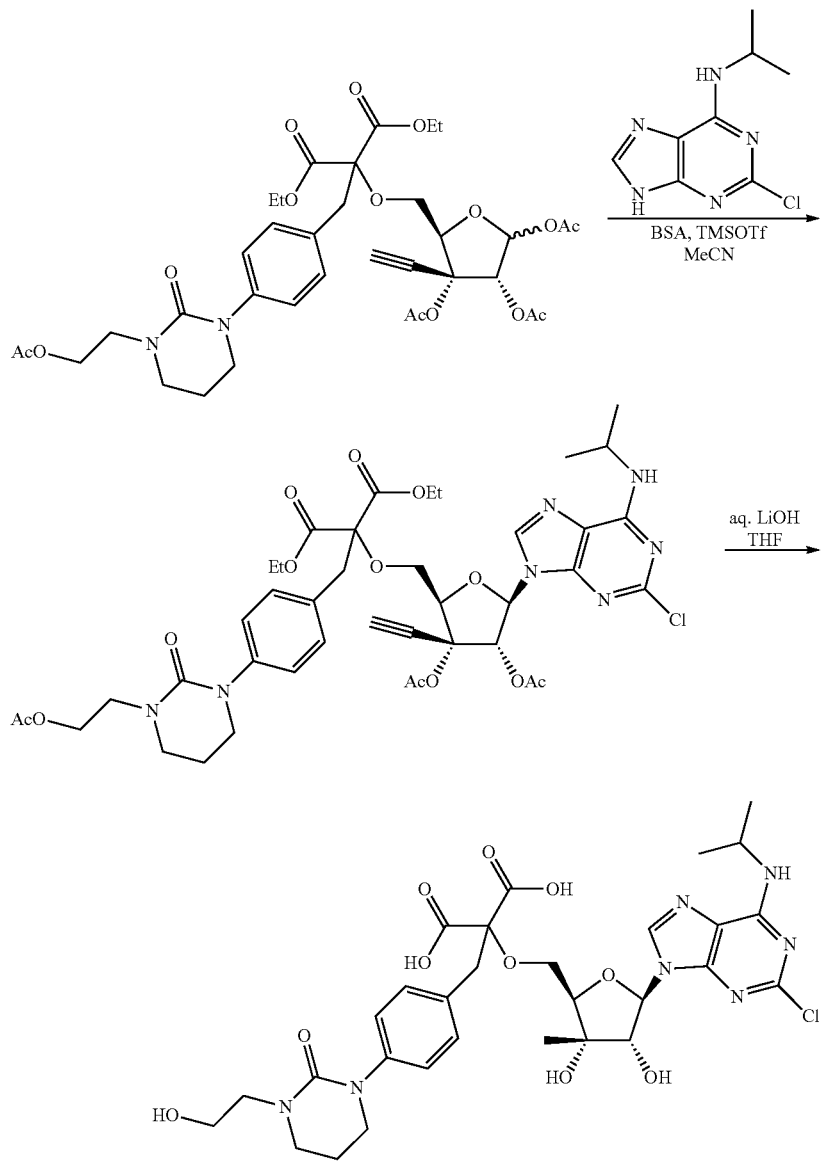

Example 139

Proceeding as described in Example 137 above but substituting 2-chloro-N-methyl-9H-purin-6-amine with 2-chloro-N-isopropyl-9H-purin-6-amine provided the title compound as a white solid.

$^1$H NMR (400 MHz, CD$_3$OD) δ ppm 8.08 (s, 1H), 7.29 (d, J=8.3 Hz, 2H), 7.02 (d, J=8.3 Hz, 2H), 5.95 (d, J=7.5 Hz, 1H), 4.73 (d, J=7.5 Hz, 1H), 4.39 (br s, 1H), 4.26 (t, J=2.5 Hz, 1H), 4.04 (d, J=2.0 Hz, 2H), 3.66 (t, J=5.8 Hz, 2H), 3.37-3.52 (m, 9H), 1.97-2.04 (m, 2H), 1.30 (d, J=6.3 Hz, 6H); LC/MS [M+H]=702.1.

Example 140

Synthesis of 2-(((2R,3S,4R,5R)-5-(2-chloro-6-(isopropylamino)-9H-purin-9-yl)-3-ethynyl-3,4-dihydroxytetrahydrofuran-2-yl)methoxy)-2-(4-(2-oxotetrahydropyrimidin-1(2H)-yl)benzyl)malonic acid

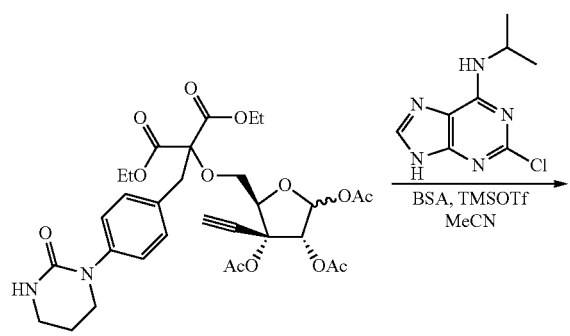

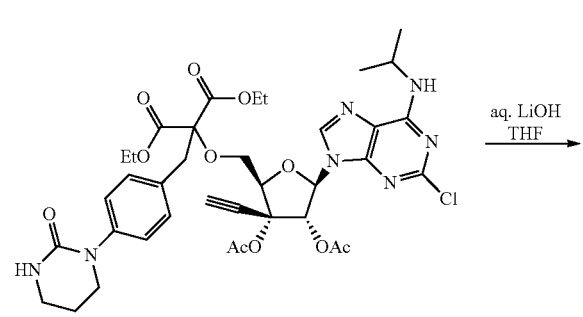

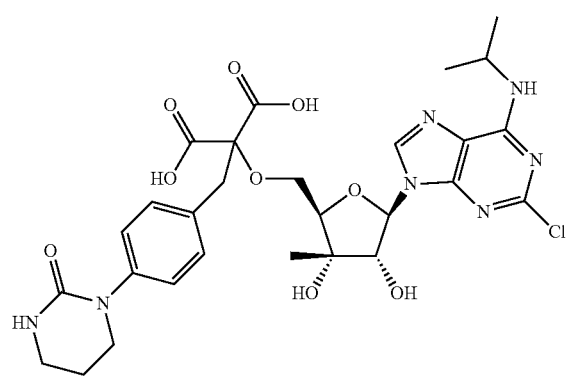

Example 140

Proceeding as described in Example 133 above but substituting thymine with 2-chloro-N-isopropyl-9H-purin-6-amine provided the title compound as a white solid.

¹H NMR (400 MHz, CD$_3$OD) δ ppm 8.16 (s, 1H) 7.32 (d, J=8.44 Hz, 2H) 7.08 (br d, J=8.31 Hz, 2H) 5.99 (d, J=7.46 Hz, 1H) 4.81 (d, J=7.46 Hz, 1H) 4.41 (br s, 1H) 4.26-4.31 (m, 1H) 3.97-4.12 (m, 2H) 3.40-3.57 (m, 4H), 3.33-3.37 (m, 2H), 3.03 (s, 1H), 1.99 (m, 2H), 1.31 (m, 6H); LC/MS [M+H]=658.3.

Example 141

Synthesis of 2-(((2R,3S,4R,5R)-5-(2-chloro-6-(methylamino)-9H-purin-9-yl)-3-ethynyl-3,4-dihydroxytetrahydrofuran-2-yl)methoxy)-2-(4-(2-oxotetrahydropyrimidin-1 (2H)-yl)benzyl)malonic acid

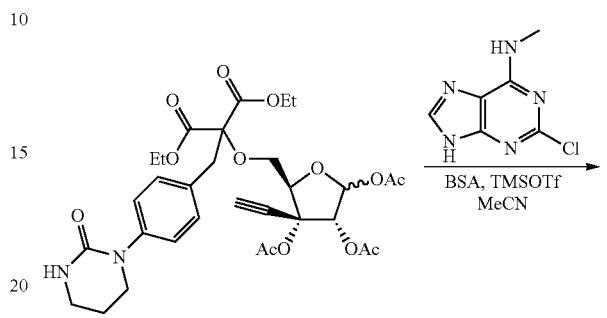

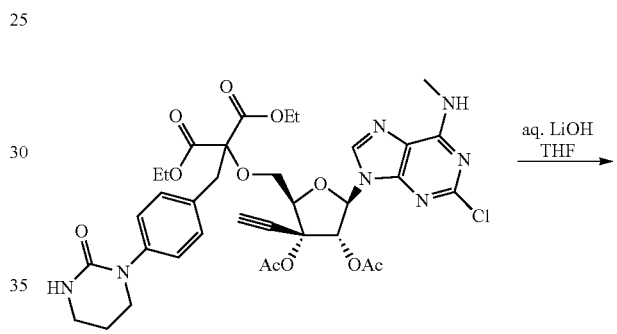

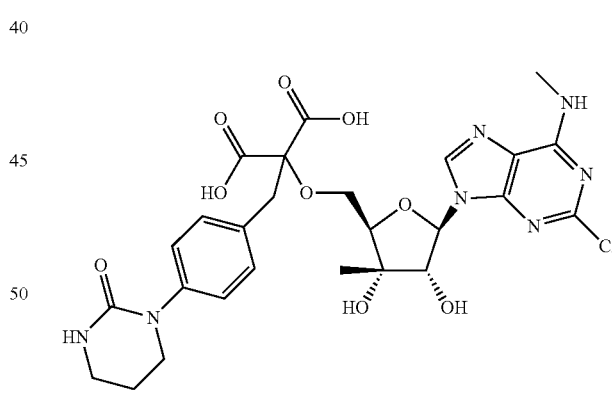

Example 141

Proceeding as described in Example 133 above but substituting thymine with 2-chloro-N-methyl-9H-purin-6-amine provided the title compound as a white solid.

¹H NMR (400 MHz, CD$_3$OD) δ ppm 8.20 (s, 1H), 7.27 (d, J=8.13 Hz, 2H), 7.00 (d, J=8.00 Hz, 2H), 5.97 (d, J=7.38 Hz, 1H), 4.80 (d, J=7.38 Hz, 1H), 4.27 (s, 1H), 4.04 (m, 2H), 3.37-3.50 (m, 4H), 3.31 (d, J=1.13 Hz, 3H), 3.06 (s, 2H) 3.04 (s, 1H), 1.90-2.00 (m, 2H); LC/MS [M+H]=630.2.

Example 142

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(thiazol-2-ylmethyl)malonic acid

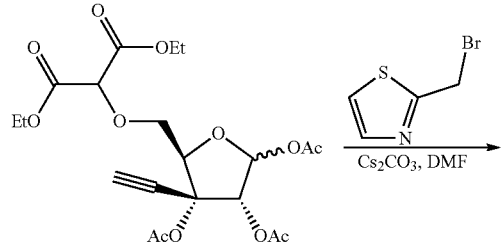

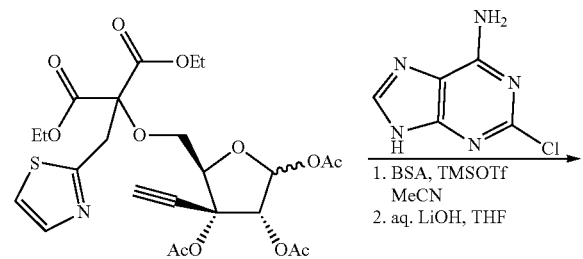

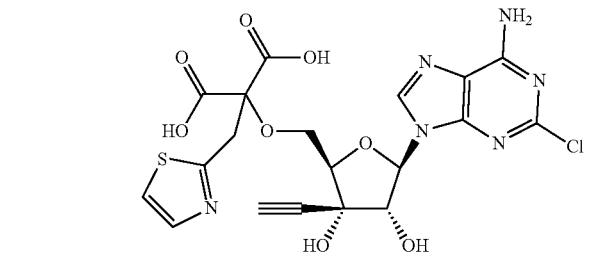

Example 142

Proceeding as described in Example 15 above but substituting allyl bromide with 2-(bromomethyl)thiazole provided the title compound as a white solid.

$^1$H NMR (400 MHz, CD$_3$OD) δ ppm 8.56 (s, 1H), 7.56 (d, J=3.4 Hz, 1H), 7.33 (d, J=3.4 Hz, 1H), 6.00 (d, J=5.6 Hz, 1H), 4.68-4.73 (m, 1H), 4.38 (dd, J=6.3, 3.4 Hz, 1H), 3.98-4.07 (m, 2H), 3.85 (s, 2H), 3.00 (s, 1H); LC/MS [M+H]=524.9.

Example 143

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(thiazol-5-ylmethyl)malonic acid

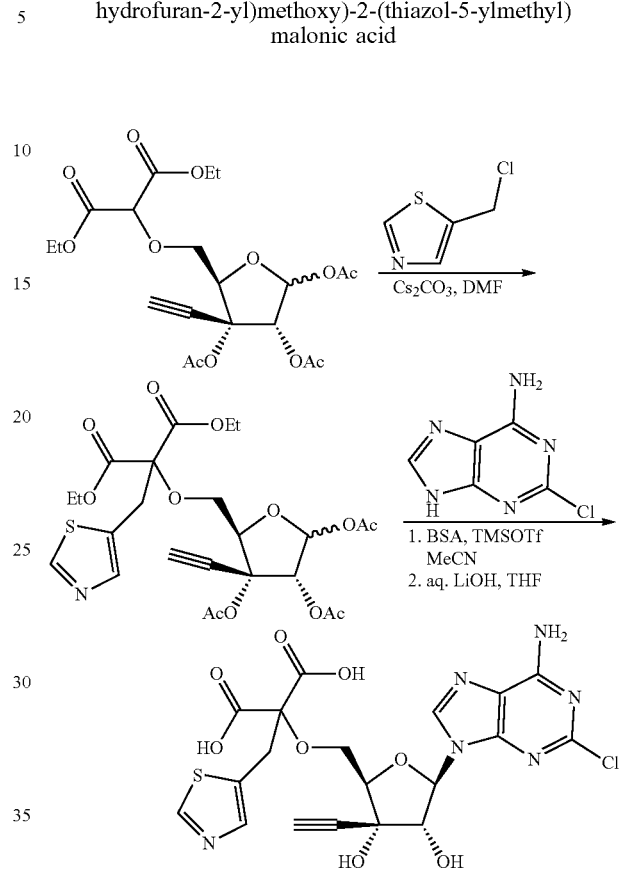

Example 143

Proceeding as described in Example 15 above but substituting allyl bromide with 5-(chloromethyl)thiazole provided the title compound as a white solid.

$^1$H NMR (400 MHz, CD$_3$OD) δ ppm 8.75 (s, 1H), 8.47 (s, 1H), 7.72 (s, 1H), 6.03 (d, J=7.3 Hz, 1H), 4.97 (d, J=7.3 Hz, 1H), 4.36 (dd, J=4.3, 3.0 Hz, 1H), 4.12-4.18 (m, 1H), 4.04-4.10 (m, 1H), 3.63-3.79 (m, 2H), 3.00 (s, 1H); LC/MS [M+H]=524.9.

Example 144

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(pyrrolidin-1-yl)benzyl)malonic acid

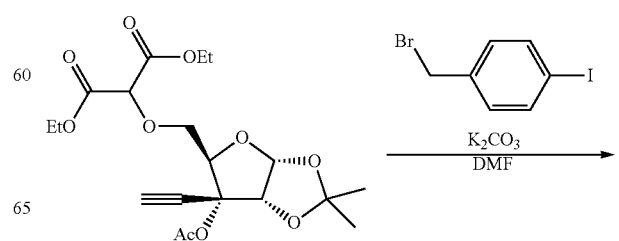

-continued

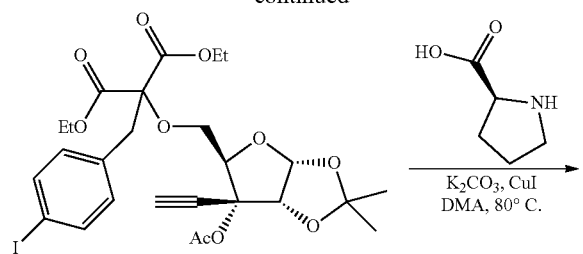

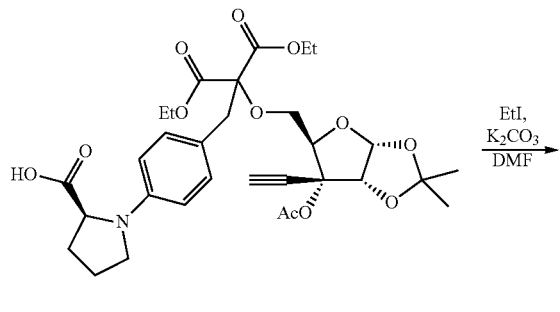

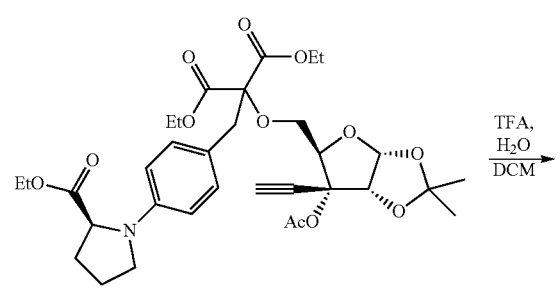

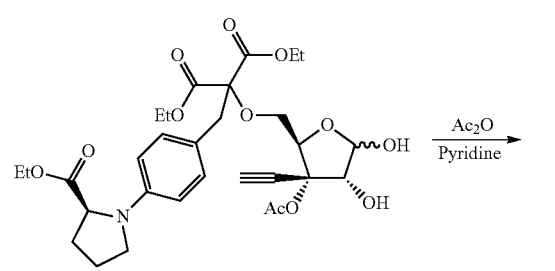

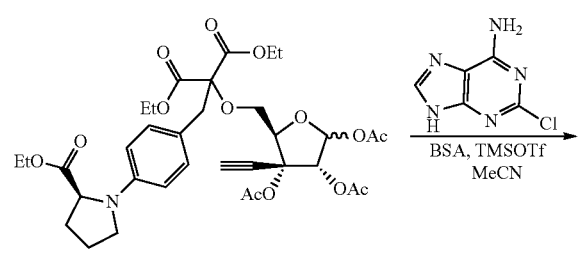

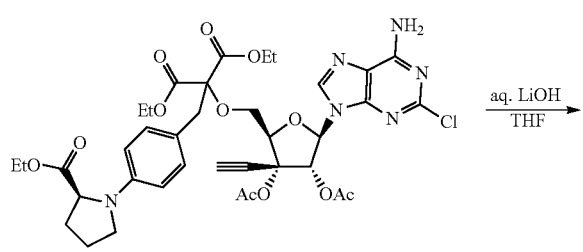

-continued

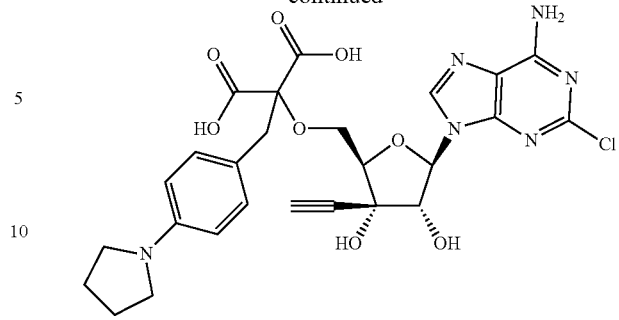

Example 144

Step 1:
To a solution of diethyl 2-(((3aR,5R,6R,6aR)-6-acetoxy-6-ethynyl-2,2-dimethyltetra-hydrofuro[2,3-d][1,3]dioxol-5-yl)methoxy)malonate (10.0 g, 24.13 mmol, 1 eq) in DMF (100 mL) was added $Cs_2CO_3$ (23.59 g, 72.39 mmol, 3 eq) and 1-(bromomethyl)-4-iodo-benzene (10.75 g, 36.20 mmol, 1.5 eq). The suspension was stirred at 20° C. for 1 h before it was diluted with water (200 mL). The resulting mixture was extracted with EtOAc (4×50 mL). The combined organic layer was washed with water (2×200 mL), brine (200 mL), dried over anhydrous $Na_2SO_4$, filtered and concentrated. The crude residue was purified by flash column chromatography on silica gel (5-20% of EtOAc in petroleum ether) to provide diethyl 2-(((3aR,5R,6R,6aR)-6-acetoxy-6-ethynyl-2,2-dimethyltetrahydrofuro[2,3-d][1,3]-dioxol-5-yl)methoxy)-2-(4-iodobenzyl)malonate (11.83 g, 74% yield) as a white solid as a white solid.

Step 2:
To a solution of diethyl 2-(((3aR,5R,6R,6aR)-6-acetoxy-6-ethynyl-2,2-dimethyltetra-hydrofuro[2,3-d][1,3]dioxol-5-yl)methoxy)-2-(4-iodobenzyl)malonate (2.00 g, 3.17 mmol, 1 eq) in DMA (22 mL) was added $K_2CO_3$ (1.32 g, 9.52 mmol, 3 eq), CuI (120.84 mg, 634.50 umol, 0.2 eq) and proline (438.30 mg, 3.81 mmol, 1.2 eq). The green suspension was stirred at 80° C. under $N_2$ atmosphere for 16 h before it was allowed to cool and poured into water (40 mL) and 2N aq. LiOH (1 mL). The mixture was extracted with ethyl acetate (2×30 mL). The resulting aq. layer was acidified to pH 5 with 1N aq. HCl solution and then extracted with ethyl acetate (2×40 mL). The combined organic layer was washed with water (80 mL), brine (80 mL), dried over $Na_2SO_4$, filtered and concentrated to give crude (S)-1-(4-(2-(((3aR,5R,6R,6aR)-6-acetoxy-6-ethynyl-2,2-dimethyl-tetrahydrofuro[2,3-d][1,3]dioxol-5-yl)methoxy)-3-ethoxy-2-(ethoxycarbonyl)-3-oxopropyl)phenyl)pyrrolidine-2-carboxylic acid (390 mg) as a yellow gum.

Step 3:
To a solution of crude (S)-1-(4-(2-(((3aR,5R,6R,6aR)-6-acetoxy-6-ethynyl-2,2-dimethyltetrahydrofuro[2,3-d][1,3]dioxol-5-yl)methoxy)-3-ethoxy-2-(ethoxycarbonyl)-3-oxopropyl)phenyl)pyrrolidine-2-carboxylic acid (420 mg, 680.01 umol, 1 eq) in DMF (5 mL) was added $K_2CO_3$ (282 mg, 2.04 mmol, 3 eq) and EtI (81.58 uL, 1.02 mmol, 1.5 eq). The mixture was stirred at 20° C. for 0.5 h before it was diluted with water (10 mL), and extracted with ethyl acetate (2×10 mL). The combined organic layer was washed with water (20 mL), brine (20 mL), dried over $Na_2SO_4$, and filtered and concentrated to give crude diethyl 2-(((3aR,5R,6R,6aR)-6-acetoxy-6-ethynyl-2,2-dimethyltetrahydrofuro

[2,3-d][1,3]dioxol-5-yl)methoxy)-2-(4-((S)-2-(ethoxycarbonyl)pyrrolidin-1-yl)benzyl)malonate (330 mg) as a yellow foam.

Step 4:

To a solution of crude diethyl 2-(((3aR,5R,6R,6aR)-6-acetoxy-6-ethynyl-2,2-dimethyltetrahydrofuro[2,3-d][1,3]dioxol-5-yl)methoxy)-2-(4-((S)-2-(ethoxycarbonyl)pyrrolidin-1-yl)benzyl)malonate (330 mg, crude) in DCM (4 mL) was added H$_2$O (0.8 mL) and TFA (4 mL) at 0° C. The solution was stirred at 20° C. for 4.5 h before it was quenched with saturated aq. NaHCO$_3$ to adjust the pH to 9. The mixture was extracted with ethyl acetate (2×8 mL). The combined organic layer was washed with brine (20 mL), dried over Na$_2$SO$_4$, filtered and concentrated to crude diethyl 2-(((2R,3S,4R)-3-acetoxy-3-ethynyl-4,5-dihydroxytetrahydrofuran-2-yl)methoxy)-2-(4-((S)-2-(ethoxycarbonyl)pyrrolidin-1-yl)benzyl)malonate (285 mg) as a yellow foam.

Step 5:

To a solution of crude diethyl 2-(((2R,3S,4R)-3-acetoxy-3-ethynyl-4,5-dihydroxytetra-hydrofuran-2-yl)methoxy)-2-(4-((S)-2-(ethoxycarbonyl)pyrrolidin-1-yl)benzyl)malonate (285 mg) in pyridine (4 mL) was added 4-DMAP (172 mg, 1.41 mmol, 3 eq) and Ac$_2$O (352.60 uL, 3.76 mmol, 8 eq). The solution was stirred at 20° C. for 16 h before it was diluted with water (10 mL), and extracted with ethyl acetate (3×10 mL). The combined organic layer was washed with brine (20 mL), dried by Na$_2$SO$_4$, filtered and concentrated. The crude residue was purified by flash column chromatography on silica gel (20-50% of ethyl acetate in petrol ether) to give diethyl 2-(4-((S)-2-(ethoxycarbonyl)pyrolidin-1-yl)benzyl)-2-(((2R,3R,4R)-3,4,5-triacetoxy-3-ethynyltetrahydrofuran-2-yl)methoxy)-malonate (220 mg, 51% yield for four steps) as a yellow gum.

Step 6:

To a suspension of diethyl 2-(4-((S)-2-(ethoxycarbonyl)pyrrolidin-1-yl)benzyl)-2-(((2R,3R,4R)-3,4,5-triacetoxy-3-ethynyltetrahydrofuran-2-yl)methoxy)malonate (50 mg, 72.50 umol, 1 eq) and 6-chloropurine (15 mg, 86.99 umol, 1.2 eq) in MeCN (1 mL) was added BSA (44.80 uL, 181.24 umol, 2.5 eq). The suspension was stirred at 65° C. for 0.5 h before it was cooled down to 0° C. and followed by addition of TMSOTf (32.75 uL, 181.24 umol, 2.5 eq). The mixture was stirred at 65° C. for 1 h before it was poured into saturated aq. NaHCO$_3$ (3 mL). The reaction mixture was extracted with ethyl acetate (3×3 mL). The combined organic layer was concentrated. The crude residue was purified by preparative TLC (petroleum ether:EtOAc=2:1) to give diethyl 2-(((2R,3R,4R,5R)-3,4-diacetoxy-5-(6-amino-2-chloro-9H-purin-9-yl)-3-ethynyltetrahydrofuran-2-yl)methoxy)-2-(4-((S)-2-(ethoxy-carbonyl)pyrrolidin-1-yl)benzyl)malonate (33 mg, 57% yield) as a yellow gum.

Step 7:

To a solution of diethyl 2-(((2R,3R,4R,5R)-3,4-diacetoxy-5-(6-amino-2-chloro-9H-purin-9-yl)-3-ethynyltetrahydrofuran-2-yl)methoxy)-2-(4-((S)-2-(ethoxycarbonyl)pyrrolidin-1-yl)benzyl)malonate (28 mg, 35.03 umol, 1 eq) in THF (2 mL) was added 1M aq. LiOH (701 uL, 20 eq). The mixture was stirred at 20° C. for 4.5 h before the organic volatile was removed under reduced pressure. The aq. layer was acidified to pH 6 with 1N aq. HCl solution before it was concentrated. The crude residue was purified by preparative HPLC (Column: YMC-Triart Prep C18 150*40 mm*7 um; mobile phase: [water (0.225% FA)-ACN]; B %: 15%-35%, 10 min.) and dried by lyophilization to provide 2-(((2R,3S,4R,5R)-5-(6-amino-2-chloro-9H-purin-9-yl)-3-ethynyl-3,4-dihydroxytetrahydrofuran-2-yl)methoxy)-2-(4-(pyrrolidin-1-yl)benzyl)malonic acid (2.6 mg) as a white solid.

$^1$H NMR (400 MHz, CD$_3$OD) δ ppm 8.21 (s, 1H), 7.05 (d, J=8.53 Hz, 2H), 6.26 (d, J=8.53 Hz, 2H), 5.98 (d, J=7.53 Hz, 1H), 4.92-5.02 (m, 1H), 4.29-4.33 (m, 1H), 4.09 (dd, J=10.16, 2.38 Hz, 1H), 3.97 (dd, J=10.04, 3.01 Hz, 1H), 3.38 (d, J=14.56 Hz, 1H), 3.23 (d, J=14.56 Hz, 1H), 3.02-3.09 (m, 4H), 3.00 (s, 1H), 1.89-1.97 (m, 4H); LC/MS [M+H]=587.1.

Example 145

Synthesis of 2-(((2R,3S,4R,5R)-5-(6-amino-2-(ethylthio)-9H-purin-9-yl)-3-ethynyl-3,4-dihydroxytetrahydrofuran-2-yl)methoxy)-2-benzylmalonic acid

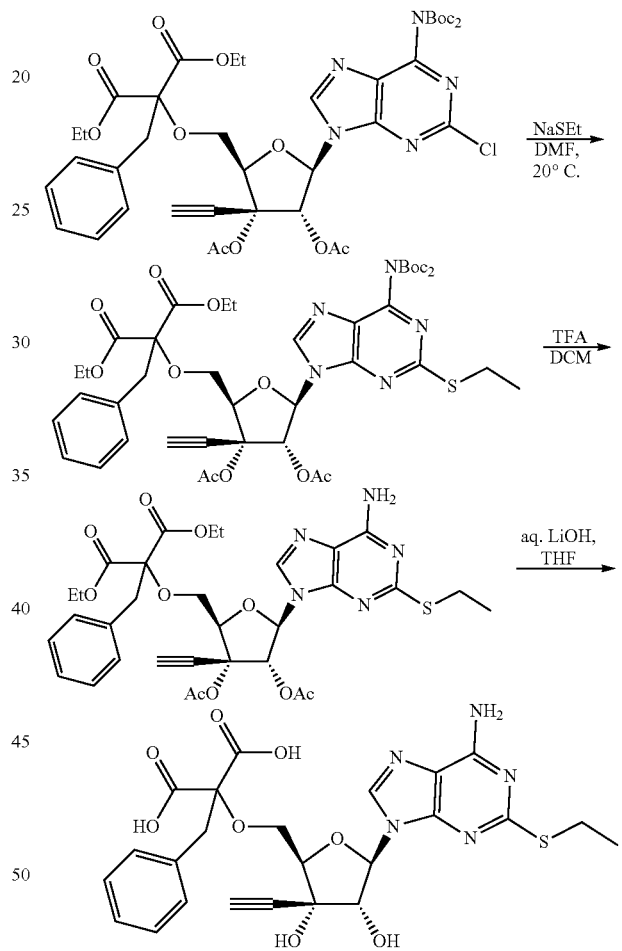

Example 145

Step 1:

To a mixture of diethyl 2-benzyl-2-(((2R,3R,4R,5R)-3,4-diacetoxy-5-(6-(bis-(tert-butoxycarbonyl)amino)-2-chloro-9H-purin-9-yl)-3-ethynyltetrahydrofuran-2-yl)methoxy)-malonate (300 mg, 349.53 umol, 1 eq) in DMF (3 mL) was added NaSEt (88.20 mg, 1.05 mmol, 3 eq). The mixture was stirred at 20° C. for 20 h before it was partitioned between water (15 mL) and EtOAc (15 mL). The aqueous phase was extracted with EtOAc (2×10 mL). The combined organic layer was washed with brine (10 mL), dried over anhydrous Na$_2$SO$_4$, and filtered and concentrated under reduced pressure to to provide crude diethyl 2-benzyl-2-(((2R,3R,4R,5R)-3,4-diacetoxy-5-(6-amino-2-(ethylthio)-9H-purin-9-yl)-3-ethynyl-tetrahydrofuran-2-yl)methoxy)malonate (310 mg) as an oil which was used for next step without further purification.

Step 2:

To a mixture of crude diethyl 2-benzyl-2-(((2R,3R,4R,5R)-3,4-diacetoxy-5-(6-amino-2-(ethylthio)-9H-purin-9-yl)-3-ethynyltetrahydrofuran-2-yl)methoxy)malonate (310 mg) in DCM (3 mL) was added TFA (1.5 mL, 20.26 mmol). The mixture was stirred at 20° C. for 2 h before it was neutralized to pH 7-8 with saturated aq. NaHCO$_3$. The reaction mixture was extracted with EtOAc (3×20 mL). The combined extract was washed with brine (15 mL), dried over anhydrous Na$_2$SO$_4$, filtered and concentrated under reduced pressure to provide crude diethyl 2-benzyl-2-(((2R,3R,4R,5R)-3,4-diacetoxy-5-(6-amino-2-(ethylthio)-9H-purin-9-yl)-3-ethynyltetrahydrofuran-2-yl)methoxy)malonate as a foam.

Step 3:

To a mixture of crude diethyl 2-benzyl-2-(((2R,3R,4R,5R)-3,4-diacetoxy-5-(6-amino-2-(ethylthio)-9H-purin-9-yl)-3-ethynyltetrahydrofuran-2-yl)methoxy)malonate (280 mg, crude) in THF (3 mL) was added saturated aq. LiOH (3 mL). The mixture was stirred at 55° C. for 1 h before it was cooled to room temperature. The reaction mixture was extracted with EtOAc (3×8 mL). The aqueous phase was adjusted to pH 2-3 with 2M aq. HCl before it was extracted with EtOAc (4×10 mL), dried over anhydrous Na$_2$SO$_4$, filtered and concentrated. The crude product was purified by preparative HPLC (column: YMC-Triart Prep C18 150*40 mm*7 um; mobile phase: [water (0.225% FA)-ACN]; B %: 23%-43%,11 min) and dried by lyophilization to give 2-(((2R,3S,4R,5R)-5-(6-amino-2-(ethylthio)-9H-purin-9-yl)-3-ethynyl-3,4-dihydroxytetrahydrofuran-2-yl)methoxy)-2-benzylmalonic acid (4.4 mg) as a white powder.

$^1$H NMR (400 MHz, DMSO-d$_6$) δ ppm 12.59-14.32 (m, 2H), 8.30 (s, 1H), 7.33 (s, 2H), 7.00-7.21 (m, 5H), 6.15 (s, 1H), 6.00 (d, J=6.78 Hz, 1H), 5.82 (d, J=7.53 Hz, 1H), 5.01 (s, 1H), 4.14 (dd, J=6.40, 2.64 Hz, 1H), 3.99 (d, J=13.05 Hz, 1H), 3.83 (s, 1H), 3.58 (s, 1H), 3.17-3.18 (m, 2H), 2.99-3.13 (m, 2H), 1.31 (t, J=7.28 Hz, 3H); LC/MS [M+H]=544.0.

Example 146

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(1-(2-methoxyethyl)-2-oxo-1,2-dihydropyridin-3-yl)benzyl)malonic acid

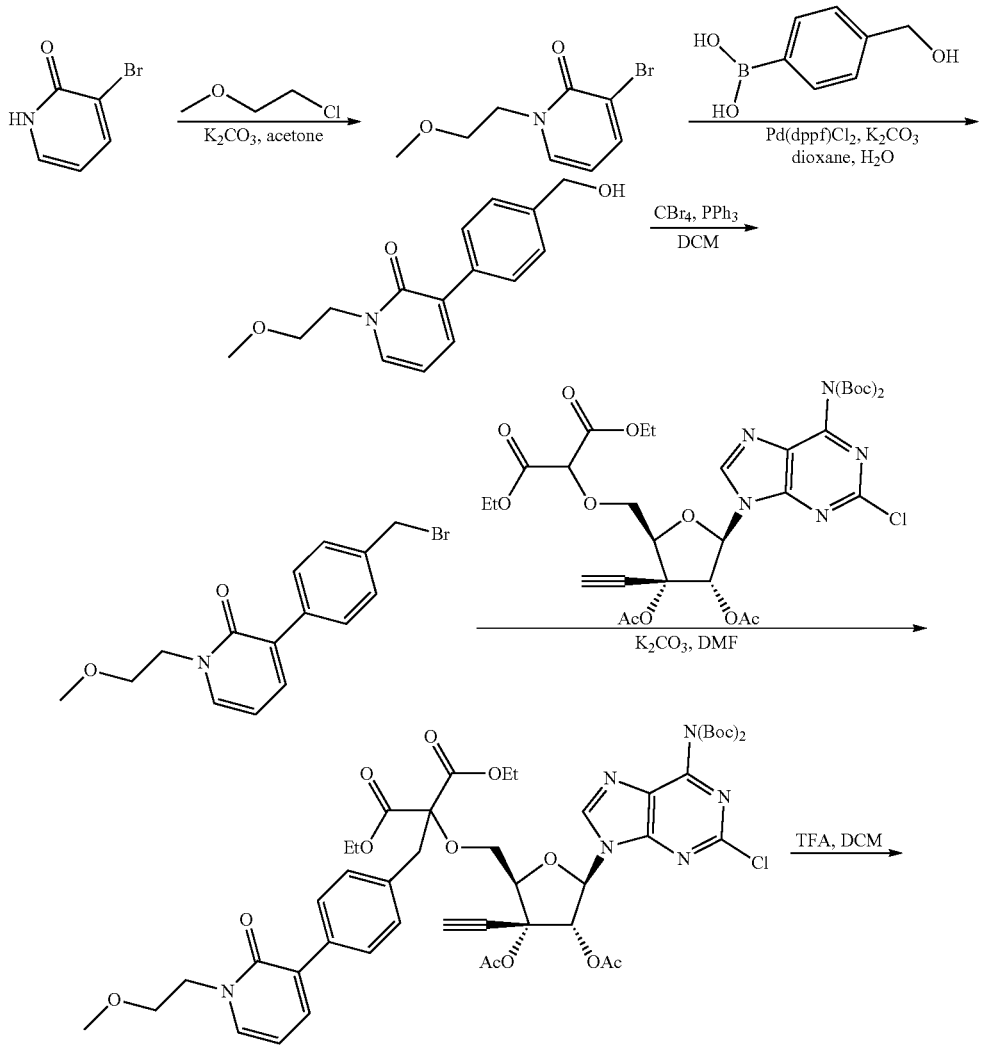

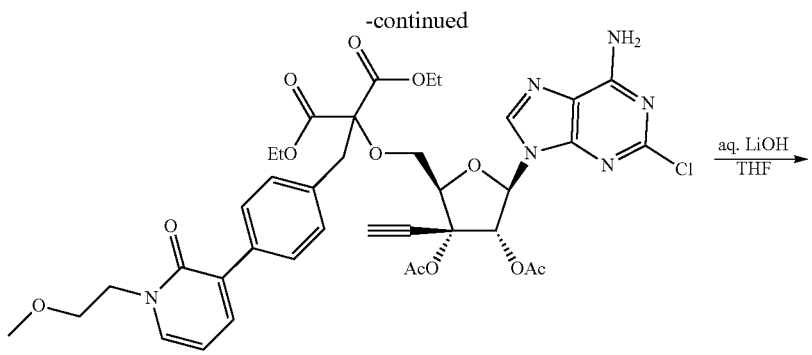

aq. LiOH / THF

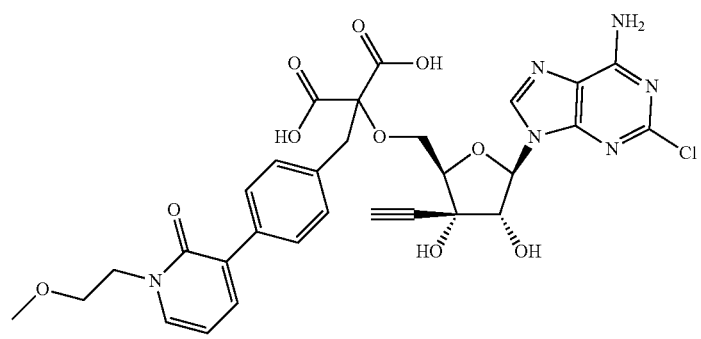

Example 146

Proceeding as described in Example 11 above but substituting chloro(methoxy)-methane with 1-chloro-2-methoxyethane provided the title compound as a white solid.

$^{1}$H NMR (400 MHz, DMSO-d$_{6}$) δ ppm 8.41 (s, 1H), 7.80 (s, 2H), 7.60 (dd, J=6.78, 2.01 Hz, 1H), 7.46 (dd, J=7.03, 2.01 Hz, 1H), 7.35 (d, J=8.28 Hz, 2H), 7.21 (d, J=8.28 Hz, 2H), 7.19-7.24 (m, 1H), 6.26-6.31 (m, 1H), 5.82 (d, J=7.78 Hz, 1H) 4.86 (d, J=7.78 Hz, 1H), 4.17 (d, J=1.76 Hz, 1H), 4.10 (t, J=5.14 Hz, 2H), 4.02 (dd, J=10.29, 4.77 Hz, 1H), 3.78-3.85 (m, 1H), 3.54-3.64 (m, 3H), 3.29 (d, J=2.01 Hz, 2H), 3.24 (s, 3H); LC/MS [M+H]=669.0.

Example 147

Synthesis of 2-(((2R,3S,4R,5R)-5-(2-chloro-6-(methylamino)-9H-purin-9-yl)-3-ethynyl-3,4-dihydroxytetrahydrofuran-2-yl)methoxy)-2-(4-(2-oxo-1,2-dihydropyridin-3-yl)benzyl)malonic acid

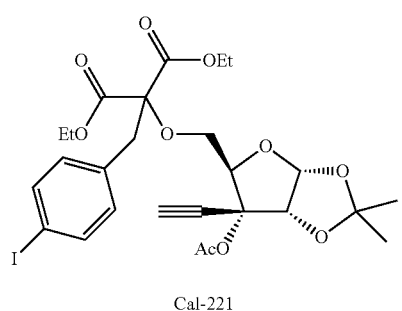

Cal-221

TFA/DCM/H$_2$O →

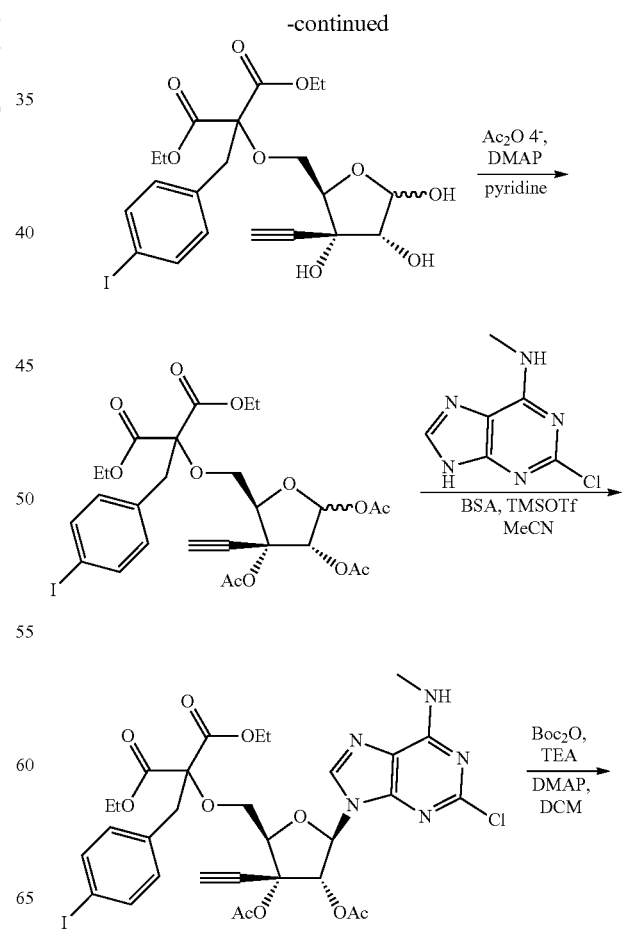

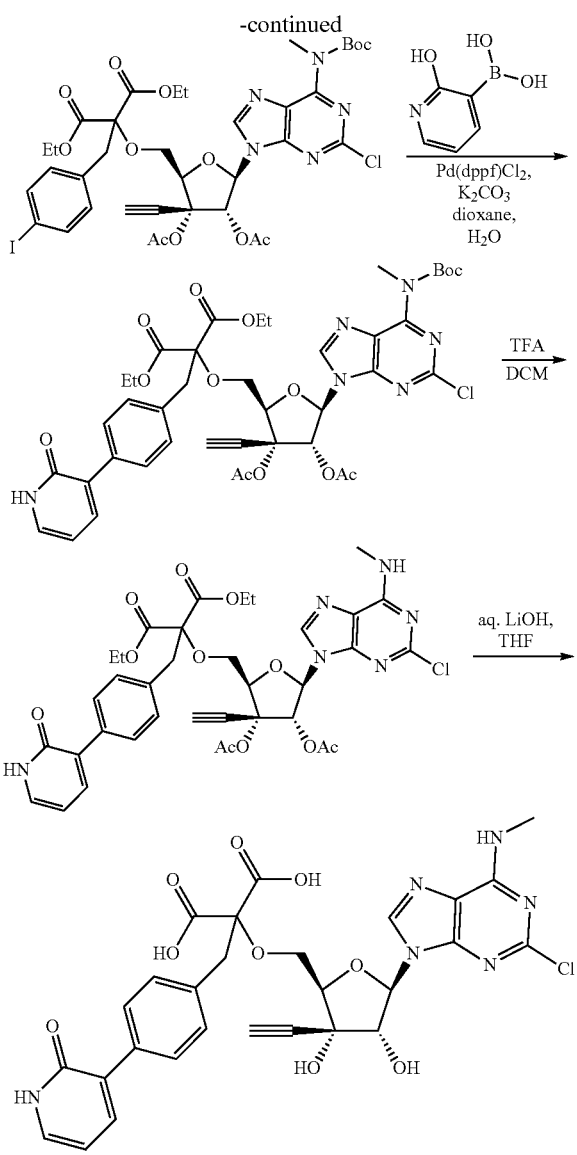

Example 147

Step 1:

To a solution of diethyl 2-(((3aR,5R,6R,6aR)-6-acetoxy-6-ethynyl-2,2-dimethyltetra-hydrofuro[2,3-d][1,3]dioxol-5-yl)methoxy)-2-(4-iodobenzyl)malonate (2.0 g, 3.17 mmol, 1 eq) in DCM (15 mL) was added H$_2$O (3 mL) and TFA (15 mL) at 0° C. The solution was stirred at 25° C. for 16 h before it was quenched with saturated aq. NaHCO$_3$ (150 mL). The mixture was extracted with ethyl acetate (2×100 mL). The combined organic layer was washed with brine (200 mL), dried over Na$_2$SO$_4$, filtered and concentrated to give crude diethyl 2-(((2R,3S,4R)-3-ethynyl-3,4,5-trihydroxytetrahydrofuran-2-yl)methoxy)-2-(4-iodobenzyl)malonate (1.74 g) as a yellow foam.

Step 2:

To a solution of diethyl 2-(((2R,3S,4R)-3-ethynyl-3,4,5-trihydroxytetrahydrofuran-2-yl)methoxy)-2-(4-iodobenzyl)malonate (1.74 g, 3.17 mmol, 1 eq) in pyridine (20 mL) was added 4-DMAP (1.16 g, 9.52 mmol, 3 eq) and Ac$_2$O (2.38 mL, 25.39 mmol, 8 eq). The solution was stirred at 25° C. for 3 h before it was diluted with water (60 mL) and extracted with ethyl acetate (2×60 mL). The combined organic layer was washed with water (100 mL), brine (100 mL), dried over Na$_2$SO$_4$, filtered and concentrated. The crude residue was purified by flash column chromatography on silica gel (10-50% of ethyl acetate in petroleum ether) to give diethyl 2-(4-iodobenzyl)-2-(((2R,3R,4R)-3,4,5-triacetoxy-3-ethynyl-tetrahydrofuran-2-yl)methoxy)malonate (1.85 g, 86% yield for two steps) as a yellow foam.

Step 3:

To a solution of diethyl 2-(4-iodobenzyl)-2-(((2R,3R,4R)-3,4,5-triacetoxy-3-ethynyl-tetrahydrofuran-2-yl)methoxy)malonate (1.00 g, 1.48 mmol, 1 eq) in MeCN (12 mL) was added 2-chloro-N-methyl-9H-purin-6-amine (327 mg, 1.78 mmol, 1.2 eq) and BSA (916 uL, 3.71 mmol, 2.5 eq). The suspension was stirred at 65° C. for 0.5 h before it was cooled down to 0° C. and followed by addition of TMSOTf (804 uL, 4.45 mmol, 3 eq). The resulting mixture was stirred at 65° C. for 1.5 h before it was diluted with saturated aq. NaHCO$_3$ (10 mL) and extracted with ethyl acetate (2×10 mL). The combined organic layer was washed with brine (25 mL), dried over Na$_2$SO$_4$, filtered and concentrated. The crude residue was purified by flash column chromatography on silica gel (10-50% ethyl acetate in petroleum ether) to give diethyl 2-(((2R,3R,4R,5R)-3,4-diacetoxy-5-(2-chloro-6-(methylamino)-9H-purin-9-yl)-3-ethynyltetrahydrofuran-2-yl)methoxy)-2-(4-iodobenzyl)malonate (595 mg, 50% yield) as a yellow solid.

Step 4:

To a solution of diethyl 2-(((2R,3R,4R,5R)-3,4-diacetoxy-5-(2-chloro-6-(methyl-amino)-9H-purin-9-yl)-3-ethynyltetrahydrofuran-2-yl)methoxy)-2-(4-iodobenzyl)malonate (592 mg, 741.88 umol, 1 eq) in DCM (8 mL) was added 4-DMAP (18 mg, 148.38 umol, 0.2 eq), TEA (413 uL, 2.97 mmol, 4 eq) and (Boc)$_2$O (324 mg, 1.48 mmol, 2 eq). The solution was stirred at 20° C. for 2 h before it was diluted with saturated aq. NH$_4$Cl (20 mL) and extracted with ethyl acetate (2×20 mL). The combined organic layer was washed with brine (40 mL), dried over Na$_2$SO$_4$, filtered and concentrated. The crude was purified by flash column chromatography on silica gel (15-50% of ethyl acetate in petroleum ether) to give diethyl 2-(((2R,3R,4R,5R)-3,4-diacetoxy-5-(6-((tert-butoxycarbonyl)(methyl)amino)-2-chloro-9H-purin-9-yl)-3-ethynyltetrahydrofuran-2-yl)methoxy)-2-(4-iodobenzyl)malonate (560 mg, 84% yield) as a foam.

Step 5:

To a mixture of diethyl 2-(((2R,3R,4R,5R)-3,4-diacetoxy-5-(6-((tert-butoxycarbonyl)-(methyl)amino)-2-chloro-9H-purin-9-yl)-3-ethynyltetrahydrofuran-2-yl)methoxy)-2-(4-iodobenzyl)malonate (660 mg, 734.89 umol, 1 eq) and (2-hydroxypyridin-3-yl)boronic acid (204.18 mg, 1.47 mmol, 2 eq) in dioxane (6 mL) and H$_2$O (2 mL) was added Pd(dppf)Cl$_2$ (53.77 mg, 73.49 umol, 0.1 eq) and K$_2$CO$_3$ (304.70 mg, 2.20 mmol, 3 eq). The yellow mixture was degassed with N$_2$ gas for 10 min before the mixture was stirred at 70° C. for 2.5 h The mixture was diluted with water (5 mL) and extracted with ethyl acetate (3×5 mL). The combined organic layer was dried over Na$_2$SO$_4$, filtered and concentrated. The crude was purified by flash column chromatography on silica gel (50-100% of ethyl acetate in petroleum ether) to give diethyl 2-(((2R,3R,4R,5R)-3,4-diacetoxy-5-(6-((tert-butoxy-carbonyl)(methyl)amino)-2-chloro-9H-purin-9-yl)-3-ethynyltetrahydrofuran-2-yl)methoxy)-2-(4-(2-oxo-1,2-dihydropyridin-3-yl)benzyl)malonate (146 mg) as a foam.

Step 6:

To a solution of diethyl 2-(((2R,3R,4R,5R)-3,4-diacetoxy-5-(6-((tert-butoxycarbonyl)-(methyl)amino)-2- chloro-9H-purin-9-yl)-3-ethynyltetrahydrofuran-2-yl)methoxy)-2-(4-(2-oxo-1,2-dihydropyridin-3-yl)benzyl)malonate (145 mg, 167.58 umol, 1 eq) in DCM (6 mL) was added TFA (1.5 mL, 20.26 mmol, 121 eq). The solution was stirred at 25° C. for 1 h before it was neutralized with saturated aq. NaHCO$_3$ solution. The mixture was extracted with ethyl acetate (3×12 mL). The combined organic layer was washed with brine (30 mL), dried over Na$_2$SO$_4$, filtered and concentrated. The crude was purified by preparative TLC (ethyl acetate) to give diethyl 2-(((2R,3R,4R,5R)-3,4-diacetoxy-5-(2-chloro-6-(methylamino)-9H-purin-9-yl)-3-ethynyltetrahydrofuran-2-yl)methoxy)-2-(4-(2-oxo-1,2-dihydropyridin-3-yl)benzyl)malonate (110 mg) as a solid.

Step 7:

To a solution of diethyl 2-(((2R,3R,4R,5R)-3,4-diacetoxy-5-(2-chloro-6-(methyl-amino)-9H-purin-9-yl)-3-ethynyltetrahydrofuran-2-yl)methoxy)-2-(4-(2-oxo-1,2-dihydro-pyridin-3-yl)benzyl)malonate (105 mg, 137.23 umol, 1 eq) in THF (4.5 mL) was added aq.

LiOH solution (1 M, 1.5 mL, 11 eq). The mixture was stirred at 25° C. for 4 h before the organic volatile was removed under reduced pressure. The aq. layer was acidified to pH 6 with 1N aq. HCl solution and concentrated. The crude residue was purified by preparative HPLC (Column: YMC-Triart Prep C18 150*40 mm*7 um; mobile phase: [water (0.225% FA)-ACN]; B %: 20%-40%, 10 min) and dried by lyophilization to give 2-(((2R,3S,4R,5R)-5-(2-chloro-6-(methylamino)-9H-purin-9-yl)-3-ethynyl-3,4-dihydroxytetrahydrofuran-2-yl)-methoxy)-2-(4-(2-oxo-1,2-dihydropyridin-3-yl)benzyl)malonic acid (6.6 mg) as a white solid.

$^1$H NMR (400 MHz, DMSO-d$_6$) δ ppm 8.44 (s, 1H), 8.23 (d, J=3.75 Hz, 1H), 7.48 (d, J=6.63 Hz, 1H), 7.39 (d, J=7.00 Hz, 2H), 7.34 (d, J=5.63 Hz, 1H), 7.13-7.22 (m, 2H), 6.15-6.29 (m, 2H), 6.00 (d, J=6.75 Hz, 1H), 5.82 (d, J=7.38 Hz, 1H), 4.71-4.89 (m, 1H), 4.16 (dd, J=4.94, 2.56 Hz, 1H), 3.86-4.05 (m, 1H), 3.53-3.83 (m, 1H), 3.51 (s, 1H), 3.48-3.30 (m, 5H overlapped under water peak), 2.90 (d, J=4.38 Hz, 3H); LC/MS [M+H]=624.9.

Example 148

Synthesis of 2-(((2R,3S,4R,5R)-5-(2-chloro-6-(methylamino)-9H-purin-9-yl)-3-ethynyl-3,4-dihydroxytetrahydrofuran-2-yl)methoxy)-2-(4-(3-methyl-2-oxotetrahydropyrimidin-1 (2H)-yl)benzyl)malonic acid

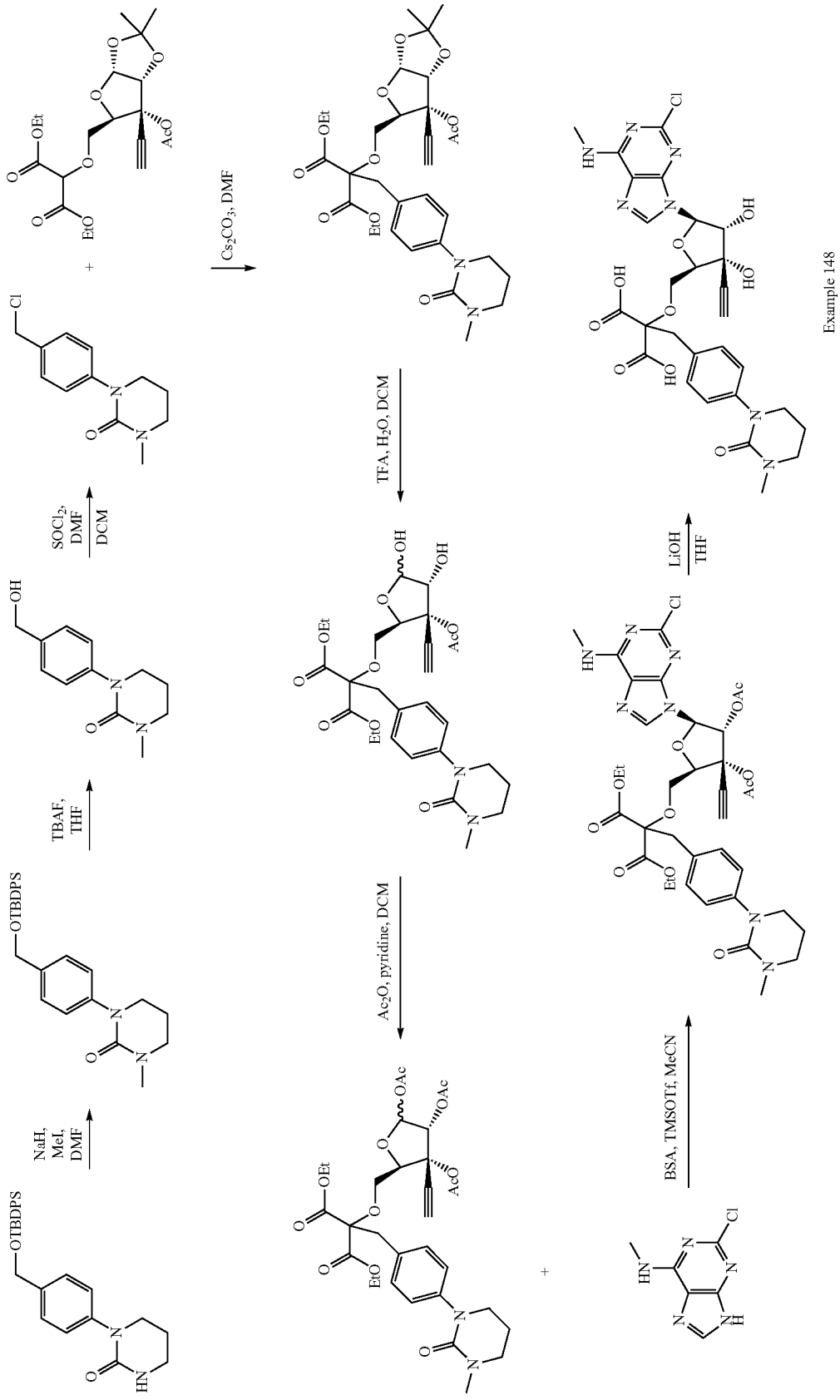

Step 1:
To a solution of 1-(4-(((tert-butyldiphenylsilyl)oxy) methyl)phenyl)tetrahydro-pyrimidin-2(1H)-one (7.33 g, 16.48 mmol, 1 eq) in DMF at 0° C. was added NaH (725 mg, 60% in mineral oil, 18.13 mmol, 1.1 eq). The mixture was stirred for 15 min and followed by addition of $CH_3I$ (4.10 mL, 65.92 mmol, 4 eq). The reaction mixture was stirred from 0-25° C. over 16 h before it was diluted with $H_2O$ (100 mL) and extracted with EtOAc (3×50 mL). The combined organic layer was washed with brine (100 mL), dried over $Na_2SO_4$, filtered and concentrated. The crude was purified by flash column chromatography on silica gel (0-50% EtOAc in petroleum ether) to provide 1-(4-(((tert-butyldiphenylsilyl)oxy)-methyl)phenyl)-3-methyltetrahydropyrimidin-2(1H)-one (3.68 g, 48% yield) as a colourless gum.

Step 2:
To a solution of 1-(4-(((tert-butyldiphenylsilyl)oxy) methyl)phenyl)-3-methyltetrahydropyrimidin-2(1H)-one (3.68 g, 8.02 mmol, 1 eq) in THF (35 mL) was added TBAF in THF (1.5 M, 10.70 mL, 2 eq) at 0° C. The reaction mixture was stirred at 25° C. for 1.5 h before it was diluted with $H_2O$ (20 mL) and extracted with EtOAc (3×50 mL). The combined organic layer was washed with brine (50 mL), dried over $Na_2SO_4$, filtered and concentrated. The crude was purified by flash column chromatography on silica gel (0-5% MeOH in DCM) to provide 1-(4-(hydroxymethyl)phenyl)-3-methyltetrahydropyrimidin-2(1H)-one (1.06 g, 60% yield) as a yellow solid.

Step 3:
To a solution of 1-(4-(hydroxymethyl)phenyl)-3-methyl-tetrahydropyrimidin-2(1H)-one (1.06 g, 4.81 mmol, 1 eq) in DCM (10 mL) and DMF (0.1 mL) was added $SOCl_2$ (698 uL, 9.62 mmol, 2 eq) at 20-25° C. The reaction mixture was stirred for 0.5 h and additional amount of $SOCl_2$ (419 uL, 5.77 mmol, 1.2 eq) was added. The resulting mixture was stirred at 40° C. for 1 h before it was concentrated. The residue was azeotroped with DCM (3×10 mL) under reduced pressure to provide crude 1-(4-(chloromethyl)phenyl)-3-methyltetrahydropyrimidin-2(1H)-one which was used in the next step without further purification.

Step 4:
To a solution of diethyl 2-(((3aR,5R,6R,6aR)-6-acetoxy-6-ethynyl-2,2-dimethyltetra-hydrofuro[2,3-d][1,3]dioxol-5-yl)methoxy)malonate (1.78 g, 4.30 mmol, 1 eq) in DMF (20 mL) was added $Cs_2CO_3$ (4.21 g, 12.91 mmol, 3 eq) at 25° C. The reaction mixture was stirred for 0.5 h and followed by addition of crude 1-(4-(chloromethyl)phenyl)-3-methyltetrahydro-pyrimidin-2(1H)-one (1.13 g). The reaction mixture was stirred at 25° C. for 16 h before it was diluted with $H_2O$ (50 mL) and extracted with EtOAc (3×20 mL). The combined organic layer was washed with brine (30 mL), dried over $Na_2SO_4$, filtered and concentrated. The crude was purified by column chromatography on silica gel (0-10% of MeOH in DCM) to provide diethyl 2-(((3aR,5R,6R,6aR)-6-acetoxy-6-ethynyl-2,2-dimethyl-tetrahydrofuro[2,3-d][1,3]dioxol-5-yl)methoxy)-2-(4-(3-methyl-2-oxotetrahydropyrimidin-1(2H)-yl)benzyl)malonate (2.63 g, 78% yield) as a brown foam.

Step 5:
To a solution of diethyl 2-(((3aR,5R,6R,6aR)-6-acetoxy-6-ethynyl-2,2-dimethyltetra-hydrofuro[2,3-d][1,3]dioxol-5-yl)methoxy)-2-(4-(3-methyl-2-oxotetrahydropyrimidin-1(2)-yl)benzyl)malonate (2.62 g, 4.25 mmol, 1 eq) in DCM (25 mL) at 0° C. was added TFA (25 mL, 337.65 mmol, 79 eq) and $H_2O$ (2.5 mL, 138.77 mmol, 33 eq). The reaction mixture was stirred at 20-25° C. for 16 h before it was concentrated under reduced pressure. The residue was azeotroped with DCM (3×20 mL) under reduced pressure to provide crude diethyl 2-(((2R,3S,4R)-3-acetoxy-3-ethynyl-4,5-dihydroxytetrahydrofuran-2-yl)methoxy)-2-(4-(3-methyl-2-oxotetrahydropyrimidin-1(2H)-yl)benzyl)malonate (2.57 g) as a syrup which was used in the next step without further purification.

Step 6:
To a solution of crude diethyl 2-(((2R,3S,4R)-3-acetoxy-3-ethynyl-4,5-dihydroxytetra-hydrofuran-2-yl)methoxy)-2-(4-(3-methyl-2-oxotetrahydropyrimidin-1(2H)-yl)benzyl)-malonate (2.57 g) in DCM (25 mL) at 20-25° C. was added $Ac_2O$ (2.39 mL, 25.50 mmol, 6 eq), 4-DMAP (51.92 mg, 425.00 umol, 0.1 eq) and pyridine (2.74 mL, 34.00 mmol, 8 eq).

The reaction mixture was stirred at 25° C. for 16 h before it was concentrated under reduced pressure. The residue was re-dissolved in EtOAc (50 mL), washed with 1N aq. HCl (40 mL), 10% aq. $Cu_2SO_4$ (40 mL), saturated aq. $NaHCO_3$ (40 mL) and brine (40 mL), dried over $Na_2SO_4$, filtered and concentrated to provide crude diethyl 2-(4-(3-methyl-2-oxotetrahydro-pyrimidin-1 (2H)-yl)benzyl)-2-(((2R,3R, 4R)-3,4,5-triacetoxy-3-ethynyltetrahydrofuran-2-yl) methoxy)malonate (2.62 g, 53% yield for two steps) which was used in the next step without further purification.

Step 7:
To a solution of 2-chloro-N-methyl-9H-purin-6-amine (181 mg, 983.86 umol, 1.3 eq) in MeCN (2.5 mL) under $N_2$ atmosphere was added BSA (468 uL, 1.89 mmol, 2.5 eq) at 20-25° C. The reaction mixture was stirred at 65° C. for 0.5 h before it was cooled to 25° C. To this mixture was added crude diethyl 2-(4-(3-methyl-2-oxotetrahydropyrimidin-1 (2H)-yl)benzyl)-2-(((2R,3R,4R)-3,4,5-triacetoxy-3-ethynyltetrahydrofuran-2-yl)methoxy)malonate (500 mg, 756.81 umol, 1 eq) in MeCN (2.5 mL) and TMSOTf (205 uL, 1.14 mmol, 1.5 eq) and stirred at 65° C. for 5 h before it was quenched with saturated aq. $NaHCO_3$ (10 mL). The mixture was then extracted with EtOAc (3×10 mL). The combined organic layer was washed with brine (20 mL), dried over anhydrous $Na_2SO_4$, filtered, and concentrated. The crude was purified by flash column chromatography on silica gel column (0-10% MeOH in DCM) to provide diethyl 2-(((2R, 3R,4R,5R)-3,4-diacetoxy-5-(2-chloro-6-(methylamino)-9H-purin-9-yl)-3-ethynyltetrahydrofuran-2-yl)methoxy)-2-(4-(3-methyl-2-oxotetrahydro-pyrimidin-1(2H)-yl)benzyl) malonate (530 mg, 60% yield) as a foam.

Step 8:
To a solution of diethyl 2-(((2R,3R,4R,5R)-3,4-diacetoxy-5-(2-chloro-6-(methyl-amino)-9H-purin-9-yl)-3-ethynyltetrahydrofuran-2-yl)methoxy)-2-(4-(3-methyl-2-oxotetrahydropyrimidin-1(2H)-yl)benzyl)malonate (540 mg, 688.59 umol, 1 eq) in THF (6 mL) was added $LiOH \cdot H_2O$ (288.96 mg, 6.89 mmol, 10 eq) in $H_2O$ (3 mL) at 25° C. The reaction mixture was stirred at 40° C. for 2 h before the organic volatile was removed under reduced pressure. The aq. phase was acidified to pH 2-3 with 1N aq. HCl solution and then concentrated. The crude was purified by preparative HPLC (column: YMC-Actus Triart C18 150*30 mm*5 um; mobile phase: [water (0.225% FA)-ACN]; B %: 23%-43%, 10 min) and dried by lyophilization to provide 2-(((2R,3S,4R,5R)-5-(2-chloro-6-(methylamino)-9H-purin-9-yl)-3-ethynyl-3,4-dihydroxytetrahydrofuran-2-yl)methoxy)-2-(4-(3-methyl-2-oxotetrahydropyrimidin-1(2H)-yl)benzyl)malonic acid (77.6 mg, 17% yield) as a white solid.

$^1H$ NMR (400 MHz, DMSO-$d_6$) δ ppm 13.00-13.93 (s, 2H), 8.37 (s, 1H), 8.23 (d, J=5.01 Hz, 1H), 7.11 (d, J=8.31 Hz, 2H), 6.90 (d, J=8.19 Hz, 2H), 6.15 (s, 1H), 5.98 (s, 1H), 5.81 (d, J=7.58 Hz, 1H), 4.82 (s, 1H), 4.15 (dd, J=4.34, 3.00 Hz, 1H), 3.96 (m, 1H), 3.78 (m, 1H), 3.53 (s, 1H), 3.43-3.52 (m, 2H), 3.23 (m, 2H), 3.20-3.10 (m, 4H overlapped with solvent water peak), 2.91 (m, 2H), 2.81 (s, 3H), 1.95 (m, 2H); LC/MS [M+H]=644.1.

Example 149

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(3-methyl-2-oxotetrahydropyrimidin-1 (2H)-yl)benzyl)malonic acid

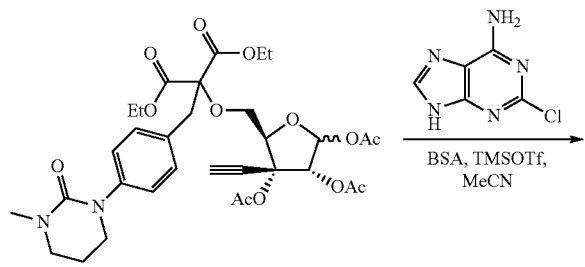

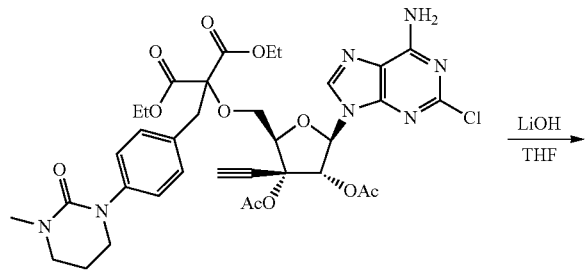

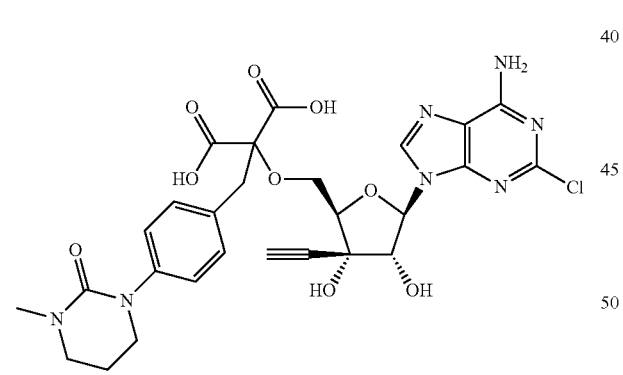

Example 149

Proceeding as described in Example 148 above but substituting 2-chloro-N-methyl-9H-purin-6-amine with 2-chloro-9H-purin-6-amine provided the title compound as a white solid.

$^1$H NMR (400 MHz, CD$_3$OD) δ ppm 8.21 (s, 1H), 7.26 (m, J=8.28 Hz, 2H), 6.96 (m, J=8.28 Hz, 2H), 5.97 (d, J=7.53 Hz, 1H), 4.70-4.83 (m, 1H), 4.27 (t, J=2.76 Hz, 1H), 3.99-4.07 (m, 2H), 3.32-3.52 (m, 6H), 3.05 (s, 1H), 2.87 (s, 3H), 2.00 (quin, J=5.83 Hz, 2H); LC/MS [M+H]=630.2.

Example 150

Synthesis of 2-(((2R,3S,4R,5R)-5-(2-chloro-6-((cyclopropylmethyl)amino)-9H-purin-9-yl)-3-ethynyl-3,4-dihydroxytetrahydrofuran-2-yl)methoxy)-2-(4-(3-methyl-2-oxotetrahydropyrimidin-1 (2H)-yl)benzyl) malonic acid

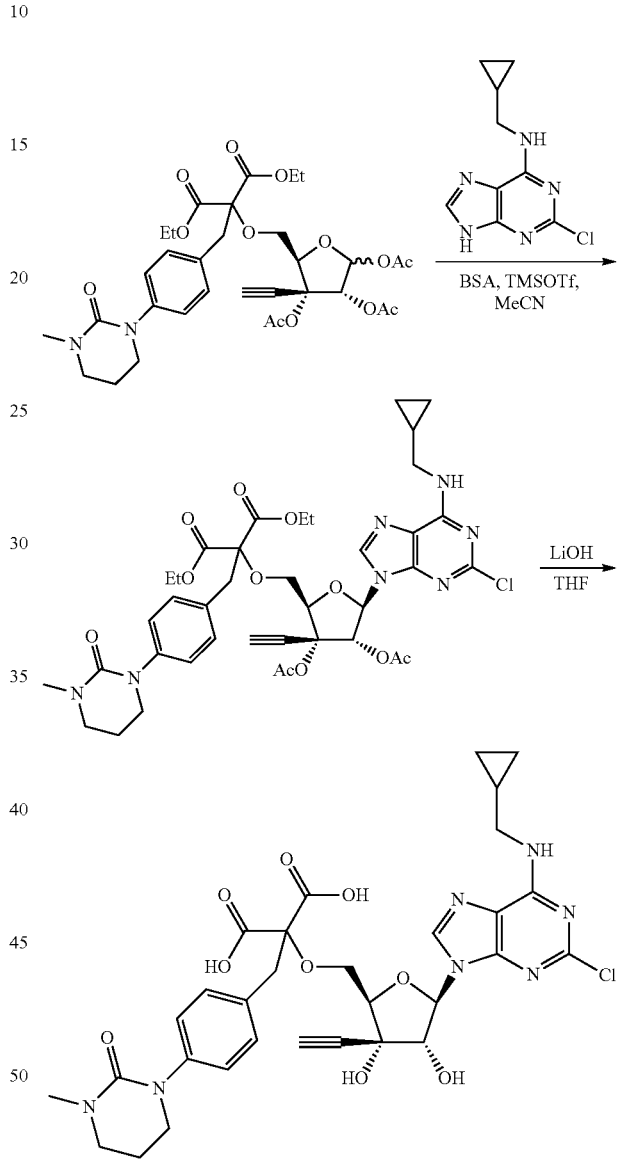

Example 150

Proceeding as described in Example 148 above but substituting 2-chloro-N-methyl-9H-purin-6-amine with 2-chloro-N-(cyclopropylmethyl)-9H-purin-6-amine provided the title compound as a white solid.

$^1$H NMR (400 MHz, CD$_3$OD) δ ppm 8.12 (s, 1H), 7.27 (d, J=8.28 Hz, 2H), 7.00 (d, J=7.68 Hz, 2H), 5.96 (d, J=7.53 Hz, 1H), 4.70 (d, J=7.53 Hz, 1H), 4.26 (t, J=2.89 Hz, 1H), 4.03 (br s, 2H), 3.33-3.54 (m, 8H), 3.05 (s, 1H), 2.88 (s, 3H), 1.97-2.04 (m, 2H), 1.11-1.20 (m, 1H), 0.53-0.59 (m, 2H), 0.34 (m, 2H); LC/MS [M+H]=684.3.

Example 151

Synthesis of 2-(((2R,3S,4R,5R)-5-(2-chloro-6-(isopropylamino)-9H-purin-9-yl)-3-ethynyl-3,4-dihydroxytetrahydrofuran-2-yl)methoxy)-2-(4-(3-methyl-2-oxotetrahydropyrimidin-1(2H)-yl)benzyl)malonic acid

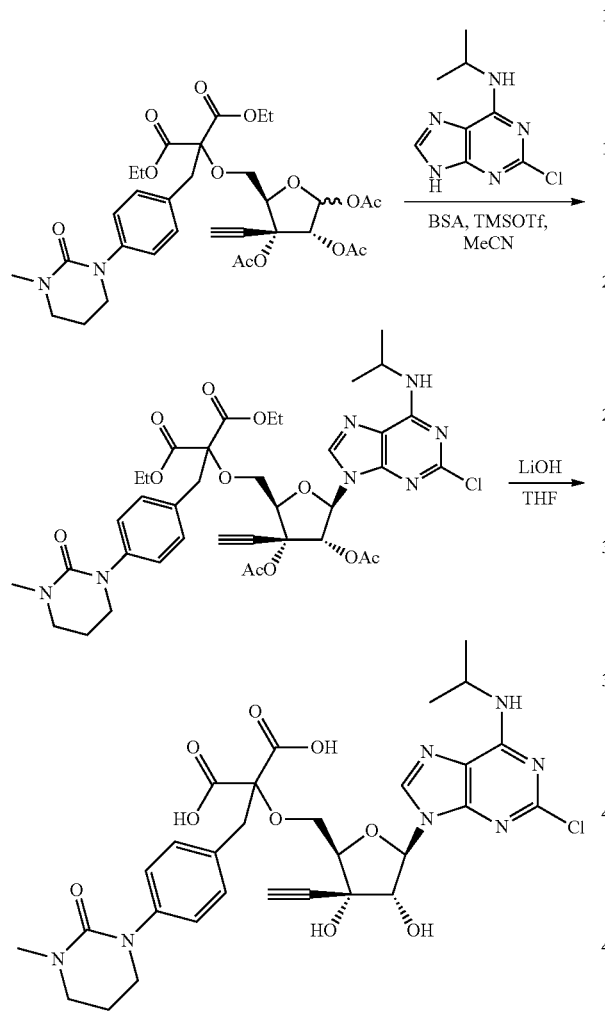

Example 151

Proceeding as described in Example 148 above but substituting 2-chloro-N-methyl-9H-purin-6-amine with 2-chloro-N-isopropyl-9H-purin-6-amine provided the title compound as a white solid.

$^1$H NMR (400 MHz, CD$_3$OD) δ ppm 8.08 (s, 1H), 7.28 (d, J=8.28 Hz, 2H), 7.00 (d, J=8.53 Hz, 2H), 5.95 (d, J=7.53 Hz, 1H), 4.66-4.80 (m, 1H), 4.32-4.48 (m, 1H), 4.25 (t, J=2.89 Hz, 1H), 4.00-4.08 (m, 2H), 3.34-3.53 (m, 6H), 3.05 (s, 1H), 2.88 (s, 3H), 1.94-2.06 (m, 2H), 1.24-1.35 (m, 6H); LC/MS [M+H]=672.1.

Example 152

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(2-oxo-3-propyltetrahydropyrimidin-1(2H)-yl)benzyl)malonic acid

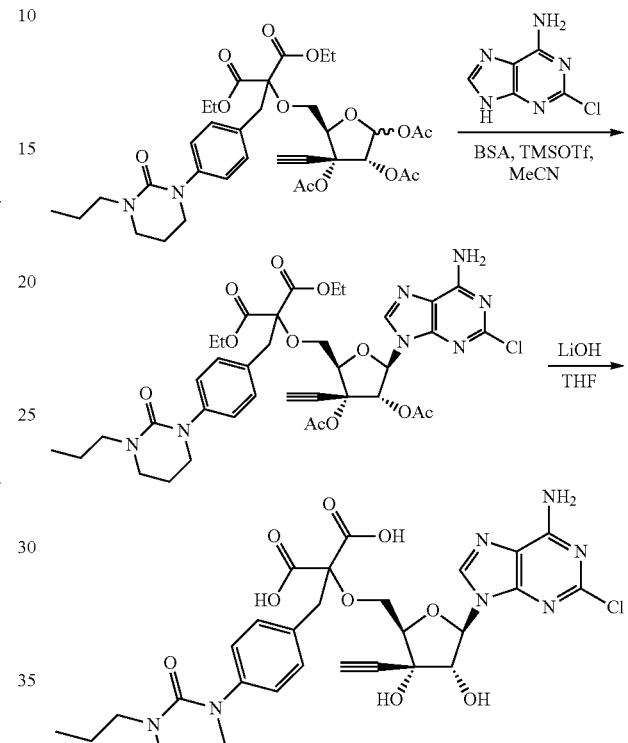

Example 152

Proceeding as described in Example 148 above but substituting MeI and 2-chloro-N-methyl-9H-purin-6-amine with 1-bromopropane and 2-chloro-9H-purin-6-amine provided the title compound as a white solid.

$^1$H NMR (400 MHz, CD$_3$OD) δ ppm 8.15 (s, 1H), 7.28 (d, J=8.4 Hz, 2H), 6.99 (d, J=8.4 Hz, 2H), 5.97 (d, J=7.5 Hz, 1H), 4.75 (d, J=7.6 Hz, 1H), 4.27 (s, 1H), 3.99-4.11 (m, 2H), 3.46-3.54 (m, 2H), 3.35-3.44 (m, 4H), 3.16-3.27 (m, 2H), 3.05 (s, 1H), 1.97-2.03 (m, 2H), 1.50-1.58 (m, 2H), 0.88 (t, J=7.4 Hz, 3H); LC/MS [M+H]=658.1.

Example 153

Synthesis of 2-(((2R,3S,4R,5R)-5-(2-chloro-6-(isopropylamino)-9H-purin-9-yl)-3-ethynyl-3,4-dihydroxytetrahydrofuran-2-yl)methoxy)-2-(4-(1-(2-hydroxyethyl)-2-oxo-1,2-dihydropyridin-3-yl)benzyl)malonic acid

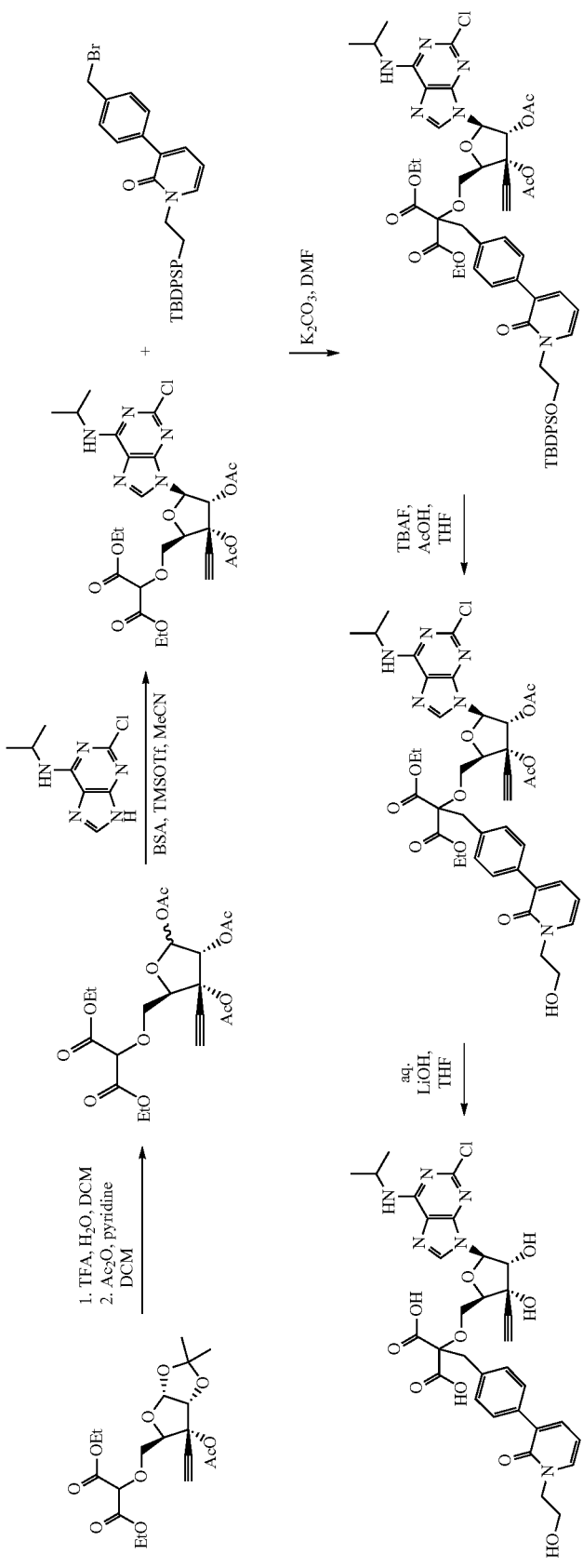

Step 1:

To a solution of diethyl 2-(((3aR,5R,6R,6aR)-6-acetoxy-6-ethynyl-2,2-dimethyltetra-hydrofuro[2,3-d][1,3]dioxol-5-yl)methoxy)malonate (4.13 g, 9.97 mmol, 1 eq) in DCM (40 mL) at 20° C. was added TFA (40 mL, 540.24 mmol, 54 eq) and H₂O (4 mL, 222.03 mmol, 22 eq). The mixture was stirred at 20° C. for 15 h before it was quenched by saturated aq. NaHCO₃ (200 mL) and extracted with EtOAc (5×50 mL). The combined organic layer was washed brine (200 mL), dried over anhydrous Na₂SO₄, filtered and concentrated to give crude diethyl 2-(((2R,3S,4R)-3-acetoxy-3-ethynyl-4,5-dihydroxytetrahydrofuran-2-yl)-methoxy)malonate (4.14 g) as a light yellow syrup which was used in the next step directly.

To a solution of the above crude product (4.14 g, 12.46 mmol, 1 eq) in pyridine (40 mL) was added Ac₂O (9.33 mL, 99.67 mmol, 8 eq) and 4-DMAP (3.81 g, 31.15 mmol, 2.5 eq). The mixture was stirred at 20° C. for 16 h before it was quenched by water (150 mL) and the resulting solution was extracted with EtOAc (4×50 mL). The combined organic layer was washed with 0.5 N aq. HCl (120 mL) and water (2×100 mL), brine (100 mL), dried over anhydrous Na₂SO₄, filtered and concentrated. The crude residue was purified by flash column chromatography on silica gel (30-50% EtOAc in petroleum ether) to provide diethyl 2-(((2R,3R,4R)-3,4,5-triacetoxy-3-ethynyltetrahydrofuran-2-yl)methoxy)malonate (2.60 g) as a syrup.

Step 2:

To a solution of diethyl 2-(((2R,3R,4R)-3,4,5-triacetoxy-3-ethynyltetrahydrofuran-2-yl)methoxy)malonate (1.2 g, 2.62 mmol, 1 eq) and 2-chloro-N-isopropyl-9H-purin-6-amine (665 mg, 3.14 mmol, 1.2 eq) in MeCN (15 mL) was added BSA (1.62 mL, 6.54 mmol, 2.5 eq). The suspension was stirred at 65° C. for 0.5 h before it was cooled down to 0° C. To this solution was added TMSOTf (1.45 g, 6.54 mmol, 1.18 mL, 2.5 eq). Then the mixture was stirred at 65° C. for 2.5 h before it was quenched by saturated aq. NaHCO₃ (50 mL) and the resulting solution was extracted with EtOAc (4×30 mL). The combined organic layer was dried over anhydrous Na₂SO₄, filtered and concentrated. The residue was purified by flash column chromatography on silica gel (30-50% of EtOAc in petroleum ether) to provide diethyl 2-(((2R,3R,4R,5R)-3,4-diacetoxy-5-(2-chloro-6-(isopropylamino)-9H-purin-9-yl)-3-ethynyltetrahydrofuran-2-yl)methoxy)malonate (814 mg, 51% yield).

Step 3:

To a solution of diethyl 2-(((2R,3R,4R,5R)-3,4-diacetoxy-5-(2-chloro-6-(isopropyl-amino)-9H-purin-9-yl)-3-ethynyltetrahydrofuran-2-yl)methoxy)malonate (120 mg, 197 umol, 1 eq) in DMF (1 mL) was added K₂CO₃ (81.56 mg, 590.15 umol, 3 eq) and 3-(4-(bromo-methyl)phenyl)-1-(2-((tert-butyldiphenylsilyl)oxy)ethyl)pyridin-2(1H)-one (161 mg, 295 umol, 1.5 eq). The mixture was stirred at 20° C. for 1.5 h before it was diluted with water (10 mL) and extracted with EtOAc (4×5 mL). The combined organic layer was washed with water (2×30 mL), dried over anhydrous Na₂SO₄, filtered and concentrated. The residue was purified by flash column chromatography on silica gel (30-60% of EtOAc in petroleum ether) to provide diethyl 2-(4-(1-(2-((tert-butyldiphenylsilyl)oxy)ethyl)-2-oxo-1,2-dihydro-pyridin-3-yl)benzyl)-2-(((2R,3R,4R,5R)-3,4-diacetoxy-5-(2-chloro-6-(isopropyl-amino)-9H-purin-9-yl)-3-ethynyltetrahydrofuran-2-yl)methoxy)malonate (154 mg) as a colorless oil.

Step 4:

To a solution of diethyl 2-(4-(1-(2-((tert-butyldiphenylsilyl)oxy)ethyl)-2-oxo-1,2-dihydropyridin-3-yl)benzyl)-2-(((2R,3R,4R,5R)-3,4-diacetoxy-5-(2-chloro-6-(isopropyl-amino)-9H-purin-9-yl)-3-ethynyltetrahydrofuran-2-yl)methoxy)malonate (150 mg, 139 umol, 1 eq) in THF (1 mL) was added TBAF (1 M, 209 uL, 1.5 eq) and AcOH (5.98 uL, 104.59 umol, 0.75 eq) at 0° C. The mixture was stirred at 20° C. for 16 h before it was diluted with water (5 mL) and the resulting solution was extracted with EtOAc (3×5 mL). The combined organic layer was dried over anhydrous Na₂SO₄, filtered and concentrated. The residue was purified by preparative TLC (petroleum ether:EtOAc=1:4) to provide diethyl 2-(((2R,3R,4R,5R)-3,4-diacetoxy-5-(2-chloro-6-(isopropylamino)-9H-purin-9-yl)-3-ethynyl-tetrahydrofuran-2-yl)methoxy)-2-(4-(1-(2-hydroxyethyl)-2-oxo-1,2-dihydropyridin-3-yl)benzyl)malonate (51 mg, 32% yield) as a white solid.

Step 5:

To a solution of diethyl 2-(((2R,3R,4R,5R)-3,4-diacetoxy-5-(2-chloro-6-(isopropyl-amino)-9H-purin-9-yl)-3-ethynyltetrahydrofuran-2-yl)methoxy)-2-(4-(1-(2-hydroxy-ethyl)-2-oxo-1,2-dihydropyridin-3-yl)benzyl)malonate (50 mg, 60 umol, 1 eq) in THF (0.5 mL) was added sat.LiOH.aq (2.51 mg, 60 umol, 0.5 mL, 1 eq). The mixture was stirred at 20° C. for 2.5 h before the organic volatile was removed under reduced pressure. The resulting aq. solution was acidified to pH 2 with 2 N aq. HCl solution and concentrated. The residue was further purification by preparative HPLC (column: YMC-Triart Prep C18 150*40 mm*7 um; mobile phase: [water (0.225% FA)-ACN]; B %: 28%-48%, 10 min) to provide 2-(((2R,3S,4R,5R)-5-(2-chloro-6-(isopropylamino)-9H-purin-9-yl)-3-ethynyl-3,4-dihydroxy-tetrahydrofuran-2-yl)methoxy)-2-(4-(1-(2-hydroxyethyl)-2-oxo-1,2-dihydropyridin-3-yl)benzyl)malonic acid (10.8 mg, 26% yield) as a white solid.

¹H NMR (400 MHz, CD₃OD) δ ppm 8.08 (s, 1H), 7.55 (dd, J=6.7, 1.9 Hz, 1H), 7.21-7.42 (m, 5H), 6.34 (t, J=6.8 Hz, 1H), 5.95 (d, J=7.3 Hz, 1H), 4.74 (d, J=7.3 Hz, 1H), 4.24-4.39 (m, 2H), 4.00-4.14 (m, 4H), 3.76-3.87 (m, 2H), 3.40-3.54 (m, 2H), 3.06 (s, 1H), 1.24 (dd, J=6.4, 2.9 Hz, 6H); LC/MS [M+H]=697.0.

Examples 154 & 155

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(4-methyl-2-oxopiperazin-1-yl)benzyl)malonic acid and 2-(((2R,3S,4R,5R)-5-(6-amino-2-chloro-9H-purin-9-yl)-3-ethynyl-3,4-dihydroxytetrahydrofuran-2-yl)methoxy)-2-(4-((2-((carboxymethyl)(methyl)amino)ethyl)amino)benzyl)malonic acid

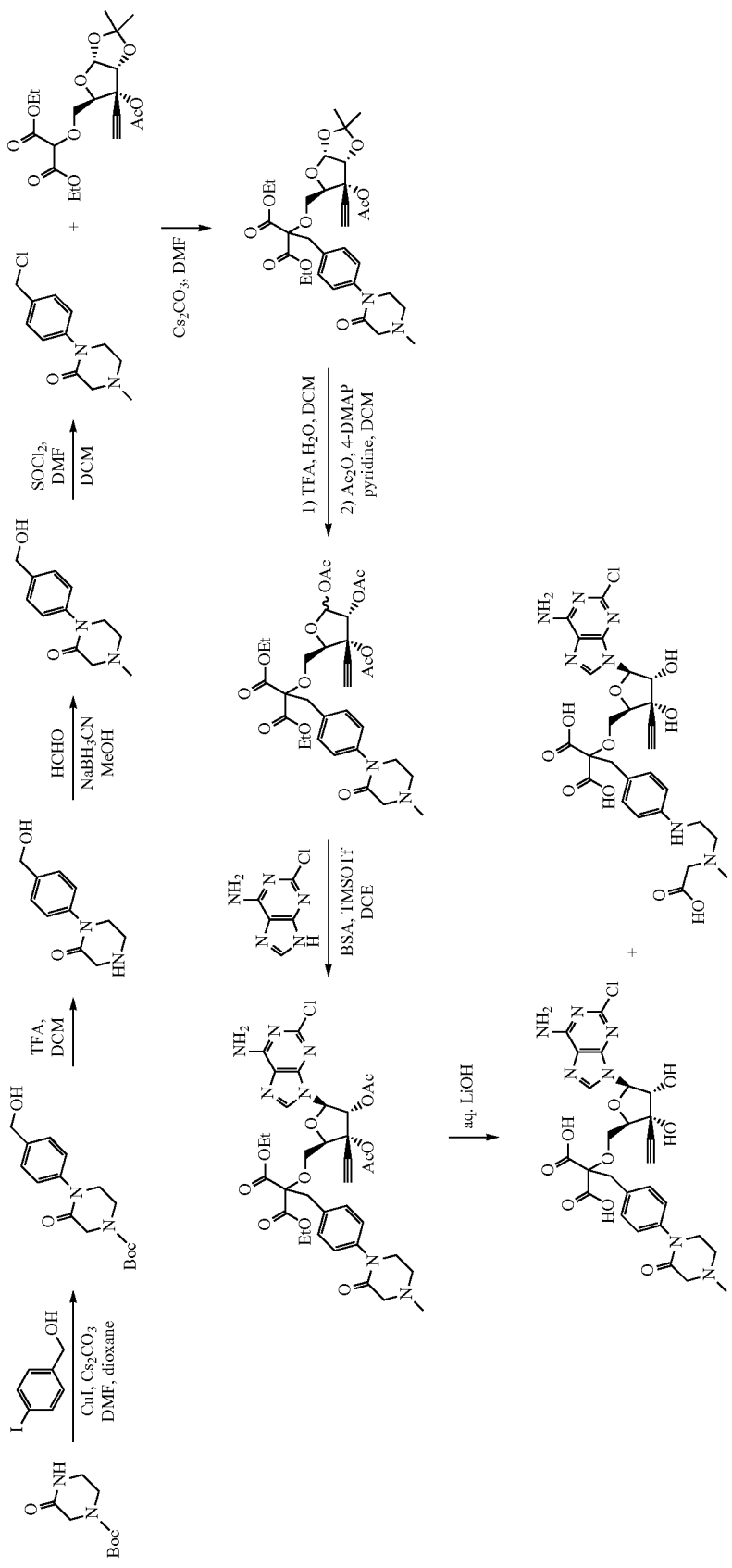

Step 1:
To a mixture of tert-butyl 3-oxopiperazine-1-carboxylate (8.7 g, 43.45 mmol, 1.2 eq) and (4-iodophenyl) methanol (8.5 g, 36.32 mmol, 1 eq) in DMF (10 mL) and dioxane (90 mL) was added CuI (1.03 g, 5.43 mmol, 0.15 eq), 2-(hydroxymethyl)-2-methyl-propane-1,3-diol (653 mg, 5.43 mmol, 0.15 eq) and $Cs_2CO_3$ (35.39 g, 108.62 mmol, 3 eq). The mixture was stirred at 110° C. under $N_2$ atmosphere for 14 hours before it was cooled. The inorganic solid was filtered off and the filtrate was concentrated in vacuo. The residue was diluted with water (50 mL) and extracted with ethyl acetate (3×50 mL). The combined organic layer was washed with brine (50 mL), dried by $Na_2SO_4$, filtered and concentrated. The crude residue was purified by flash silica gel chromatography (0-10% of EtOAc in petroleum ether) to provide tert-butyl 4-(4-(hydroxymethyl)phenyl)-3-oxopiperazine-1-carboxylate (6.1 g, 55% yield) as a white solid.

Step 2:
To a solution of tert-butyl 4-(4-(hydroxymethyl)phenyl)-3-oxopiperazine-1-carboxylate (2 g, 6.53 mmol, 1 eq) in DCM (10 mL) was added TFA (5.00 mL, 67.53 mmol, 10.34 eq) at 0° C. The mixture was stirred at 25° C. for 3 h before it was concentrated. The residue was diluted with water (20 mL) and extracted with a mixture of DCM and MeOH (50:1=v:v, 2×20 mL). The combined organic layer was concentrated to provide crude 1-(4-(hydroxymethyl)phenyl)piperazin-2-one (2.45 g) as a colorless oil.

Step 3:
To a solution of crude 1-(4-(hydroxymethyl)phenyl)piperazin-2-one (2.45 g, 11.88 mmol, 1 eq) in MeOH (15 mL) was added HCHO (720 uL, 26.12 mmol, 2.2 eq), AcOH (5 mL, 87.42 mmol, 7.4 eq). The mixture was stirred at 25° C. under $N_2$ atmosphere for 15 h before $NaBH_3CN$ (2.05 g, 32.65 mmol, 2.75 eq) was added and the resulting mixture was stirred for 2 h. The reaction mixture was concentrated in vacuo. The residue was purified by flash column chromatography on silica gel (10-40% of MeOH in EtOAc) to give 1-(4-(hydroxymethyl)phenyl)-4-methylpiperazin-2-one (1.23 g) as a colorless oil.

Step 4:
To a solution of 1-(4-(hydroxymethyl)phenyl)-4-methylpiperazin-2-one (1.23 g, 5.58 mmol, 1 eq) in DCM (2 mL) was added DMF (0.2 mL) and $SOCl_2$ (810 uL, 11.17 mmol, 2 eq). The mixture was stirred at 25° C. for 30 min to give white suspension before it was concentrated under reduced pressure to give crude 1-(4-(chloromethyl)phenyl)-4-methyl-piperazin-2-one (1.27 g, 95% yield) as a white solid which was used in the next step directly.

Step 5:
To a solution of diethyl 2-(((3aR,5R,6R,6aR)-6-acetoxy-6-ethynyl-2,2-dimethyltetra-hydrofuro[2,3-d][1,3]dioxol-5-yl)methoxy)malonate (1.4 g, 3.38 mmol, 1 eq) in DMF (15 mL) was added $Cs_2CO_3$ (3.30 g, 10.14 mmol, 3 eq) and crude 1-(4-(chloromethyl)-phenyl)-4-methylpiperazin-2-one (1.21 g, 5.07 mmol, 1.5 eq). The mixture was stirred at 25° C. for 1 h before it was filtered and the filtrate was concentrated. The crude residue was purified by flash column chromatography on silica gel (0-50% MeOH in EtOAc) to give diethyl 2-(((3aR,5R,6R,6aR)-6-acetoxy-6-ethynyl-2,2-dimethyltetrahydrofuro[2,3-d][1,3]dioxol-5-yl)methoxy)-2-(4-(4-methyl-2-oxopiperazin-1-yl)benzyl)malonate (1.02 g).

Step 6:
To a solution of diethyl 2-(((3aR,5R,6R,6aR)-6-acetoxy-6-ethynyl-2,2-dimethyltetra-hydrofuro[2,3-d][1,3]dioxol-5-yl)methoxy)-2-(4-(4-methyl-2-oxopiperazin-1-yl)benzyl)-malonate (1.02 g, 1.65 mmol, 1 eq) in DCM (5 mL) and water (1 mL, 55.51 mmol, 34 eq) was added TFA (4.99 mL, 67.36 mmol, 41 eq). The mixture was stirred at 25° C. for 20 h before it was concentrated to give crude diethyl 2-(((2R,3S,4R)-3-ethynyl-3,4,5-trihydroxy-tetrahydrofuran-2-yl)methoxy)-2-(4-(4-methyl-2-oxopiperazin-1-yl)benzyl)malonate (1.13 g) as an oil.

To a solution of diethyl 2-[[(2R,3S,4R)-3-ethynyl-3,4,5-trihydroxy-tetrahydrofuran-2-yl]methoxy]-2-[[4-(4-methyl-2-oxo-piperazin-1-yl)phenyl]methyl]propanedioate (1.13 g, 2.11 mmol, 1 eq) in DCM (10 mL) was added 4-DMAP (25.78 mg, 211.00 umol, 0.1 eq), pyridine (1.07 mL, 13.2 mmol, 6.3 eq) and $Ac_2O$ (927 uL, 9.9 mmol, 4.7 eq). The mixture was stirred at 25° C. for 16 h before it was concentrated. The residue was diluted with EtOAc (20 mL) and 1N aq. HCl (10 mL). The organic layer was separated and the aqueous layer was extracted with EtOAc (4×20 mL). The combined organic layer was washed with water (50 mL), brine (50 mL) and dried over anhydrous $Na_2SO_4$, filtered and concentrated to provide crude diethyl 2-(4-(4-methyl-2-oxopiperazin-1-yl)benzyl)-2-(((2R,3R,4R)-3,4,5-triacetoxy-3-ethynyltetrahydrofuran-2-yl)methoxy)malonate (674 mg) as an syrup.

Step 7:
To a solution of 2-chloro-9H-purin-6-amine (76 mg, 450.46 umol, 1.2 eq) in dichloroethane (3 mL) was added BSA (204 uL, 825.84 umol, 2.2 eq). The mixture was stirred at 65° C. for 0.5 h before it was cooled to 0° C. and crude diethyl 2-(4-(4-methyl-2-oxopiperazin-1-yl)benzyl)-2-(((2R,3R,4R)-3,4,5-triacetoxy-3-ethynyltetrahydrofuran-2-yl)methoxy)malonate (248 mg, 375.38 umol, 1 eq) in dichloroethane (1 mL) and TMSOTf (102 uL, 563.07 umol, 1.5 eq) was added. The mixture was stirred at 65° C. for 2 h under $N_2$ atmosphere before it was quenched with saturated aq. $NaHCO_3$ (15 mL) and extracted with EtOAc (4×20 mL). The combined organic layer was dried over anhydrous $Na_2SO_4$, filtered and concentrated. The residue was purified by flash column chromatography on silica gel (0-30% of MeOH in EtOAc) to provide diethyl 2-(((2R,3R,4R,5R)-3,4-diacetoxy-5-(6-amino-2-chloro-9H-purin-9-yl)-3-ethynyltetrahydrofuran-2-yl)methoxy)-2-(4-(4-methyl-2-oxopiperazin-1-yl)benzyl)malonate (62 mg) as a white solid.

Step 8:
To a solution of diethyl 2-(((2R,3R,4R,5R)-3,4-diacetoxy-5-(6-amino-2-chloro-9H-purin-9-yl)-3-ethynyltetrahydrofuran-2-yl)methoxy)-2-(4-(4-methyl-2-oxopiperazin-1-yl)benzyl)malonate (171 mg, 222.02 umol, 1 eq) in THF (2 mL) was added aq. LiOH (5.32 mg, 222.02 umol, 2 mL, 1 eq). The mixture was stirred at 25° C. for 2.5 h before it was acidified to pH 2-3 with 2N aq. HCl. The mixture was concentrated under reduced pressure. The crude residue was further purified by preparative HPLC to provide 2-(((2R,3S,4R,5R)-5-(6-amino-2-chloro-9H-purin-9-yl)-3-ethynyl-3,4-dihydroxy-tetrahydro-furan-2-yl)methoxy)-2-(4-(4-methyl-2-oxopiperazin-1-yl)benzyl)-malonic acid (3.3 mg) as an off-white solid and 2-(((2R,3S,4R,5R)-5-(6-amino-2-chloro-9H-purin-9-yl)-3-ethynyl-3,4-dihydroxytetrahydrofuran-2-yl)methoxy)-2-(4-((2-((carboxymethyl)(methyl)amino) ethyl)-amino)benzyl)malonic acid (3.7 mg) as a white solid.

2-(((2R,3S,4R,5R)-5-(6-amino-2-chloro-9H-purin-9-yl)-3-ethynyl-3,4-dihydroxytetrahydro-furan-2-yl)methoxy)-2-(4-(4-methyl-2-oxopiperazin-1-yl)benzyl)malonic acid: $^1$H NMR (400 MHz, $CD_3OD$) δ ppm 8.35 (s, 1H), 7.35 (d, J=8.3 Hz, 2H), 6.97 (d, J=8.5 Hz, 2H), 5.95 (d, J=5.5 Hz, 1H), 4.70-4.79 (m, 1H), 4.33 (dd, J=9.0, 3.3 Hz, 1H), 3.96-4.14 (m, 2H), 3.54-3.66 (m, 2H), 3.49 (s, 2H), 3.35 (s, 1H), 3.21

(s, 2H), 2.83 (t, J=5.4 Hz, 2H), 2.32-2.48 (m, 3H), 1.89 (s, 3H); LC/MS [M+H]=630.2.

2-(((2R,3S,4R,5R)-5-(6-amino-2-chloro-9H-purin-9-yl)-3-ethynyl-3,4-dihydroxytetrahydro-furan-2-yl)methoxy)-2-(4-((2-((carboxymethyl)(methyl)amino)ethyl)amino)benzyl)malonic acid: ¹H NMR (400 MHz, CD₃OD) δ ppm 8.56 (s, 1H), 7.03 (d, J=8.5 Hz, 2H), 6.49 (d, J=8.3 Hz, 2H), 6.01 (d, J=6.0 Hz, 1H), 4.70 (d, J=6.0 Hz, 1H), 4.34 (br d, J=4.3 Hz, 1H), 3.94 (dd, J=9.7, 6.9 Hz, 1H), 3.83 (dd, J=9.9, 2.4 Hz, 1H), 3.59 (s, 2H), 3.34-3.42 (m, 2H), 3.22-3.27 (m, 2H), 3.20 (s, 2H), 3.04 (s, 1H), 2.83 (s, 3H); LC/MS [M+H]=649.3.

Example 156

Synthesis of 2-(((2R,3S,4R,5R)-5-(5-chloro-7-((2,4-dimethoxybenzyl)amino)-3H-imidazo[4,5-b]pyridin-3-yl)-3-ethynyl-3,4-dihydroxytetrahydrofuran-2-yl)methoxy)-2-(4-(2-oxotetrahydropyrimidin-1 (2H)-yl)benzyl)malonic acid

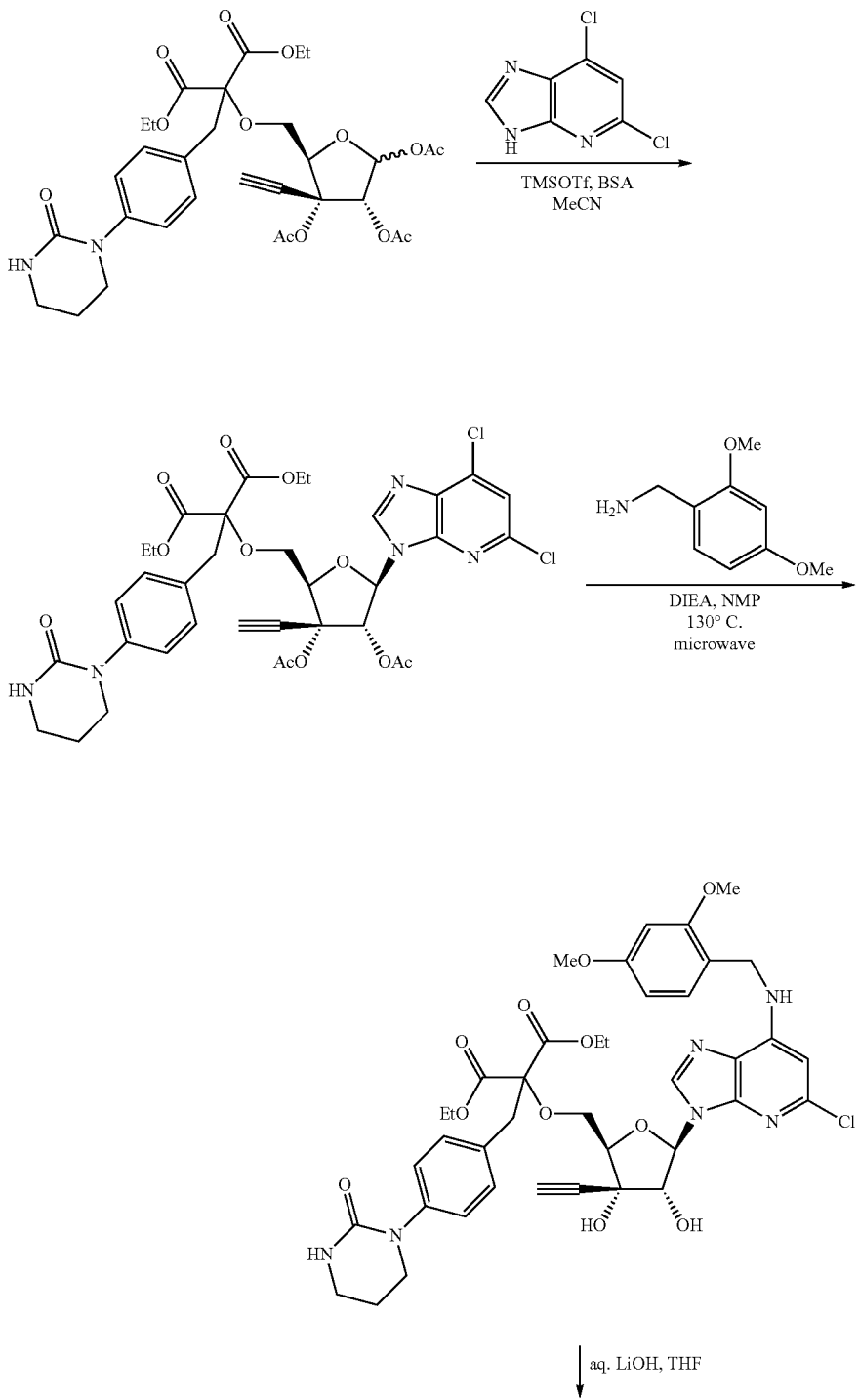

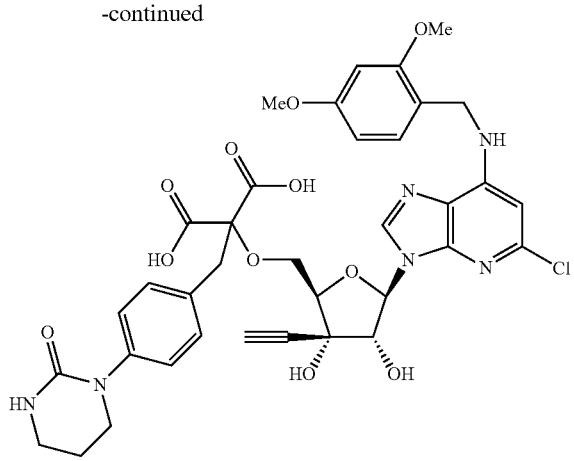

Example 156

Step 1:

To a mixture of 5,7-dichloro-3H-imidazo[4,5-b]pyridine (317 mg, 1.69 mmol, 1 eq) in MeCN (6 mL) was added BSA (1.04 mL, 4.22 mmol, 2.5 eq). The mixture was stirred at 65° C. under $N_2$ atmosphere for 0.5 h before it was cooled to 0° C. To the mixture was added diethyl 2-(4-(2-oxotetrahydropyrimidin-1(2H)-yl)benzyl)-2-(((2R,3R,4R)-3,4,5-triacetoxy-3-ethynyltetrahydrofuran-2-yl)methoxy)malonate (1.20 g, 1.85 mmol, 1.1 eq) and TMSOTf (913.99 uL, 5.06 mmol, 3 eq). The mixture was stirred at 65° C. under $N_2$ atmosphere for 6 h before it was quenched with $NaHCO_3$ (15 mL). The reaction mixture was extracted with EtOAc (3×15 mL). The combined organic layer was washed with brine (2×5 mL), dried over $Na_2SO_4$, filtered and concentrated under reduced pressure. The crude residue was purified by flash column chromatography on silica gel (0-100% of EtOAc in petroleum ether) to provide diethyl 2-(((2R,3R,4R,5R)-3,4-diacetoxy-5-(5,7-dichloro-3H-imidazo[4,5-b]pyridin-3-yl)-3-ethynyltetrahydrofuran-2-yl)methoxy)-2-(4-(2-oxotetrahydropyrimidin-1(2H)-yl)benzyl)malonate (752 mg) as a foam.

Step 2:

To a mixture of diethyl 2-(((2R,3R,4R,5R)-3,4-diacetoxy-5-(5,7-dichloro-3H-imidazo[4,5-b]pyridin-3-yl)-3-ethynyltetrahydrofuran-2-yl)methoxy)-2-(4-(2-oxotetrahydropyrimidin-1(2H)-yl)benzyl)malonate (752 mg, 970.82 umol, 1 eq) and 2,4-dimethoxybenzylamine (292 uL, 1.94 mmol, 2 eq) and DIEA (507 uL, 2.91 mmol, 3 eq) were taken up into a microwave tube in NMP (4 mL). The sealed tube was irradiated in a microwave reactor at 130° C. for 2 h before it was diluted with $H_2O$ (10 mL) and extracted with EtOAc (3×15 mL). The combined organic layer was washed with brine (10 mL), dried over $Na_2SO_4$, filtered and concentrated under reduced pressure. The crude residue was purified by flash column chromatography on silica gel (0-100% of EtOAc in petroleum) to provide diethyl 2-(((2R,3S,4R,5R)-5-(5-chloro-7-((2,4-dimethoxybenzyl)amino)-3H-imidazo[4,5-b]pyridin-3-yl)-3-ethynyl-3,4-dihydroxytetrahydrofuran-2-yl)methoxy)-2-(4-(2-oxotetrahydropyrimidin-1(2H)-yl)benzyl)malonate (249 mg, 26% yield) as a foam.

Step 3:

To a mixture of diethyl 2-(((2R,3S,4R,5R)-5-(5-chloro-7-((2,4-dimethoxybenzyl)-amino)-3H-imidazo[4,5-b]pyridin-3-yl)-3-ethynyl-3,4-dihydroxytetrahydrofuran-2-yl)-methoxy)-2-(4-(2-oxotetrahydropyrimidin-1 (2H)-yl) benzyl)malonate (239 mg, 291.01 umol, 1 eq) in THF (4 mL) and $H_2O$ (3 mL) was added LiOH (69.69 mg, 2.91 mmol, 10 eq). The mixture was stirred at 25° C. for 20 h before it was acidified to pH 6-7 with 2N aqueous HCl and concentrated under reduced pressure. The crude residue was purified by preparative HPLC (column: Phenomenex Gemini-NX 150*30 mm*5 um; mobile phase: [water (0.1% TFA)-ACN]; B %: 25%-65%, 10 min) and dried by lyophilization to provide 2-(((2R,3S,4R,5R)-5-(5-chloro-7-((2,4-dimethoxybenzyl)amino)-3H-imidazo[4,5-b]pyridin-3-yl)-3-ethynyl-3,4-dihydroxytetrahydrofuran-2-yl)methoxy)-2-(4-(2-oxotetrahydropyrimidin-1(2H)-yl)benzyl)malonic acid (9.5 mg) as a white solid.

$^1$H NMR (400 MHz, $CD_3OD$) δ ppm 8.23 (s, 1H), 7.27 (d, J=8.44 Hz, 2H), 7.21 (d, J=8.31 Hz, 1H), 7.00 (d, J=8.44 Hz, 2H), 6.58 (d, J=2.32 Hz, 1H), 6.46-6.51 (m, 2H), 6.04 (d, J=7.34 Hz, 1H), 4.73 (d, J=7.34 Hz, 1H), 4.43 (s, 2H), 4.27 (t, J=3.06 Hz, 1H), 4.01 (d, J=2.93 Hz, 2H), 3.87 (s, 3H), 3.78 (s, 3H), 3.37-3.47 (m, 2H), 3.31-3.37 (m, 2H), 3.22 (t, J=5.87 Hz, 2H), 3.03 (s, 1H), 1.78-1.85 (m, 2H); LC/MS [M+H]=765.1.

Example 157

Synthesis of 2-(((2R,3S,4R,5R)-5-(7-amino-5-chloro-3H-imidazo[4,5-b]pyridin-3-yl)-3-ethynyl-3,4-dihydroxytetrahydrofuran-2-yl)methoxy)-2-(4-(2-oxotetrahydropyrimidin-1(2H)-yl)benzyl)malonic acid

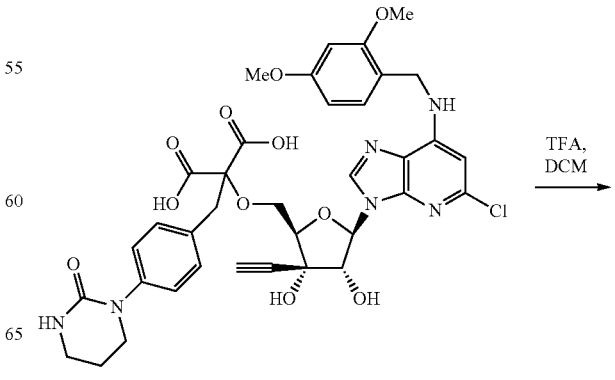

TFA, DCM

287

-continued

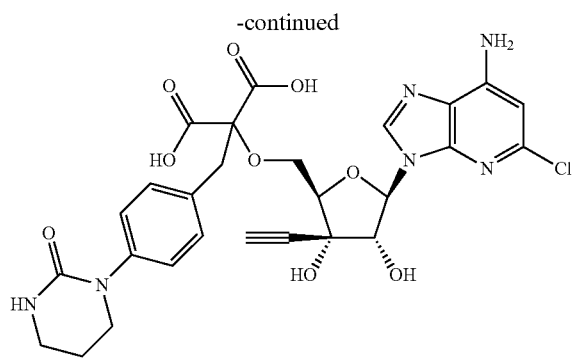

Example 157

To a mixture of 2-(((2R,3S,4R,5R)-5-(5-chloro-7-((2,4-dimethoxybenzyl)amino)-3H-imidazo[4,5-b]pyridin-3-yl)-3-ethynyl-3,4-dihydroxytetrahydrofuran-2-yl)methoxy)-2-(4-(2-oxotetrahydropyrimidin-1(2H)-yl)benzyl)malonic acid (160 mg, 209.11 umol, 1 eq) in DCM (3 mL) was added TFA (1 mL, 13.51 mmol, 64.59 eq). The mixture was stirred at 25° C. for 2 h before it was concentrated. The residue was purified by preparative HPLC (column: YMC-Actus Triart C18 150*30 mm*5 um; mobile phase: [water (0.225% FA)-ACN]; B %: 20%-40%, 10 min) and dried by lyophilization to provide 2-(((2R,3S,4R,5R)-5-(7-amino-5-chloro-3H-imidazo[4,5-b]pyridin-3-yl)-3-ethynyl-3,4-dihydroxytetrahydrofuran-2-yl)-methoxy)-2-(4-(2-oxotetrahydropyrimidin-1(2H)-yl)benzyl)malonic acid (5.4 mg) as a white solid.

$^1$H NMR (400 MHz, CD$_3$OD) δ ppm 8.34 (s, 1H), 7.28 (d, J=8.31 Hz, 2H), 7.02 (d, J=8.44 Hz, 2H), 6.49 (s, 1H), 6.07 (d, J=7.21 Hz, 1H), 4.78 (d, J=7.21 Hz, 1H), 4.30 (t, J=3.18 Hz, 1H), 3.93-4.08 (m, 2H), 3.45-3.54 (m, 2H), 3.35-3.49 (m, 4H), 3.04 (s, 1H), 1.94-2.00 (m, 2H); LC/MS [M+H]= 615.1.

Example 158

Synthesis of 2-((1H-pyrazol-5-yl)methyl)-2-(((2R,3S,4R,5R)-5-(6-amino-2-chloro-9H-purin-9-yl)-3-ethynyl-3,4-dihydroxytetrahydrofuran-2-yl)methoxy)malonic acid

288

-continued

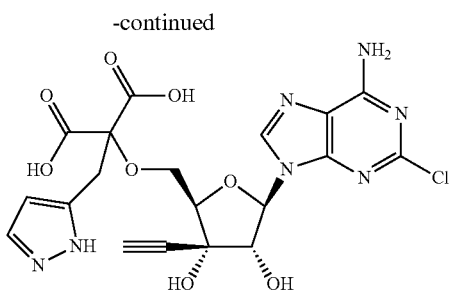

Example 158 Cal-210

Proceeding as described in Example 1 above but substituting benzyl bromide with tert-butyl 5-(bromomethyl)-1H-pyrazole-1-carboxylate provided the title compound as a white solid.

$^1$H NMR (400 MHz, CD$_3$OD) δ ppm 8.46 (s, 1H), 7.32 (s, 1H), 6.17 (s, 1H), 6.02 (d, J=7.13 Hz, 1H), 4.83 (s, 1H), 4.34 (s, 1H), 3.98-4.11 (m, 2H), 3.43-3.54 (m, 2H), 2.95 (s, 1H); LC/MS [M+H]=508.1.

Example 159

Synthesis of 2-benzyl-2-((((2R,3S,4R,5R)-5-(2-chloro-6-(1-tosyl-1H-pyrazol-4-yl)-9H-purin-9-yl)-3-ethynyl-3,4-dihydroxytetrahydrofuran-2-yl)methoxy)malonic acid

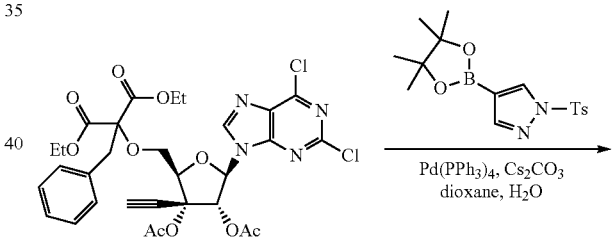

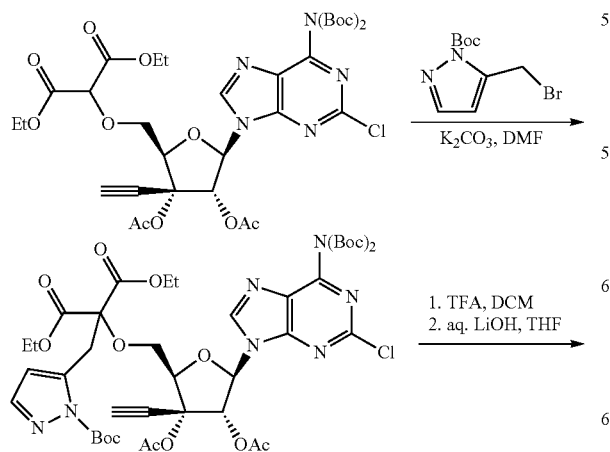

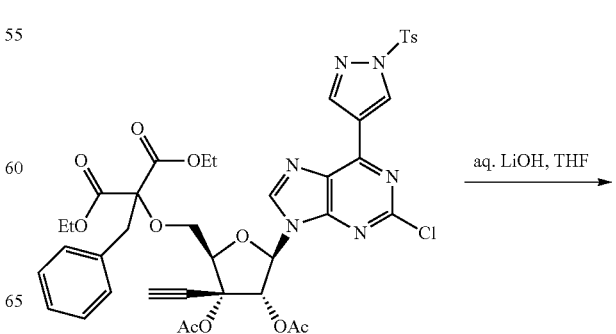

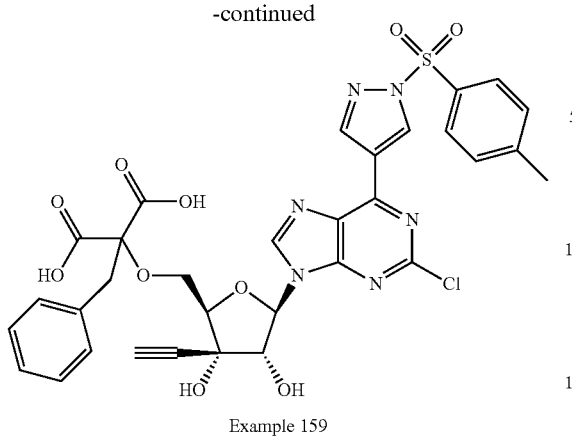

Example 159

Step 1:

To a mixture of diethyl 2-benzyl-2-(((2R,3R,4R,5R)-3,4-diacetoxy-5-(2,6-dichloro-9H-purin-9-yl)-3-ethynyltetrahydrofuran-2-yl)methoxy)malonate (1.3 g, 1.92 mmol, 1 eq) and 4-(4,4,5,5-tetramethyl-1,3,2-dioxaborolan-2-yl)-1-tosyl-1H-pyrazole (669 mg, 1.92 mmol, 1 eq) in dioxane (10 mL) and H$_2$O (3 mL) under a N$_2$ atmosphere was added Pd(PPh$_3$)$_4$ (222 mg, 192 umol, 0.1 eq) and Cs$_2$CO$_3$ (1.88 g, 5.76 mmol, 3 eq). The mixture was stirred at 100° C. for 3 h before it was filtered and the filtrate was concentrated under reduced pressure. The crude residue was purified by flash silica gel column chromatography (0-50% of EtOAc in petroleum ether) to provide diethyl 2-benzyl-2-(((2R,3R,4R,5R)-3,4-diacetoxy-5-(2-chloro-6-(1-tosyl-1H-pyrazol-4-yl)-9H-purin-9-yl)-3-ethynyltetrahydrofuran-2-yl)methoxy)malonate (170 mg) as a foam.

Step 2:

To a solution diethyl 2-benzyl-2-(((2R,3R,4R,5R)-3,4-diacetoxy-5-(2-chloro-6-(1-tosyl-1H-pyrazol-4-yl)-9H-purin-9-yl)-3-ethynyltetrahydrofuran-2-yl)methoxy)malonate (50 mg, 58 umol, 1 eq) in THF (1 mL) was added 1M aq. LiOH (1 mL, 18 eq). The mixture was stirred at 25° C. for 14 h before it was diluted with EtOAc (10 mL) and water (10 mL). The aqueous phase was adjusted to pH 2-3 with 2M aq. HCl solution and extracted with EtOAc (2×40 mL), dried over anhydrous Na$_2$SO$_4$, filtered and concentrated under reduced pressure. The crude residue was purified by preparative HPLC (column: YMC-Triart Prep C18 150*40 mm*7 um; mobile phase: [water (0.225% FA)-AC]; B %: 40%-60%,10 min) to provide 2-benzyl-2-(((2R,3S,4R,5R)-5-(2-chloro-6-(1-tosyl-1H-pyrazol-4-yl)-9H-purin-9-yl)-3-ethynyl-3,4-dihydroxytetrahydrofuran-2-yl)methoxy)malonic acid (2.0 mg) as a white solid.

$^1$H NMR (400 MHz, CD$_3$OD) δ ppm 8.98 (s, 1H), 8.69 (s, 2H) 7.47 (d, J=8.25 Hz, 2H), 7.30 (d, J=6.88 Hz, 2H), 7.07-7.19 (m, 4H), 6.92 (d, J=8.00 Hz, 2H), 6.24 (d, J=7.63 Hz, 1H), 5.85 (d, J=7.63 Hz, 1H), 4.35 (t, J=2.56 Hz, 1H), 4.03-4.09 (m, 1H), 3.90 (d, J=10.63 Hz, 1H), 3.40-3.50 (m, 1H), 2.92 (s, 1H), 2.05 (s, 3H); LC/MS [M+H]=723.2.

Example 160

Synthesis of 2-(((2R,3S,4R,5R)-5-(2-chloro-6-(methylamino)-9H-purin-9-yl)-3-ethynyl-3,4-dihydroxytetrahydrofuran-2-yl)methoxy)-2-(4-(2-oxo-1-propy-1,2-dihydropyridin-3-yl)benzyl)malonic acid

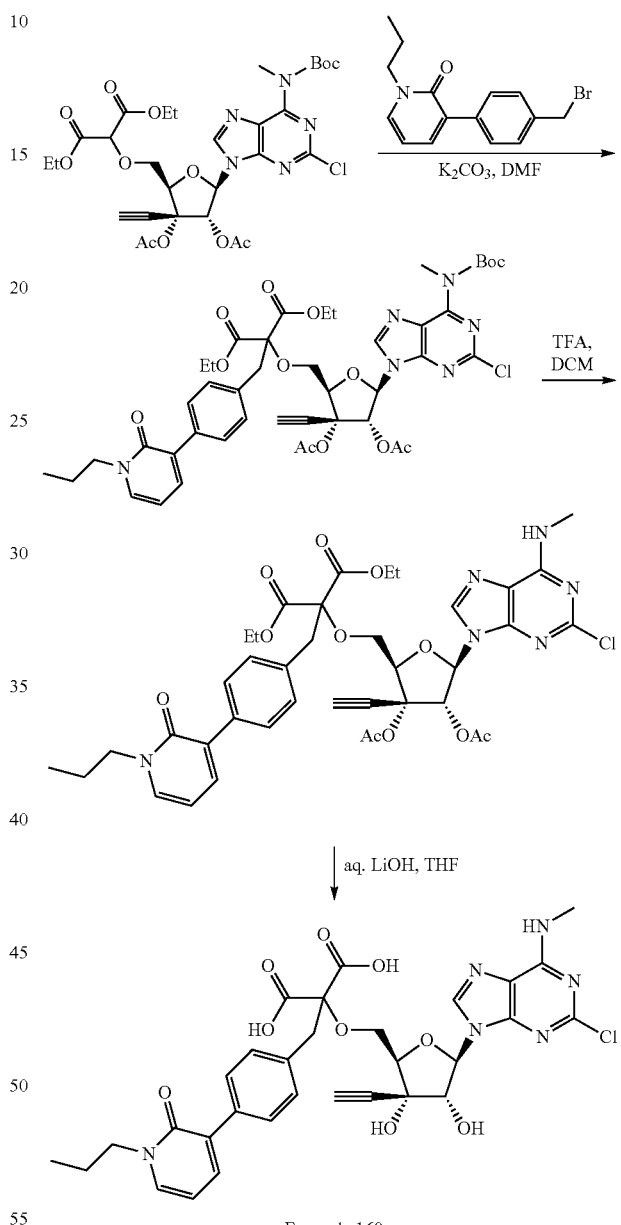

Example 160

Proceeding as described in Example 19 above but substituting diethyl 2-(((2R,3R,4R,5R)-3,4-diacetoxy-5-(6-N,N'-(bis-(tert-butoxycarbonyl)amino)-2-chloro-9H-purin-9-yl)-3-ethynyltetrahydrofuran-2-yl)methoxy)malonate with diethyl 2-(((2R,3R,4R,5R)-3,4-diacetoxy-5-(6-((tert-butoxycarbonyl)(methyl)amino)-2-chloro-9H-purin-9-yl)-3-ethynyl-tetrahydrofuran-2-yl)methoxy)malonate provided the title compound as a white solid.

$^1$H NMR (400 MHz, DMSO-d$_6$) δ ppm 8.44 (s, 1H), 8.25 (d, J=4.3 Hz, 1H), 7.68 (dd, J=6.7, 1.8 Hz, 1H), 7.29-7.51

(m, 3H), 7.18 (d, J=7.5 Hz, 2H), 6.28 (t, J=6.8 Hz, 1H), 6.21 (s, 1H), 6.01 (d, J=6.8 Hz, 1H), 5.83 (d, J=7.3 Hz, 1H), 4.82 (s, 1H), 4.17 (dd, J=5.1, 2.6 Hz, 1H), 3.96 (s, 1H), 3.89 (t, J=7.3 Hz, 2H), 3.79 (s, 1H), 3.58 (s, 1H), 3.25 (s, 1H), 2.90 (d, J=4.5 Hz, 3H), 1.67 (sxt, J=7.3 Hz, 2H), 0.88 (t, J=7.4 Hz, 3H); LC/MS [M+H]=667.1.

Example 161

Synthesis of 2-(((2R,3S,4R,5R)-5-(6-amino-2-(1-hydroxyethyl)-9H-purin-9-yl)-3-ethynyl-3,4-dihydroxytetrahydrofuran-2-yl)methoxy)-2-benzylmalonic acid

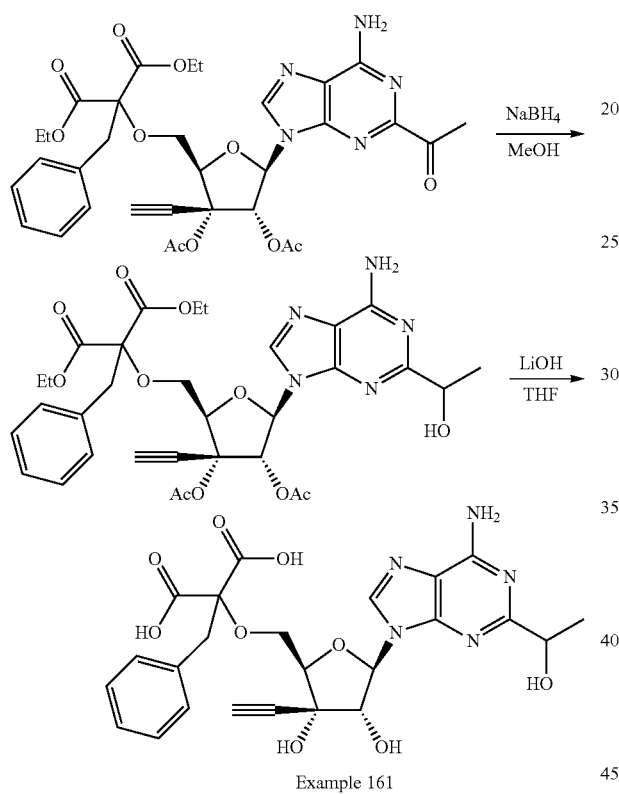

Example 161

Step 1:
To a solution of diethyl 2-benzyl-2-(((2R,3R,4R,5R)-3,4-diacetoxy-5-(2-acetyl-6-amino-9H-purin-9-yl)-3-ethynyltetrahydrofuran-2-yl)methoxy)malonate (48 mg, 72.11 umol, 1 eq) in MeOH (2 mL) at 0° C. was added NaBH$_4$ (4.09 mg, 108.17 umol, 1.5 eq). The solution was stirred at 0° C. for 1 h. Additional NaBH$_4$ (4.1 mg) was added to the reaction mixture and it was stirred at 0° C. for 0.5 h before it was diluted with water (6 mL) and extracted with ethyl acetate (3×6 mL). The combined organic layer was dried by Na$_2$SO$_4$, filtered and concentrated. The crude residue was purified by preparative TLC (ethyl acetate) to give diethyl 2-benzyl-2-(((2R,3R,4R,5R)-3,4-diacetoxy-5-(6-amino-2-(1-hydroxyethyl)-9H-purin-9-yl)-3-ethynyltetrahydrofuran-2-yl)methoxy)malonate (20 mg) as a syrup.

Step 2:
To a solution of diethyl 2-benzyl-2-(((2R,3R,4R,5R)-3,4-diacetoxy-5-(6-amino-2-(1-hydroxyethyl)-9H-purin-9-yl)-3-ethynyltetrahydrofuran-2-yl)methoxy)malonate (16 mg, 23.96 umol, 1 eq) in THF (2 mL) was added 1M aq. LiOH (0.5 mL, 21 eq). The mixture was stirred at 20° C. for 3 h before it was acidified to pH 5 with 1N aq. HCl solution. The mixture was extracted with ethyl acetate (5×3 mL). The combined organic layer was concentrated. The crude residue was purified by preparative HPLC (Column: YMC-Triart Prep C18 150*40 mm*7 um; mobile phase: [water (0.225% FA)-ACN]; B %: 13%-33%, 10 min) and dried by lyophilization to give 2-(((2R,3S,4R,5R)-5-(6-amino-2-(1-hydroxyethyl)-9H-purin-9-yl)-3-ethynyl-3,4-dihydroxytetrahydrofuran-2-yl)methoxy)-2-benzylmalonic acid (4.0 mg) as a white solid.

$^1$H NMR (400 MHz, CD$_3$OD) δ ppm 8.49 (d, J=8.88 Hz, 1H), 7.18-7.25 (m, 2H), 7.07-7.14 (m, 3H), 6.09 (dd, J=9.82, 6.94 Hz, 1H), 4.76-4.84 (m, 2H), 4.29-4.36 (m, 1H), 3.89-4.03 (m, 2H), 3.32-3.45 (m, 1H), 3.24-3.28 (m, 1H), 3.02 (d, J=10.13 Hz, 1H), 1.52 (d, J=6.50 Hz, 3H); LC/MS [M+H]=528.1.

Example 162

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(4-(1-methyl-2-oxo-1,2-dihydropyridin-3-yl)benzyl)malonic acid

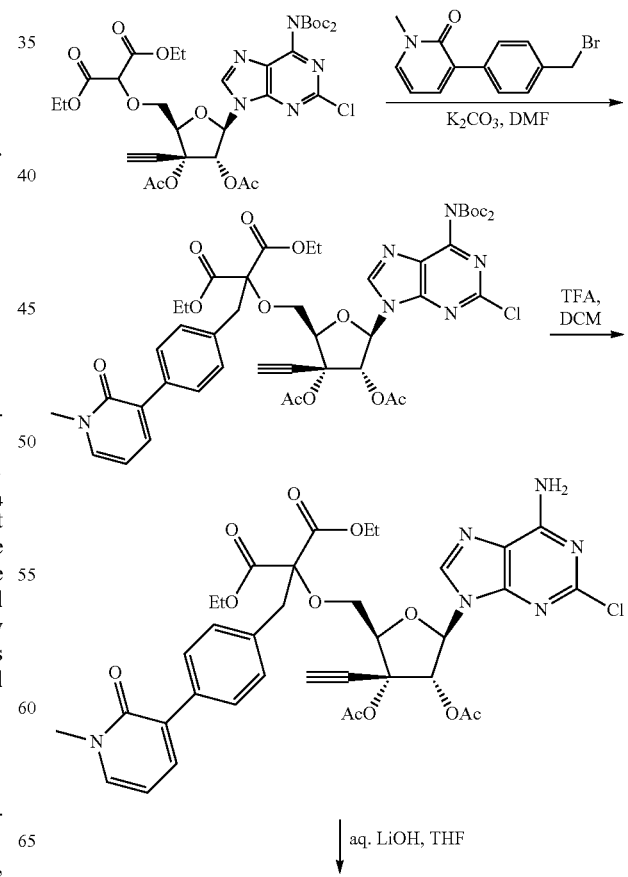

293

-continued

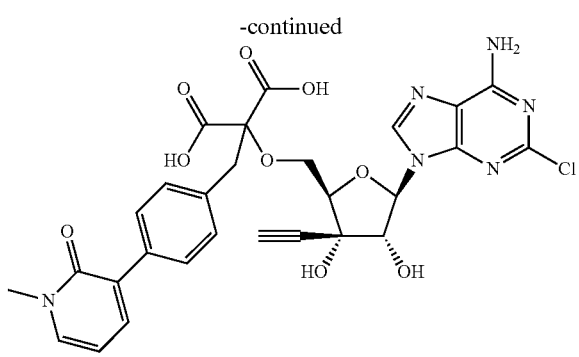

Example 162

Proceeding as described in Example 19 above but substituting 3-(4-(bromomethyl)-phenyl)-1-propylpyridin-2

294

(1H)-one with 3-(4-(bromomethyl)phenyl)-1-methylpyridin-2(1H)-one provided the title compound as a white solid.

$^1$H NMR (400 MHz, CD$_3$OD) δ ppm 8.12 (s, 1H), 7.55-7.53 (m, 1H), 7.38-7.28 (m, 5H), 6.33 (t, J=6.8 Hz, 1H), 5.94 (d, J=7.6 Hz, 1H), 4.75 (d, J=7.6 Hz, 1H), 4.27-4.26 (m, 1H), 4.09-4.01 (m, 2H), 3.55 (s, 3H), 3.53-3.44 (m, 2H), 3.05 (s, 1H); LC/MS [M+H]=625.0.

Example 163

Synthesis of 2-benzyl-2-(((2R,3S,4R,5R)-5-(6-(3-carboxypropyl)-2-chloro-9H-purin-9-yl)-3-ethynyl-3,4-dihydroxytetrahydrofuran-2-yl)methoxy)malonic acid

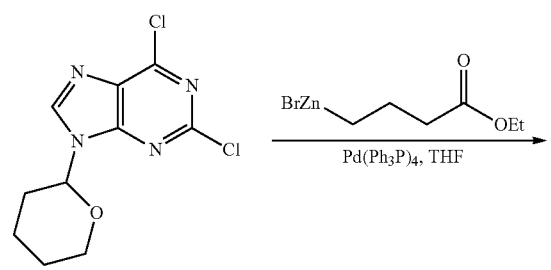

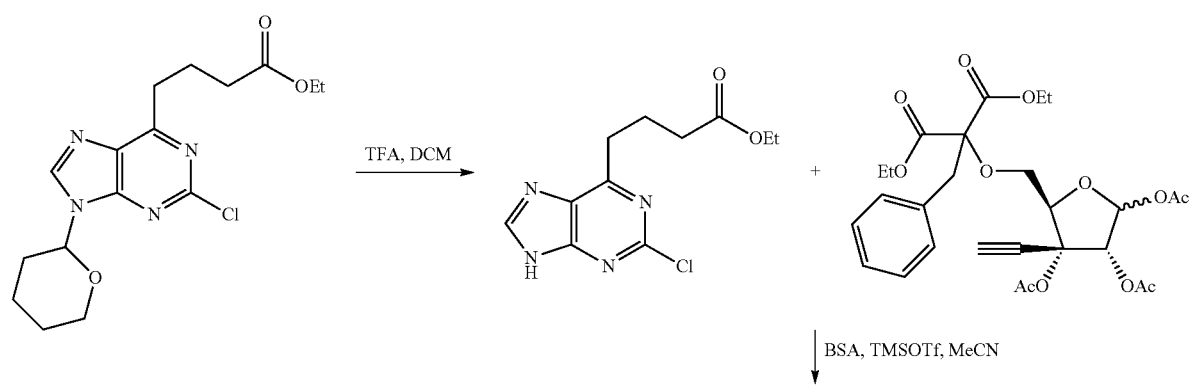

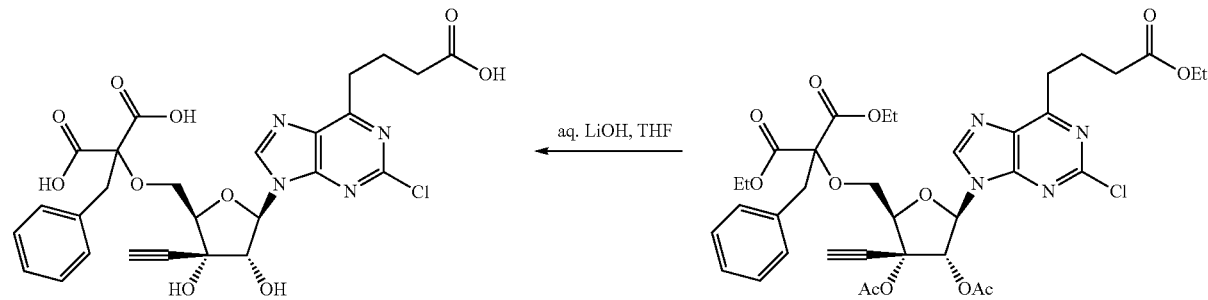

Example 163

Step 1:

To a solution of 2,6-dichloro-9-(tetrahydro-2H-pyran-2-yl)-9H-purine (4.00 g, 14.65 mmol, 1 eq) and Pd(Ph3P)4 (1.69 g, 1.46 mmol, 0.1 eq) in THF (30 mL) under N2 atmosphere at 0° C. was added a solution of 0.5 M (4-ethoxy-4-oxobutyl)zinc(II) bromide (73.23 mL, 36.61 mmol, 2.5 eq) dropwise. The mixture was stirred from 0-25° C. over 16 h before it was cooled to 0° C. and quenched with 0.5N aq. HCl solution. The reaction mixture was extracted with EtOAc (3×100 mL). The combined organic extract was washed with H2O (100 mL), brine (50 mL), dried over Na2SO4, filtered and concentrated. The crude residue was purified by flash column chromatography on silica gel (10-75% EtOAc in petroleum ether) to provide ethyl 4-(2-chloro-9-(tetrahydro-2H-pyran-2-yl)-9H-purin-6-yl)butanoate (2.83 g).

Step 2:

To a solution of thyl 4-(2-chloro-9-(tetrahydro-2H-pyran-2-yl)-9H-purin-6-yl)-butanoate (1.50 g, 4.25 mmol) in DCM (15 mL) was added TFA (10 mL). The mixture was stirred at 25° C. for 7 h before it was concentrated under reduced pressure. The residue was re-taken up in H2O (50 mL) and neutralized to pH 7 with saturated aq. NaHCO3. The resulting mixture was extracted with EtOAc (3×75 mL). The combined organic layer was washed with brine, dried over Na2SO4, filtered and concentrated to provide ethyl 4-(2-chloro-9H-purin-6-yl)butanoate (1.05 g).

Steps 3-4:

Proceeding as described in Example 5 above but substituting uracil with ethyl 4-(2-chloro-9H-purin-6-yl)butanoate provided the title compound as a white solid.

$^1$H NMR (400 MHz, CD$_3$OD) δ ppm 8.74 (s, 1H), 7.27-7.24 (m, 2H), 7.09-7.08 (m, 3H), 6.09 (d, J=7.6 Hz, 1H), 5.05 (d, J=7.6 Hz, 1H), 4.31-4.14 (m, 1H), 4.10-4.06 (m, 2H), 3.18-3.16 (m, 3H), 2.41 (t, J=7.2 Hz, 2H), 2.17-2.15 (m, 2H), 1.22 (t, J=7.6 Hz, 2H); LC/MS [M+H]=589.1.

Examples 164 and 165

Synthesis of (R)-2-(((2R,3S,4R,5R)-5-(6-amino-2-chloro-9H-purin-9-yl)-3-ethynyl-3,4-dihydroxytetrahydrofuran-2-yl)methoxy)-3-ethoxy-3-oxo-2-(4-(2-oxotetrahydropyrimidin-1 (2H)-yl)benzyl)propanoic acid and (S)-2-(((2R,3S,4R,5R)-5-(6-amino-2-chloro-9H-purin-9-yl)-3-ethynyl-3,4-dihydroxytetrahydrofuran-2-yl)methoxy)-3-ethoxy-3-oxo-2-(4-(2-oxotetrahydropyrimidin-1(2H)-yl)benzyl)propanoic acid

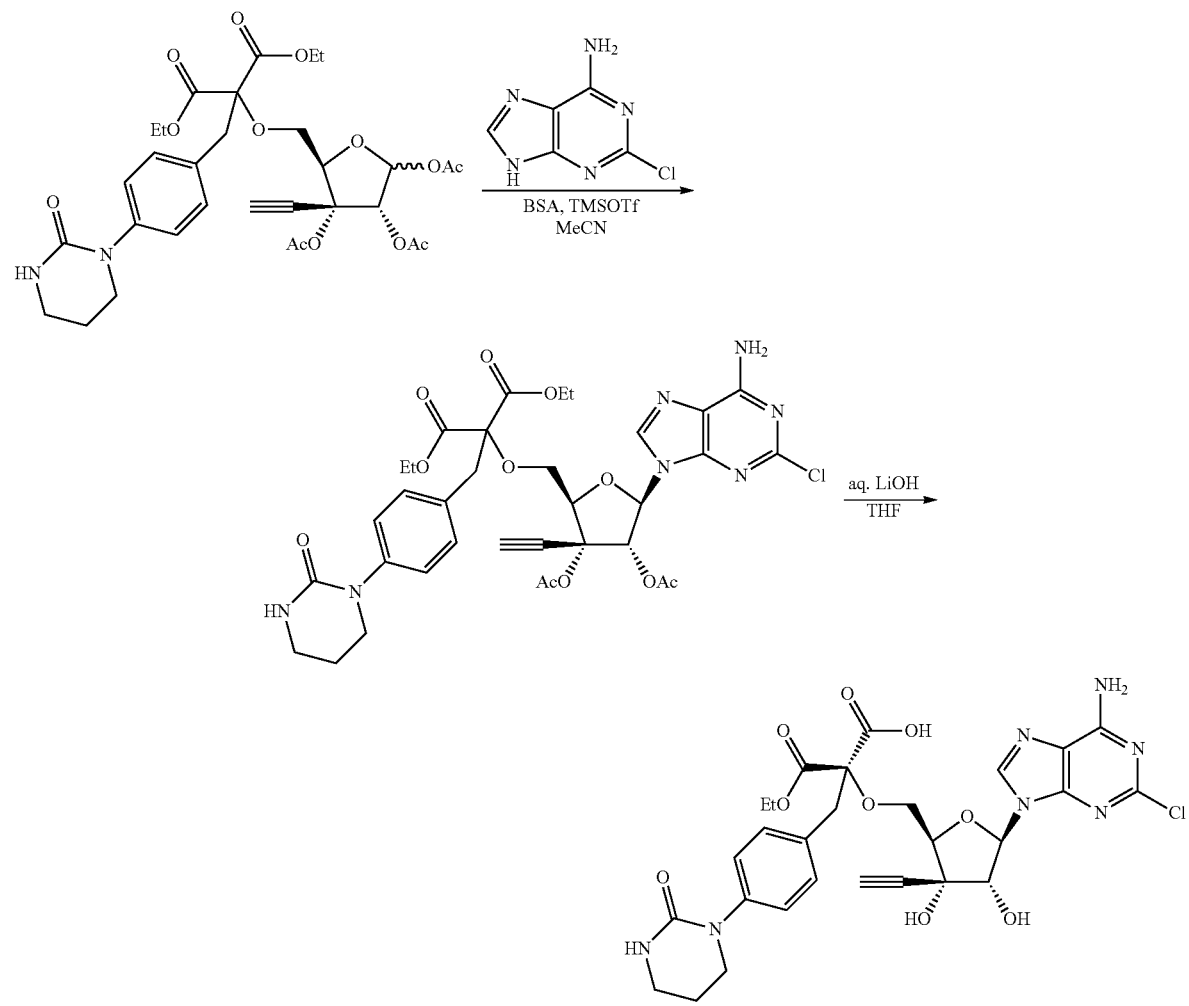

Example 164

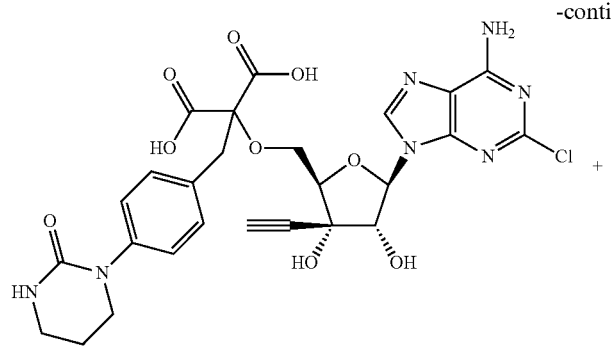

Example 9

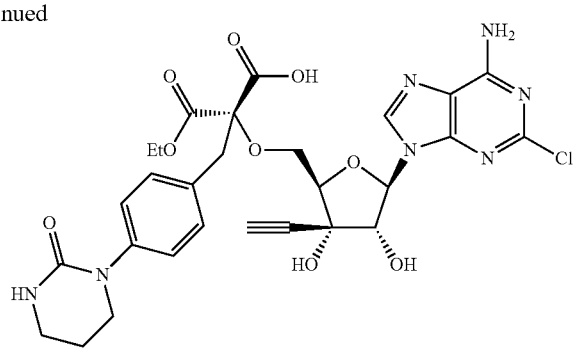

Example 165

Step 1:

To a suspension of 2-chloro-9H-purin-6-amine (1.04 g, 6.15 mmol, 1.7 eq) in MeCN (10 mL) at 25° C. was added N,O-bis(trimethylsilyl)acetamide (BSA) (3.1 mL, 0.0127 mol, 3.5 eq). The resulting suspension was heated at 85° C. for 30 min as it became clear. The reaction mixture was allowed to cool to 25° C. followed by addition of a solution of diethyl 2-(4-(2-oxotetrahydropyrimidin-1(2H)-yl)benzyl)-2-(((2R,3R,4R)-3,4,5-triacetoxy-3-ethynyltetrahydrofuran-2-yl)methoxy)malonate (2.34 g, 0.0036 mol, 1.0 eq) in MeCN (10 mL) and TMSOTf (1.12 mL, 0.00615 mol, 1.7 eq) dropwise. The reaction mixture was then heated at 70-80° C. overnight as all of the starting material was consumed. The reaction was allowed to cool to 25° C. before it was diluted with MeCN (100 mL) and quenched with saturated aq. NaHCO3 solution (150 mL). The insoluble was removed by filtration. The organic layer of the filtrate was separated, washed with H2O (50 mL), brine (50 mL), dried over Na2SO4 and concentrated. The crude residue was purified by flash silica gel column chromatography (0-5% MeOH in CH2Cl2) to provide diethyl 2-(((2R,3R,4R,5R)-3,4-diacetoxy-5-(6-amino-2-chloro-9H-purin-9-yl)-3-ethynyltetrahydrofuran-2-yl)methoxy)-2-(4-(2-oxotetrahydropyrimidin-1(2H)-yl)benzyl)malonate (1.1 g, 40% yield) as a white solid.

Step 2:

To a solution of diethyl 2-(((2R,3R,4R,5R)-3,4-diacetoxy-5-(6-amino-2-chloro-9H-purin-9-yl)-3-ethynyltetrahydrofuran-2-yl)methoxy)-2-(4-(2-oxotetrahydropyrimidin-1 (2H)-yl)benzyl)malonate (400 mg, 0.53 mmol, 1 eq) in THF (4 mL) and H2O (4 mL) at 0° C. was added LiOH monohydrate (89 mg, 2.12 mmol, 4 eq). The resulting mixture was stirred at room temperature overnight before the organic volatile was removed under reduced pressure.

The mixture was cooled to 0° C. and acidified to pH 6 with 1N aq. HCl solution and concentrated under reduced pressure. The crude residue was purified by preparative reversed-phase HPLC to provide a pair of diastereomers as a white solid: (R)-2-(((2R,3S,4R,5R)-5-(6-amino-2-chloro-9H-purin-9-yl)-3-ethynyl-3,4-dihydroxytetrahydro-furan-2-yl)methoxy)-3-ethoxy-3-oxo-2-(4-(2-oxotetrahydropyrimidin-1(2H)-yl)benzyl)-propanoic acid and (S)-2-(((2R,3S,4R,5R)-5-(6-amino-2-chloro-9H-purin-9-yl)-3-ethynyl-3,4-dihydroxytetrahydrofuran-2-yl)methoxy)-3-ethoxy-3-oxo-2-(4-(2-oxotetrahydropyrimidin-1(2H)-yl)benzyl)propanoic acid which the stereo configuration was arbitrarily assigned. In addition, Example 9 was also isolated as a white solid.

(R)-2-(((2R,3S,4R,5R)-5-(6-amino-2-chloro-9H-purin-9-yl)-3-ethynyl-3,4-dihydroxytetra-hydrofuran-2-yl) methoxy)-3-ethoxy-3-oxo-2-(4-(2-oxotetrahydropyrimidin-1(2H)-yl)benzyl)propanoic acid: $^1$H NMR (300 MHz, CD3OD) δ 8.32 (s, 1H), 7.28 (d, J=8.1 Hz, 2H), 7.01 (d, J=8.1 Hz, 2H), 6.00 (d, J=7.5 Hz, 1H), 4.84 (d, J=7.5, 1H), 4.28-4.06 (m, 3H), 3.99-3.95 (m, 2H), 3.52-3.35 (m, 6H), 3.08 (s, 1H), 2.02-1.97 (m, 2H), 1.21 (t, J=7.1, 3H); LC/MS [M+H]=644.05.

(S)-2-(((2R,3S,4R,5R)-5-(6-amino-2-chloro-9H-purin-9-yl)-3-ethynyl-3,4-dihydroxytetra-hydrofuran-2-yl) methoxy)-3-ethoxy-3-oxo-2-(4-(2-oxotetrahydropyrimidin-1(2H)-yl)benzyl)propanoic acid: $^1$H NMR (300 MHz, CD3OD) δ 8.08 (s, 1H), 7.26-7.29 (d, J=6.8 Hz, 2H), 7.03-7.01 (d, J=7.23 Hz, 2H), 5.96-5.99 (d, J=7.14 Hz, 1H), 4.75-4.77 (d, J=7.5, 1H), 4.02-4.24 (m, 5H), 3.32-3.66 (m, 6H), 3.15 (s, 1H), 1.95-2.19 (m, 2H), 1.22-1.27 (m, 3H); LC/MS [M+H]=644.05.

Examples 166 and 167

Synthesis of (R)-2-(((2R,3S,4R,5R)-5-(6-amino-2-chloro-9H-purin-9-yl)-3-ethynyl-3,4-dihydroxytetrahydrofuran-2-yl)methoxy)-3-(4-(2-oxotetrahydropyrimidin-1 (2H)-yl)phenyl)propanoic acid and (S)-2-(((2R,3S,4R,5R)-5-(6-amino-2-chloro-9H-purin-9-yl)-3-ethynyl-3,4-dihydroxytetrahydrofuran-2-yl) methoxy)-3-(4-(2-oxotetrahydropyrimidin-1 (2H)-yl)phenyl)propanoic acid

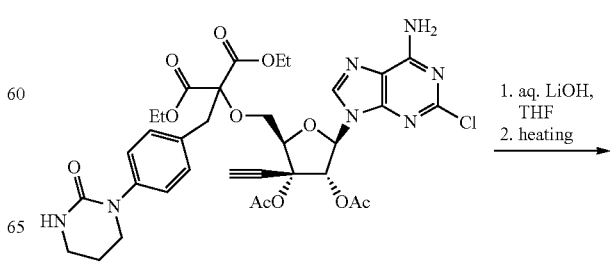

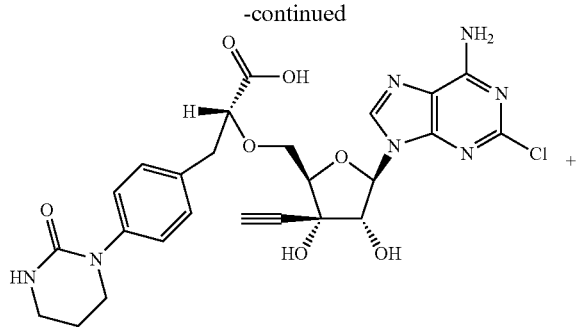

Example 165

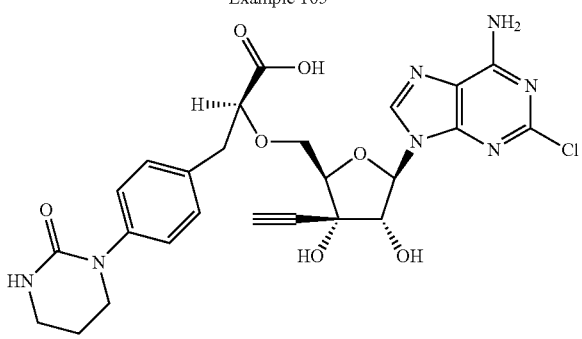

Example 166

The crude product of Example 9 from the work up was dried in the vacuum oven at 60° C. for 2 days before it was purified by preparative HPLC to provide a pair of diastereomers: (R)-2-(((2R,3S,4R,5R)-5-(6-amino-2-chloro-9H-purin-9-yl)-3-ethynyl-3,4-dihydroxytetrahydrofuran-2-yl)methoxy)-3-(4-(2-oxotetrahydropyrimidin-1(2H)-yl)phenyl)-propanoic acid and (S)-2-(((2R,3S,4R,5R)-5-(6-amino-2-chloro-9H-purin-9-yl)-3-ethynyl-3,4-dihydroxytetrahydrofuran-2-yl)methoxy)-3-(4-(2-oxotetrahydropyrimidin-1(2H)-yl)phenyl)-propanoic acid which the stereo configuration was arbitrarily assigned. Both were isolated as white solids.

(R)-2-(((2R,3S,4R,5R)-5-(6-amino-2-chloro-9H-purin-9-yl)-3-ethynyl-3,4-dihydroxytetra-hydrofuran-2-yl)methoxy)-3-(4-(2-oxotetrahydropyrimidin-1(2H)-yl)phenyl)propanoic acid: $^1$H NMR (300 MHz, CD$_3$OD) δ 8.38 (s, 1H), 7.22 (d, J=8.3 Hz, 2H), 7.04 (d, J=8.3 Hz, 2H), 5.92 (d, J=7.3 Hz, 1H), 4.36-4.32 (m, 1H), 4.30 (d, J=7.3 Hz, 1H), 4.17 (t, J=2.3 Hz, 1H), 4.07-4.03 (m, 1H), 3.80-3.75 (m, 1H), 3.54-3.49 (m, 2H), 3.33-3.31 (m, 2H), 3.25-3.19 (m, 1H), 3.12 (s, 1H), 3.09-3.02 (m, 1H), 2.02-1.97 (m, 2H); LC/MS [M+H]=572.0.

(S)-2-(((2R,3S,4R,5R)-5-(6-amino-2-chloro-9H-purin-9-yl)-3-ethynyl-3,4-dihydroxytetra-hydrofuran-2-yl)methoxy)-3-(4-(2-oxotetrahydropyrimidin-1(2H)-yl)phenyl)propanoic acid: $^1$H NMR (300 MHz, CD$_3$OD) δ 8.47 (s, 1H), 7.26 (d, J=8.2 Hz, 2H), 7.15 (d, J=8.3 Hz, 2H), 5.97 (d, J=7.0 Hz, 1H), 4.97 (d, J=7.0 Hz, 1H), 4.31 (t, J=6.4 Hz, 1H), 4.20 (t, J=3.4 Hz, 1H), 3.91 (d, J=3.4 Hz, 1H), 3.65 (t, J=6.0 Hz, 2H), 3.39-3.33 (m, 2H), 3.23-3.17 (m, 2H), 3.08 (s, 1H), 3.06-3.01 (m, 1H), 2.10-1.95 (m, 2H); LC/MS [M+H]=572.0.

Example 168

Synthesis of 2-benzyl-2-(((2R,3S,4R,5R)-5-(2-chloro-6-(hydroxyamino)-9H-purin-9-yl)-3-ethynyl-3,4-dihydroxytetrahydrofuran-2-yl)methoxy)malonic acid

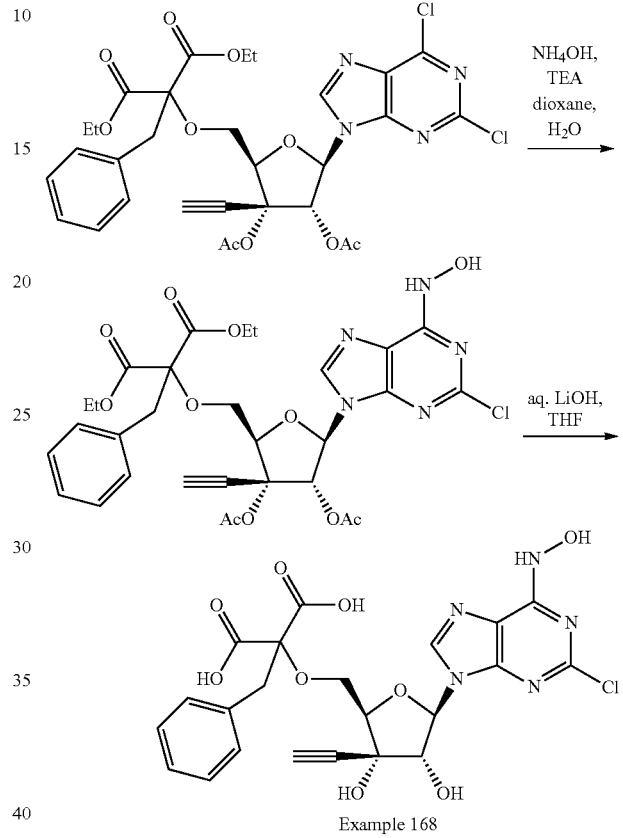

Example 168

Step 1:
To a solution of diethyl 2-benzyl-2-(((2R,3S,4R,5R)-5-(5-chloro-7-(hydroxyamino)-3H-imidazo[4,5-b]pyridin-3-yl)-3-ethynyl-3,4-dihydroxytetrahydrofuran-2-yl)methoxy)-malonate (98 mg, 0.144 mmol) in dioxane (2 mL) was added an aqueous solution of hydroxylamine (0.1 mL, 1.6 mmol, 16 M) and Et$_3$N (35 uL, 0.16 mmol). The reaction mixture was stirred for 2.5 h and then it was diluted with EtOAc (15 mL) and H$_2$O (5 mL). The organic layer was separated, washed with H$_2$O (20 mL), brine (20 mL), dried over Na$_2$SO$_4$ and concentrated to provide crude diethyl 2-benzyl-2-(((2R,3R,4R,5R)-3,4-diacetoxy-5-(2-chloro-6-(hydroxyamino)-9H-purin-9-yl)-3-ethynyltetrahydrofuran-2-yl)methoxy)-malonate (88 mg) as an off-solid which was used in the next step without further purification.

Step 2:
To a solution of crude diethyl 2-benzyl-2-(((2R,3R,4R,5R)-3,4-diacetoxy-5-(2-chloro-6-(hydroxyamino)-9H-purin-9-yl)-3-ethynyltetrahydrofuran-2-yl)methoxy)malonate (88 mg, 0.14 mmol) in a mixture of THF (0.2 mL), MeOH (0.62 mL) and H$_2$O (0.15 mL) was added LiOH.H$_2$O (31 mg, 0.75 mmol). The resulting mixture was stirred at 25° C. for 5.5 h before the organic volatile was removed under reduced pressure. The aq. layer was cooled to 0° C. and acidified to pH 6.5 with 1N aq. HCl solution before it was concentrated. The crude residue was purified by preparative reversed-phase HPLC to provide 2-benzyl-2-(((2R,3S,4R,5R)-5-(5-chloro-7-(hydroxyamino)-3H-imidazo[4,5-b]pyridin-3-yl)-3-ethynyl-3,4-dihydroxytetrahydrofuran-2-yl)methoxy)malonic acid (17 mg) as a reddish solid.

$^1$H NMR (CD$_3$OD, 300 MHz) δ 8.25 (s, 1H), 7.25-7.28 (m, 2H), 7.05 (m, 3H), 6.43 (s, 1H), 6.06-6.08 (d, J=7.17 Hz, 1H), 4.95-4.98 (d, J=7.05 Hz, 1H), 4.32 (s, 1H), 4.05-4.11 (m, 2H), 3.89-3.93 (m, 1H), 3.31-3.39 (m, 2H), 2.99 (s, 1H), 1.30-1.33 (m, 6H); LC/MS [M+H]=533.1.

Example 169

Synthesis of 2-(((2R,3S,4R,5R)-5-(2-chloro-6-(isopropylamino)-9H-purin-9-yl)-3-ethynyl-3,4-dihydroxytetrahydrofuran-2-yl)methoxy)-2-(thiazol-4-yl)-3-(thiophen-3-yl)propanoic acid

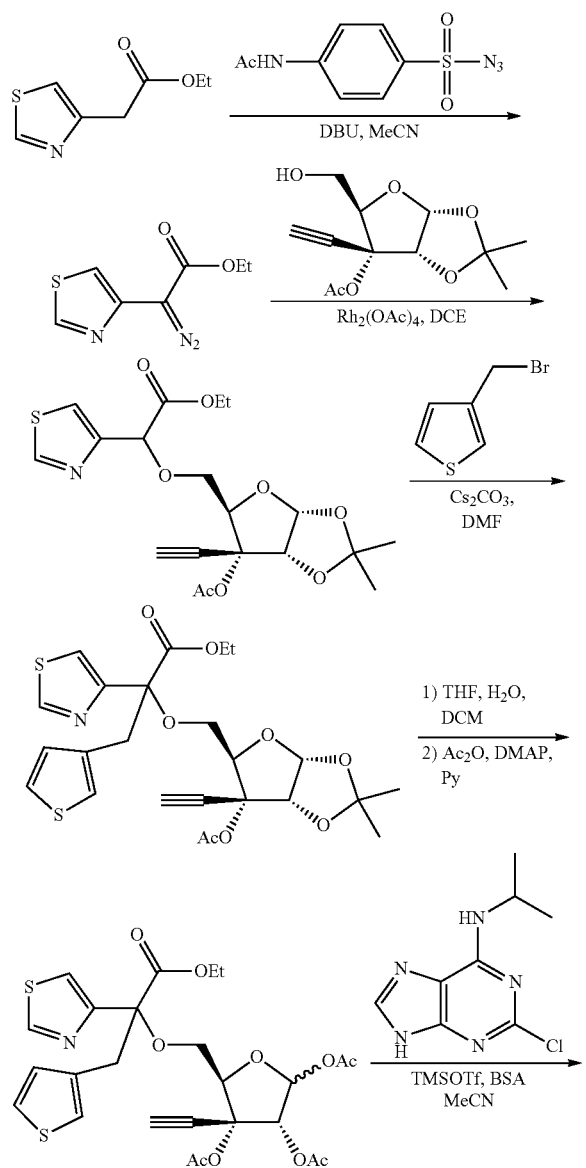

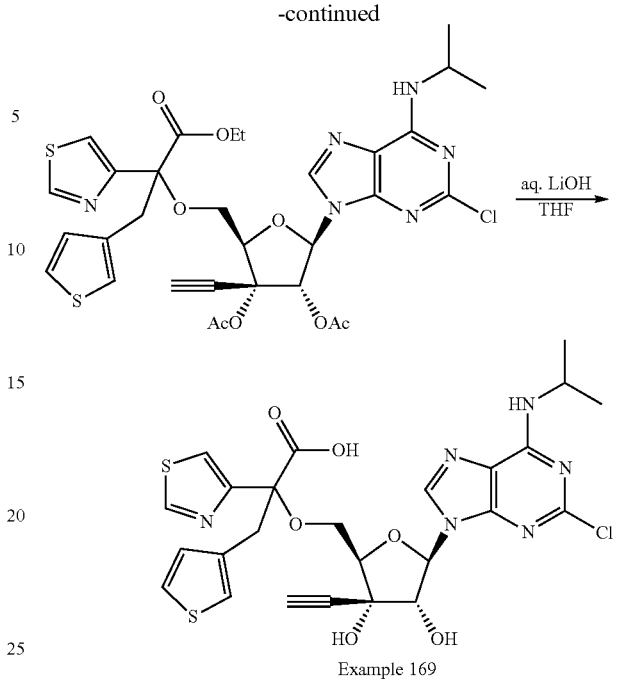

Example 169

Step 1:
To a solution of ethyl 2-(thiazol-4-yl)acetate (2 g, 11.7 mmole) in CH$_3$CN (15 mL) at 0° C. was added DBU (2.62 ml, 17.6 mmole) and 4-acetamidibenzenesulfonylazide (3.4 g, 14.1 mmole) in CH$_3$CN (10 mL). The reaction mixture was stirred at room temperature for 1.5 h before it was concentrated under reduced pressure to dryness. The resulting crude was purified by silica gel column chromatography (0-40% EtOAc in hexanes) to provide ethyl 2-diazo-2-(thiazol-4-yl)acetate (2.0 g).

Step 2:
To a mixture of (3aR,5R,6R,6aR)-6-ethynyl-5-(hydroxymethyl)-2,2-dimethyltetra-hydrofuro[2,3-d][1,3]dioxol-6-yl acetate (7 g, 27.32 mmol, 1 eq) in DCE (15 mL) was added Rh(OAc)$_2$ (603.69 mg, 2.73 mmol, 0.1 eq) and ethyl 2-diazo-2-(thiazol-4-yl)acetate (6.46 g, 32.78 mmol, 1.2 eq) in DCE (15 mL) dropwise at 0° C. The mixture was stirred at 25° C. under N$_2$ atmosphere for 14 h before the insoluble was filtered and the filtrate was concentrated under reduced pressure. The crude residue was purified by flash silica gel column chromatography (0-50% of EtOAc in petroleum ether) to provide ethyl 2-(((3aR,5R,6R,6aR)-6-acetoxy-6-ethynyl-2,2-dimethyltetrahydrofuro[2,3-d][1,3]dioxol-5-yl)methoxy)-2-(thiazol-4-yl)acetate (10.81 g, 93% yield) as an oil.

Step 3:
To a mixture of ethyl 2-(((3aR,5R,6R,6aR)-6-acetoxy-6-ethynyl-2,2-dimethyltetra-hydrofuro[2,3-d][1,3]dioxol-5-yl)methoxy)-2-(thiazol-4-yl)acetate (2.69 g, 6.33 mmol, 1 eq) in DMF (5 mL) was added Cs$_2$CO$_3$ (6.18 g, 18.98 mmol, 3 eq). The mixture was stirred at 25° C. under N$_2$ atmosphere for 0.5 h before 3-(bromomethyl)thiophene (2.8 g, 15.81 mmol, 2.5 eq) was added. The resulting mixture was stirred at 25° C. for 14 h before the insoluble was filtered and the filtrate was diluted with H$_2$O (15 mL) and extracted with EtOAc (3×15 mL). The combined organic layer was washed with saturated aq. NH$_4$Cl (3×15 mL), dried over Na$_2$SO$_4$, filtered and concentrated under reduced pressure. The crude residue was purified by flash silica gel column chromatography (0-50% of EtOAc in petroleum) to provide ethyl 2-(((3aR,5R,6R,6aR)-6-acetoxy-6-ethynyl-2,2-dimethyltetrahydrofuro[2,3-d][1,3]dioxol-5-yl)methoxy)-2-(thiazol-4-yl)-3-(thiophen-3-yl)propanoate (2.27 g, 69% yield) as an oil.

Step 4:

To a mixture of ethyl 2-(((3aR,5R,6R,6aR)-6-acetoxy-6-ethynyl-2,2-dimethyltetra-hydrofuro[2,3-d][1,3]dioxol-5-yl)methoxy)-2-(thiazol-4-yl)-3-(thiophen-3-yl)propanoate (2.27 g, 4.35 mmol, 1 eq) in DCM (5 mL) and H₂O (0.5 mL) was added TFA (5 mL, 67.53 mmol, 15.5 eq). The mixture was stirred at 15° C. under N₂ atmosphere for 14 h before it was adjusted to 7-8 pH with saturated aq. NaHCO₃(50 mL) and concentrated under reduced pressure. The residue was diluted with H₂O (5 mL) and extracted with EtOAc (4×15 mL). The combined organic layer was washed with brine (10 mL), dried over Na₂SO₄, filtered and concentrated under reduced pressure to provide crude ethyl 2-[[(2R,3S,4R)-3-acetoxy-3-ethynyl-4,5-dihydroxy-tetrahydrofuran-2-yl]methoxy]-2-thiazol-4-yl-3-(3-thienyl)propanoate (1.82 g) as a syrup.

To a solution of ethyl 2-[[(2R,3S,4R)-3-acetoxy-3-ethynyl-4,5-dihydroxy-tetrahydro-furan-2-yl]methoxy]-2-thiazol-4-yl-3-(3-thienyl)propanoate (1.82 g, 3.78 mmol, 1 eq) in pyridine (8 mL) under a N₂ atmosphere at 0° C. was added 4-DMAP (1.39 g, 11.34 mmol, 3 eq) and Ac₂O (2.83 mL, 30.24 mmol, 8 eq). The mixture was stirred at 15° C. for 15 before it was diluted with H₂O (20 mL) and extracted with EtOAc (3×15 mL). The combined organic layer was washed with 10% CuSO₄ solution (2×15 mL), dried over Na₂SO₄, filtered and concentrated under reduced pressure to give crude (3R,4R,5R)-5-(((1-ethoxy-1-oxo-2-(thiazol-4-yl)-3-(thiophen-3-yl)propan-2-yl)oxy)methyl)-4-ethynyltetrahydrofuran-2,3,4-triyl triacetate (2.42 g) as a syrup.

Step 5:

To a mixture of 2-chloro-N-isopropyl-9H-purin-6-amine (606.20 mg, 2.86 mmol, 1 eq) in DCE (20 mL) was added BSA (1.77 mL, 7.16 mmol, 2.5 eq). The mixture was stirred at 85° C. under a N₂ atmosphere for 0.5 h before it was allowed to cool to 0° C. and followed by addition of crude (3R,4R,5R)-5-(((1-ethoxy-1-oxo-2-(thiazol-4-yl)-3-(thiophen-3-yl)-propan-2-yl)oxy)methyl)-4-ethynyltetrahydrofuran-2,3,4-triyl triacetate (1.62 g, 2.86 mmol, 1 eq) and TMSOTf (1.55 mL, 8.59 mmol, 3 eq). The resulting mixture was stirred at 65° C. under N₂ for 14 h before it was quenched with saturated aq. NaHCO₃(20 mL). The reaction mixture was diluted with H₂O (10 mL) and extracted with DCM (3×20 mL). The combined organic layer was washed with brine (3×15 mL), dried over Na₂SO₄, filtered and concentrated under reduced pressure. The crude residue was purified by flash silica gel column chromatography (0-50% of EtOAc in petroleum ether) to provide (2R,3R,4R,5R)-5-(2-chloro-6-(isopropylamino)-9H-purin-9-yl)-2-(((1-ethoxy-1-oxo-2-(thiazol-4-yl)-3-(thio-phen-3-yl)propan-2-yl)oxy)methyl)-3-ethynyltetrahydrofuran-3,4-diyl diacetate (402 mg, crude) as a syrup.

Step 6:

To a mixture of (2R,3R,4R,5R)-5-(2-chloro-6-(isopropylamino)-9H-purin-9-yl)-2-(((1-ethoxy-1-oxo-2-(thiazol-4-yl)-3-(thiophen-3-yl)propan-2-yl)oxy)methyl)-3-ethynyltetra-hydrofuran-3,4-diyl diacetate (384 mg, crude) in THF (2 mL) and H₂O (1 mL) was added LiOH (128 mg, 5.35 mmol). The mixture was stirred at 50° C. for 6 h before it was diluted with H₂O (40 mL) and extracted with EtOAc (10 mL). The aqueous phase was acidified to pH 2-3 with 2 N aqueous HCl until pH-2-3 and then concentrated under reduced pressure. The crude residue was purified by preparative HPLC (column: YMC-Actus Triart C18 150*30 mm*5 um; mobile phase: [water (0.225% FA)-ACN]; B %: 40%-60%, 10 min) and dried by lyophilization to provide a diastereomeric mixture (ca. 1:1) of 2-(((2R,3S,4R,5R)-5-(2-chloro-6-(isopropylamino)-9H-purin-9-yl)-3-ethynyl-3,4-dihydroxytetrahydrofuran-2-yl)methoxy)-2-(thiazol-4-yl)-3-(thiophen-3-yl)propanoic acid (17.5 mg) as a white solid.

¹H NMR (400 MHz, CD₃OD) δ ppm 8.92-9.01 (m, 1H), 8.04-8.28 (m, 1H), 7.60-7.71 (m, 1H), 7.10-7.15 (m, 1H), 6.98-7.06 (m, 1H), 6.77-6.94 (m, 1H), 5.90-6.02 (m, 1H), 4.91-5.06 (m, 2H), 4.40 (br s, 1H), 4.19-4.32 (m, 1H), 3.89-3.99 (m, 1H), 3.65-3.87 (m, 3H), 2.89-3.02 (m, 1H), 1.25-1.35 (m, 6H); LC/MS [M+H]=605.2.

Examples 170 & 171

Synthesis of (S)-2-(((2R,3S,4R,5R)-5-(2-chloro-6-(isopropylamino)-9H-purin-9-yl)-3-ethynyl-3,4-dihydroxytetrahydrofuran-2-yl)methoxy)-3-phenyl-2-(thiazol-4-yl)propanoic acid and (R)-2-(((2R,3S,4R,5R)-5-(2-chloro-6-(isopropylamino)-9H-purin-9-yl)-3-ethynyl-3,4-dihydroxytetrahydrofuran-2-yl)methoxy)-3-phenyl-2-(thiazol-4-yl)propanoic acid

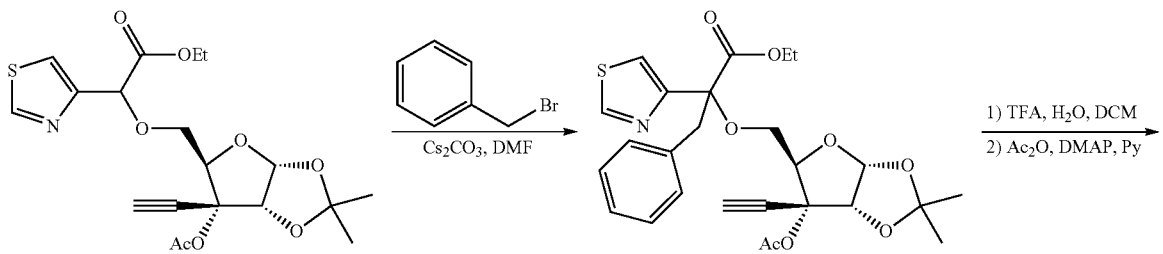

-continued

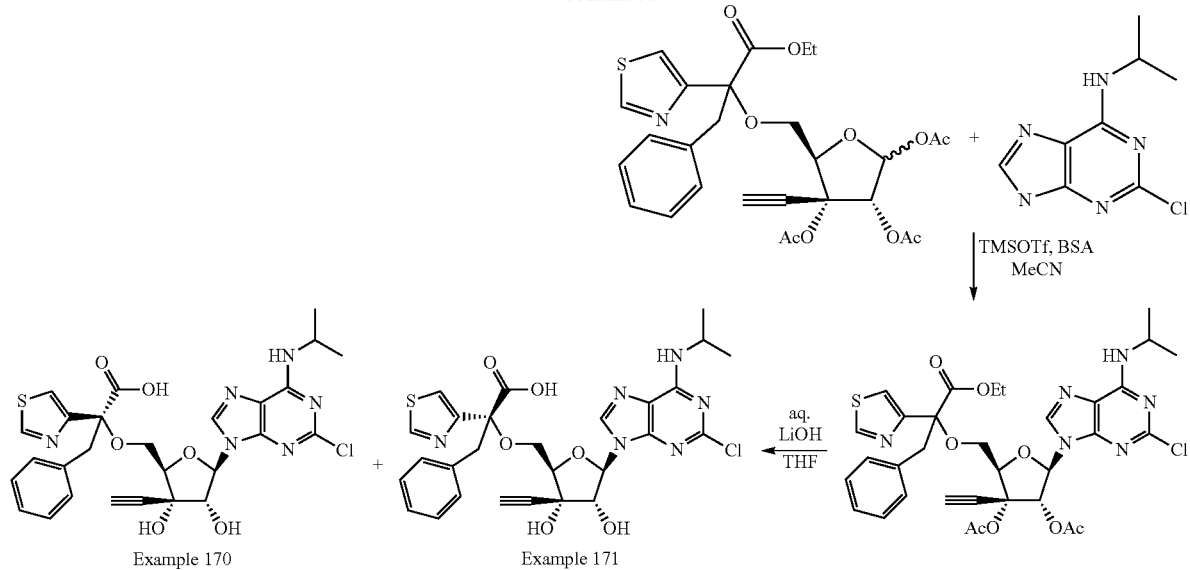

Proceeding as described in Example 169 above but substituting 3-(bromomethyl)thiophene with benzyl bromide provided a pair of diastereomeric products which the stereo configuration was assigned arbitrarily. Both products were purified by preparative HPLC and isolated as white solids.

(S)-2-(((2R,3S,4R,5R)-5-(2-chloro-6-(isopropylamino)-9H-purin-9-yl)-3-ethynyl-3,4-dihydroxytetrahydrofuran-2-yl)methoxy)-3-phenyl-2-(thiazol-4-yl)propanoic: $^1$H NMR (CD$_3$OD, 300 MHz) δ 8.99 (s, 1H), 7.91 (s, 1H), 7.70 (s, 1H), 7.07-7.23 (m, 5H), 5.91-5.94 (d, J=6.9 Hz, 1H), 4.87-4.90 (d, J=7.0 Hz, 1H), 4.21-4.45 (m, 2H), 3.59-3.94 (m, 4H), 3.02 (s, 1H), 1.29-1.31 (d, J=6.48 Hz, 6H); LC/MS [M+H]=599.0.

(R)-2-(((2R,3S,4R,5R)-5-(2-chloro-6-(isopropylamino)-9H-purin-9-yl)-3-ethynyl-3,4-dihydroxytetrahydrofuran-2-yl)methoxy)-3-phenyl-2-(thiazol-4-yl)propanoic: $^1$H NMR (CD$_3$OD, 300 MHz) δ 8.97-8.98 (d, J=1.83 Hz, 1H), 8.07 (s, 1H), 7.573-7.579 (d, J=1.86 Hz, 1H), 6.94-7.09 (m, 5H), 5.97-5.99 (d, J=7.17 Hz, 1H), 4.98-5.00 (d, J=7.23 Hz, 1H), 4.40-4.42 (m, 1H), 4.27-4.29 (t, J=3.84 Hz, 1H), 3.93-3.97 (m, 2H), 3.59-3.81 (q, J=14.31, 37.47 Hz, 2H), 2.95 (s, 1H), 1.29-1.33 (d, J=6.39 Hz, 6H); LC/MS [M+H]=599.0.

Examples 172 & 173

Synthesis of (S)-2-(((2R,3S,4R,5R)-5-(2-chloro-6-((cyclopropylmethyl)amino)-9H-purin-9-yl)-3-ethynyl-3,4-dihydroxytetrahydrofuran-2-yl)methoxy)-3-phenyl-2-(thiazol-4-yl)propanoic acid and (R)-2-(((2R,3S,4R,5R)-5-(2-chloro-6-((cyclopropylmethyl)amino)-9H-purin-9-yl)-3-ethynyl-3,4-dihydroxytetrahydrofuran-2-yl)methoxy)-3-phenyl-2-(thiazol-4-yl)propanoic acid Example 172

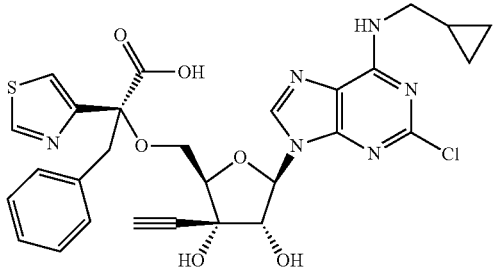

-continued

Example 173

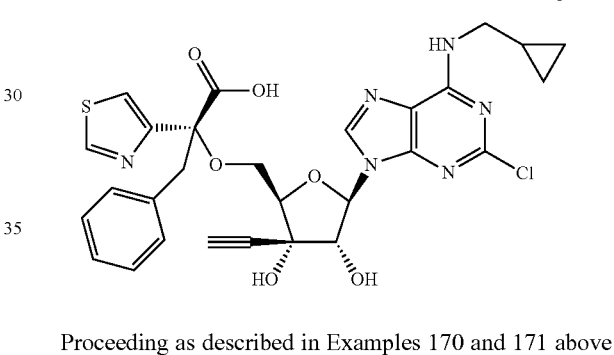

Proceeding as described in Examples 170 and 171 above but substituting 2-chloro-N-isopropyl-9H-purin-6-amine with 2-chloro-N-(cyclopropylmethyl)-9H-purin-6-amine provided a pair of diastereomeric products which the stereo configuration was assigned arbitrarily. Both products were purified by preparative HPLC and isolated as white solids.

(S)-2-(((2R,3S,4R,5R)-5-(2-chloro-6-((cyclopropylmethyl)amino)-9H-purin-9-yl)-3-ethynyl-3,4-dihydroxytetrahydrofuran-2-yl)methoxy)-3-phenyl-2-(thiazol-4-yl)propanoic acid: $^1$H NMR (CD$_3$OD, 300 MHz) δ 8.99-8.99 (d, J=1.95 Hz, 1H), 7.93 (s, 1H), 7.69-7.70 (d, J=1.86 Hz, 1H), 7.03-7.23 (m, 5H), 5.92-5.94 (d, J=6.96 Hz, 1H), 4.87-4.89 (d, J=7.11 Hz, 1H), 4.19-4.22 (m, 1H), 3.59-3.94 (m, 4H), 3.42-3.43 (m, 2H), 3.02 (s, 1H), 1.12-1.22 (m, 1H), 0.54-0.61 (m, 2H), 0.32-0.37 (m, 2H); LC/MS [M+H]=611.0.

(R)-2-(((2R,3S,4R,5R)-5-(2-chloro-6-((cyclopropylmethyl)amino)-9H-purin-9-yl)-3-ethynyl-3,4-dihydroxytetrahydrofuran-2-yl)methoxy)-3-phenyl-2-(thiazol-4-yl)propanoic acid: $^1$H NMR (CD$_3$OD, 300 MHz) δ 8.96-8.97 (d, J=1.89 Hz, 1H), 8.07 (s, 1H), 7.55-7.56 (d, J=2.07 Hz, 1H), 6.94-7.11 (m, 5H), 5.97-5.99 (d, J=7.17 Hz, 1H), 4.98-5.00 (d, J=7.29 Hz, 1H), 4.27-4.29 (t, J=3.66 Hz, 1H), 3.94-3.95 (m, 2H), 3.59-3.80 (q, J=14.64, 32.46 Hz, 2H), 3.39-3.50 (m, 2H), 2.96 (s, 1H), 1.13-1.23 (m, 1H), 0.55-0.62 (m, 2H), 0.32-0.38 (m, 2H); LC/MS [M+H]=611.0.

Example 174

Synthesis of 2-(((2R,3S,4R,5R)-5-(2-chloro-6-(isopropylamino)-9H-purin-9-yl)-3-ethynyl-3,4-dihydroxytetrahydrofuran-2-yl)methoxy)-2-(thiazol-4-yl)-3-(4-(trifluoromethoxy)phenyl)propanoic acid

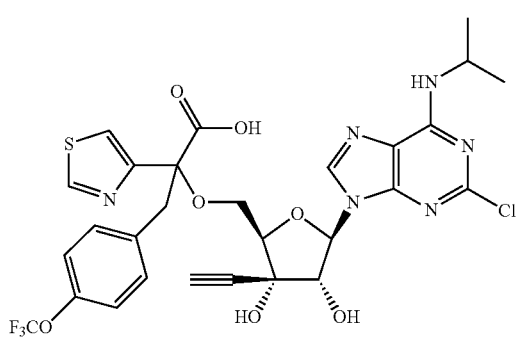

Example 174

Proceeding as described in Example 169 above but substituting 3-(bromomethyl)thiophene with 1-(bromomethyl)-4-(trifluoromethoxy)benzene provided the title compound as a mixture of diastereomers (ca. 1:1) and isolated as a white solid.

$^1$H NMR (400 MHz, $CD_3OD$) δ ppm 8.95-9.02 (m, 1H), 8.05-8.27 (m, 1H), 7.59-7.74 (m, 1H), 7.15-7.32 (m, 2H), 6.78-6.98 (m, 2H), 5.89-6.00 (m, 1H), 4.92-5.10 (m, 1H), 4.32-4.46 (m, 1H), 4.22-4.32 (m, 1H), 3.76-3.98 (m, 2H), 3.57-3.71 (m, 2H), 2.98-3.04 (m, 1H), 1.26-1.32 (m, 6H); LC/MS [M+H]=682.8.

Example 175

Synthesis of 2-(((2R,3S,4R,5R)-5-(6-amino-2-chloro-9H-purin-9-yl)-3-ethynyl-3,4-dihydroxytetrahydrofuran-2-yl)methoxy)-3-(4-(2-oxotetrahydropyrimidin-1(2H)-yl)phenyl)-2-(thiazol-4-yl)propanoic acid

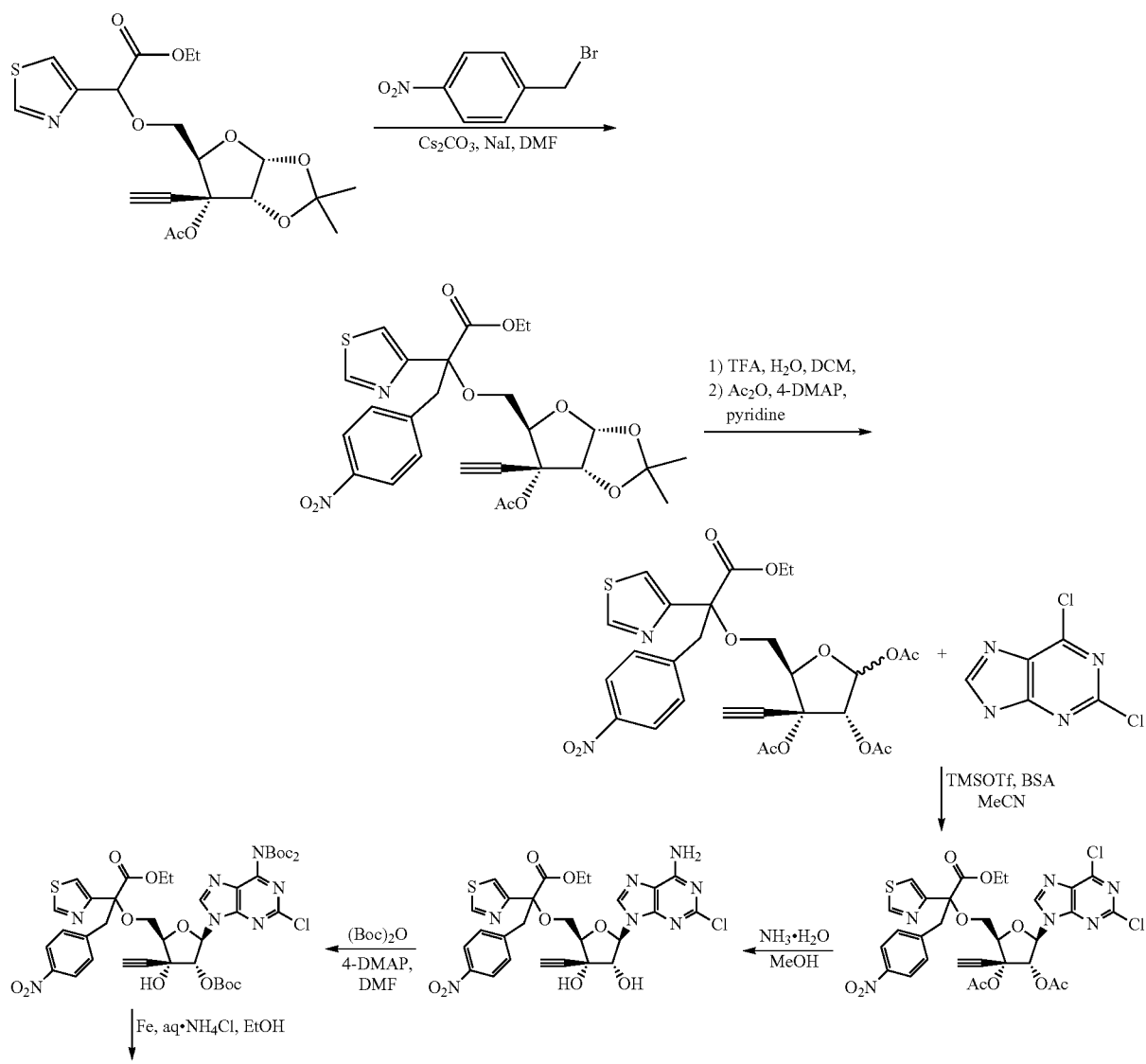

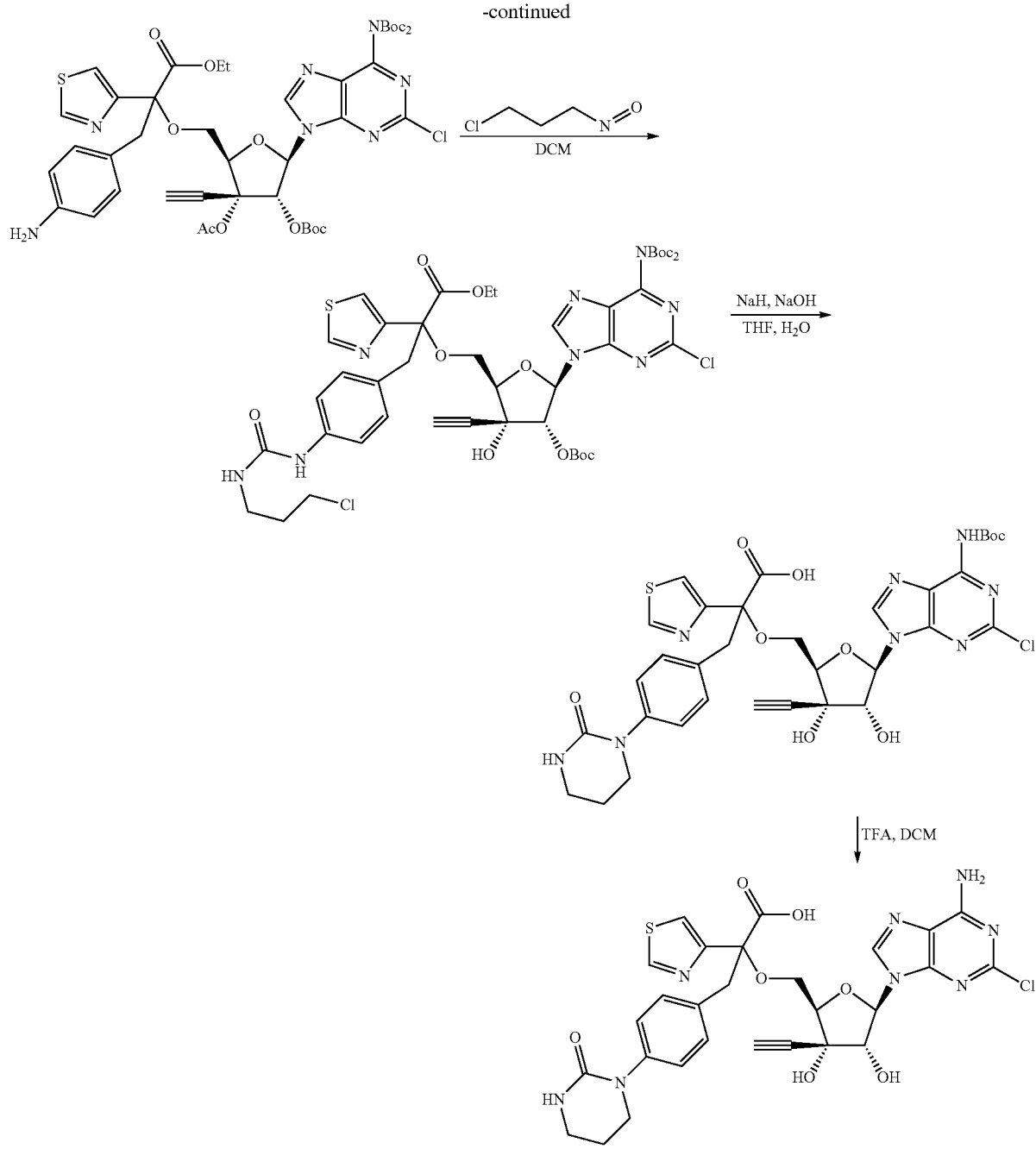

Example 175

Step 1:

A mixture of 1-(bromomethyl)-4-nitro-benzene (7.62 g, 35.26 mmol, 3 eq) and NaI (352.31 mg, 2.35 mmol, 0.2 eq) in DMF (50 mL) was stirred at 15° C. for 30 min. Then this mixture was added to a solution of ethyl 2-(((3aR,5R,6R,6aR)-6-acetoxy-6-ethynyl-2,2-dimethyltetrahydrofuro[2,3-d][1,3]dioxol-5-yl)methoxy)-2-(thiazol-4-yl)acetate (5 g, 11.75 mmol, 1 eq) and Cs₂CO₃ (19.15 g, 58.76 mmol, 5 eq) in DMF (50 mL) at 15° C. was stirred for 30 min. The resulting mixture was stirred for 8 h before it was quenched by water (200 mL). The mixture was extracted with EtOAc (4×30 mL). The combined organic layer was washed with water (3×100 mL), dried over anhydrous Na₂SO₄, filtered and concentrated.

The residue was purified by flash column chromatography on silica gel (0-40% of EtOAc in petroleum ether) to provide ethyl 2-(((3aR,5R,6R,6aR)-6-acetoxy-6-ethynyl-2,2-dimethyl-tetrahydrofuro[2,3-d][1,3]dioxol-5-yl)methoxy)-3-(4-nitrophenyl)-2-(thiazol-4-yl)propanoate (4.89 g) as a syrup.

Step 2:

To a solution of ethyl 2-(((3aR,5R,6R,6aR)-6-acetoxy-6-ethynyl-2,2-dimethyltetra-hydrofuro[2,3-d][1,3]dioxol-5-yl)methoxy)-3-(4-nitrophenyl)-2-(thiazol-4-yl)propanoate (4.89 g, impure) in DCM (25 mL) and H₂O (2.5 mL) was added TFA (25 mL 337.65 mmol). The mixture was stirred at 30° C. for 23 h before it was diluted with water (100 mL) and the resulting mixture was extracted with DCM (6×30 mL). The combined organic layer was washed with saturated aq. NaHCO$_3$(2×100 mL), dried over anhydrous Na$_2$SO$_4$, filtered and concentrated to provide crude ethyl 2-(((2R,3S,4R)-3-ethynyl-3,4,5-trihydroxytetrahydro-furan-2-yl)methoxy)-3-(4-nitrophenyl)-2-(thiazol-4-yl)propanoate (4.56 g) as a brown oil.

To a solution of crude ethyl 2-(((2R,3S,4R)-3-ethynyl-3,4,5-trihydroxytetrahydro-furan-2-yl)methoxy)-3-(4-nitrophenyl)-2-(thiazol-4-yl)propanoate (4.56 g) in DCM (50 mL) was added 4-DMAP (232.86 mg, 1.91 mmol), pyridine (6.15 mL, 76.24 mmol) and Ac$_2$O (8.93 mL, 95.30 mmol) dropwise. The mixture was stirred at 15° C. for 19 h before it was quenched with water (100 mL) and the resulting mixture was extracted with DCM (4×30 mL). The combined organic layer was washed with water (3×100 mL), and dried over anhydrous Na$_2$SO$_4$, filtered and concentrated. The crude residue was purified by flash column chromatography on silica gel (10-55% EtOAc in petroleum ether) to provide (3R,4R,5R)-5-(((1-ethoxy-3-(4-nitrophenyl)-1-oxo-2-(thiazol-4-yl)propan-2-yl)oxy)methyl)-4-ethynyltetrahydrofuran-2,3,4-triyl triacetate (1.02 g) as a yellow oil.
Step 3:

To a solution of 2,6-dichloro-9H-purine (382.64 mg, 2.02 mmol) in MeCN (5 mL) was added BSA (1.04 mL, 4.22 mmol). The suspension was stirred at 65° C. for 0.5 h as it became clear. The resulting solution was cooled down to 0° C. and followed by addition of a solution of (3R,4R,5R)-5-(((1-ethoxy-3-(4-nitrophenyl)-1-oxo-2-(thiazol-4-yl)propan-2-yl)oxy)methyl)-4-ethynyltetrahydrofuran-2,3,4-triyl triacetate (1.02 g) in MeCN (5 mL) and TMSOTf (4.22 mmol, 762.15 uL). Then the mixture was stirred at 65° C. for 1 h before it was quenched with saturated aq. NaHCO$_3$(40 mL) and the resulting mixture was extracted EtOAc (4×20 mL). The combined organic layer was dried over anhydrous Na$_2$SO$_4$, filtered and concentrated to provide crude (2R,3R,4R,5R)-5-(2,6-dichloro-9H-purin-9-yl)-2-(((1-ethoxy-3-(4-nitrophenyl)-1-oxo-2-(thiazol-4-yl)propan-2-yl)oxy)methyl)-3-ethynyltetrahydrofuran-3,4-diyl diacetate (1.71 g) as a yellow solid.
Step 4:

To a solution of crude (2R,3R,4R,5R)-5-(2,6-dichloro-9H-purin-9-yl)-2-(((1-ethoxy-3-(4-nitrophenyl)-1-oxo-2-(thiazol-4-yl)propan-2-yl)oxy)methyl)-3-ethynyltetrahydrofuran-3,4-diyl diacetate (1.0 g) in MeOH (20 mL) in a seal tube was added NH$_4$.OH (28.04 mmol, 4.00 mL, 27% concentration). The mixture was sealed and stirred at 100° C. for 1.5 h before it was allowed to cool and diluted with water (20 mL) and the resulting mixture was extracted with EtOAc (3×10 mL). The combined organic layer was dried over anhydrous Na$_2$SO$_4$, filtered and concentrated to give crude ethyl 2-(((2R,3S,4R,5R)-5-(6-amino-2-chloro-9H-purin-9-yl)-3-ethynyl-3,4-dihydroxytetrahydrofuran-2-yl)methoxy)-3-(4-nitrophenyl)-2-(thiazol-4-yl)propanoate (752 mg) as a yellow solid.
Step 5:

To a solution of crude ethyl 2-(((2R,3S,4R,5R)-5-(6-amino-2-chloro-9H-purin-9-yl)-3-ethynyl-3,4-dihydroxytetrahydrofuran-2-yl)methoxy)-3-(4-nitrophenyl)-2-(thiazol-4-yl)-propanoate (752 mg), 4-DMAP (58.33 mg, 477.44 umol) and Et$_3$N (7.16 mmol, 996.81 uL) in DMF (8 mL) at 0° C. was added Boc$_2$O (1.04 g, 4.77 mmol). The mixture was stirred at 20° C. for 2 h before it was diluted with water (40 mL) and the resulting mixture was extracted with EtOAc (4×20 mL). The combined organic layer was dried over anhydrous Na$_2$SO$_4$, filtered and concentrated to give crude ethyl 2-(((2R,3R,4R,5R)-5-(6-(bis-(tert-butoxycarbonyl)amino)-2-chloro-9H-purin-9-yl)-4-((tert-butoxycarbonyl)oxy)-3-ethynyl-3-hydroxytetrahydrofuran-2-yl)methoxy)-3-(4-nitrophenyl)-2-(thiazol-4-yl)propanoate (911 mg) as a brown solid.
Step 6:

To a solution of crude ethyl 2-(((2R,3R,4R,5R)-5-(6-(bis-(tert-butoxycarbonyl)-amino)-2-chloro-9H-purin-9-yl)-4-((tert-butoxycarbonyl)oxy)-3-ethynyl-3-hydroxytetrahydrofuran-2-yl)methoxy)-3-(4-nitrophenyl)-2-(thiazol-4-yl) propanoate (711 mg) in EtOH (7 mL) was added saturated aq. NH$_4$Cl (764.21 umol, 7 mL) and iron (426.77 mg, 7.64 mmol). The mixture was stirred at 50° C. for 2 h before it was filtered through a pad of Celite and the filtrate was concentrated. Then the crude residue was taken up in water (20 mL) and the resulting mixture was extracted with EtOAc (3×15 mL). The combined organic layer was dried over anhydrous Na$_2$SO$_4$, filtered and concentrated to give crude ethyl 3-(4-amino-phenyl)-2-(((2R,3R,4R,5R)-5-(6-(bis-(tert-butoxycarbonyl)amino)-2-chloro-9H-purin-9-yl)-4-((tert-butoxycarbonyl)oxy)-3-ethynyl-3-hydroxytetrahydrofuran-2-yl)methoxy)-2-(thiazol-4-yl)propanoate (552 mg) as a brown solid.
Step 7:

To a solution of crude ethyl 3-(4-aminophenyl)-2-(((2R,3R,4R,5R)-5-(6-(bis-(tert-butoxycarbonyl)amino)-2-chloro-9H-purin-9-yl)-4-((tert-butoxycarbonyl)oxy)-3-ethynyl-3-hydroxytetrahydrofuran-2-yl)methoxy)-2-(thiazol-4-yl) propanoate (552 mg) in DCM (5 mL) was added 1-chloro-3-isocyanato-propane (109.94 mg, 919.60 umol). The mixture was stirred at 15° C. for 16 h before it was concentrated under reduce pressure. The crude residue was purified by flash column chromatography on silica gel (20-100% EtOAc in petroleum ether) to provide ethyl 2-(((2R,3R,4R,5R)-5-(6-(bis-(tert-butoxycarbonyl)amino)-2-chloro-9H-purin-9-yl)-4-((tert-butoxycarbonyl)oxy)-3-ethynyl-3-hydroxytetrahydrofuran-2-yl)methoxy)-3-(4-(3-(3-chloropropyl)ureido)phenyl)-2-(thiazol-4-yl)propanoate (283 mg) as an off-white solid.
Step 8:

To a solution of ethyl 2-(((2R,3R,4R,5R)-5-(6-(bis-(tert-butoxycarbonyl)amino)-2-chloro-9H-purin-9-yl)-4-((tert-butoxycarbonyl)oxy)-3-ethynyl-3-hydroxytetrahydrofuran-2-yl)methoxy)-3-(4-(3-(3-chloropropyl)ureido)phenyl)-2-(thiazol-4-yl)propanoate (283 mg, 277.47 umol, 1 eq) in THF (3 mL) was added NaH (55.49 mg, 1.39 mmol, 60% in mineral oil, 5 eq). The mixture was stirred at 15° C. for 5 h before it was quenched with H$_2$O (1.5 mL). To this mixture was added NaOH (166.48 mg, 4.16 mmol, 15 eq) and the resulting mixture was stirred at 40° C. for 48 h before the organic volatile was removed under reduced pressure. The aq. layer was acidified with 2N aq. HCl (1 mL) and concentrated under reduced pressure to give crude 2-(((2R,3S,4R,5R)-5-(6-((tert-butoxycarbonyl)amino)-2-chloro-9H-purin-9-yl)-3-ethynyl-3,4-dihydroxytetrahydrofuran-2-yl)methoxy)-3-(4-(2-oxotetrahydropyrimidin-1 (2H)-yl) phenyl)-2-(thiazol-4-yl)propanoic acid (238 mg) as a yellow solid.
Step 9:

A mixture of crude 2-(((2R,3S,4R,5R)-5-(6-((tert-butoxycarbonyl)amino)-2-chloro-9H-purin-9-yl)-3-ethynyl-3,4-dihydroxytetrahydrofuran-2-yl)methoxy)-3-(4-(2-oxotetrahydropyrimidin-1(2H)-yl)phenyl)-2-(thiazol-4-yl)propanoic acid (238 mg) in DCM (2 mL) was added TFA (9.45 mmol, 0.7 mL). The mixture was stirred at 15° C. for 2 h before it was concentrated under reduced pressure. The crude residue was purified by Preparative HPLC ([water (0.225% FA)-ACN]; B %: 20%-40%, 10 min) to provide a diastereomeric mixture (ca. 1:1) of 2-(((2R,3S,4R,5R)-5-(6-amino-2-chloro-9H-purin-9-yl)-3-ethynyl-3,4-dihydroxytetra-hydrofuran-2-yl)methoxy)-3-(4-(2-oxotetrahydropyrimidin-1 (2H)-yl)phenyl)-2-(thiazol-4-yl)propanoic acid (22.9 mg) as a white solid.

¹H NMR (400 MHz, CD₃OD) δ ppm 9.01 (m, 1H), 7.98-8.32 (m, 1H), 7.59-7.83 (m, 1H), 6.91-7.34 (m, 4H), 5.88-6.07 (m, 1H), 4.72-4.96 (m, 1H), 4.13-4.32 (m, 1H), 3.60-4.00 (m, 4H), 3.43-3.56 (m, 2H), 3.35-3.42 (m, 2H), 2.96-3.14 (m, 1H), 1.89-2.08 (m, 2H); LC/MS [M+H] =655.3.

Example 176

Synthesis of 2-(((2R,3S,4R,5R)-5-(2-chloro-6-(isopropylamino)-9H-purin-9-yl)-3-ethynyl-3,4-dihydroxytetrahydrofuran-2-yl)methoxy)-3-(4-(2-oxotetrahydropyrimidin-1(2H)-yl)phenyl)-2-(thiazol-4-yl)propanoic acid azol-4-yl)propan-2-yl)oxy)methyl)-3-ethynyltetrahydrofuran-3,4-diyl diacetate (1.17 g) in MeCN (10 mL) was added propan-2-amine (1.0 mL, 11.64 mmol) and DIEA (0.9 mL). The mixture was stirred at 15° C. for 16 h before it was diluted with water (30 mL) and the resulting mixture was extracted EtOAc (4×20 mL). The combined organic layer was dried over anhydrous Na₂SO₄, filtered and concentrated to give crude (2R,3R,4R,5R)-5-(2-chloro-6-(isopropylamino)-9H-purin-9-yl)-2-(((1-ethoxy-3-(4-nitrophenyl)-1-oxo-2-(thiazol-4-yl)propan-2-yl)oxy)methyl)-3-ethynyltetrahydrofuran-3,4-diyl diacetate (1.16 g) as a yellow solid.

Step 2:

To a solution of crude (2R,3R,4R,5R)-5-(2-chloro-6-(isopropylamino)-9H-purin-9-yl)-2-(((1-ethoxy-3-(4-nitrophenyl)-1-oxo-2-(thiazol-4-yl)propan-2-yl)oxy)methyl)-3-ethynyltetrahydrofuran-3,4-diyl diacetate (1.16 g) in EtOH (5 mL) was added Fe powder (856.75 mg, 15.34 mmol) and saturated aq. NH₄Cl (1.53 mmol, 5 mL). The mixture was stirred at 50° C. for 2 h before it was filtered through a pad

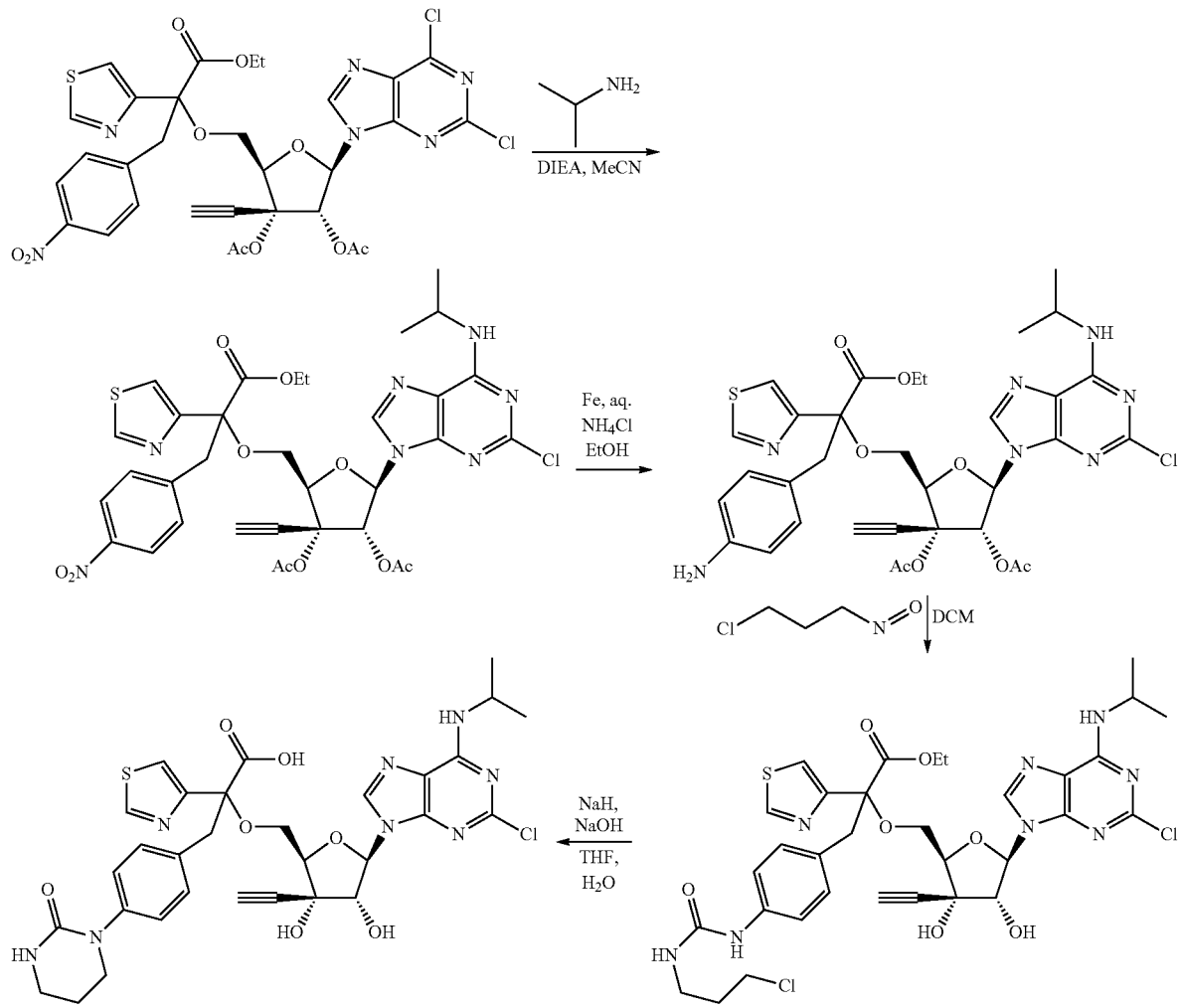

Example 176

Step 1:

A solution of crude (2R,3R,4R,5R)-5-(2,6-dichloro-9H-purin-9-yl)-2-(((1-ethoxy-3-(4-nitrophenyl)-1-oxo-2-(thiof Celite and the filtrate was concentrated to give crude (2R,3R,4R,5R)-2-(((3-(4-aminophenyl)-1-ethoxy-1-oxo-2-(thiazol-4-yl)propan-2-yl)oxy)methyl)-5-(2-chloro-6-(isopropylamino)-9H-purin-9-yl)-3-ethynyltetrahydrofuran-3,4-diyl diacetate (1.05 g) as a yellow solid.

Step 3:

To a solution of crude (2R,3R,4R,5R)-2-(((3-(4-aminophenyl)-1-ethoxy-1-oxo-2-(thiazol-4-yl)propan-2-yl)oxy)methyl)-5-(2-chloro-6-(isopropylamino)-9H-purin-9-yl)-3-ethynyltetrahydrofuran-3,4-diyl diacetate (1.05 g) in DCM (10 mL) was added 1-chloro-3-isocyanato-propane (172.85 mg, 1.45 mmol). The mixture was stirred at 15° C. for 16 h before it was quenched with water (20 mL) and the resulting mixture was extracted with DCM (3×10 mL). The combined organic layer was dried over anhydrous $Na_2SO_4$, filtered and concentrated to give crude ethyl 2-(((2R,3R,4R,5R)-5-(2-chloro-6-(isopropylamino)-9H-purin-9-yl)-3-ethynyl-3,4-dihydroxytetrahydrofuran-2-yl)methoxy)-3-(4-(3-(3-chloropropyl)-ureido)phenyl)-2-(thiazol-4-yl)propanoate (1.33 g) as a yellow solid.

Step 4:

To a solution of crude ethyl 2-(((2R,3S,4R,5R)-5-(2-chloro-6-(isopropylamino)-9H-purin-9-yl)-3-ethynyl-3,4-dihydroxytetrahydrofuran-2-yl)methoxy)-3-(4-(3-(3-chloropropyl)-ureido)phenyl)-2-(thiazol-4-yl)propanoate (1.23 g) in THF (12 mL) was added NaH (290.84 mg, 7.27 mmol, 60% in mineral oil). The mixture was stirred at 15° C. for 5 h before it was quenched with $H_2O$ (6 mL) and followed by addition of NaOH (290.85 mg, 7.27 mmol). The mixture was stirred at 15° C. for 16 h and then at 40° C. for 8 h. Additional NaOH (600 mg) was added to mixture and the mixture was stirred at 40° C. for 4 h before it was quenched with water (20 mL). The resulting solution was extracted with EtOAc (15 mL). The aq. layer was acidified with 2N aq. HCl (15 mL) to produce a precipitate. The solid was collected by filtration and purified by preparative HPLC (column: YMC-Actus Triart C18 150*30 mm*5 um; mobile phase: [water (0.225% FA)-ACN]; B %: 30%-50%, 10 min) to provide a diastereomeric mixture (ca. 1:1) of 2-(((2R,3S,4R,5R)-5-(2-chloro-6-(isopropyl-amino)-9H-purin-9-yl)-3-ethynyl-3,4-dihydroxytetrahydrofuran-2-yl)methoxy)-3-(4-(2-oxotetrahydropyrimidin-1(2H)-yl)phenyl)-2-(thiazol-4-yl)propanoic acid (245 mg) as a white solid $^1$H NMR (400 MHz, $CD_3OD$) δ ppm 8.99 (d, J=1.6 Hz, 1H), 7.88-8.18 (m, 1H), 7.53-7.79 (m, 1H), 7.30 (d, J=8.3 Hz, 1H), 7.03-7.13 (m, 2H), 6.95 (d, J=8.4 Hz, 1H), 5.83-6.03 (m, 1H), 4.63-4.74 (m, 1H), 4.33-4.43 (m, 1H), 4.09-4.29 (m, 1H), 3.72-4.01 (m, 3H), 3.59-3.70 (m, 1H), 3.41-3.53 (m, 2H), 3.33-3.38 (m, 2H), 2.91-3.14 (m, 1H), 1.83-2.05 (m, 2H), 1.25-1.35 (m, 6H); LC/MS [M+H]=697.4.

Example 177

Synthesis of 2-(((2R,3S,4R,5R)-5-(6-chloro-4-(isopropylamino)-1H-pyrazolo[3,4-d]pyrimidin-1-yl)-3-ethynyl-3,4-dihydroxytetrahydrofuran-2-yl)methoxy)-3-phenyl-2-(thiazol-4-yl)propanoic acid

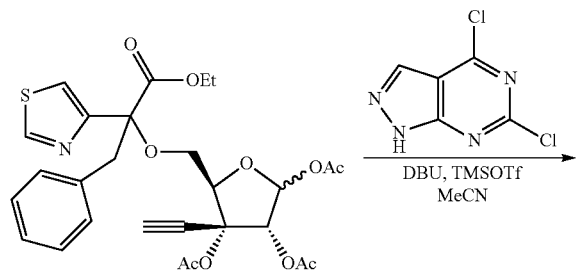

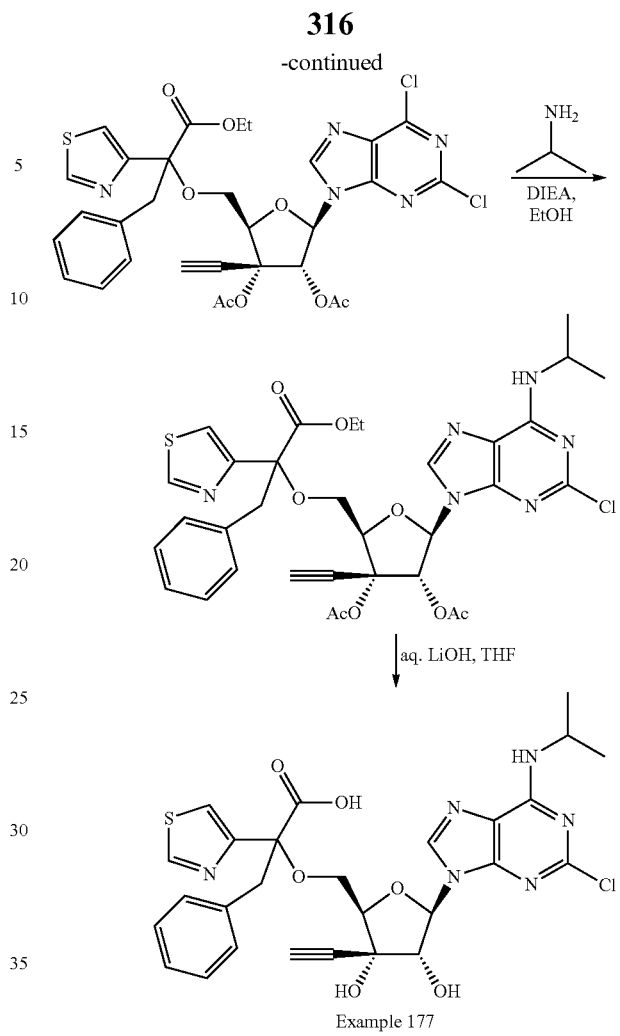

Example 177

Step 1:

To a solution of 4,6-dichloro-1H-pyrazolo[3,4-d]pyrimidine (620 mg, 1.11 mmol, 1 eq) and (3R,4R,5R)-5-(((1-ethoxy-1-oxo-3-phenyl-2-(thiazol-4-yl)propan-2-yl)oxy)methyl)-4-ethynyltetrahydrofuran-2,3,4-triyl triacetate (230.35 mg, 1.22 mmol, 1.1 eq) in MeCN (6.5 mL) under a $N_2$ atmosphere at 0° C. was added DBU (501 uL, 3.32 mmol, 3 eq). The mixture was stirred at 0° C. for 5 min and followed by addition of TMSOTf (900.93 uL, 4.99 mmol, 4.5 eq) dropwise. The mixture was stirred at 0° C. for 30 min and then stirred at 65° C. for 16 h before it was quenched with saturated aq. $NaHCO_3$(10 mL) and extracted with EtOAc (3×6 mL). The combined organic phase was dried over anhydrous $Na_2SO_4$, filtered and concentrated. The crude residue was purified by flash column chromatography on silica gel (10-40% of EtOAc in petroleum ether) to provide (2R,3R,4R,5R)-5-(4,6-dichloro-1H-pyrazolo[3,4-d]pyrimidin-1-yl)-2-(((1-ethoxy-1-oxo-3-phenyl-2-(thiazol-4-yl)propan-2-yl)oxy)methyl)-3-ethynyltetrahydrofuran-3,4-diyl diacetate (220 mg) as a foam.

Step 2:

To (2R,3R,4R,5R)-5-(4,6-dichloro-1H-pyrazolo[3,4-d]pyrimidin-1-yl)-2-(((1-ethoxy-1-oxo-3-phenyl-2-(thiazol-4-yl)propan-2-yl)oxy)methyl)-3-ethynyltetrahydrofuran-3,4-diyl diacetate (260 mg, 377.61 umol, 1 eq) in EtOH (2 mL) was added propan-2-amine (64.89 uL, 755.23 umol, 2 eq) and DIEA (131.55 uL, 755.23 umol, 2 eq). The mixture was stirred at 15° C. for 4 h before it was diluted with EtOAc (30 mL), washed with water (8 mL), brine (8 mL), dried over anhydrous Na₂SO₄, filtered and concentrated. The crude residue was purified by preparative TLC (EtOAc:petroleum ether=2:1) to give (2R,3R,4R,5R)-5-(6-chloro-4-(isopropylamino)-1H-pyrazolo[3,4-d]pyrimidin-1-yl)-2-(((1-ethoxy-1-oxo-3-phenyl-2-(thiazol-4-yl)propan-2-yl)oxy)methyl)-3-ethynyltetrahydrofuran-3,4-diyl diacetate (70 mg) as a foam.

Step 3:

To a solution of (2R,3R,4R,5R)-5-(6-chloro-4-(isopropylamino)-1H-pyrazolo[3,4-d]pyrimidin-1-yl)-2-(((1-ethoxy-1-oxo-3-phenyl-2-(thiazol-4-yl)propan-2-yl)oxy)methyl)-3-ethynyltetrahydrofuran-3,4-diyl diacetate (70 mg, 98.43 umol, 1 eq) in THF (1 mL) was added LiOH.H₂O (4.13 mg). The mixture was stirred at 50° C. for 14 h before it was concentrated to dryness. The crude residue was purified by preparative HPLC (column: YMC-Actus Triart C18 150*30 mm*5 um; mobile phase: [water (0.225% FA)-ACN]; B %: 43%-63%, 10 min) and dried by lyophilization to provide a diastereomeric mixture (ca. 1:1) of 2-(((2R,3S,4R,5R)-5-(6-chloro-4-(isopropylamino)-1H-pyrazolo[3,4-d]pyrimidin-1-yl)-3-ethynyl-3,4-dihydroxytetrahydro-furan-2-yl)methoxy)-3-phenyl-2-(thiazol-4-yl)propanoic acid (15.7 mg) as a white solid.

¹H NMR (400 MHz, CD₃OD) δ ppm 8.76-9.10 (m, 1H), 7.93-8.08 (m, 1H), 7.40-7.65 (m, 1H), 6.89-7.08 (m, 4H), 6.80-6.88 (m, 1H), 6.11-6.20 (m, 1H), 5.14-5.28 (m, 1H), 4.38-4.50 (m, 1H), 4.29-4.37 (m, 1H), 3.93-4.11 (m, 1H), 3.78-3.86 (m, 1H), 3.47-3.63 (m, 2H), 2.97-3.09 (m, 1H), 1.25-1.31 (m, 6H); LC/MS [M+H]=598.7.

Example 178

Synthesis of 2-(((2R,3S,4R,5R)-5-(4-amino-6-chloro-1H-pyrazolo[3,4-d]pyrimidin-1-yl)-3-ethynyl-3,4-dihydroxytetrahydrofuran-2-yl)methoxy)-3-phenyl-2-(thiazol-4-yl)propanoic acid

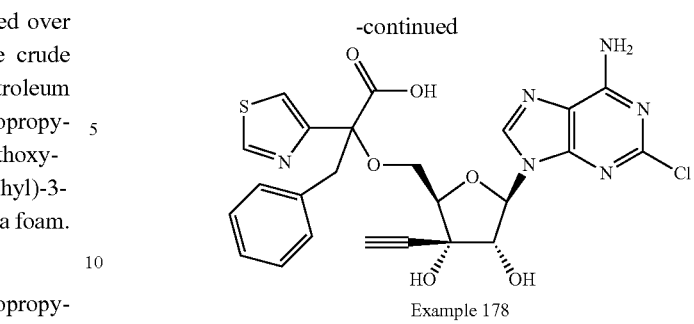

Example 178

Step 1:

To a solution of (2R,3R,4R,5R)-5-(4,6-dichloro-1H-pyrazolo[3,4-d]pyrimidin-1-yl)-2-(((1-ethoxy-1-oxo-3-phenyl-2-(thiazol-4-yl)propan-2-yl)oxy)methyl)-3-ethynyltetrahydro-furan-3,4-diyl diacetate (100 mg, 145.24 umol, 1 eq) in THF (1 mL) was added NH₄OH (199.76 uL, 1.45 mmol, 10 eq). The mixture was stirred at 15° C. for 14 h before it was concentrated to dryness to provide crude (2R,3R,4R,5R)-5-(4-amino-6-chloro-1H-pyrazolo-[3,4-d]pyrimidin-1-yl)-2-(((1-ethoxy-1-oxo-3-phenyl-2-(thiazol-4-yl)propan-2-yl)oxy)-methyl)-3-ethynyltetrahydrofuran-3,4-diyl diacetate (120 mg) as a white solid.

Step 2:

To a solution of crude (2R,3R,4R,5R)-5-(4-amino-6-chloro-1H-pyrazolo[3,4-d]pyrimidin-1-yl)-2-(((1-ethoxy-1-oxo-3-phenyl-2-(thiazol-4-yl)propan-2-yl)oxy)methyl)-3-ethynyltetrahydrofuran-3,4-diyl diacetate (145.24 umol, 1 eq) in THF (4 mL) and H₂O (2 mL) was added LiOH.H₂O (60.94 mg, 1.45 mmol, 10 eq). The mixture was stirred at 50° C. for 16 h before it was concentrated to dryness. The crude residue was purified by preparative HPLC (column: YMC-Actus Triart C18 150*30 mm*5 um; mobile phase: [water (0.225% FA)-ACN]; B %: 28%-48%,10 min) and dried by lyophilization to provide a diastereomeric mixture (ca. 1:1) of 2-(((2R,3S,4R,5R)-5-(4-amino-6-chloro-1H-pyrazolo[3,4-d]pyrimidin-1-yl)-3-ethynyl-3,4-dihydroxytetrahydrofuran-2-yl)methoxy)-3-phenyl-2-(thiazol-4-yl)-propanoic acid (32.8 mg) as a white solid.

¹H NMR (400 MHz, CD₃OD) δ ppm 8.87-9.01 (m, 1H), 7.91-8.06 (m, 1H), 7.47-7.67 (m, 1H), 7.01-7.06 (m, 2H), 6.93-7.00 (m, 2H), 6.84-6.90 (m, 1H), 6.12-6.20 (m, 1H), 5.14-5.27 (m, 1H), 4.26-4.33 (m, 1H), 3.76-4.03 (m, 2H), 3.48-3.70 (m, 2H), 2.96-3.05 (m, 1H); LC/MS [M+H]= 557.0.

Example 179

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(thiazol-4-yl)acetic acid

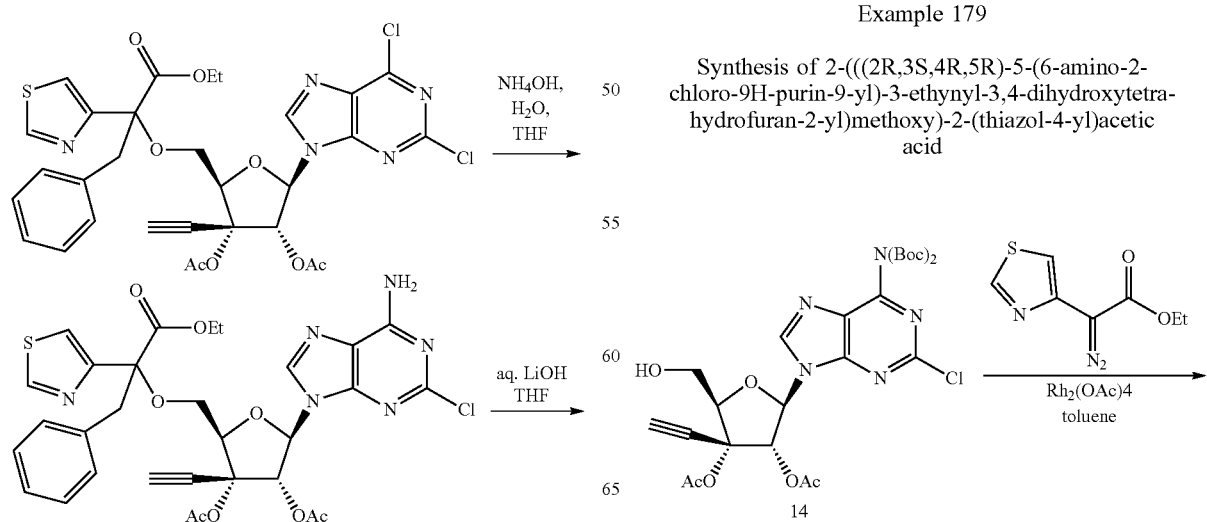

319

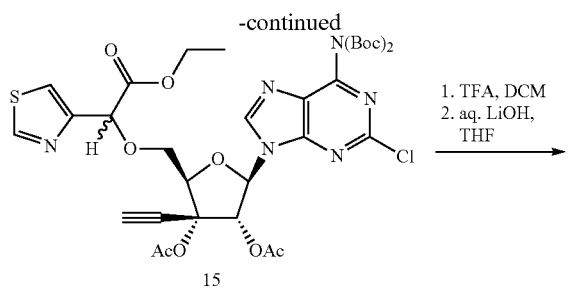

1. TFA, DCM
2. aq. LiOH, THF

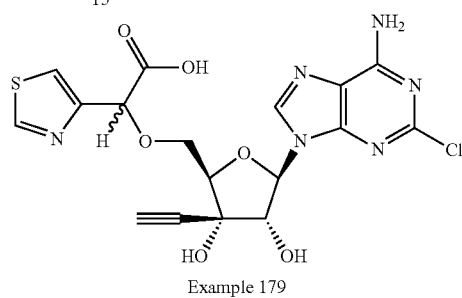

Example 179

Step 1:

To a solution of (2R,3R,4R,5R)-5-(((6-N,N'-bis-(tert-butoxycarbonyl)amino)-2-chloro-9H-purin-9-yl)-3-ethynyl-2-(hydroxymethyl)tetrahydrofuran-3,4-diyl diacetate (2 g, 3.28 mmol) in toluene (10 mL) was added ethyl 2-diazo-2-(thiazol-4-yl)acetate (841 mg, 4.26 mmol) and Rh$_2$(OAc)$_4$ (145 mg, 0.328 mmol) under an argon atmosphere. The resulting mixture was stirred at 70° C. for 2 h before it was allowed to cool to room temperature. The organic volatile was removed under reduced pressure. The resulting crude was purified by silica gel column chromatography (0-40% EtOAc in hexanes) to provide (2R,3R,4R,5R)-5-(6-(bis-(tert-butoxycarbonyl)amino)-2-chloro-9H-purin-9-yl)-2-((2-ethoxy-2-oxo-1-(thiazol-4-yl)ethoxy)methyl)-3-ethynyltetrahydrofuran-3,4-diyl diacetate (1.78 g) as a syrup.

320

Step 2:

To a solution of (2R,3R,4R,5R)-5-(6-(bis-(tert-butoxycarbonyl)amino)-2-chloro-9H-purin-9-yl)-2-((2-ethoxy-2-oxo-1-(thiazol-4-yl)ethoxy)methyl)-3-ethynyltetrahydrofuran-3,4-diyl diacetate (310 mg) in DCM (3 mL) at 25° C. was added TFA (2 mL). The mixture was stirred for 2 h before it was concentrated under reduced pressure to provide crude (2R,3R,4R,5R)-5-(6-amino-2-chloro-9H-purin-9-yl)-2-((2-ethoxy-2-oxo-1-(thiazol-4-yl)ethoxy)methyl)-3-ethynyltetrahydrofuran-3,4-diyl diacetate.

To a solution of crude (2R,3R,4R,5R)-5-(6-amino-2-chloro-9H-purin-9-yl)-2-((2-ethoxy-2-oxo-1-(thiazol-4-yl)ethoxy)methyl)-3-ethynyltetrahydrofuran-3,4-diyl diacetate in THF (1 mL) and H$_2$O (1 mL) at 0° C. was added LiOH monohydrate (100 mg). The resulting mixture was stirred at 25° C. overnight before the organic volatile was removed under reduced pressure. The mixture was cooled to 0° C. before it was acidified to pH ~6 with 1N aq. HCl solution and concentrated under reduced pressure. The crude residue was purified by preparative reversed-phase HPLC to provide a diastereomeric mixture (ca. 1:1) of 2-(((2R,3S,4R,5R)-5-(6-amino-2-chloro-9H-purin-9-yl)-3-ethynyl-3,4-dihydroxytetrahydro-furan-2-yl)methoxy)-2-(thiazol-4-yl)acetic acid as a white solid.

$^1$H NMR (CD$_3$OD, 300 MHz) δ 8.84-9.00 (m, 2H), 7.67-7.68 (m, 1H), 6.02-6.06 (m, 1H), 5.28-5.32 (d, J=12.27 Hz, 1.5H), 5.14-5.16 (d, J=7.56 Hz, 0.5H), 4.24-4.28 (m, 1H), 3.69-4.09 (m, 2H), 3.16 (s, 0.5H), 2.95 (s, 0.5H); LC/MS [M+H]=467.0.

Examples 180 and 181

Synthesis of (S)-2-(((2R,3S,4R,5R)-5-(6-amino-2-chloro-9H-purin-9-yl)-3-ethynyl-3,4-dihydroxytetrahydrofuran-2-yl)methoxy)-3-phenyl-2-(thiazol-4-yl)propanoic acid and (R)-2-(((2R,3S,4R,5R)-5-(6-amino-2-chloro-9H-purin-9-yl)-3-ethynyl-3,4-dihydroxytetrahydrofuran-2-yl)methoxy)-3-phenyl-2-(thiazol-4-yl)propanoic acid

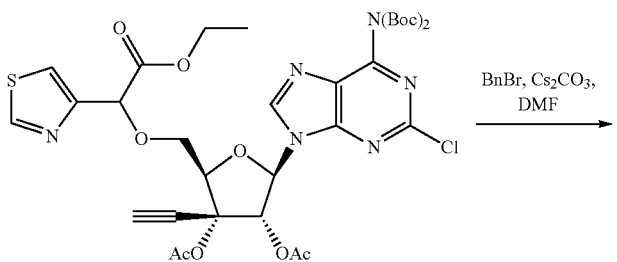

BnBr, Cs$_2$CO$_3$, DMF

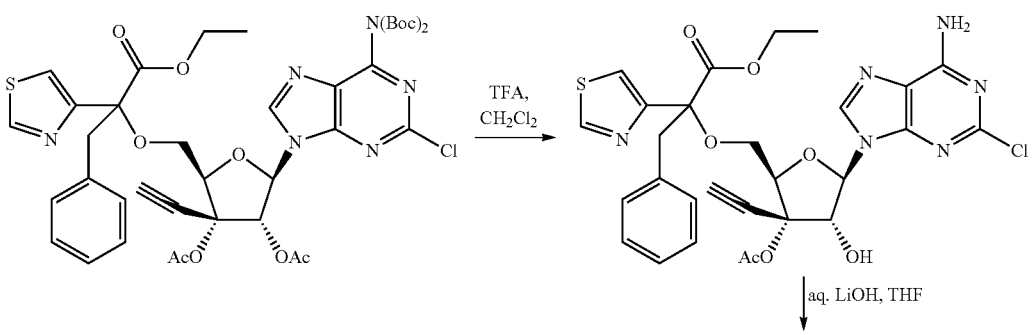

TFA, CH$_2$Cl$_2$ aq. LiOH, THF

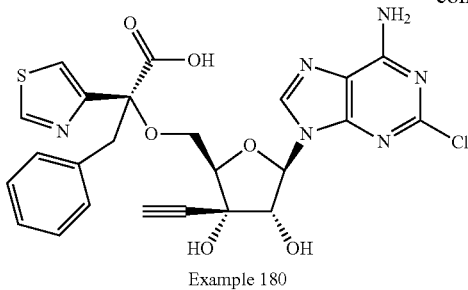

Example 180

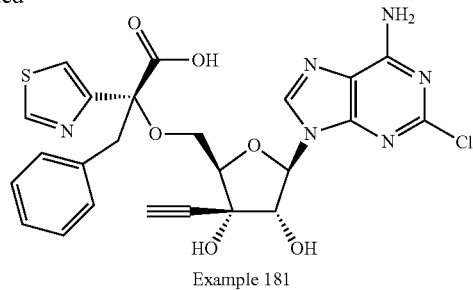

Example 181

Proceeding as described in Example 169 above but substituting 3-(bromomethyl)thiophene and 2-chloro-N-isopropyl-9purin-6-amine with benzyl bromide and 2-chloroadenine provided a pair of diastereomeric products which the stereo configuration was assigned arbitrarily. Both products were purified by preparative HPLC and isolated as white solids.

(S)-2-(((2R,3S,4R,5R)-5-(6-amino-2-chloro-9H-purin-9-yl)-3-ethynyl-3,4-dihydroxytetra-hydrofuran-2-yl)methoxy)-3-phenyl-2-(thiazol-4-yl)propanoic acid: $^1$H NMR (CD$_3$OD, 300 MHz) δ 8.95-8.96 (d, J=2.01 Hz, 1H), 8.34 (s, 1H), 7.54-7.55 (d, J=2.01 Hz, 1H), 6.97-7.12 (m, 5H), 5.97-5.99 (d, J=6.99 Hz, 1H), 4.97-4.99 (d, J=7.08 Hz, 1H), 4.27-4.29 (t, J=4.23, 3.18 Hz, 1H), 3.88-3.99 (m, 2H), 3.62-3.79 (q, J=14.82, 39.24 Hz, 2H), 2.97 (s, 1H); LC/MS [M+H]=557.0.

(R)-2-(((2R,3S,4R,5R)-5-(6-amino-2-chloro-9H-purin-9-yl)-3-ethynyl-3,4-dihydroxytetra-hydrofuran-2-yl)methoxy)-3-phenyl-2-(thiazol-4-yl)propanoic acid: $^1$H NMR (CD$_3$OD, 300 MHz) δ 8.95-8.96 (m, 1H), 7.99 (s, 1H), 7.70-7.71 (d, J=1.98 Hz, 1H), 7.05-7.25 (m, 5H), 5.92-5.94 (d, J=7.02 Hz, 1H), 4.85-4.87 (d, J=7.29 Hz, 1H), 4.20-4.22 (q, J=2.64 Hz, 1H), 3.58-3.90 (m, 4H), 3.02 (s, 1H); LC/MS [M+H]=557.0.

Example 182

Synthesis of 3-(2-(((2R,3S,4R,5R)-5-(6-amino-2-chloro-9H-purin-9-yl)-3-ethynyl-3,4-dihydroxytetra-hydrofuran-2-yl)methoxy)-2-carboxy-2-(thiazol-4-yl)ethyl)benzoic acid

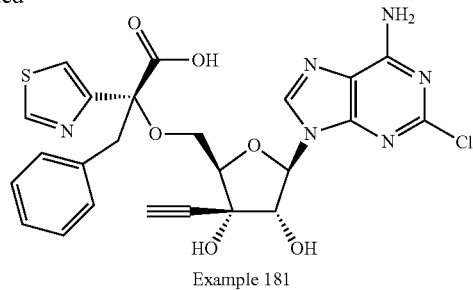

Example 182

Proceeding as described in Example 179 above but substituting BnBr with methyl 3-(bromomethyl)benzoate provided the title compound as a mixture of diastereomers (ca. 1:1) and isolated as a white solid.

$^1$H NMR (CD$_3$OD, 300 MHz) δ 8.99-9.01 (m, 1H), 8.33 (s, 0.5H), 8.14 (s, 0.5H), 7.66-7.88 (m, 3H), 7.45-7.48 (d, J=7.29 Hz, 0.5H), 7.36-7.39 (d, J=7.86 Hz, 0.5H), 7.17-7.22 (t, J=7.56 Hz, 0.5H), 7.00-7.05 (d, J=7.47 Hz, 0.5H), 5.99-6.01 (d, J=7.29 Hz, 0.5H), 5.93-5.95 (d, J=6.87 Hz, 0.5H), 5.00-5.03 (d, J=7.38 Hz, 0.5H), 4.90-4.95 (d, J=6.80 Hz, 0.5H), 4.23-4.31 (m, 1H), 3.80-4.01 (m, 2H), 3.63-3.69 (m, 2H), 3.01 (s, 0.5H), 2.92 (s, 0.5H); LC/MS [M+H]=601.0.

Example 183

Synthesis of 2-(((2R,3S,4R,5R)-5-(6-amino-2-chloro-9H-purin-9-yl)-3-ethynyl-3,4-dihydroxytetra-hydrofuran-2-yl)methoxy)-2-(thiazol-4-yl)-3-(3-(trifluoromethoxy)phenyl)propanoic acid

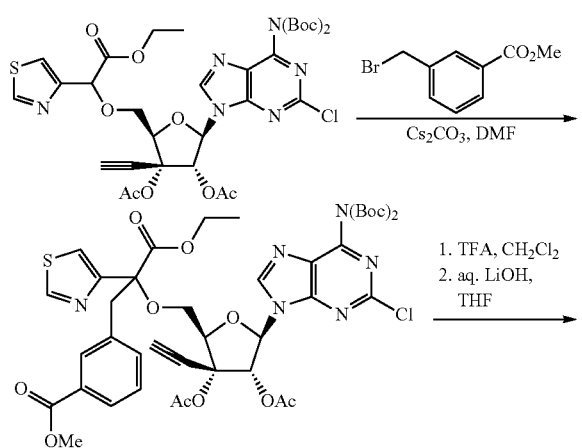

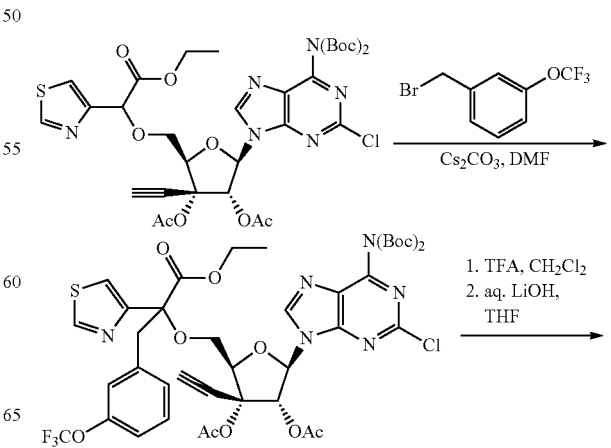

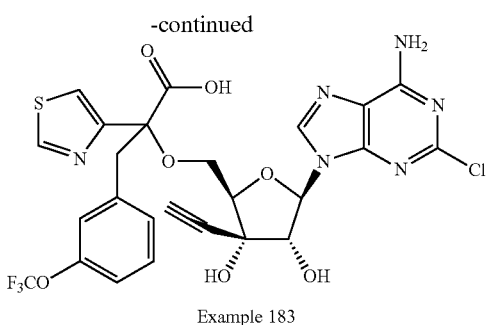

Example 183

Proceeding as described in Example 179 above but substituting BnBr with 1-(bromomethyl)-3-(trifluoromethoxy)benzene provided the title compound as a mixture of diastereomers (ca. 1:1) and isolated as a white solid.

$^1$H NMR (CD$_3$OD, 300 MHz) δ 8.97-9.00 (m, 1H), 8.41 (s, 0.5H), 8.26 (s, 0.5H), 7.68-7.69 (d, J=1.92 Hz, 0.5H), 7.62-7.63 (d, J=1.83 Hz, 0.5H), 6.88-7.21 (m, 4H), 6.00-6.02 (d, J=7.14 Hz, 0.5H), 5.94-5.96 (d, J=6.78 Hz, 0.5H), 5.04-5.07 (d, J=7.44 Hz, 0.5H), 4.91-4.94 (d, J=6.87 Hz, 0.5H), 4.28-4.33 (m, 1H), 3.62-3.96 (m, 4H), 2.98 (s, 0.5H), 2.96 (s, 0.5H); LC/MS [M+H]=641.0.

Example 184

Synthesis of 2-(((2R,3S,4R,5R)-5-(6-amino-2-chloro-9H-purin-9-yl)-3-ethynyl-3,4-dihydroxytetrahydrofuran-2-yl)methoxy)-2-(thiazol-4-yl)pent-4-ynoic acid

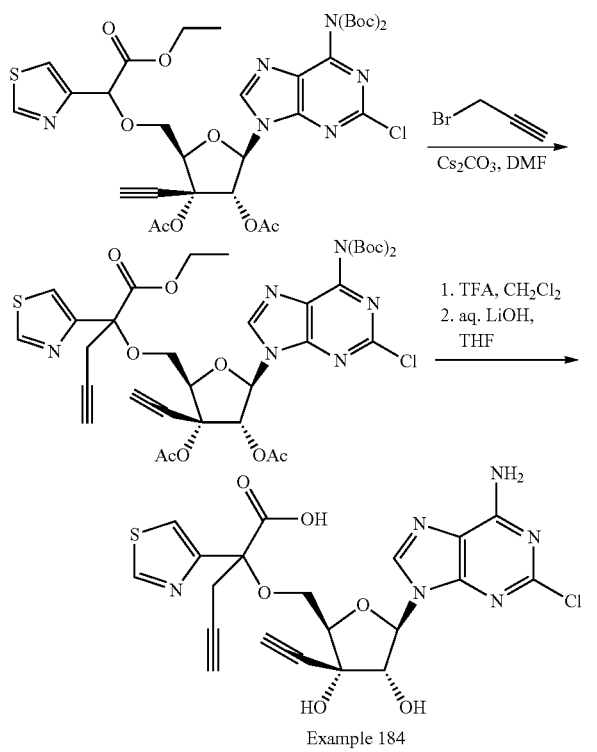

Example 184

Proceeding as described in Example 179 above but substituting BnBr with propargyl bromide provided the title compound as a mixture of diastereomers (ca. 1:1) and isolated as a white solid.

$^1$H NMR (CD$_3$OD, 300 MHz) δ 8.95 (s, 1H), 8.79-8.83 (d, J=13.95 Hz, 1H), 7.73 (s, 1H), 6.04-6.06 (d, J=7.05 Hz, 1H), 4.97-5.05 (dd, J=7.29, 17.91 Hz, 1H), 4.24-4.30 (m, 1H), 3.69-3.94 (m, 2H), 3.34-3.38 (m, 2H), 3.04 (s, 0.5H), 2.93 (s, 0.5H), 2.22-2.30 (dt, J=1.74, 19.62 Hz, 1H); LC/MS [M+H]=505.0.

Examples 185 and 186

Synthesis of (S)-2-(((2R,3S,4R,5R)-5-(6-amino-2-chloro-9H-purin-9-yl)-3-ethynyl-3,4-dihydroxytetrahydrofuran-2-yl)methoxy)-N-hydroxy-2-(thiazol-4-yl)acetamide and (S)-2-(((2R,3S,4R,5R)-5-(6-amino-2-chloro-9H-purin-9-yl)-3-ethynyl-3,4-dihydroxytetrahydrofuran-2-yl)methoxy)-N-hydroxy-2-(thiazol-3-yl)acetamide

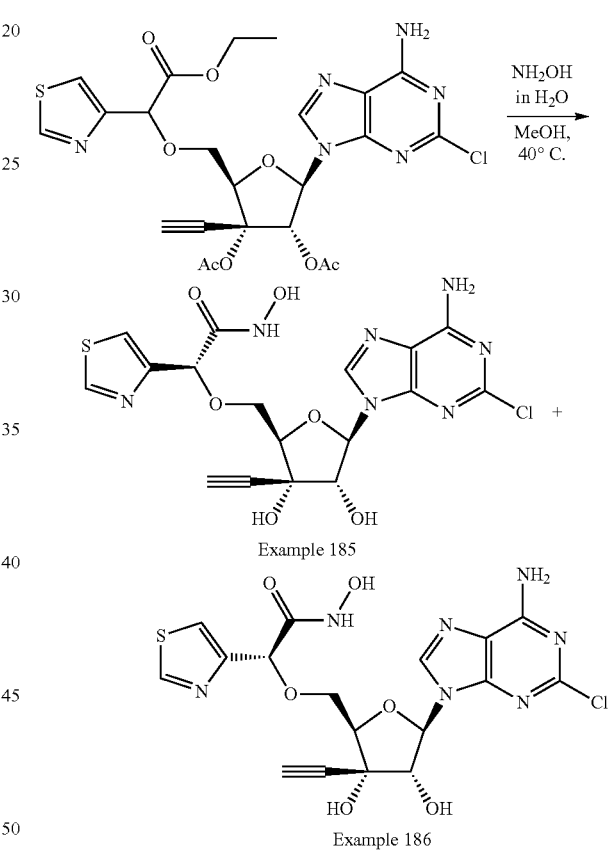

To a solution of (2R,3R,4R,5R)-5-(6-amino-2-chloro-9H-purin-9-yl)-2-((2-ethoxy-2-oxo-1-(thiazol-4-yl)ethoxy)methyl)-3-ethynyltetrahydrofuran-3,4-diyl diacetate (2 g, 3.45 mmole) in MeOH (20 mL) was added 50% NH$_2$OH in H$_2$O (30 mL). The reaction mixture was stirred at 40° C. for 1 h before it was concentrated under reduced pressure. The crude residue was purified by preparative reversed-phase HPLC to provide a pair of diastereomeric title products which the stereo configuration was assigned arbitrarily. Both products were isolated as white solids.

(S)-2-(((2R,3S,4R,5R)-5-(6-amino-2-chloro-9H-purin-9-yl)-3-ethynyl-3,4-dihydroxytetrahydrofuran-2-yl)methoxy)-N-hydroxy-2-(thiazol-4-yl)acetamide: $^1$H NMR (CD$_3$OD, 300 MHz) δ 9.02-9.03 (d, J=1.77 Hz, 1H), 8.45 (s, 1H), 7.68-7.69 (d, J=1.8 Hz, 1H), 5.98-6.01 (d, J=6.96 Hz, 1H), 4.92-4.95 (d, J=6.93 Hz, 1H), 4.29-4.32 (q, J=2.82, 2.28 Hz, 1H), 3.91-4.10 (m, 2H), 3.18 (s, 1H); LC/MS [M+H]=482.0.

(R)-2-(((2R,3S,4R,5R)-5-(6-amino-2-chloro-9H-purin-9-yl)-3-ethynyl-3,4-dihydroxytetra-hydrofuran-2-yl)methoxy)-N-hydroxy-2-(thiazol-4-yl)acetamide: ¹H NMR (CD₃OD, 300 MHz) δ 8.97 (s, 1H), 8.46 (s, 1H), 7.68 (s, 1H), 5.97-6.00 (d, J=6.96 Hz, 1H), 4.88-4.90 (d, J=6.93 Hz, 1H), 4.33-4.35 (m, 1H), 3.96-4.08 (m, 2H), 3.12 (s, 1H); LC/MS [M+H]=482.0.

Examples 187 and 188

Synthesis of (S)-2-(((2R,3S,4R,5R)-5-(2-chloro-6-(methylamino)-9H-purin-9-yl)-3-ethynyl-3,4-dihydroxytetrahydrofuran-2-yl)methoxy)-3-phenyl-2-(thiazol-4-yl)propanoic acid and (R)-2-(((2R,3S,4R, 5R)-5-(2-chloro-6-(methylamino)-9H-purin-9-yl)-3-ethynyl-3,4-dihydroxytetrahydrofuran-2-yl)methoxy)-3-phenyl-2-(thiazol-4-yl)propanoic acid

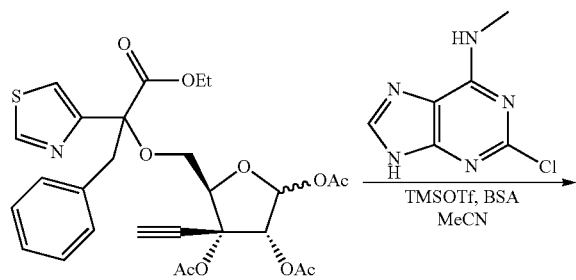

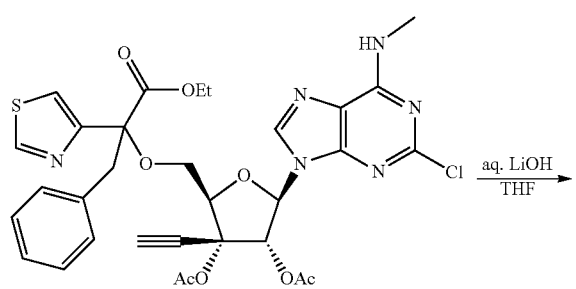

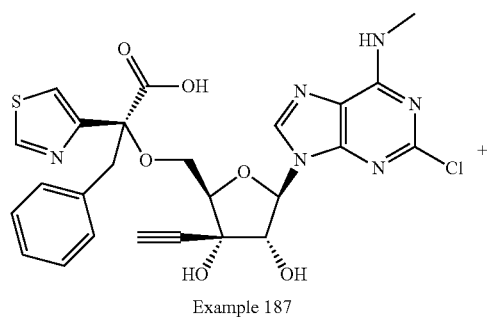

Example 187

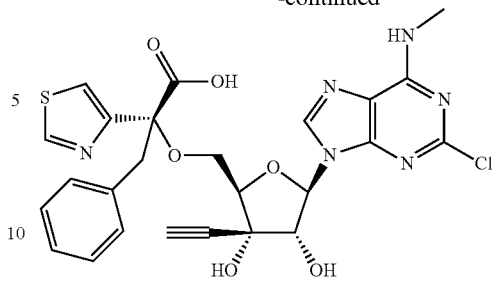

Example 188

Proceeding as described in Examples 170 and 171 above but substituting 2-chloro-N-isopropyl-9H-purin-6-amine with 2-chloro-N-methyl-9H-purin-6-amine provided the title compounds as a pair of diastereomers (ca. 1:1) and isolated as white solids.

(S)-2-(((2R,3S,4R,5R)-5-(2-chloro-6-(methylamino)-9H-purin-9-yl)-3-ethynyl-3,4-dihydroxy-tetrahydrofuran-2-yl)methoxy)-3-phenyl-2-(thiazol-4-yl)propanoic acid: ¹H NMR (CD₃OD, 300 MHz) δ 8.99 (s, 1H), 7.97 (s, 1H), 7.69 (s, 1H), 7.08-7.22 (m, 5H), 5.93-5.95 (d, J=6.9 Hz, 1H), 4.96-4.98 (d, J=6.0 Hz, 1H), 3.59-4.22 (m, 5H), 3.01-3.06 (m, 4H); LC/MS [M+H]=571.0.

(R)-2-(((2R,3S,4R,5R)-5-(2-chloro-6-(methylamino)-9H-purin-9-yl)-3-ethynyl-3,4-dihydroxytetrahydrofuran-2-yl)methoxy)-3-phenyl-2-(thiazol-4-yl)propanoic acid: ¹H NMR (CD₃OD, 300 MHz) δ 8.97-8.98 (d, J=1.83 Hz, 1H), 8.15 (s, 1H), 7.58-7.59 (d, J=1.77 Hz, 1H), 6.94-7.09 (m, 5H), 5.98-6.00 (d, J=7.17 Hz, 1H), 4.98-5.01 (d, J=7.26 Hz, 1H), 4.27-4.29 (t, J=3.48 Hz, 1H), 3.93 (m, 2H), 3.58-3.80 (q, J=14.46, 38.7 Hz, 2H), 3.07 (s, 3H), 2.94 (s, 1H); LC/MS [M+H]=571.0.

Examples 189 and 190

Synthesis of (S)-2-(((2R,3S,4R,5R)-5-(6-amino-2-chloro-9H-purin-9-yl)-3-ethynyl-3,4-dihydroxytetrahydrofuran-2-yl)methoxy)-2-cyano-3-phenylpropanoic acid and (R)-2-(((2R,3S,4R,5R)-5-(6-amino-2-chloro-9H-purin-9-yl)-3-ethynyl-3,4-dihydroxytetrahydrofuran-2-yl)methoxy)-2-cyano-3-phenylpropanoic acid

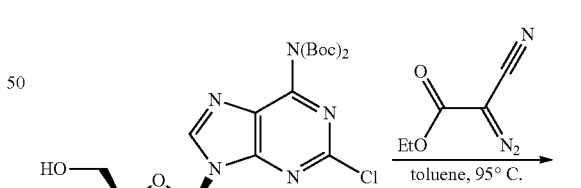

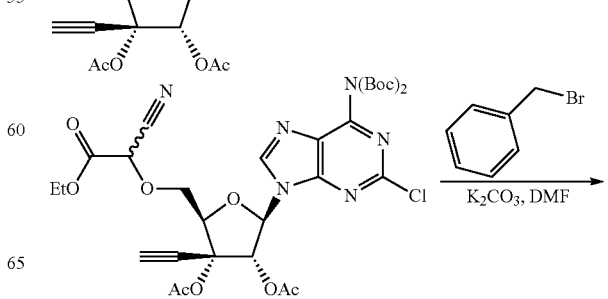

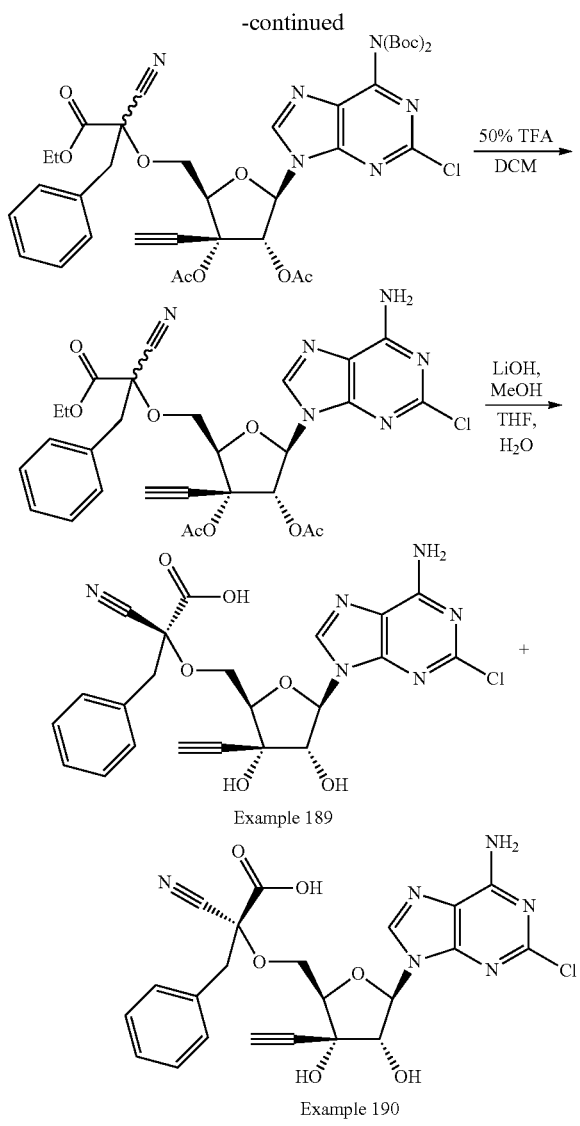

Example 189

Example 190

Step 1:

To a solution of R, 3R,4R,5R)-5-(6-N,N'-(bis-(tert-butoxycarbonyl)amino)-2-chloro-9H-purin-9-yl)-3-ethynyl-2-(hydroxymethyl)tetrahydrofuran-3,4-diyl diacetate (510 mg, 0.836 mmol) in toluene (5 mL) was added ethyl 2-cyano-2-diazoacetate (134 mg, 0.961 mmol). The mixture was concentrated in vacuo. The mixture was taken up in dry toluene (2 mL) and followed by addition of $Rh_2(OAc)_4$ (8 mg, 17 umol) under argon atmosphere. The material was stirred and heated at 80° C. for 30 minutes before additional ethyl 2-cyano-2-diazoacetate (254 mg, 1.82 mmol) was added over 60 min at 80° C. The reaction was further heated at 80° C. for 80 minutes before it was cooled to room temperature and concentrated. The crude product was purified by CombiFlash silica gel chromatography (5-65% of EtOAc in hexanes) to provide a diastereomeric mixture of (2R,3R,4R,5R)-5-(6-N,N'-(bis-(tert-butoxycarbonyl)amino)-2-chloro-9H-purin-9-yl)-2-((1-cyano-2-ethoxy-2-oxoethoxy)methyl)-3-ethynyltetrahydrofuran-3,4-diyl diacetate (230 mg, 38% yield) as an off-white foam.

Step 2:

An oven dried flask was charged with ((2R,3R,4R,5R)-5-(6-N,N'-(bis-(tert-butoxycarbonyl)amino)-2-chloro-9H-purin-9-yl)-2-((1-cyano-2-ethoxy-2-oxoethoxy)methyl)-3-ethynyltetrahydrofuran-3,4-diyl diacetate (230 mg, 0.319 mmol) and taken up in dry DMF (4 mL). To this mixture was added $Cs_2CO_3$ (208 mg, 0.639 mmol) and followed by the addition of benzyl bromide (109 mg, 0.639 mmol). The mixture was stirred at 25° C. for 30 minutes before it was diluted with cold saturated aqueous $NH_4Cl$ (40 mL) and extracted with EtOAc (40 mL). The aqueous phases were extracted with EtOAc (2×40 mL). The combined organic layer was dried over $Na_2SO_4$, filtered and concentrated. The crude product was purified by CombiFlash silica gel column chromatography (10-70% EtOAc in hexanes) to provide (2R,3R,4R,5R)-5-(6-N,N'-(bis-(tert-butoxycarbonyl)amino)-2-chloro-9H-purin-9-yl)-2-(((2-cyano-1-ethoxy-1-oxo-3-phenylpropan-2-yl)oxy)methyl)-3-ethynyltetrahydrofuran-3,4-diyl diacetate as a pair of diastereomers (215 mg, 83% yield) as an off-white solid.

Step 3:

A solution (2R,3R,4R,5R)-5-(6-N,N'-(bis-(tert-butoxycarbonyl)amino)-2-chloro-9H-purin-9-yl)-2-(((2-cyano-1-ethoxy-1-oxo-3-phenylpropan-2-yl)oxy)methyl)-3-ethynyltetra-hydrofuran-3,4-diyl diacetate (215 mg, 0.265 mmol) in a solution of TFA (1 mL) in DCM (1 mL) was stirred for 2 h before it was concentrated under reduced pressure. The residue was azetroped with DCM (8×8 mL) under reduced pressure. The residue was taken up in a mixture of MeOH in $H_2O$ (2.2 mL, 5:1=v:v) and followed by addition of $LiOH·H_2O$ (77 mg, 1.86 mmol, 7 eq) and THF (0.5 mL). The mixture was stirred at ambient temperature for 40 minutes before it was concentrated to dryness. The residue was dissolved in $H_2O$ (15 mL). The aqueous phase was extracted with EtOAc (2×10 mL). The aqueous phase was acidified to pH 2.5 with 1N aq. HCl solution. The aqueous phase was extracted with EtOAc (3×50 mL). The combined organic layer was washed with brine (50 mL), dried over $Na_2SO_4$, filtered and concentrated. The crude residue was purified by preparative reversed-phase HPLC to provide the title compounds as a pair of diastereomers: (S)-2-(((2R,3S,4R,5R)-5-(6-amino-2-chloro-9H-purin-9-yl)-3-ethynyl-3,4-dihydroxytetrahydrofuran-2-yl)methoxy)-2-cyano-3-phenylpropanoic acid (33.7 mg, 26% yield) and (R)-2-(((2R,3S,4R,5R)-5-(6-amino-2-chloro-9H-purin-9-yl)-3-ethynyl-3,4-dihydroxytetrahydrofuran-2-yl)methoxy)-2-cyano-3-phenylpropanoic acid (30 mg, 23% yield) which the stereo configuration was assigned arbitrarily. Both were isolated as off-white solids.

(S)-2-(((2R,3S,4R,5R)-5-(6-amino-2-chloro-9H-purin-9-yl)-3-ethynyl-3,4-dihydroxytetra-hydrofuran-2-yl) methoxy)-2-cyano-3-phenylpropanoic acid: $^1H$ NMR ($CD_3OD$, 300 MHz) δ 8.32 (bs, 1H), 7.20-7.36 (m, 5H), 6.02 (d, J=7.00 Hz, 1H), 4.68 (d, J=7.02 Hz, 1H), 4.33-4.37 (m, 1H), 4.18 (dd, J=9.91, 3.96 Hz, 1H), 3.99 (dd, J=9.94, 2.19 Hz, 1H), 3.41 (bs, 2H), 3.03 (s, 1H); LC/MS [M+H]=499.1.

(R)-2-(((2R,3S,4R,5R)-5-(6-amino-2-chloro-9H-purin-9-yl)-3-ethynyl-3,4-dihydroxytetra-hydrofuran-2-yl) methoxy)-2-cyano-3-phenylpropanoic acid: $^1H$ NMR ($CD_3OD$, 300 MHz) δ 8.04 (bs, 1H), 7.21-7.39 (m, 5H), 5.99 (d, J=6.90 Hz, 1H), 4.79 (d, J=6.93 Hz, 1H), 4.31-4.36 (m, 1H), 4.19 (dd, J=10.07, 4.34 Hz, 1H), 4.12 (dd, J=10.10, 3.30 Hz, 1H), 3.38-3.44 (m, 2H), 3.09 (s, 1H); LC/MS [M+H]=499.1.

Examples 191 and 192

Synthesis of (S)-2-(((2R,3S,4R,5R)-5-(6-amino-2-chloro-9H-purin-9-yl)-3-ethynyl-3,4-dihydroxytetrahydrofuran-2-yl)methoxy)-3-phenyl-2-(1H-tetrazol-5-yl)propanoic acid and (R)-2-(((2R,3S,4R,5R)-5-(6-amino-2-chloro-9H-purin-9-yl)-3-ethynyl-3,4-dihydroxytetrahydrofuran-2-yl)methoxy)-3-phenyl-2-(1H-tetrazol-5-yl)propanoic acid

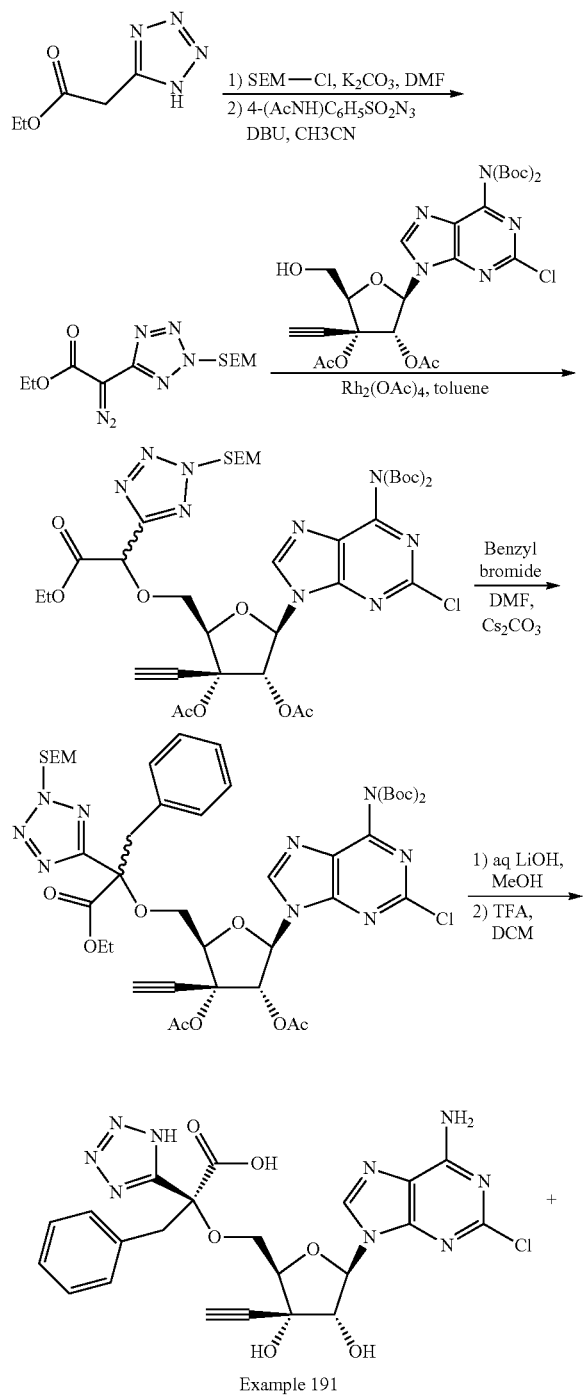

Example 191

Example 192

Step 1:

To a solution of ethyl 1H-tetrazole-5-acetate (3 g, 19.21 mmol) in DMF (40 mL) under argon atmosphere at 25° C. was added 2-(trimethylsilyl)ethoxymethyl chloride (4.1 mL, 23.05 mmol) and powdered potassium carbonate (5.31 g, 38.42 mmol). The reaction mixture was stirred overnight before it was diluted with brine (70 mL) and EtOAc (70 mL). The aqueous phase was extracted with EtOAc (2×70 mL). The combined organic layer was washed with brine (70 mL) and water (70 mL), dried over $Na_2SO_4$ and concentrated. The residue was purified by silica gel column chromatography (15-48% EtOAc in hexanes) to provide ethyl 2-(2-((2-(trimethylsilyl)ethoxy)methyl)-2H-tetrazol-5-yl)acetate (2.379 g) as a light yellow oil.

Step 2:

To a solution of ethyl 2-(2-((2-(trimethylsilyl)ethoxy)methyl)-2H-tetrazol-5-yl)acetate (2.379 g, 8.31 mmol) in dry acetonitrile (25 mL) under argon atmosphere was added DBU (1.87 mL, 12.47 mmol). To this mixture was added 4-acetamidobenzenesulfonyl azide (2.395 g, 9.96 mmol) in 3 equal portions over 5 minutes. The reaction mixture was stirred for 3.5 h the organic volatile was removed under reduced pressure. The residue was purified by silica gel column chromatography (20% EtOAc in hexanes) to provide ethyl 2-diazo-2-(2-((2-(trimethylsilyl)ethoxy)methyl)-2H-tetrazol-5-yl)acetate (2.316 g) as an oil.

Step 3:

To a solution of (2R,3R,4R,5R)-5-(6-(bis-(tert-butoxycarbonyl)amino)-2-chloro-9H-purin-9-yl)-3-ethynyl-2-(hydroxymethyl)tetrahydrofuran-3,4-diyl diacetate (2 g, 3.28 mmol) in toluene (8 mL) at 20° C. under $N_2$ atmosphere was added $Rh_2(OAc)_4$ (29 mg, 0.066 mmol, 0.066 eq) and ethyl 2-diazo-2-(2-((2-(trimethylsilyl)ethoxy)-methyl)-2H-tetrazol-5-yl)acetate (1.08 g, 3.44 mmol, 1.05 eq). The mixture was stirred at 75° C. for 1 h before additional ethyl 2-diazo-2-(2-((2-(trimethylsilyl)ethoxy)methyl)-2H-tetrazol-5-yl)acetate (720 mg) was added over 80 min. The reaction mixture was cooled to ambient temperature and concentrated. The crude material was purified by Combi-Flash silica gel column (5-80% EtOAc in hexanes) to provide a diastereomeric mixture of (2R,3R,4R,5R)-5-(6-(bis-(tert-butoxycarbonyl)amino)-2-chloro-9H-purin-9-yl)-2-((2-ethoxy-2-oxo-1-(2-((2-(trimethylsilyl)ethoxy)methyl)-2H-tetrazol-5-yl)ethoxy)methyl)-3-ethynyltetrahydrofuran-3,4-diyl diacetate (1.608 g) as a gum.

Step 4:

To a solution of (2R,3R,4R,5R)-5-(6-(bis-(tert-butoxycarbonyl)amino)-2-chloro-9H-purin-9-yl)-2-((2-ethoxy-2-oxo-1-(2-((2-(trimethylsilyl)ethoxy)methyl)-2H-tetrazol-5-yl)ethoxy)methyl)-3-ethynyltetrahydrofuran-3,4-diyl diacetate (1.555 g, 1.739 mmol) in dry toluene (10 mL). The mixture was concentrated under reduced pressure. The residue was taken up in dry DMF (10 mL) and followed by addition of benzyl bromide (1.189 g, 6.96 mmol) and dried Cs$_2$CO$_3$ (1.133 g, 3.478 mmol). The mixture was stirred at 25° C. for 5.5 h before it was diluted with saturated aq. NH$_4$Cl solution (60 mL). The aqueous phase was extracted with EtOAc (3×60 mL). The combined organic layer was washed with brine (60 mL), dried over Na$_2$SO$_4$, filtered and concentrated. The crude product was purified by flash silica gel column chromatography (5-65% EtOAc in hexanes) to provide a diastereomeric mixture of (2R,3R,4R,5R)-5-(6-(bis-(tert-butoxycarbonyl)amino)-2-chloro-9H-purin-9-yl)-2-(((1-ethoxy-1-oxo-3-phenyl-2-(2-((2-(trimethylsilyl)ethoxy) methyl)-2H-tetrazol-5-yl)propan-2-yl)oxy)methyl)-3-ethynyltetrahydrofuran-3,4-diyl diacetate (1.041 g) as a foam.

Step 5:

To a solution of (2R,3R,4R,5R)-5-(6-(bis-(tert-butoxycarbonyl)amino)-2-chloro-9H-purin-9-yl)-2-(((1-ethoxy-1-oxo-3-phenyl-2-(2-((2-(trimethylsilyl)ethoxy)methyl)-2H-tetrazol-5-yl)propan-2-yl)oxy)methyl)-3-ethynyltetrahydrofuran-3,4-diyl diacetate (1.041 g, 1.057 mmol) in a mixture of MeOH and H$_2$O (12 mL, 6:1=v:v) was added powdered LiOH.H$_2$O (349 mg, 8.5 mmol). The mixture was stirred at 23° C. for 16 h before it was concentrated to dryness. The residue was dissolved in H$_2$O (40 mL) and it was extracted with EtOAc (40 mL). The aqueous phase was acidified to pH 2.5 with 1N aq. HCl solution and extracted with EtOAc (3×40 mL). The combined organic layer was washed with brine (40 mL), dried over Na$_2$SO$_4$, filtered and concentrated to provide a diastereomeric mixture of 2-(((2R,3S,4R,5R)-5-(6-((tert-butoxycarbonyl)amino)-2-chloro-9H-purin-9-yl)-3-ethynyl-3,4-dihydroxytetrahydrofuran-2-yl)methoxy)-3-phenyl-2-(2-((2-(trimethylsilyl)ethoxy)methyl)-2H-tetrazol-5-yl)propanoic acid (784 mg) as an oil.

Step 6:

To a solution of 2-(((2R,3S,4R,5R)-5-(6-((tert-butoxycarbonyl)amino)-2-chloro-9H-purin-9-yl)-3-ethynyl-3,4-dihydroxytetrahydrofuran-2-yl)methoxy)-3-phenyl-2-(2-((2-(trimethylsilyl)ethoxy)methyl)-2H-tetrazol-5-yl)propanoic acid (138 mg, 0.179 mmol) in DCM (0.9 mL) under argon atmosphere at 0° C. was added TFA (0.9 mL). The mixture was stirred at 0° C. for 5 h and then stirred to ambient for 15 min before the organic volatile was removed under the reduced pressure. The residue was azetroped with DCM (3×15 mL) under reduced pressure. The crude residue was purified by preparative reversed-phase HPLC to provide the two title products as a pair of diastereomers: (S)-2-(((2R,3S,4R,5R)-5-(6-amino-2-chloro-9H-purin-9-yl)-3-ethynyl-3,4-dihydroxytetrahydrofuran-2-yl)methoxy)-3-phenyl-2-(1H-tetrazol-5-yl)propanoic from the first fraction and (R)-2-(((2R,3S,4R,5R)-5-(6-amino-2-chloro-9H-purin-9-yl)-3-ethynyl-3,4-dihydroxytetrahydrofuran-2-yl)methoxy)-3-phenyl-2-(1H-tetrazol-5-yl)propanoic acid from the later fraction. Both isolated as off-white solids.

(S)-2-(((2R,3S,4R,5R)-5-(6-amino-2-chloro-9H-purin-9-yl)-3-ethynyl-3,4-dihydroxytetra-hydrofuran-2-yl)methoxy)-3-phenyl-2-(1H-tetrazol-5-yl)propanoic acid: $^1$H NMR (CD$_3$OD, 300 MHz); δ 8.37 (s, 1H), 7.11-7.23 (m, 5H), 5.96 (d, J=6.57 Hz, 1H), 4.81 (d, J=6.57 Hz, 1H), 4.25-4.30 (m, 1H), 4.01 (dd, J=10.19, 2.29 Hz, 1H), 3.78 (d, J=13.90 Hz, 1H), 3.67 (d, J=13.90 Hz 1H), 3.72-3.79 (m, 1H), 3.06 (s, 1H); LC/MS [M+H]=542.2.

(R)-2-(((2R,3S,4R,5R)-5-(6-amino-2-chloro-9H-purin-9-yl)-3-ethynyl-3,4-dihydroxytetra-hydrofuran-2-yl)methoxy)-3-phenyl-2-(1H-tetrazol-5-yl)propanoic acid: $^1$H NMR (CD$_3$OD, 300 MHz); δ 8.37 (s, 1H), 6.92-7.11 (m, 5H), 6.01 (d, J=7.11 Hz, 1H), 5.06 (d, J=7.11 Hz, 1H), 4.35-4.39 (m, 1H), 4.11 (dd, J=10.06, 2.52 Hz, 1H), 4.01 (dd, J=10.06, 5.49 Hz, 1H), 3.80 (d, J=14.75 Hz 1H), 3.67 (d, J=14.75 Hz 1H), 2.96 (s, 1H); LC/MS [M+H]=542.2.

Examples 193 and 194

Synthesis of (S)-2-(((2R,3S,4R,5R)-5-(6-amino-2-chloro-9H-purin-9-yl)-3-ethynyl-3,4-dihydroxytetrahydrofuran-2-yl)methoxy)-2-(2-phenylthiazol-4-yl) acetic acid and (R)-2-(((2R,3S,4R,5R)-5-(6-amino-2-chloro-9H-purin-9-yl)-3-ethynyl-3,4-dihydroxytetrahydrofuran-2-yl)methoxy)-2-(2-phenylthiazol-4-yl)acetic acid

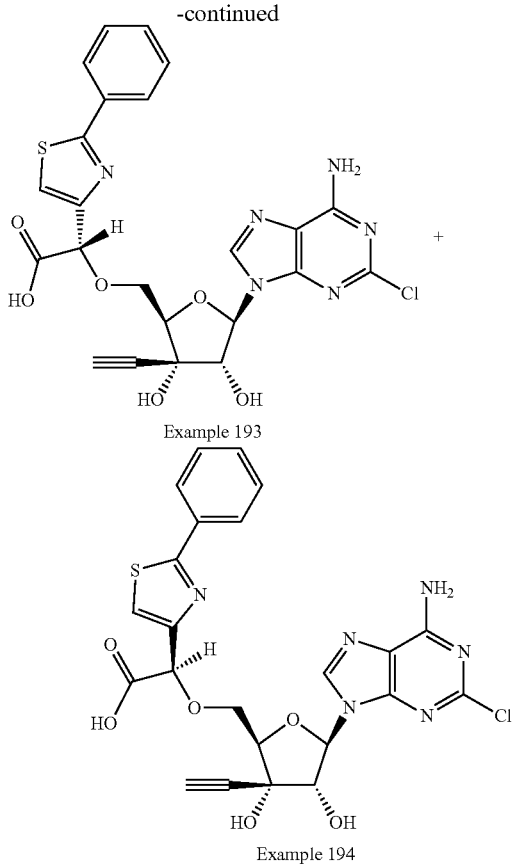

Example 193

Example 194

Proceeding as described in Example 179 but substituting ethyl 2-diazo-2-(thiazol-4-yl)acetate with ethyl (2-phenylthiazol-4-yl)diazoacetate which was prepared via the procedure described by Lefebvre, Quentin, et al., (*Chemical Communications* 2014, 50, 6617-6619) provided the title compounds as a pair of diastereomers (ca. 1:1). The stereo configuration was assigned arbitrarily. Both were isolated as off-white solids.

(S)-2-(((2R,3S,4R,5R)-5-(6-amino-2-chloro-9H-purin-9-yl)-3-ethynyl-3,4-dihydroxytetra-hydrofuran-2-yl)methoxy)-2-(2-phenylthiazol-4-yl)acetic acid: $^1$H NMR (CD$_3$OD, 300 MHz); δ 9.03 (bs, 1H), 7.91-7.97 (m, 2H), 7.60 (s, 1H), 7.39-7.45 (m, 3H), 6.06 (d, J=7.45 Hz, 1H), 5.28 (s, 1H), 4.92 (d, J=7.45 Hz, 1H), 4.29-4.33 (m, 1H), 4.12 (dd, J=10.45, 2.51 Hz, 1H), 4.01 (dd, J=10.46, 2.56 Hz, 1H), 2.92 (s, 1H); LC/MS [M+H]=543.1.

(R)-2-(((2R,3S,4R,5R)-5-(6-amino-2-chloro-9H-purin-9-yl)-3-ethynyl-3,4-dihydroxytetra-hydrofuran-2-yl)methoxy)-2-(2-phenylthiazol-4-yl)acetic acid: $^1$H NMR (CD$_3$OD, 300 MHz); δ 9.15 (s, 1H), 7.90-7.96 (m, 2H), 7.61 (s, 1H), 7.38-7.44 (m, 3H), 6.09 (d, J=7.48 Hz, 1H), 5.23 (d, J=7.48 Hz, 1H), 5.30 (s, 1H), 4.26-4.29 (m, 1H), 3.93 (dd, J=10.67, 2.18 Hz, 1H), 3.76 (dd, J=10.64, 2.48 Hz, 1H), 3.17 (s, 1H); LC/MS [M+H]=543.2.

Example 195

Synthesis of 4-((((2R,3S,4R,5R)-5-(6-amino-2-chloro-9H-purin-9-yl)-3-ethynyl-3,4-dihydroxytetra-hydrofuran-2-yl)methoxy)(carboxy)methyl)thiazole-2-carboxylic acid

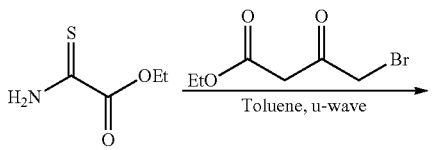

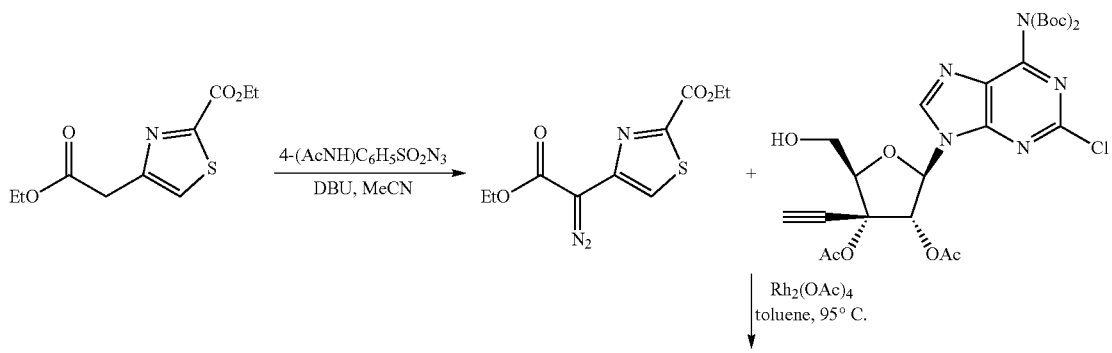

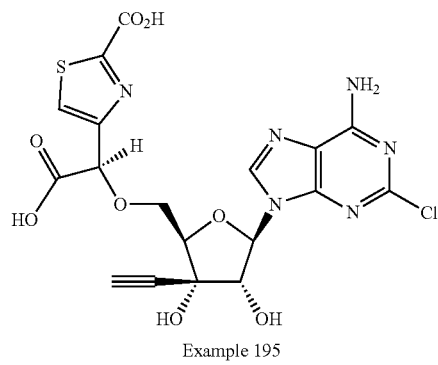

Example 195

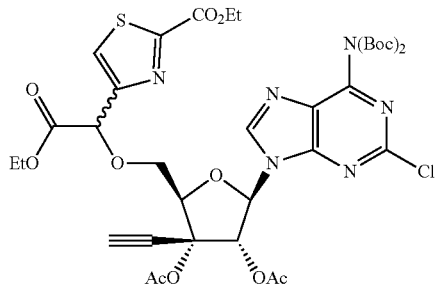

Step 1:

To a microwave vial was charged with ethyl thiooxamate (1.91 g, 14.36 mmol) and ethyl 4-bromoacetoacetate (3 g, 14.36 mmol) in dry toluene (27 mL). The mixture was irradiated in a microwave reactor at 90° C. for 1 hour. The reaction mixture was cooled to ambient and the solvent decanted and then was concentrated. The crude residue was purified by CombiFlash silica gel chromatography (2-56% EtOAc in hexanes) to provide ethyl 4-(2-ethoxy-2-oxoethyl) thiazole-2-carboxylate (890 mg, 26% yield) as a thick oil.

Step 2:

To a solution of ethyl 4-(2-ethoxy-2-oxoethyl)thiazole-2-carboxylate (890 mg, 3.66 mmol) in dry acetonitrile (12 mL) under argon atmosphere was added DBU (0.82 mL, 5.49 mmol) and 4-acetamidobenzenesulfonyl azide (1.055 g, 4.39 mmol). The reaction mixture was stirred for 1.5 hours before it was concentrated under reduced pressure. The residue was purified by silica gel column chromatography (20% EtOAc in hexanes) to provide ethyl 4-(1-diazo-2-ethoxy-2-oxo-ethyl)thiazole-2-carboxylate (894 mg, 90% yield) as a yellowish solid.

Step 3:

Proceeding as described in Example 179 but substituting ethyl 2-diazo-2-(thiazol-4-yl)acetate with ethyl 4-(1-diazo-2-ethoxy-2-oxoethyl)thiazole-2-carboxylate provided the title compound as a mixture of diastereomers (ca. 1:1) and isolated as off-white solids.

Isomer 1: $^1$H NMR (CD$_3$OD, 300 MHz): δ 8.93 (s, 1H), 7.91 (s, 1H), 6.06 (d, J=7.42 Hz, 1H), 5.39 (s, 1H), 5.13 (d, J=7.42 Hz, 1H), 4.24-4.31 (m, 1H), 4.03-4.09 (m, 1H), 3.75-3.83 (m, 1H), 2.95 (s, 1H); LC/MS [M+H]=511.1.

Isomer 2: $^1$H NMR (CD$_3$OD, 300 MHz): δ 8.87 (s, 1H), 7.93 (s, 1H), 6.04 (d, J=7.42 Hz, 1H), 5.33 (s, 1H), 4.91 (d, J=7.45 Hz, 1H), 4.24-4.31 (m, 1H), 3.92-4.01 (m, 2H), 3.19 (s, 1H); LC/MS [M+H]=511.1.

Example 196

Synthesis of 4-(1-(((2R,3S,4R,5R)-5-(6-amino-2-chloro-9H-purin-9-yl)-3-ethynyl-3,4-dihydroxytetrahydrofuran-2-yl)methoxy)-1-carboxy-2-phenylethyl) thiazole-2-carboxylic acid

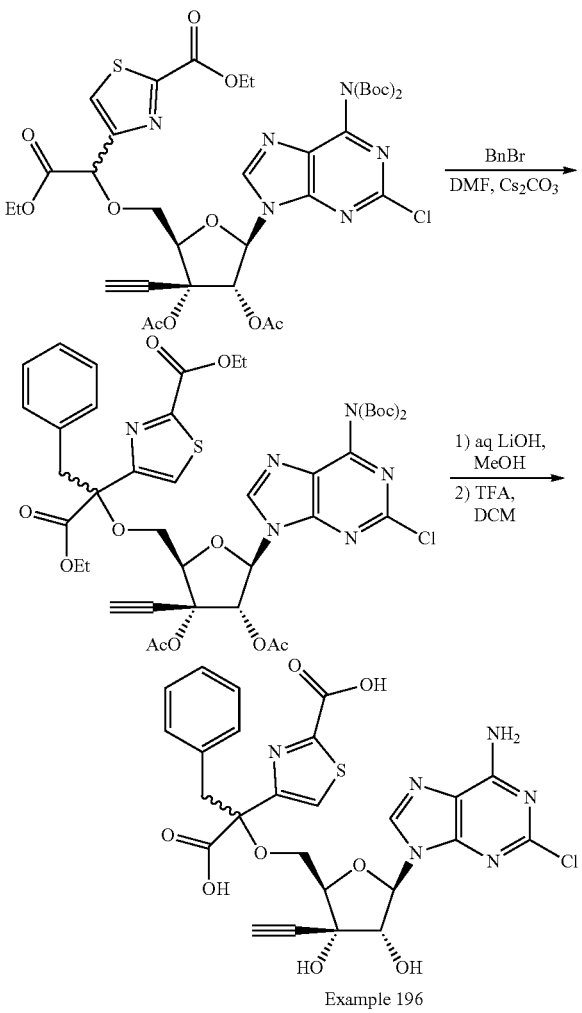

Example 196

Proceeding as described in Example 179 above but substituting (2R,3R,4R,5R)-5-(6-N,N'-(bis-(tert-butoxycarbonyl)amino)-2-chloro-9H-purin-9-yl)-3-ethynyl-2-(hydroxyl-methyl)tetrahydrofuran-3,4-diyl diacetate with (2R, 3R,4R,5R)-5-(6-N,N'-(bis-(tert-butoxy-carbonyl)amino))-2-chloro-9H-purin-9-yl)-2-((2-ethoxy-1-(2-(ethoxycarbonyl)thiazol-4-yl)-2-oxoethoxy)methyl)-3-ethynyltetrahydrofuran-3,4-diyl diacetate provided the title compound as a mixture of diastereomers (ca. 1:1) and isolated as an off-white solid.

Isomer 1: ¹H NMR (CD₃OD, 300 MHz): δ 8.17 (bs, 1H), 7.81 (s, 1H), 6.92-7.25 (m, 5H), 5.95 (d, J=7.02 Hz, 1H), 4.89 (d, J=7.02 Hz, 1H), 4.29-4.34 (m, 1H), 3.59-4.05 (m, 4H), 3.01 (s, 1H); LC/MS [M+H]=601.1.

Isomer 2: ¹H NMR (CD₃OD, 300 MHz): δ 8.05 (bs, 1H), 7.90 (s, 1H), 6.92-7.25 (m, 5H), 6.00 (d, J=7.41 Hz, 1H), 5.04 (d, J=7.42 Hz, 1H), 4.21-4.26 (m, 1H), 3.59-4.05 (m, 4H), 3.06 (s, 1H); LC/MS [M+H]=601.1.

Examples 197

Synthesis of 2-(((2R,3S,4R, 5R)-5-(6-amino-2-chloro-9H-purin-9-yl)-3-ethynyl-3,4-dihydroxytetrahydrofuran-2-yl)methoxy)-2-(4-(2-aminopyridin-3-yl)benzyl)malonic acid

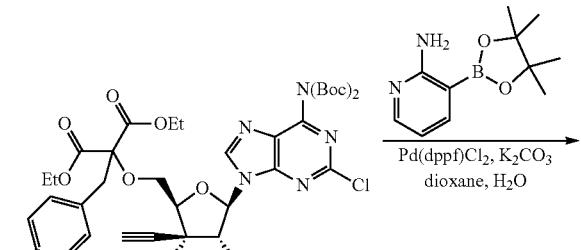

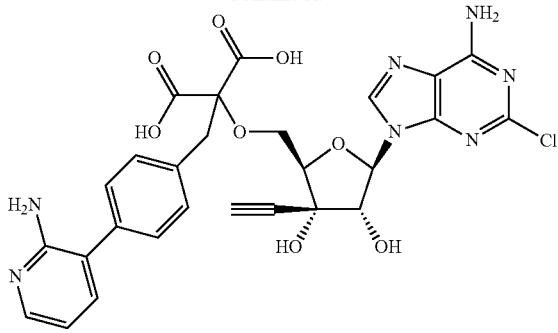

Example 197

Proceeding as described in Example 22 above but substituting (2-oxo-1,2-dihydropyridin-3-yl)boronic acid with 3-(4,4,5,5-tetramethyl-1,3,2-dioxaborolan-2-yl)pyridin-2-amine provided the title compound as a white solid.

¹H NMR (CD₃OD, 300 MHz) δ 8.43 (s, 1H), 7.85-7.87 (dd, J=1.5, 6.42 Hz, 1H), 7.65-7.68 (dd, J=1.53, 7.38 Hz, 1H), 7.37-7.40 (d, J=8.13 Hz, 2H), 7.09-7.12 (d, J=8.07 Hz, 2H), 6.88-6.93 (t, J=6.9 Hz, 1H), 5.99-6.01 (d, J=6.72 Hz, 1H), 4.77-4.79 (d, J=7.0, 1H), 4.37-4.40 (m, 1H), 3.98-4.12 (m, 2H), 3.34-3.42 (m, 2H), 3.09 (s, 1H); LC/MS [M+H]=610.1.

Examples 198 & 199

Synthesis of (S)-3-([1,1'-biphenyl]-4-yl)-2-(((2R,3S, 4R, 5R)-5-(6-amino-2-chloro-9H-purin-9-yl)-3,4-dihydroxy-3-methyltetrahydrofuran-2-yl)methoxy)-2-(thiazol-4-yl)propanoic acid and (R)-3-([1,1'-biphenyl]-4-yl)-2-(((2R,3S,4R, 5R)-5-(6-amino-2-chloro-9H-purin-9-yl)-3,4-dihydroxy-3-methyltetrahydrofuran-2-yl)methoxy)-2-(thiazol-4-yl)propanoic acid

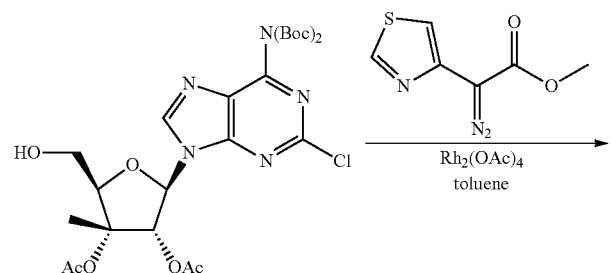

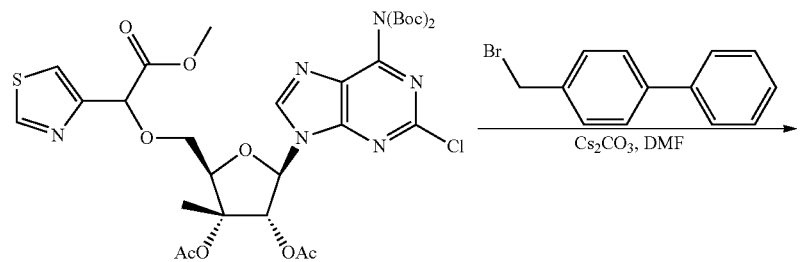

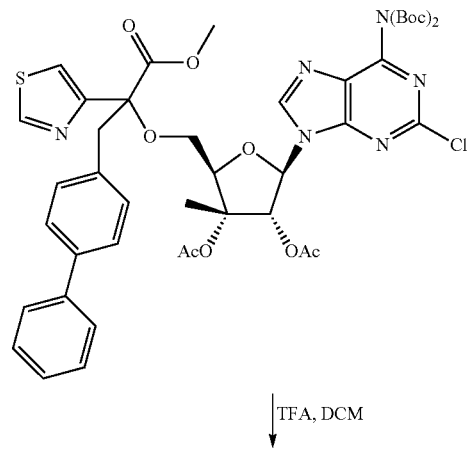

↓ TFA, DCM

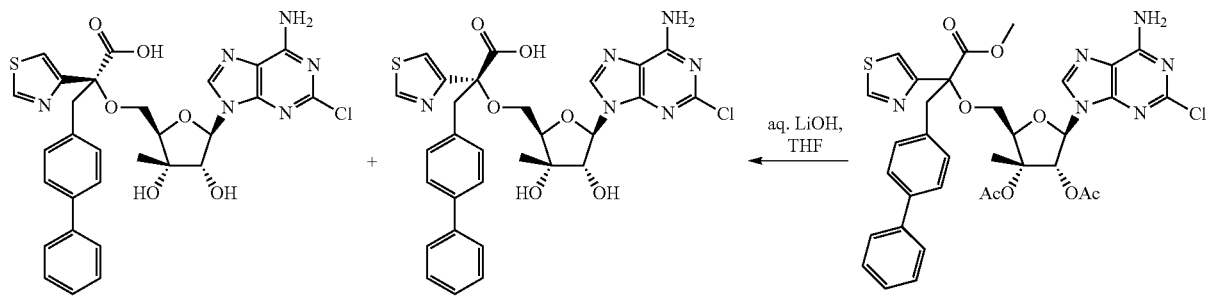

Example 198     Example 199

← aq. LiOH, THF

Proceeding as described in Example 1 above but substituting (2R,3R,4R,5R)-5-(6-(bis-(tert-butoxycarbonyl)amino)-2-chloro-9H-purin-9-yl)-2-(((tert-butyldiphenylsilyl)oxy)-methyl)-3-ethynyltetrahydrofuran-3,4-diyl diacetate and diethyl 2-diazomalonate with (2R,3R,4R,5R)-5-(6-(N,N'-bis-(tert-butoxycarbonyl)amino)-2-chloro-9H-purin-9-yl)-2-(hydroxylmethyl)-3-methyltetrahydrofuran-3,4-diyl diacetate and methyl 2-diazo-2-(thiazol-4-yl)acetate provided a pair of diastereomeric title products (ca. 1:1) which the stereo configuration was assigned arbitrarily. Both products were purified by preparative HPLC and isolated as white solids.

(S)-3-([1,1'-biphenyl]-4-yl)-2-(((2R,3S,4R,5R)-5-(6-amino-2-chloro-9H-purin-9-yl)-3,4-dihydroxy-3-methyltetrahydrofuran-2-yl)methoxy)-2-(thiazol-4-yl)propanoic acid:
¹H NMR (CD₃OD, 300 MHz) δ 9.04 (s, 1H), 8.42 (s, 1H), 7.74 (s, 1H), 7.21-7.45 (m, 9H), 6.00-6.03 (d, J=8 Hz, 1H), 4.67-4.70 (d, J=7 Hz, 1H), 4.13 (s, 1H), 3.88-3.85 (m, 2H), 3.62-3.66 (d, J=14 Hz, 1H), 3.44-3.47 (d, J=11 Hz, 1H), 1.37 (s, 3H); LC/MS [M+H]=623.2.

(R)-3-([1,1'-biphenyl]-4-yl)-2-(((2R,3S,4R,5R)-5-(6-amino-2-chloro-9H-purin-9-yl)-3,4-dihydroxy-3-methyltetrahydrofuran-2-yl)methoxy)-2-(thiazol-4-yl)propanoic acid:
¹H NMR (CD₃OD, 300 MHz) δ 9.04 (s, 1H), 8.21 (s, 1H), 7.27-7.69 (m, 10H), 5.93-5.95 (d, J=7 Hz, 1H), 4.52-4.55 (d, J=8 Hz, 1H), 4.04 (s, 1H), 3.79-3.85 (m, 3H), 1.36 (s, 3H); LC/MS [M+H]=623.2.

Example 200

Synthesis of 4'-(2-(((2R,3S,4R,5R)-5-(6-amino-2-chloro-9H-purin-9-yl)-3,4-dihydroxy-3-methyltetrahydrofuran-2-yl)methoxy)-2-carboxy-2-(thiazol-4-yl)ethyl)-[1,1'-biphenyl]-2-carboxylic acid

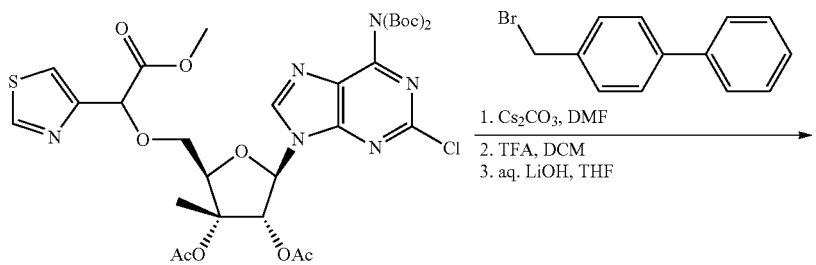

1. Cs₂CO₃, DMF
2. TFA, DCM
3. aq. LiOH, THF

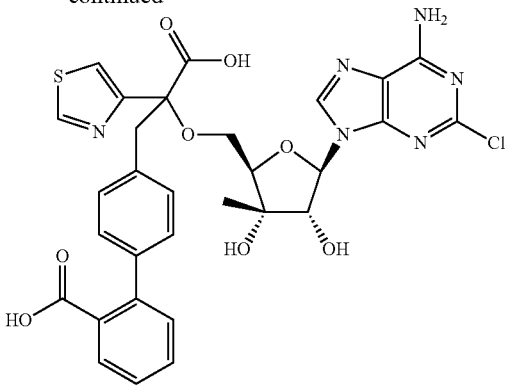

Example 200

Proceeding as described in Example 179 above but substituting (2R,3R,4R,5R)-5-((6-N,N'-bis-(tert-butoxycarbonyl)amino)-2-chloro-9H-purin-9-yl)-3-ethynyl-2-(hydroxyl-methyl)tetrahydrofuran-3,4-diyl diacetate and BnBr with (2R,3R,4R,5R)-5-(6-(N,N'-bis-(tert-butoxycarbonyl)amino)-2-chloro-9H-purin-9-yl)-2-((2-methoxy-2-oxo-1-(thiazol-4-yl)ethoxy)methyl)-3-methyltetrahydrofuran-3,4-diyl diacetate and 4-(bromomethyl)-1,1'-biphenyl provided the title compound as a mixture of diastereomers (ca. 1:1) and isolated as an off-white solid.

LC/MS [M+H]=667.2.

Example 201

Synthesis of 4'-(2-(((2R,3S,4R,5R)-5-(6-amino-2-chloro-9H-purin-9-yl)-3,4-dihydroxy-3-methyltetrahydrofuran-2-yl)methoxy)-2-carboxy-2-(1H-tetrazol-5-yl)ethyl)-[1,1'-biphenyl]-2-carboxylic acid

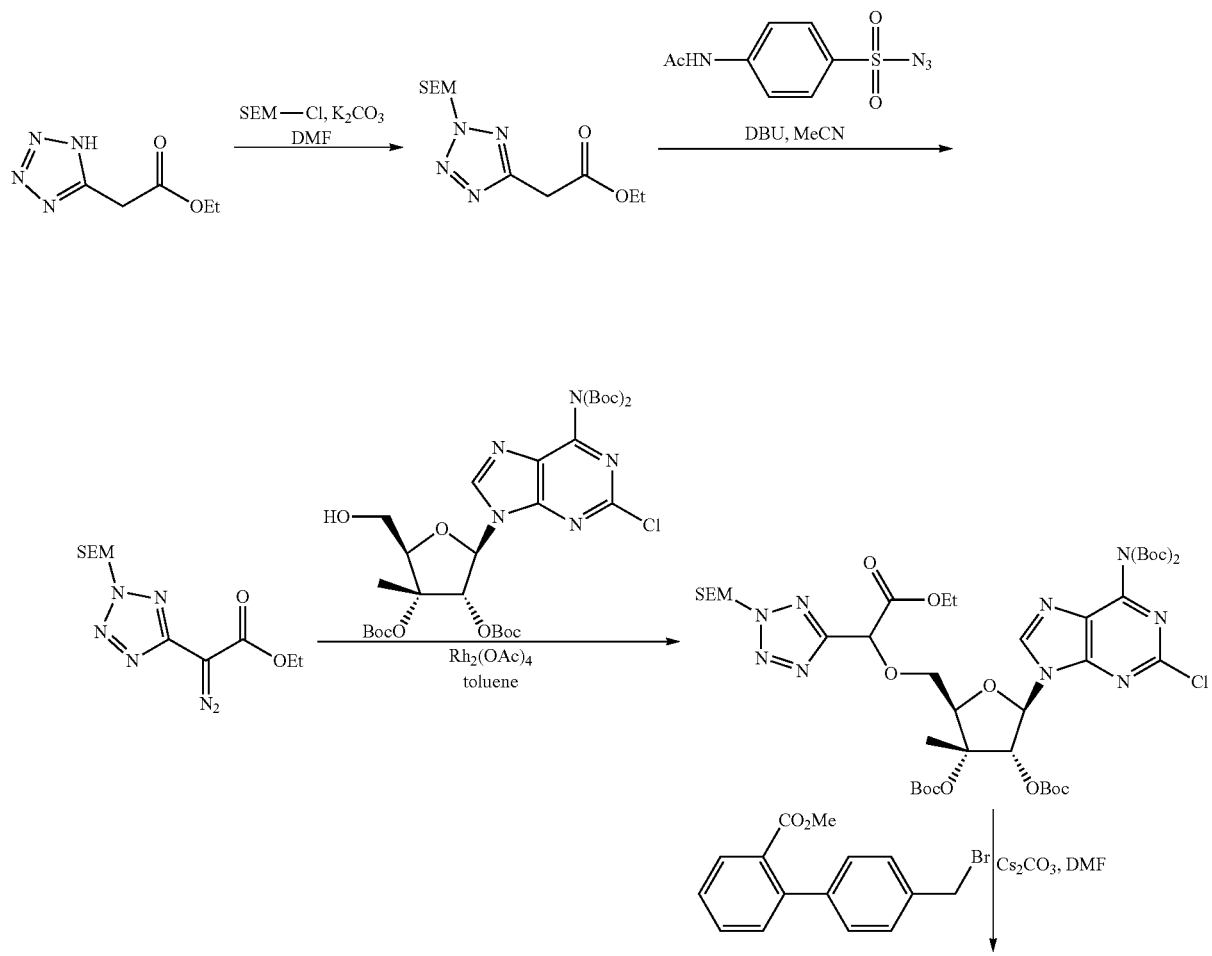

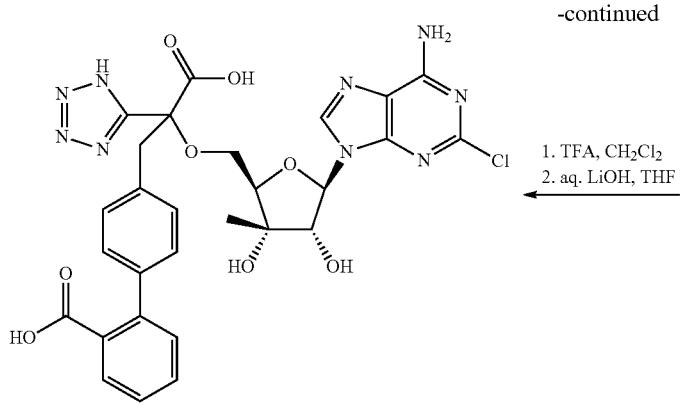

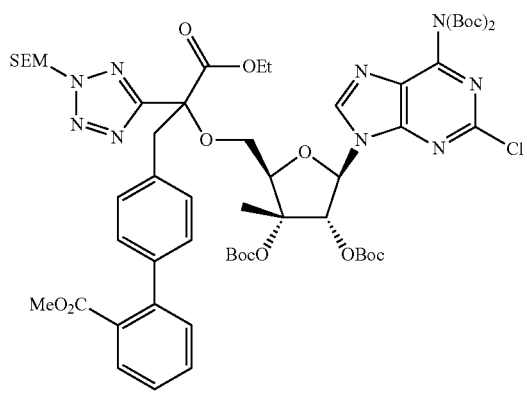

Example 201

Step 1:

To a solution of ethyl 2-(1H-tetrazol-5-yl)acetate (500 mg, 3.24 mmol) and trimethylsilyl)ethoxymethyl chloride (0.69 mL, 3.89 mmol) in dry DMF (7 mL) under argon atmosphere at 25° C. was added powdered potassium carbonate (896 mg, 6.48 mmol). The reaction mixture was stirred overnight before it was diluted with H$_2$O (30 mL) and extracted with EtOAc (3×30 mL). The combined organic layer was washed with brine (30 mL) and water (30 mL) and then dried over Na$_2$SO$_4$ and concentrated. The residue was purified by CombiFlash silica gel column chromatography (8-58% EtOAc in hexanes) to provide ethyl 2-(2-((2-(trimethylsilyl)ethoxy)methyl)-2H-tetrazol-5-yl)acetate (200 mg) as an oil.

Steps 2-6:

Proceeding as described in Example 1 above but substituting methyl 2-(thiazol-4-yl)acetate with ethyl 2-(2-((2-(trimethylsilyl)ethoxy)methyl)-2H-tetrazol-5-yl)acetate provided a pair of diastereomeric title products (ca. 1:1) which the stereo configuration was assigned arbitrarily. Both products were purified by preparative HPLC and isolated as off-white solids.

$^1$H NMR (CD$_3$OD, 300 MHz): Isomer 1: δ 8.50 (s, 1H), 7.73-7.79 (m, 2H), 7.31-7.56 (m, 3H), 7.01-7.24 (m, 4H), 6.04 (d, J=7.87 Hz, 1H), 4.64 (d, J=7.88 Hz, 1H), 4.10-4.14 (m, 1H), 3.46-4.00 (m, 4H), 1.35 (s, 3H); Isomer 2: δ 8.31 (s, 1H), 7.73-7.79 (m, 2H), 7.31-7.56 (m, 3H), 7.01-7.24 (m, 4H), 5.99 (d, J=7.75 Hz, 1H), 4.48 (d, J=7.72 Hz, 1H), 4.19-4.23 (m, 1H), 3.46-4.00 (m, 4H), 1.42 (s, 3H); LC/MS [M+H]=652.2.

Example 202

Synthesis of (((((2R,3S,4R,5R)-5-(6-amino-2-chloro-9H-purin-9-yl)-3-ethynyl-3,4-dihydroxytetrahydrofuran-2-yl)methoxy)(hydroxy)phosphoryl)methyl)phosphonic acid

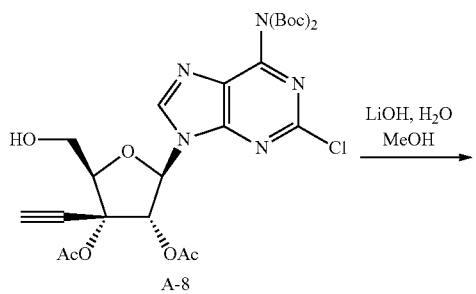

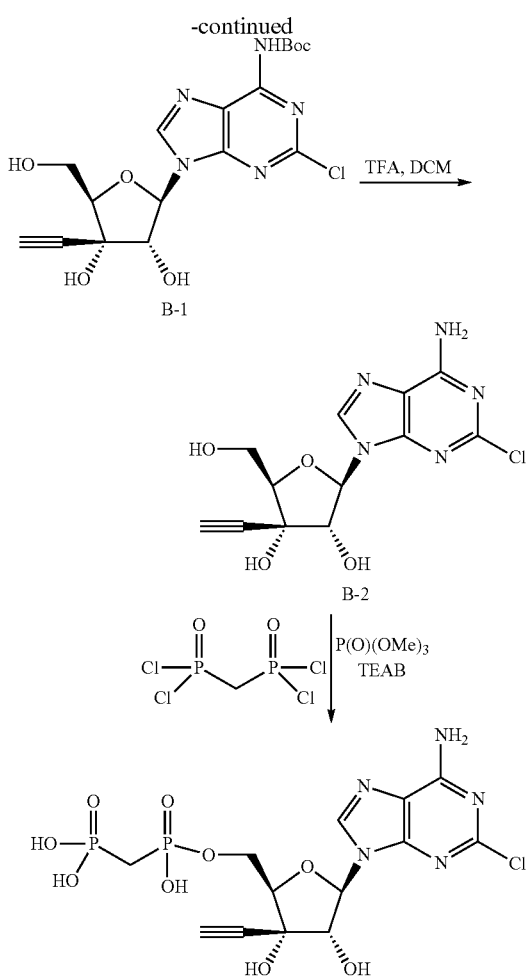

Example 202

Step 1:

To a solution of (2R,3R,4R,5R)-5-(6-(bis-(tert-butoxycarbonyl)amino)-2-chloro-9H-purin-9-yl)-3-ethynyl-2-(hydroxymethyl)tetrahydrofuran-3,4-diyl diacetate (329 mg, 0.539 mmol) in i-PrOH (1.6 mL), MeOH (1.1 mL) and H$_2$O (0.8 mL) was added powdered LiOH (111 mg, 2.69 mmol). The mixture was stirred for 30 minutes before the organic volatile was removed under reduced pressure and the residue was diluted with H$_2$O (12 mL). The pH of the aq. layer was adjusted to ~3 with 1N aq. HCl and extracted with EtOAc (3×12 mL). The combined organic layer was dried over MgSO$_4$, filtered and concentrated to provide tert-butyl (2-chloro-9-((2R,3R,4S,5R)-4-ethynyl-3,4-dihydroxy-5-(hydroxymethyl)tetrahydro-furan-2-yl)-9H-purin-6-yl)carbamate which was used in the next step directly without further purification.

Step 2:

Tert-butyl (2-chloro-9-((2R,3R,4S,5R)-4-ethynyl-3,4-dihydroxy-5-(hydroxymethyl)-tetrahydrofuran-2-yl)-9H-purin-6-yl)carbamate (0.539 mmol) was taken up in a mixture of DCM (1 mL) and TFA (0.5 mL). The reaction mixture was stirred for 3 h before it was concentrated. The residue was taken up in DCM (10 mL) and concentrated again (repeated 5 cycles). The residue was dried further in the vacuum oven for 18 h to provide crude (2R,3S,4R,5R)-5-(6-amino-2-chloro-9H-purin-9-yl)-3-ethynyl-2-(hydroxymethyl)tetrahydro-furan-3,4-diol as an off-white solid.

Step 3:

To an oven dried flask was charged with crude (2R,3S,4R,5R)-5-(6-amino-2-chloro-9H-purin-9-yl)-3-ethynyl-2-(hydroxymethyl)tetrahydrofuran-3,4-diol and dry trimethyl phosphate (2.5 mL) under argon atmosphere. The mixture was cooled at 0° C. and followed by dropwise addition of a solution of methylenebis(phosphonic dichloride) (673 mg, 2.7 mmol) in dry trimethyl phosphate (1.1 mL) over 10 minutes. The reaction mixture was stirred at 0° C. for 3 h before a solution of triethylammonium carbonate (1 M, 1.9 mL) was added dropwise. The mixture was stirred for 15 minutes at 0° C. and then stirred for 2 h at ambient temperature. The crude mixture was purified by preparative reversed-phase HPLC to provide a impure product. This impure product was further purified by reserved-phase HLPC twice to provide the desired (((((2R,3S,4R,5R)-5-(6-amino-2-chloro-9H-purin-9-yl)-3-ethynyl-3,4-dihydroxytetrahydrofuran-2-yl)methoxy)(hydroxy)phosphoryl)methyl)-phosphonic acid (34 mg) as a light brown solid.

$^1$H NMR (CD$_3$OD, 300 MHz): δ 8.75 (bs, 1H), 6.07 (br, 1H), 4.86 (bs, 1H), 4.31-4.61 (m, 3H), 3.20 (s, 1H), 2.54 (br, 1H); LC/MS [M+H]=484.0.

Example 203

Synthesis of (((((2R,3S,4R,5R)-5-(6-(benzylamino)-2-chloro-9H-purin-9-yl)-3-ethynyl-3,4-dihydroxytetrahydrofuran-2-yl)methoxy)(hydroxy)phosphoryl)methyl)phosphonic acid

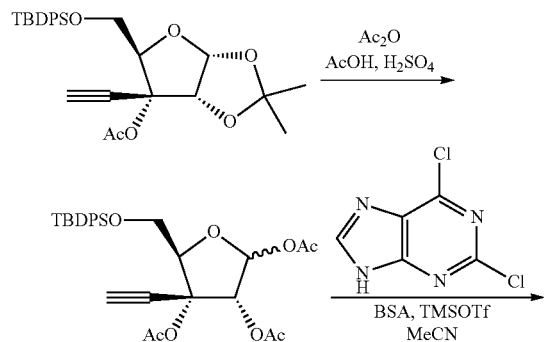

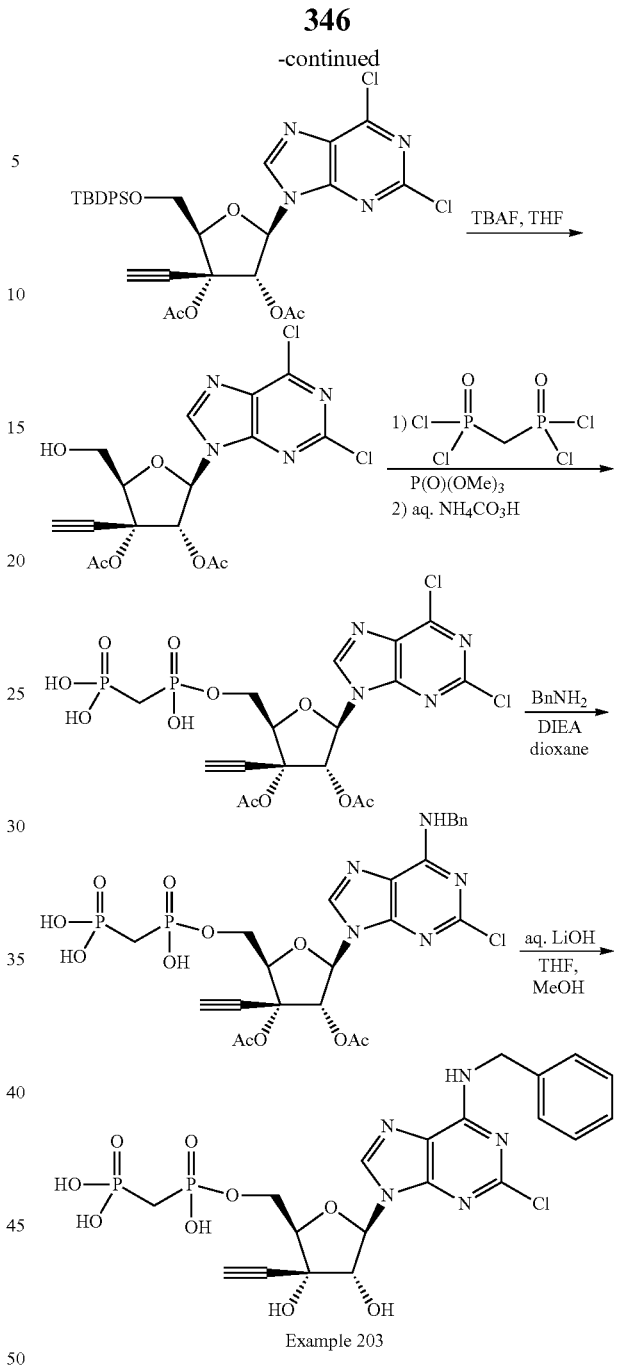

Example 203

Step 1:

While under nitrogen, a solution of (3aR,5R,6R,6aR)-5-(((tert-butyldiphenylsilyl)-oxy)methyl)-6-ethynyl-2,2-dimethyltetrahydrofuro[2,3-d][1,3]dioxol-6-ol (14.48 g, 32 mmoL) (prepared using the methods described in Hulpia, F. et al. Bioorg. Med. Chem. Lett. 2016, 26, 1970-1972) in acetic acid (130 mL) was cooled to 14-17° C. and treated with acetic anhydride (32.01 mL, 341 mmoL, 10.7 eq) and concentrated sulfuric acid (576 uL, 10.8 mmoL, 0.34 eq). After stirring at for 2.5 h. The mixture was diluted with ethyl acetate (200 mL each) and washed with water. The aqueous phase was extracted with ethyl acetate (25 mL), and the combined organic solution washed with sodium bicarbonate (aqueous, saturated, 200 mL), dried over Na$_2$SO$_4$, filtered, and concentrated. The residual oil was purified by flash column chromatography on silica gel column (0-3% ethyl acetate in dichloromethane) to provide (3R,4R,5R)-5-(((tert-butyldiphenylsilyl)oxy)methyl)-4-ethynyltetrahydrofuran-2,3,4-triyl triacetate as a mixture of anomers and isolated as a white solid in good yield (9.5 g, 55%).

Step 2:

While under nitrogen, 2,6-dichloroadenine (2.91 g, 15.4 mmoL, 1.01 eq) and N,O-bis(trimethylsilyl)acetamide (4.87 mL, 19.6 mmoL, 1.29 eq) in anhydrous acetonitrile (90 mL) was stirred at room temperature. Next, a solution of (2R,3R,4R,5R)-2,4-bis(acetyloxy)-5-{[(tert-butyldiphenylsilyl)oxy]methyl}-4-ethynyloxolan-3-yl acetate (8.2 g, 15.22 mmoL) in anhydrous acetonitrile (10 mL) was added, followed by dropwise addition of trimethylsilyl trifluoromethanesulfonate (3.67 mL, 20.3 mmoL, 1.33 eq). The reaction was warmed to 50° C. for 18 h, then cooled to room temperature. Saturated aqueous sodium bicarbonate (10 mL), was added and the mixture was stirred for ten minutes. The resulting mixture was extracted with ethyl acetate (3×100 mL) and the combined organic layer was dried ($Na_2SO_4$), filtered, and concentrated. The residue was purified by flash column chromatography on silica gel column (0-30% ethyl acetate in hexanes) to provide (2R,3R,4R,5R)-2-(((tert-butyldiphenylsilyl)oxy)methyl)-5-(2,6-dichloro-9H-purin-9-yl)-3-ethynyltetrahydrofuran-3,4-diyl diacetate as a white solid (8.2 g, 81%).

Step 3:

A solution of (2R,3R,4R,5R)-2-(((tert-butyldiphenylsilyl)oxy)methyl)-5-(2,6-dichloro-9H-purin-9-yl)-3-ethynyltetrahydrofuran-3,4-diyl diacetate (1.6 g, 2.4 mmoL) in anhydrous THF (25 mL) was cooled to 0° C. and treated with acetic acid (0.192 mL, 3.36 mmoL) and tetrabutylammonium fluoride in THF (1N, 3.36 mL, 3.36 mmoL). After the addition was complete, the reaction was warmed to room temperature with continued stirring for 3 h. The reaction mixture was concentrated. The crude residue was purified via flash column chromatography on silica gel (0-50% ethyl acetate in hexanes) to afford (2R,3R,4R,5R)-5-(2,6-dichloro-9H-purin-9-yl)-3-ethynyl-2-(hydroxymethyl)tetrahydrofuran-3,4-diyl diacetate (0.88 g, 86%) as a white foam.

Step 4:

A solution of (2R,3R,4R,5R)-5-(2,6-dichloro-9H-purin-9-yl)-3-ethynyl-2-(hydroxyl-methyl)tetrahydrofuran-3,4-diyl diacetate (100 mg, 0.233 mmoL) in trimethylphosphate (4 mL) was cooled to 0° C. and treated with a second solution of methylenebis(phosphonic dichloride) (116 mg, 0.467 mmoL, 2 eq) in trimethylphosphate (4 mL). After the addition was complete, stirring was continued for 2 h then the cooling bath was removed and stirring was continued for 18 h. Ammonium bicarbonate (0.7 M aqueous TEAB, pH 8.5) was added slowly with vigorous stirring until no more gas evolution was observed. Once quenched, $NaHCO_3$ (satd., aqueous; 5 mL) was added and mixture stirred for 1 h at room temperature. The reaction mixture was washes with dichloromethane, acidified with 2N HCl to pH-1 and extracted with ethyl acetate (10×50 mL). The combined organic layer was dried over sodium sulfate, filtered and concentrated in vacuo. The residual oil was azeotroped with toluene (3×10 mL) to give (((((2R,3R,4R,5R)-3,4-diacetoxy-5-(2,6-dichloro-9H-purin-9-yl)-3-ethynyltetrahydrofuran-2-yl)methoxy)(hydroxy)phosphoryl)-methyl)phosphonic acid as an off-white solid that was used in the next step without further purification.

Step 5:

A solution of (((((2R,3R,4R,5R)-3,4-diacetoxy-5-(2,6-dichloro-9H-purin-9-yl)-3-ethynyltetrahydrofuran-2-yl)methoxy)(hydroxy)phosphoryl)methyl)phosphonic acid from Step 4 (~90 mg) was dissolved in anhydrous dioxane (8 mL), cooled to 0° C., then treated with diisopropylethylamine (0.085 mL, 0.513 mmoL, 2.2 eq) and benzylamine (0.036 mL, 0.33 mmoL, 1.4 eq). After the addition was complete, the reaction was stirred at room temperature for 18 h and concentrated to provide (((((2R,3R,4R,5R)-3,4-diacetoxy-5-(6-(benzylamino)-2-chloro-9H-purin-9-yl)-3-ethynyltetrahydrofuran-2-yl)methoxy)(hydroxy)-phosphoryl)methyl)phosphonic acid. The crude product was used directly in the subsequent hydrolysis without further purification.

The crude product from Step 5 was dissolved in 1:1 MeOH/THF (2 mL) and treated with LiOH (84 mg, 3.5 mmoL, 15 eq) in water (1 mL). After the addition was complete, the reaction was stirred at room temperature for 18 h before it was acidified to pH~1 with 2N HCl and concentrated. The resulting reaction mixture was diluted in 1:1 acetonitrile in water with 0.1% TFA (4 mL) and purified via reverse phase HPLC to give (((((2R,3S,4R,5R)-5-(6-(benzylamino)-2-chloro-9H-purin-9-yl)-3-ethynyl-3,4-dihydroxytetrahydrofuran-2-yl)methoxy)(hydroxy)phosphoryl)methyl)phosphonic acid as a white solid (9.2 mg, 7%) after lyophilization.

$^1$H NMR ($D_2O$) δ 8.63 (s, 1H), 7.41 (m, 5H), 6.07 (d, J=6.9 Hz, 1H), 4.96 (d, J=7.0 Hz, 1H), 4.46 (s, 1H), 4.37 (d, J=12.0 Hz, 1H), 4.25 (d, J=11.5 Hz, 1H), 3.21 (s, 1H), 2.38 (t, J=20.0 Hz, 2H). HPLC: Rt=17.2 min, 97.9%. ESI-MS for $C_{21}H_{24}ClN_5O_9P_2$ calcd. 587.07, found 586.8 (M−); ESI-MS for $C_{12}H_9ClN_5$ calcd. 258.05, found 258.4 (M-ribose fragment).

Example 204

Synthesis of (((((2R,3S,4R,5R)-5-(6-(benzylamino)-2-chloro-9H-purin-9-yl)-3-ethynyl-3,4-dihydroxytetrahydrofuran-2-yl)methoxy)methyl)phosphonic acid

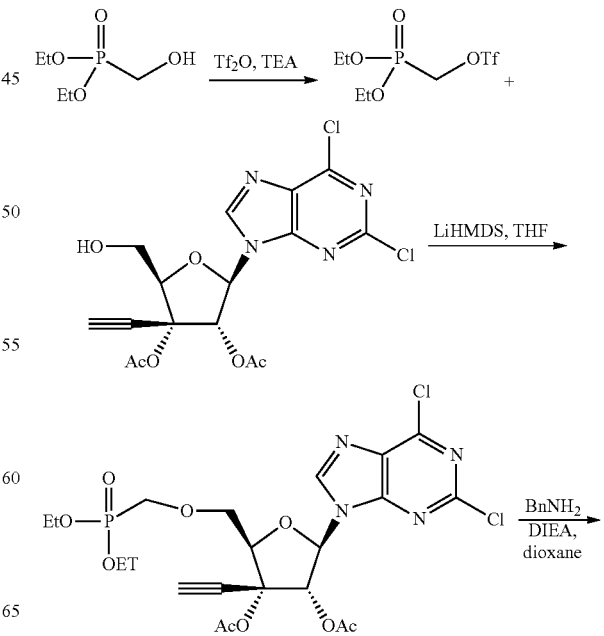

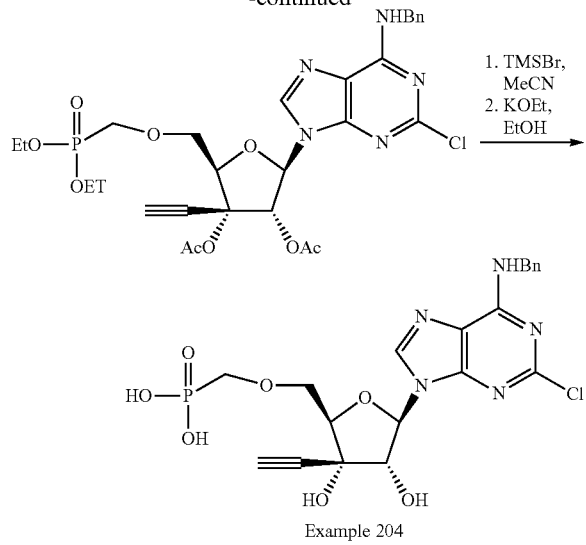

Example 204

Step 1:

A flamed dried round bottom flask was charged with diethyl hydroxymethylphosphonate (780 mg, 4.64 mmol) and triethylamine (0.838 mL, 6.031 mmoL, 1.3 eq) in anhydrous dichloromethane (20 mL) was cooled to −78° C. and treated trifluoromethane-sulfonic anhydride (0.847 mL, 5.10 mmoL, 1.3 eq) dropwise. The reaction was stirred for 10 min as the reaction was warmed to 0° C. After 30 min, the reaction mixture was poured into ether (precooled to 0° C.) and the crystalline precipitate filtered. The filtrate was then washed sequentially with water (1×100 mL), 1 M HCl (1×100 mL), and saturated aqueous sodium chloride (1×125 mL). Organic layer was dried ($MgSO_4$), filtered, and concentrated to provide crude (diethoxyphosphoryl)methyl trifluoromethanesulfonate obtained as a yellow oil, was dissolved in anhydrous THF and this solution used directly in the next step without further purification.

Step 2:

A solution of (2R,3R,4R,5R)-5-(2,6-dichloro-9H-purin-9-yl)-3-ethynyl-2-(hydroxyl-methyl)tetrahydrofuran-3,4-diyl diacetate (350 mg, 0.815 mmoL) and (diethoxyphosphoryl)-methyl trifluoromethanesulfonate (294 mg, 0.978 mmoL, 1.2 eq) in THF (20 mL) was cooled to −78° C. and treated with LiHMDS (1M in THF; 0.980 mL, 0.978 mmoL, 1.2 eq) in a dropwise. After stirring for 1.5 h, reaction was quenched with solid $NH_4Cl$, diluted with water and extracted with ethyl acetate. The organic layer was dried ($MgSO_4$), filtered, and concentrated. Purification by flash column chromatography on silica gel (0-100% ethyl acetate in hexanes) afforded (2R,3R,4R,5R)-5-(2,6-dichloro-9H-purin-9-yl)-2-(((diethoxy-phosphoryl)methoxy)methyl)-3-ethynyltetrahydrofuran-3,4-diyl diacetate (140 mg, 30%) as a pale yellow oil.

Step 3:

A solution of (2R,3R,4R,5R)-5-(2,6-dichloro-9H-purin-9-yl)-2-(((diethoxyphosphoryl)methoxy)methyl)-3-ethynyltetrahydrofuran-3,4-diyl diacetate (85 mg, 0.147 mmoL) and diisopropylethylamine (40 µL, 0.235 mmoL, 1.6 eq) in anhydrous dioxane (8 mL) was cooled to 0° C. was treated with benzylamine (19 µL, 0.176 mmoL, 1.2 eq). After the addition was complete, the reaction was warmed to room temperature and stirred for 18 h. The mixture was diluted with water and extracted with ethyl acetate. The organic layer was dried ($Na_2SO_4$), filtered, and concentrated to provide crude (2R,3R,4R,5R)-5-(6-(benzylamino)-2-chloro-9H-purin-9-yl)-2-(((diethoxyphosphoryl)methoxy)methyl)-3-ethynyltetrahydrofuran-3,4-diyl diacetate (93 mg, 96%) as a white solid which was used directly in the subsequent step without further purification.

Step 4:

The crude product from the previous step was dissolved in anhydrous acetonitrile (10 mL) and treated with bromotrimethylsilane (0.24 mL, 1.8 mmoL, 12 eq) dropwise. After the addition was complete, the solution was stirred at room temperature for 22 h and quenched with water (5 mL). After stirring an additional 2-3 min, the solution was extracted with ethyl acetate (4×100 mL). The organic layer was, dried ($Na_2SO_4$), filtered, and concentrated to afford ((((2R,3S,4R,5R)-5-(6-(benzylamino)-2-chloro-9H-purin-9-yl)-3-ethynyl-3,4-dihydroxytetra-hydrofuran-2-yl)methoxy)methyl) phosphonic acid as an off-white solid. This crude solid was dissolved in absolute EtOH at 0° C. and treated with KOEt (51 mg, 0.61 mmoL, 4 eq) in one portion. The reaction was stirred at room temperature for 20 min before it was acidified with AcOH (0.52 mL, 0.91 mmoL, 6 eq) and stirred an additional 10 min. The crude product was purified via reverse-phase HPLC and dried by lyophilization to give ((((2R,3S,4R,5R)-5-(6-(benzylamino)-2-chloro-9H-purin-9-yl)-3-ethynyl-3,4-dihydroxytetrahydrofuran-2-yl) methoxy)methyl)phosphonic acid (6 mg, 7%) as a white solid.

$^1$H NMR ($D_2O$) δ 8.41 (s, 1H), 7.19 (m, 5H), 5.84 (d, J=7.2 Hz, 1H), 4.82 (d, J=7.1 Hz, 1H), 4.21 (m, 1H), 4.19 (m, 2H), 3.79 (d, J=3.8 Hz, 2H), 3.57 (m, 2H), 2.98 (s, 1H). HPLC: Rt=7.19 min, 97.5%. ESI-MS for $C_{20}H_{21}ClN_5O_7P$ calcd, 509.09, found 509 (M+); ESI-MS for $C_{11}H_5ClN_6$ calcd. 258.05, found 259 (M-ribose fragment).

Example 205

Synthesis of (((((2R,3S,4R,5R)-5-(6-(benzylamino)-2-chloro-9H-purin-9-yl)-3,4-dihydroxy-3-methyltetrahydrofuran-2-yl)methoxy)(hydroxy)phosphoryl) methyl)phosphonic acid

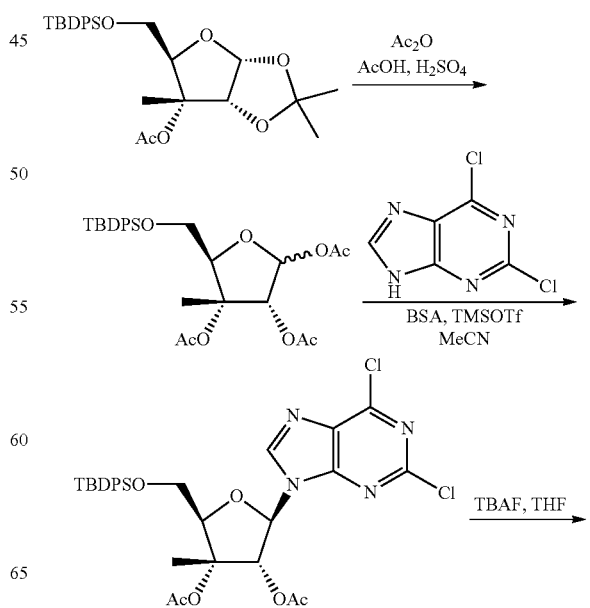

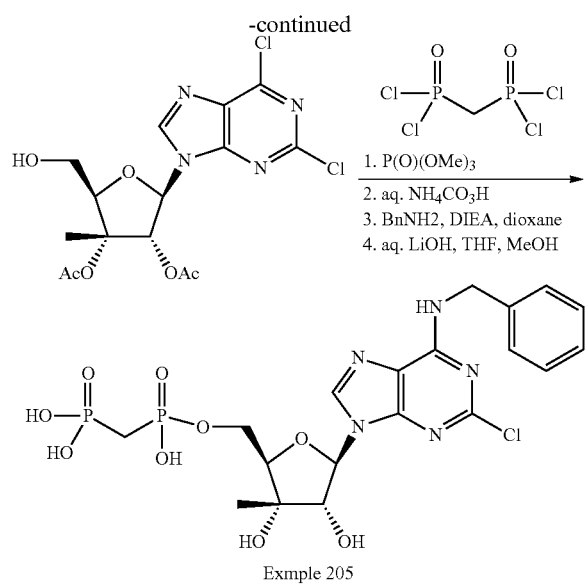

Exmple 205

Step 1:

While under nitrogen an ice-cooled solution of (3aR,5R,6aS)-5-(((tert-butyldiphenyl-silyl)oxy)methyl)-2,2-dimethyldihydrofuro[2,3-d][1,3]dioxol-6(5H)-one (6 g, 14.1 mmoL) in anhydrous THF (100 mL) was treated with 3M methyl magnesium chloride in THF (5.9 mL, 1.4 eq) dropwise. After the addition was complete, the cooling bath was removed, and stirring was continuing for 1 h. The mixture was cooled back to 0° C. and quenched with a saturated aqueous ammonium chloride (10 mL), diluted with ethyl acetate (100 mL) and washed with water (80 mL). The aqueous was re-extracted with ethyl acetate (1×50 mL) and the combined organic layer was dried over sodium sulfate, filtered, and concentrated. The residual oil was purified by flash column chromatography on silica (0-30% ethyl acetate in hexanes) to provide (3aR,5R,6R,6aR)-5-(((tert-butyldiphenylsilyl)oxy)methyl)-2,2,6-trimethyltetrahydrofuro[2,3-d][1,3]dioxol-6-ol as a pale viscous oil (4.2 g, 67%).

Step 2:

While under nitrogen, a solution of (3aR,5R,6aS)-5-(((tert-butyldiphenylsilyl)oxy)-methyl)-2,2-dimethyldihydrofuro[2,3-d][1,3]dioxol-6(5H)-one (2.25 g, 5.08 mmoL) in dichloromethane (35 mL) and water (3.5 mL) cooled to 0° C. and treated with trifluoroacetic acid (15 mL). After 2.5 h, saturated aqueous NaHCO₃ was added until the solution was pH-8 and mixture was extracted with dichloromethane (2×150 mL). The combined organic layer was dried over sodium sulfate, filtered, and concentrated. The crude oil was azeotroped with toluene (3×5 mL), diluted with dichloromethane (45 mL) was treated with pyridine (12 mL), acetic anhydride (4.77 mL, 50.83 mmoL) and catalytic 4-DMAP (142 mg, 1.17 mmoL). After stirring 18 h, the reaction was diluted with ethyl acetate (200 mL each) and washed sequentially with saturated aqueous NH₄Cl (3×100 mL), 0.5 N HCl (2×100 mL), and saturated aqueous sodium chloride (1×120 mL). The organic layer was dried over sodium sulfate, filtered, and concentrated. The residual oil was purified by flash column chromatography on silica gel (0-30% ethyl acetate in hexanes) to provide (3R,4R,5R)-5-(((tert-butyldiphenylsilyl)oxy)methyl)-4-methyltetrahydrofuran-2,3,4-triyl triacetate (2.1 g, 78%) as colorless solid.

Steps 3-6:

Proceeding as described in Example 203 above but substituting (3aR,5R,6R,6aR)-5-(((tert-butyldiphenylsilyl)oxy)methyl)-6-ethynyl-2,2-dimethyltetrahydrofuro[2,3-d][1,3]-dioxol-6-ol with (3aR,5R,6aS)-5-(((tert-butyldiphenyl-silyl)oxy)methyl)-2,2-dimethyldihydrofuro[2,3-d][1,3]dioxol-6(5H)-one provided the title compound (8 mg, 3%) as as a white solid.

¹H NMR (D₂O:DMSO-d6, 6:1) 8.46 (bs, 1H), 7.23 (m, 5H), 5.84 (d, J=6.9 Hz, 1H), 4.45 (d, J=7.0 Hz, 1H), 4.12 (s, 1H), 3.95 (m, 3H), 3.54 (m, 1H), 2.18 (bs, 2H), 1.31 (s, 3H). ESI-MS for $C_{19}H_{24}ClN_5O_9P_2$ calcd. 563.1, found 562.1 (M−).

Example 206

Assay 1: Inhibition of the CD73 Enzyme In Vitro

For measurements of soluble CD73 enzyme activity, recombinant CD73 was obtained from R&D Systems, Cat. No. 5795-EN-010. Serial dilutions of test compounds were incubated with recombinant CD73 and AMP in reaction buffer (25 mM Tris HCl pH7.5, 5 mM MgCl2, 50 mM NaCl, 0.25 mM DTT, 0.005% Triton X-100). The final reaction volume was 25 µL and the final concentrations of recombinant CD73 and AMP were 0.5 nM and 50 M, respectively. Reactions were allowed to proceed for 30 minutes at room temperature before the addition of 100 µL Malachite Green (Cell Signaling Technology, Cat. No. 12776). After 5 minutes at room temperature, absorbance at 630 nm was determined on a microplate spectrophotometer. The concentration of inorganic phosphate was determined using a phosphate standard curve.

Assay 2: Inhibition of the CD73 Enzyme In Vitro

For measurements of soluble CD73 enzyme activity, recombinant CD73 was obtained from R&D Systems, Cat. No. 5795-EN-010. Serial dilutions of test compounds were incubated with recombinant CD73 and AMP in reaction buffer (25 mM Tris HCl pH7.5, 5 mM MgCl2, 50 mM NaCl, 0.25 mM DTT, 0.005% Triton X-100). The final reaction volume was 25 µL and the final concentrations of recombinant CD73 and AMP were 0.05 nM and 50 µM, respectively. Reactions were allowed to proceed for 1 hour at 37° C. before the addition of 100 µL Malachite Green (Cell Signaling Technology, Cat. No. 12776). After 5 minutes at room temperature, absorbance at 630 nm was determined on a microplate spectrophotometer. The concentration of inorganic phosphate was determined using a phosphate standard curve.

The IC₅₀ data for both assays is given below in Table 2. ND indicates not determined.

TABLE 2

| Example # | Compound | Assay 1 CD73 IC50 (nM) | Assay 2 CD73 IC50 (nM) |
|---|---|---|---|
| 1 | | ND | 1.7 |
| 2 | | ND | 147 |
| 3 | | ND | 1 |
| 4 | | ND | 0.5 |
| 5 | | ND | 4 |

TABLE 2-continued

| Example # | Compound | Assay 1 CD73 IC50 (nM) | Assay 2 CD73 IC50 (nM) |
|---|---|---|---|
| 6 | | 52 | ND |
| 7 | | ND | 8 |
| 8 | | ND | 2 |
| 9 | | ND | 0.17 |
| 10 | | ND | 0.26 |

TABLE 2-continued

| Example # | Compound | Assay 1 CD73 IC50 (nM) | Assay 2 CD73 IC50 (nM) |
|---|---|---|---|
| 11 | | ND | 0.06 |
| 12 | | ND | 0.1 |
| 13 | | ND | 0.3 |
| 14 | | ND | 0.6 |

TABLE 2-continued

| Example # | Compound | Assay 1 CD73 IC50 (nM) | Assay 2 CD73 IC50 (nM) |
|---|---|---|---|
| 15 | | ND | 20 |
| 16 | | ND | 24 |
| 17 | | ND | 347 |
| 18 | | ND | 0.3 |
| 19 | | ND | 0.2 |

TABLE 2-continued

| Example # | Compound | Assay 1 CD73 IC50 (nM) | Assay 2 CD73 IC50 (nM) |
|---|---|---|---|
| 20 | | ND | 0.2 |
| 21 | | ND | 0.3 |
| 22 | | ND | 0.3 |
| 23 | | 5 | ND |

TABLE 2-continued

| Example # | Compound | Assay 1 CD73 IC50 (nM) | Assay 2 CD73 IC50 (nM) |
|---|---|---|---|
| 24 | | 1.8 | ND |
| 25 | | 7 | ND |
| 26 | | 58 | ND |
| 27 | | 18 | ND |
| 28 | | 3 | ND |

TABLE 2-continued

| Example # | Compound | Assay 1 CD73 IC50 (nM) | Assay 2 CD73 IC50 (nM) |
|---|---|---|---|
| 29 | | 2 | ND |
| 30 | | ND | 5 |
| 31 | | ND | 2 |
| 32 | | ND | 3 |

TABLE 2-continued

| Example # | Compound | Assay 1 CD73 IC50 (nM) | Assay 2 CD73 IC50 (nM) |
|---|---|---|---|
| 33 | | ND | 2 |
| 34 | | ND | 2 |
| 35 | | ND | 4 |
| 36 | | ND | 4 |

TABLE 2-continued

| Example # | Compound | Assay 1 CD73 IC50 (nM) | Assay 2 CD73 IC50 (nM) |
|---|---|---|---|
| 37 | | ND | 6 |
| 38 | | ND | 3 |
| 39 | | ND | 3 |
| 40 | | ND | 3 |

TABLE 2-continued

| Example # | Compound | Assay 1 CD73 IC50 (nM) | Assay 2 CD73 IC50 (nM) |
|---|---|---|---|
| 41 | | ND | 0.6 |
| 42 | | ND | 1 |
| 43 | | ND | 2 |
| 44 | | ND | 62 |

TABLE 2-continued

| Example # | Compound | Assay 1 CD73 IC50 (nM) | Assay 2 CD73 IC50 (nM) |
|---|---|---|---|
| 45 | | ND | 1 |
| 46 | | ND | 1 |
| 47 | | ND | 2 |
| 48 | | ND | 0.5 |

TABLE 2-continued

| Example # | Compound | Assay 1 CD73 IC50 (nM) | Assay 2 CD73 IC50 (nM) |
|---|---|---|---|
| 49 | | 273 | ND |
| 50 | | 3 | ND |
| 51 | | 3 | ND |
| 52 | | 4 | ND |

TABLE 2-continued

| Example # | Compound | Assay 1 CD73 IC50 (nM) | Assay 2 CD73 IC50 (nM) |
|---|---|---|---|
| 53 | | ND | 0.3 |
| 54 | | ND | 0.2 |
| 55 | | 35 | ND |
| 56 | | ND | >200 |
| 57 | | ND | 103 |

TABLE 2-continued

| Example # | Compound | Assay 1 CD73 IC50 (nM) | Assay 2 CD73 IC50 (nM) |
|---|---|---|---|
| 58 | | ND | 1.6 |
| 59 | | 1 | ND |
| 60 | | 3 | ND |
| 61 | | 1.5 | ND |
| 62 | | ND | 2 |
| 63 | | ND | 1 |

TABLE 2-continued

| Example # | Compound | Assay 1 CD73 IC50 (nM) | Assay 2 CD73 IC50 (nM) |
|---|---|---|---|
| 64 | | ND | 3 |
| 65 | | ND | 1 |
| 66 | | ND | 0.3 |
| 67 | | ND | 0.8 |
| 68 | | ND | 0.8 |
| 69 | | ND | 3 |

TABLE 2-continued

| Example # | Compound | Assay 1 CD73 IC50 (nM) | Assay 2 CD73 IC50 (nM) |
|---|---|---|---|
| 70 | | ND | 1 |
| 71 | | ND | 6 |
| 72 | | ND | 3 |
| 73 | | ND | 1 |
| 74 | | ND | 2 |
| 75 | | ND | 0.6 |

TABLE 2-continued

| Example # | Compound | Assay 1 CD73 IC50 (nM) | Assay 2 CD73 IC50 (nM) |
|---|---|---|---|
| 76 | ![structure] | ND | 6 |
| 77 | ![structure] | ND | 2 |
| 78 | ![structure] | ND | 2 |
| 79 | ![structure] | ND | 4 |
| 80 | ![structure] | ND | 2 |
| 81 | ![structure] | ND | 0.4 |

TABLE 2-continued
| Example # | Compound | Assay 1 CD73 IC50 (nM) | Assay 2 CD73 IC50 (nM) |
|---|---|---|---|
| 82 | 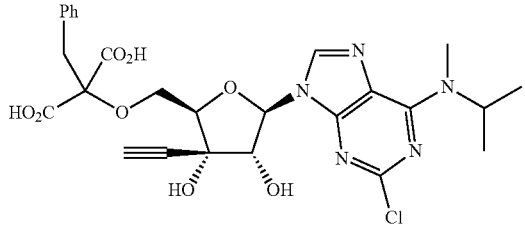 [SMILES: C#C[C@@]1(O)[C@@H](COC(Cc2ccccc2)(C(=O)O)C(=O)O)O[C@@H](n2cnc3c(N(C)C(C)C)nc(Cl)nc32)[C@@H]1O] | ND | 2 |
| 83 | 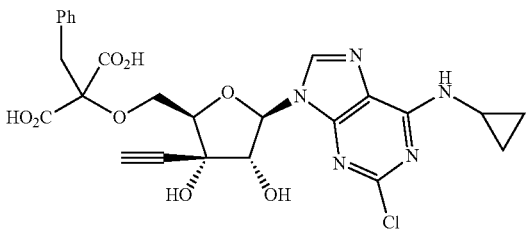 [SMILES: C#C[C@@]1(O)[C@@H](COC(Cc2ccccc2)(C(=O)O)C(=O)O)O[C@@H](n2cnc3c(NC4CC4)nc(Cl)nc32)[C@@H]1O] | ND | 1 |
| 84 | 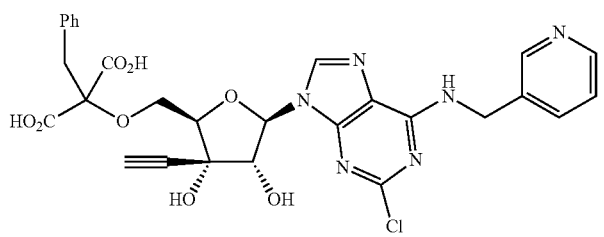 [SMILES: C#C[C@@]1(O)[C@@H](COC(Cc2ccccc2)(C(=O)O)C(=O)O)O[C@@H](n2cnc3c(NCc4cccnc4)nc(Cl)nc32)[C@@H]1O] | ND | 3 |
| 85 | 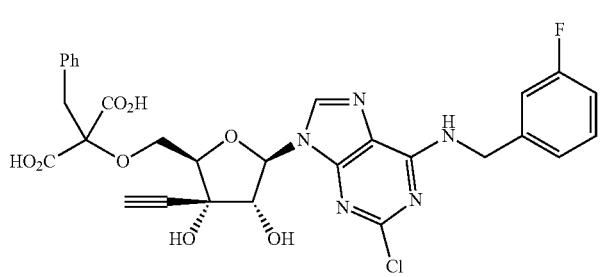 [SMILES: C#C[C@@]1(O)[C@@H](COC(Cc2ccccc2)(C(=O)O)C(=O)O)O[C@@H](n2cnc3c(NCc4cccc(F)c4)nc(Cl)nc32)[C@@H]1O] | ND | 2 |
| 86 | 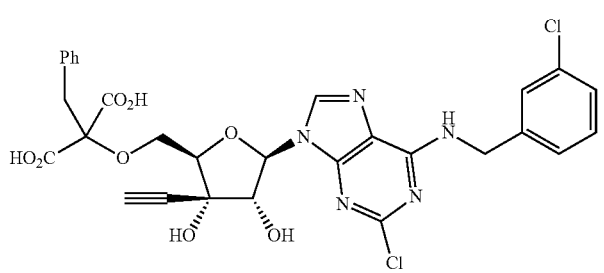 [SMILES: C#C[C@@]1(O)[C@@H](COC(Cc2ccccc2)(C(=O)O)C(=O)O)O[C@@H](n2cnc3c(NCc4cccc(Cl)c4)nc(Cl)nc32)[C@@H]1O] | ND | 1 |
| 87 | 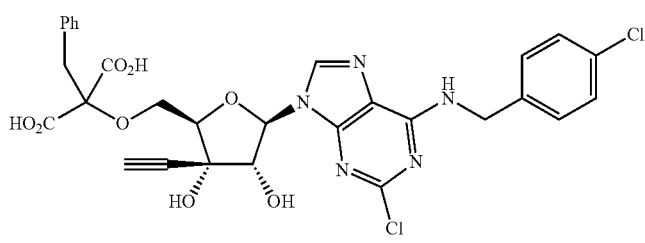 [SMILES: C#C[C@@]1(O)[C@@H](COC(Cc2ccccc2)(C(=O)O)C(=O)O)O[C@@H](n2cnc3c(NCc4ccc(Cl)cc4)nc(Cl)nc32)[C@@H]1O] | ND | 0.6 |

TABLE 2-continued

| Example # | Compound | Assay 1 CD73 IC50 (nM) | Assay 2 CD73 IC50 (nM) |
|---|---|---|---|
| 88 | [structure: azetidinyl-substituted chloropurine nucleoside with Ph/CO2H/HO2C ether and ethynyl] | ND | 1.2 |
| 89 | [structure: N,N-dimethylamino-substituted chloropurine nucleoside] | ND | 1.1 |
| 90 | [structure: pyrrolidinyl-substituted chloropurine nucleoside] | 0.9 | ND |
| 91 | [structure: N-cyclopentyl-substituted chloropurine nucleoside] | 0.3 | ND |
| 92 | [structure: N-cyclopropylmethyl-substituted chloropurine nucleoside] | 0.8 | ND |
| 93 | [structure: N-isopropyl-substituted chloropurine nucleoside] | 1.7 | ND |
| 94 | [structure: N-(2-hydroxy-2-methylpropyl)-substituted chloropurine nucleoside] | ND | 5 |

TABLE 2-continued

| Example # | Compound | Assay 1 CD73 IC50 (nM) | Assay 2 CD73 IC50 (nM) |
|---|---|---|---|
| 95 | | ND | 7 |
| 96 | | ND | 3 |
| 97 | | ND | 2 |
| 98 | | ND | 2 |
| 99 | | ND | 6 |
| 100 | | ND | 2 |

TABLE 2-continued

| Example # | Compound | Assay 1 CD73 IC50 (nM) | Assay 2 CD73 IC50 (nM) |
|---|---|---|---|
| 101 | | ND | 1 |
| 102 | | ND | 1 |
| 103 | | ND | 3 |
| 104 | | ND | 2 |
| 105 | | ND | 2 |
| 106 | | ND | 296 |

TABLE 2-continued

| Example # | Compound | Assay 1 CD73 IC50 (nM) | Assay 2 CD73 IC50 (nM) |
|---|---|---|---|
| 107 | (structure) | ND | 506 |
| 108 | (structure) | ND | 3 |
| 109 | (structure) | ND | 284 |
| 110 | (structure) | ND | 3 |
| 111 | (structure) | ND | 2,666 |

TABLE 2-continued
| Example # | Compound | Assay 1 CD73 IC50 (nM) | Assay 2 CD73 IC50 (nM) |
|---|---|---|---|
| 112 | 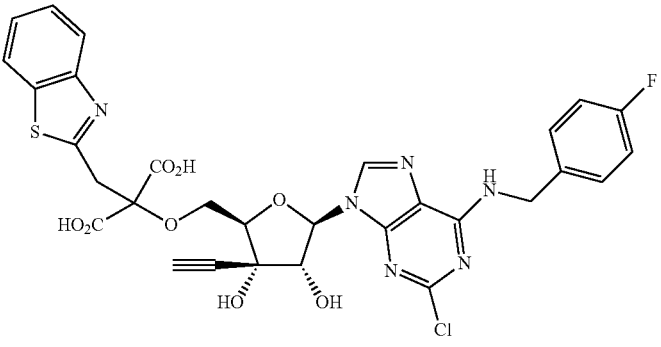 [SMILES: C#C[C@@]1(O)[C@@H](COC(Cc2nc3ccccc3s2)(C(=O)O)C(=O)O)O[C@@H](n2cnc3c(NCc4ccc(F)cc4)nc(Cl)nc32)[C@@H]1O] | ND | 1,357 |
| 113 | 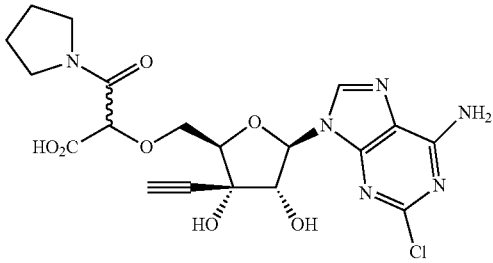 [SMILES: C#C[C@@]1(O)[C@@H](COC(C(=O)O)C(=O)N2CCCC2)O[C@@H](n2cnc3c(N)nc(Cl)nc32)[C@@H]1O] | 331 | ND |
| 114 | 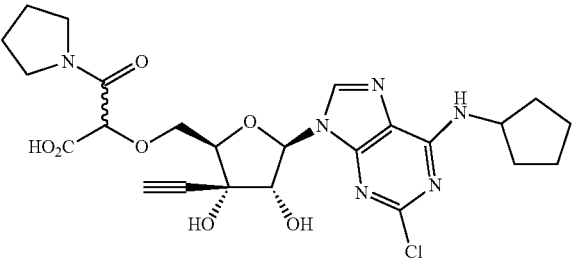 [SMILES: C#C[C@@]1(O)[C@@H](COC(C(=O)O)C(=O)N2CCCC2)O[C@@H](n2cnc3c(NC4CCCC4)nc(Cl)nc32)[C@@H]1O] | 177 | ND |
| 115 | 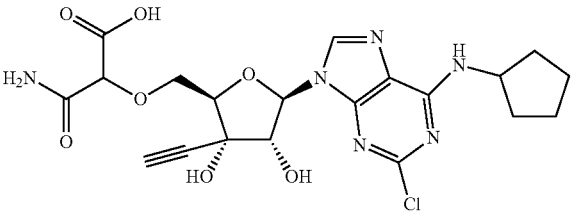 [SMILES: C#C[C@@]1(O)[C@@H](COC(C(N)=O)C(=O)O)O[C@@H](n2cnc3c(NC4CCCC4)nc(Cl)nc32)[C@@H]1O] | 135 | ND |
| 116 | 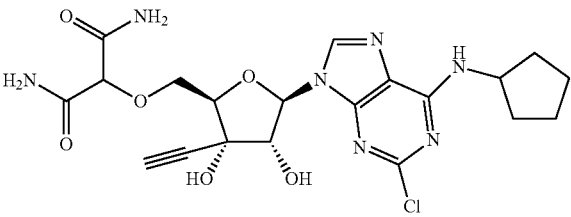 [SMILES: C#C[C@@]1(O)[C@@H](COC(C(N)=O)C(N)=O)O[C@@H](n2cnc3c(NC4CCCC4)nc(Cl)nc32)[C@@H]1O] | 8,049 | ND |

TABLE 2-continued

| Example # | Compound | Assay 1 CD73 IC50 (nM) | Assay 2 CD73 IC50 (nM) |
|---|---|---|---|
| 117 | [structure] | ND | 58 |
| 118 | [structure] | ND | 48 |
| 119 | [structure] | ND | 4,612 |
| 120 | [structure] | 4,628 | ND |
| 121 | [structure] | ND | 1,711 |
| 122 | [structure] | ND | 40 |

TABLE 2-continued

| Example # | Compound | Assay 1 CD73 IC50 (nM) | Assay 2 CD73 IC50 (nM) |
|---|---|---|---|
| 123 | | 71 | ND |
| 124 | | 27 | ND |
| 125 | | ND | 235 |
| 126 | | ND | 9 |
| 127 | | ND | 170 |

TABLE 2-continued

| Example # | Compound | Assay 1 CD73 IC50 (nM) | Assay 2 CD73 IC50 (nM) |
|---|---|---|---|
| 128 | | ND | 6 |
| 129 | | 1,580 | ND |
| 130 | | ND | 0.36 |
| 131 | | ND | >100 |

TABLE 2-continued

| Example # | Compound | Assay 1 CD73 IC50 (nM) | Assay 2 CD73 IC50 (nM) |
|---|---|---|---|
| 132 | | ND | ND |
| 133 | | ND | 7 |
| 134 | | ND | 16 |
| 135 | | ND | 91 |

TABLE 2-continued

| Example # | Compound | Assay 1 CD73 IC50 (nM) | Assay 2 CD73 IC50 (nM) |
|---|---|---|---|
| 136 | | ND | 0.24 |
| 137 | | ND | 0.31 |
| 138 | | ND | 0.15 |

TABLE 2-continued

| Example # | Compound | Assay 1 CD73 IC50 (nM) | Assay 2 CD73 IC50 (nM) |
|---|---|---|---|
| 139 | | ND | 0.13 |
| 140 | | ND | 0.29 |
| 141 | | ND | 0.23 |
| 142 | | ND | 5 |

TABLE 2-continued

| Example # | Compound | Assay 1 CD73 IC50 (nM) | Assay 2 CD73 IC50 (nM) |
|---|---|---|---|
| 143 | | ND | 13 |
| 144 | | ND | 1 |
| 145 | | ND | 108 |
| 146 | | ND | 0.41 |

TABLE 2-continued

| Example # | Compound | Assay 1 CD73 IC50 (nM) | Assay 2 CD73 IC50 (nM) |
|---|---|---|---|
| 147 | | ND | 0.58 |
| 148 | | ND | 0.08 |
| 149 | | ND | 0.11 |
| 150 | | ND | 0.16 |

TABLE 2-continued

| Example # | Compound | Assay 1 CD73 IC50 (nM) | Assay 2 CD73 IC50 (nM) |
|---|---|---|---|
| 151 | | ND | 0.25 |
| 152 | | ND | 0.05 |
| 153 | | ND | 0.48 |
| 154 | | ND | 2 |

TABLE 2-continued

| Example # | Compound | Assay 1 CD73 IC50 (nM) | Assay 2 CD73 IC50 (nM) |
|---|---|---|---|
| 155 | | ND | 2 |
| 156 | | ND | 0.14 |
| 157 | | ND | 0.37 |
| 158 | | ND | 8 |

TABLE 2-continued
| Example # | Compound | Assay 1 CD73 IC50 (nM) | Assay 2 CD73 IC50 (nM) |
|---|---|---|---|
| 159 | 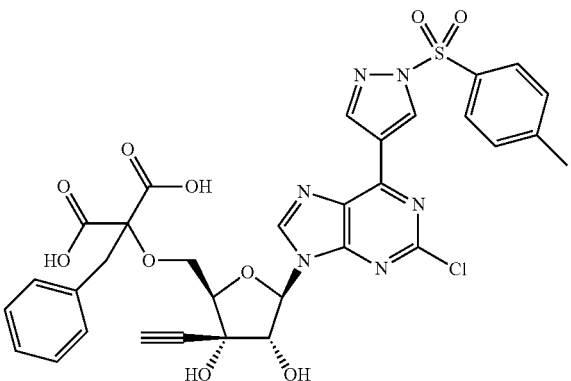 [SMILES: C#C[C@@]1(O)[C@@H](COC(Cc2ccccc2)(C(=O)O)C(=O)O)O[C@@H](n2cnc3c(-c4cnn(S(=O)(=O)c5ccc(C)cc5)c4)nc(Cl)nc32)[C@@H]1O] | ND | 476 |
| 160 | 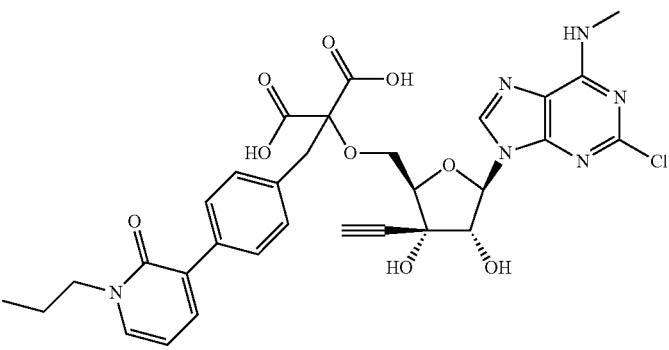 [SMILES: C#C[C@@]1(O)[C@@H](COC(Cc2ccc(-c3cccn(CCC)c3=O)cc2)(C(=O)O)C(=O)O)O[C@@H](n2cnc3c(NC)nc(Cl)nc32)[C@@H]1O] | ND | 0.31 |
| 161 | 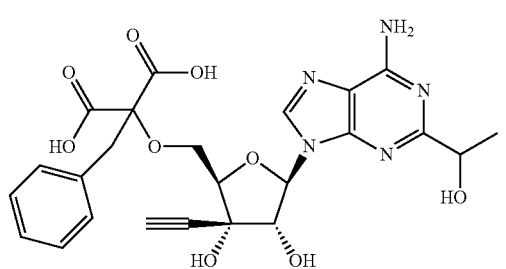 [SMILES: C#C[C@@]1(O)[C@@H](COC(Cc2ccccc2)(C(=O)O)C(=O)O)O[C@@H](n2cnc3c(N)nc(C(C)O)nc32)[C@@H]1O] | ND | 561 |
| 162 | 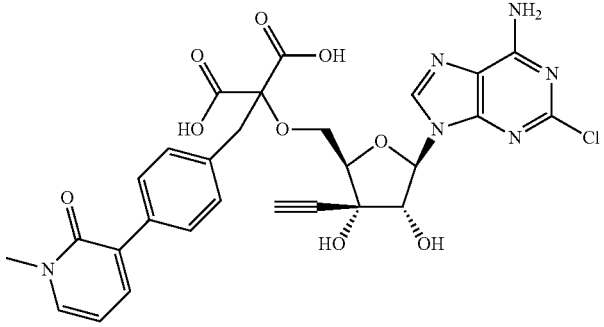 [SMILES: C#C[C@@]1(O)[C@@H](COC(Cc2ccc(-c3cccn(C)c3=O)cc2)(C(=O)O)C(=O)O)O[C@@H](n2cnc3c(N)nc(Cl)nc32)[C@@H]1O] | ND | 0.42 |

TABLE 2-continued

| Example # | Compound | Assay 1 CD73 IC50 (nM) | Assay 2 CD73 IC50 (nM) |
|---|---|---|---|
| 163 | | ND | >100 |
| 164 | | ND | 261 |
| 165 | | ND | 45 |
| 166 | | ND | 145 |

TABLE 2-continued

| Example # | Compound | Assay 1 CD73 IC50 (nM) | Assay 2 CD73 IC50 (nM) |
|---|---|---|---|
| 167 | | ND | 139 |
| 168 | | ND | 14 |
| 169 | | ND | 162 |
| 170 | | ND | 8 |

TABLE 2-continued

| Example # | Compound | Assay 1 CD73 IC50 (nM) | Assay 2 CD73 IC50 (nM) |
|---|---|---|---|
| 171 | | ND | 96 |
| 172 | | ND | 6 |
| 173 | | ND | 112 |
| 174 | | ND | 17 |

TABLE 2-continued

| Example # | Compound | Assay 1 CD73 IC50 (nM) | Assay 2 CD73 IC50 (nM) |
|---|---|---|---|
| 175 | | ND | 1 |
| 176 | | ND | 5 |
| 177 | | ND | ND |
| 178 | | ND | ND |

TABLE 2-continued

| Example # | Compound | Assay 1 CD73 IC50 (nM) | Assay 2 CD73 IC50 (nM) |
|---|---|---|---|
| 179 | | 320 | ND |
| 180 | | 9 | ND |
| 181 | | 21 | ND |
| 182 | | 24 | ND |
| 183 | | 56 | ND |

TABLE 2-continued

| Example # | Compound | Assay 1 CD73 IC50 (nM) | Assay 2 CD73 IC50 (nM) |
|---|---|---|---|
| 184 | | 102 | ND |
| 185 | | 11748 | ND |
| 186 | | 8833 | ND |
| 187 | | 10 | ND |
| 188 | | 134 | ND |

TABLE 2-continued

| Example # | Compound | Assay 1 CD73 IC50 (nM) | Assay 2 CD73 IC50 (nM) |
|---|---|---|---|
| 189 | | 1851 | ND |
| 190 | | 9316 | ND |
| 191 | | 7 | ND |
| 192 | | 25 | ND |
| 193 | | 263 | ND |

TABLE 2-continued

| Example # | Compound | Assay 1 CD73 IC50 (nM) | Assay 2 CD73 IC50 (nM) |
|---|---|---|---|
| 194 | | 336 | ND |
| 195 | | 236 | ND |
| 196 | | 82 | ND |
| 197 | | ND | 0.73 |

TABLE 2-continued

| Example # | Compound | Assay 1 CD73 IC50 (nM) | Assay 2 CD73 IC50 (nM) |
|---|---|---|---|
| 198 | | 2268 | ND |
| 199 | | 5757 | ND |
| 200 | | 6091 | ND |

TABLE 2-continued

| Example # | Compound | Assay 1 CD73 IC50 (nM) | Assay 2 CD73 IC50 (nM) |
|---|---|---|---|
| 201 | | 204 | ND |
| 202 | | 148 | ND |
| 203 | | 4.2 | ND |
| 204 | | 100 | ND |

TABLE 2-continued

| Example # | Compound | Assay 1 CD73 IC50 (nM) | Assay 2 CD73 IC50 (nM) |
|---|---|---|---|
| 205 | (structure) | 12 | ND |

Example 207

Activation of Tumor-Directed Immune Response with CD73 Inhibitors

Figure 1B:
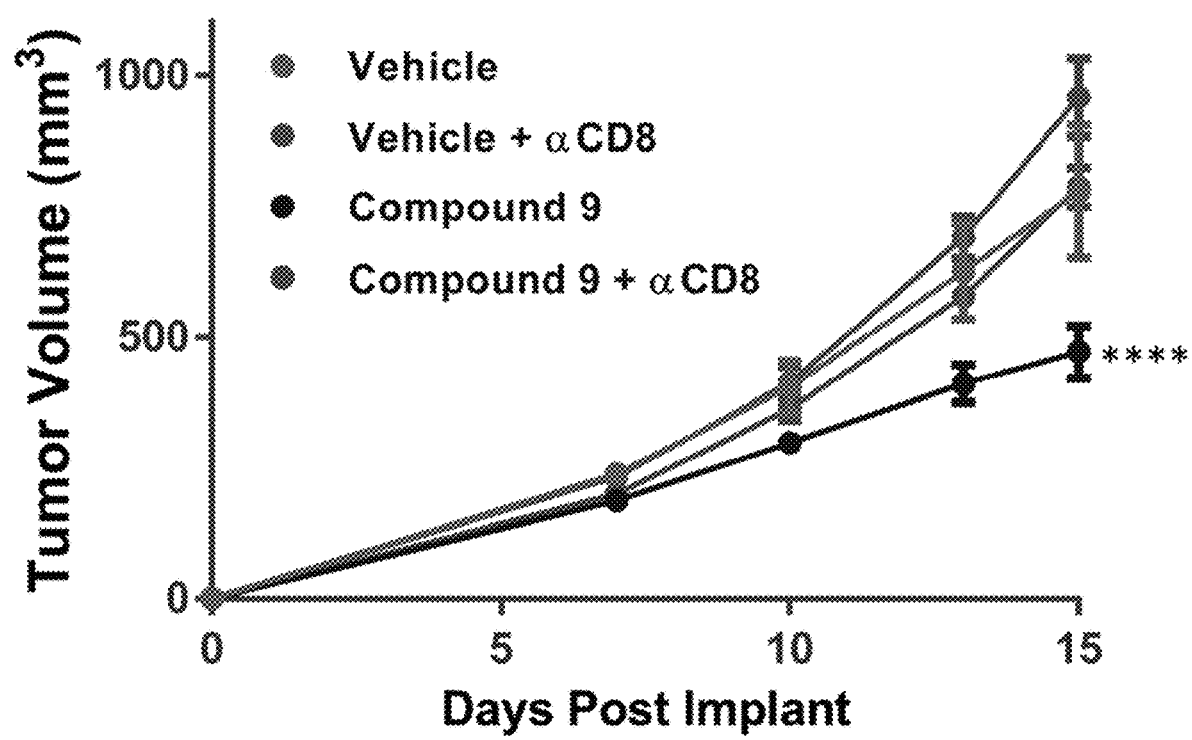
FIG. 1B depicts the reversal of efficacy using Compound 9 when CD8+ cells are depleted with an anti-CD8 antibody.

EG7 cells were implanted subcutaneously into C57BL/6 mice. Compound 9 (50 mg/kg) or vehicle was orally administered BID starting day one post implant (N=10 per group). Tumors were excised on day 14 and analyzed by flow cytometry. Compound 9 increased the % CD8+ cells of CD45+ cells as shown in FIG. 1A (* indicates p<0.05). EG7 cells were implanted subcutaneously into C57BL/6 mice. Anti-CD8 antibody was dosed i.p. on days −1, 0, 5, and 10. Compound 9 (50 mg/kg) or vehicle was orally dosed BID starting on day 1. FIG. 1B shows that depletion of CD8+ T cells reverses efficacy (**** indicates p<0.0001 vs Compound 9+anti-CD8). Compound 9 alone showed more of a tumor volume reduction that the combination of Compound 9 than the anti-CD8 antibody.

Example 208

Reversal of AMP-Mediated Suppression of CD8+ T Cells Using CD73 Inhibitors

Figure 2A:
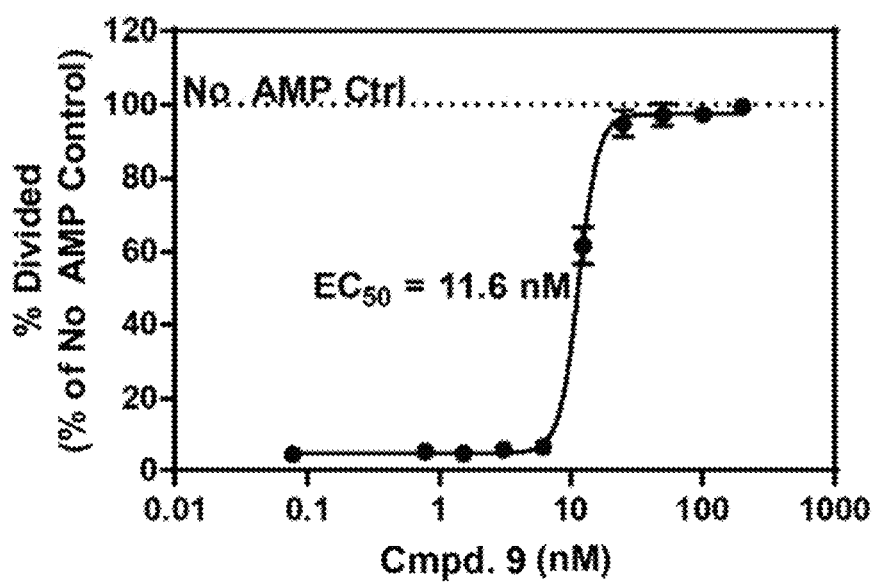
FIG. 2A depicts the reversal of AMP-mediated suppression of CD8+ T cells using the CD73 inhibitor Compound 9, including the $EC_{50}$=11.6 nM for CD8+ T cell proliferation.
Figure 2B:
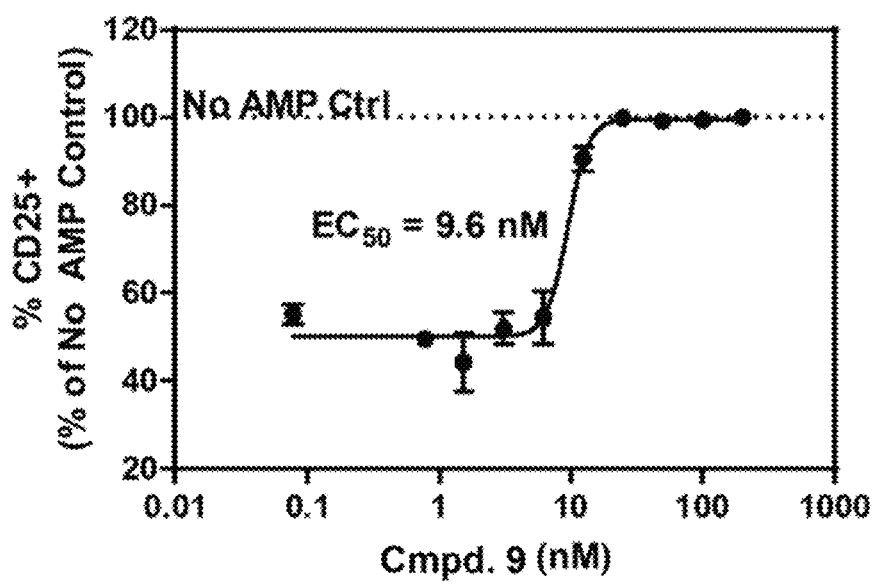
FIG. 2B depicts the $EC_{50}$=9.6 nM for CD8+ T cell activation.
Figure 2C:
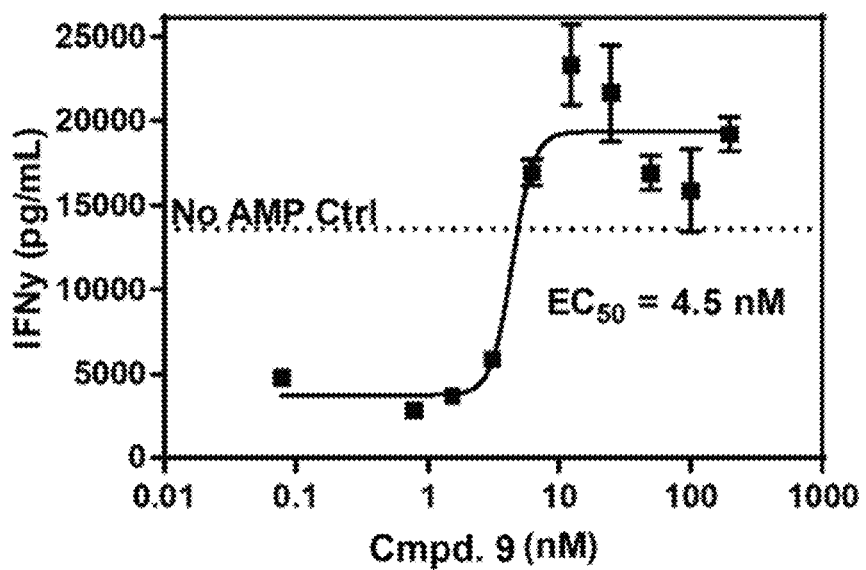
FIG. 2C depicts the $EC_{50}$=4.5 nM for IFN-gamma production.
Figure 2D:
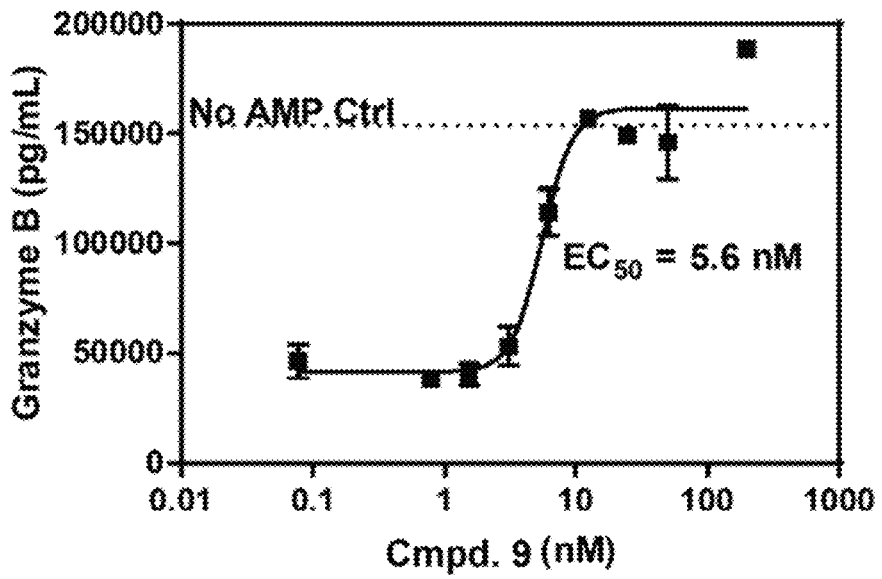
FIG. 2D depicts the $EC_{50}$=5.6 nM for Granzyme B production.

Human CD8+ T cells were labeled with CellTrace CFSE and then pre-incubated with an adenosine deaminase inhibitor and Compound 9 or vehicle for 20 minutes. 20 µM AMP was added for assessing T cell proliferation and CD25 expression. 10 µM AMP was added for assessing cytokine production. T cells were activated with α-CD3, α-CD28, and hIL2. After 4 days, proliferation and CD25 expression were assessed by flow cytometry and cytokine levels in the supernatant were measured by ELISA. EC$_{50}$s were determined using a four-parameter dose-response curve equation. FIG. 2A depicts the EC$_{50}$=11.6 nM for CD8+ T cell proliferation. FIG. 2B depicts the EC$_{50}$=9.6 nM for CD8+ T cell activation. FIG. 2C depicts the EC$_{50}$=4.5 nM for IFNγ production. FIG. 2D depicts the EC$_{50}$=5.6 nM for Granzyme B production.

Example 209

Selectivity of CD73 Inhibitors

Compounds of the invention are selective for CD73 and do not exhibit proliferative effects. Using Compound 9, the activity of cell surface CD39 was assessed using K562 cells expressing human CD39 and Kinase-Glo. Activity of recombinant human ENTPD2 and ENTPD3 was assessed using a malachite green assay. Each of the enzymes CD39, ENTPD2 AND ENTPD3 all showed an IC$_{50}$ of >10,000 nM. Compound 9 was screened in the Eurofins Safety Screen Panel and the Eurofins Express Diversity Kinase Profile Panel. In the Safety Panel, 1/87 targets were inhibited at >50% at 10 µM of Compound 9. The PDE3 enzyme was inhibited at 59%. In the Kinase Panel, none of the 45 targets were inhibited at >50%.

Figure 3A:
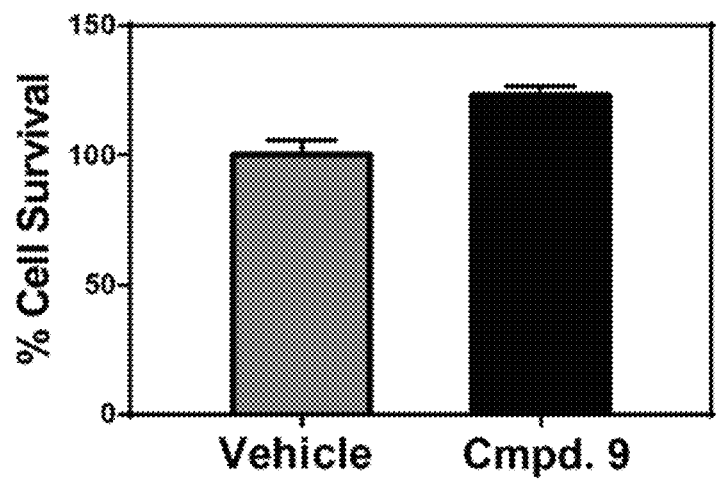
FIG. 3A depicts the effect of Compound 9 on proliferation of certain cell lines, including the comparable % cell survival of EG7 cells, a mouse T cell lymphoma cell line.
Figure 3B:
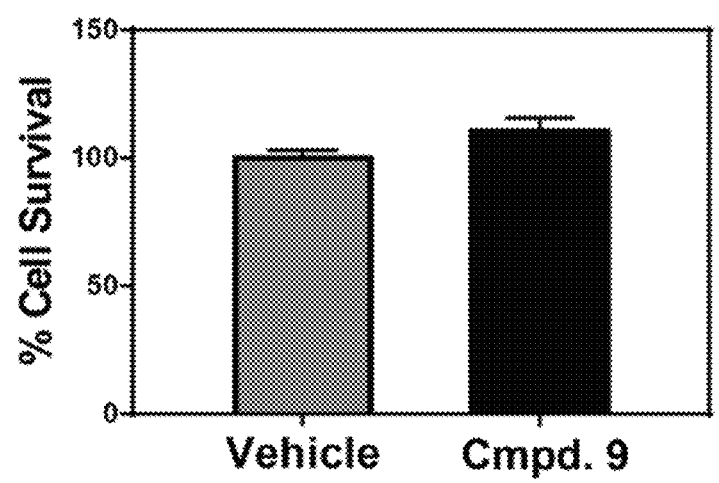
FIG. 3B depicts the comparable % cell survival of A375 cells, a human melanoma cell line.
Figures 3C, 4A:
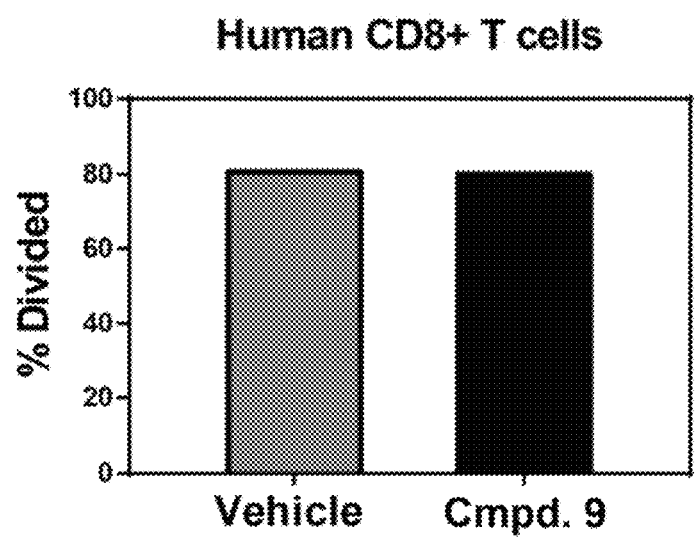
FIG. 3C depicts the comparable % divided cells of human CD8+ T cells.
FIG. 4A depicts the potency of Compound 9 as evaluated against CD73 and CD73-expressing SK-MEL-28 cells.

Further, Compound 9 did not show anti-proliferative effects against three cell lines. Viability of EG7 and A375 cells treated with 100 µM Compound 9 was measured using CellTiter-Glo after 3 days. Proliferation of human CD8+ T cells was measured by flow cytometry after 4 days of treatment with 100 µM Compound 9 using CellTrace CFSE Cell Proliferation Kit. FIG. 3A shows the comparable % cell survival of EG7 cells, a mouse T cell lymphoma cell line. FIG. 3B shows the comparable % cell survival of A375 cells, a human melanoma cell line. FIG. 3C shows the comparable % divided cells of human CD8+ T cells.

Example 210

CD73 Inhibition

Figure 4B:
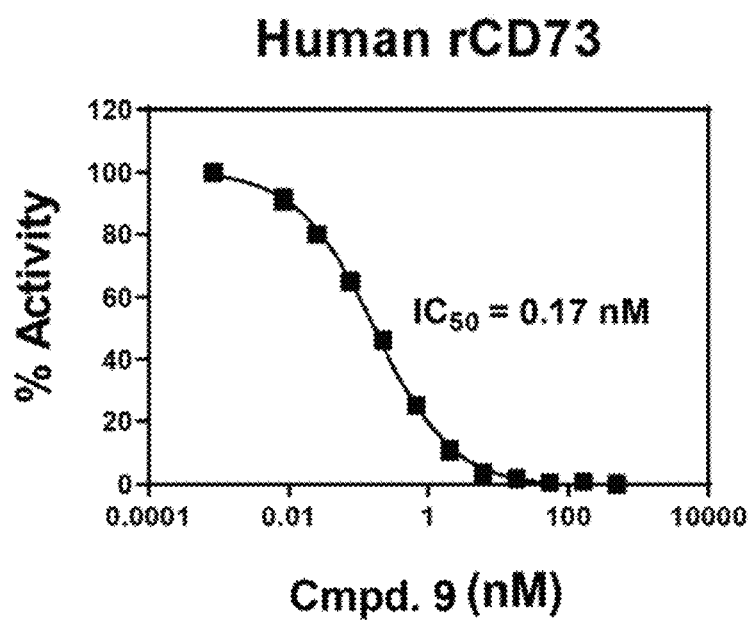
FIG. 4B depicts the $IC_{50}$=0.17 nM for human recombinant CD73.
Figure 4C:
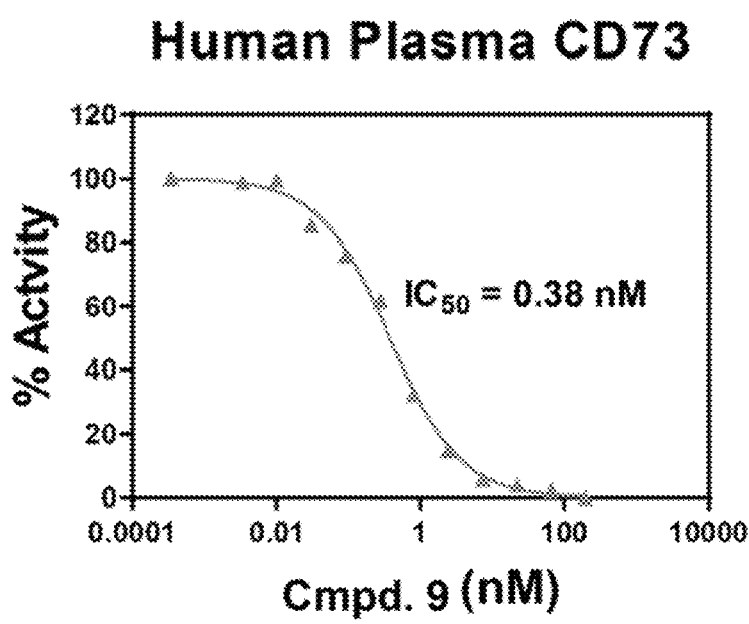
FIG. 4C depicts the $IC_{50}$=0.38 nM for human plasma CD73.
Figure 4D:
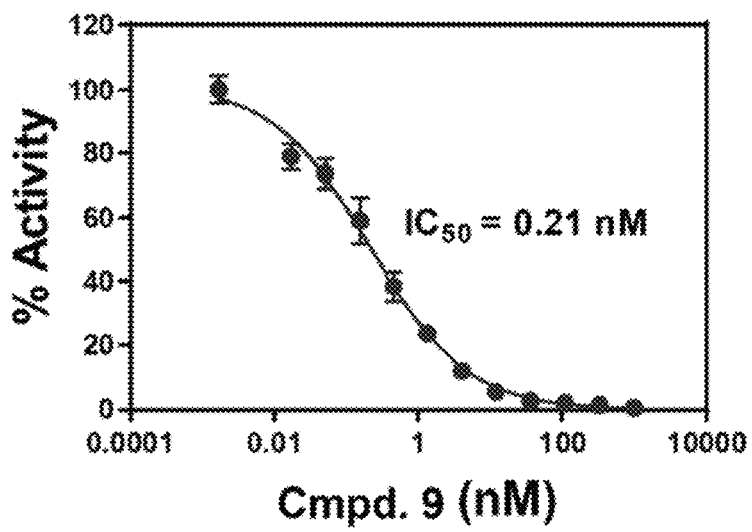
FIG. 4D depicts the $IC_{50}$=0.21 nM for human CD73 cell surface assay.

The potency of Compound 9 was evaluated against recombinant CD73 and CD73-expressing SK-MEL-28 cells using a malachite green assay. Inhibition of CD73 in plasma was measured using LC/MS to assess conversion of $^{15}N_5$-AMP into $^{15}N_5$-ADO. FIG. 4A indicates the nanomolar inhibition of CD73 cells from both human and mouse sources. FIG. 4B depicts the IC$_{50}$=0.17 nM for human recombinant CD73 cells. FIG. 4C depicts the IC$_{50}$=0.38 nM for human plasma CD73 cells. Inhibition of CD73 in plasma was measured using LC/MS to assess conversion of $^{15}N_5$-AMP into $^{15}N_5$-ADO. FIG. 4D depicts the IC$_{50}$=0.21 nM for human CD73 cell surface.

Example 211

CD73 Inhibitor Oral Dosing Phamacodynamics

Figure 5A:
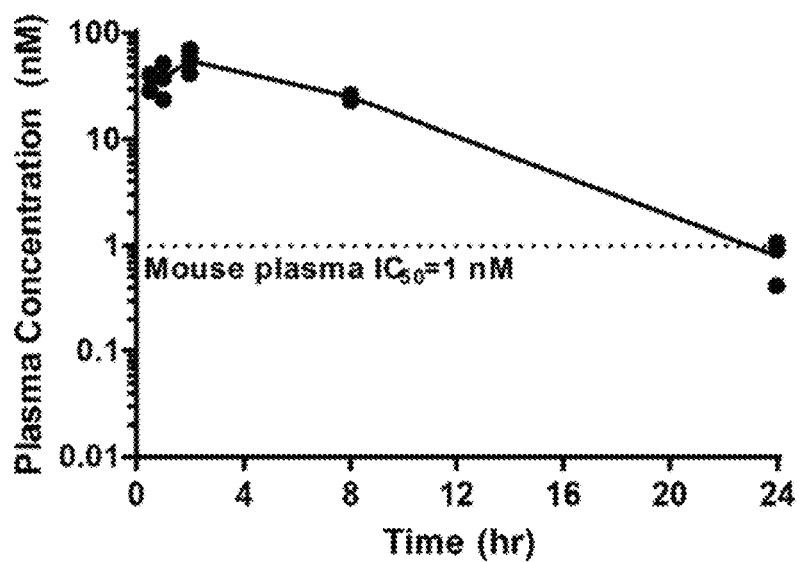
FIG. 5A depicts the level of Compound 9 in mouse plasma.
Figure 5B:
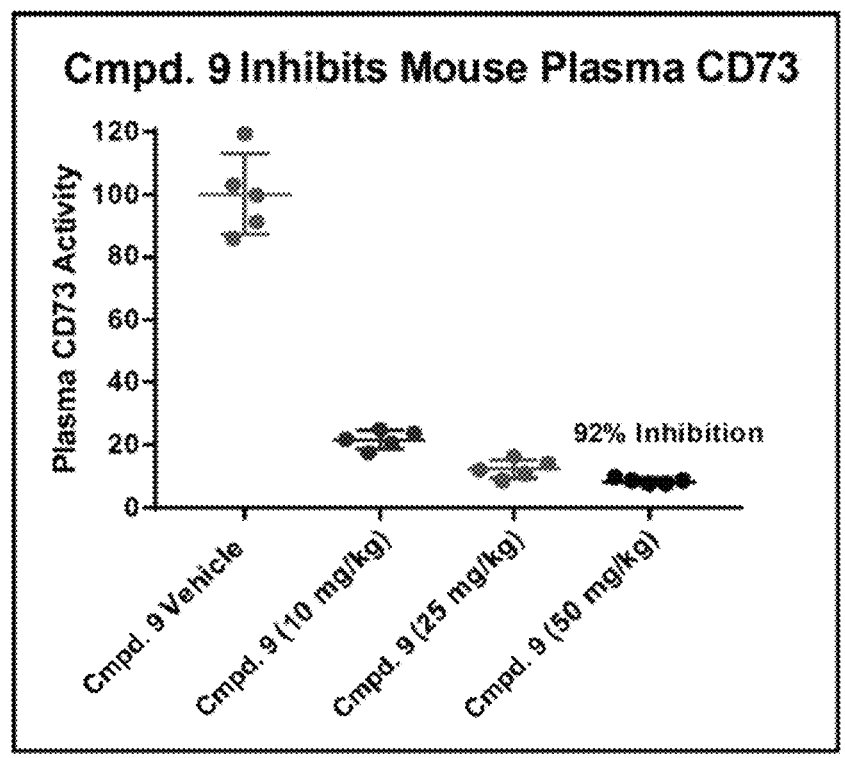
FIG. 5B depicts the inhibition of CD73 in mouse plasma.

Single dose Compound 9 (50 mg/kg) was administered orally to mice and plasma was collected at indicated time points. Compound 9 levels were measured by LC/MS. The IC$_{50}$ in mouse plasma was 1 nM as shown in FIG. 5A. Plasma was harvested from mice 2 hours post dose and spiked with $^{15}N_5$-AMP and a TNAP inhibitor. $^{15}N_5$-ADO levels were measured by LC/MS. FIG. 5B depicts the 92% inhibition of mouse plasma CD73 cells.

Example 212

Single-Agent Efficacy of Orally Dosed CD73 Inhibitors

Figure 6A:
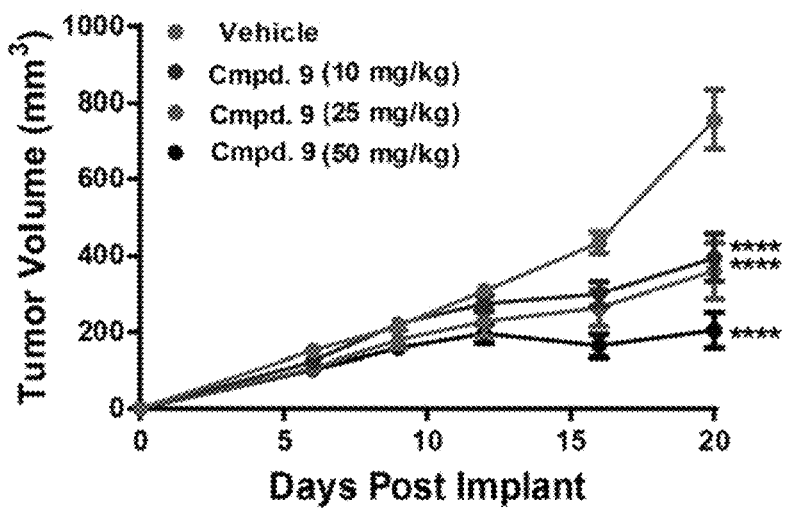
FIG. 6A depicts the efficacy of Compound 9 against EG7 tumors.
Figure 6B:
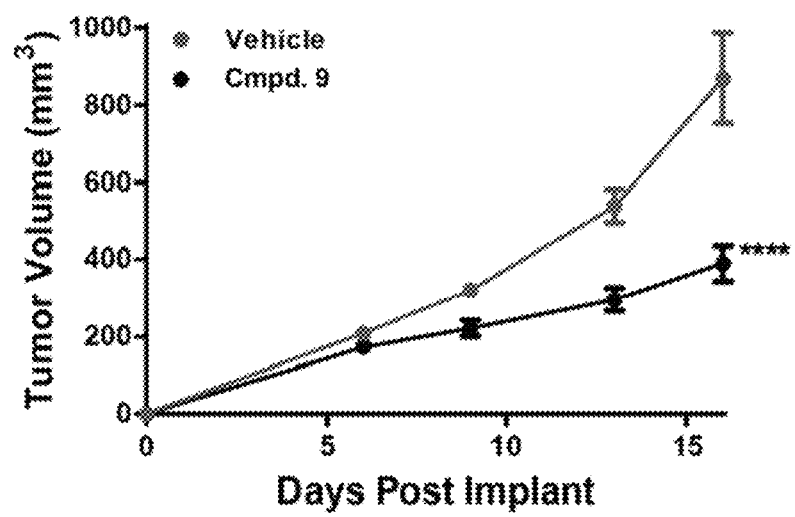
FIG. 6B depicts the efficacy of Compound 9 against CT26 tumors.
Figure 13A:
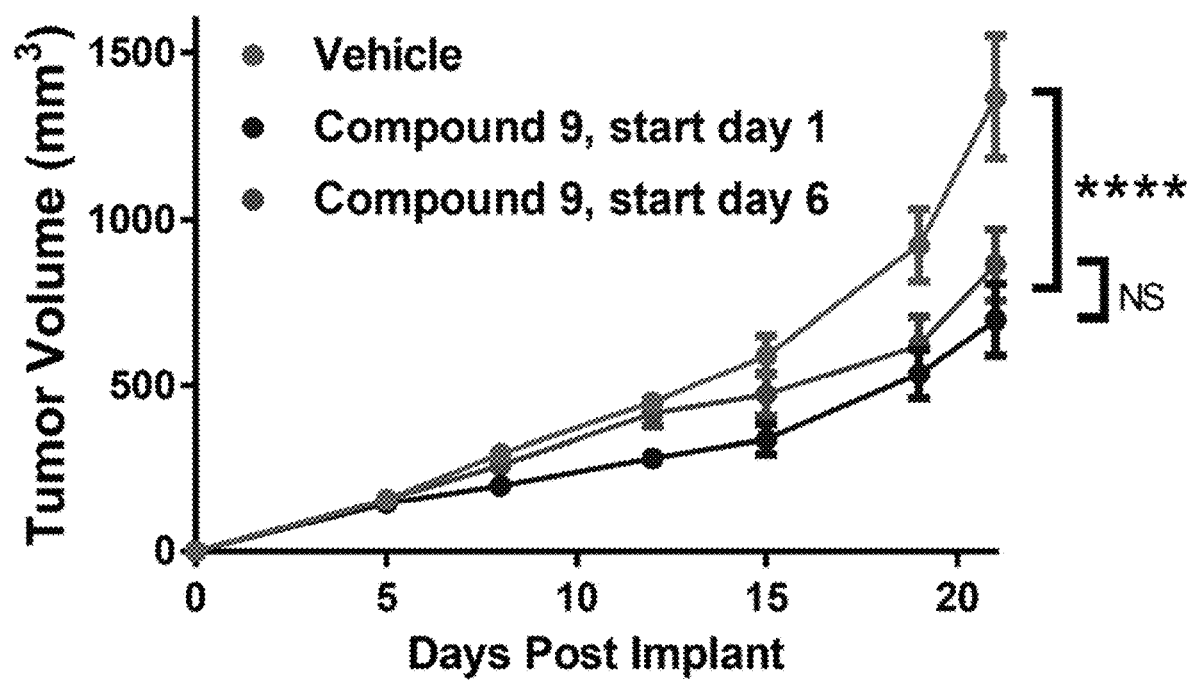
FIG. 13A depicts Compound 9 reduced the growth of established EG7 tumors.
Figure 13B:
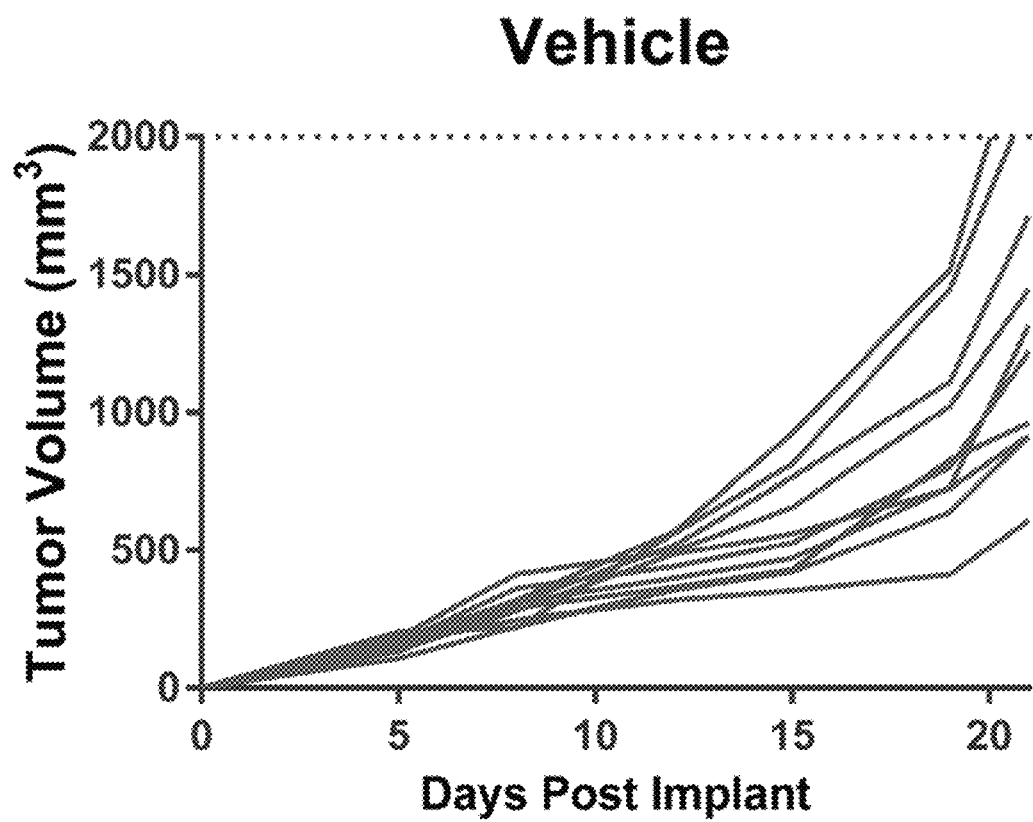
FIGS. 13B-13D depict individual replications of the reduction in tumor growth.
Figure 13C:
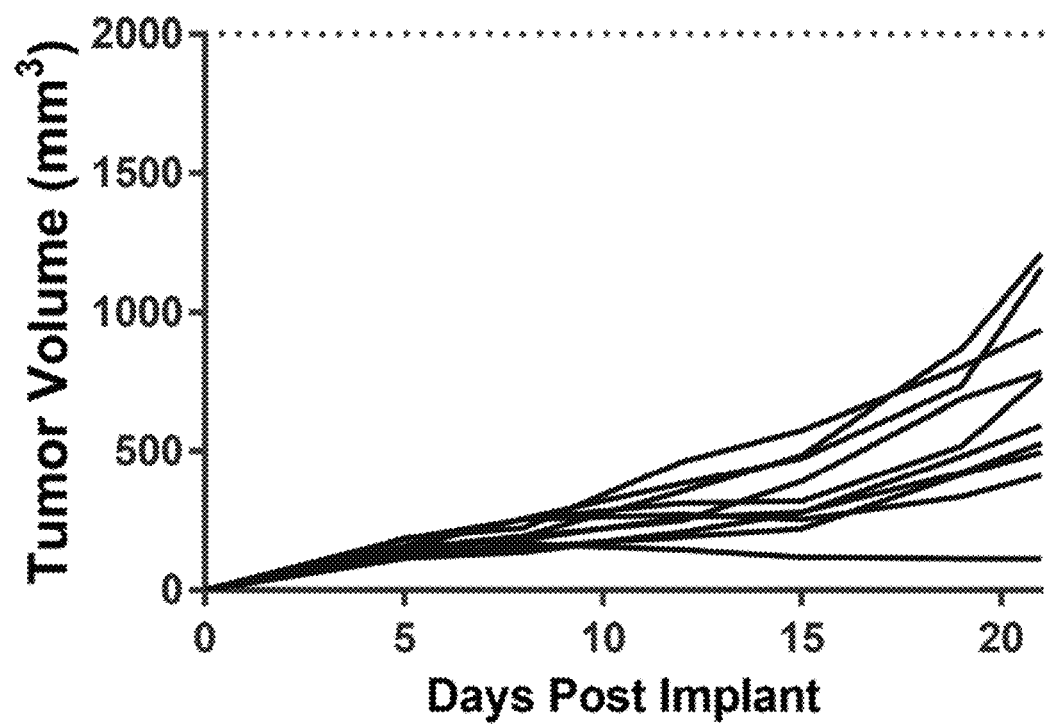
Figure 13D:
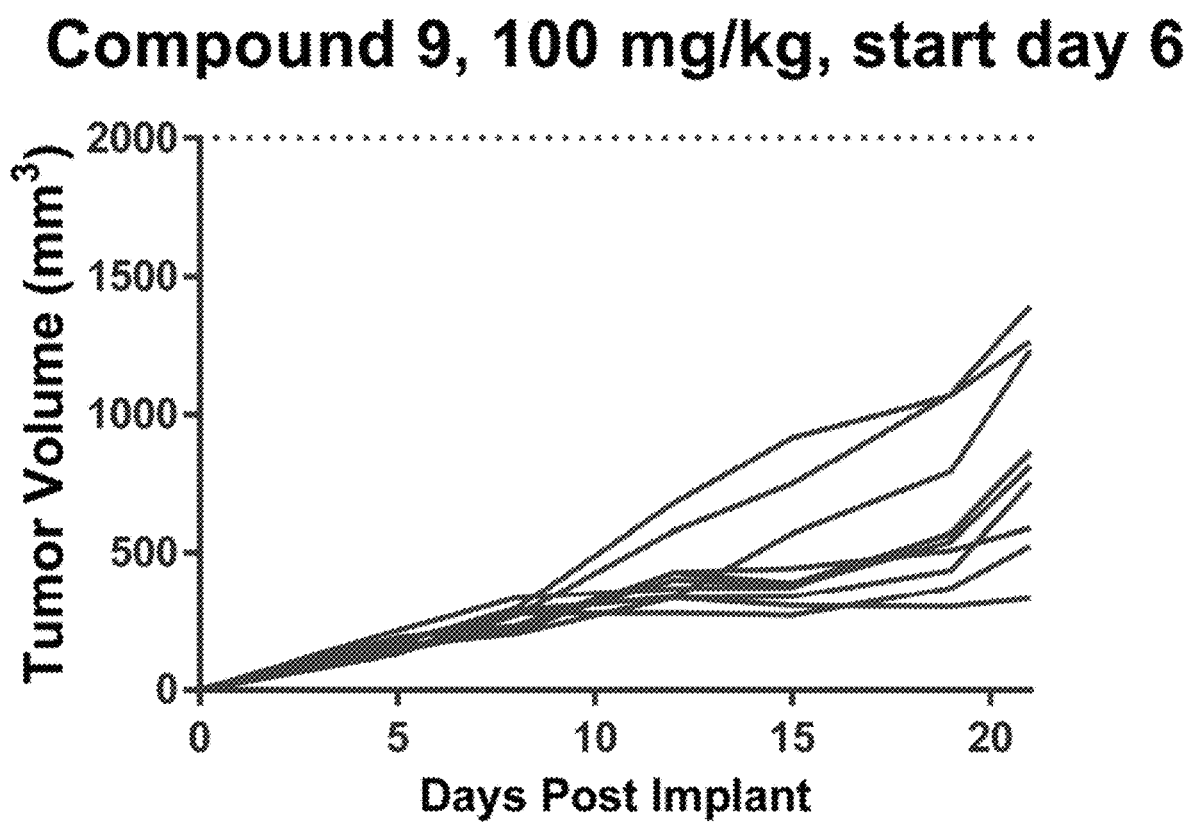

Compounds of the invention show potent anti-tumor effects, evidenced in reducing tumor volume in a mouse model. In one model, EG7 cells were implanted subcutaneously into C57BL/6 mice. Compound 9 or vehicle was orally administered BID starting day one post implant (N=10 per group). FIG. 6A depicts the further decrease in tumor volume with increasing doses of Compound 9. In another model, EG7 cells were implanted subcutaneously into C57BL/6 mice. Compound 9 was orally administered BID (100 mg/kg) starting day one post implant (N=10 per group). Vehicle was orally administered BID starting day one post implant (N=20) until day five post implant, at which time, mice were randomized by tumor volume into two groups. Compound 9 (100 mg/kg) or vehicle was orally administered BID to N=10 per group starting day six post implant. FIG. 13A depicts the decrease in tumor volume with administration of Compound 9 to mice harboring established tumors. FIGS. 13B-D show individual replications of this measurement for each dosing. FIG. 13B is vehicle. FIG. 13C is dosing of Compound 9 started on day 1. FIG. 13D is Compound 9 started on day 6. In another model, CT26 cells were implanted subcutaneously into Balb/c mice. 100 mg/kg Compound 9 or vehicle was orally administered BID starting day one post implant (N=10 per group). FIG. 6B depicts the decrease in tumor volume compared to vehicle. **** indicates $p<0.0001$ vs vehicle; NS indicates not significant (two-way ANOVA).

Example 213

Figure 7A:
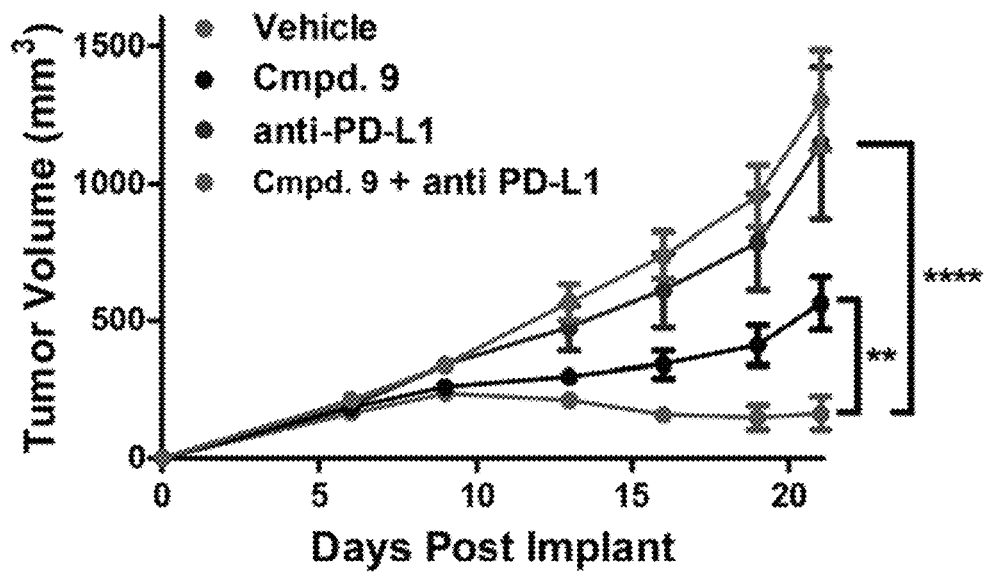
FIG. 7A depicts the reduction in tumor volume with single agent Compound 9 and combination therapy with anti-PD-L1 antibody.
Figure 7B:
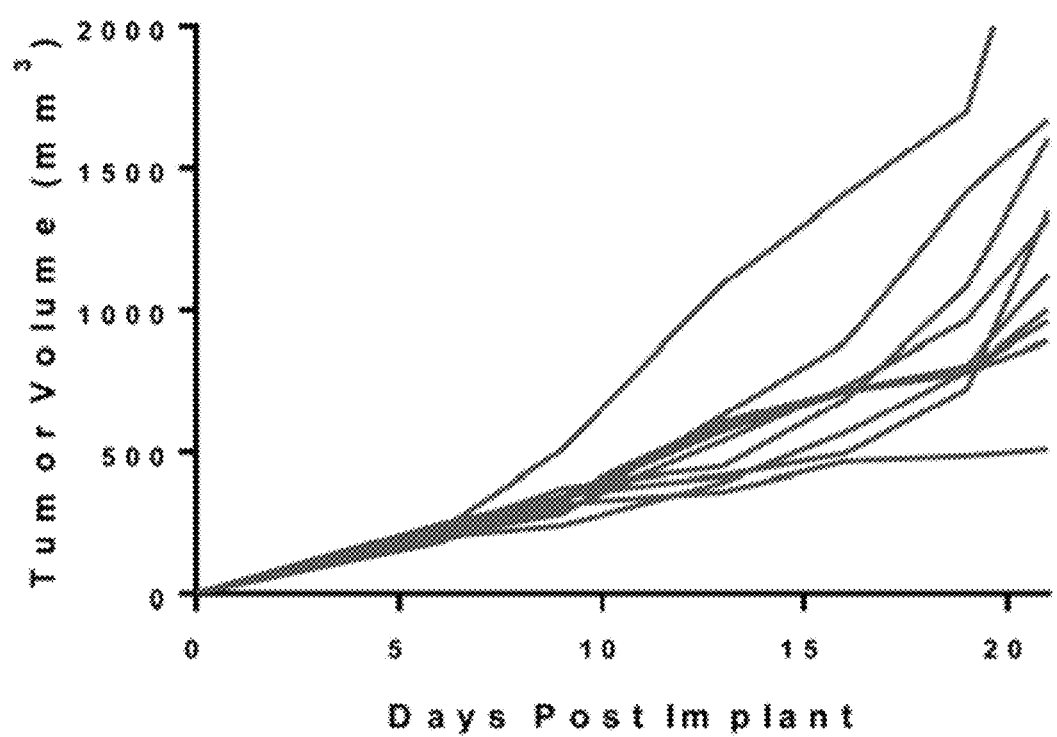
FIGS. 7B-7E show individual replications of this measurement for each dosing.
Figure 7C:
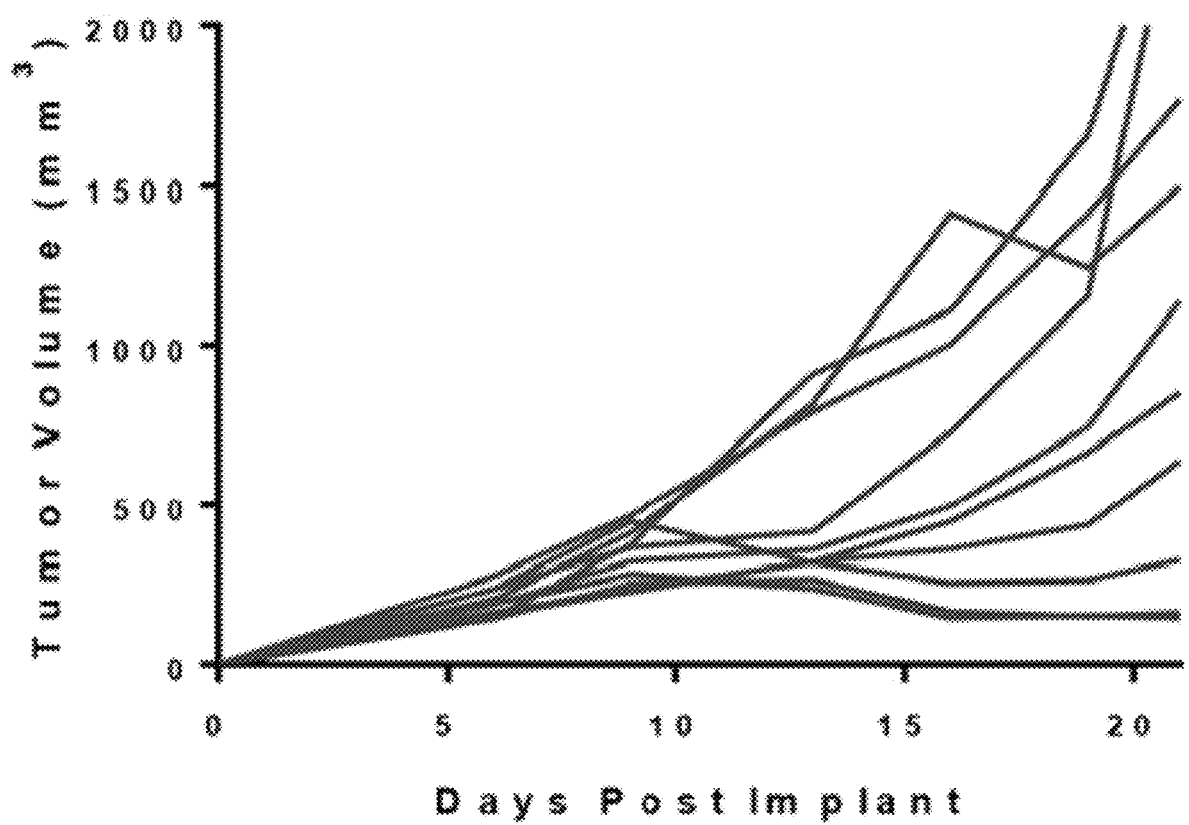
Figure 7D:
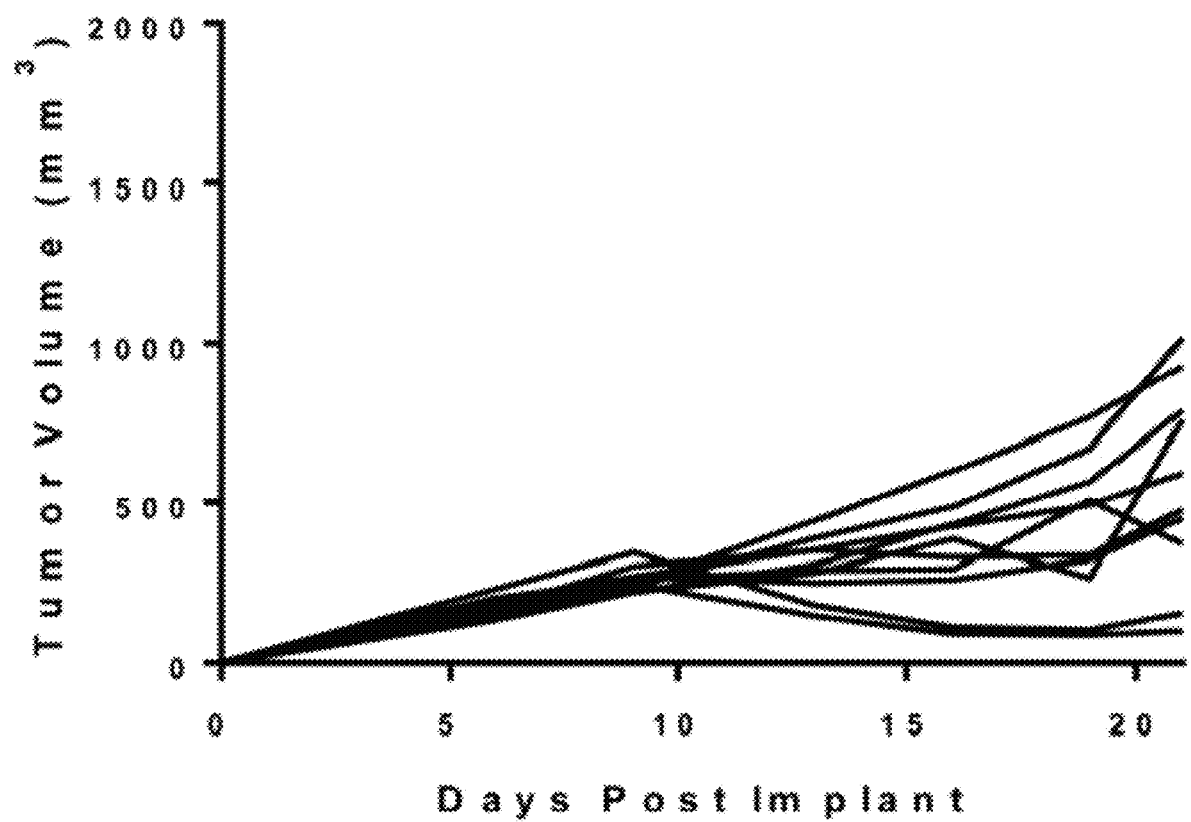
Figure 7E:
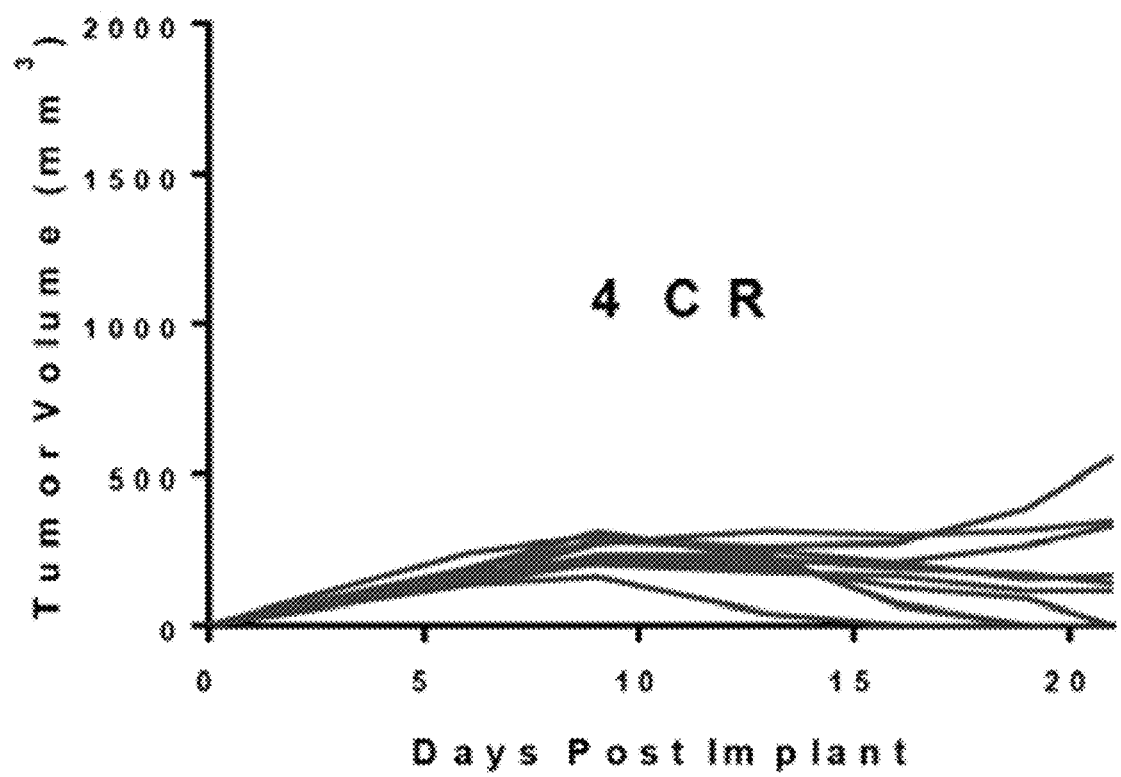

CD73 Inhibitor Efficacy in Combination with Immunooncology and Chemotherapeutic Agents EG7 cells were implanted subcutaneously into C57BL/6 mice for each experiment. Anti-PD-L1 antibody (5 mg/kg) was dosed i.p. on Study Days 3, 5, 7, 9, 11, 13. Compound 9 (100 mg/kg) or vehicle was orally administered BID starting one day post implant. FIG. 7A depicts the reduction in tumor volume with single agent and combination therapy.  indicates $p<0.01$; ** indicates $p<0.0001$ (two-way ANOVA). FIGS. 7B-7E show the individual replications of this measurement for each dosing. FIG. 7B is vehicle, FIG. 7C is anti-PD-L1 antibody, FIG. 7D is Compound 9, and FIG. 7E is Compound 9+ Anti-PD-L1.

Figure 8A:
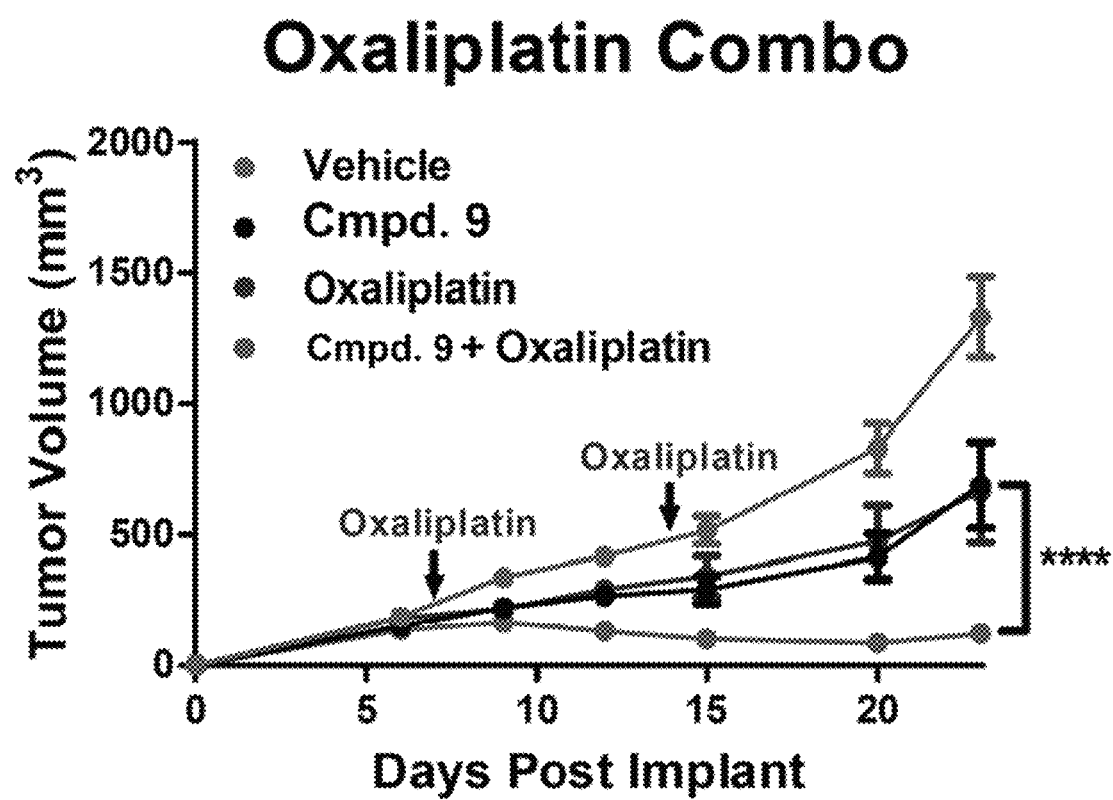
FIG. 8A depicts the reduction in tumor volume with single agent Compound 9 and combination therapy with oxaliplatin.
Figure 8B:
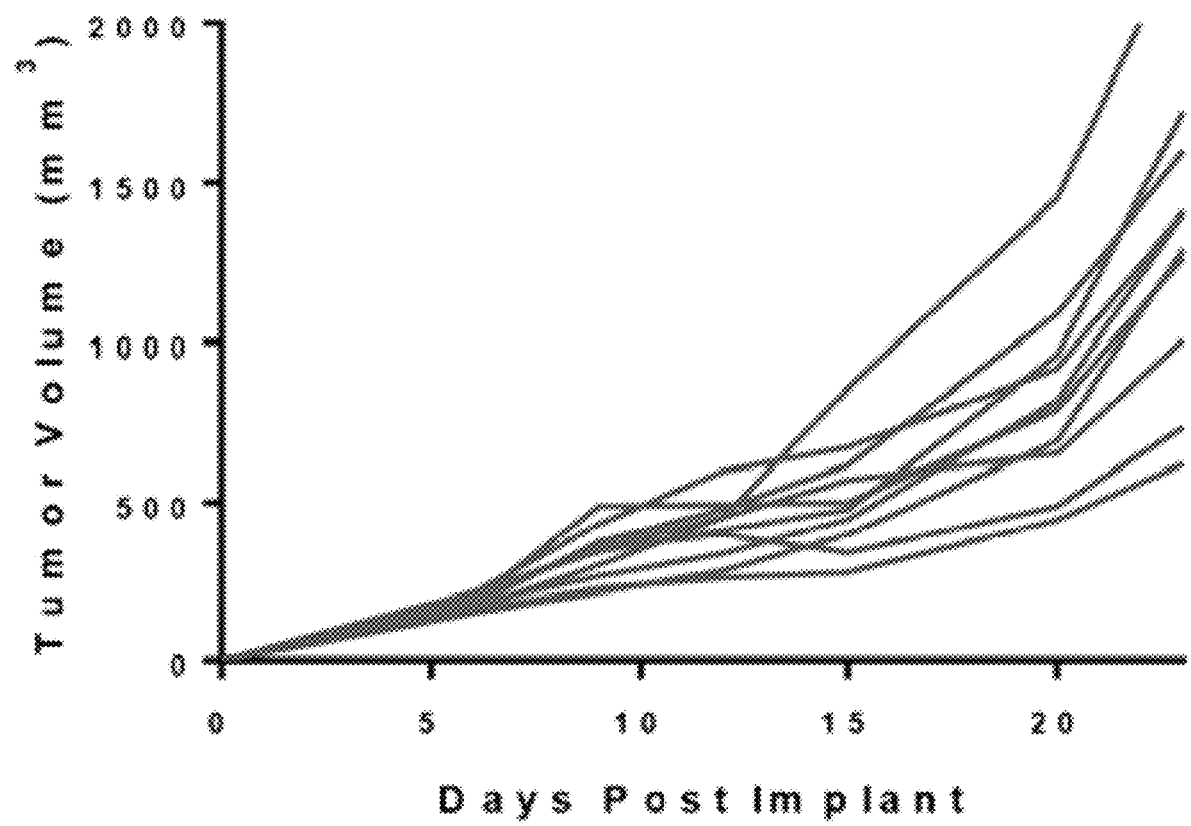
FIGS. 8B-8E show individual replications of this measurement for each dosing.
Figure 8C:
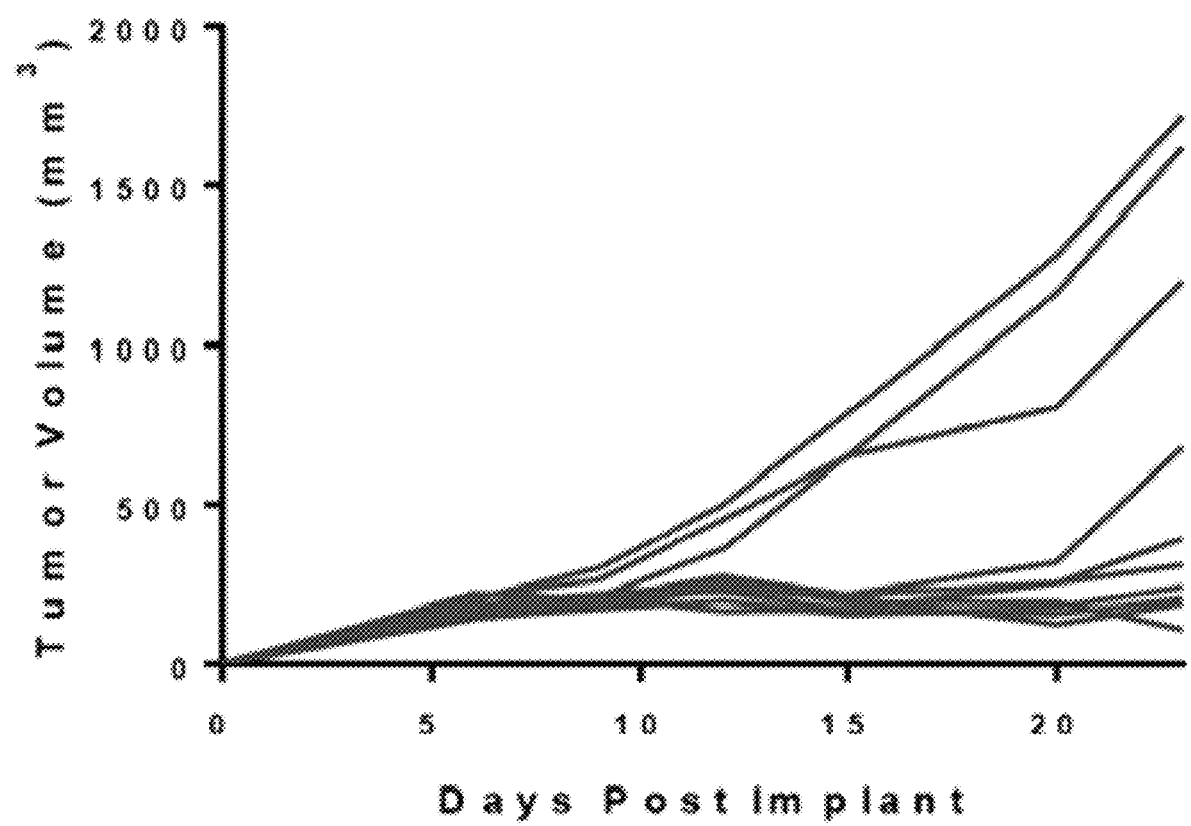
Figure 8D:
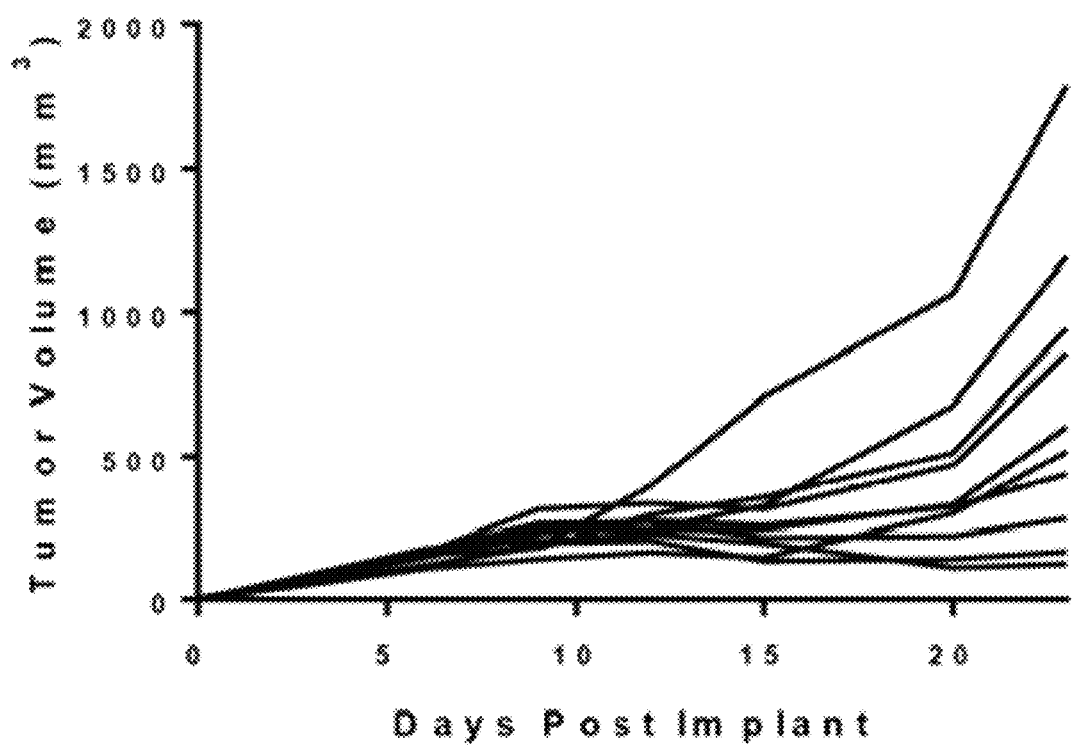
Figure 8E:
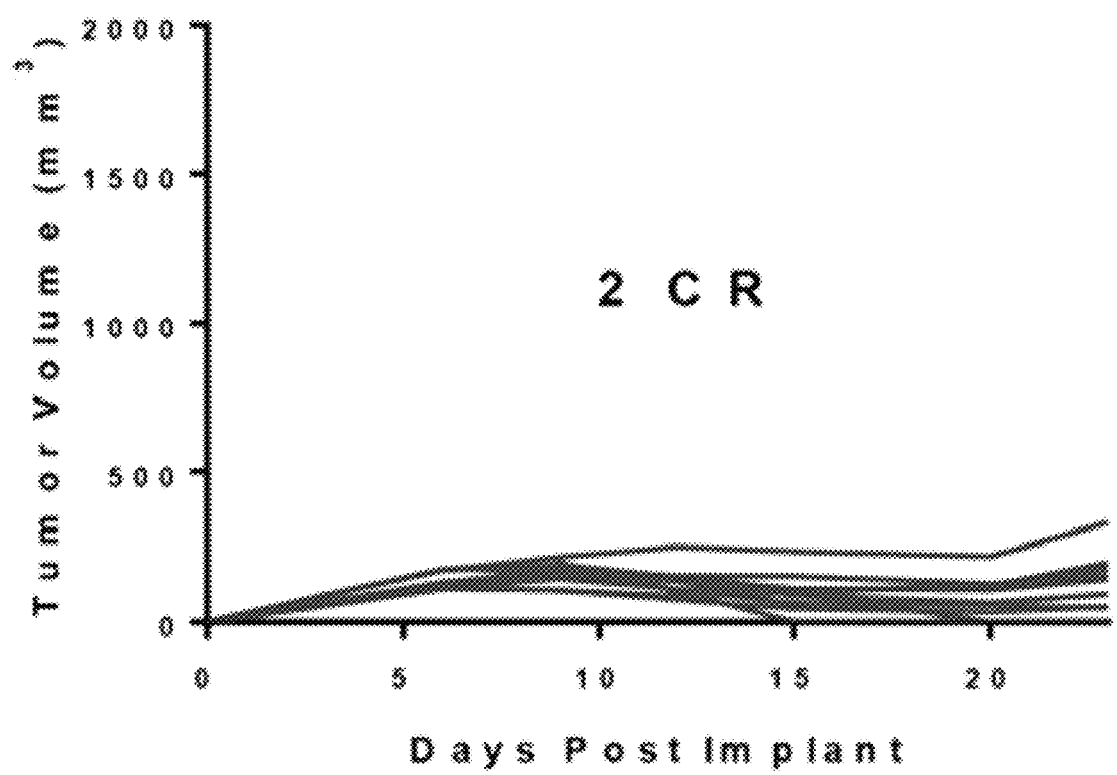

Oxaliplatin was dosed i.p. 6 mg/kg on Study Days 7 and 14. Compound 9 (100 mg/kg) or vehicle was orally administered BID starting one day post implant. FIG. 8A depicts the reduction in tumor volume with single agent and combination therapy. **** indicates $p<0.0001$ (two-way ANOVA). FIGS. 8B-8E show the individual replications of this measurement for each dosing. FIG. 8B is vehicle, FIG. 8C is oxaliplatin, FIG. 8D is Compound 9, and FIG. 8E is Compound 9+oxaliplatin.

Figure 9A:
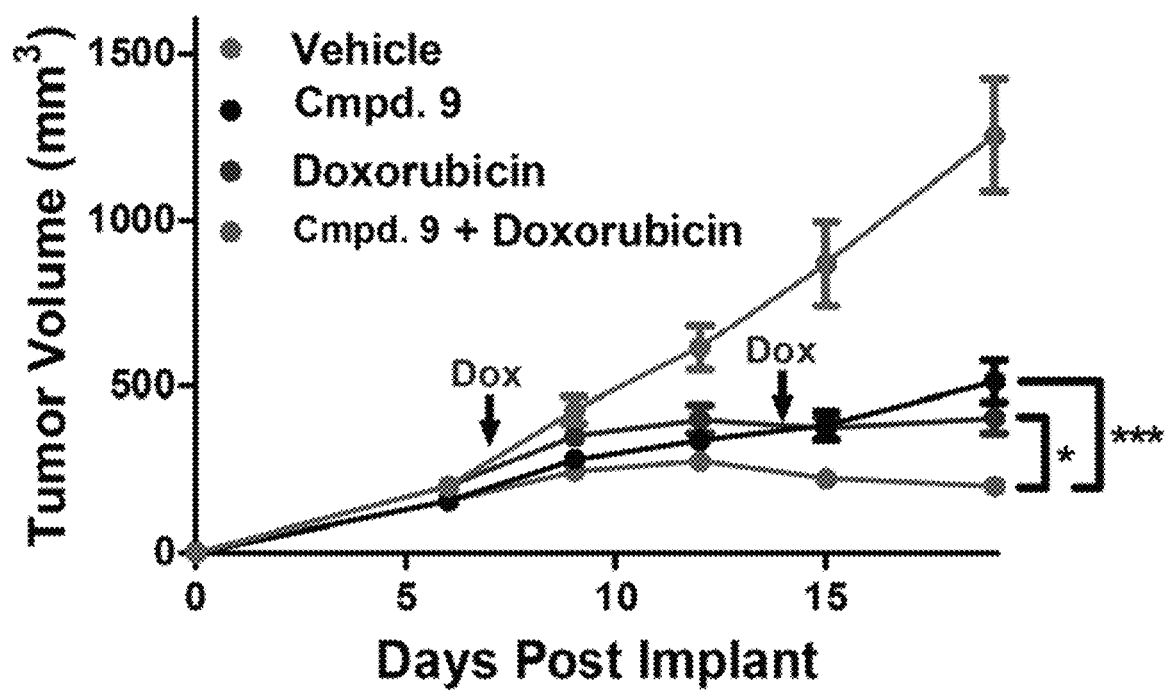
FIG. 9A depicts the reduction in tumor volume with single agent Compound 9 and combination therapy with doxorubicin.
Figure 9B:
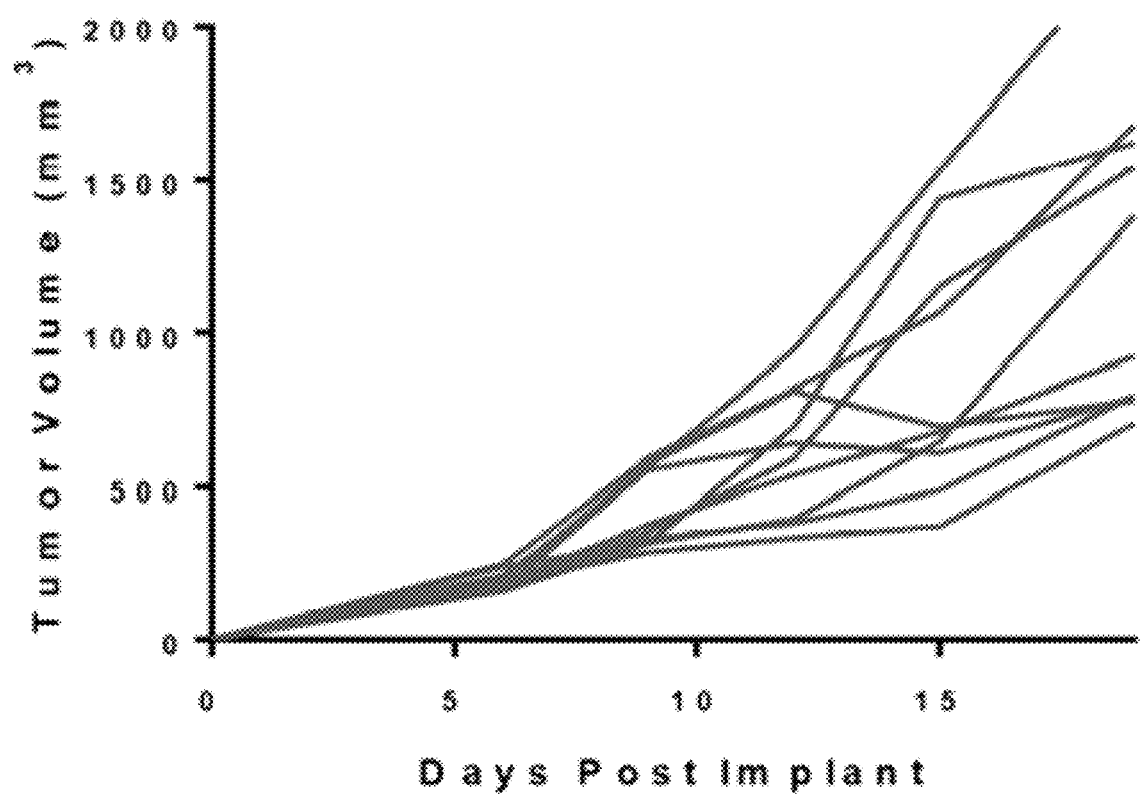
Figure 9C:
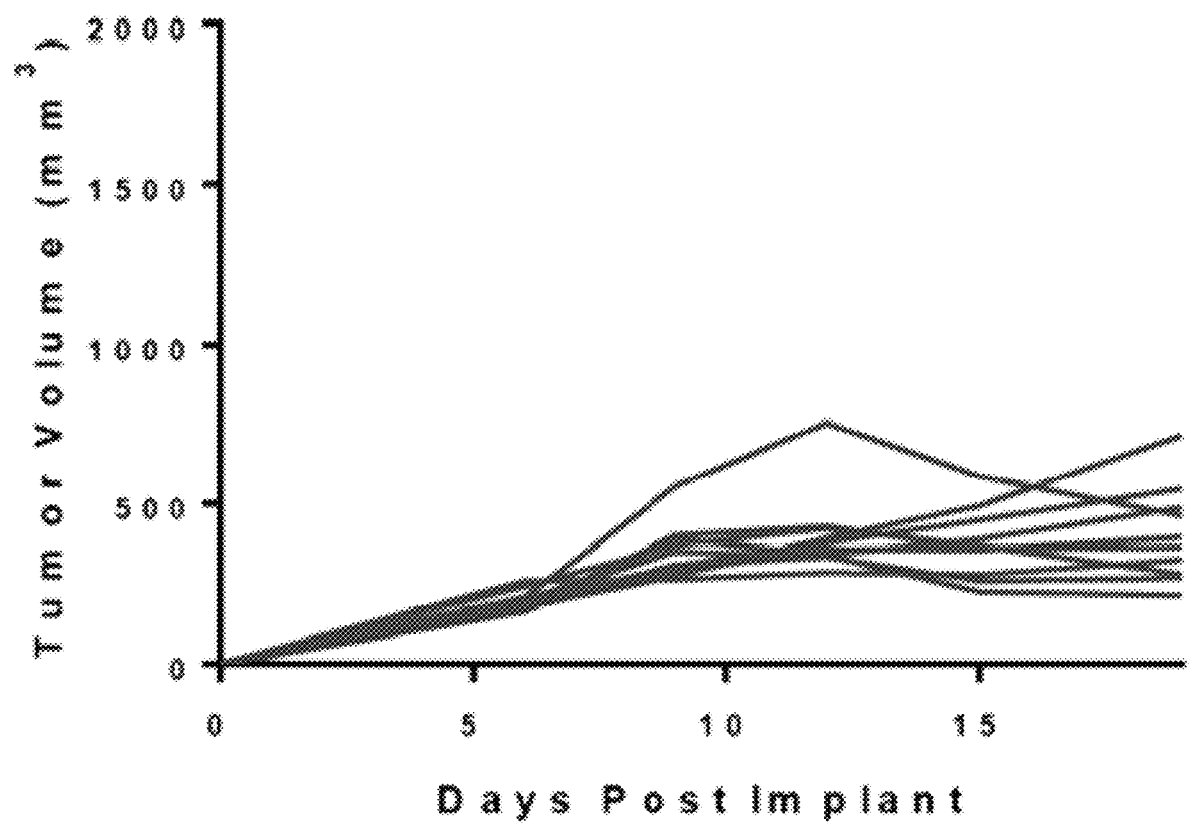
Figure 9E:
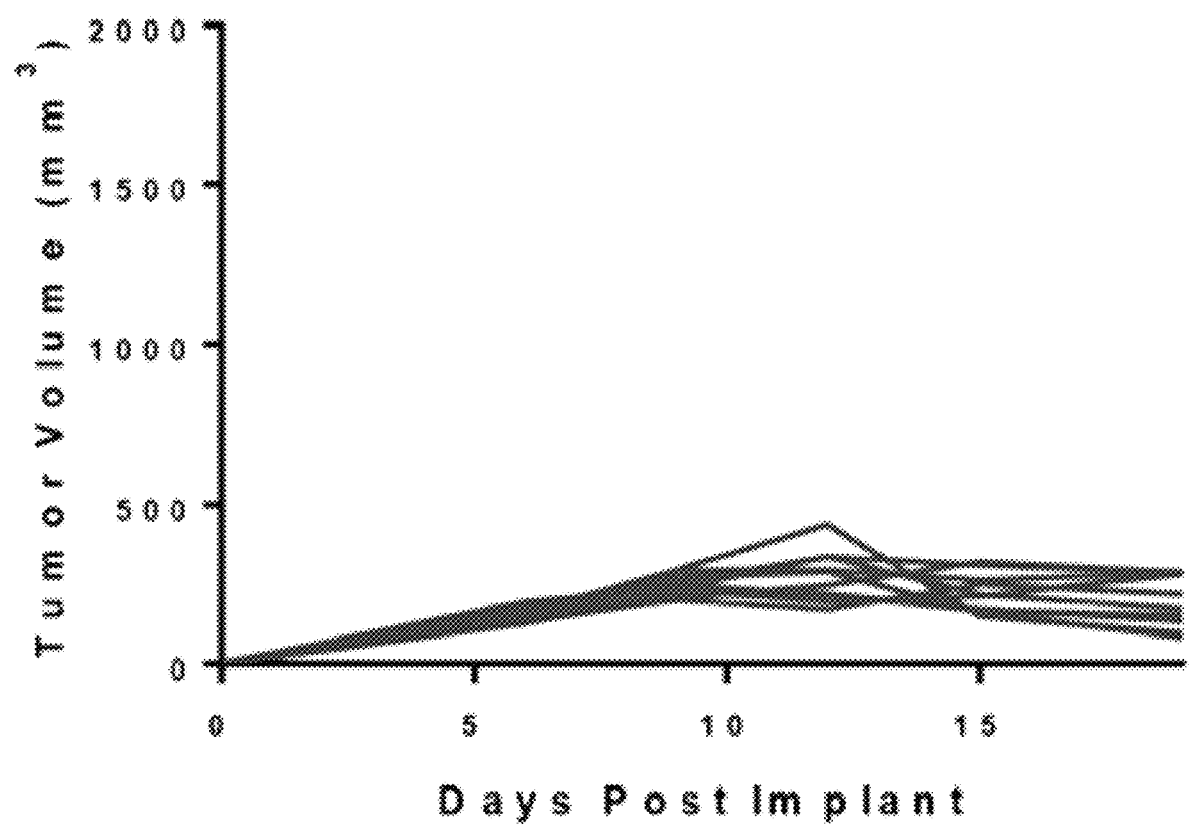

Doxorubicin was dosed i.v. 2.5 mg/kg on Study Days 7 and 14. Compound 9 (50 mg/kg) or vehicle was orally administered BID starting one day post implant. FIG. 9A depicts the reduction in tumor volume with single agent and combination therapy. * indicates $p<0.05$; *** indicates $p<0.001$ (two-way ANOVA). FIGS. 9B-9E show the individual replications of this measurement for each dosing. FIG. 9B is vehicle, FIG. 9C is doxorubicin, FIG. 9D is Compound 9, and FIG. 9E is Compound 9+doxorubicin.

Figure 12A:
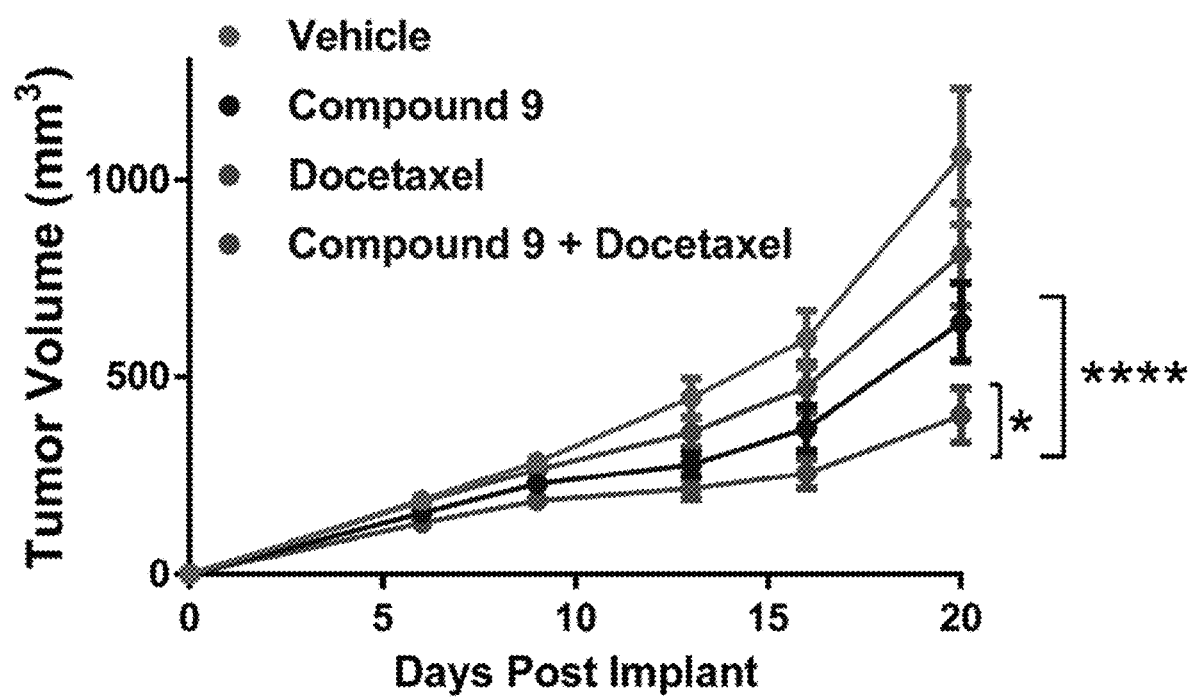
FIG. 12A depicts the reduction in tumor volume with single agent Compound 9 and combination therapy with docetaxel in EG7 tumor model.
Figure 12B:
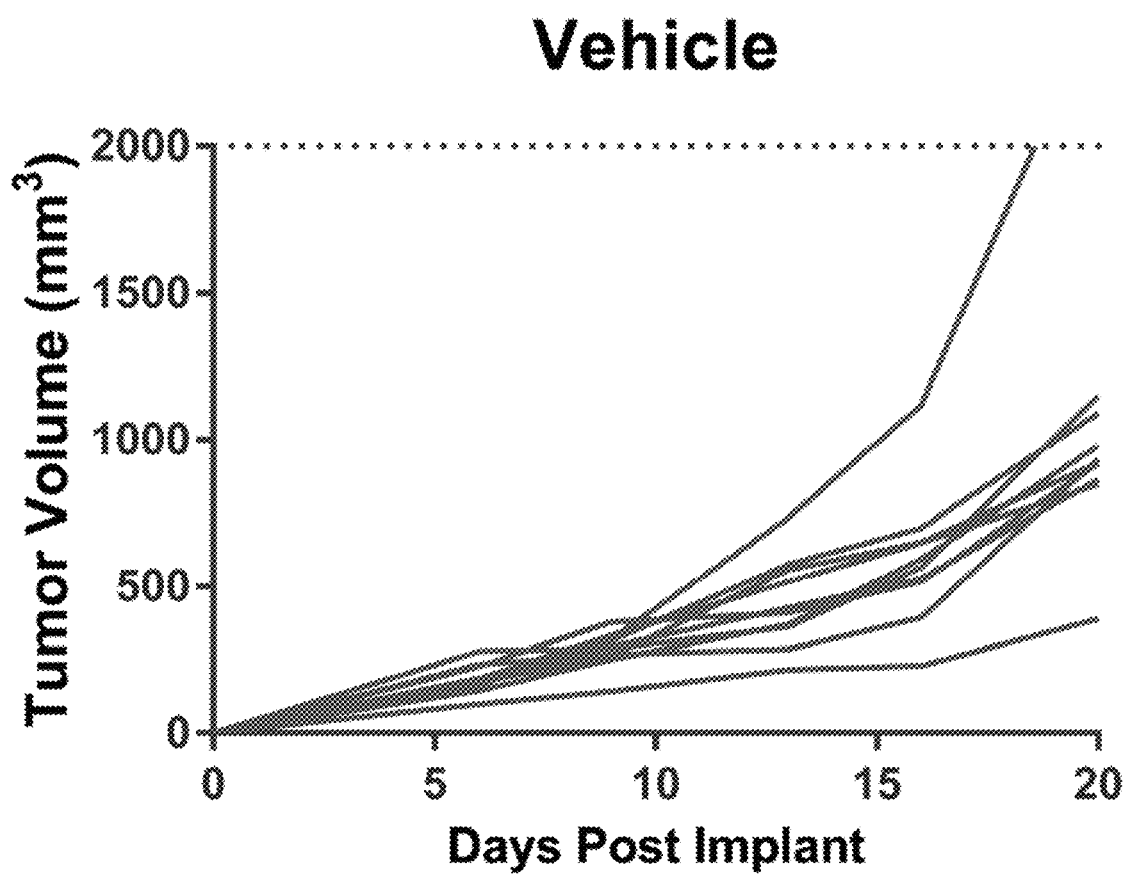
FIGS. 12B-12E depict individual replications of the reduction in tumor volume.
Figure 12C:
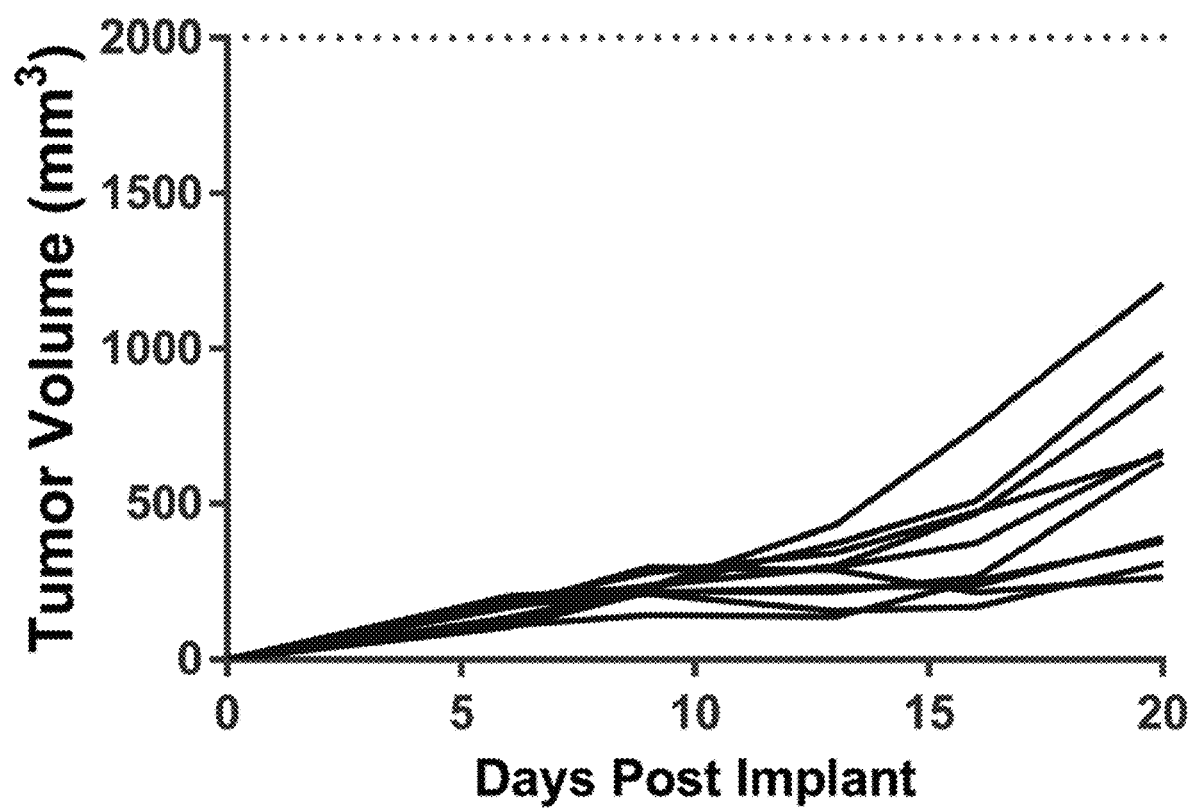
Figure 12D:
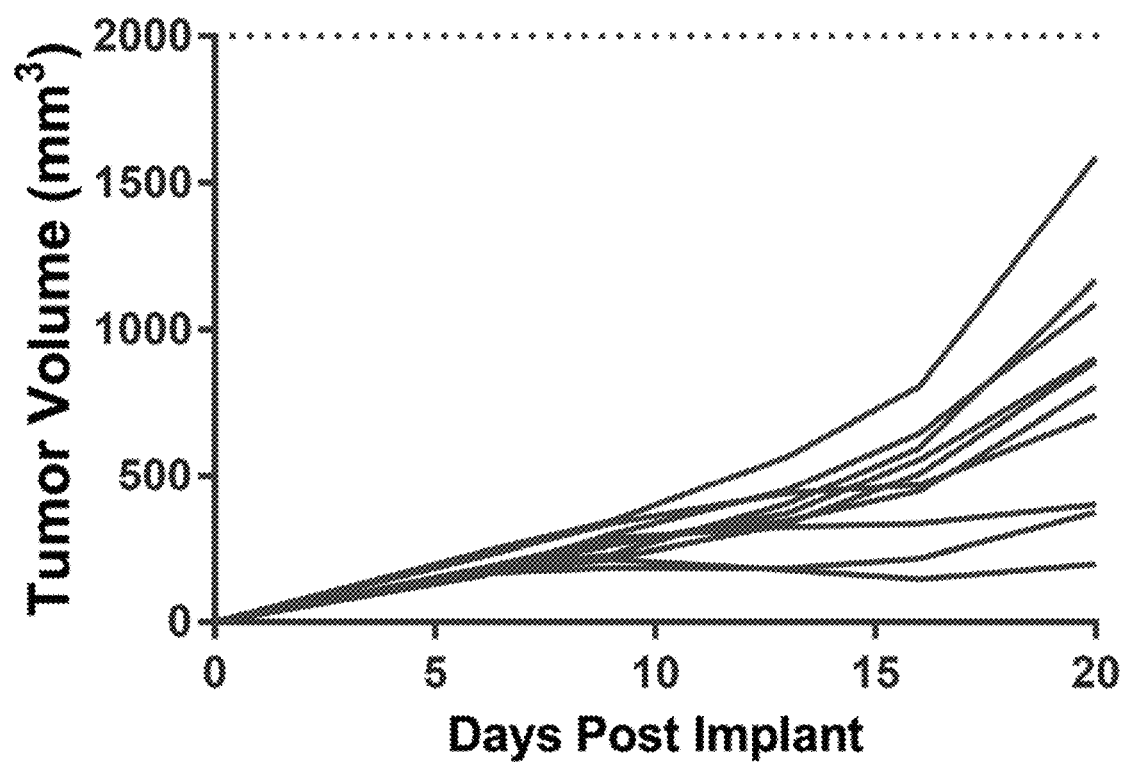
Figure 12E:
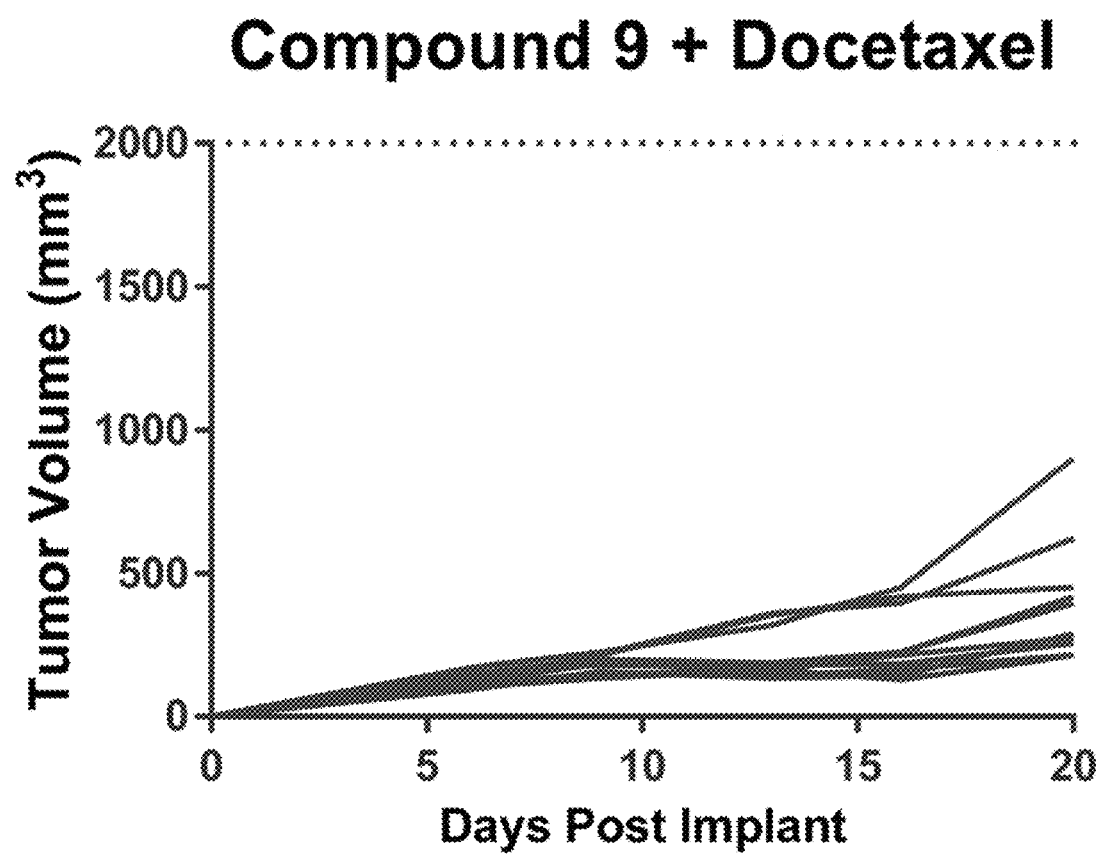

Docetaxel was dosed i.p. 5 mg/kg on Study Days 5, 12, and 19. Compound 9 (100 mg/kg) or vehicle was orally administered BID starting one day post implant. FIG. 12A depicts the reduction in tumor volume with single agent and combination therapy. * indicates $p<0.05$; **** indicates $p<0.0001$ (two-way ANOVA). FIGS. 12B-10E show the individual replications of this measurement for each dosing. FIG. 12B is vehicle, FIG. 12C is docetaxel, FIG. 12D is Compound 9, and FIG. 12E is Compound 9+docetaxel.

Example 214

CD73 Inhibitor Efficacy in Multiple Tumors

Figure 10A:
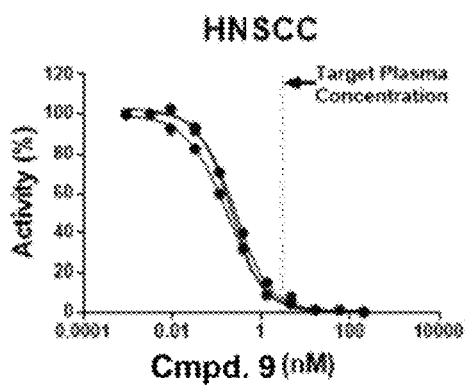
FIG. 10A depicts the sub-nanomolar inhibition of CD73 activity in head and neck squamous cell carcinoma (HNSCC) serum by Compound 9.
Figure 10B:
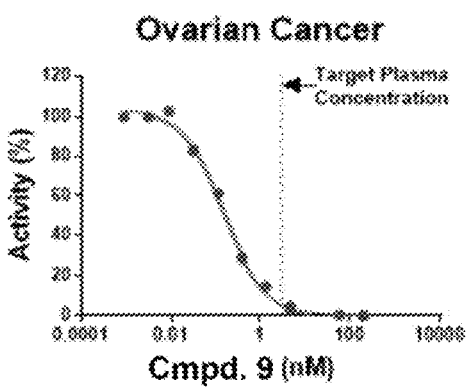
FIG. 10B depicts the sub-nanomolar inhibition of CD73 activity in ovarian cancer serum by Compound 9.
Figure 10C:
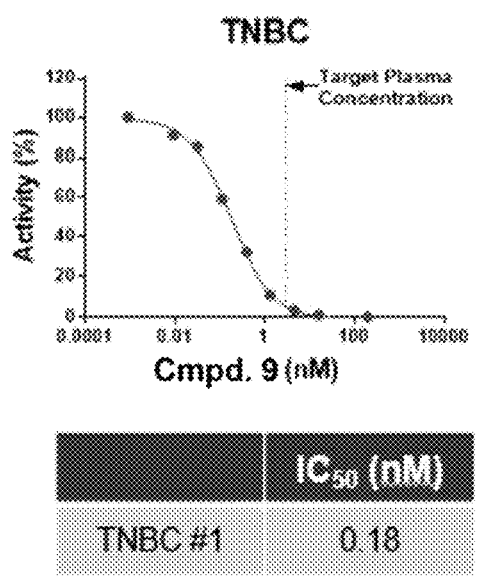
FIG. 10C depicts the sub-nanomolar inhibition of CD73 activity in triple-negative breast cancer (TNBC) serum by compound 9.
Figure 10D:
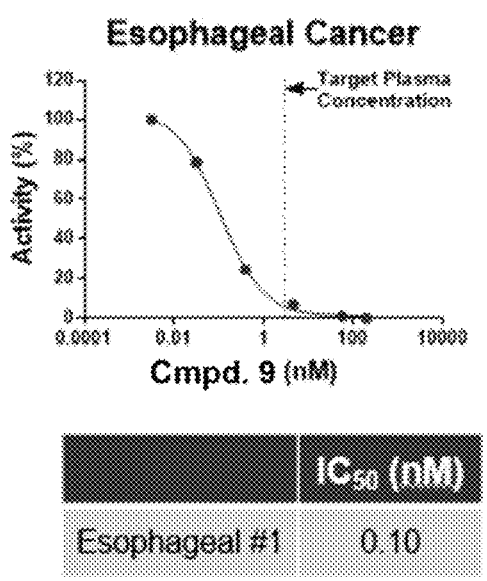
FIG. 10D depicts the sub-nanomolar inhibition of CD73 activity in esophageal cancer serum by Compound 9.

Serum was procured from Discovery Life Sciences. Serum from head and neck squamous cell carcinoma (HNSCC), ovarian cancer, triple-negative breast cancer and esophageal cancer patients were incubated with a serial dilution of Compound 9 in the presence of a TNAP inhibitor. Conversion of $^{15}N_5$-AMP to $^{15}N_5$-ADO was measured by LC/MS. FIG. 10A depicts the sub-nanomolar inhibition of HNSCC serum. FIG. 10B depicts the sub-nanomolar inhibition of ovarian cancer serum. FIG. 10C depicts the sub-nanomolar inhibition of TNBC serum. FIG. 10D depicts the sub-nanomolar inhibition of esophageal cancer serum.

Example 215

Expression of CD73 in Multiple Human Tumors

Figure 11:
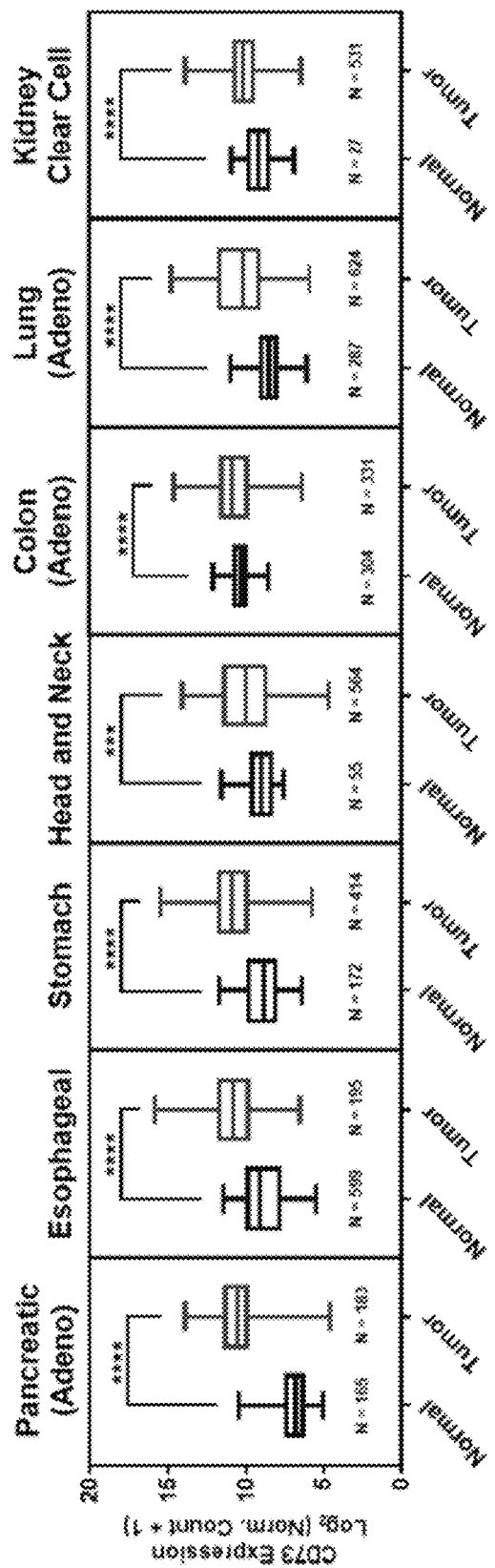
FIG. 11 depicts normalized mRNA expression levels of CD73 in tumor and normal tissues.

FIG. 11 depicts normalized mRNA expression levels of CD73 in tumor and normal tissues. Expression levels of CD73 (NT5E) were obtained from the TCGA (tumor) or GTEX (normal) databases using the UCSC Xena platform and analyzed using an unpaired t-test. The expression of CD73 as measured by a $Log_2$ (Normalized Count +1) was greater than vehicle for pancreatic, esophageal, stomach, head and neck, colon, lung and kidney clear cell tumors.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:
1. A compound of formula (I):

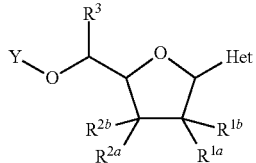

or a pharmaceutically acceptable salt and/or prodrug thereof, wherein
Y is

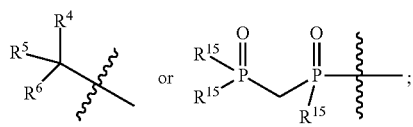

Het is an optionally substituted purinyl ring or an optionally substituted 5-methyl-pyrimidin-2,4-dione ring;
$R^{1a}$ is selected from H, halo, hydroxy, cyano, azido, amino, $C_{1-6}$alkyl, hydroxy$C_{1-6}$alkyl, amino-$C_{1-6}$alkyl, —O—C(O)—O—$C_{1-6}$alkyl, $C_{1-6}$acyloxy, $C_{1-6}$alkoxy, $C_{2-6}$alkenyl, and $C_{2-6}$alkynyl;
$R^{1b}$ is selected from H, halo, $C_{1-6}$alkyl, hydroxy-$C_{1-6}$ alkyl, amino-$C_{1-6}$alkyl, $C_{2-6}$alkenyl, and $C_{2-6}$alkynyl;
$R^{2a}$ is selected from halo, hydroxy, cyano, azido, amino, $C_{1-6}$alkyl, hydroxy-$C_{1-6}$alkyl, amino-$C_{1-6}$alkyl, $C_{1-6}$acyloxy, —O—C(O)—O—$C_{1-6}$alkyl, $C_{1-6}$alkoxy, $C_{2-6}$alkenyl, and $C_{2-6}$alkynyl;
$R^{2b}$ is $C_{2-6}$alkynyl;
$R^3$ is selected from H and alkyl;
$R^4$ is selected from H, alkyl, CN, aryl, heteroaryl, —C(O) $OR^9$, —C(O)$NR^{11}R^{12}$, —S(O)$_2R^{10}$, —P(O)($OR^{11}$)($OR^{12}$), and —P(O)($OR^{11}$)($NR^{13}R^{14}$);
$R^5$ is aralkyl or heteroaralkyl wherein the aralkyl is substituted with one or more substituents selected from halo, haloalkyl, alkyl, alkoxy, carbonyl, aryl amino, amino, cycloalkyl, heterocyclyl, and heteroaryl;
$R^6$ is selected from —C(O)$OR^9$, —C(O)$NR^{16}R^{17}$, and —P(O)($OR^{11}$)($OR^{12}$);
$R^9$ is independently selected from H, alkyl, cycloalkyl, cycloalkylalkyl, heterocyclyl, heterocyclylalkyl, aryl, aralkyl, heteroaryl, and heteroaralkyl;
$R^{10}$ is independently selected from alkyl, alkenyl, alkynyl, amino, cycloalkyl, cycloalkylalkyl, heterocyclyl, heterocyclylalkyl, aryl, aralkyl, heteroaryl, and heteroaralkyl; and
each $R^{11}$ and $R^{12}$ is independently selected from H, alkyl, cycloalkyl, cycloalkylalkyl, heterocyclyl, heterocyclylalkyl, aryl, aralkyl, heteroaryl, and heteroaralkyl; or
$R^{11}$ and $R^{12}$, together with the nitrogen atom to which they are attached, form a 5- to 7-membered heterocyclyl;
$R^{13}$ is, independently for each occurrence, H or alkyl;
$R^{14}$ is, independently for each occurrence, alkyl or aralkyl;
each $R^{15}$ is independently selected from hydroxy, alkoxy acyloxy and $NR^{13}R^{14}$;
each $R^{16}$ and $R^{17}$ is independently selected from H, hydroxy, alkyl, cycloalkyl, cycloalkylalkyl, heterocyclyl, heterocyclylalkyl, aryl, aralkyl, heteroaryl, heteroaralkyl; or $R^{16}$ and $R^{17}$, together with the nitrogen atom to which they are attached, form a 5- to 7-membered heterocyclyl.

2. The compound of claim 1, wherein:
a) if $R^4$ and $R^6$ are each —C(O)OH and $R^5$ is benzyl substituted on the phenyl ring with a heterocyclyl or heteroaryl substituent, then the heterocyclyl or heteroaryl substituent is selected from unsubstituted or substituted pyrrolidinyl, piperazinonyl, piperidonyl, tetrahydropyrimidonyl, pyridonyl, and pyridyl; and
b) if $R^4$ is —C(O)OH or tetrazolyl, $R^6$ is —C(O)OH, and $R^5$ is benzyl substituted on the phenyl ring with a second phenyl ring, then either the benzyl phenyl ring or the second phenyl ring is substituted with —C(O) $OR^9$ where $R^9$ is H or alkyl.

3. The compound of claim 1, wherein
$R^5$ is aralkyl or heteroaralkyl with a para substituent on the aryl or heteroaryl ring selected from heterocyclyl, heteroaryl, and aryl; and
$R^{2b}$ is substituted or unsubstituted $C_2$alkynyl.

4. The compound of claim 1, wherein Y is R

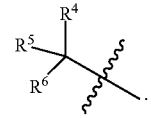

5. The compound of claim 1, wherein $R^5$ is benzyl substituted on the phenyl ring with a heterocyclyl or heteroaryl substituent.

6. The compound of claim 1, wherein $R^5$ is benzyl substituted on the phenyl ring at the 4-position with

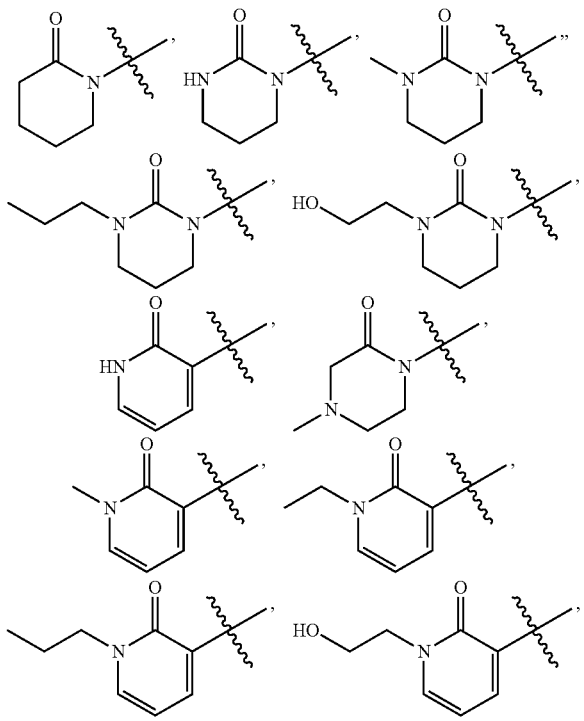

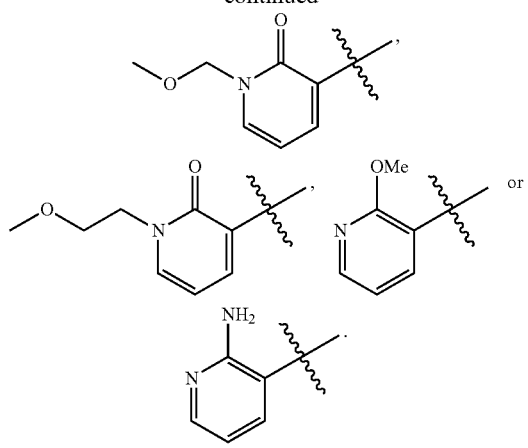
7. The compound of claim 1, wherein
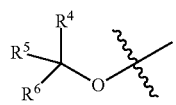
represents
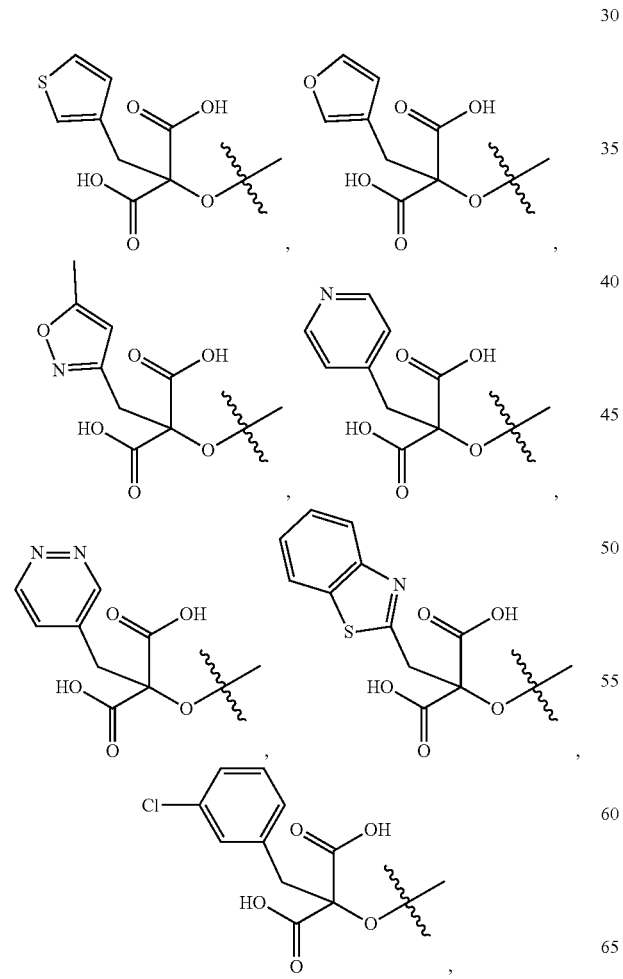
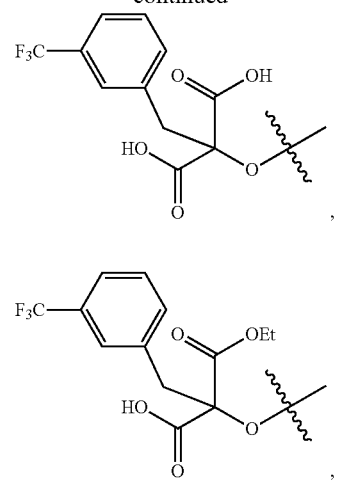
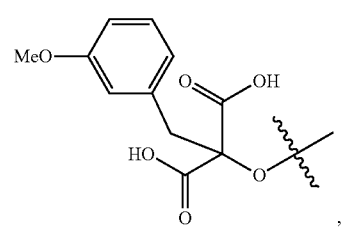
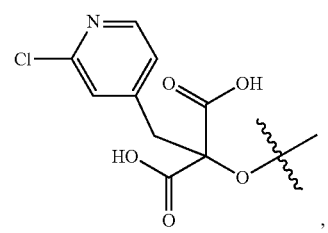
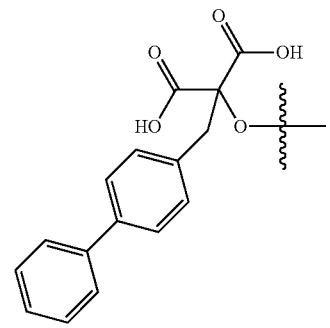
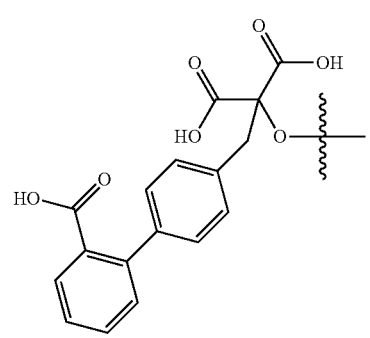

449
-continued
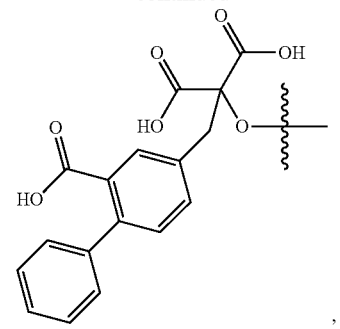
,
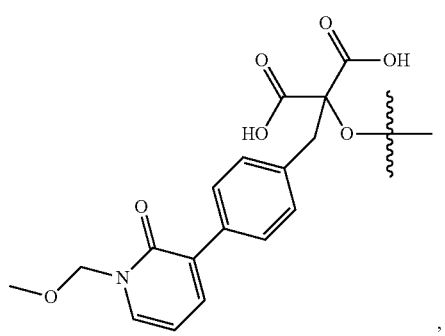
,
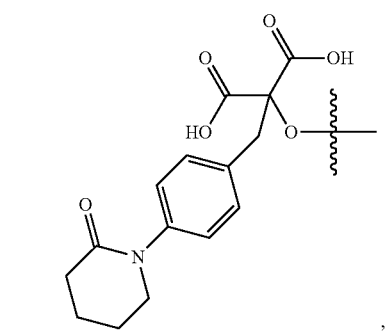
,
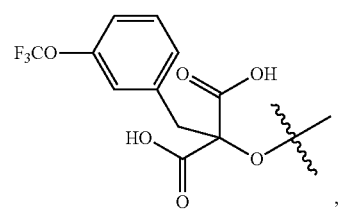
,
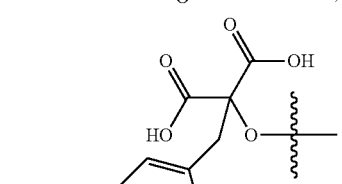
,
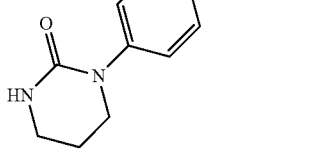
,
450
-continued
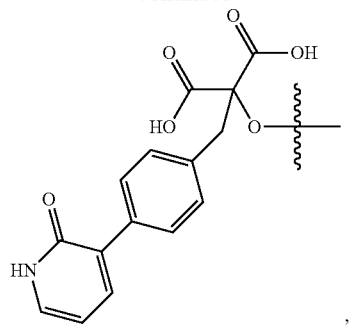
,
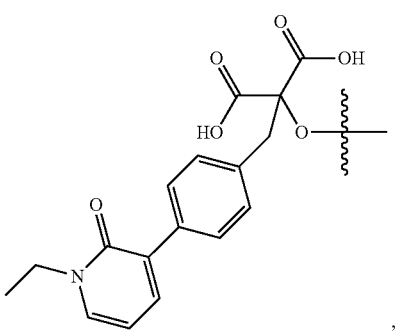
,
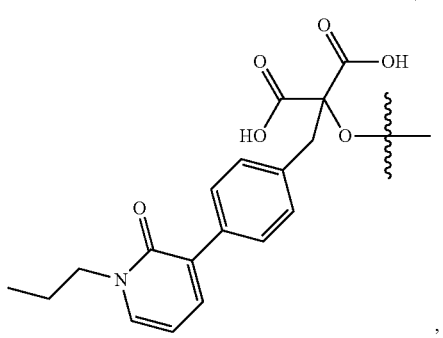
,
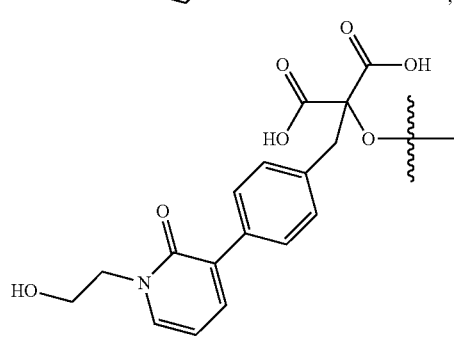
,
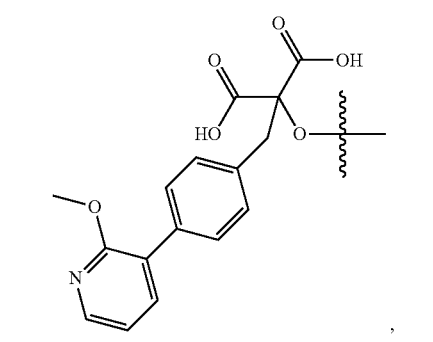
, 451
-continued
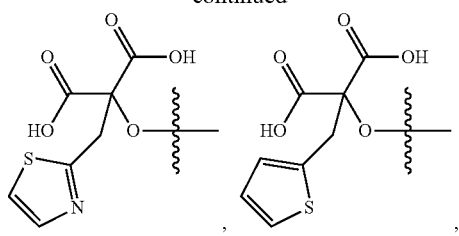
,
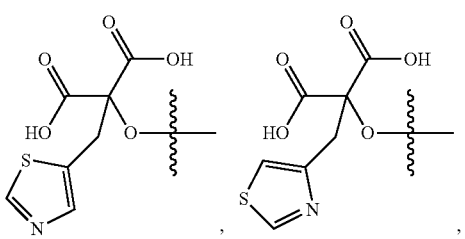
,
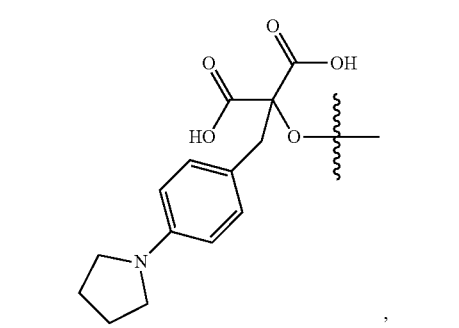
,
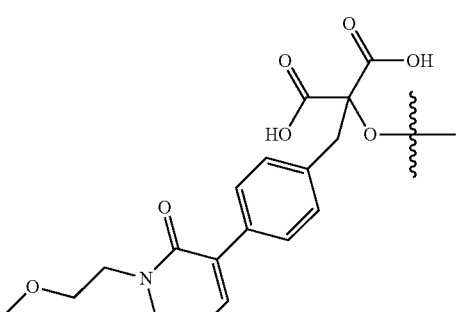
,
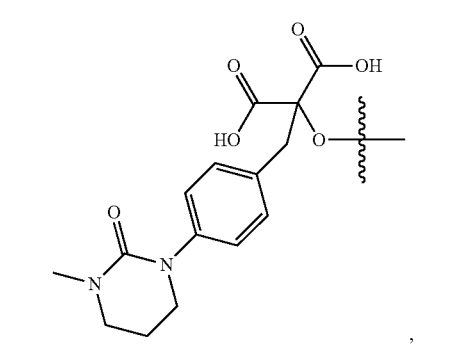
,
452
-continued
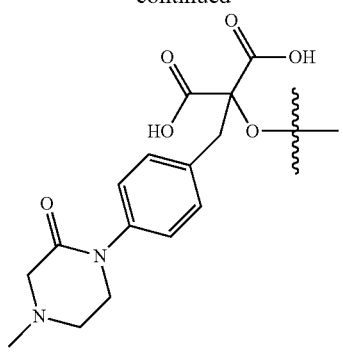
,
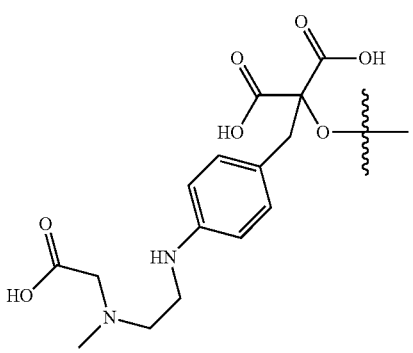
,
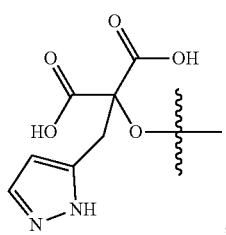
,
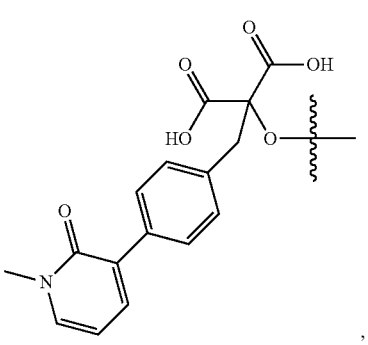
,
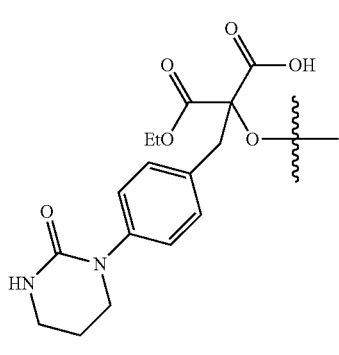
,

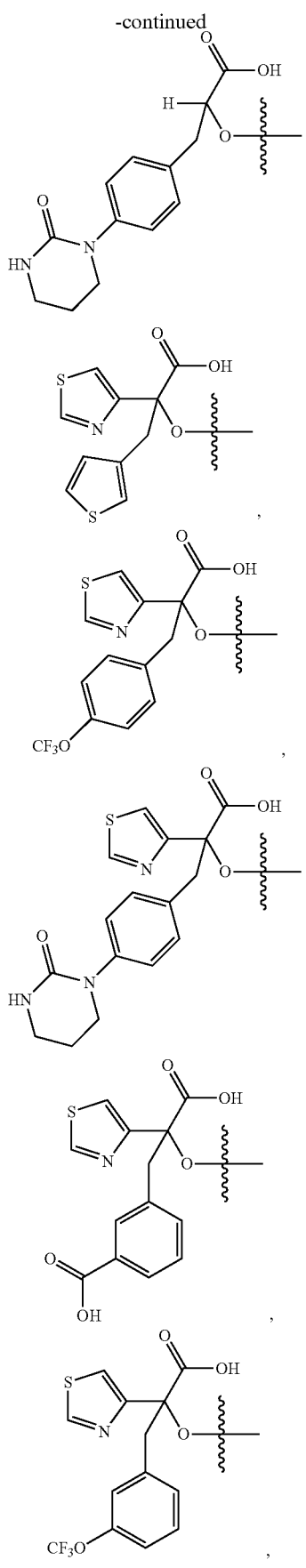
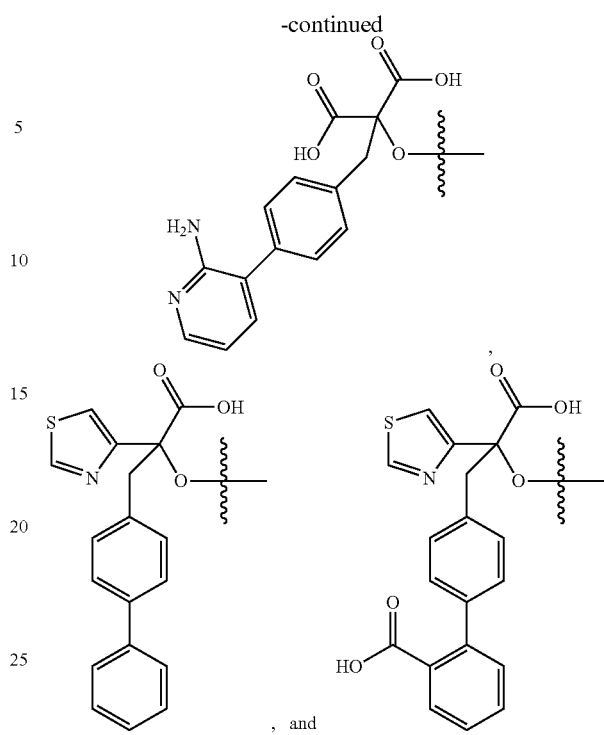
, and
8. The compound of claim 1, wherein Y is
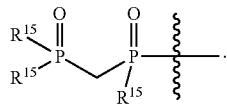
9. The compound of claim 8, wherein each $R^{15}$ is hydroxy.
10. The compound of claim 1, wherein Het is
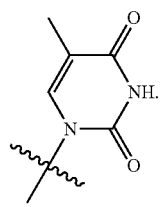 [SMILES: *n1cc(C)c(=O)[nH]c1=O]
11. The compound of claim 1, wherein Het is
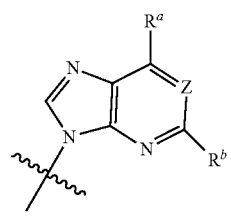
wherein
Z is N;
$R^a$ is selected from H, halo, hydroxy, alkyl, thiophenyl, —$NR^7R^8$, aralkyl, aryl, and heteroaryl;

$R^b$ is selected from halo, alkyl, haloalkyl, hydroxy alkyl, alkylthio, amido, carbonyl, amido, and heteroaryl; and $R^7$ is selected from H, hydroxy, alkyl, aralkyl, heteroaralkyl, cycloalkyl, and heterocyclyl and $R^8$ is H or alkyl; or $R^7$ and $R^8$, together with the nitrogen atom to which they are attached, form a 4- to 7-membered heterocyclyl ring.

12. The compound of claim 11, wherein $R^a$ is selected from H, Cl, —$NR^7R^8$, and phenyl.

13. The compound of claim 11, wherein $R^b$ is selected from Cl, —$CF_3$, carbonyl, and —$CONH_2$.

14. The compound of claim 11, wherein $R^7$ is selected from H, alkyl, aralkyl, heteroaralkyl, cycloalkyl, and heterocyclyl.

15. The compound of claim 1, wherein $R^{1a}$ and $R^{2a}$ are each hydroxy.

16. The compound of claim 1, wherein $R^{1a}$ is hydroxy and $R^{1b}$ is H.

17. The compound of claim 1, wherein $R^{2a}$ is hydroxy or $C_{1-6}$alkyl.

18. The compound of claim 1, wherein $R^{2b}$ is substituted or unsubstituted $C_2$alkynyl.

19. The compound of claim 1, wherein $R^{2a}$ is Me and $R^{2b}$ is ethynyl.

20. The compound of claim 1, wherein $R^{2a}$ is hydroxy and $R^{2b}$ is ethynyl.

21. The compound of claim 1, wherein $R^{2b}$ is propynyl, butynyl,

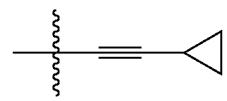 [SMILES: *C#CC1CC1]

or unsubstituted or substituted

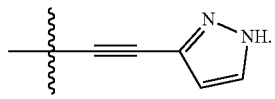

22. The compound of claim 1, wherein $R^4$ is selected from —$C(O)OR^9$, —$C(O)NR^{11}R^{12}$, —$S(O)_2R^{10}$, and —$P(O)(OR^{11})(OR^{12})$.

23. The compound of claim 22, wherein $R^4$ is —$C(O)OR^9$ and $R^9$ is H or alkyl.

24. The compound of claim 22, wherein $R^4$ is —$C(O)NR^{11}R^{12}$.

25. The compound of claim 24, wherein each $R^{11}$ and $R^{12}$ is independently selected from H and alkyl; or $R^{11}$ and $R^{12}$, together with the nitrogen atom to which they are attached, form a 5- to 7-membered heterocyclyl.

26. The compound of claim 1, wherein $R^6$ is —$C(O)OR^9$ and $R^9$ is H or alkyl.

27. The compound of claim 1, wherein $R^6$ is —$C(O)NR^{16}R^{17}$.

28. The compound of claim 1, wherein $R^4$ and $R^6$ are each —$C(O)OH$.

29. A compound selected from:

| Example # | Compound |
|---|---|
| 2 | 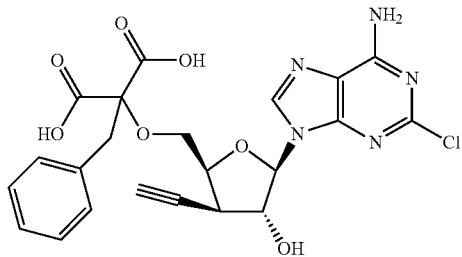 [SMILES: C#C[C@@H]1[C@@H](O)[C@H](n2cnc3c(N)nc(Cl)nc32)O[C@@H]1COC(Cc1ccccc1)(C(=O)O)C(=O)O] |
| 3 | 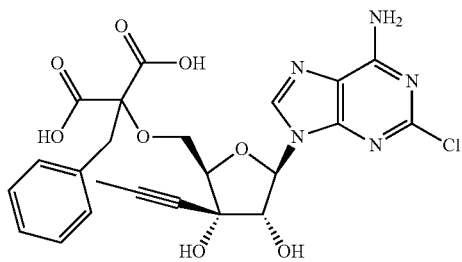 [SMILES: CC#C[C@@]1(O)[C@@H](COC(Cc2ccccc2)(C(=O)O)C(=O)O)O[C@@H](n2cnc3c(N)nc(Cl)nc32)[C@@H]1O] |

-continued
| Example # | Compound |
|---|---|
| 4 | 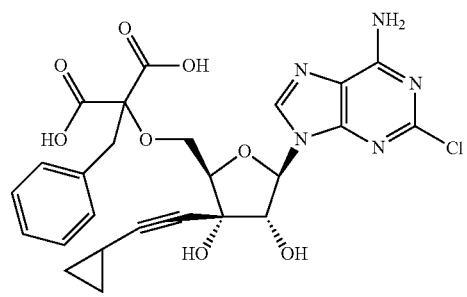 [SMILES: Nc1nc(Cl)nc2c1ncn2[C@@H]1O[C@H](COC(Cc2ccccc2)(C(=O)O)C(=O)O)[C@](O)(C#CC2CC2)[C@H]1O] |
| 5 | 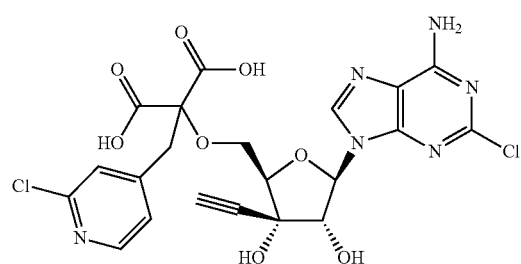 [SMILES: C#C[C@@]1(O)[C@@H](COC(Cc2ccnc(Cl)c2)(C(=O)O)C(=O)O)O[C@@H](n2cnc3c(N)nc(Cl)nc32)[C@@H]1O] |
| 6 | 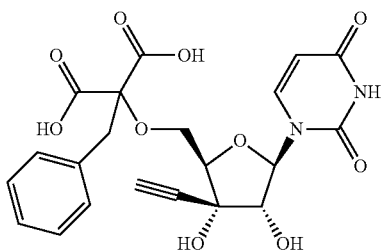 [SMILES: C#C[C@@]1(O)[C@@H](COC(Cc2ccccc2)(C(=O)O)C(=O)O)O[C@@H](n2ccc(=O)[nH]c2=O)[C@@H]1O] |
| 7 | 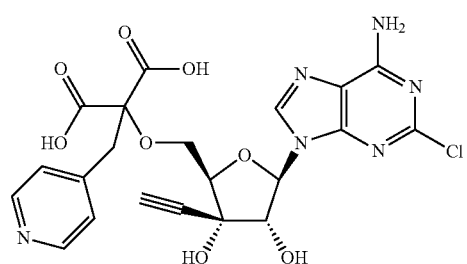 [SMILES: C#C[C@@]1(O)[C@@H](COC(Cc2ccncc2)(C(=O)O)C(=O)O)O[C@@H](n2cnc3c(N)nc(Cl)nc32)[C@@H]1O] |
| 8 | 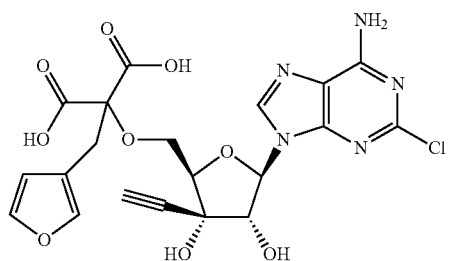 [SMILES: C#C[C@@]1(O)[C@@H](COC(Cc2ccoc2)(C(=O)O)C(=O)O)O[C@@H](n2cnc3c(N)nc(Cl)nc32)[C@@H]1O] |

| Example # | Compound |
|---|---|
| 9 | 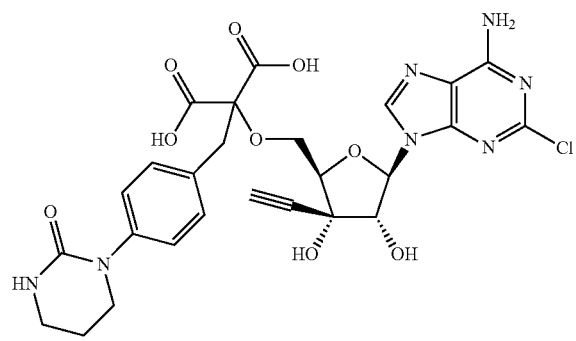 [SMILES: C#C[C@@]1(O)[C@@H](COC(Cc2ccc(N3CCCNC3=O)cc2)(C(=O)O)C(=O)O)O[C@@H](n2cnc3c(N)nc(Cl)nc32)[C@@H]1O] |
| 10 | 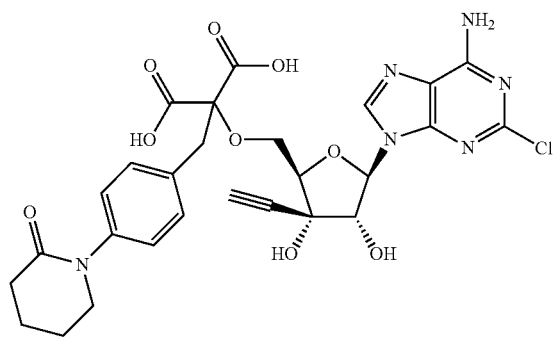 [SMILES: C#C[C@@]1(O)[C@@H](COC(Cc2ccc(N3CCCCC3=O)cc2)(C(=O)O)C(=O)O)O[C@@H](n2cnc3c(N)nc(Cl)nc32)[C@@H]1O] |
| 11 | 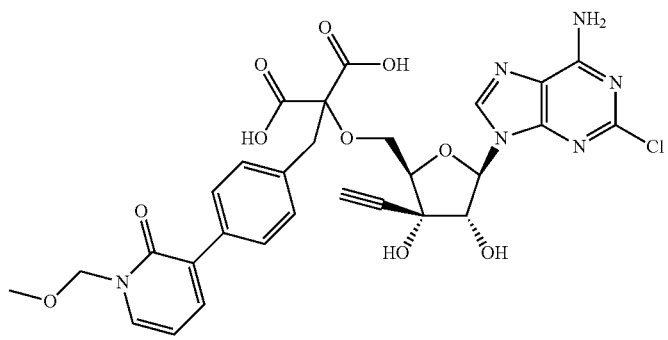 [SMILES: C#C[C@@]1(O)[C@@H](COC(Cc2ccc(-c3cccn(COC)c3=O)cc2)(C(=O)O)C(=O)O)O[C@@H](n2cnc3c(N)nc(Cl)nc32)[C@@H]1O] |
| 12 | 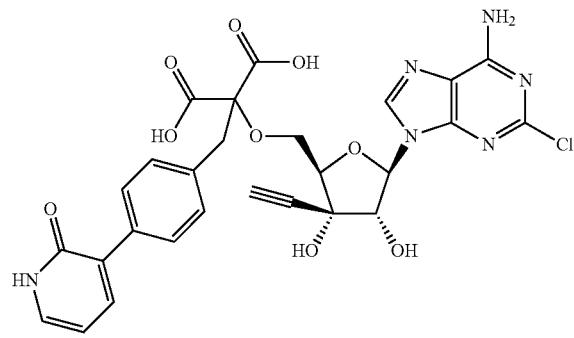 [SMILES: C#C[C@@]1(O)[C@@H](COC(Cc2ccc(-c3ccc[nH]c3=O)cc2)(C(=O)O)C(=O)O)O[C@@H](n2cnc3c(N)nc(Cl)nc32)[C@@H]1O] |

-continued
| Example # | Compound |
|---|---|
| 13 | 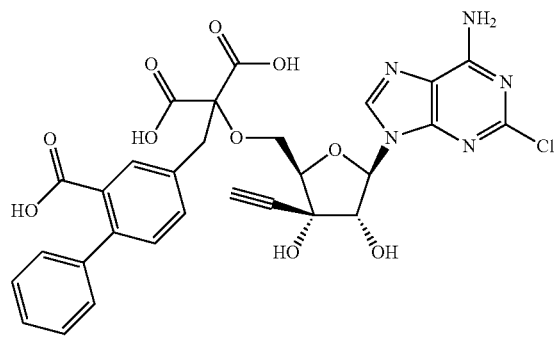 [SMILES: C#C[C@@]1(O)[C@@H](COC(Cc2ccc(-c3ccccc3)c(C(=O)O)c2)(C(=O)O)C(=O)O)O[C@@H](n2cnc3c(N)nc(Cl)nc32)[C@@H]1O] |
| 14 | 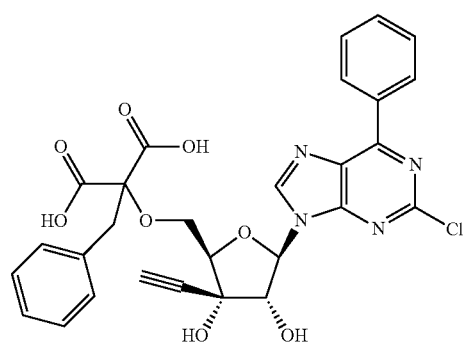 [SMILES: C#C[C@@]1(O)[C@@H](COC(Cc2ccccc2)(C(=O)O)C(=O)O)O[C@@H](n2cnc3c(-c4ccccc4)nc(Cl)nc32)[C@@H]1O] |
| 15 | 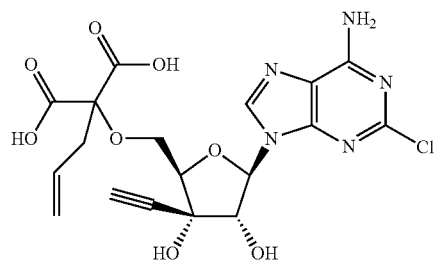 [SMILES: C#C[C@@]1(O)[C@@H](COC(CC=C)(C(=O)O)C(=O)O)O[C@@H](n2cnc3c(N)nc(Cl)nc32)[C@@H]1O] |
| 16 | 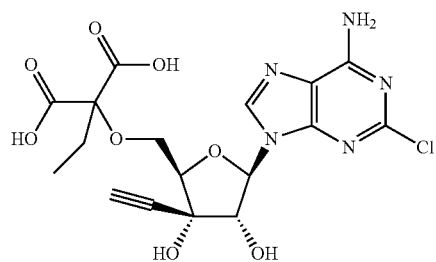 [SMILES: C#C[C@@]1(O)[C@@H](COC(CC)(C(=O)O)C(=O)O)O[C@@H](n2cnc3c(N)nc(Cl)nc32)[C@@H]1O] |
| 17 | 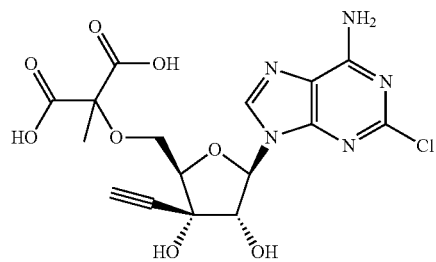 [SMILES: C#C[C@@]1(O)[C@@H](COC(C)(C(=O)O)C(=O)O)O[C@@H](n2cnc3c(N)nc(Cl)nc32)[C@@H]1O] |

-continued
| Example # | Compound |
|---|---|
| 18 | 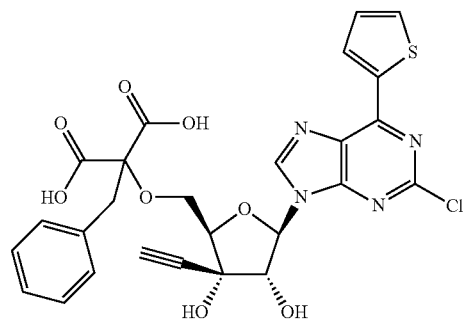 [SMILES: C#C[C@@]1(O)[C@@H](COC(Cc2ccccc2)(C(=O)O)C(=O)O)O[C@@H](n2cnc3c(-c4cccs4)nc(Cl)nc32)[C@@H]1O] |
| 19 | 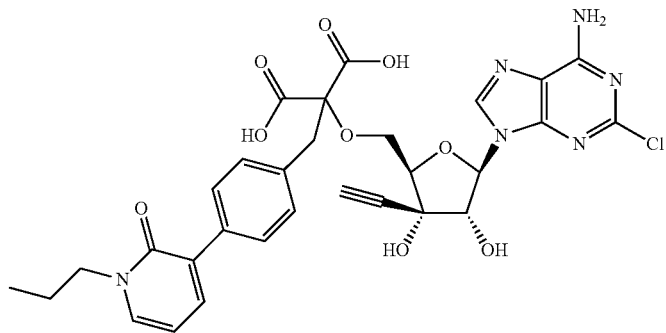 |
| 20 | 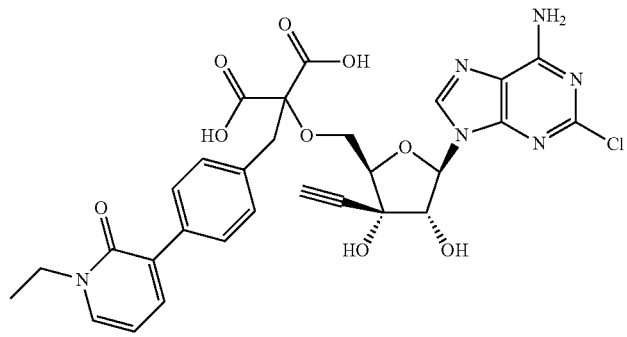 [SMILES: C#C[C@@]1(O)[C@@H](COC(Cc2ccc(-c3cccn(CC)c3=O)cc2)(C(=O)O)C(=O)O)O[C@@H](n2cnc3c(N)nc(Cl)nc32)[C@@H]1O] |
| 21 | 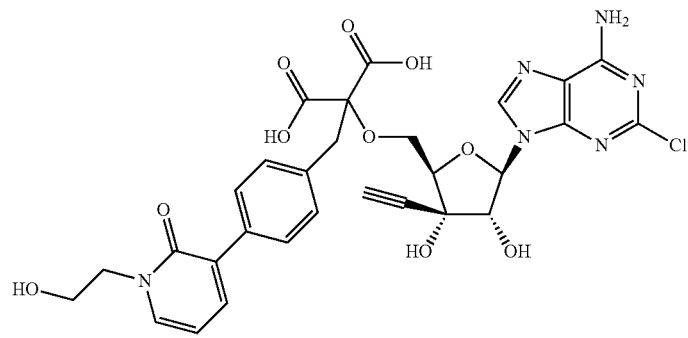 [SMILES: C#C[C@@]1(O)[C@@H](COC(Cc2ccc(-c3cccn(CCO)c3=O)cc2)(C(=O)O)C(=O)O)O[C@@H](n2cnc3c(N)nc(Cl)nc32)[C@@H]1O] |

-continued
| Example # | Compound |
|---|---|
| 22 | 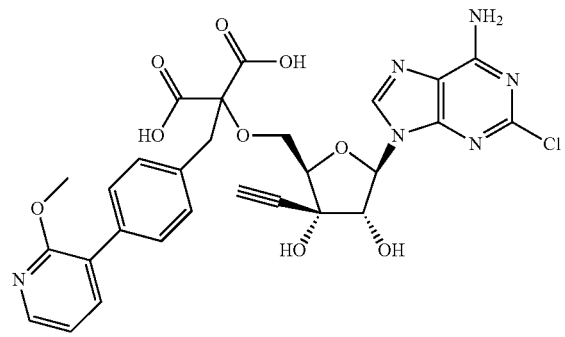 [SMILES: C#C[C@@]1(O)[C@@H](COC(Cc2ccc(-c3cccnc3OC)cc2)(C(=O)O)C(=O)O)O[C@@H](n2cnc3c(N)nc(Cl)nc32)[C@@H]1O] |
| 23 | 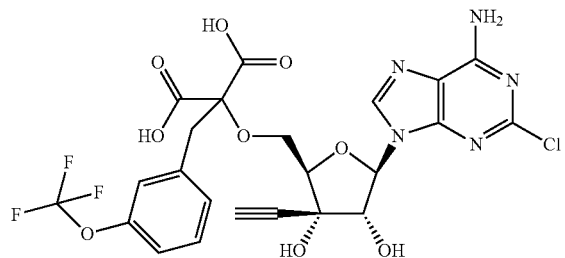 [SMILES: C#C[C@@]1(O)[C@@H](COC(Cc2cccc(OC(F)(F)F)c2)(C(=O)O)C(=O)O)O[C@@H](n2cnc3c(N)nc(Cl)nc32)[C@@H]1O] |
| 24 | 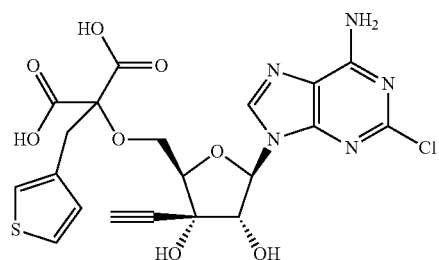 [SMILES: C#C[C@@]1(O)[C@@H](COC(Cc2ccsc2)(C(=O)O)C(=O)O)O[C@@H](n2cnc3c(N)nc(Cl)nc32)[C@@H]1O] |
| 25 | 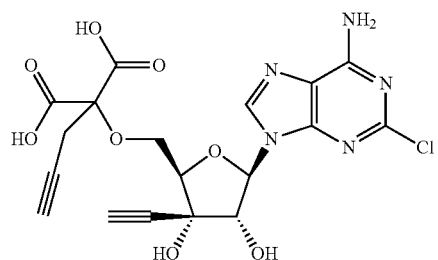 [SMILES: C#CCC(OC[C@H]1O[C@@H](n2cnc3c(N)nc(Cl)nc32)[C@H](O)[C@@]1(O)C#C)(C(=O)O)C(=O)O] |
| 26 | 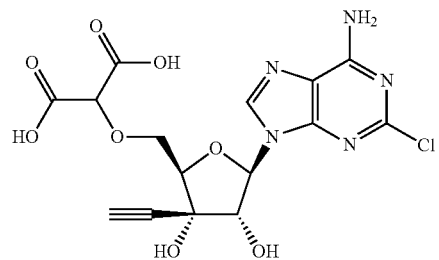 [SMILES: C#C[C@@]1(O)[C@@H](COC(C(=O)O)C(=O)O)O[C@@H](n2cnc3c(N)nc(Cl)nc32)[C@@H]1O] |

-continued
| Example # | Compound |
|---|---|
| 27 | 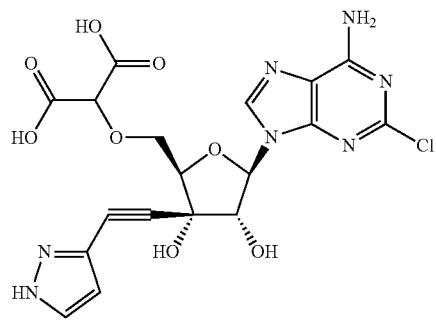 [SMILES: Nc1nc(Cl)nc2c1ncn2[C@@H]1O[C@H](COC(C(=O)O)C(=O)O)[C@](O)(C#Cc2cc[nH]n2)[C@H]1O] |
| 28 | 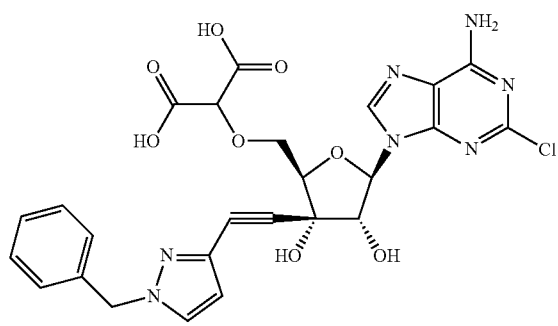 [SMILES: Nc1nc(Cl)nc2c1ncn2[C@@H]1O[C@H](COC(C(=O)O)C(=O)O)[C@](O)(C#Cc2ccn(Cc3ccccc3)n2)[C@H]1O] |
| 29 | 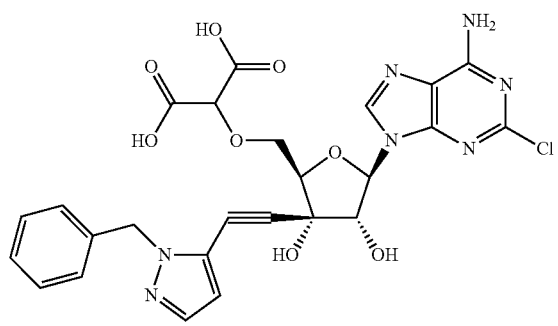 [SMILES: Nc1nc(Cl)nc2c1ncn2[C@@H]1O[C@H](COC(C(=O)O)C(=O)O)[C@](O)(C#Cc2ccnn2Cc2ccccc2)[C@H]1O] |
| 30 | 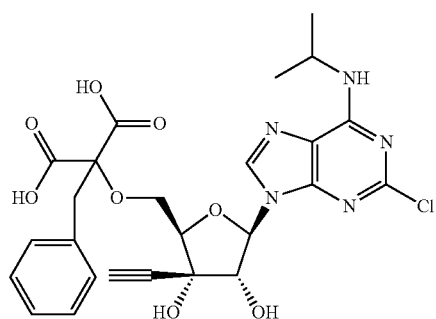 |
| 31 | 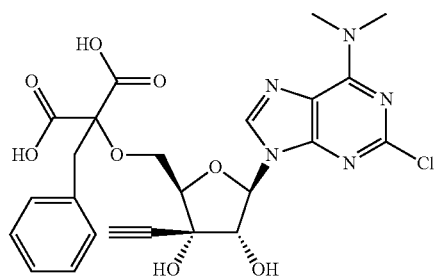 |

-continued

| Example # | Compound |
|---|---|
| 32 | |
| 33 | |
| 34 | |
| 35 | |
| 36 | |

-continued
| Example # | Compound |
|---|---|
| 37 | 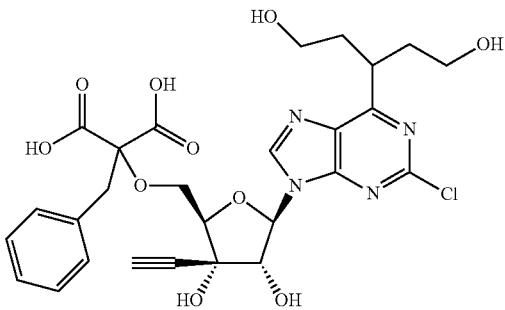 [SMILES: C#C[C@@]1(O)[C@@H](COC(Cc2ccccc2)(C(=O)O)C(=O)O)O[C@@H](n2cnc3c(C(CCO)CCO)nc(Cl)nc32)[C@@H]1O] |
| 38 | 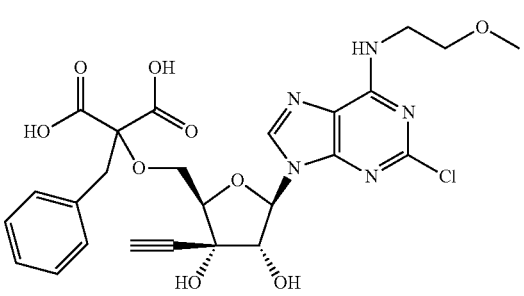 |
| 39 | 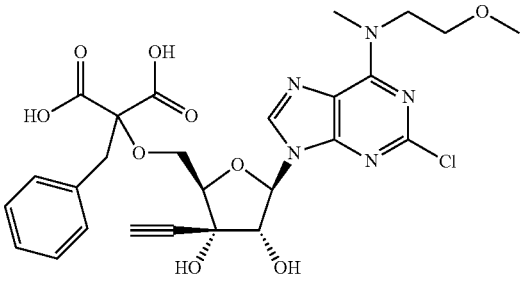 [SMILES: C#C[C@@]1(O)[C@@H](COC(Cc2ccccc2)(C(=O)O)C(=O)O)O[C@@H](n2cnc3c(N(C)CCOC)nc(Cl)nc32)[C@@H]1O] |
| 40 | 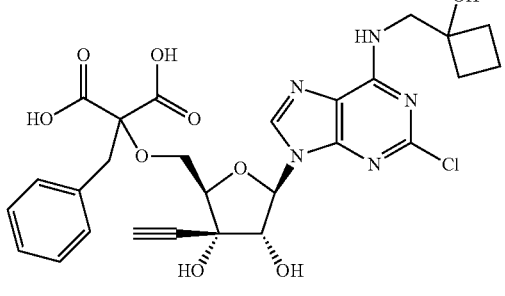 |
| 41 | 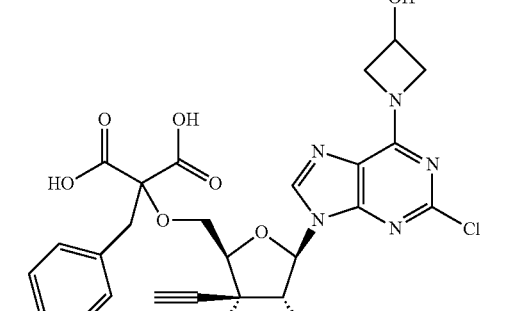 |

-continued
| Example # | Compound |
|---|---|
| 42 | 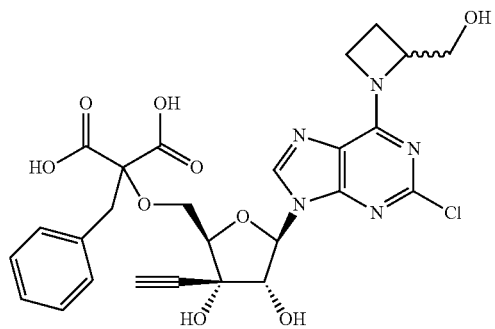 [SMILES: C#C[C@@]1(O)[C@@H](COC(Cc2ccccc2)(C(=O)O)C(=O)O)O[C@@H](n2cnc3c(N4CCC4CO)nc(Cl)nc32)[C@@H]1O] |
| 43 | 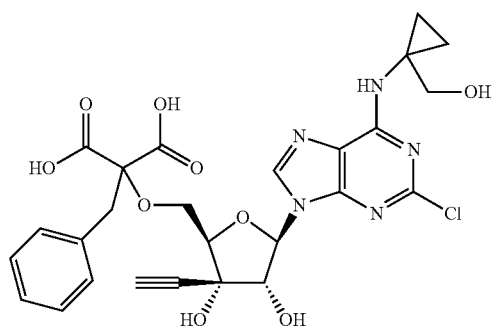 [SMILES: C#C[C@@]1(O)[C@@H](COC(Cc2ccccc2)(C(=O)O)C(=O)O)O[C@@H](n2cnc3c(NC4(CO)CC4)nc(Cl)nc32)[C@@H]1O] |
| 44 | 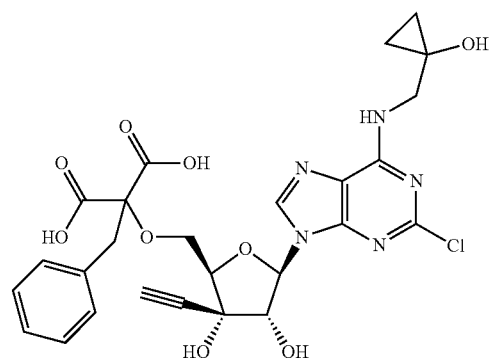 [SMILES: C#C[C@@]1(O)[C@@H](COC(Cc2ccccc2)(C(=O)O)C(=O)O)O[C@@H](n2cnc3c(NCC4(O)CC4)nc(Cl)nc32)[C@@H]1O] |
| 45 | 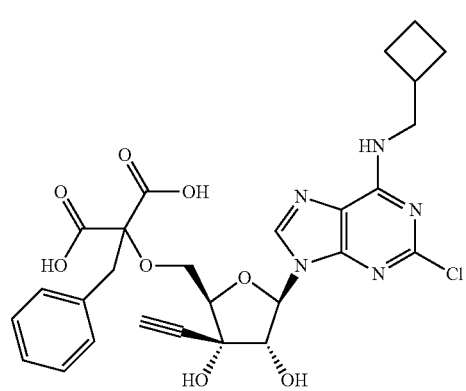 [SMILES: C#C[C@@]1(O)[C@@H](COC(Cc2ccccc2)(C(=O)O)C(=O)O)O[C@@H](n2cnc3c(NCC4CCC4)nc(Cl)nc32)[C@@H]1O] |

-continued
| Example # | Compound |
|---|---|
| 46 | 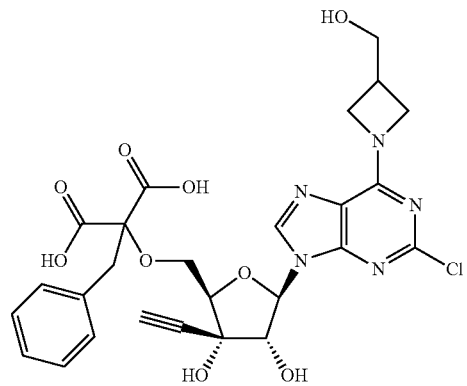 [SMILES: C#C[C@@]1(O)[C@@H](COC(Cc2ccccc2)(C(=O)O)C(=O)O)O[C@@H](n2cnc3c(N4CC(CO)C4)nc(Cl)nc32)[C@@H]1O] |
| 47 | 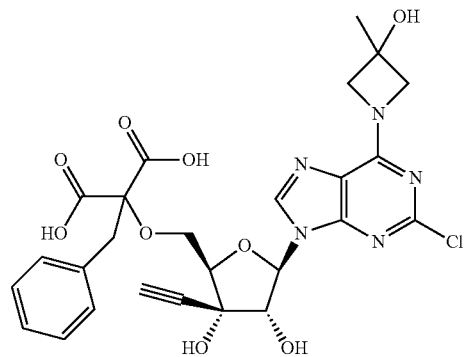 [SMILES: C#C[C@@]1(O)[C@@H](COC(Cc2ccccc2)(C(=O)O)C(=O)O)O[C@@H](n2cnc3c(N4CC(C)(O)C4)nc(Cl)nc32)[C@@H]1O] |
| 48 | 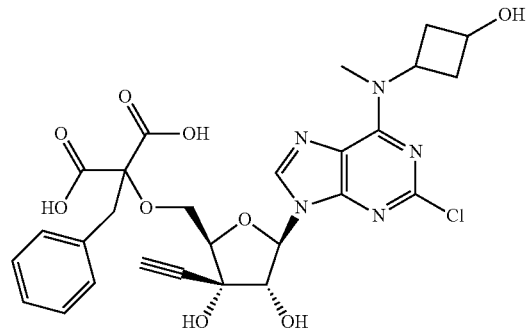 [SMILES: C#C[C@@]1(O)[C@@H](COC(Cc2ccccc2)(C(=O)O)C(=O)O)O[C@@H](n2cnc3c(N(C)C4CC(O)C4)nc(Cl)nc32)[C@@H]1O] |
| 49 | 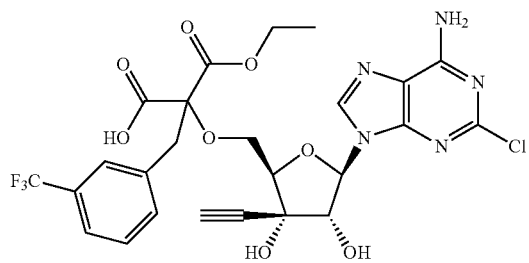 [SMILES: C#C[C@@]1(O)[C@@H](COC(Cc2cccc(C(F)(F)F)c2)(C(=O)O)C(=O)OCC)O[C@@H](n2cnc3c(N)nc(Cl)nc32)[C@@H]1O] |

-continued
| Example # | Compound |
|---|---|
| 50 | 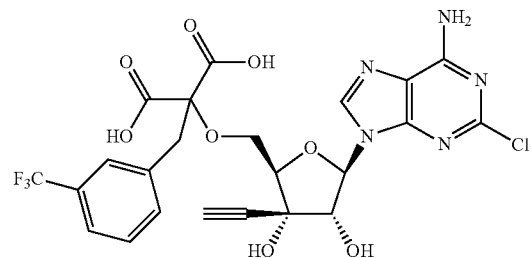 [SMILES: C#C[C@@]1(O)[C@@H](COC(Cc2cccc(C(F)(F)F)c2)(C(=O)O)C(=O)O)O[C@@H](n2cnc3c(N)nc(Cl)nc32)[C@@H]1O] |
| 51 | 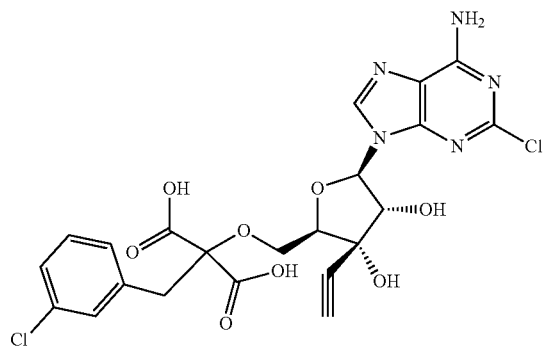 [SMILES: C#C[C@@]1(O)[C@@H](COC(Cc2cccc(Cl)c2)(C(=O)O)C(=O)O)O[C@@H](n2cnc3c(N)nc(Cl)nc32)[C@@H]1O] |
| 52 | 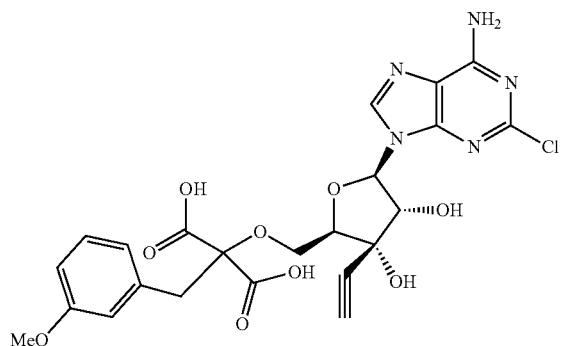 [SMILES: C#C[C@@]1(O)[C@@H](COC(Cc2cccc(OC)c2)(C(=O)O)C(=O)O)O[C@@H](n2cnc3c(N)nc(Cl)nc32)[C@@H]1O] |
| 53 | 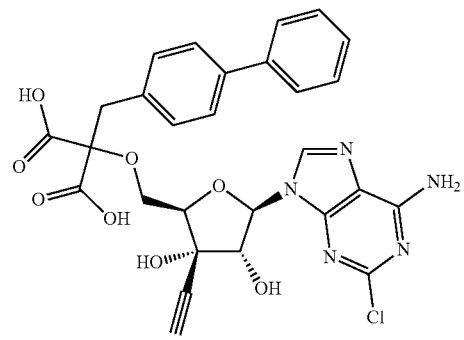 [SMILES: C#C[C@@]1(O)[C@@H](COC(Cc2ccc(-c3ccccc3)cc2)(C(=O)O)C(=O)O)O[C@@H](n2cnc3c(N)nc(Cl)nc32)[C@@H]1O] |

-continued
| Example # | Compound |
|---|---|
| 54 | 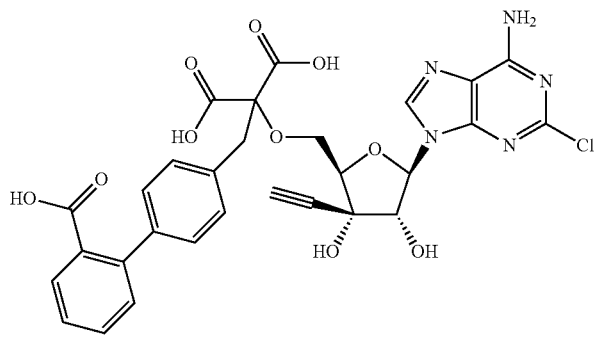 [SMILES: C#C[C@@]1(O)[C@@H](COC(Cc2ccc(-c3ccccc3C(=O)O)cc2)(C(=O)O)C(=O)O)O[C@@H](n2cnc3c(N)nc(Cl)nc32)[C@@H]1O] |
| 55 | 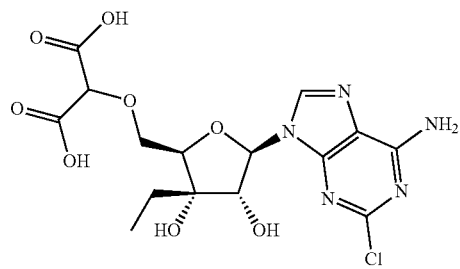 [SMILES: CC[C@@]1(O)[C@@H](COC(C(=O)O)C(=O)O)O[C@@H](n2cnc3c(N)nc(Cl)nc32)[C@@H]1O] |
| 56 | 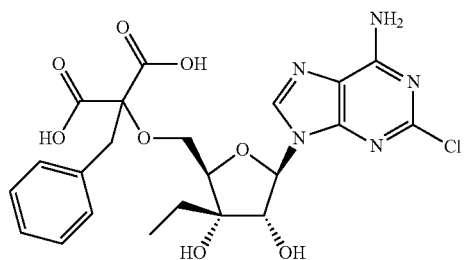 [SMILES: CC[C@@]1(O)[C@@H](COC(Cc2ccccc2)(C(=O)O)C(=O)O)O[C@@H](n2cnc3c(N)nc(Cl)nc32)[C@@H]1O] |
| 57 | 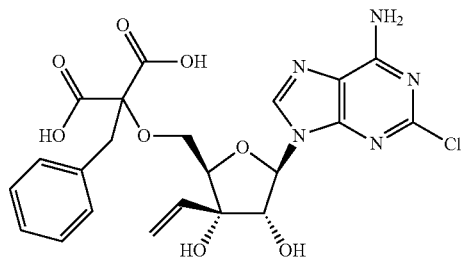 [SMILES: C=C[C@@]1(O)[C@@H](COC(Cc2ccccc2)(C(=O)O)C(=O)O)O[C@@H](n2cnc3c(N)nc(Cl)nc32)[C@@H]1O] |
| 58 | 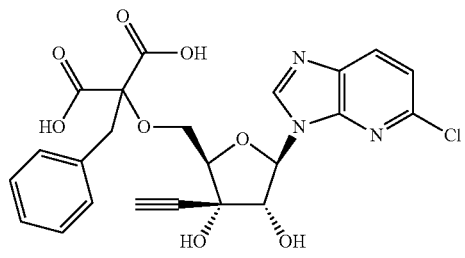 [SMILES: C#C[C@@]1(O)[C@@H](COC(Cc2ccccc2)(C(=O)O)C(=O)O)O[C@@H](n2cnc3ccc(Cl)nc32)[C@@H]1O] |

-continued

| Example # | Compound |
|---|---|
| 59 | |
| 60 | |
| 61 | |
| 62 | |
| 63 | |
| 64 | |
| 65 | |

-continued
| Example # | Compound |
|---|---|
| 66 | 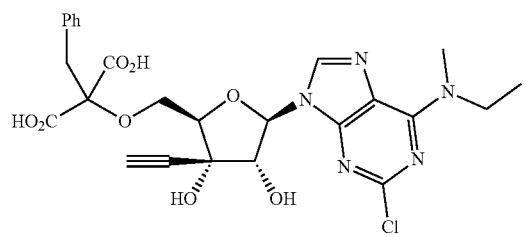 [SMILES: C#C[C@@]1(O)[C@@H](COC(Cc2ccccc2)(C(=O)O)C(=O)O)O[C@@H](n2cnc3c(N(C)CC)nc(Cl)nc32)[C@@H]1O] |
| 67 | 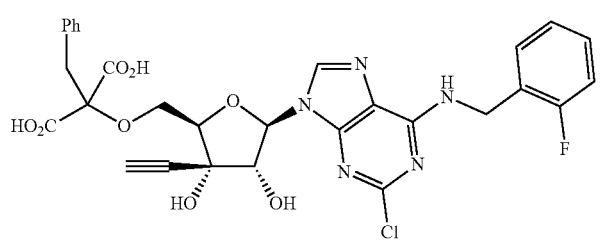 [SMILES: C#C[C@@]1(O)[C@@H](COC(Cc2ccccc2)(C(=O)O)C(=O)O)O[C@@H](n2cnc3c(NCc4ccccc4F)nc(Cl)nc32)[C@@H]1O] |
| 68 | 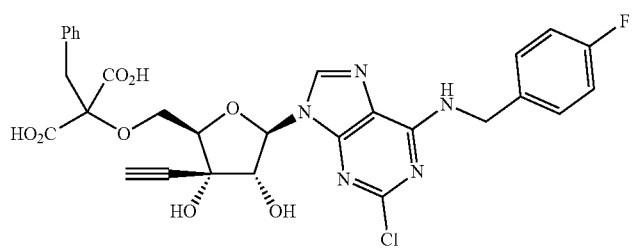 [SMILES: C#C[C@@]1(O)[C@@H](COC(Cc2ccccc2)(C(=O)O)C(=O)O)O[C@@H](n2cnc3c(NCc4ccc(F)cc4)nc(Cl)nc32)[C@@H]1O] |
| 69 | 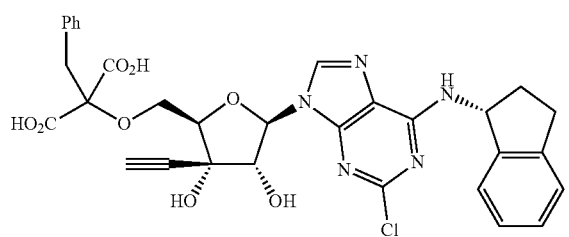 [SMILES: C#C[C@@]1(O)[C@@H](COC(Cc2ccccc2)(C(=O)O)C(=O)O)O[C@@H](n2cnc3c(N[C@@H]4CCc5ccccc54)nc(Cl)nc32)[C@@H]1O] |
| 70 | 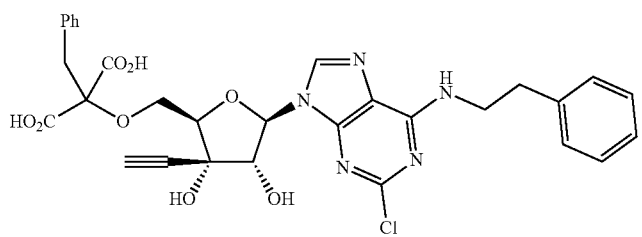 [SMILES: C#C[C@@]1(O)[C@@H](COC(Cc2ccccc2)(C(=O)O)C(=O)O)O[C@@H](n2cnc3c(NCCc4ccccc4)nc(Cl)nc32)[C@@H]1O] |
| 71 | 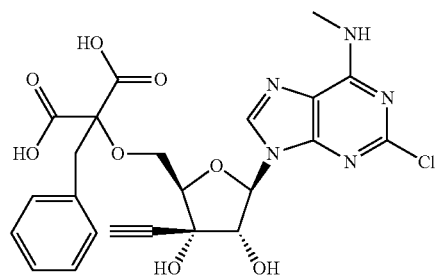 [SMILES: C#C[C@@]1(O)[C@@H](COC(Cc2ccccc2)(C(=O)O)C(=O)O)O[C@@H](n2cnc3c(NC)nc(Cl)nc32)[C@@H]1O] |

-continued
| Example # | Compound |
|---|---|
| 72 | 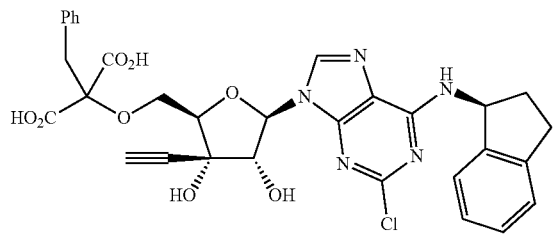 [SMILES: C#C[C@@]1(O)[C@@H](COC(Cc2ccccc2)(C(=O)O)C(=O)O)O[C@@H](n2cnc3c(N[C@H]4CCc5ccccc54)nc(Cl)nc32)[C@@H]1O] |
| 73 | 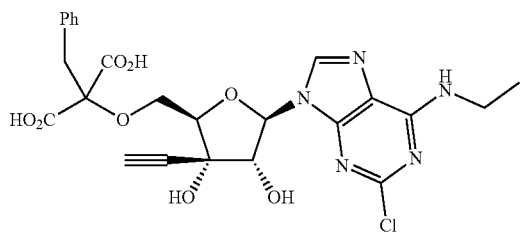 |
| 74 | 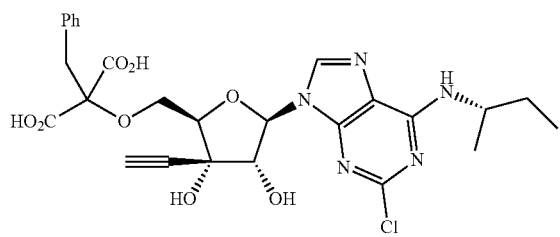 [SMILES: C#C[C@@]1(O)[C@@H](COC(Cc2ccccc2)(C(=O)O)C(=O)O)O[C@@H](n2cnc3c(N[C@@H](C)CC)nc(Cl)nc32)[C@@H]1O] |
| 75 | 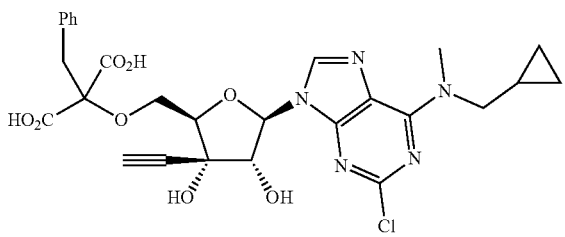 [SMILES: C#C[C@@]1(O)[C@@H](COC(Cc2ccccc2)(C(=O)O)C(=O)O)O[C@@H](n2cnc3c(N(C)CC4CC4)nc(Cl)nc32)[C@@H]1O] |
| 76 | 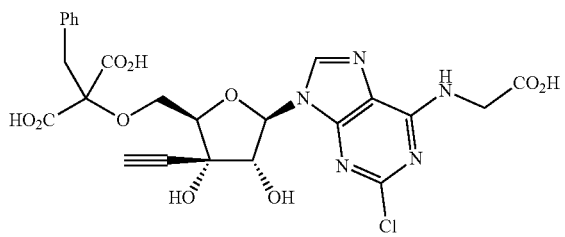 [SMILES: C#C[C@@]1(O)[C@@H](COC(Cc2ccccc2)(C(=O)O)C(=O)O)O[C@@H](n2cnc3c(NCC(=O)O)nc(Cl)nc32)[C@@H]1O] |
| 77 | 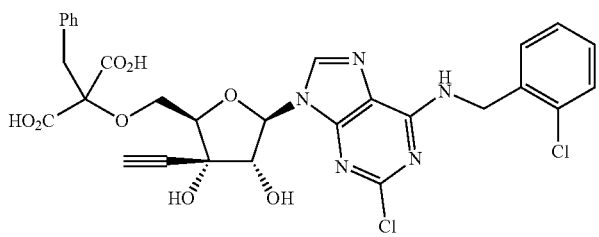 [SMILES: C#C[C@@]1(O)[C@@H](COC(Cc2ccccc2)(C(=O)O)C(=O)O)O[C@@H](n2cnc3c(NCc4ccccc4Cl)nc(Cl)nc32)[C@@H]1O] |

-continued
| Example # | Compound |
|---|---|
| 78 | 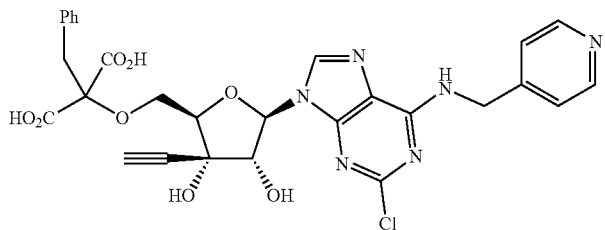 [SMILES: C#C[C@@]1(O)[C@@H](COC(Cc2ccccc2)(C(=O)O)C(=O)O)O[C@@H](n2cnc3c(NCc4ccncc4)nc(Cl)nc32)[C@@H]1O] |
| 79 | 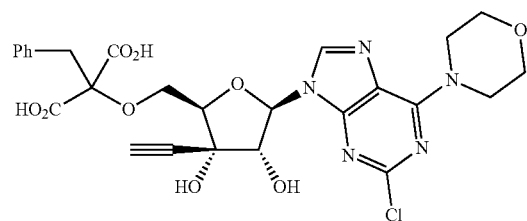 |
| 80 | 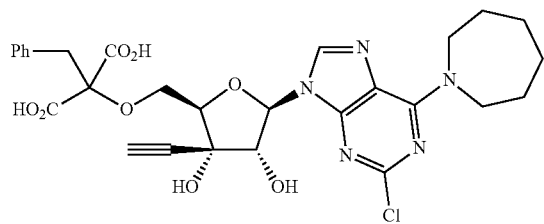 [SMILES: C#C[C@@]1(O)[C@@H](COC(Cc2ccccc2)(C(=O)O)C(=O)O)O[C@@H](n2cnc3c(N4CCCCCC4)nc(Cl)nc32)[C@@H]1O] |
| 81 | 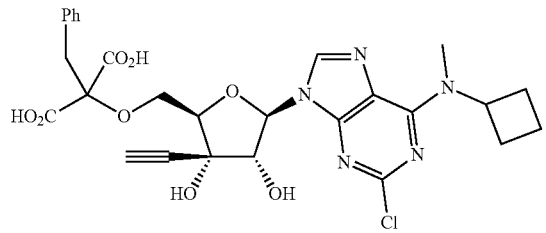 [SMILES: C#C[C@@]1(O)[C@@H](COC(Cc2ccccc2)(C(=O)O)C(=O)O)O[C@@H](n2cnc3c(N(C)C4CCC4)nc(Cl)nc32)[C@@H]1O] |
| 82 | 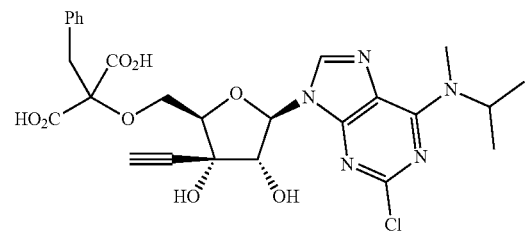 [SMILES: C#C[C@@]1(O)[C@@H](COC(Cc2ccccc2)(C(=O)O)C(=O)O)O[C@@H](n2cnc3c(N(C)C(C)C)nc(Cl)nc32)[C@@H]1O] |
| 83 | 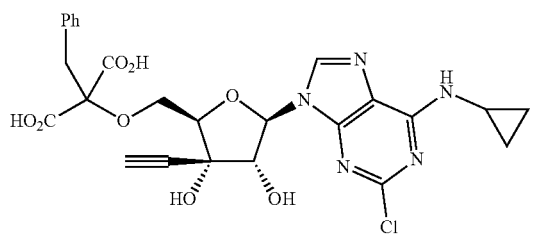 [SMILES: C#C[C@@]1(O)[C@@H](COC(Cc2ccccc2)(C(=O)O)C(=O)O)O[C@@H](n2cnc3c(NC4CC4)nc(Cl)nc32)[C@@H]1O] |

-continued

| Example # | Compound |
|---|---|
| 84 | |
| 85 | |
| 86 | |
| 87 | |
| 88 | |
| 89 | |

-continued

| Example # | Compound |
|---|---|
| 90 | |
| 91 | |
| 92 | |
| 93 | |
| 94 | |
| 95 | |
| 96 | |

-continued

| Example # | Compound |
|---|---|
| 97 | (structure) |
| 98 | (structure) |
| 99 | (structure) |
| 100 | (structure) |
| 101 | (structure) |
| 102 | (structure) |
| 103 | (structure) |

-continued
| Example # | Compound |
|---|---|
| 104 | 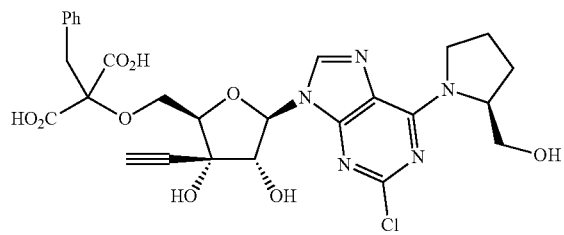 [SMILES: C#C[C@@]1(O)[C@@H](COC(Cc2ccccc2)(C(=O)O)C(=O)O)O[C@@H](n2cnc3c(N4CCC[C@H]4CO)nc(Cl)nc32)[C@@H]1O] |
| 105 | 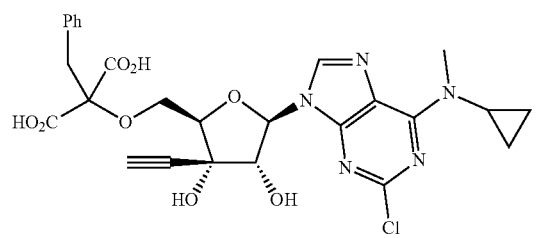 [SMILES: C#C[C@@]1(O)[C@@H](COC(Cc2ccccc2)(C(=O)O)C(=O)O)O[C@@H](n2cnc3c(N(C)C4CC4)nc(Cl)nc32)[C@@H]1O] |
| 106 | 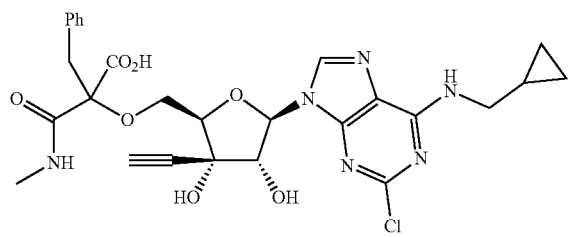 [SMILES: C#C[C@@]1(O)[C@@H](COC(Cc2ccccc2)(C(=O)O)C(=O)NC)O[C@@H](n2cnc3c(NCC4CC4)nc(Cl)nc32)[C@@H]1O] |
| 107 | 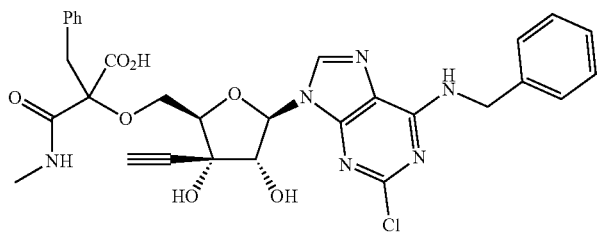 [SMILES: C#C[C@@]1(O)[C@@H](COC(Cc2ccccc2)(C(=O)O)C(=O)NC)O[C@@H](n2cnc3c(NCc4ccccc4)nc(Cl)nc32)[C@@H]1O] |
| 108 | 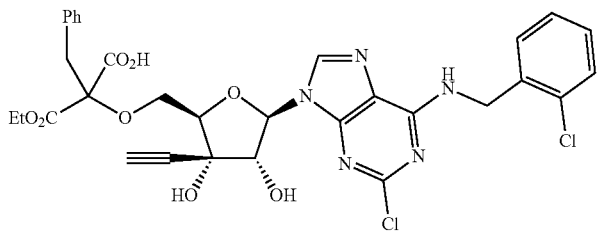 [SMILES: C#C[C@@]1(O)[C@@H](COC(Cc2ccccc2)(C(=O)O)C(=O)OCC)O[C@@H](n2cnc3c(NCc4ccccc4Cl)nc(Cl)nc32)[C@@H]1O] |
| 109 | 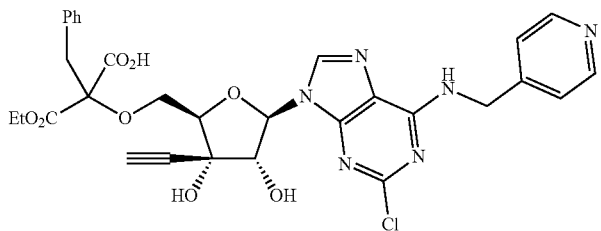 [SMILES: C#C[C@@]1(O)[C@@H](COC(Cc2ccccc2)(C(=O)O)C(=O)OCC)O[C@@H](n2cnc3c(NCc4ccncc4)nc(Cl)nc32)[C@@H]1O] |

-continued

| Example # | Compound |
|---|---|
| 110 | |
| 111 | |
| 112 | |
| 113 | |
| 114 | |

| Example # | Compound |
|---|---|
| 115 | 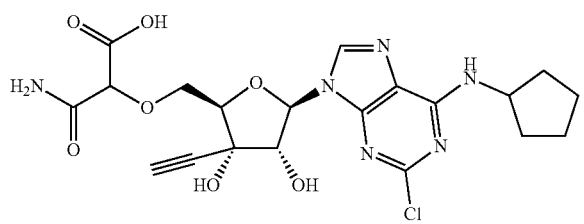 |
| 116 | 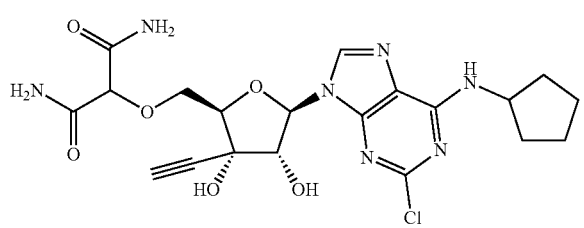 [SMILES: C#C[C@@]1(O)[C@@H](COC(C(N)=O)C(=O)O)O[C@@H](n2cnc3c(NC4CCCC4)nc(Cl)nc32)[C@@H]1O] |
| 117 | 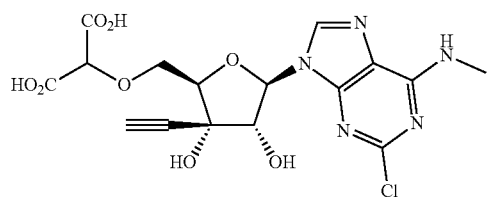 [SMILES: C#C[C@@]1(O)[C@@H](COC(C(=O)O)C(=O)O)O[C@@H](n2cnc3c(NC)nc(Cl)nc32)[C@@H]1O] |
| 118 | 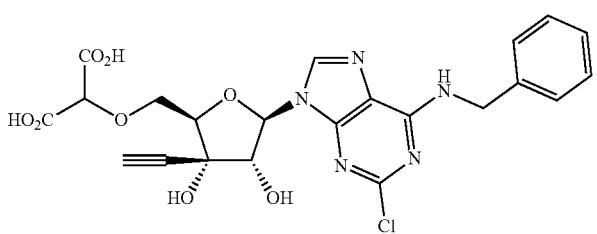 [SMILES: C#C[C@@]1(O)[C@@H](COC(C(=O)O)C(=O)O)O[C@@H](n2cnc3c(NCc4ccccc4)nc(Cl)nc32)[C@@H]1O] |
| 119 | 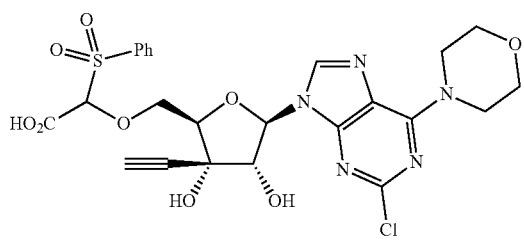 [SMILES: C#C[C@@]1(O)[C@@H](COC(C(=O)O)S(=O)(=O)c2ccccc2)O[C@@H](n2cnc3c(N4CCOCC4)nc(Cl)nc32)[C@@H]1O] |
| 120 | 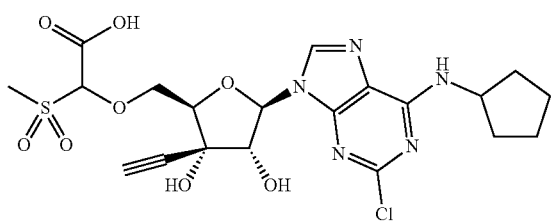 [SMILES: C#C[C@@]1(O)[C@@H](COC(C(=O)O)S(C)(=O)=O)O[C@@H](n2cnc3c(NC4CCCC4)nc(Cl)nc32)[C@@H]1O] |

-continued
| Example # | Compound |
|---|---|
| 121 | 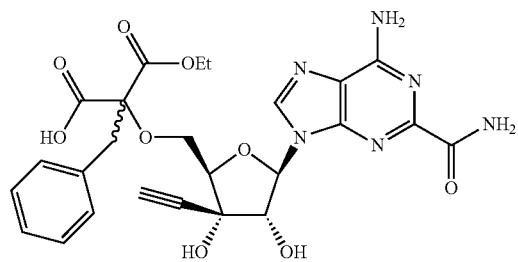 [SMILES: C#C[C@@]1(O)[C@@H](COC(Cc2ccccc2)(C(=O)O)C(=O)O)O[C@@H](n2cnc3c(N)nc(C(N)=O)nc32)[C@@H]1O] |
| 122 | 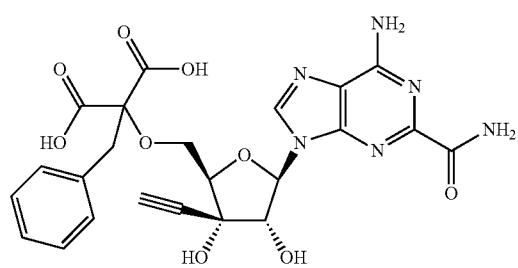 |
| 123 | 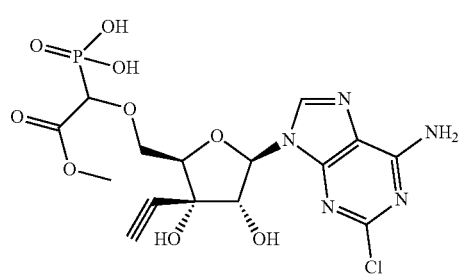 [SMILES: C#C[C@@]1(O)[C@@H](COC(C(=O)OC)P(=O)(O)O)O[C@@H](n2cnc3c(N)nc(Cl)nc32)[C@@H]1O] |
| 124 | 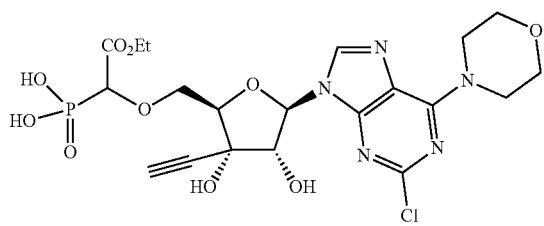 [SMILES: C#C[C@@]1(O)[C@@H](COC(C(=O)OCC)P(=O)(O)O)O[C@@H](n2cnc3c(N4CCOCC4)nc(Cl)nc32)[C@@H]1O] |
| 125 | 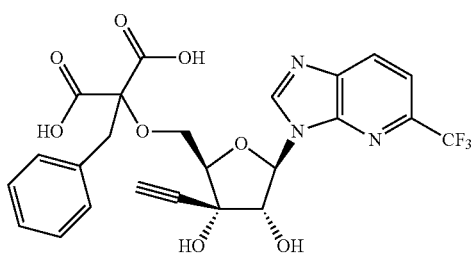 [SMILES: C#C[C@@]1(O)[C@@H](COC(Cc2ccccc2)(C(=O)O)C(=O)O)O[C@@H](n2cnc3ccc(C(F)(F)F)nc32)[C@@H]1O] |
| 126 | 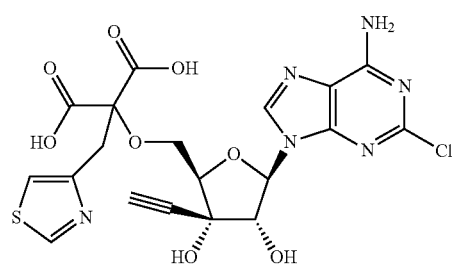 [SMILES: C#C[C@@]1(O)[C@@H](COC(Cc2cscn2)(C(=O)O)C(=O)O)O[C@@H](n2cnc3c(N)nc(Cl)nc32)[C@@H]1O] |

-continued
| Example # | Compound |
|---|---|
| 127 | 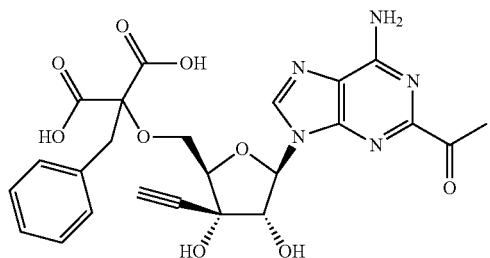 [SMILES: C#C[C@@]1(O)[C@@H](COC(Cc2ccccc2)(C(=O)O)C(=O)O)O[C@@H](n2cnc3c(N)nc(C(C)=O)nc32)[C@@H]1O] |
| 128 | 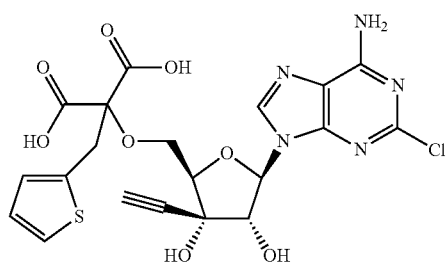 [SMILES: C#C[C@@]1(O)[C@@H](COC(Cc2cccs2)(C(=O)O)C(=O)O)O[C@@H](n2cnc3c(N)nc(Cl)nc32)[C@@H]1O] |
| 129 | 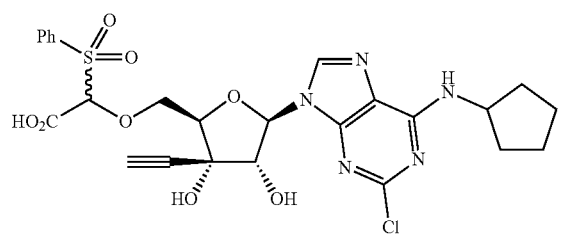 [SMILES: C#C[C@@]1(O)[C@@H](COC(C(=O)O)S(=O)(=O)c2ccccc2)O[C@@H](n2cnc3c(NC4CCCC4)nc(Cl)nc32)[C@@H]1O] |
| 130 | 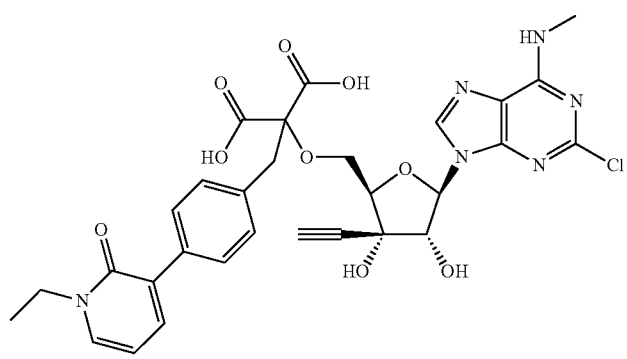 [SMILES: C#C[C@@]1(O)[C@@H](COC(Cc2ccc(-c3cccn(CC)c3=O)cc2)(C(=O)O)C(=O)O)O[C@@H](n2cnc3c(NC)nc(Cl)nc32)[C@@H]1O] |
| 131 | 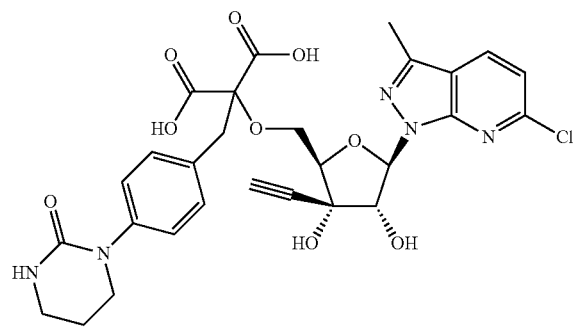 [SMILES: C#C[C@@]1(O)[C@@H](COC(Cc2ccc(N3CCCNC3=O)cc2)(C(=O)O)C(=O)O)O[C@@H](n2nc(C)c3ccc(Cl)nc32)[C@@H]1O] |

-continued
| Example # | Compound |
|---|---|
| 132 | 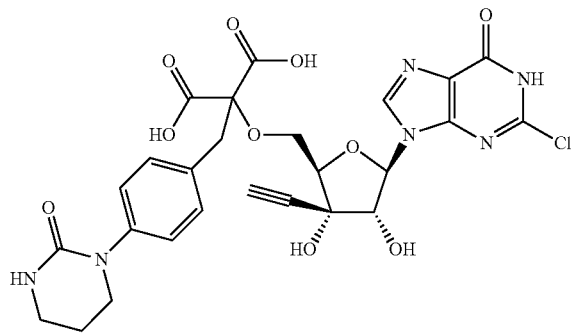 [SMILES: C#C[C@@]1(O)[C@@H](COC(Cc2ccc(N3CCCNC3=O)cc2)(C(=O)O)C(=O)O)O[C@@H](n2cnc3c(=O)[nH]c(Cl)nc32)[C@@H]1O] |
| 133 | 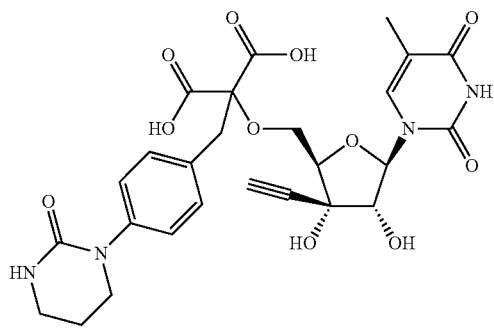 |
| 134 | 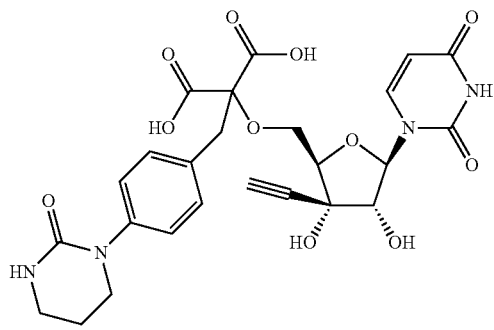 |
| 135 | 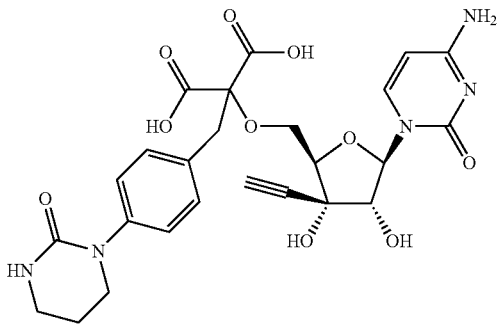 [SMILES: C#C[C@@]1(O)[C@@H](COC(Cc2ccc(N3CCCNC3=O)cc2)(C(=O)O)C(=O)O)O[C@@H](n2ccc(N)nc2=O)[C@@H]1O] |

-continued
| Example # | Compound |
|---|---|
| 136 | 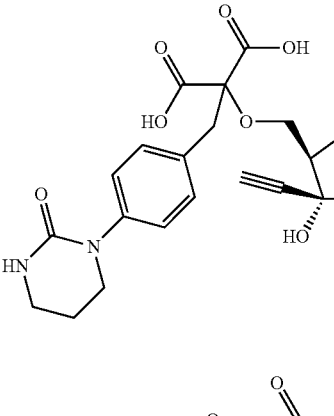 |
| 137 | 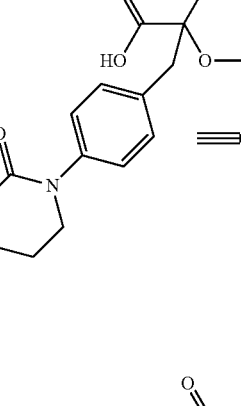 |
| 138 | 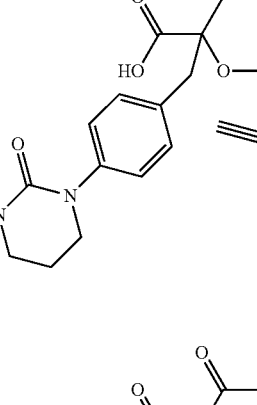 |
| 139 | 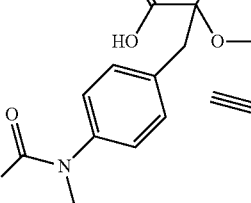 |

-continued
| Example # | Compound |
|---|---|
| 140 | 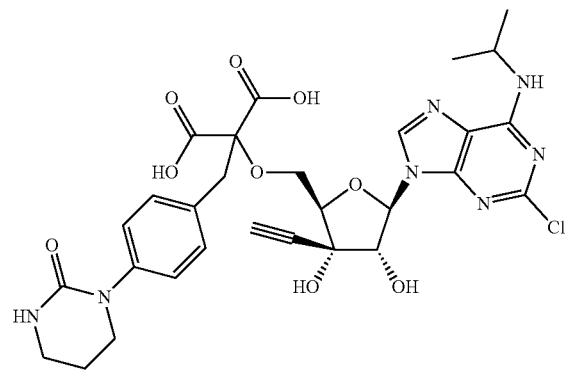 [SMILES: C#C[C@@]1(O)[C@@H](COC(Cc2ccc(N3CCCNC3=O)cc2)(C(=O)O)C(=O)O)O[C@@H](n2cnc3c(NC(C)C)nc(Cl)nc32)[C@@H]1O] |
| 141 | 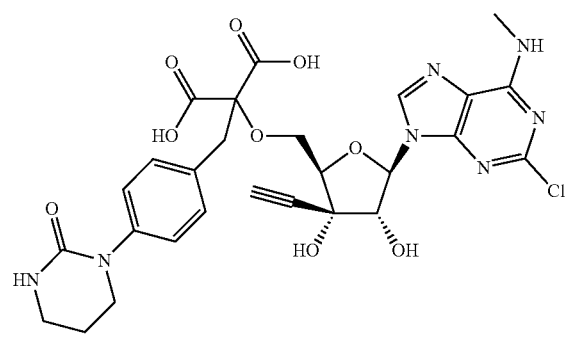 [SMILES: C#C[C@@]1(O)[C@@H](COC(Cc2ccc(N3CCCNC3=O)cc2)(C(=O)O)C(=O)O)O[C@@H](n2cnc3c(NC)nc(Cl)nc32)[C@@H]1O] |
| 142 | 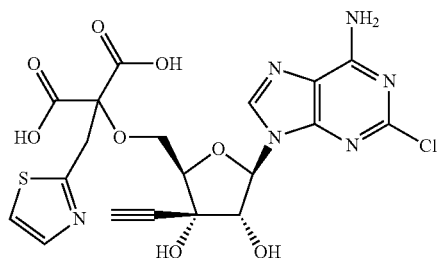 [SMILES: C#C[C@@]1(O)[C@@H](COC(Cc2nccs2)(C(=O)O)C(=O)O)O[C@@H](n2cnc3c(N)nc(Cl)nc32)[C@@H]1O] |
| 143 | 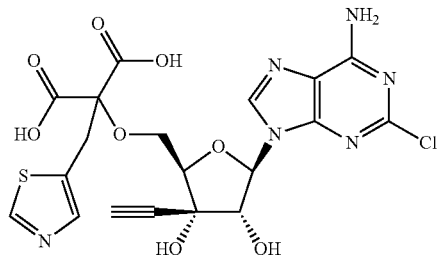 [SMILES: C#C[C@@]1(O)[C@@H](COC(Cc2cncs2)(C(=O)O)C(=O)O)O[C@@H](n2cnc3c(N)nc(Cl)nc32)[C@@H]1O] |
| 144 | 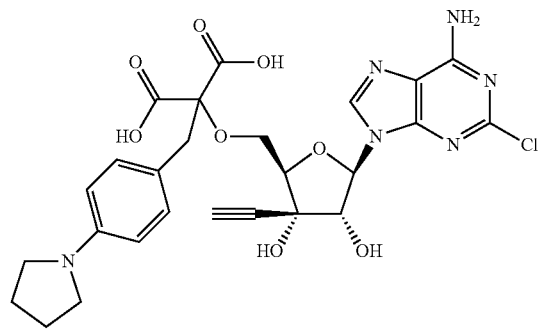 [SMILES: C#C[C@@]1(O)[C@@H](COC(Cc2ccc(N3CCCC3)cc2)(C(=O)O)C(=O)O)O[C@@H](n2cnc3c(N)nc(Cl)nc32)[C@@H]1O] |

-continued
| Example # | Compound |
|---|---|
| 145 | 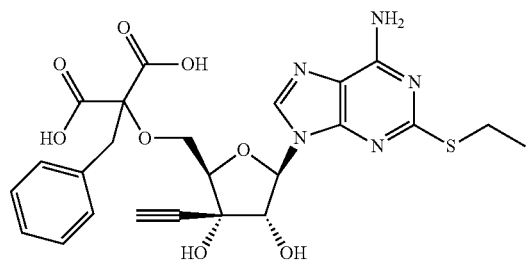 [SMILES: C#C[C@@]1(O)[C@@H](COC(Cc2ccccc2)(C(=O)O)C(=O)O)O[C@@H](n2cnc3c(N)nc(SCC)nc32)[C@@H]1O] |
| 146 | 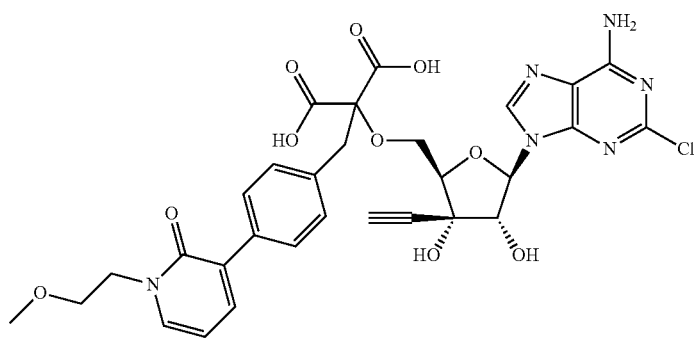 [SMILES: C#C[C@@]1(O)[C@@H](COC(Cc2ccc(-c3cccn(CCOC)c3=O)cc2)(C(=O)O)C(=O)O)O[C@@H](n2cnc3c(N)nc(Cl)nc32)[C@@H]1O] |
| 147 | 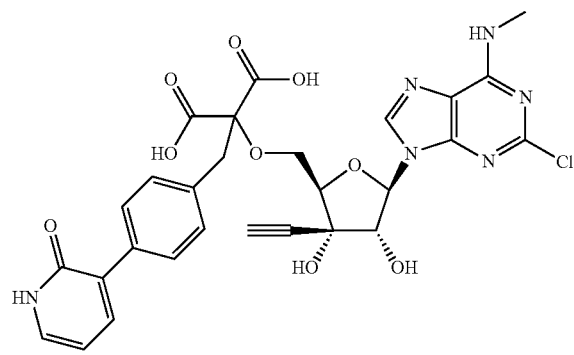 [SMILES: C#C[C@@]1(O)[C@@H](COC(Cc2ccc(-c3ccc[nH]c3=O)cc2)(C(=O)O)C(=O)O)O[C@@H](n2cnc3c(NC)nc(Cl)nc32)[C@@H]1O] |
| 148 | 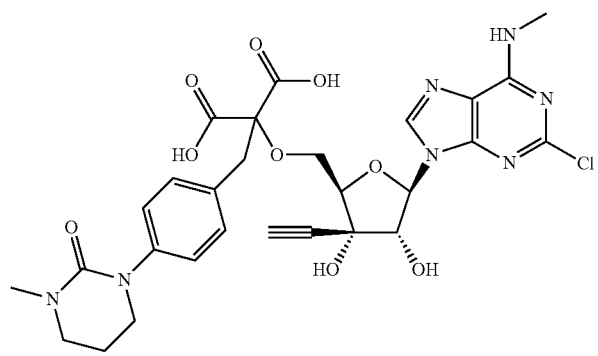 [SMILES: C#C[C@@]1(O)[C@@H](COC(Cc2ccc(N3CCCN(C)C3=O)cc2)(C(=O)O)C(=O)O)O[C@@H](n2cnc3c(NC)nc(Cl)nc32)[C@@H]1O] |

-continued
| Example # | Compound |
|---|---|
| 149 | 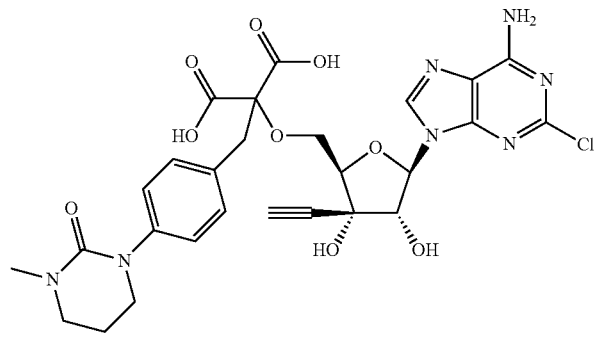 [SMILES: C#C[C@@]1(O)[C@@H](COC(Cc2ccc(N3CCCN(C)C3=O)cc2)(C(=O)O)C(=O)O)O[C@@H](n2cnc3c(N)nc(Cl)nc32)[C@@H]1O] |
| 150 | 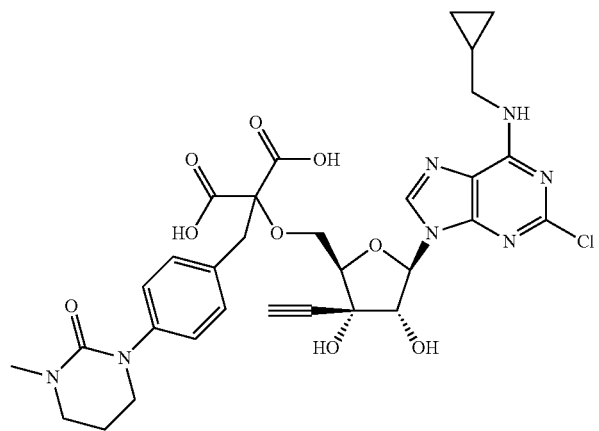 [SMILES: C#C[C@@]1(O)[C@@H](COC(Cc2ccc(N3CCCN(C)C3=O)cc2)(C(=O)O)C(=O)O)O[C@@H](n2cnc3c(NCC4CC4)nc(Cl)nc32)[C@@H]1O] |
| 151 | 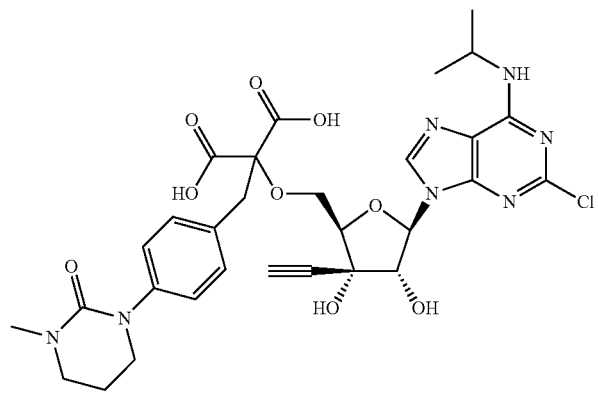 [SMILES: C#C[C@@]1(O)[C@@H](COC(Cc2ccc(N3CCCN(C)C3=O)cc2)(C(=O)O)C(=O)O)O[C@@H](n2cnc3c(NC(C)C)nc(Cl)nc32)[C@@H]1O] |
| 152 | 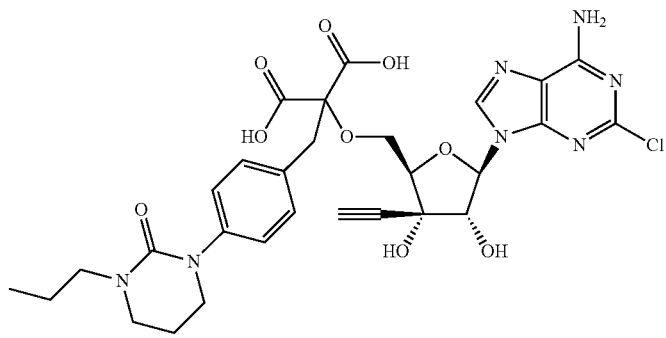 [SMILES: C#C[C@@]1(O)[C@@H](COC(Cc2ccc(N3CCCN(CCC)C3=O)cc2)(C(=O)O)C(=O)O)O[C@@H](n2cnc3c(N)nc(Cl)nc32)[C@@H]1O] |

-continued
| Example # | Compound |
|---|---|
| 153 | 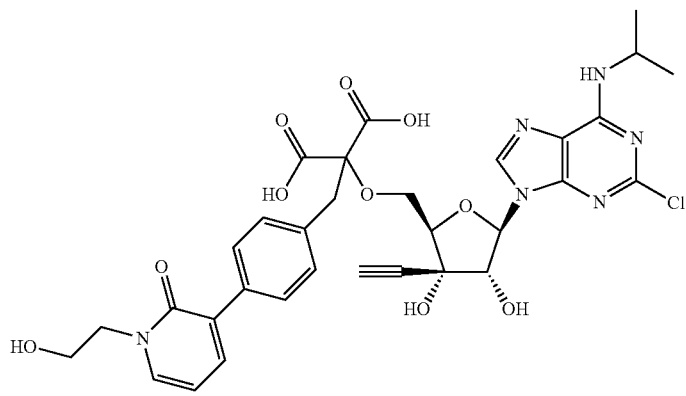 [SMILES: C#C[C@@]1(O)[C@@H](COC(Cc2ccc(-c3cccn(CCO)c3=O)cc2)(C(=O)O)C(=O)O)O[C@@H](n2cnc3c(NC(C)C)nc(Cl)nc32)[C@@H]1O] |
| 154 | 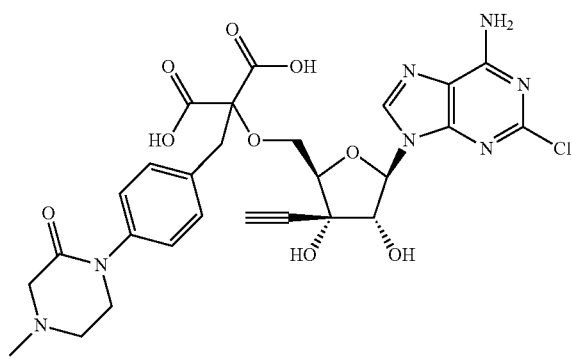 [SMILES: C#C[C@@]1(O)[C@@H](COC(Cc2ccc(N3CCN(C)CC3=O)cc2)(C(=O)O)C(=O)O)O[C@@H](n2cnc3c(N)nc(Cl)nc32)[C@@H]1O] |
| 155 | 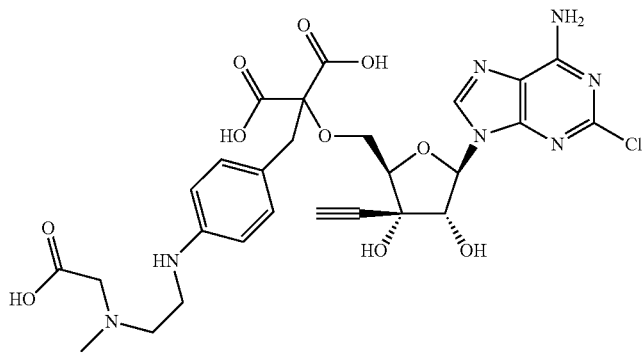 [SMILES: C#C[C@@]1(O)[C@@H](COC(Cc2ccc(NCCN(C)CC(=O)O)cc2)(C(=O)O)C(=O)O)O[C@@H](n2cnc3c(N)nc(Cl)nc32)[C@@H]1O] |
| 156 | 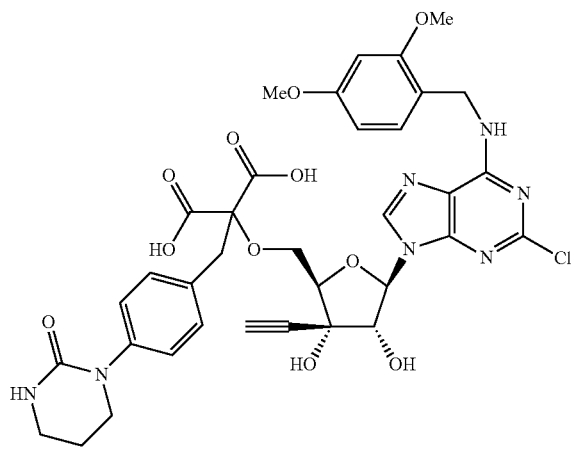 [SMILES: C#C[C@@]1(O)[C@@H](COC(Cc2ccc(N3CCCNC3=O)cc2)(C(=O)O)C(=O)O)O[C@@H](n2cnc3c(NCc4ccc(OC)cc4OC)nc(Cl)nc32)[C@@H]1O] |

| Example # | Compound |
|---|---|
| 157 | 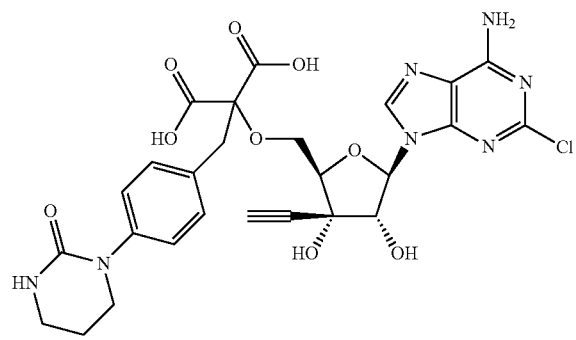 |
| 158 | 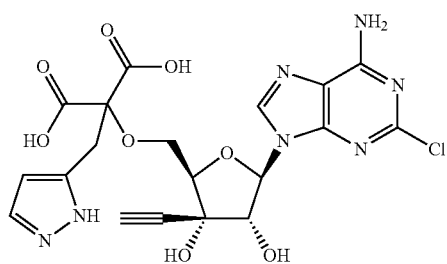 [SMILES: C#C[C@@]1(O)[C@@H](COC(Cc2ccn[nH]2)(C(=O)O)C(=O)O)O[C@@H](n2cnc3c(N)nc(Cl)nc32)[C@@H]1O] |
| 159 | 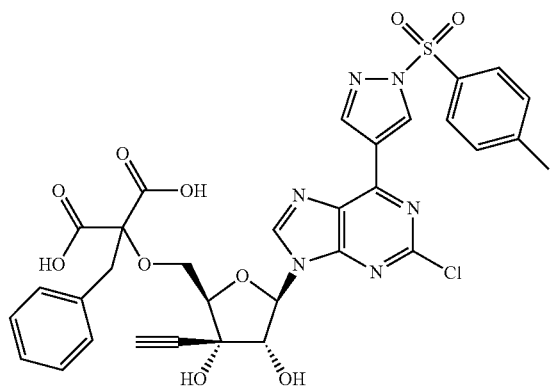 [SMILES: C#C[C@@]1(O)[C@@H](COC(Cc2ccccc2)(C(=O)O)C(=O)O)O[C@@H](n2cnc3c(-c4cnn(S(=O)(=O)c5ccc(C)cc5)c4)nc(Cl)nc32)[C@@H]1O] |
| 160 | 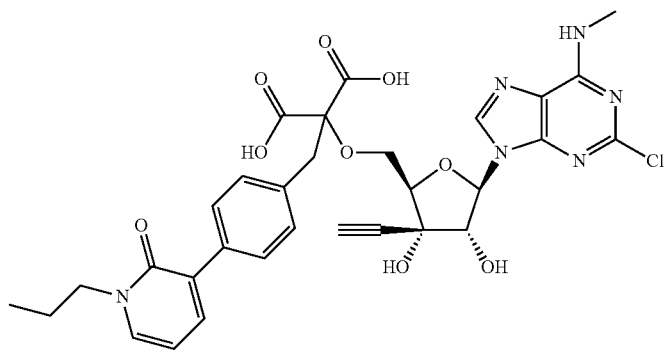 [SMILES: C#C[C@@]1(O)[C@@H](COC(Cc2ccc(-c3cccn(CCC)c3=O)cc2)(C(=O)O)C(=O)O)O[C@@H](n2cnc3c(NC)nc(Cl)nc32)[C@@H]1O] |

-continued

| Example # | Compound |
|---|---|
| 161 | |
| 162 | |
| 163 | |
| 164 | |

-continued

| Example # | Compound |
|---|---|
| 165 | |
| 166 | |
| 167 | |
| 168 | |

-continued
| Example # | Compound |
|---|---|
| 169 | 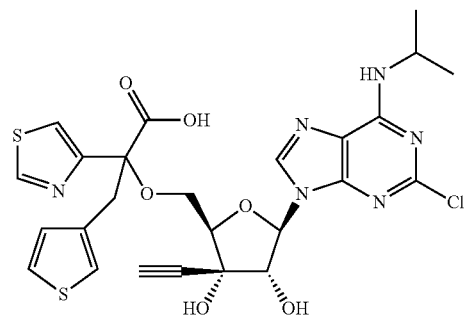 [SMILES: C#C[C@@]1(O)[C@@H](COC(Cc2ccsc2)(C(=O)O)c2cscn2)O[C@@H](n2cnc3c(NC(C)C)nc(Cl)nc32)[C@@H]1O] |
| 170 | 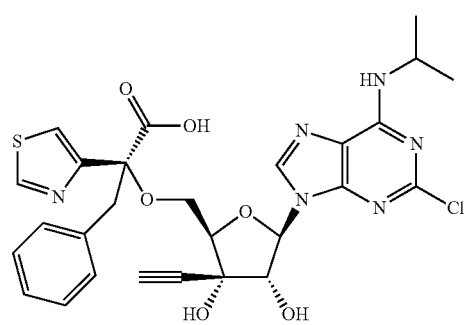 [SMILES: C#C[C@@]1(O)[C@@H](CO[C@](Cc2ccccc2)(C(=O)O)c2cscn2)O[C@@H](n2cnc3c(NC(C)C)nc(Cl)nc32)[C@@H]1O] |
| 171 | 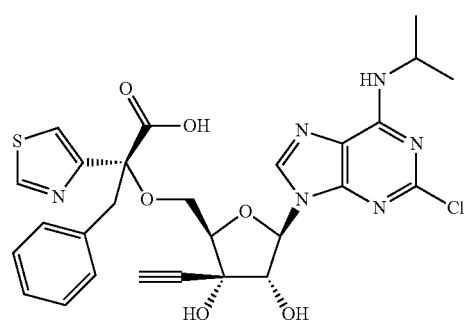 [SMILES: C#C[C@@]1(O)[C@@H](CO[C@@](Cc2ccccc2)(C(=O)O)c2cscn2)O[C@@H](n2cnc3c(NC(C)C)nc(Cl)nc32)[C@@H]1O] |
| 172 | 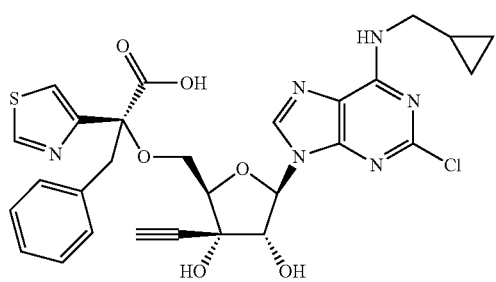 [SMILES: C#C[C@@]1(O)[C@@H](CO[C@](Cc2ccccc2)(C(=O)O)c2cscn2)O[C@@H](n2cnc3c(NCC4CC4)nc(Cl)nc32)[C@@H]1O] |
| 173 | 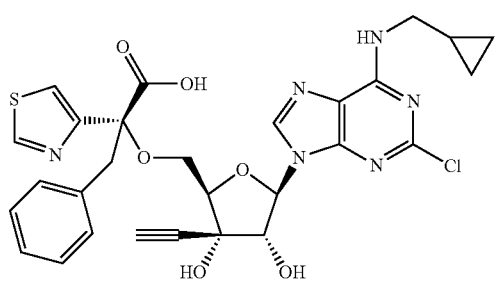 [SMILES: C#C[C@@]1(O)[C@@H](CO[C@@](Cc2ccccc2)(C(=O)O)c2cscn2)O[C@@H](n2cnc3c(NCC4CC4)nc(Cl)nc32)[C@@H]1O] |

| Example # | Compound |
|---|---|
| 174 | 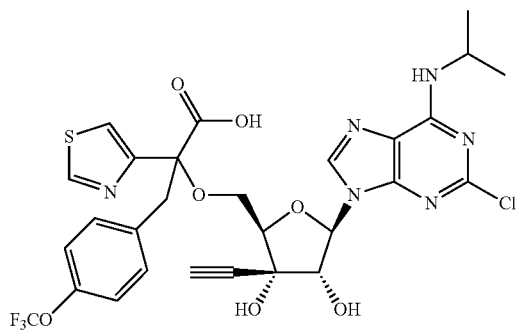 [SMILES: C#C[C@@]1(O)[C@@H](COC(Cc2ccc(OC(F)(F)F)cc2)(C(=O)O)c2cscn2)O[C@@H](n2cnc3c(NC(C)C)nc(Cl)nc32)[C@@H]1O] |
| 175 | 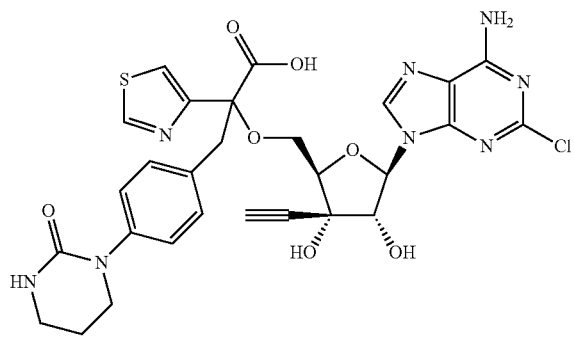 [SMILES: C#C[C@@]1(O)[C@@H](COC(Cc2ccc(N3CCCNC3=O)cc2)(C(=O)O)c2cscn2)O[C@@H](n2cnc3c(N)nc(Cl)nc32)[C@@H]1O] |
| 176 | 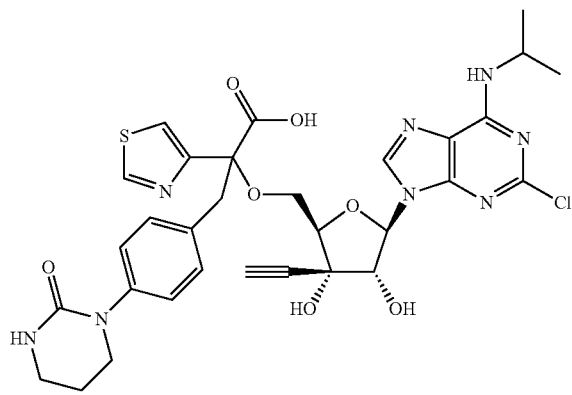 [SMILES: C#C[C@@]1(O)[C@@H](COC(Cc2ccc(N3CCCNC3=O)cc2)(C(=O)O)c2cscn2)O[C@@H](n2cnc3c(NC(C)C)nc(Cl)nc32)[C@@H]1O] |
| 177 | 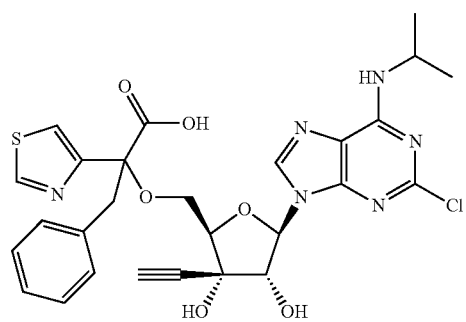 [SMILES: C#C[C@@]1(O)[C@@H](COC(Cc2ccccc2)(C(=O)O)c2cscn2)O[C@@H](n2cnc3c(NC(C)C)nc(Cl)nc32)[C@@H]1O] |

-continued

| Example # | Compound |
|---|---|
| 178 | |
| 179 | |
| 180 | |
| 181 | |
| 182 | |

-continued

| Example # | Compound |
|---|---|
| 183 | |
| 184 | |
| 185 | |
| 186 | |
| 187 | |

US 11,078,228 B2
-continued
| Example # | Compound |
|---|---|
| 188 | 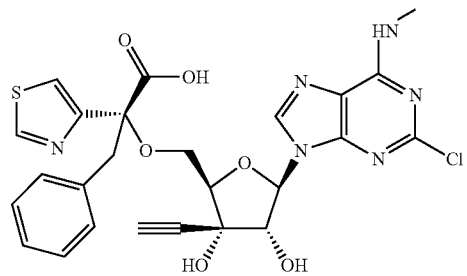 [SMILES: C#C[C@@]1(O)[C@@H](CO[C@@](Cc2ccccc2)(C(=O)O)c2cscn2)O[C@@H](n2cnc3c(NC)nc(Cl)nc32)[C@@H]1O] |
| 189 | 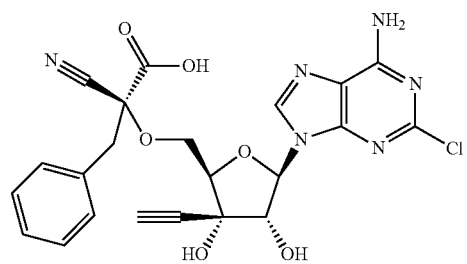 [SMILES: C#C[C@@]1(O)[C@@H](CO[C@](C#N)(Cc2ccccc2)C(=O)O)O[C@@H](n2cnc3c(N)nc(Cl)nc32)[C@@H]1O] |
| 190 | 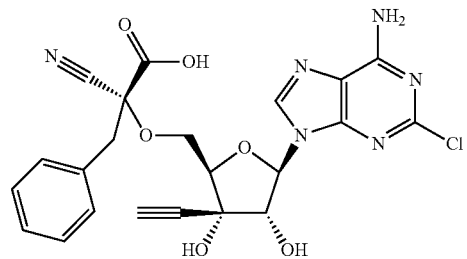 [SMILES: C#C[C@@]1(O)[C@@H](CO[C@@](C#N)(Cc2ccccc2)C(=O)O)O[C@@H](n2cnc3c(N)nc(Cl)nc32)[C@@H]1O] |
| 191 | 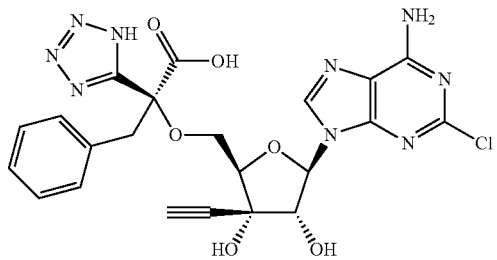 [SMILES: C#C[C@@]1(O)[C@@H](CO[C@](Cc2ccccc2)(C(=O)O)c2nnn[nH]2)O[C@@H](n2cnc3c(N)nc(Cl)nc32)[C@@H]1O] |
| 192 | 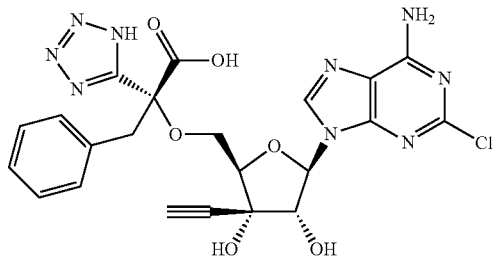 [SMILES: C#C[C@@]1(O)[C@@H](CO[C@@](Cc2ccccc2)(C(=O)O)c2nnn[nH]2)O[C@@H](n2cnc3c(N)nc(Cl)nc32)[C@@H]1O] |

| Example # | Compound |
|---|---|
| 193 | 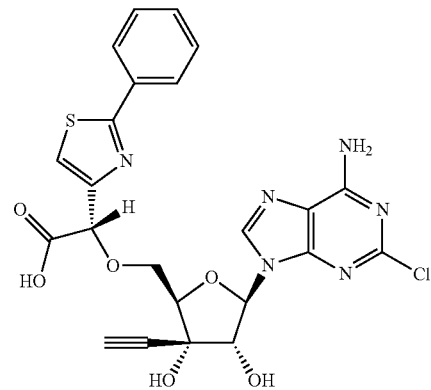 [SMILES: C#C[C@@]1(O)[C@@H](CO[C@H](C(=O)O)c2csc(-c3ccccc3)n2)O[C@@H](n2cnc3c(N)nc(Cl)nc32)[C@@H]1O] |
| 194 | 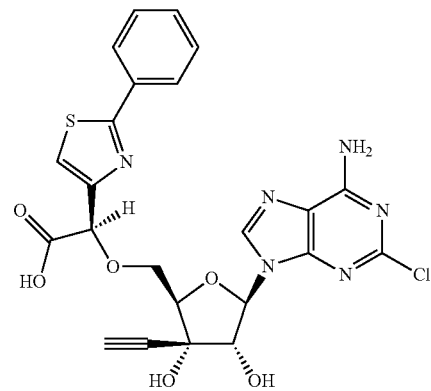 [SMILES: C#C[C@@]1(O)[C@@H](CO[C@@H](C(=O)O)c2csc(-c3ccccc3)n2)O[C@@H](n2cnc3c(N)nc(Cl)nc32)[C@@H]1O] |
| 195 | 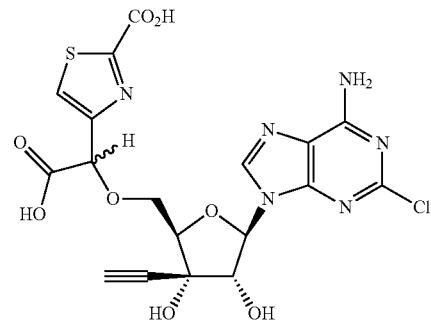 [SMILES: C#C[C@@]1(O)[C@@H](COC(C(=O)O)c2csc(C(=O)O)n2)O[C@@H](n2cnc3c(N)nc(Cl)nc32)[C@@H]1O] |
| 196 | 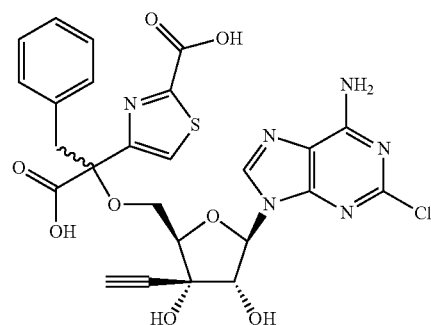 [SMILES: C#C[C@@]1(O)[C@@H](COC(Cc2ccccc2)(C(=O)O)c2csc(C(=O)O)n2)O[C@@H](n2cnc3c(N)nc(Cl)nc32)[C@@H]1O] |

-continued
| Example # | Compound |
|---|---|
| 197 | 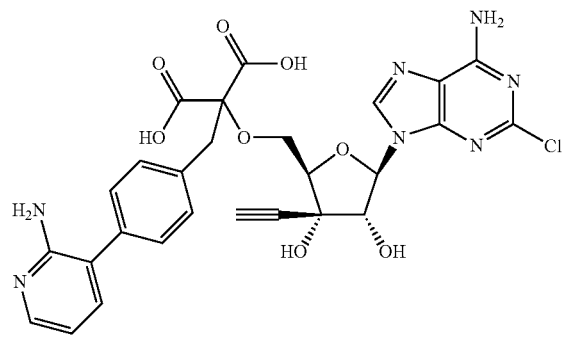 [SMILES: C#C[C@@]1(O)[C@@H](COC(Cc2ccc(-c3cccnc3N)cc2)(C(=O)O)C(=O)O)O[C@@H](n2cnc3c(N)nc(Cl)nc32)[C@@H]1O] |
| 198 | 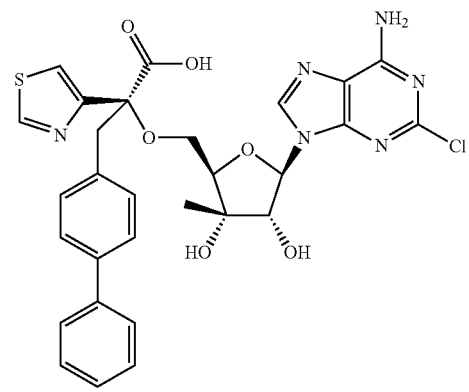 [SMILES: C[C@@]1(O)[C@@H](CO[C@](Cc2ccc(-c3ccccc3)cc2)(C(=O)O)c2cscn2)O[C@@H](n2cnc3c(N)nc(Cl)nc32)[C@@H]1O] |
| 199 | 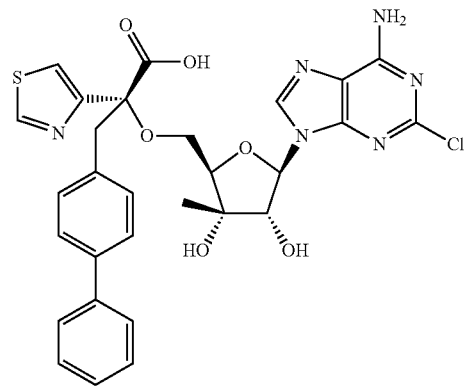 [SMILES: C[C@@]1(O)[C@@H](CO[C@@](Cc2ccc(-c3ccccc3)cc2)(C(=O)O)c2cscn2)O[C@@H](n2cnc3c(N)nc(Cl)nc32)[C@@H]1O] |
| 200 | 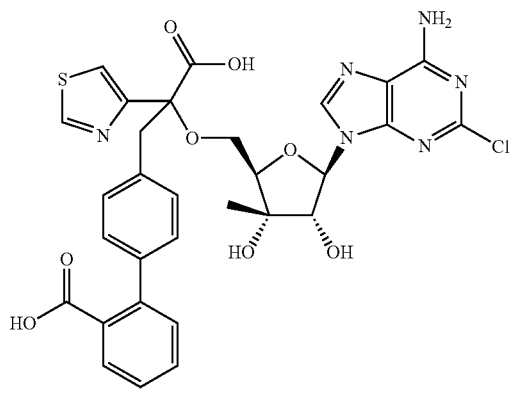 [SMILES: C[C@@]1(O)[C@@H](COC(Cc2ccc(-c3ccccc3C(=O)O)cc2)(C(=O)O)c2cscn2)O[C@@H](n2cnc3c(N)nc(Cl)nc32)[C@@H]1O] |

-continued
| Example # | Compound |
|---|---|
| 201 | 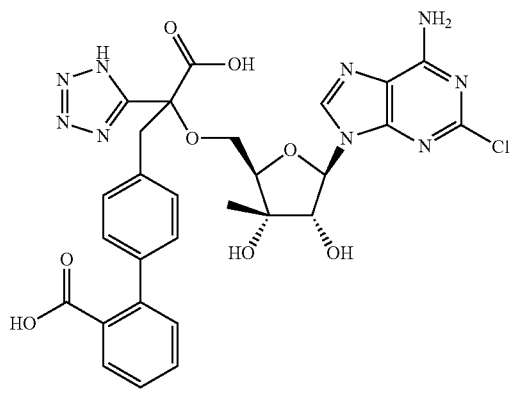 [SMILES: C[C@@]1(O)[C@@H](COC(Cc2ccc(-c3ccccc3C(=O)O)cc2)(C(=O)O)c2nnn[nH]2)O[C@@H](n2cnc3c(N)nc(Cl)nc32)[C@@H]1O] |
| 202 | 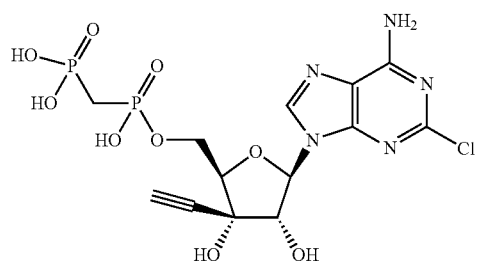 [SMILES: C#C[C@@]1(O)[C@@H](COP(=O)(O)CP(=O)(O)O)O[C@@H](n2cnc3c(N)nc(Cl)nc32)[C@@H]1O] |
| 203 | 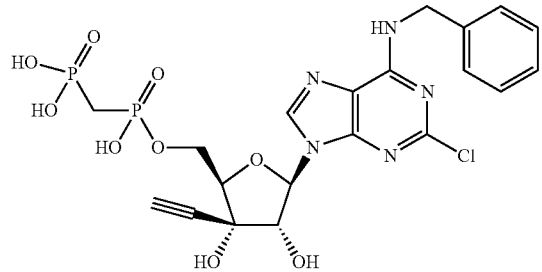 [SMILES: C#C[C@@]1(O)[C@@H](COP(=O)(O)CP(=O)(O)O)O[C@@H](n2cnc3c(NCc4ccccc4)nc(Cl)nc32)[C@@H]1O] |
| 204 | 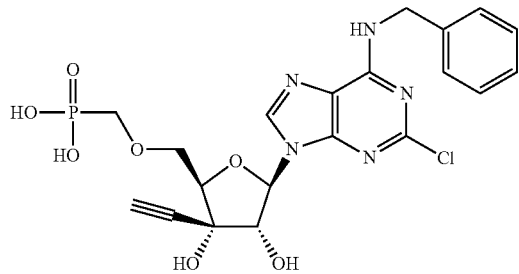 [SMILES: C#C[C@@]1(O)[C@@H](COCP(=O)(O)O)O[C@@H](n2cnc3c(NCc4ccccc4)nc(Cl)nc32)[C@@H]1O] |
| 205 | 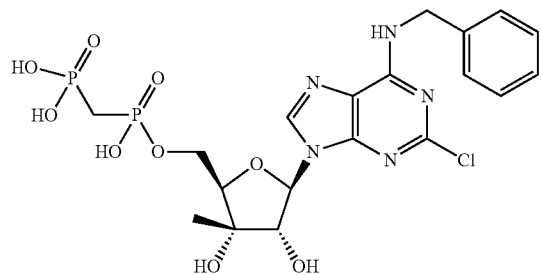 [SMILES: C[C@@]1(O)[C@@H](COP(=O)(O)CP(=O)(O)O)O[C@@H](n2cnc3c(NCc4ccccc4)nc(Cl)nc32)[C@@H]1O] |
or a pharmaceutically acceptable salt thereof.

30. A pharmaceutical composition comprising a compound according to claim 1, or a pharmaceutically acceptable salt thereof, and one or more pharmaceutically acceptable excipients.

31. The compound of claim 1, wherein $R^{2b}$ is unsubstituted $C_2$alkynyl.

32. The compound of claim 5, wherein $R^5$ is benzyl substituted on the phenyl ring at a para position.

33. The compound of claim 5, wherein:
the phenyl ring substituent is selected from substituted piperidonyl, piperazinonyl, tetrahydropyrimidonyl, pyridonyl, and pyridyl, and, optionally,
the piperidonyl, tetrahydropyrimidonyl, pyridonyl, or pyridyl is substituted with one or more of alkyl, hydroxyalkyl or alkoxyalkyl.

34. The compound of claim 28, wherein $R^5$ is benzyl substituted on the phenyl ring.

35. A compound of formula (I):

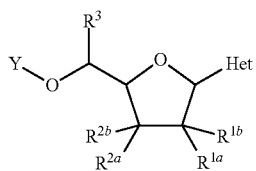

(I)

or a pharmaceutically acceptable salt and/or prodrug thereof wherein
Y is

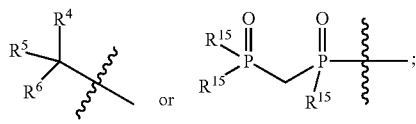

Het is

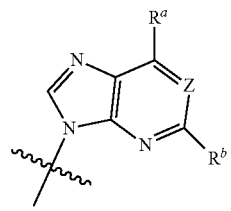

wherein Z is N; $R^a$ is selected from —$NR^7R^8$, aralkyl, aryl, and heteroaryl; $R^b$ is selected from halo, alkyl, haloalkyl, hydroxyalkyl, alkylthio, amido, carbonyl, amido, and heteroaryl; $R^7$ is selected from hydroxy, alkyl, aralkyl, heteroaralkyl, cycloalkyl, and heterocyclyl and $R^8$ is H or alkyl; or $R^7$ and $R^8$, together with the nitrogen atom to which they are attached, form a 4- to 7-membered heterocyclyl ring;

$R^{1a}$ is selected from H, halo, hydroxy, cyano, azido, amino, $C_{1-6}$alkyl, hydroxy$C_{1-6}$alkyl, amino-$C_{1-6}$alkyl, —O—C(O)—O—$C_{1-6}$alkyl, $C_{1-6}$acyloxy, $C_{1-6}$alkoxy, $C_{2-6}$alkenyl, and $C_{2-6}$alkynyl;

$R^{1b}$ is selected from H, halo, $C_{1-6}$alkyl, hydroxy-$C_{1-6}$alkyl, amino-$C_{1-6}$alkyl, $C_{2-6}$alkenyl, and $C_{2-6}$alkynyl;

$R^{2a}$ is selected from halo, hydroxy, cyano, azido, amino, $C_{1-6}$alkyl, hydroxy-$C_{1-6}$alkyl, amino-$C_{1-6}$alkyl, $C_{1-6}$acyloxy, —O—C(O)—O—$C_{1-6}$alkyl, $C_{1-6}$alkoxy, $C_{2-6}$alkenyl, and $C_{2-6}$alkynyl;

$R^{2b}$ is $C_{2-6}$alkynyl;

$R^3$ is selected from H and alkyl;

$R^4$ is selected from H, alkyl, CN, aryl, heteroaryl, —C(O)OR$^9$, —C(O)NR$^{11}$R$^{12}$, —S(O)$_2$R$^{10}$, —P(O)(OR$^{11}$)(OR$^{12}$), and —P(O)(OR$^{11}$)(NR$^{13}$R$^{14}$);

$R^5$ is aralkyl or heteroaralkyl;

$R^6$ is selected from —C(O)OR$^9$, —C(O)NR$^{16}$R$^{17}$, and —P(O)(OR$^{11}$)(OR$^{12}$);

$R^9$ is independently selected from H, alkyl, cycloalkyl, cycloalkylalkyl, heterocyclyl, heterocyclylalkyl, aryl, aralkyl, heteroaryl, and heteroaralkyl;

$R^{10}$ is independently selected from alkyl, alkenyl, alkynyl, amino, cycloalkyl, cycloalkylalkyl, heterocyclyl, heterocyclylalkyl, aryl, aralkyl, heteroaryl, and heteroaralkyl; and each $R^{11}$ and $R^{12}$ is independently selected from H, alkyl, cycloalkyl, cycloalkylalkyl, heterocyclyl, heterocyclylalkyl, aryl, aralkyl, heteroaryl, and heteroaralkyl; or $R^{11}$ and $R^{12}$, together with the nitrogen atom to which they are attached, form a 5- to 7-membered heterocyclyl;

$R^{13}$ is, independently for each occurrence, H or alkyl;

$R^{14}$ is, independently for each occurrence, alkyl or aralkyl;

each $R^{15}$ is independently selected from hydroxy, alkoxy acyloxy and NR$^{13}$R$^{14}$;

each $R^{16}$ and $R^{17}$ is independently selected from H, hydroxy, alkyl, cycloalkyl, cycloalkylalkyl, heterocyclyl, heterocyclylalkyl, aryl, aralkyl, heteroaryl, heteroaralkyl; or $R^{16}$ and $R^{17}$, together with the nitrogen atom to which they are attached, form a 5- to 7-membered heterocyclyl.

* * * * *